United States Patent
Yang et al.

(10) Patent No.: US 11,691,952 B2
(45) Date of Patent: Jul. 4, 2023

(54) NITROGEN-CONTAINING COMPOUND, AND ELECTRONIC ELEMENT AND ELECTRONIC DEVICE USING SAME

(71) Applicant: Shaanxi Lighte Optoelectronics Material Co., Ltd., Xi'an (CN)

(72) Inventors: Min Yang, Xi'an (CN); Peng Nan, Xi'an (CN)

(73) Assignee: SHAANXI LIGHTE OPTOELECTRONICS MATERIAL CO., LTD., Xi'an (CN)

(*) Notice: Subject to any disclaimer, the term of this patent is extended or adjusted under 35 U.S.C. 154(b) by 53 days.

(21) Appl. No.: 17/787,656

(22) PCT Filed: Apr. 28, 2021

(86) PCT No.: PCT/CN2021/090725
§ 371 (c)(1),
(2) Date: Jun. 21, 2022

(87) PCT Pub. No.: WO2021/223650
PCT Pub. Date: Nov. 11, 2021

(65) Prior Publication Data
US 2023/0052660 A1 Feb. 16, 2023

(30) Foreign Application Priority Data
May 8, 2020 (CN) .......... 202010383441.X
Jul. 27, 2020 (CN) .......... 202010732484.4

(51) Int. Cl.
C07D 251/24 (2006.01)
C07D 407/04 (2006.01)
(Continued)

(52) U.S. Cl.
CPC ......... *C07D 251/24* (2013.01); *C07D 215/12* (2013.01); *C07D 235/18* (2013.01);
(Continued)

(58) Field of Classification Search
CPC .. C07D 251/24; C07D 215/12; H01L 51/0071
See application file for complete search history.

(56) References Cited

FOREIGN PATENT DOCUMENTS

| CN | 107189436 A | 9/2017 |
|---|---|---|
| CN | 110128279 A | 8/2019 |

(Continued)

OTHER PUBLICATIONS

International Search Report from corresponding International Application No. PCT/CN2021/090725, dated Jul. 21, 2021, 6 pages with translation.

*Primary Examiner* — Anthony Ho
(74) *Attorney, Agent, or Firm* — Tucker Ellis LLP

(57) ABSTRACT

The present application relates to a nitrogen-containing compound. The structural formula of the nitrogen-containing compound is as shown in a Formula 1, in which a ring A and a ring B are each independently selected from a benzene ring or a fused aromatic ring with 10 to 14 ring-forming carbon atoms, and at least one of the ring A and the ring B is selected from the fused aromatic ring with 10 to 14 ring-forming carbon atoms; L is selected from a single bond, a substituted or unsubstituted arylene group with 6 to 30 carbon atoms, and a substituted or unsubstituted heteroarylene group with 3 to 30 carbon atoms; and Het is a substituted or unsubstituted nitrogen-containing heteroaryl group with 3 to 30 carbon atoms. The nitrogen-containing compound of the present application can improve the luminous efficiency of an organic electroluminescent device and the conversion efficiency of a photoelectric conversion device using the nitrogen-containing compound.

(Continued)

Formula 1

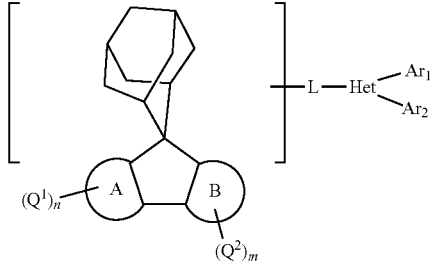

12 Claims, 2 Drawing Sheets

(51) Int. Cl.
| | |
|---|---|
| C07D 401/04 | (2006.01) |
| C07D 401/10 | (2006.01) |
| C07D 405/10 | (2006.01) |
| C07D 403/10 | (2006.01) |
| C07D 403/04 | (2006.01) |
| C07D 413/10 | (2006.01) |
| C07D 417/10 | (2006.01) |
| C07D 239/74 | (2006.01) |
| C07D 237/08 | (2006.01) |
| C07D 241/42 | (2006.01) |
| C07D 215/12 | (2006.01) |
| C07D 235/18 | (2006.01) |
| C07D 495/04 | (2006.01) |
| C07D 491/048 | (2006.01) |
| C07D 405/14 | (2006.01) |
| C07D 407/14 | (2006.01) |
| C07D 401/14 | (2006.01) |
| C07D 239/26 | (2006.01) |
| H01L 51/50 | (2006.01) |
| H01L 51/00 | (2006.01) |
| C07D 405/04 | (2006.01) |

(52) U.S. Cl.
CPC ......... *C07D 237/08* (2013.01); *C07D 239/26* (2013.01); *C07D 239/74* (2013.01); *C07D 241/42* (2013.01); *C07D 401/04* (2013.01); *C07D 401/10* (2013.01); *C07D 401/14* (2013.01); *C07D 403/04* (2013.01); *C07D 403/10* (2013.01); *C07D 405/04* (2013.01); *C07D 405/10* (2013.01); *C07D 405/14* (2013.01); *C07D 407/04* (2013.01); *C07D 407/14* (2013.01); *C07D 413/10* (2013.01); *C07D 417/10* (2013.01); *C07D 491/048* (2013.01); *C07D 495/04* (2013.01); *H01L 51/0064* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/5072* (2013.01); *H01L 51/5096* (2013.01); *C07B 2200/05* (2013.01)

(56) References Cited

FOREIGN PATENT DOCUMENTS

| CN | 110615759 A | 12/2019 |
|---|---|---|
| CN | 111018797 A | 4/2020 |
| CN | 111039881 A | 4/2020 |
| CN | 111848501 A | 10/2020 |
| CN | 111925315 A | 11/2020 |
| CN | 111961038 A | 11/2020 |
| CN | 112142548 A | 12/2020 |
| CN | 112209840 A | 1/2021 |
| EP | 1655293 B1 | 5/2006 |
| KR | 1020190118514 A | 10/2019 |
| KR | 1020200026124 A | 3/2020 |
| WO | 2020045924 A1 | 3/2020 |
| WO | 2020046049 A1 | 3/2020 |
| WO | 2020050623 A1 | 3/2020 |
| WO | 2020080849 A1 | 4/2020 |
| WO | 2020080872 A1 | 4/2020 |

NITROGEN-CONTAINING COMPOUND, AND ELECTRONIC ELEMENT AND ELECTRONIC DEVICE USING SAME

CROSS REFERENCE TO RELATED APPLICATIONS

The application claims the priority of the Chinese patent application No. 202010383441.X filed on May 8, 2020 and the priority of the Chinese patent application No. 202010732484.4 filed on Jul. 27, 2020, and the contents of the Chinese patent applications are hereby incorporated by reference in their entirety as a part of the application.

TECHNICAL FIELD

The application belongs to the technical field of organic materials, and particularly provides a nitrogen-containing compound, and an electronic element and an electronic device using the same.

BACKGROUND

An organic light-emitting element is a representative example of an organic electronic element. Generally speaking, an organic light-emitting phenomenon refers to a phenomenon that electric energy is converted into light energy by using organic substances. An organic light-emitting element using the organic light-emitting phenomenon is generally provided with a structure including an anode and a cathode, and an organic layer positioned therebetween. In order to improve the efficiency and the stability of the organic light-emitting element, the organic layer is usually formed by a multi-layer structure formed by different substances, for example, the organic layer can be formed by a hole injection layer, a hole transport layer, a light-emitting layer, an electron transport layer, an electron injection layer and the like. For the structure of such organic light-emitting element, if a voltage is applied between the two electrodes, holes are injected into the organic layer from the anode, electrons are injected into the organic layer from the cathode, when the injected holes and electrons meet each other, excitons are formed, and when the excitons undergo transition to a ground state again, light is emitted.

Generally speaking, electron transport materials are compounds with electron-deficient nitrogen-containing heterocyclic groups, and most of the electron transport materials have relatively high electron affinity, so that the electron transport materials have relatively high electron accepting capability, but compared with hole transport materials, the electron mobility of common electron transport materials such as aluminum 8-hydroxyquinolinate is far lower than the hole mobility of the hole transport materials, so that in an OLED device, on one hand, the recombination probability of holes and electrons caused by unbalanced injection and transport of carriers is reduced, and the luminous efficiency of the device is reduced; and on the other hand, the electron transport materials with lower electron mobility can cause the working voltage of the device to rise, so that the power efficiency is influenced, which is unfavorable for the energy conservation.

SUMMARY

Aiming at the problems in the prior art, the aims of the present disclosure to provide a nitrogen-containing compound, and an electronic element and an electronic device using the same. The nitrogen-containing compound can be used as a hole blocking layer and/or an electron transport layer of an organic electroluminescent device.

In a first aspect, the present disclosure provides a nitrogen-containing compound, having a structural formula as shown in Formula 1:

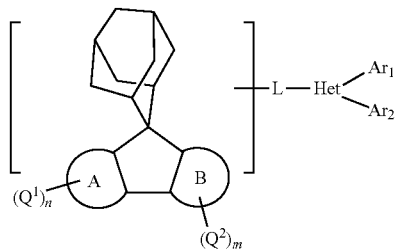

Formula 1 where ring A and ring B are the same or different, and are each independently selected from a benzene ring or a fused aromatic ring with 10 to 14 ring-forming carbon atoms, and at least one of the ring A and the ring B is the fused aromatic ring with 10 to 14 ring-forming carbon atoms;

L is selected from a single bond, substituted or unsubstituted arylene with 6 to 30 carbon atoms, and substituted or unsubstituted heteroarylene with 3 to 30 carbon atoms;

each $Q^1$ and each $Q^2$ are the same or different, and are each independently selected from deuterium, halogen group, cyano, haloalkyl with 1 to 10 carbon atoms, alkyl with 1 to 10 carbon atoms, cycloalkyl with 3 to 15 carbon atoms, alkoxy with 1 to 4 carbon atoms, alkylthio with 1 to 4 carbon atoms, trialkylsilyl with 3 to 12 carbon atoms, triarylsilyl with 18 to 24 carbon atoms, aryl with 6 to 12 carbon atoms, aralkyl with 7 to 13 carbon atoms, heteroaryl with 4 to 12 carbon atoms, and heteroaralkyl with 5 to 13 carbon atoms;

n represents the number of $Q^1$, which is selected from 0 or 1; and m represents the number of $Q^2$, which is selected from 0 or 1;

Het is substituted or unsubstituted nitrogen-containing heteroaryl with 3 to 30 carbon atoms;

$Ar_1$ and $Ar_2$ are the same or different, and are each independently selected from hydrogen, substituted or unsubstituted alkyl with 1 to 20 carbon atoms, substituted or unsubstituted cycloalkyl with 3 to 20 carbon atoms, substituted or unsubstituted aryl with 6 to 30 carbon atoms, and substituted or unsubstituted heteroaryl with 3 to 30 carbon atoms;

the substituents in L, Het, $Ar_1$ and $Ar_2$ are the same or different, and are each independently selected from deuterium, halogen group, cyano, aryl with 6 to 25 carbon atoms, heteroaryl with 3 to 25 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, trialkylsilyl with 3 to 12 carbon atoms, and triarylsilyl with 18 to 24 carbon atoms.

In a second aspect, the present disclosure provides an electronic element, comprising an anode, a cathode which are arranged oppositely to the anode, and a functional layer arranged between the anode and the cathode, and the functional layer contains the nitrogen-containing compound in the first aspect of the present disclosure; preferably, the functional layer comprises an electron transport layer, and the electron transport layer contains the nitrogen-containing compound; and preferably, the functional layer comprises a hole blocking layer, and the hole blocking layer contains the nitrogen-containing compound.

In a third aspect, the present disclosure provides an electronic device, comprising the electronic element in the second aspect of the present disclosure.

Through the above technical solution, the nitrogen-containing compound provided by the present disclosure has a molecular structure in which heteroaryl is bonded to fused-ring adamantane fluorene. On one hand, the molecular structure can reduce an energy level injection barrier, so that the working voltage of an organic electroluminescent device is reduced, and the open-circuit voltage of a photoelectric conversion device is improved. On the other hand, the molecular structure has large molecular weight, and a fused ring structure can increase steric hindrance, so that the structure is adjusted, the material is difficult to crystallize or aggregate, and the material has longer service life in the electronic element. Not only that, the molecular structure has electron-rich characteristics, the polarity of the whole molecule is enhanced, and directional arrangement of material molecules is more facilitated, so that injection and transport of electrons are enhanced, the electron conductivity of an electron transport material is enhanced, and meanwhile, the luminous efficiency of an organic electroluminescent device using the nitrogen-containing compound can be improved; and the conversion efficiency of the photoelectric conversion device using the nitrogen-containing compound is improved.

Other features and advantages of the present disclosure will be described in detail in the subsequent specific embodiments.

BRIEF DESCRIPTION OF THE DRAWINGS

The drawings are used to provide a further understanding of the present disclosure and constitute a part of the description, and are used to explain the present disclosure together with the following specific embodiments, but do not constitute limitations on the present disclosure. In the drawings.

DESCRIPTION OF REFERENCE SIGNS

Figure 1:
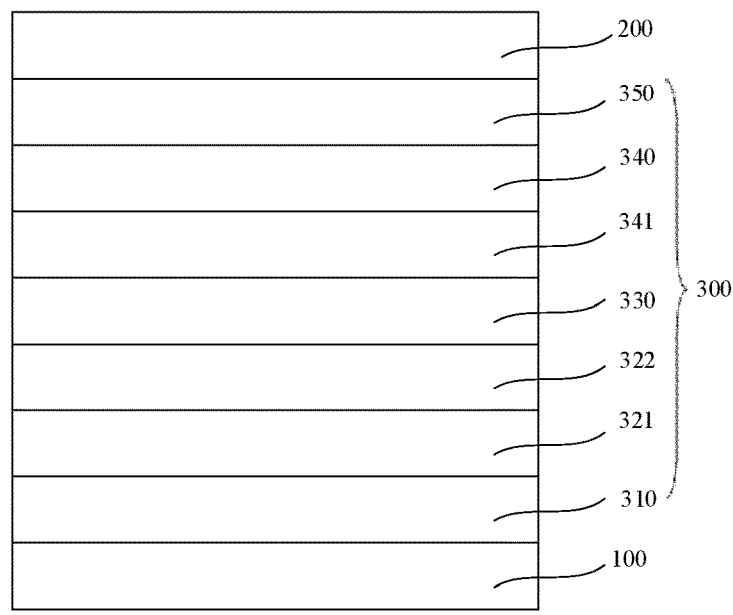
FIG. 1 is a structural schematic diagram of an organic electroluminescent device according to an embodiment of the present disclosure.

100, anode; 200, cathode; 300, functional layer; 310, hole injection layer; 321, hole transport layer; 322, electron blocking layer; 330, organic light-emitting layer; 341, hole blocking layer; 340, electron transport layer; 350, electron injection layer; 360, photoelectric conversion layer; 400, first electronic device; and 500, second electronic device.

DETAILED DESCRIPTION

The specific embodiments of the present disclosure are described in detail below in combination with the drawings. It should be understood that the specific embodiments described herein are only used to illustrate and interpret the present disclosure, but not to limit the present disclosure.

In a first aspect, the present disclosure provides a nitrogen-containing compound, having a structural formula as shown in Formula 1:

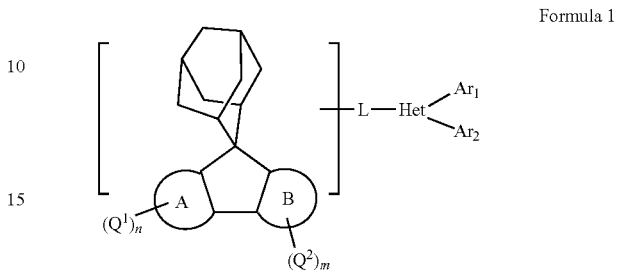

Formula 1 where ring A and ring B are the same or different, and are each independently selected from a benzene ring or a fused aromatic ring with 10 to 14 ring-forming carbon atoms, and at least one of the ring A and the ring B is the fused aromatic ring with 10 to 14 ring-forming carbon atoms;

L is connected with the ring A or the ring B;

specifically, in the present disclosure, the nitrogen-containing compound as shown in the Formula 1 can be selected from the compound as shown in Formula A or Formula B;

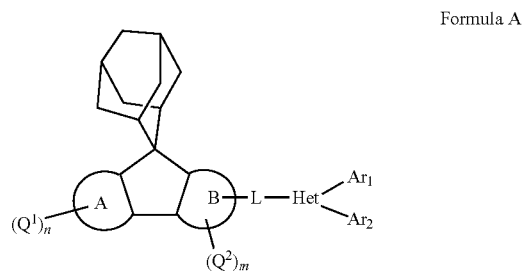

Formula A

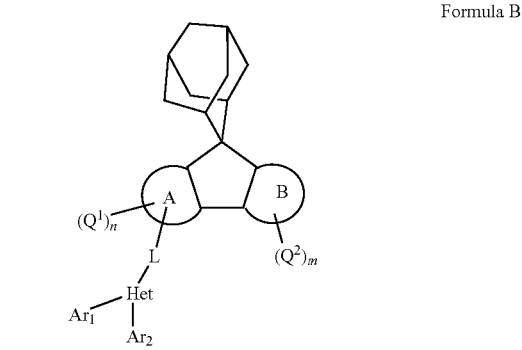

Formula B when the ring A or the ring B is provided with substituent group $Q^1$ or $Q^2$, L is only connected with the ring A itself or with the ring B itself.

L is selected from a single bond, substituted or unsubstituted arylene with 6 to 30 carbon atoms, and substituted or unsubstituted heteroarylene with 3 to 30 carbon atoms;

each $Q^1$ and each $Q^2$ are the same or different, and are each independently selected from deuterium, halogen group, cyano, haloalkyl with 1 to 10 carbon atoms, alkyl with 1 to 10 carbon atoms, cycloalkyl with 3 to 15 carbon atoms, alkoxy with 1 to 4 carbon atoms, alkylthio with 1 to 4 carbon atoms, trialkylsilyl with 3 to 12 carbon atoms, triarylsilyl with 18 to 24 carbon atoms, aryl with 6 to 12 carbon atoms, aralkyl with 7 to 13 carbon atoms, heteroaryl with 4 to 12 carbon atoms, and heteroaralkyl with 5 to 13 carbon atoms;

n represents the number of $Q^1$, which is selected from 0 or 1; and m represents the number of $Q^2$, which is selected from 0 or 1;

Het is substituted or unsubstituted nitrogen-containing heteroaryl with 3 to 30 carbon atoms;

$Ar_1$ and $Ar_2$ are the same or different, and are each independently selected from hydrogen, substituted or unsubstituted alkyl with 1 to 20 carbon atoms, substituted or unsubstituted cycloalkyl with 3 to 20 carbon atoms, substituted or unsubstituted aryl with 6 to 30 carbon atoms, and substituted or unsubstituted heteroaryl with 3 to 30 carbon atoms;

the substituents in the L, the Het, $Ar_1$ and $Ar_2$ are the same or different, and are each independently selected from deuterium, halogen group, cyano, aryl with 6 to 25 carbon atoms, heteroaryl with 3 to 25 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, trialkylsilyl with 3 to 12 carbon atoms, and triarylsilyl with 18 to 24 carbon atoms. In the present disclosure, "Het can be substituted or unsubstituted nitrogen-containing heteroaryl with 3 to 30 carbon atoms" means that Het can contain substituent group or can not contain substituent group. When Het contains substituent group, the substituent group in Het refers to substituent group except $Ar_1$ and $Ar_2$.

In the present disclosure, the ring A and the ring B are the same or different, and are each independently selected from a benzene ring or a fused aromatic ring with 10 to 14 ring-forming carbon atoms, and the fused aromatic ring can be a naphthalene ring, an anthracene ring or a phenanthrene ring.

Preferably, in the present disclosure, the ring A or the ring B is phenyl; and L is connected with phenyl.

The nitrogen-containing compound provided by the present disclosure has a molecular structure in which heteroaryl is bonded to fused-ring adamantane fluorene. On one hand, the molecular structure can reduce an energy level injection barrier, so that the working voltage of an organic electroluminescent device is reduced, and the open-circuit voltage of a photoelectric conversion device is improved. On the other hand, the molecular structure has large molecular weight, molecular asymmetry is increased, the structure can be adjusted, the material is difficult to crystallize or aggregate, and the material has longer service life in an electronic element. Not only that, the molecular structure has electron-rich characteristics, the polarity of the whole molecule is enhanced, and directional arrangement of material molecules is facilitated, so that injection and transport of electrons are enhanced. In addition, the fused ring structure can enhance the electron conductivity of an electron transport material, can improve the luminous efficiency of an organic electroluminescent device using the nitrogen-containing compound, and can improve the conversion efficiency of a photoelectric conversion device using the nitrogen-containing compound.

In one embodiment of the present disclosure, the structural formula of the nitrogen-containing compound as shown in the Formula 1 is selected from the group consisting of the following Formulae 2 to 19:

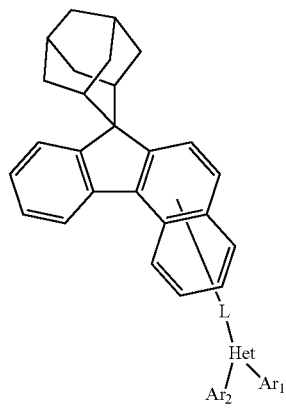

Formula 2

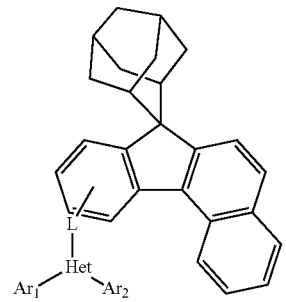

Formula 3

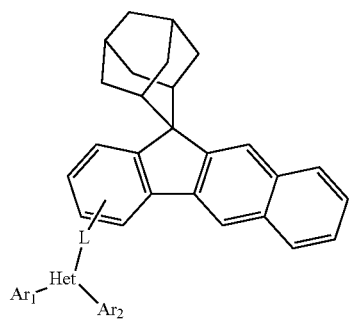

Formula 4

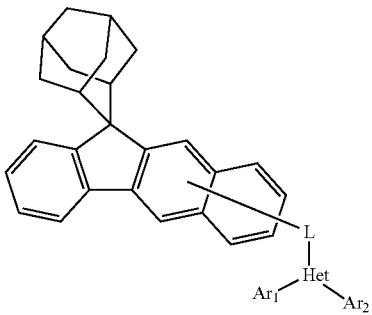

Formula 5

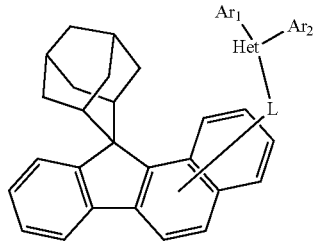

Formula 5'

Formula 6
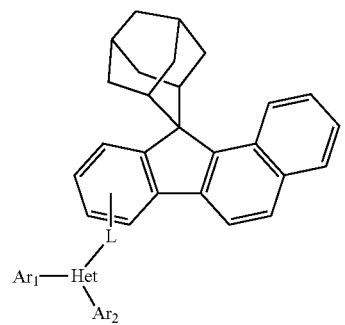
Formula 7
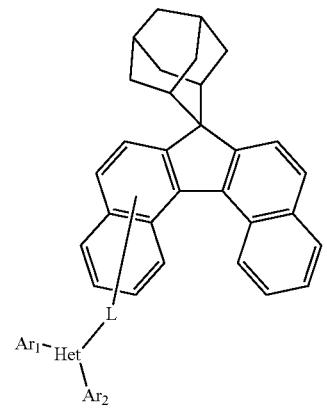
Formula 8
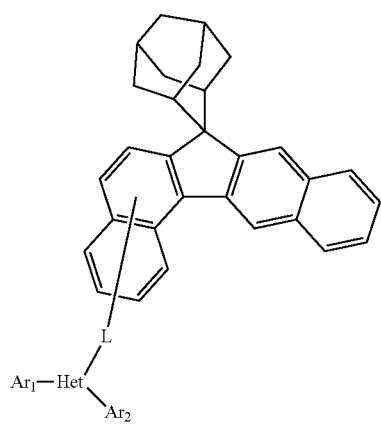
Formula 9'
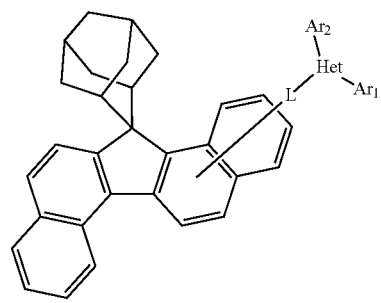
Formula 9
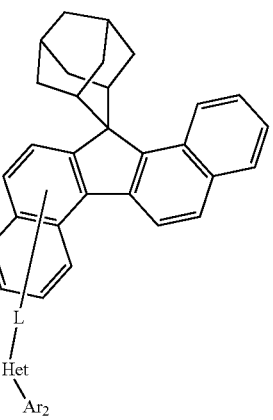
Formula 10
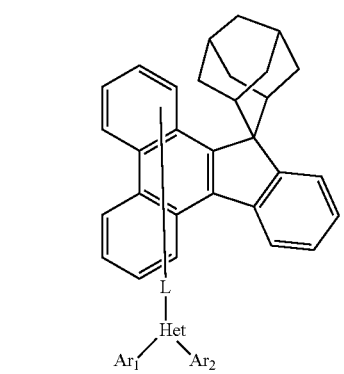
Formula 11
Formula 12
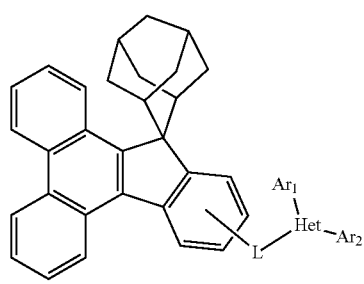

Formula 13
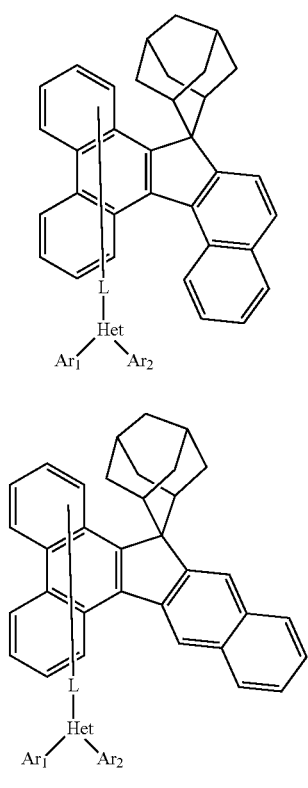
Formula 14
Formula 15
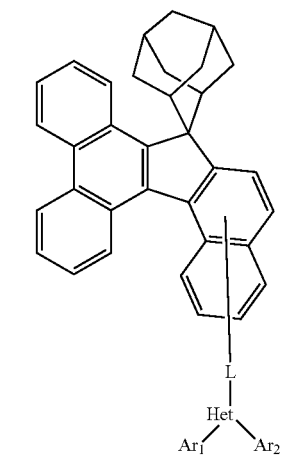
Formula 16
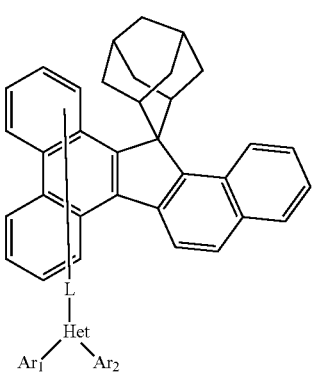
Formula 17
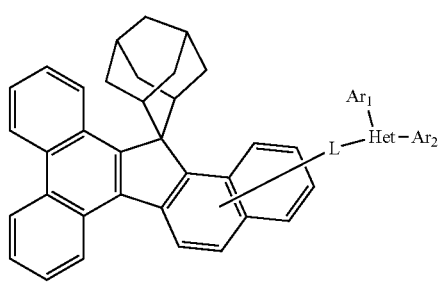
Formula 18
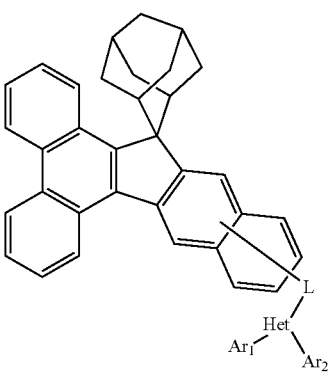
Formula 19
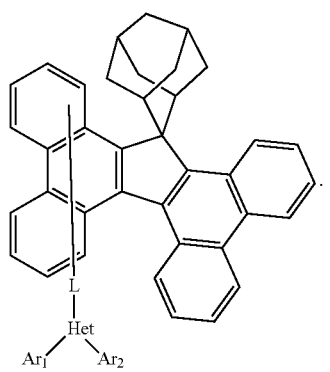
In one embodiment of the present disclosure, the structural formula of the nitrogen-containing compound as shown in the Formula 1 is selected from the group consisting of the following Formulae 20 to 28:
Formula 20
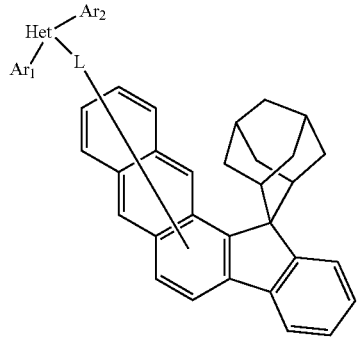

Formula 21
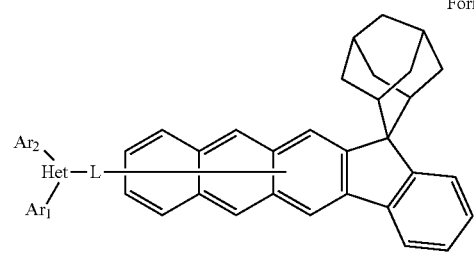
Formula 22
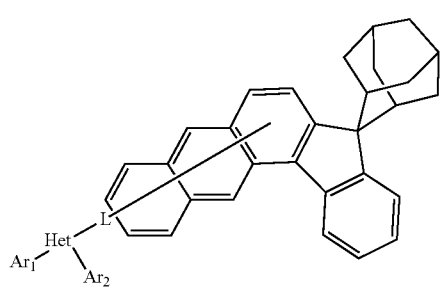
Formula 23
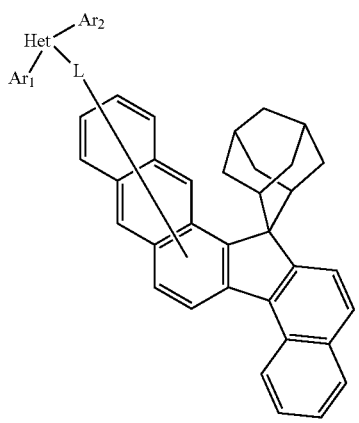
Formula 24
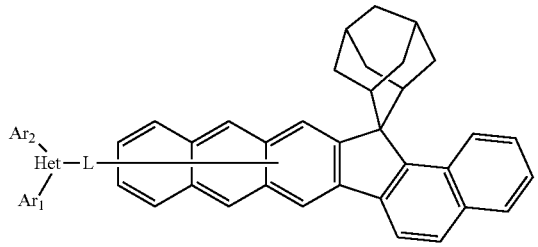
Formula 25
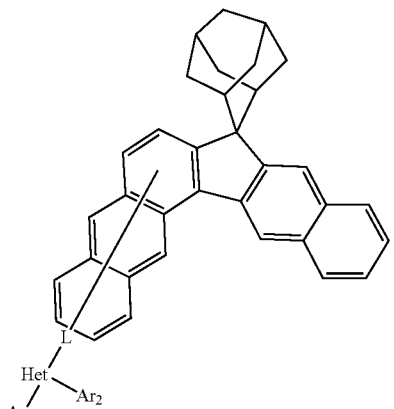
Formula 26
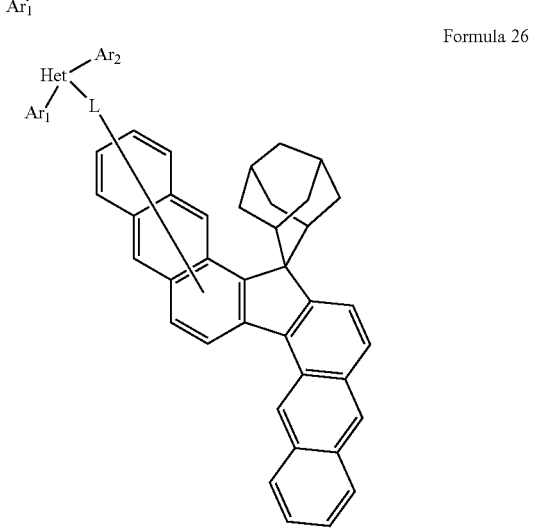
Formula 27
Formula 28
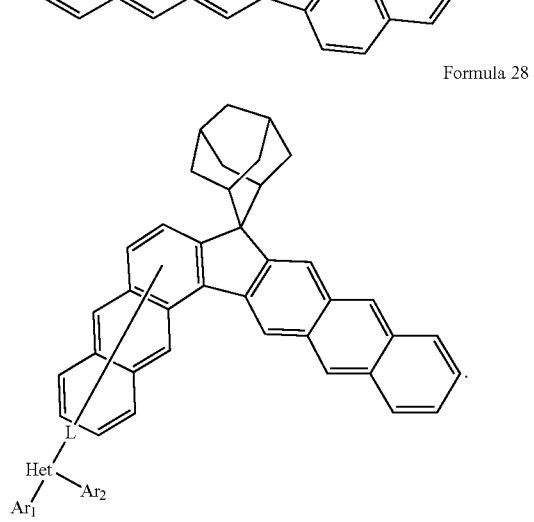

In the present disclosure, because adamantane is of a three-dimensional structure, in a compound structure diagram, due to different drawing angles, different plane shapes can be presented, cyclic structures formed on cyclopentane are all adamantane, and the connection positions are the same. For example, the following structures

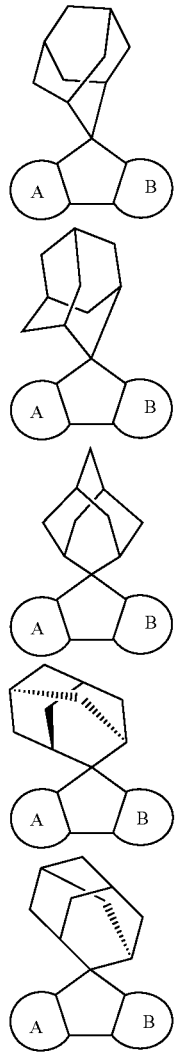

are the same.

In the present disclosure, the adopted description modes "each . . . are independently", " . . . are respectively and independently" and " . . . are independently selected from" can be interchanged, and should be understood in a broad sense, which means that in different groups, specific options expressed between the same symbols do not influence each other, or in a same group, specific options expressed between the same symbols do not influence each other. For example, the meaning of

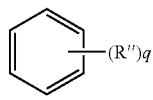

Formula Q-1

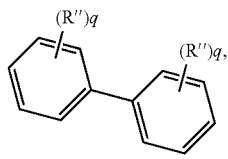

Formula Q-2

"where each q is independently 0, 1, 2 or 3, each R" is independently selected from hydrogen, deuterium, fluorine and chlorine" is as follows: Formula Q-1 represents that q substituents R" exist on a benzene ring, each R" can be the same or different, and options of each R" do not influence each other; and Formula Q-2 represents that each benzene ring of biphenyl has q substituents R", the number q of the substituents R" on the two benzene rings can be the same or different, each R" can be the same or different, and options of each R" do not influence each other.

In the present disclosure, the term such as "substituted or unsubstituted" means that a functional group described behind the term may have or do not have a substituent (hereinafter, the substituent is collectively referred to as Rc in order to facilitate description). For example, the "substituted or unsubstituted aryl" refers to aryl having the substituent Rc or unsubstituted aryl. The above substituent, namely Rc can, for example, be deuterium, halogen group, cyano, aryl with 6 to 25 carbon atoms, heteroaryl with 3 to 25 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, trialkylsilyl with 3 to 12 carbon atoms, and triarylsilyl with 18 to 24 carbon atoms. In the present disclosure, the "substituted" functional group can be substituted by one or two or more substituents in the Rc; when two substituents Rc are connected to a same atom, the two substituents Rc can independently exist or are connected with each other to form a ring with the atom; and when two adjacent substituents Rc exist on the functional group, the two adjacent substituents Rc can independently exist or are fused with the functional group connected with the two adjacent substituents Rc to form a ring.

In the present disclosure, the number of carbon atoms in the substituted or unsubstituted functional group refers to the number of all carbon atoms. For example, if $Ar_1$ is selected from substituted aryl with 30 carbon atoms, the number of all carbon atoms of the aryl and the substituents thereon are 30.

In the present disclosure, the number of carbon atoms of L, $Ar_1$, $Ar_2$ and Het refers to the number of all carbon atoms. For example, if L is substituted arylene with 12 carbon atoms, the number of all carbon atoms of the arylene and the substituents thereon are 12. For example, if $Ar_1$ is

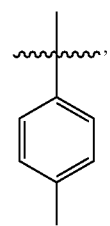 [SMILES: *c1ccc(C)cc1]

the number of carbon atoms is 7; and if L is

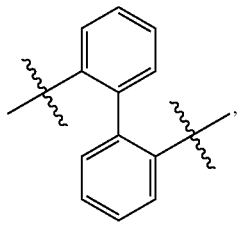 [SMILES: *c1ccccc1-c1ccccc1*]

the number of carbon atoms is 12.

In the present disclosure, aryl refers to an optional functional group or substituent derived from an aromatic carbocyclic ring. The aryl may be monocyclic aryl (e.g., phenyl) or polycyclic aryl, in other words, the aryl may be monocyclic aryl, fused aryl, which is formed by two or more monocyclic aryl conjugatedly connected through carbon-carbon bonds, formed by a monocyclic aryl and fused aryl which are conjugatedly connected through a carbon-carbon bond, or formed by two or more fused aryl conjugatedly connected through carbon-carbon bonds. That is, unless otherwise noted, two or more aromatic groups conjugatedly connected by carbon-carbon bonds can also be regarded as the aryl groups in the present present disclosure. The fused aryl may, for example, contain bicyclic fused aryl (e.g., naphthyl), tricyclic fused aryl (e.g., phenanthryl, fluorenyl, and anthryl), and the like. The aryl does not contain heteroatoms such as B, N, O, S, P, Se and Si. For example, in the present present disclosure, phenyl or the like is the aryl. Examples of the aryl may contain, but are not limited to, phenyl, naphthyl, fluorenyl, anthryl, phenanthryl, biphenyl, terphenyl, quaterphenyl, quinquephenyl, benzo[9,10] phenanthryl, pyrenyl, benzofluoranthenyl, chrysenyl, and the like. In the present disclosure, the arylene involved is a divalent group formed by further loss of one hydrogen atom from aryl.

In the present disclosure, the fused aromatic ring refers to a polyaromatic ring formed by two or more aromatic rings or heteroaromatic rings which share ring edges, such as naphthalene, anthracene, phenanthrene and pyrene.

In the present present disclosure, the substituted aryl refers to one or two or more hydrogen atoms in the aryl being substituted by a group such as a deuterium atom, halogen group, —CN, aryl, heteroaryl, trialkylsilyl, alkyl, cycloalkyl, alkoxy, alkylthio and the like. Specific examples of heteroaryl-substituted aryl contain, but are not limited to, dibenzofuranyl-substituted phenyl, dibenzothienyl-substituted phenyl, pyridyl-substituted phenyl, and the like. It should be understood that the number of carbon atoms in the substituted aryl refers to the total number of carbon atoms of the aryl and substituents on the aryl, for example, the substituted aryl with 18 carbon atoms means that the total number of carbon atoms of the aryl and the substituents thereon are 18.

In the present disclosure, the arylene involved is a divalent group formed by further loss of one hydrogen atom from aryl.

In the present disclosure, the heteroaryl refers to a monovalent aromatic ring containing at least one heteroatom in a ring or a derivative thereof, and the heteroatom can be at least one of B, O, N, P, Si, Se and S. The heteroaryl may be monocyclic heteroaryl or polycyclic heteroaryl, in other words, the heteroaryl may be a single aromatic ring system or a polycyclic systems formed by multiple aromatic rings conjugatedly connected through carbon-carbon bonds, where any one of the aromatic ring system is an aromatic monocyclic ring or an aromatic fused ring. Exemplarily, the heteroaryl may contain thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenothiazinyl, phenoxazinyl, phthalazinyl, pyridinopyrimidyl, pyridinopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuryl, phenanthrolinyl, isoxazolyl, thiadiazolyl, benzothiazolyl, phenothiazinyl, silafluorenyl, dibenzofuryl and N-arylcarbazolyl (e.g., N-phenylcarbazolyl), N-heteroarylcarbazolyl (e.g., N-pyridylcarbazolyl), N-alkylcarbazolyl (e.g., N-methylcarbazolyl), and the like, but is not limited thereto. Among them, thienyl, furyl, phenanthrolinyl etc. are heteroaryl groups of a single aromatic ring system, and the N-arylcarbazolyl and N-heteroarylcarbazolyl are heteroaryl groups of a multiple aromatic ring systems conjugatedly connected through carbon-carbon bonds.

In the present disclosure, the nitrogen-containing heteroaryl refers to a monovalent aromatic ring containing at least one heteroatom in a ring or a derivative thereof, and the heteroatom can be at least one of B, O, N, P, Si, Se and S, and at least has one N.

In the present disclosure, the heteroarylene involved refers to a divalent group formed by further loss of one hydrogen atom from heteroaryl.

In the present disclosure, the substituted heteroaryl refer to one or two or more hydrogen atoms in the heteroaryl being substituted by a group such as a deuterium atom, halogen group, —CN, aryl, heteroaryl, trialkylsilyl, alkyl, cycloalkyl, alkoxy, alkylthio and the like. Specific examples of aryl-substituted heteroaryl contain but are not limited to phenyl-substituted dibenzofuranyl, phenyl-substituted dibenzothienyl, phenyl-substituted pyridyl and the like. It should be understood that the number of carbon atoms of the substituted heteroaryl refers to the total number of carbon atoms of heteroaryl and substituents on the heteroaryl.

In the present disclosure, the alkyl with 1 to 20 carbon atoms can be linear alkyl or branched alkyl. Specifically, the alkyl with 1 to 20 carbon atoms can be linear alkyl with 1 to 20 carbon atoms or branched alkyl with 3 to 20 carbon atoms. The number of carbon atoms may, for example, be 1, 2, 3, 4, 5, 6, 7, 8, 9, 10, 11, 12, 13, 14, 15, 16, 17, 18, 19 or 20. Specific embodiments of the alkyl with 1 to 20 carbon atoms include but are not limited to methyl, ethyl, n-propyl, isopropyl, n-butyl, isobutyl, tert-butyl, n-amyl, isoamyl, neopentyl, cyclopentyl, n-hexyl, heptyl, n-octyl, 2-ethylhexyl, nonyl, decyl, 3,7-dimethyloctyl and the like.

In the present disclosure, the halogen group can be fluorine, chlorine, bromine or iodine.

In the present disclosure, an unpositioned connecting bond is a single bond "⁓" extending from a ring system, which means that one end of the connecting bond can be connected with any position in the ring system through which the bond penetrates, and the other end of the connecting bond is connected with the remaining part of a compound molecule.

For example, as shown in the following Formula (f), naphthyl represented by the Formula (f) is connected to other positions of a molecule through two unpositioned connecting bonds penetrating a dicyclic ring, and its meaning includes any one possible connecting mode represented by Formulae (f-1) to (f-10).

Formula (f)
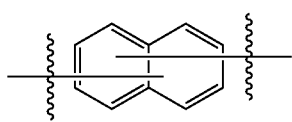

Formula (f-1)
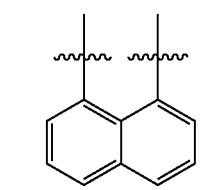

Formula (f-2)
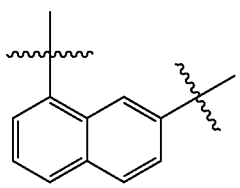

Formula (f-3)
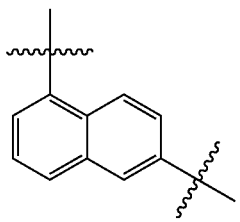

Formula (f-4)
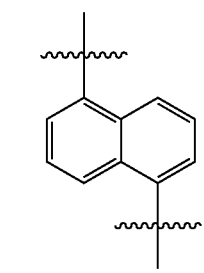

Formula (f-5)
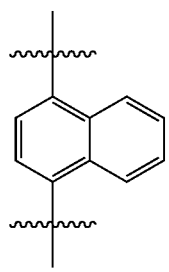

Formula (f-6)
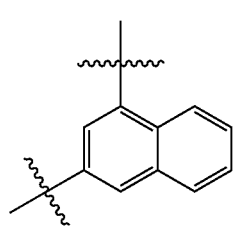

Formula (f-7)
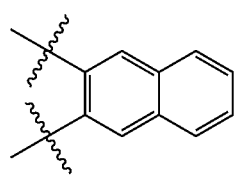

Formula (f-8)
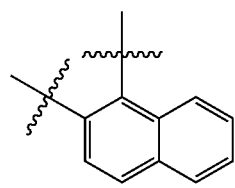

Formula (f-9)
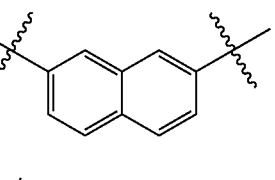

Formula (f-10)
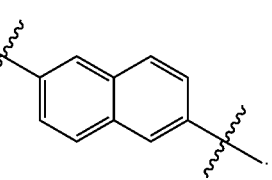

For example, as shown in the following formula (X'), dibenzofuranyl represented by the formula (X') is connected with other positions of a molecule through one unpositioned connecting bond extending from the middle of a benzene ring on one side, and its meaning includes any one possible connecting mode represented by formulae (X'-1) to (X'-4).

(X')
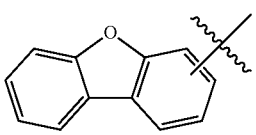

(X'-1)
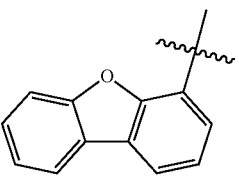

(X'-2)
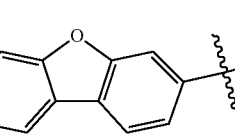

(X'-3)
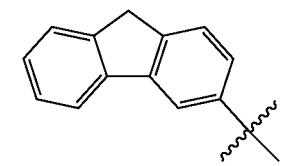

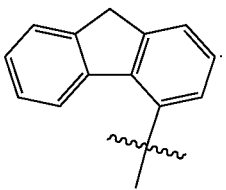
(X'-4)

In one specific embodiment of the present disclosure, the ring A and the ring B are the same or different, and are each independently selected from a benzene ring, a naphthalene ring, a phenanthrene ring and an anthracene ring, and the ring A and the ring B are not benzene rings at the same time.

In one specific embodiment of the disclosure,

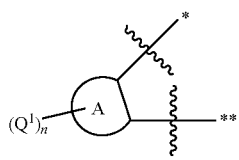

is selected from the group consisting of structures shown below:

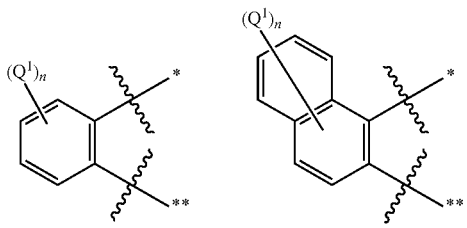

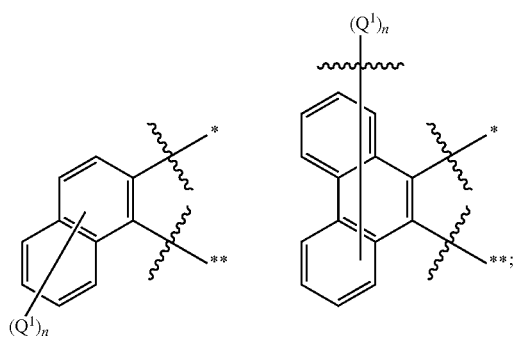

where ⁎ represents a chemical bond used for connection with

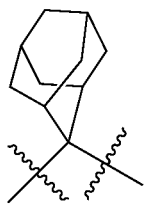 [SMILES: *C1(*)C2CC3CC(C2)CC1C3]

in the above structures, and ⁑ represents a chemical bond used for connection with

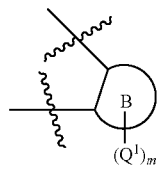

in the above structures.

In one specific embodiment of the present disclosure, in

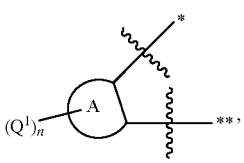

n=1 and

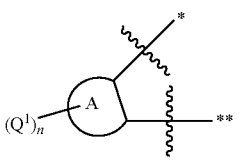

is selected from the group consisting of structures shown below:

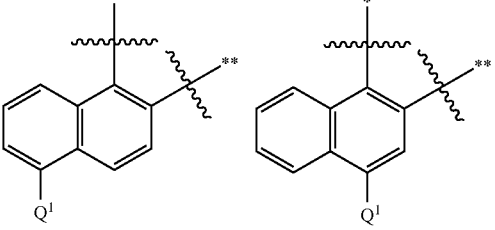

-continued
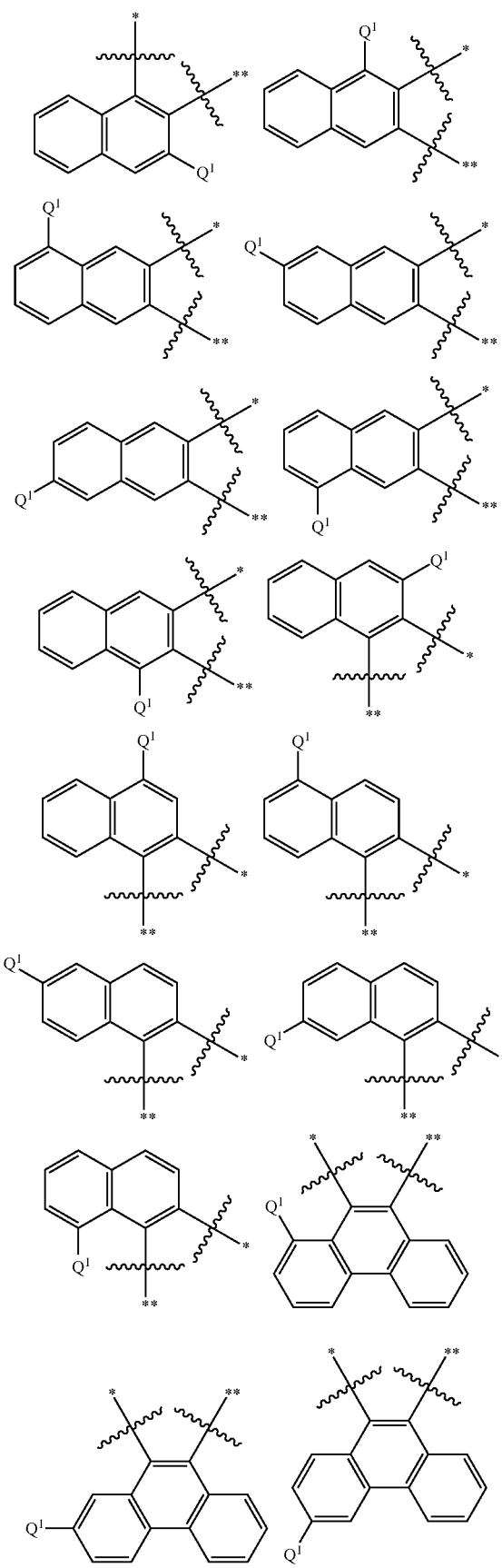
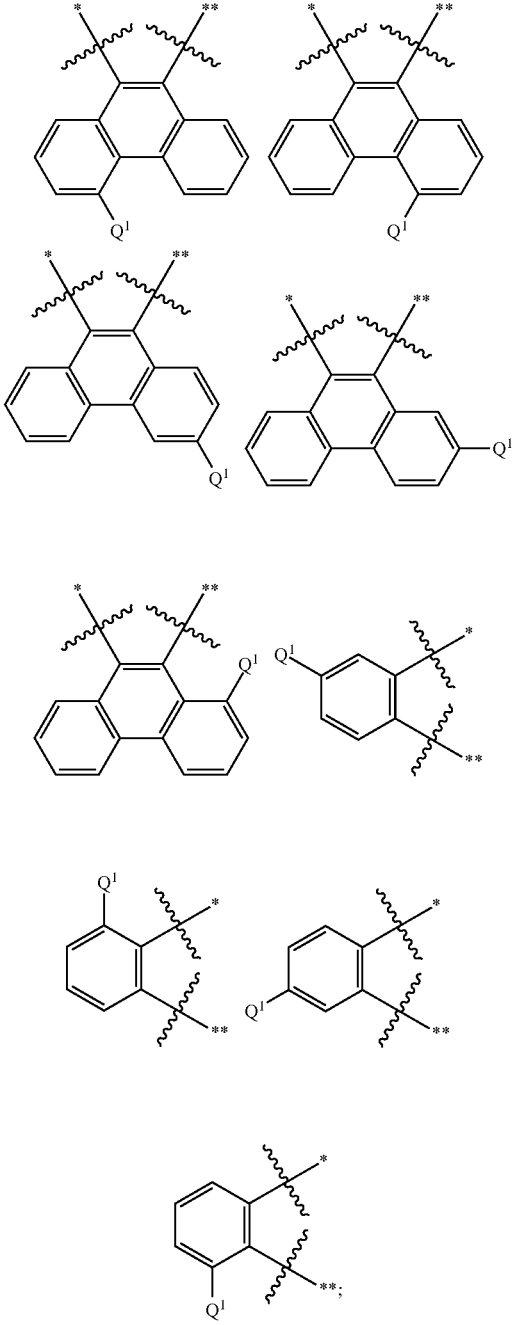
where, ⁓✶ represents a chemical bond used for connection with
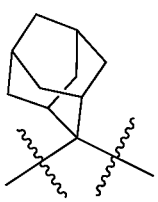 [SMILES: *C1(*)C2CC3CC(C2)CC1C3]

in the above structures, and  represents a chemical bond used for connection with

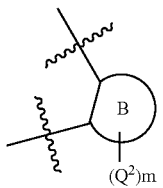

in the above structures.

In one specific embodiment of the present disclosure,

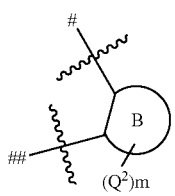

is selected from the group consisting of structures shown below:

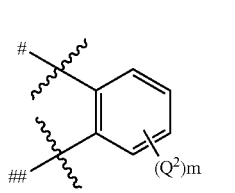 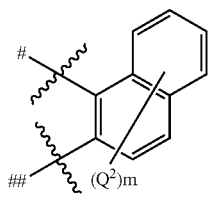

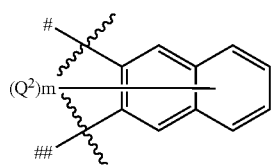 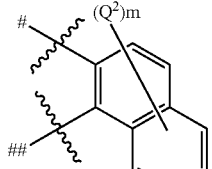

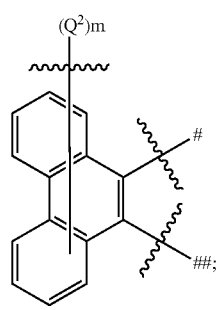

where,  represents a chemical bond used for connection with

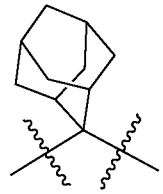 [SMILES: *C1(*)C2CC3CC(C2)CC1C3]

in the above structures, and  represents a chemical bond used for connection with

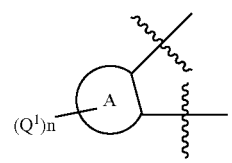

in the above structures.

In one specific embodiment of the present disclosure, in

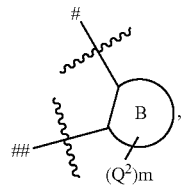

m=1 and

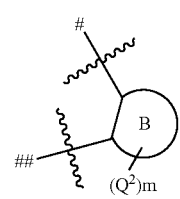

is selected from the group consisting of structures shown below:

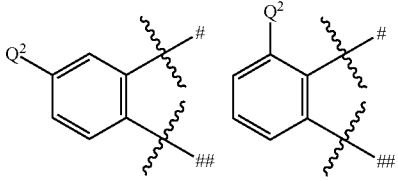

-continued
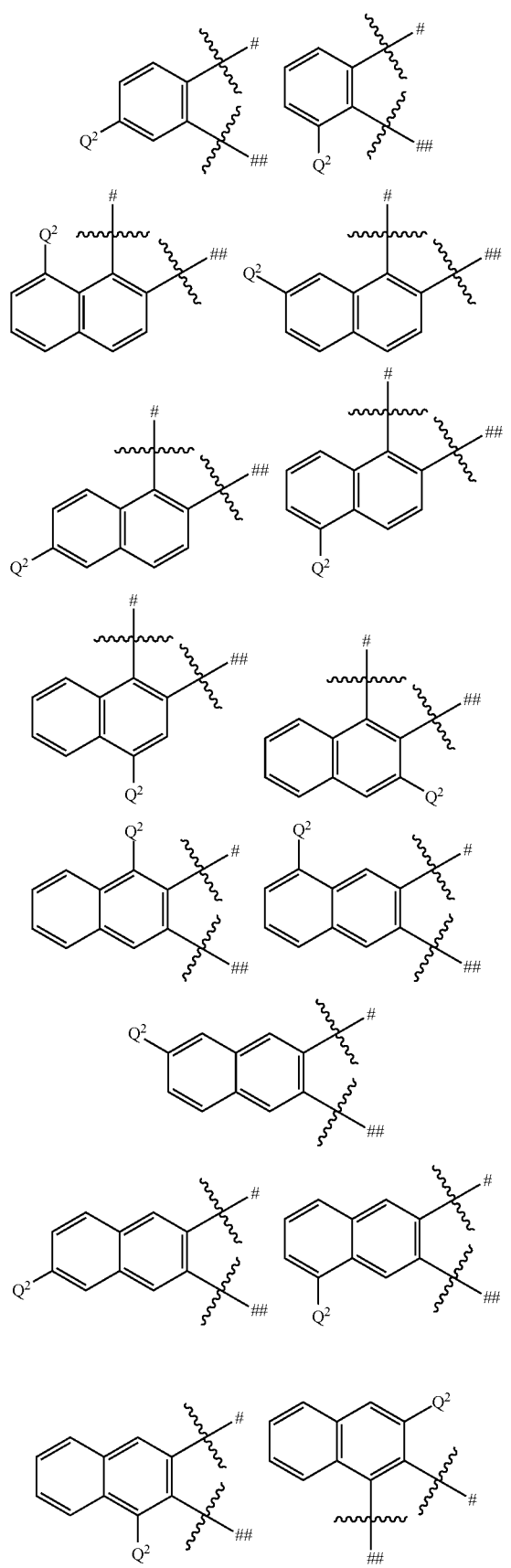
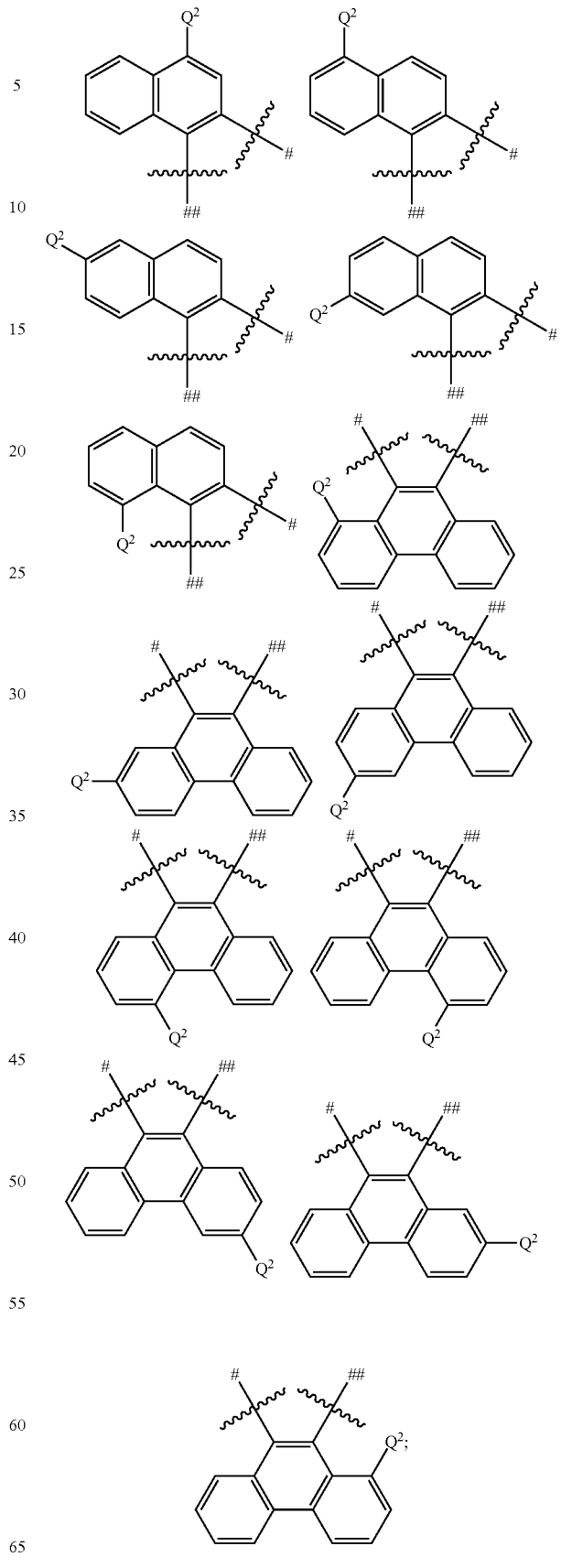

where,  represents a chemical bond used for connection with

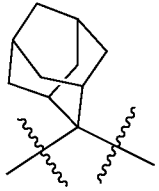 [SMILES: *C1(*)C2CC3CC(C2)CC1C3]

in the above structures, and  represents a chemical bond used for connection with

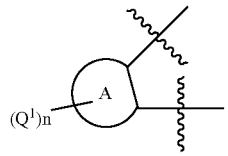

in the above structures.

In one specific embodiment of the present disclosure, the $Ar_1$ and the $Ar_2$ are the same or different, and are each independently selected from hydrogen, substituted or unsubstituted alkyl with 1 to 10 carbon atoms, substituted or unsubstituted cycloalkyl with 3 to 10 carbon atoms, substituted or unsubstituted aryl with 6 to 24 carbon atoms, and substituted or unsubstituted heteroaryl with 5 to 24 carbon atoms.

Optionally, in the present disclosure, the $Ar_1$ and the $Ar_2$ are the same or different, and are each independently selected from aryl with 6 to 21 carbon atoms and substituted or unsubstituted heteroaryl with 5 to 20 carbon atoms.

Preferably, in the present disclosure, the $Ar_1$ and the $Ar_2$ are the same or different, and are each independently selected from aryl with 6 to 20 carbon atoms and substituted or unsubstituted heteroaryl with 5 to 12 carbon atoms.

In one specific embodiment of the present disclosure, the substituents in $Ar_1$ and $Ar_2$ are the same or different, and are each independently selected from deuterium, halogen group, cyano, aryl with 6 to 20 carbon atoms, heteroaryl with 3 to 20 carbon atoms, alkyl with 1 to 5 carbon atoms, haloalkyl with 1 to 4 carbon atoms, cycloalkyl with 3 to 10 carbon atoms, alkoxy with 1 to 4 carbon atoms, alkylthio with 1 to 4 carbon atoms, trialkylsilyl with 3 to 7 carbon atoms, and triarylsilyl with 18 to 24 carbon atoms. Specifically, the substituents in $Ar_1$ and $Ar_2$ are the same or different, and are each independently selected from deuterium, fluorine, cyano, methyl, ethyl, tert-butyl, phenyl, naphthyl, biphenyl, terphenyl, dimethylfluorenyl, N-phenylcarbazolyl, dibenzofuryl, dibenzothienyl, quinolyl, pyridyl, pyrimidyl, phenothiazinyl and phenoxazinyl.

In one specific embodiment of the present disclosure, $Ar_1$ and $Ar_2$ are the same or different, and are each independently selected from hydrogen or the group consisting of groups as shown in i-1 to i-15 below:

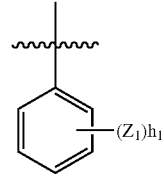 i-1

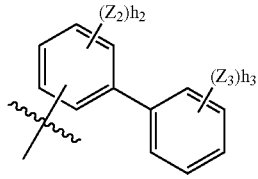 i-2

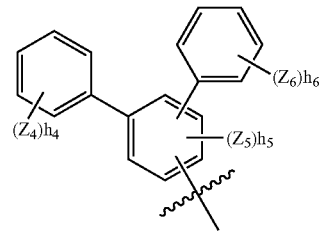 i-3

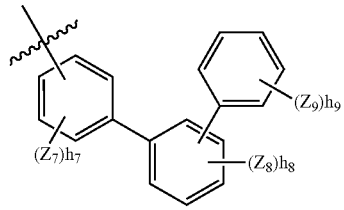 i-4

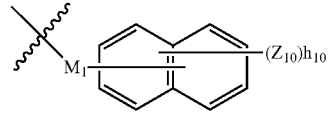 i-5

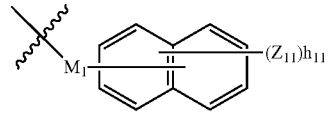 i-6

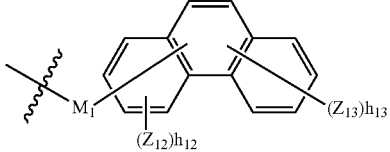 i-7

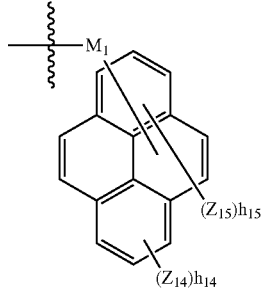 i-8

-continued

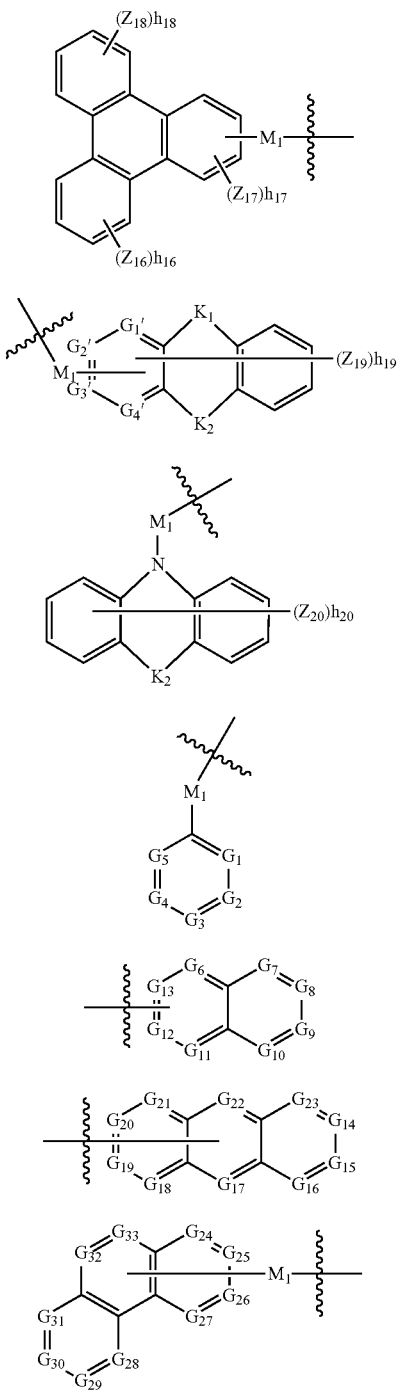

where $M_1$ is selected from a single bond or

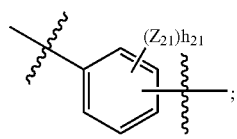

$G_1$ to $G_5$ and $G_1'$ to $G_4'$ are each independently selected from N, C or $C(J_1)$, at least one of $G_1$ to $G_5$ is selected from N, and when two or more of $G_1$ to $G_5$ are selected from $C(J_1)$, any two $J_1$s are the same or different;

$G_6$ to $G_{13}$ are each independently selected from N, C or $C(J_2)$, and at least one of $G_6$ to $G_{13}$ is selected from N; and when two or more of $G_6$ to $G_{13}$ are selected from $C(J_2)$, any two $J_2$s are the same or different;

$G_{14}$ to $G_{23}$ are each independently selected from N, C or $C(J_3)$, and at least one of $G_{14}$ to $G_{23}$ is selected from N; and when two or more of $G_{14}$ to $G_{23}$ are selected from $C(J_3)$, any two $J_3$s are the same or different;

$G_{24}$ to $G_{33}$ are each independently selected from N, C or $C(J_4)$, and at least one of $G_{24}$ to $G_{33}$ is selected from N; and when two or more of $G_{24}$ to $G_{33}$ are selected from $C(J_4)$, any two $J_4$s are the same or different;

$Z_1$ is selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms and triarylsilyl with 18 to 24 carbon atoms;

$Z_2$ to $Z_9$ and $Z_{21}$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, heteroaryl with 3 to 18 carbon atoms and triarylsilyl with 18 to 24 carbon atoms;

$Z_{10}$ to $Z_{20}$ and $J_1$ to $J_4$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, aryl with 6 to 18 carbon atoms optionally substituted by one or more of deuterium, fluorine, chlorine and cyano, heteroaryl with 3 to 18 carbon atoms, and triarylsilyl with 18 to 24 carbon atoms; in the present disclosure, "aryl with 6 to 18 carbon atoms optionally substituted by one or more of deuterium, fluorine, chlorine and cyano" means that the aryl can be substituted by deuterium, fluorine, chlorine and cyano and also can not be substituted by deuterium, fluorine, chlorine and cyano.

$h_1$ to $h_{21}$ are represented by $h_k$, $Z_1$ to $Z_{21}$ are represented by $Z_k$, k is a variable and represents any integer of 1 to 21, and $h_k$ represents the number of substituents $Z_k$; when k is selected from 5 or 17, $h_k$ is selected from 1, 2 or 3; when k is selected from 2, 7, 8, 12, 15, 16, 18 or 21, $h_k$ is selected from 1, 2, 3 or 4; when k is selected from 1, 3, 4, 6, 9 or 14, $h_k$ is selected from 1, 2, 3, 4 or 5; when k is 13, $h_k$ is selected from 1, 2, 3, 4, 5 or 6; when k is selected from 10 or 19, $h_k$ is selected from 1, 2, 3, 4, 5, 6 or 7; when k is 20, $h_k$ is selected from 1, 2, 3, 4, 5, 6, 7 or 8; when k is 11, $h_k$ is selected from 1, 2, 3, 4, 5, 6, 7, 8 or 9; and when $h_k$ is greater than one, any two $Z_k$s are the same or different;

$K_1$ is selected from O, S, $N(Z_{22})$, $C(Z_{23}Z_{24})$ and $Si(Z_{28}Z_{29})$; where $Z_{22}$, $Z_{23}$, $Z_{24}$, $Z_{28}$ and $Z_{29}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{23}$ and the $Z_{24}$ are connected with each other to form a saturated or unsaturated ring with 3 to 15 carbon atoms together with atoms to which they are jointly connected, or the $Z_{28}$ and the $Z_{29}$ are connected with each other to form a saturated or unsaturated ring with 3 to 15 carbon atoms together with atoms to which they are jointly connected;

$K_2$ is selected from a single bond, O, S, $N(Z_{25})$, $C(Z_{26}Z_{27})$, and $Si(Z_{30}Z_{31})$; where $Z_{25}$, $Z_{26}$, $Z_{27}$, $Z_{30}$ and $Z_{31}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{26}$ and the $Z_{27}$ are connected with each other to form a saturated or unsaturated ring with 3 to 15 carbon atoms together with atoms to which they are jointly connected, or the $Z_{30}$ and the $Z_{31}$ are connected with each other to form a saturated or unsaturated ring with 3 to 15 carbon atoms together with atoms to which they are jointly connected.

In one specific embodiment of the present disclosure, $Ar_1$ and $Ar_2$ are the same or different, and are each independently selected from hydrogen or the group consisting of the following groups:

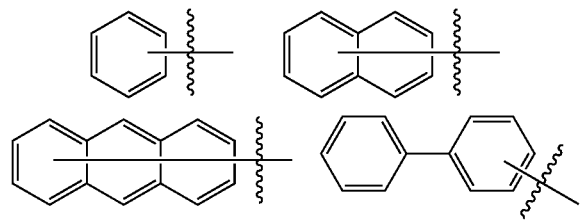
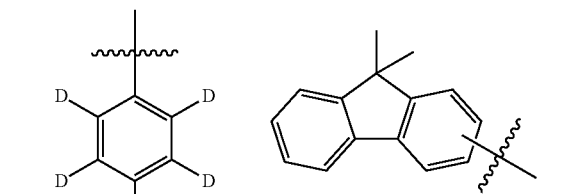
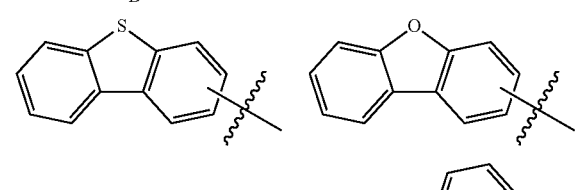
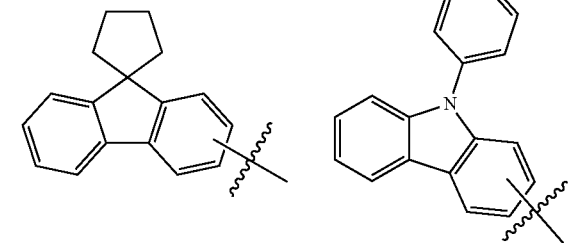
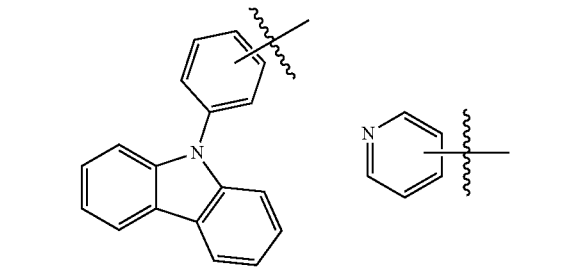
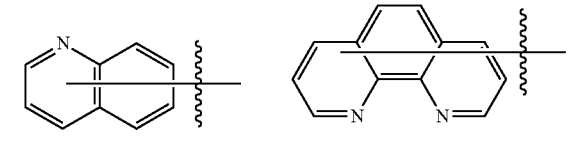

-continued

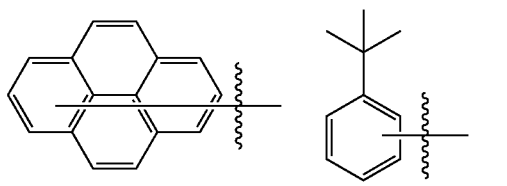
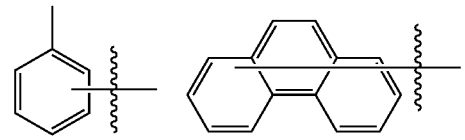
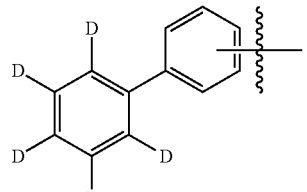
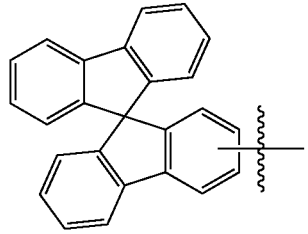
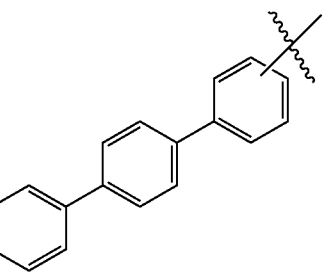
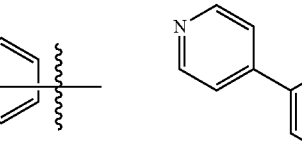
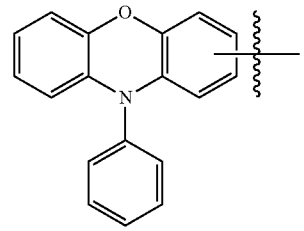
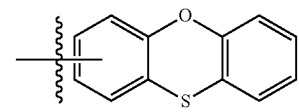

-continued
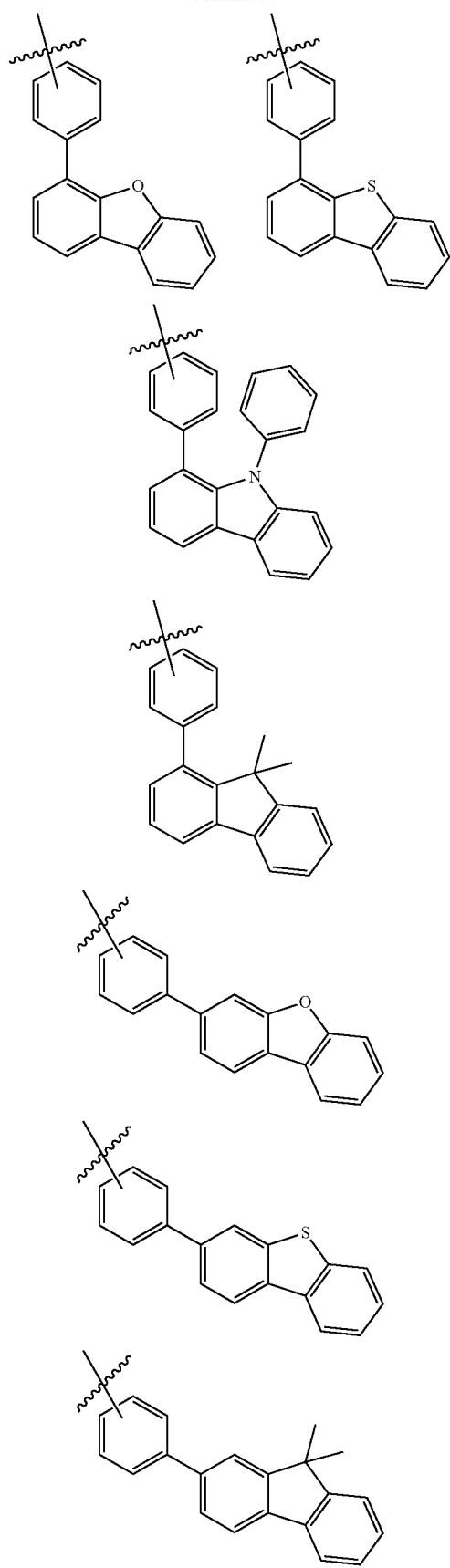
-continued
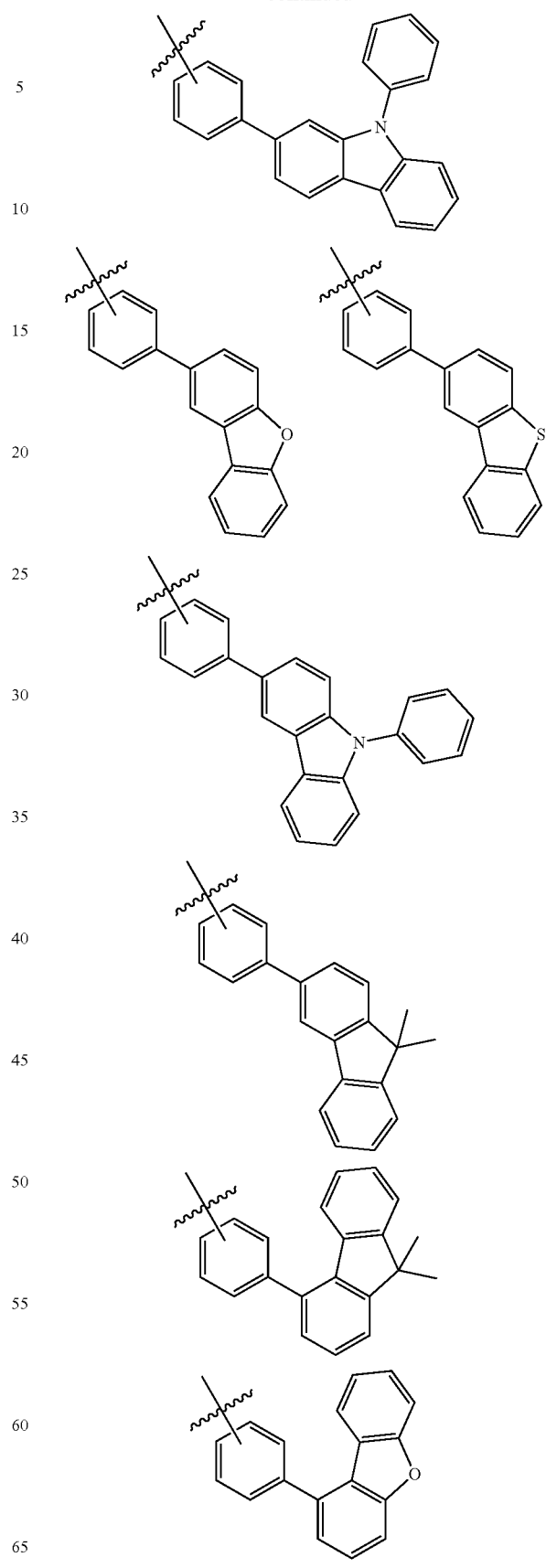

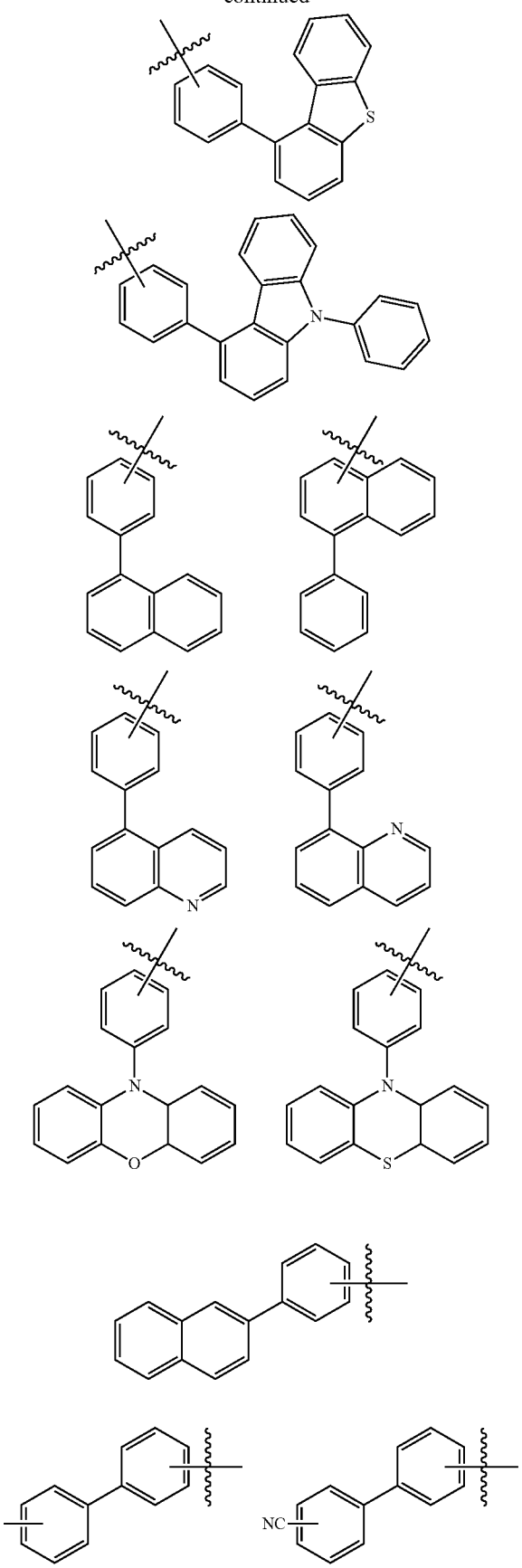
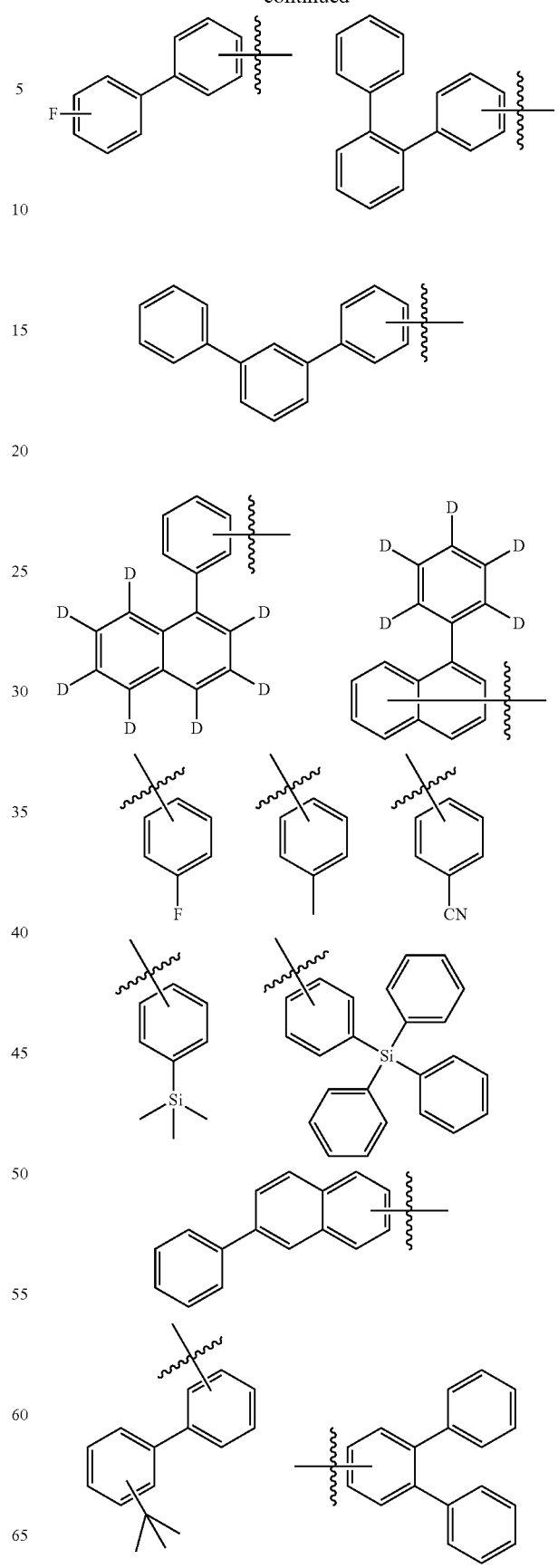

In one specific embodiment of the present disclosure, Ar$_1$ and Ar$_2$ are the same or different, and are each independently selected from hydrogen or the group consisting of the following groups:
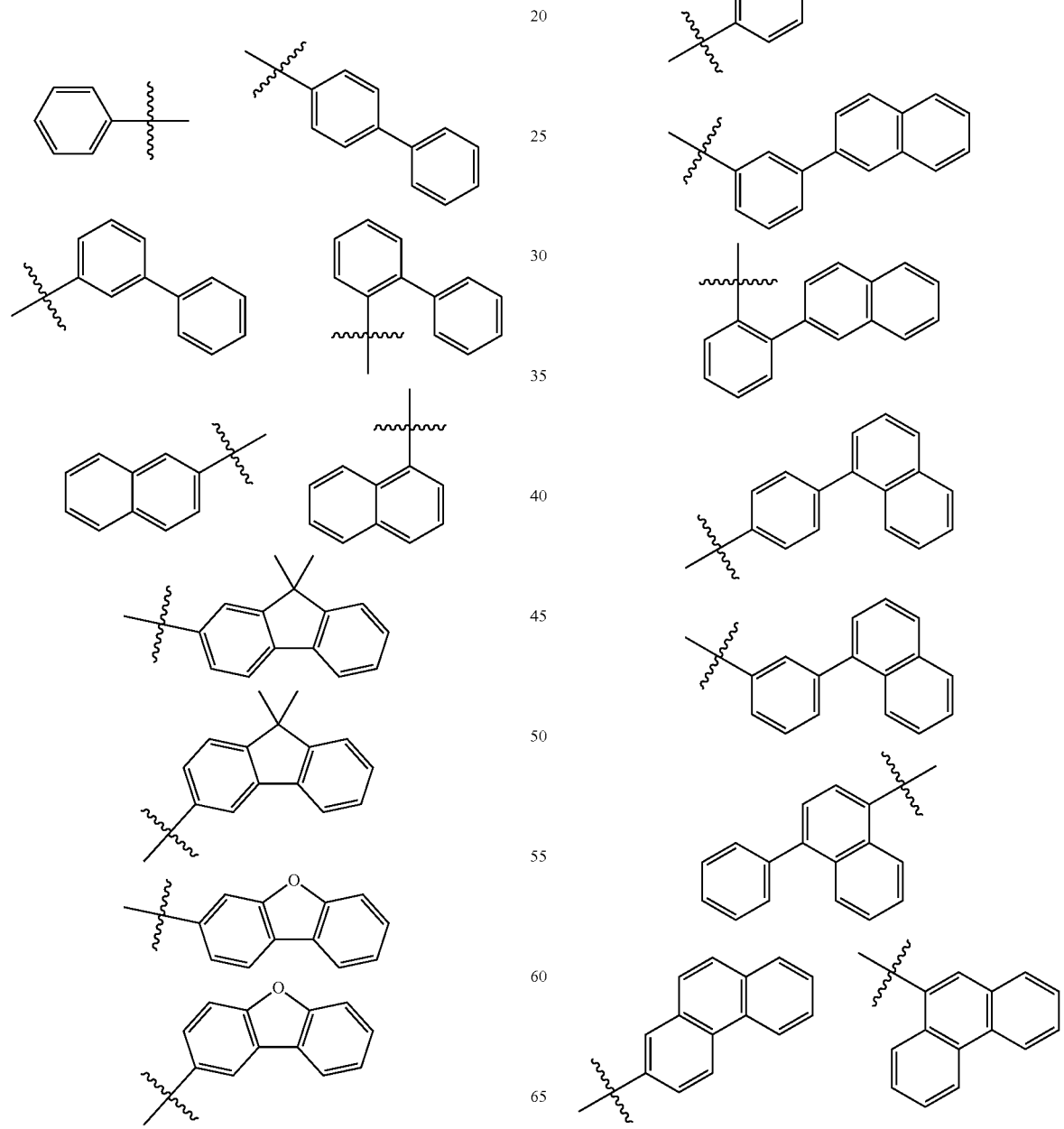

-continued
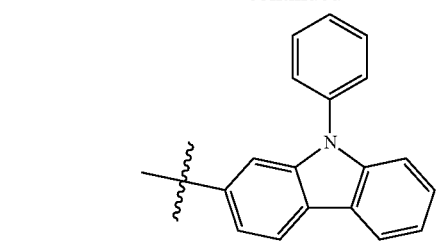
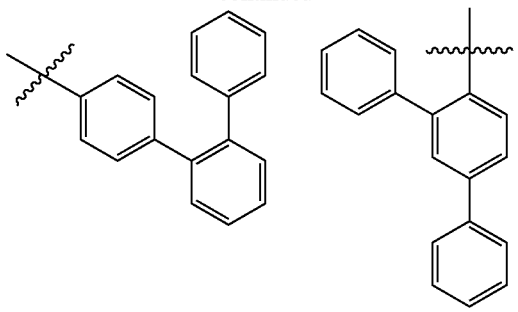
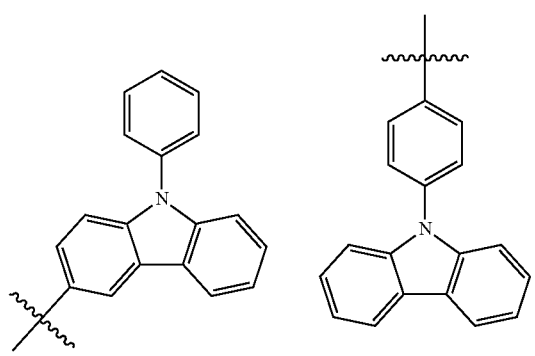
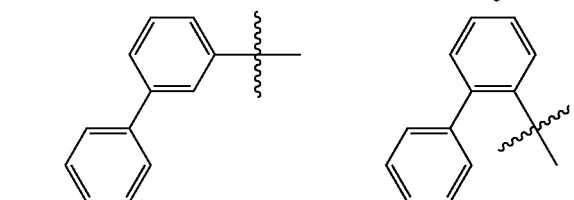
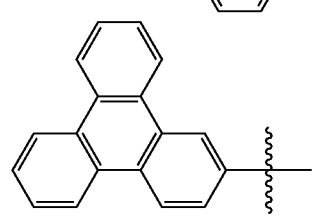
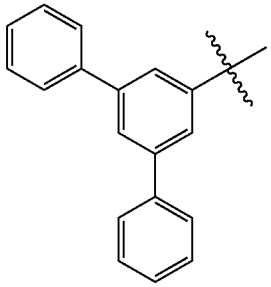
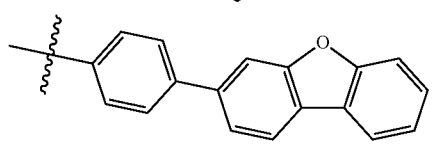
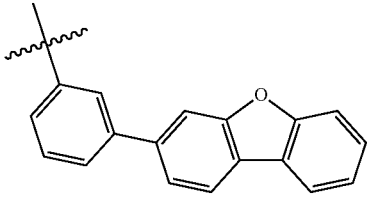
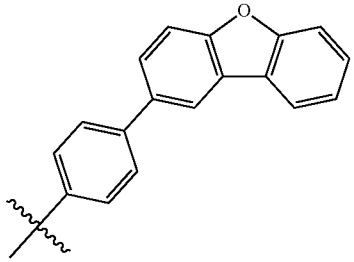

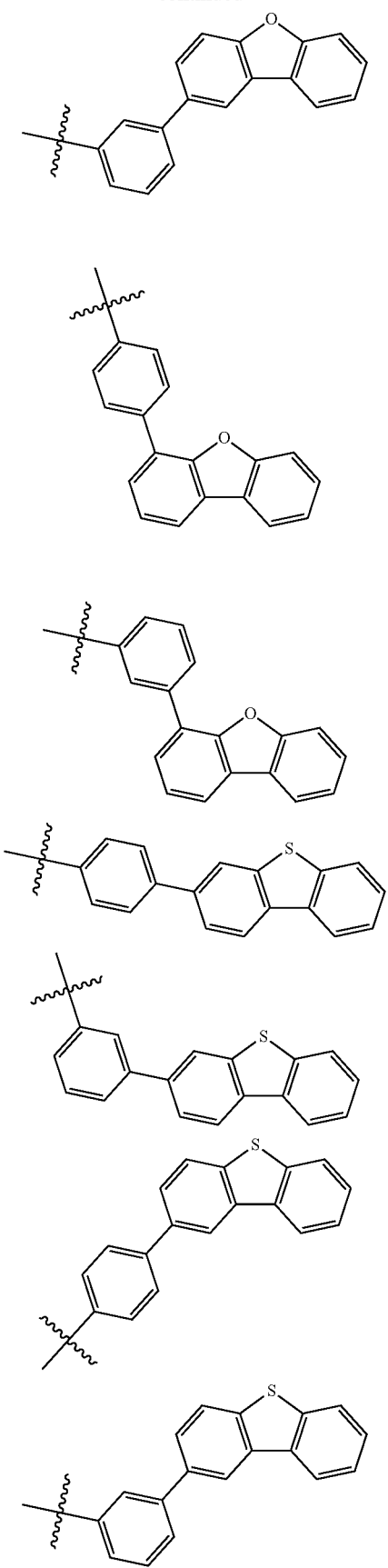

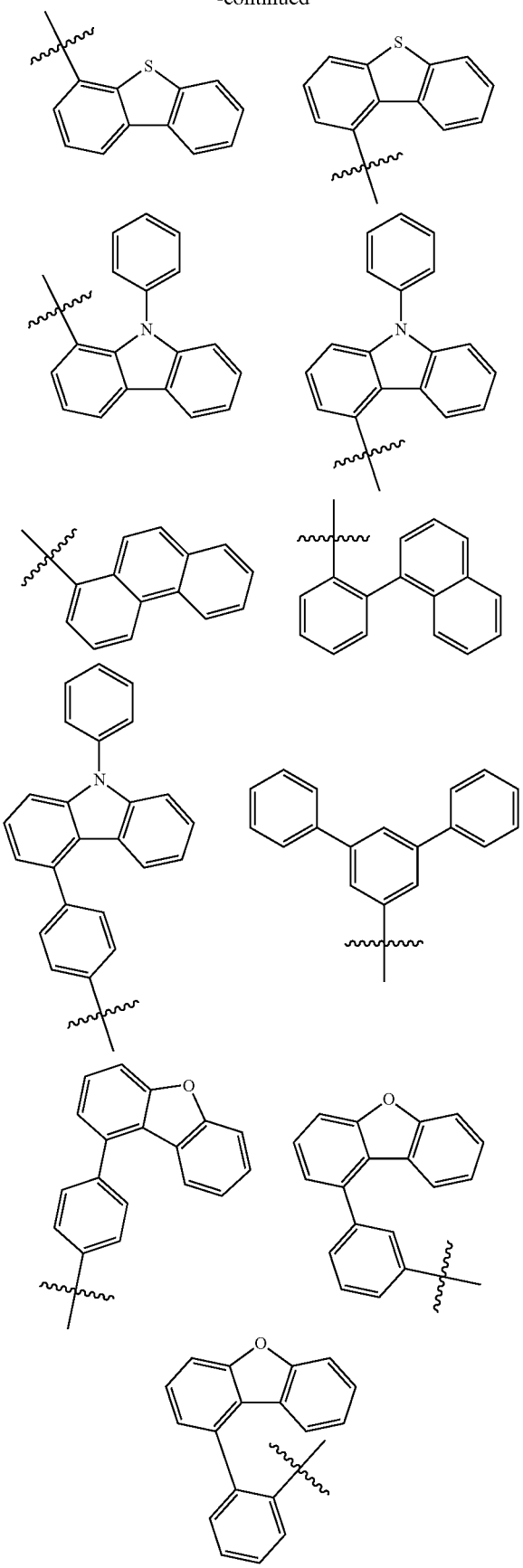
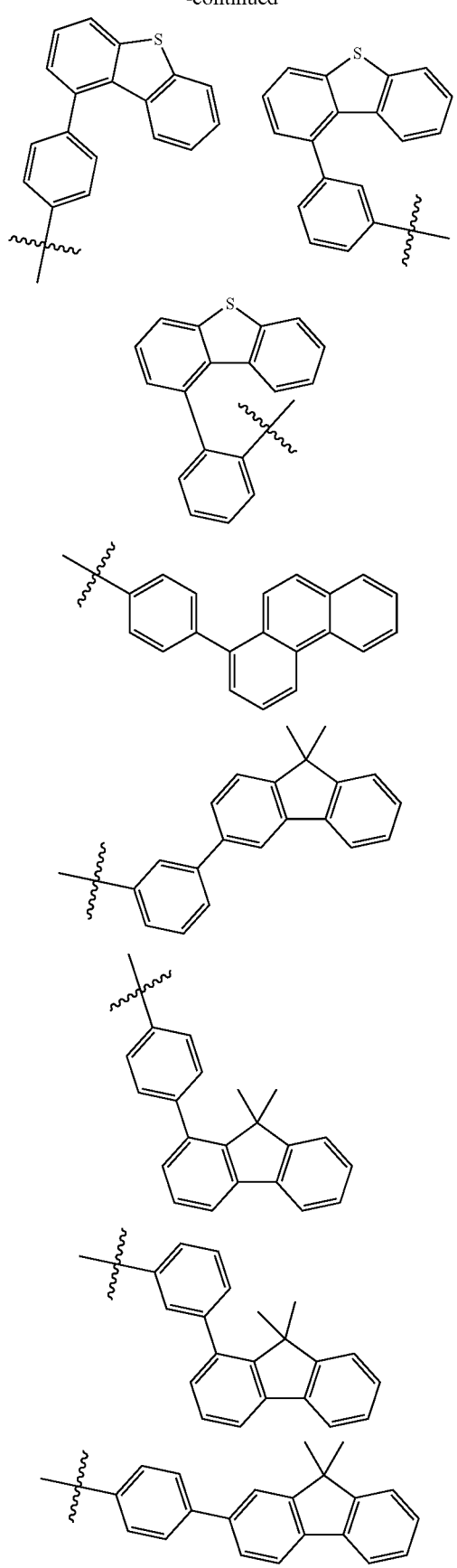

-continued
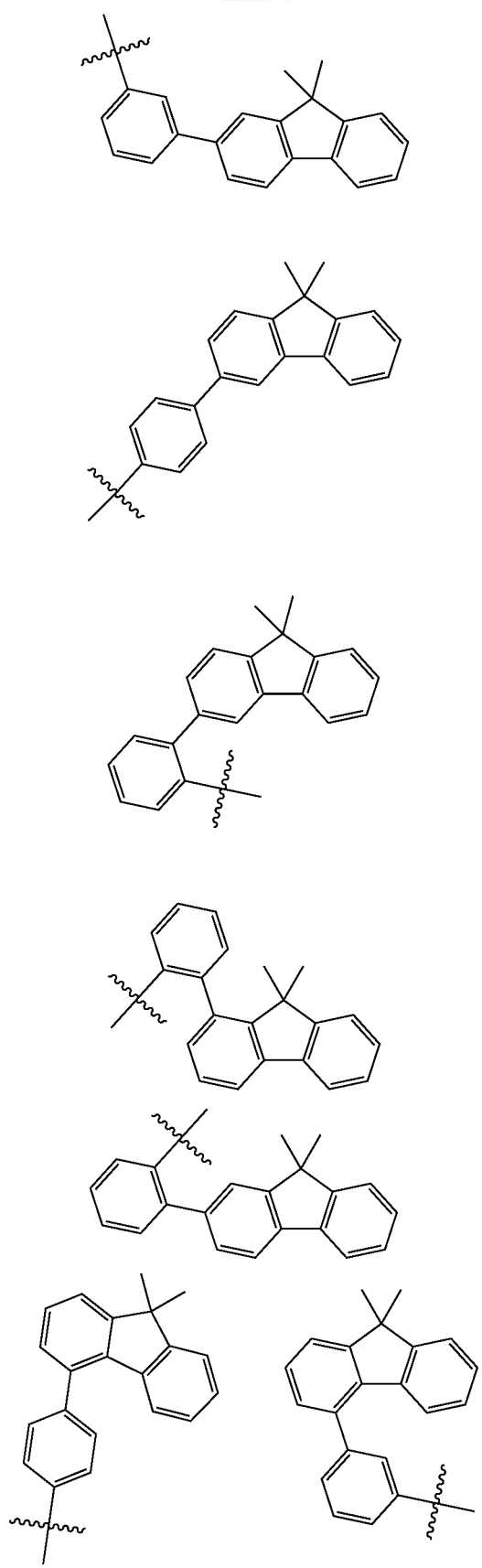
-continued
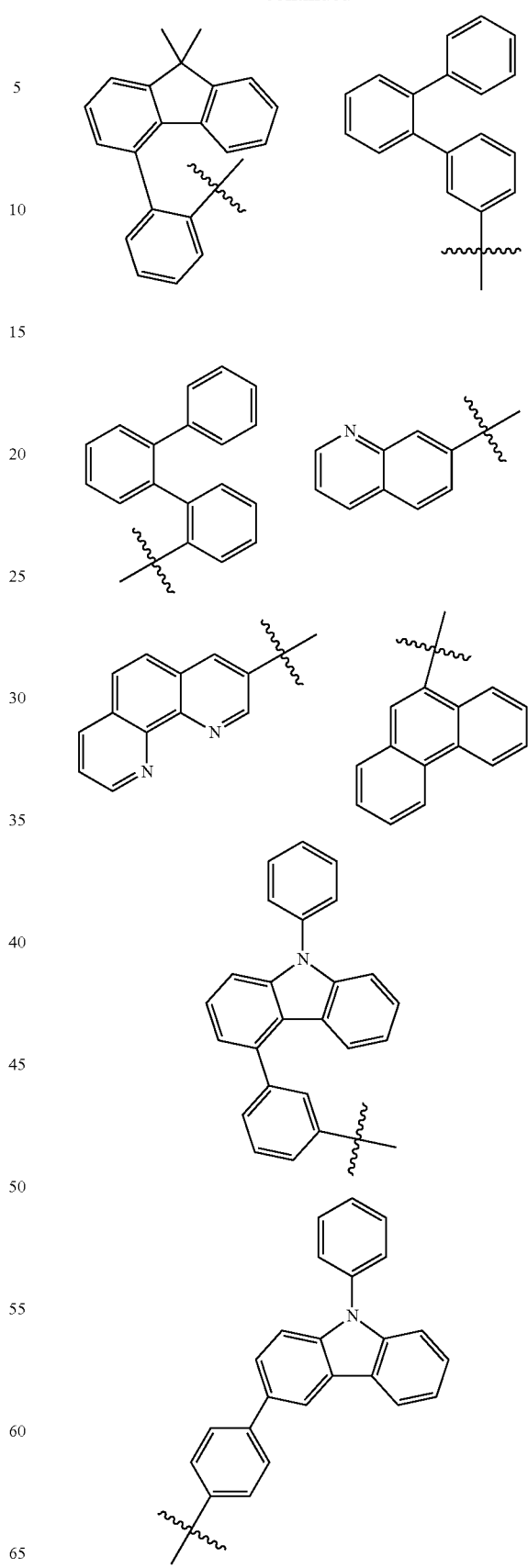

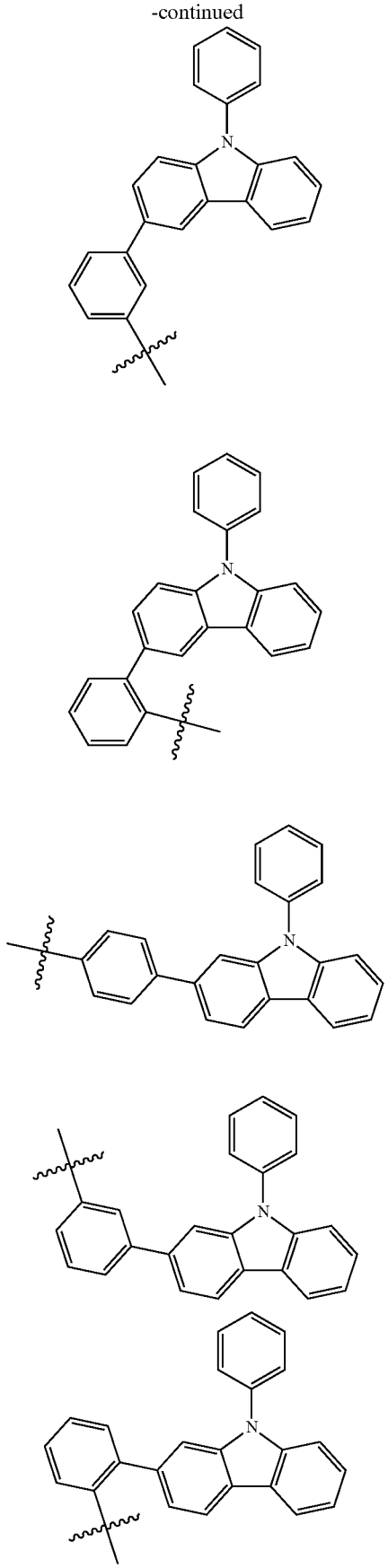
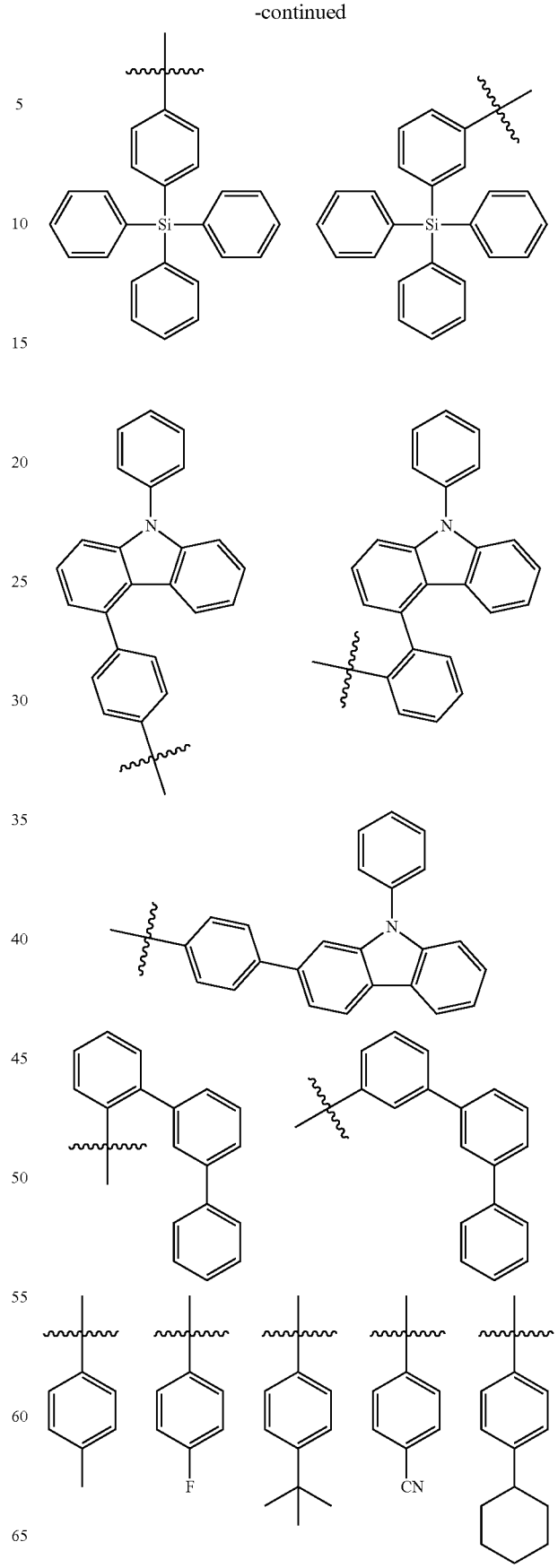

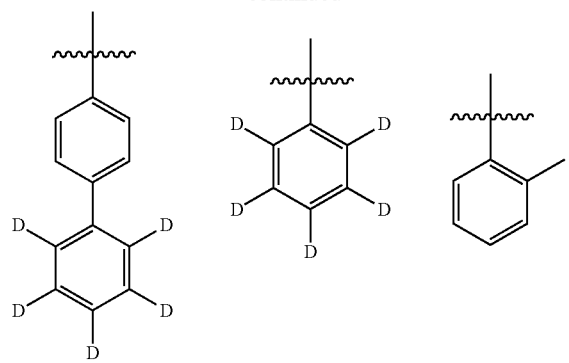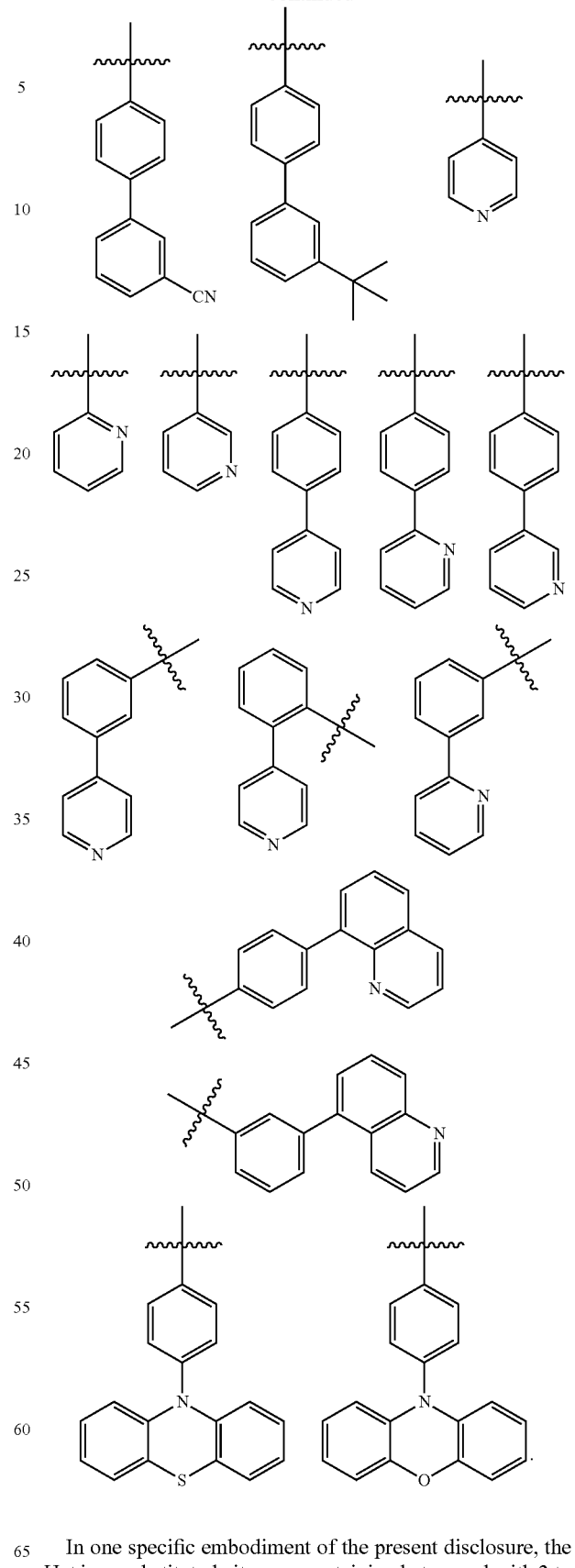
In one specific embodiment of the present disclosure, the Het is unsubstituted nitrogen-containing heteroaryl with 3 to 25 carbon atoms.

Preferably, in the present disclosure, the Het is unsubstituted nitrogen-containing heteroaryl with 3 to 20 carbon atoms.

In one specific embodiment of the present disclosure, in the Formula 1,

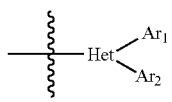

is selected from the following groups:

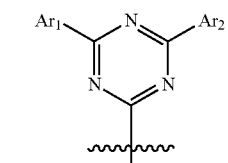 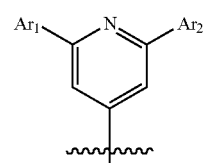

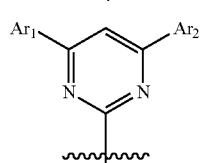 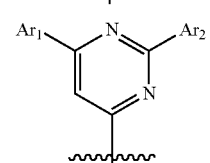

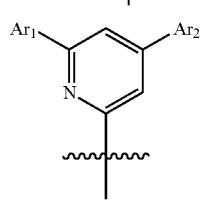 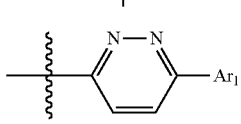

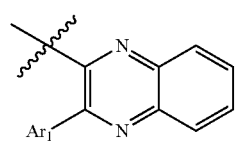 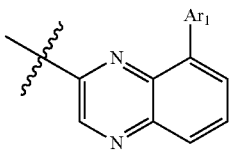

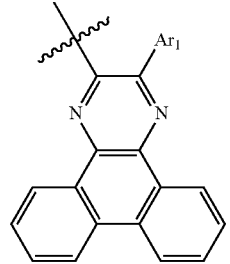 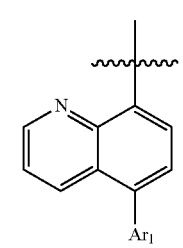

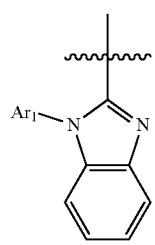 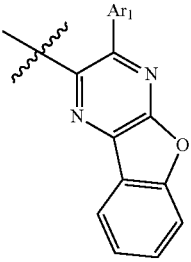

-continued

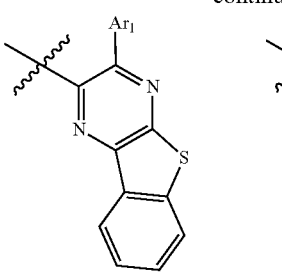 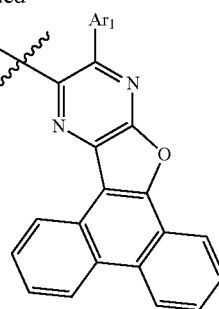

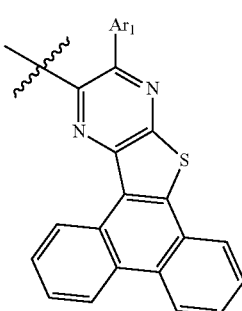

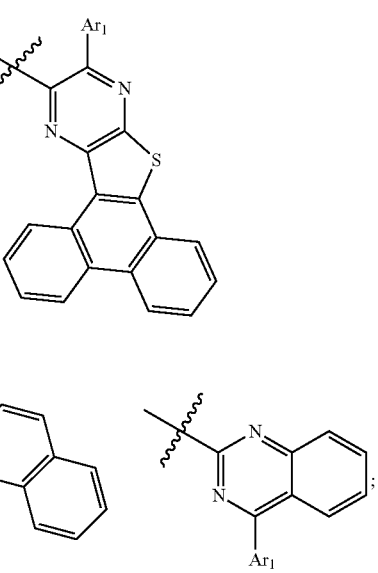

where, represents a chemical bond.

In one specific embodiment of the present disclosure,

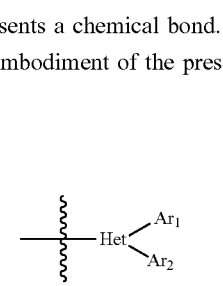

is selected from the group consisting of the following groups:

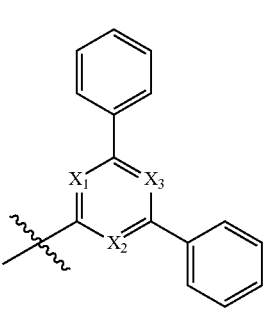

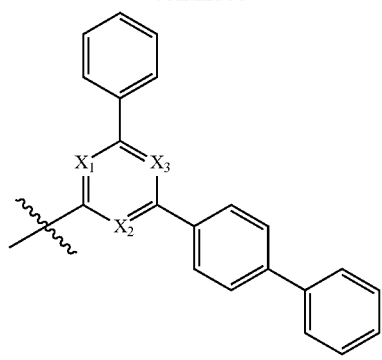
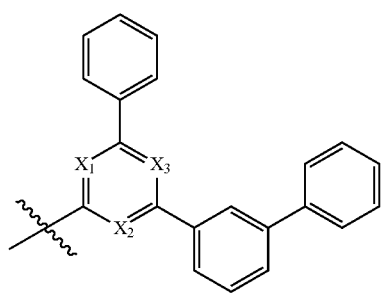
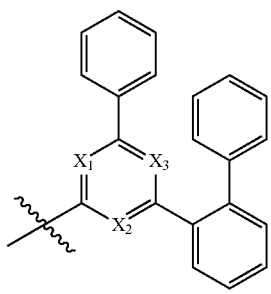
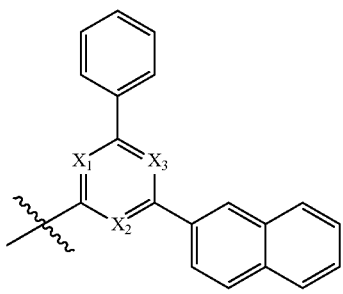
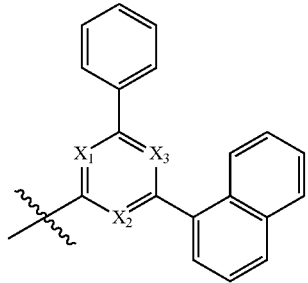
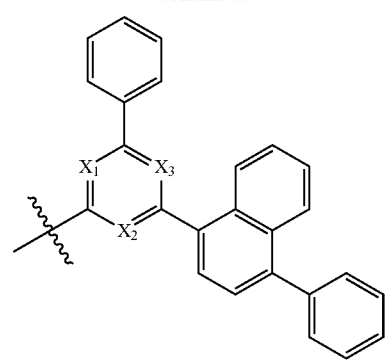
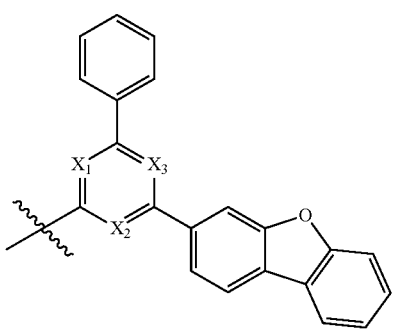
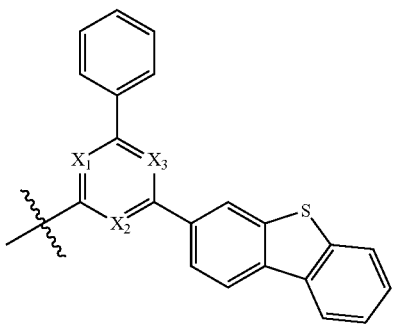
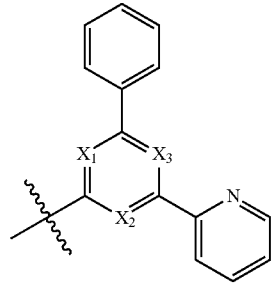
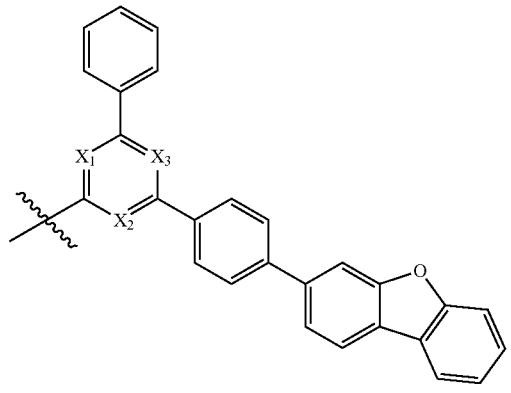

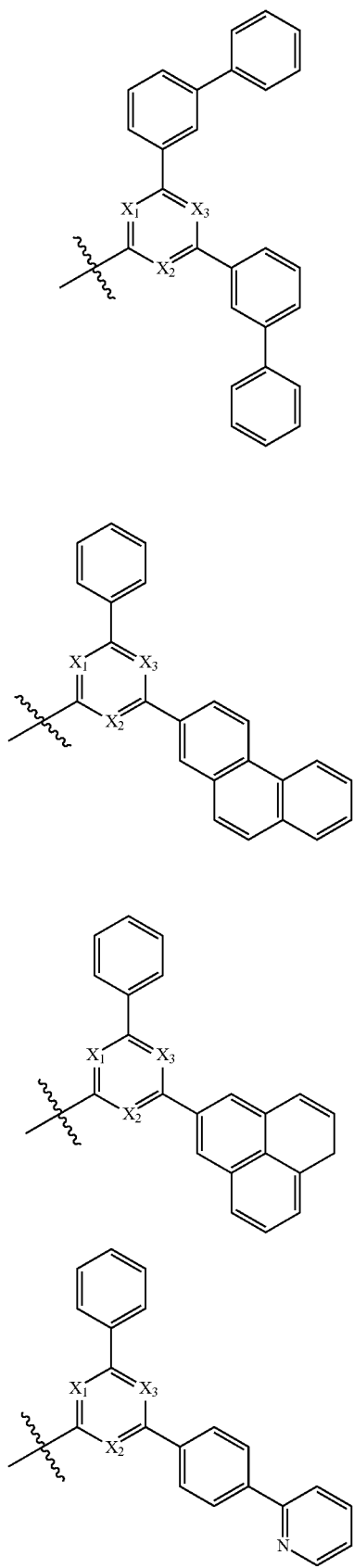
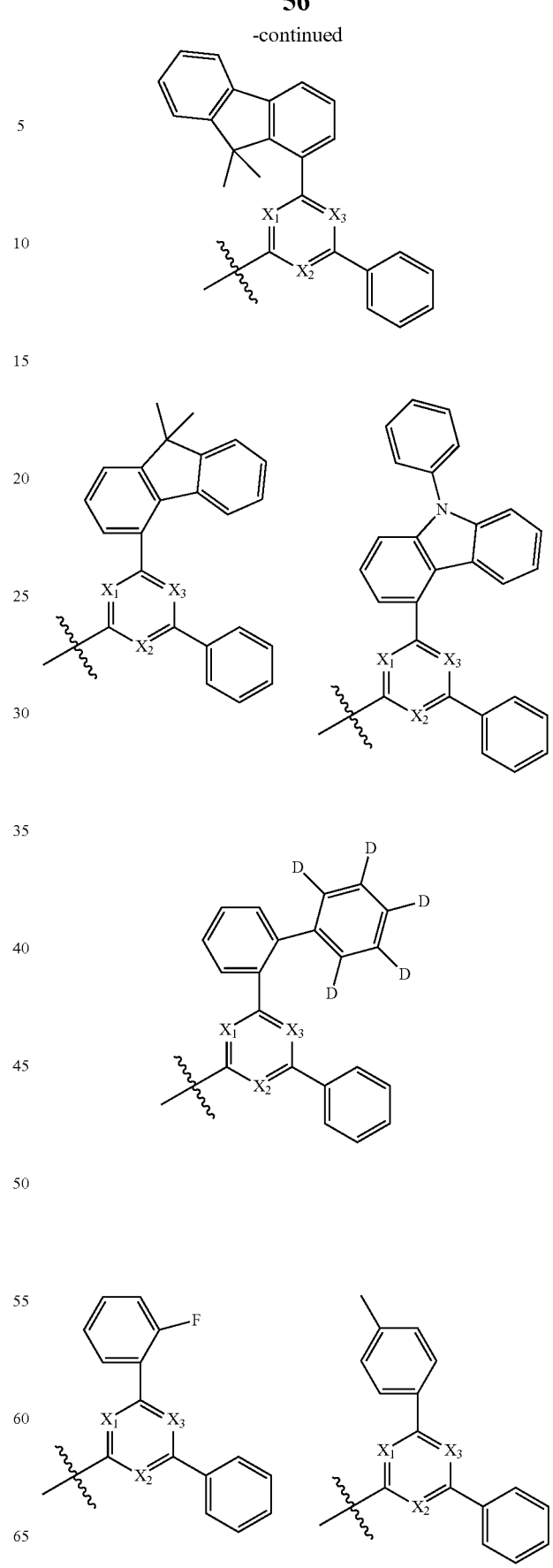

57
-continued
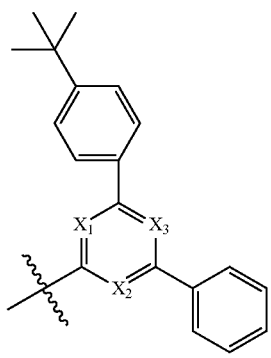
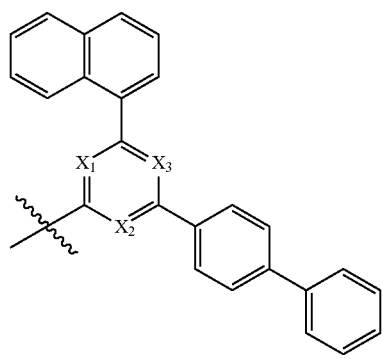
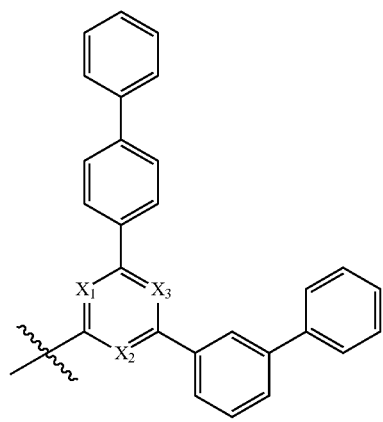
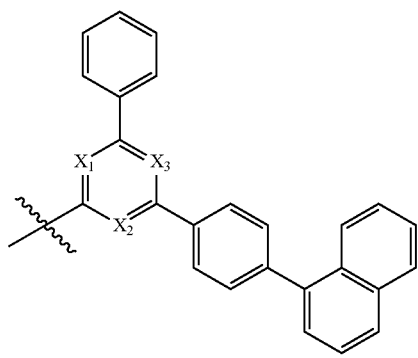
58
-continued
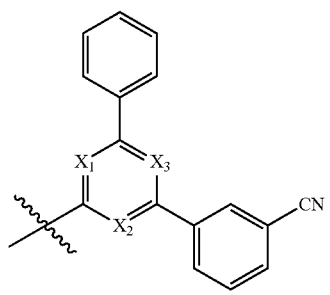
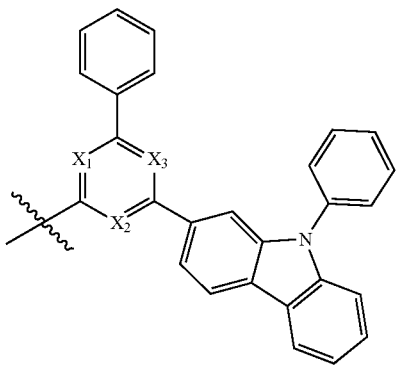
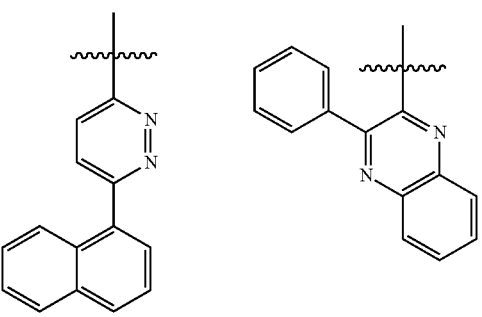
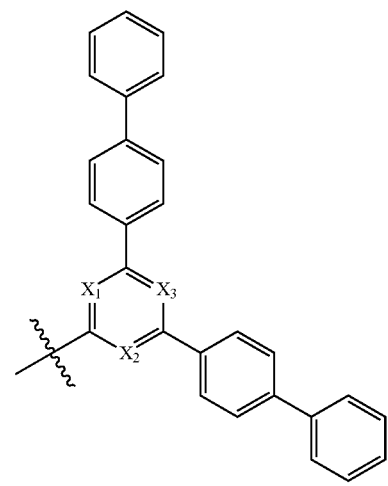

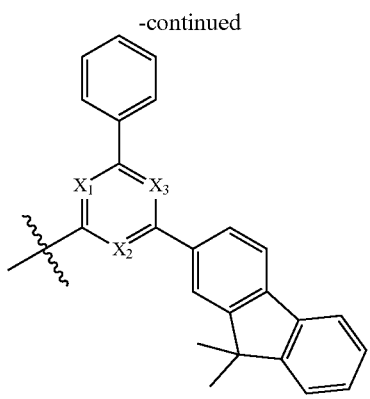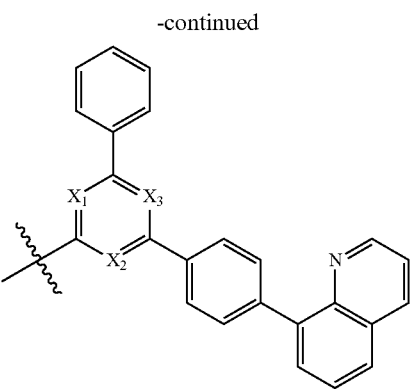

61
-continued
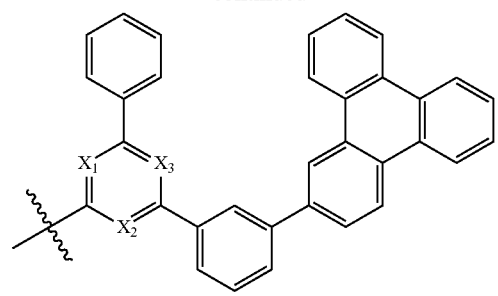
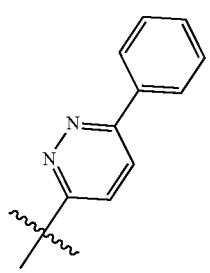
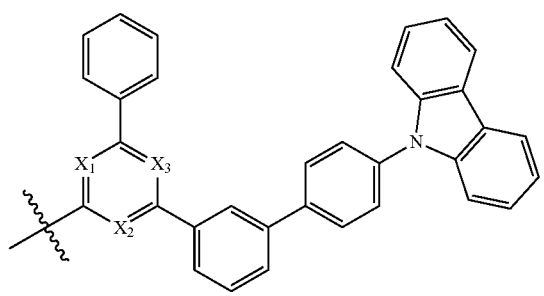
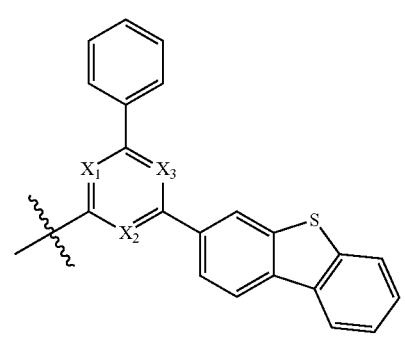
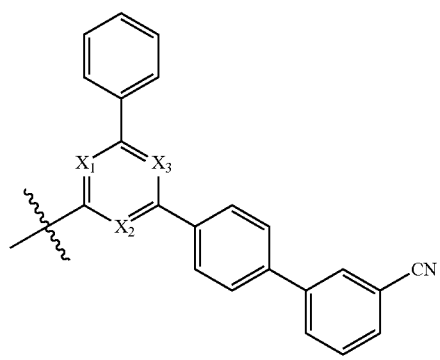
62
-continued
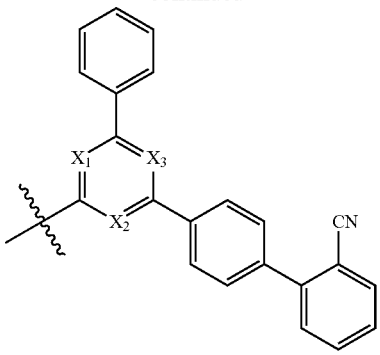
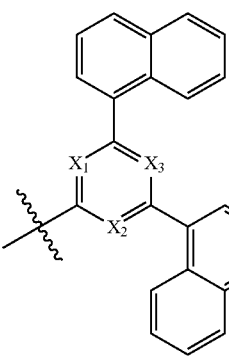
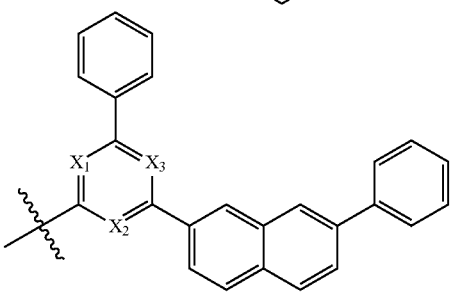
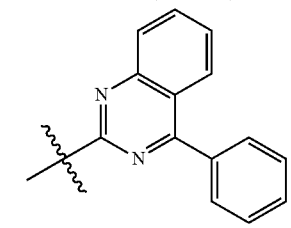
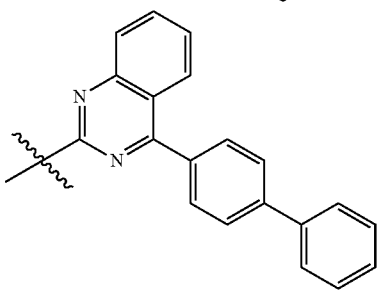
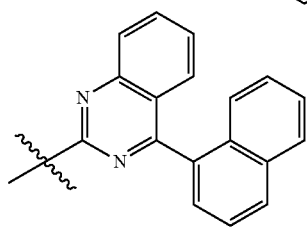

63
-continued
64
-continued
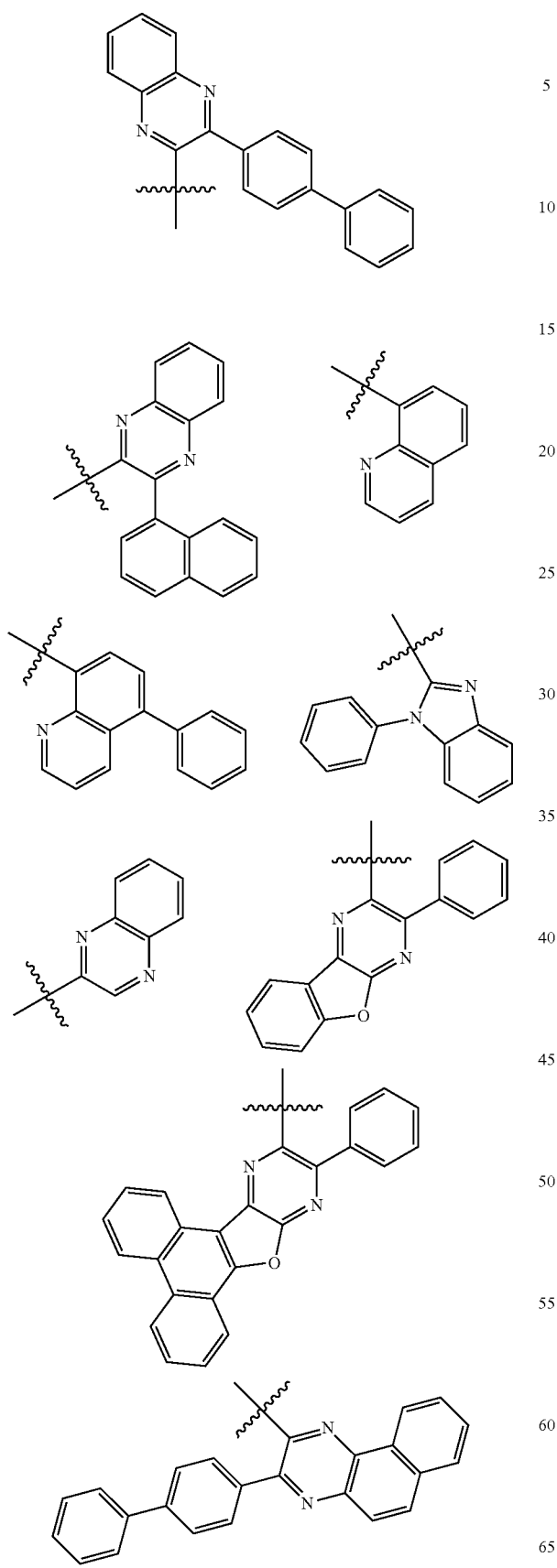
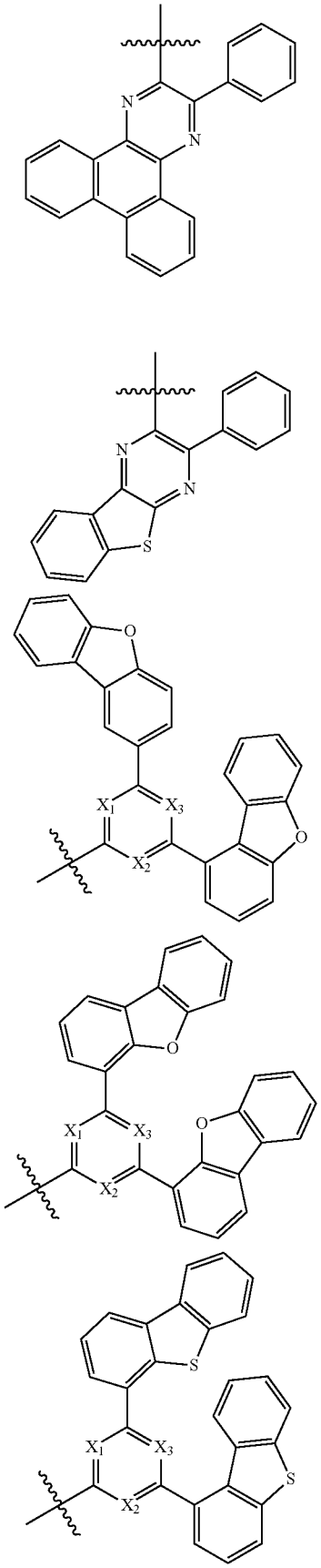

65
-continued
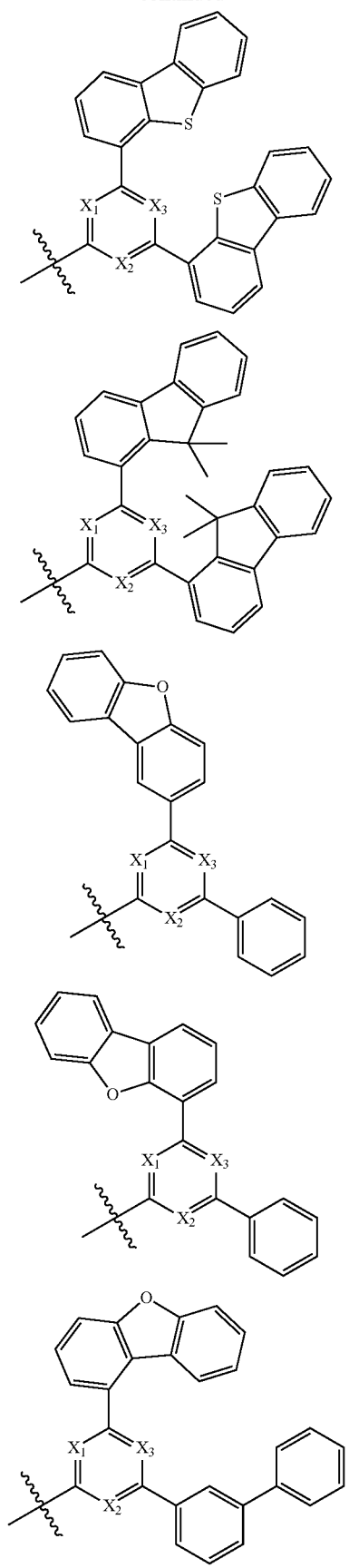
66
-continued
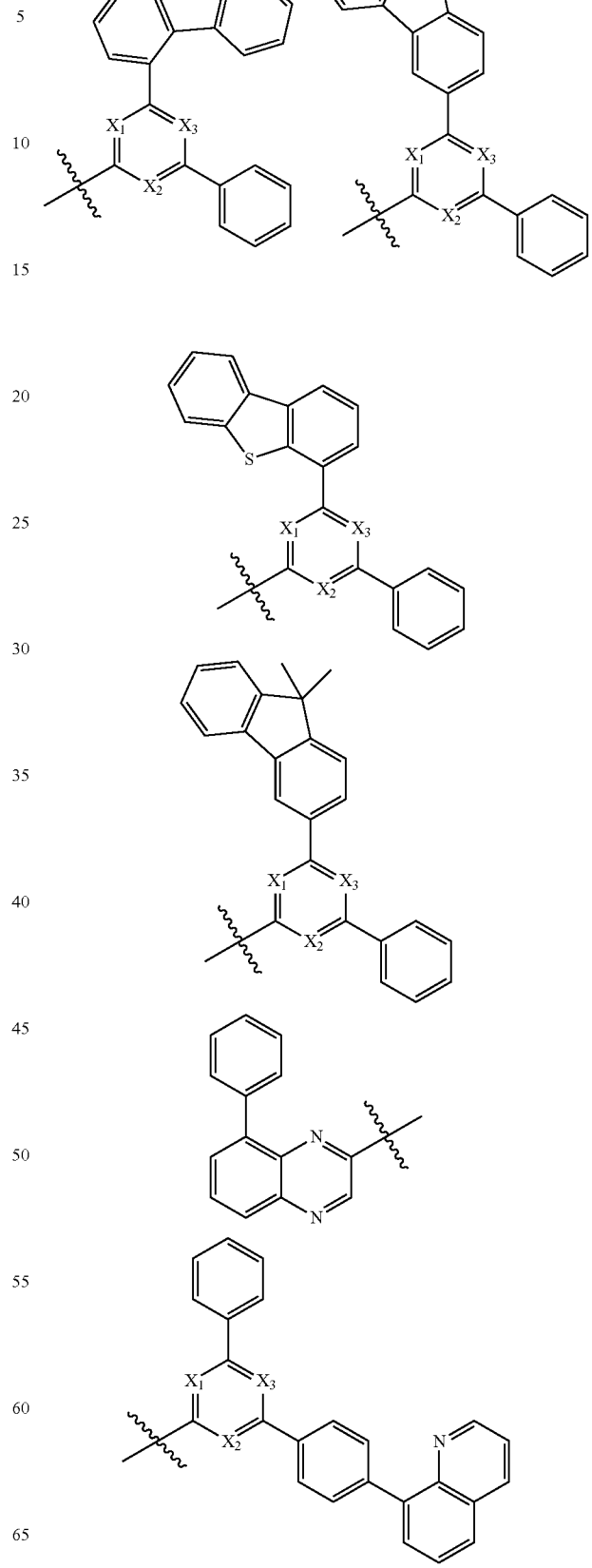

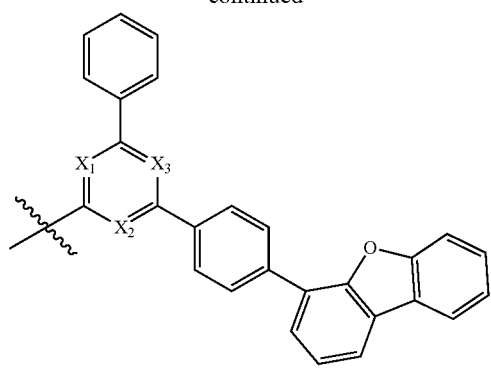
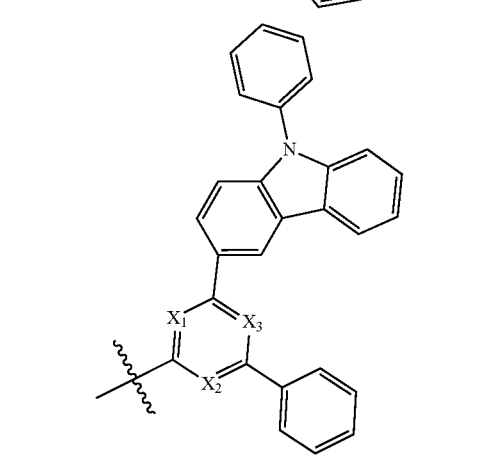
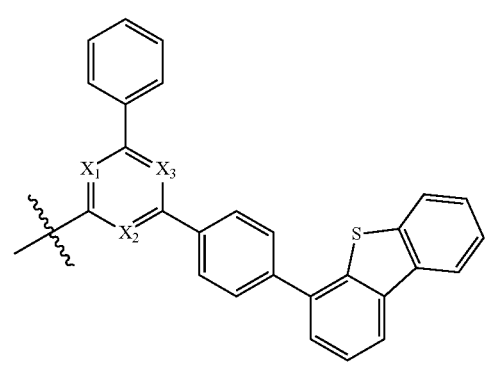
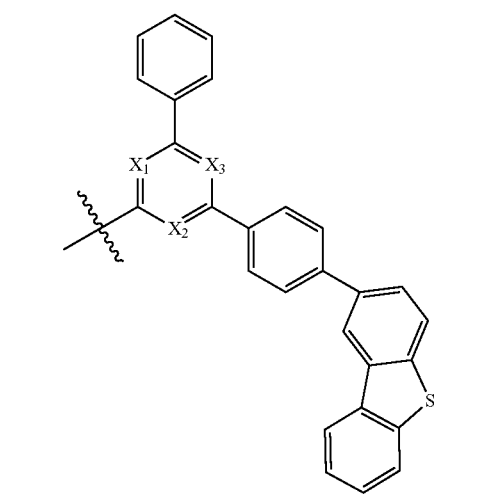
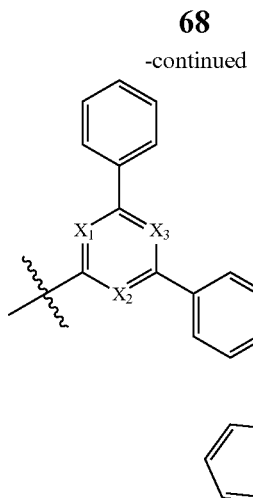
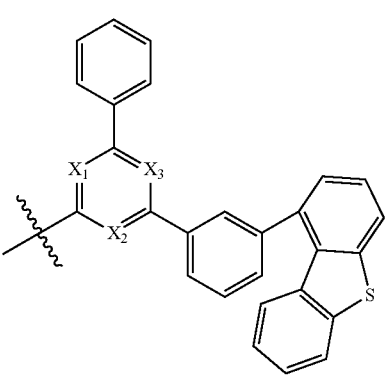
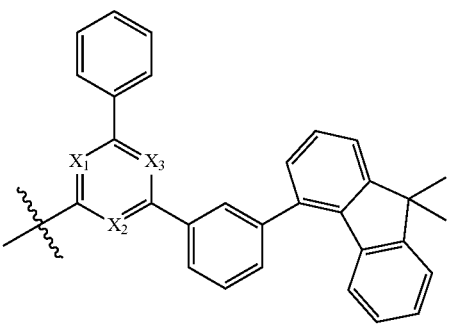
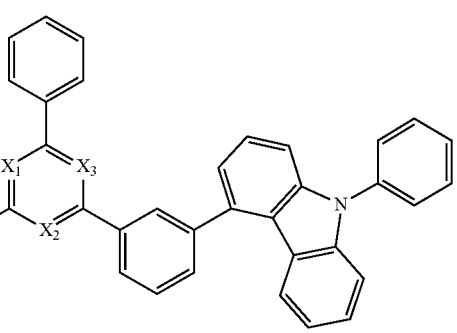

-continued
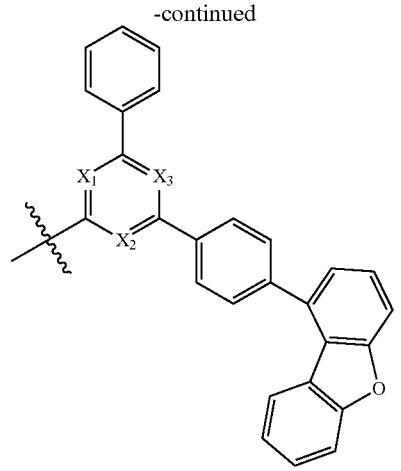
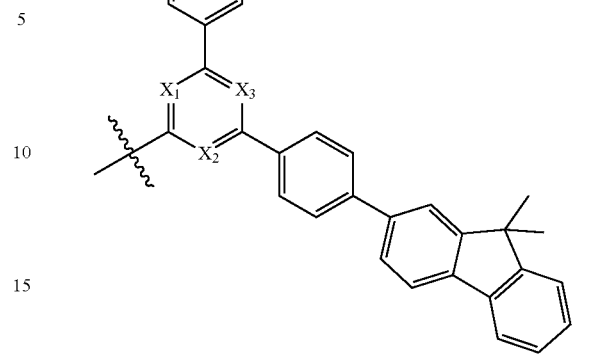
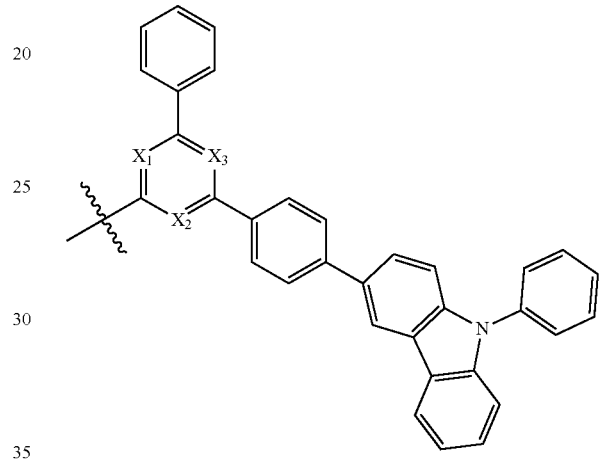
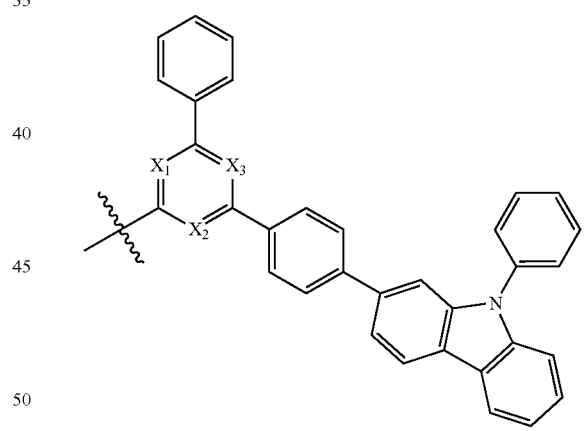
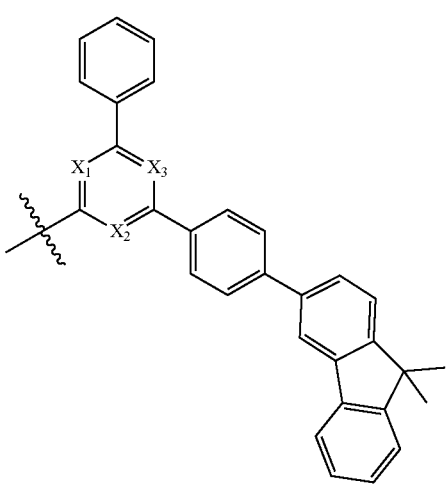
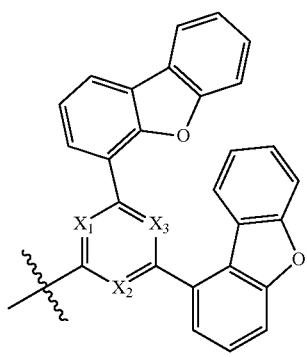

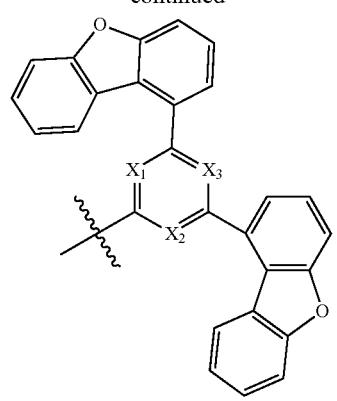
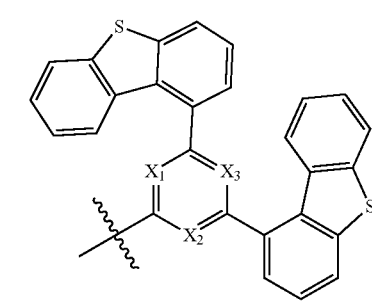
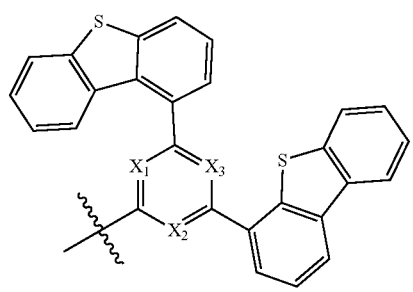
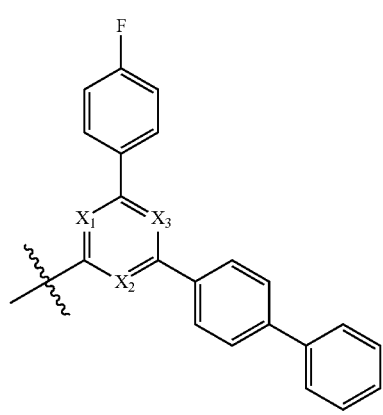
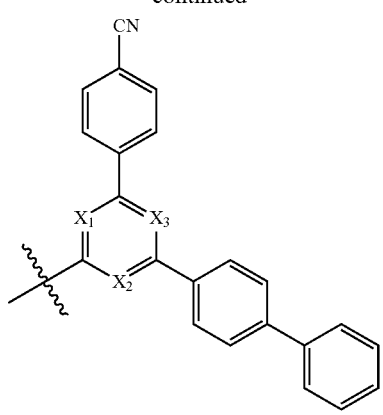
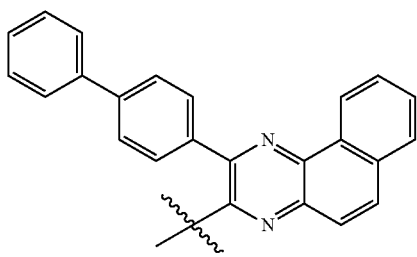
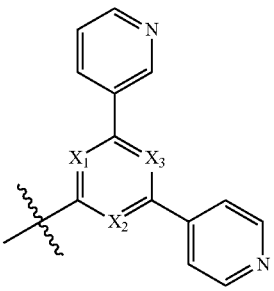
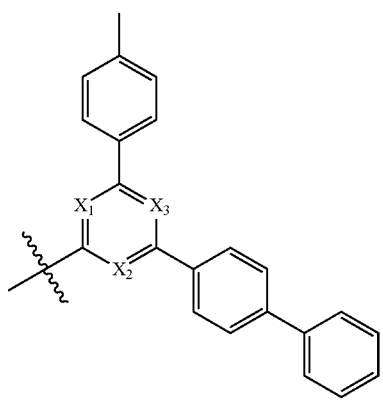
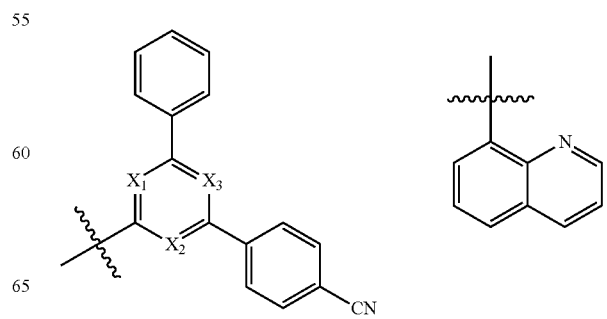

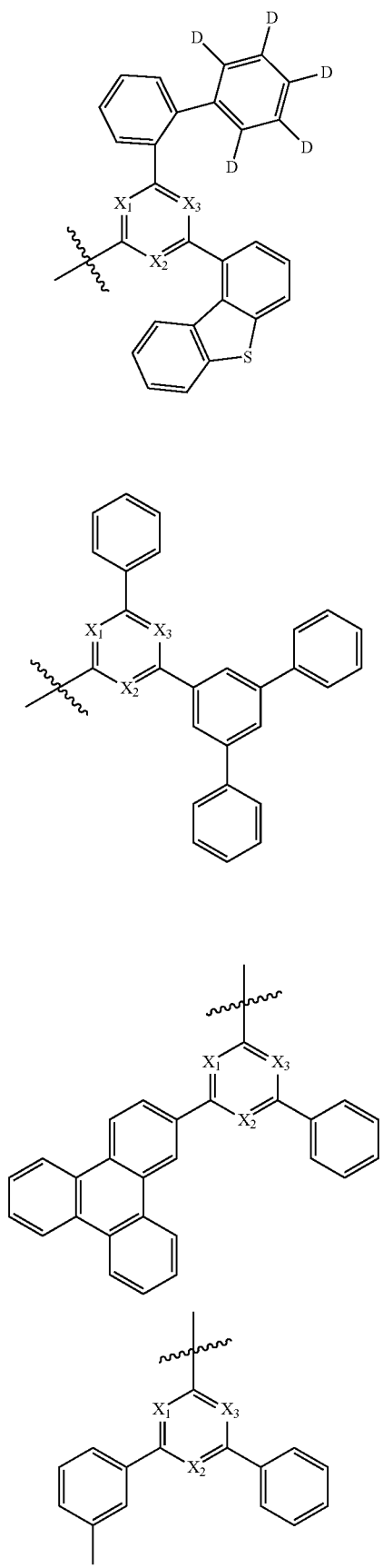
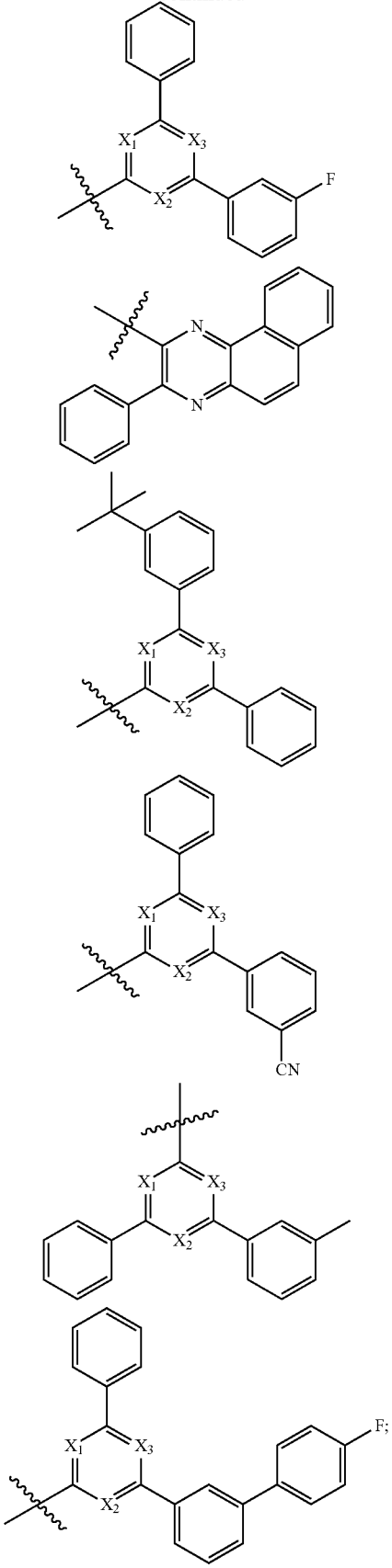

Wherein, in the above groups containing $X_1$, $X_2$ and $X_3$, the $X_1$, the $X_2$ and the $X_3$ are independently selected from CH or N, and at least one of the $X_1$, the $X_2$ and the $X_3$ is N.

In the present disclosure, L is selected from a single bond, substituted or unsubstituted arylene with 6 to 20 carbon atoms, and substituted or unsubstituted heteroarylene with 3 to 20 carbon atoms.

Preferably, L is selected from a single bond, substituted or unsubstituted arylene with 6 to 18 carbon atoms, and substituted or unsubstituted heteroarylene with 3 to 18 carbon atoms; further preferably, L is selected from a single bond, substituted or unsubstituted arylene with 6 to 15 carbon atoms, and substituted or unsubstituted heteroarylene with 5 to 12 carbon atoms.

In the present disclosure, L is selected from a single bond, substituted or unsubstituted phenylene, substituted or unsubstituted naphthylene, substituted or unsubstituted biphenylene, substituted or unsubstituted terphenylene, substituted or unsubstituted fluorenylidene, substituted or unsubstituted dibenzothienylidene, substituted or unsubstituted dibenzofurylidene, and substituted or unsubstituted pyridylidene.

In the present disclosure, the substituent in L is selected from deuterium, halogen group, cyano, alkyl with 1 to 5 carbon atoms, aryl with 6 to 12 carbon atoms, and cycloalkyl with 3 to 10 carbon atoms. Specifically, in the present disclosure, the substituent in the L is selected from deuterium, fluorine, cyano, methyl, ethyl, tert-butyl, phenyl, naphthyl, biphenyl and terphenyl.

In the present disclosure, L is selected from a single bond or the group consisting of groups as shown in j-1 to j-14:

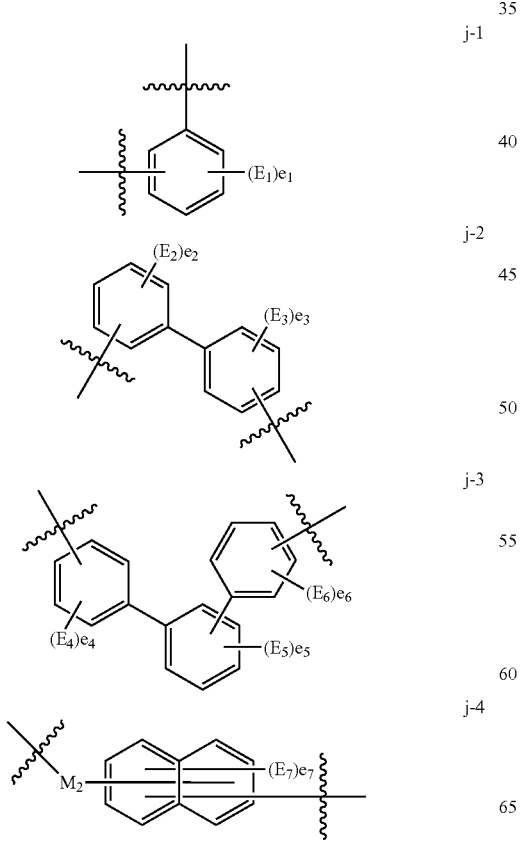

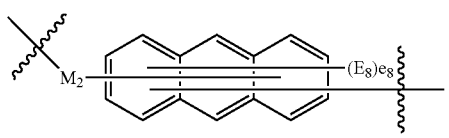

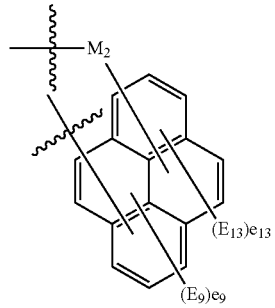

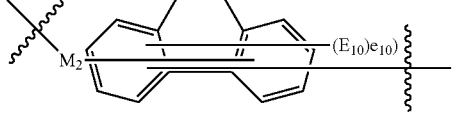

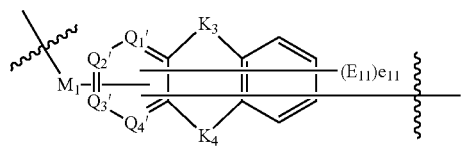

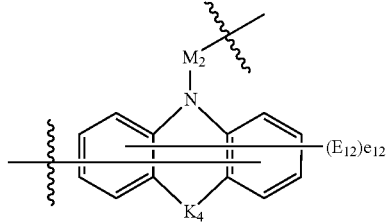

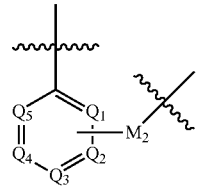

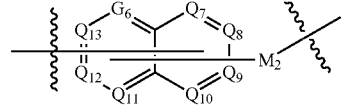

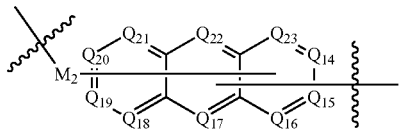

-continued

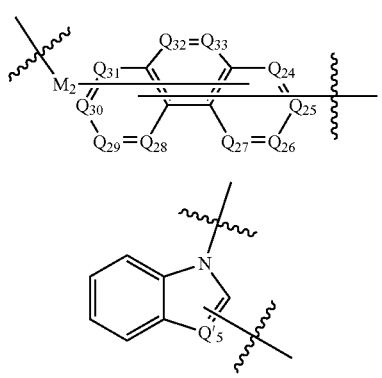

j-13 j-14

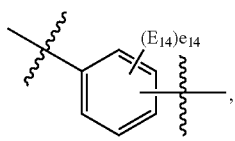

where M$_2$ is selected from a single bond or and ⊰ represents a chemical bond;

Q$_1$ to Q$_5$ and Q'$_1$ to Q'$_5$ are each independently selected from N or C(J$_5$), and at least one of Q$_1$ to Q$_5$ is selected from N; and when two or more of Q$_1$ to Q$_5$ are selected from C(J$_5$), any two J$_5$s are the same or different, and when two or more of Q'$_1$ to Q'$_4$ are selected from C(J$_5$), any two J$_5$s are the same or different;

Q$_6$ to Q$_{13}$ are each independently selected from N, C or C(J$_6$), and at least one of Q$_6$ to Q$_{13}$ is selected from N; and when two or more of Q$_6$ to Q$_{13}$ are selected from C(J$_6$), any two J$_6$s are the same or different;

Q$_{14}$ to Q$_{23}$ are each independently selected from N, C or C(J$_7$), and at least one of Q$_{14}$ to Q$_{23}$ is selected from N; and when two or more of Q$_{14}$ to Q$_{23}$ are selected from C(J$_7$), any two J$_7$s are the same or different;

Q$_{24}$ to Q$_{33}$ are each independently selected from N, C or C(J$_8$), and at least one of Q$_{24}$ to Q$_{33}$ is selected from N; and when two or more of Q$_{24}$ to Q$_{33}$ are selected from C(J$_8$), any two J$_8$s are the same or different;

E$_1$ to E$_{14}$ and J$_5$ to J$_8$ are each independently selected from hydrogen, deuterium, halogen group, cyano, heteroaryl with 3 to 20 carbon atoms, aryl with 6 to 20 carbon atoms optionally substituted by one or more of deuterium, fluorine, chlorine and cyano, trialkylsilyl with 3 to 12 carbon atoms, arylsilyl with 8 to 12 carbon atoms, alkyl with 1 to 10 carbon atoms, haloalkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, heterocycloalkenyl with 4 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, phosphinyloxy with 6 to 18 carbon atoms and triarylsilyl with 18 to 24 carbon atoms; in the present disclosure, "aryl with 6 to 20 carbon atoms optionally substituted by one or more of deuterium, fluorine, chlorine and cyano" means that the aryl can be substituted by deuterium, fluorine, chlorine and cyano and also can not be substituted by deuterium, fluorine, chlorine and cyano.

e$_1$ to e$_{14}$ are represented by er, E$_1$ to E$_{14}$ are represented by E$_r$, r is a variable and represents any integer of 1 to 14, and er represents the number of substituents E$_r$; when r is selected from 1, 2, 3, 4, 5, 6, 9, 13 or 14, er is selected from 1, 2, 3 or 4; when r is selected from 7 or 11, er is selected from 1, 2, 3, 4, 5 or 6; when r is 12, er is selected from 1, 2, 3, 4, 5, 6 or 7; when r is selected from 8 or 10, er is selected from 1, 2, 3, 4, 5, 6, 7 or 8; and when the er is greater than one, any two Ers are the same or different;

K$_3$ is selected from O, S, Se, N(E$_{15}$), C(E$_{16}$E$_{17}$) and Si(E$_{18}$E$_{19}$); where E$_{15}$, E$_{16}$, E$_{17}$, E$_{18}$ and E$_{19}$ are each independently selected from aryl with 6 to 20 carbon atoms, heteroaryl with 3 to 20 carbon atoms, alkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, and heterocloalkenyl with 4 to 10 carbon atoms; or E$_{16}$ and E$_{17}$ are connected with each other to form a saturated or unsaturated ring with 3 to 15 carbon atoms together with atoms to which they are jointly connected, or E$_{18}$ and E$_{19}$ are connected with each other to form a saturated or unsaturated ring with 3 to 15 carbon atoms together with atoms to which they are jointly connected;

K$_4$ is selected from a single bond, O, S, Se, N(E$_{20}$), C(E$_{21}$E$_{22}$) and Si(E$_{23}$E$_{24}$); where E$_{20}$-E$_{24}$ are each independently selected from aryl with 6 to 20 carbon atoms, heteroaryl with 3 to 20 carbon atoms, alkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, and heterocloalkenyl with 4 to 10 carbon atoms; or E$_{21}$ and E$_{22}$ are connected with each other to form a saturated or unsaturated ring with 3 to 15 carbon atoms together with atoms to which they are jointly connected, or E$_{23}$ and E$_{24}$ are connected with each other to form a saturated or unsaturated ring with 3 to 15 carbon atoms together with atoms to which they are jointly connected.

In one specific embodiment of the present disclosure, L is selected from a single bond or the group consisting of the following groups:

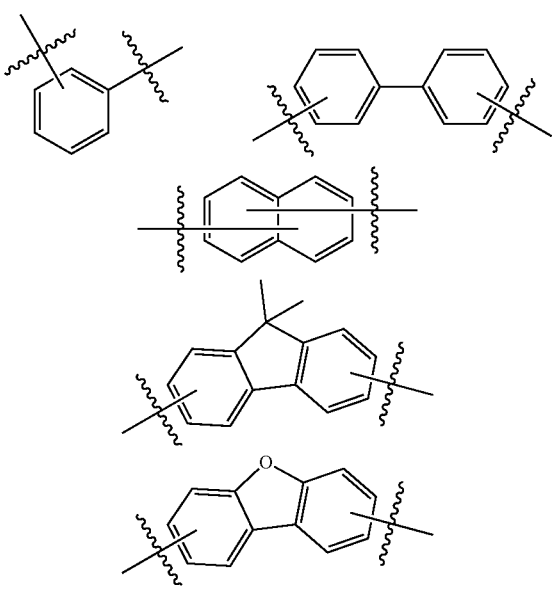

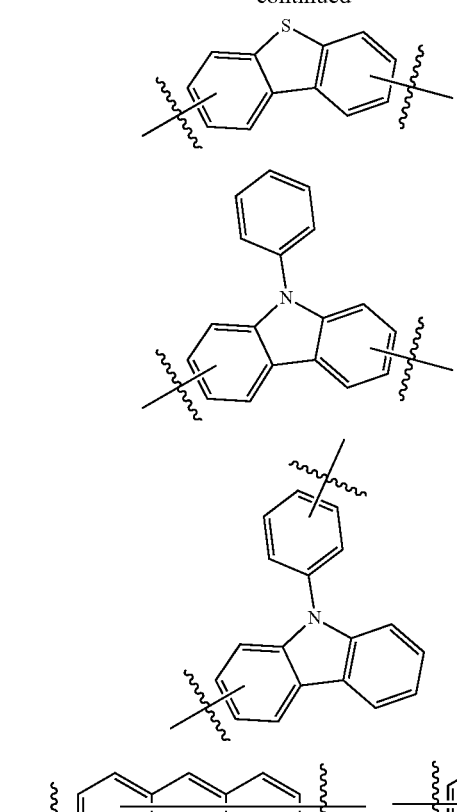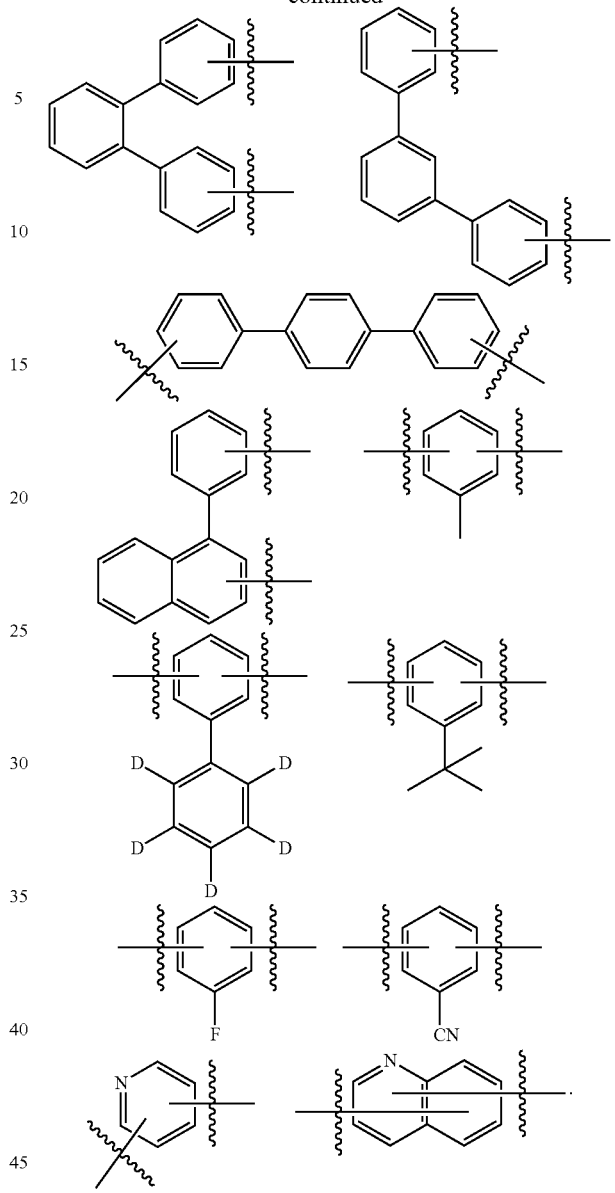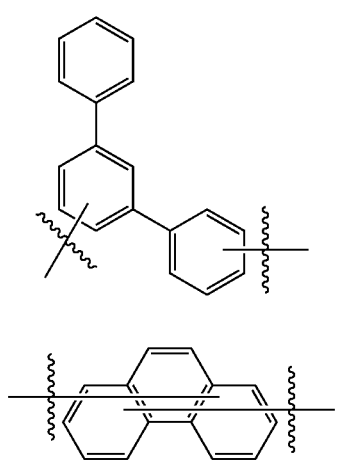
In one specific embodiment of the present disclosure, L is selected from a single bond or the group consisting of the following groups:

-continued
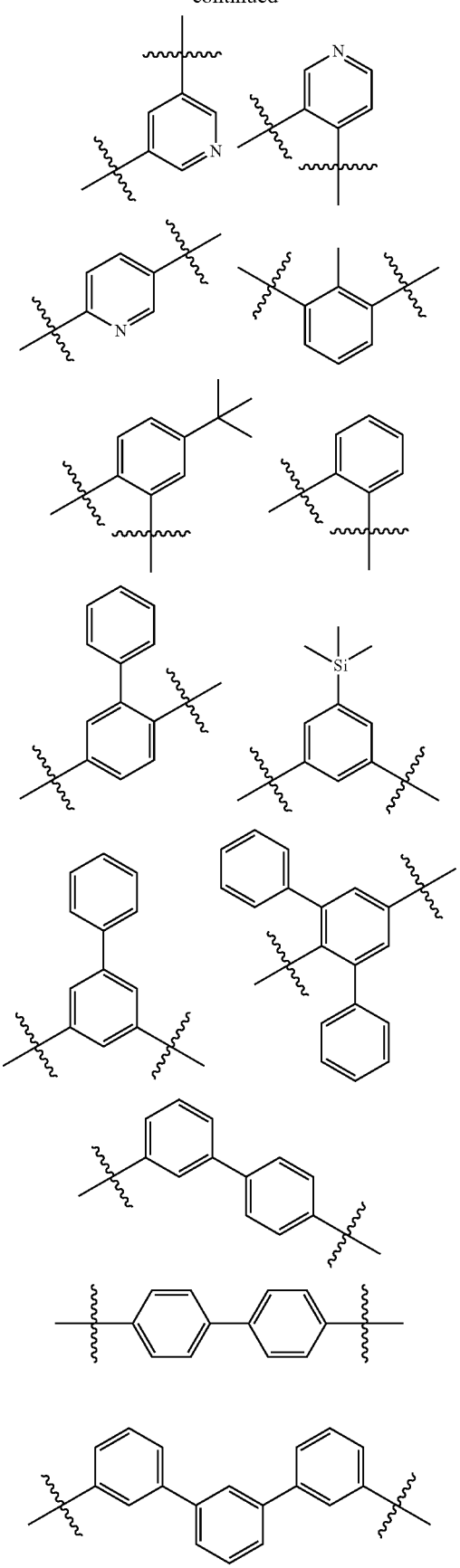
-continued
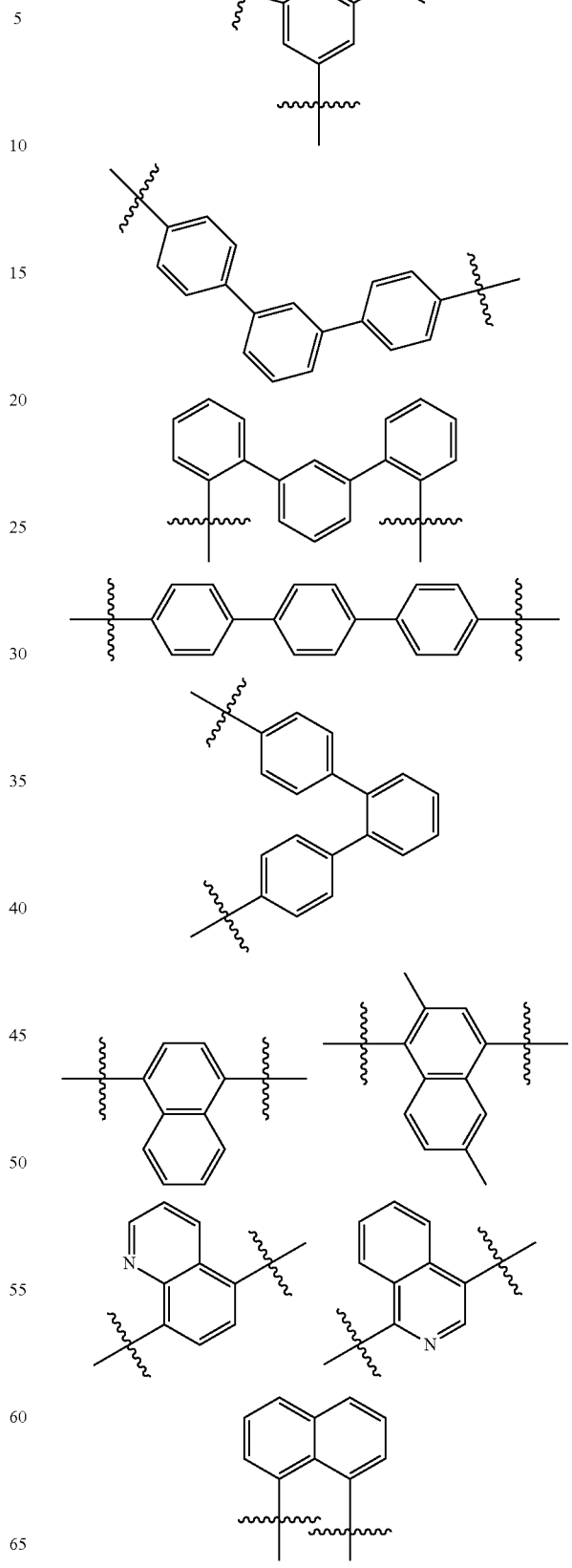

-continued
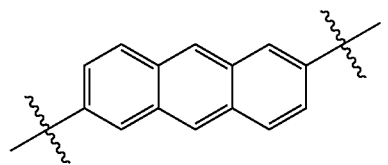
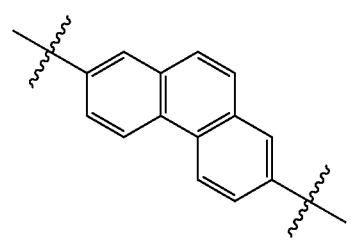
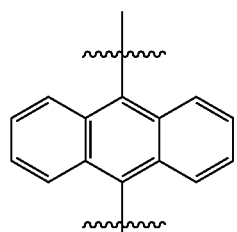
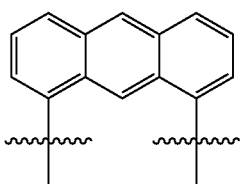
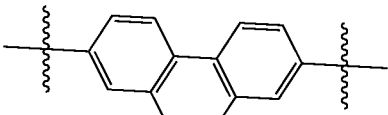
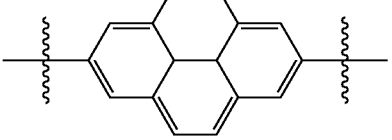
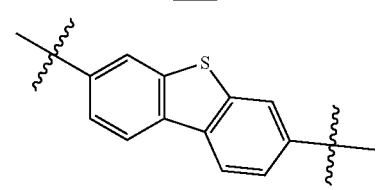
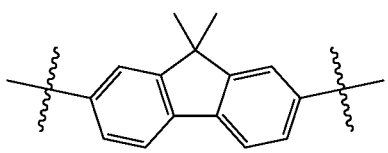
-continued
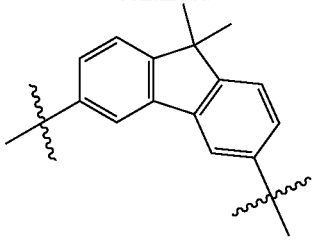
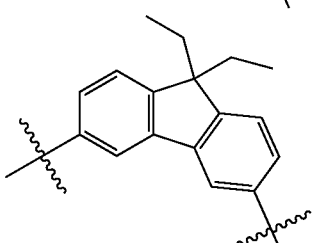
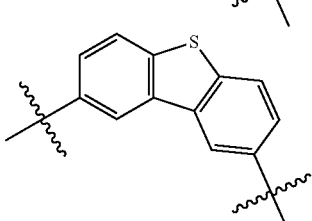
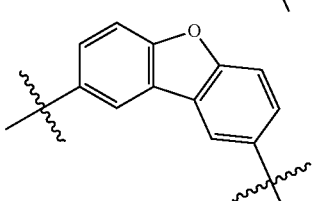
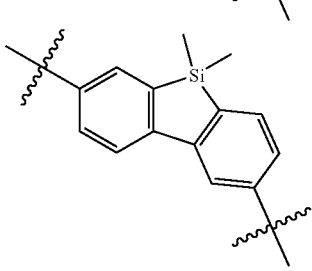
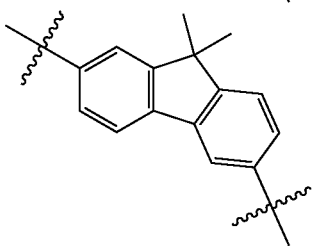
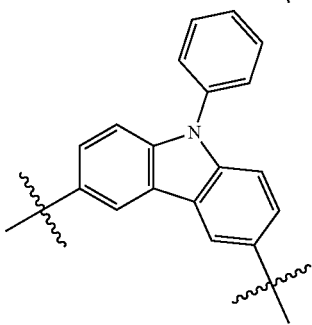

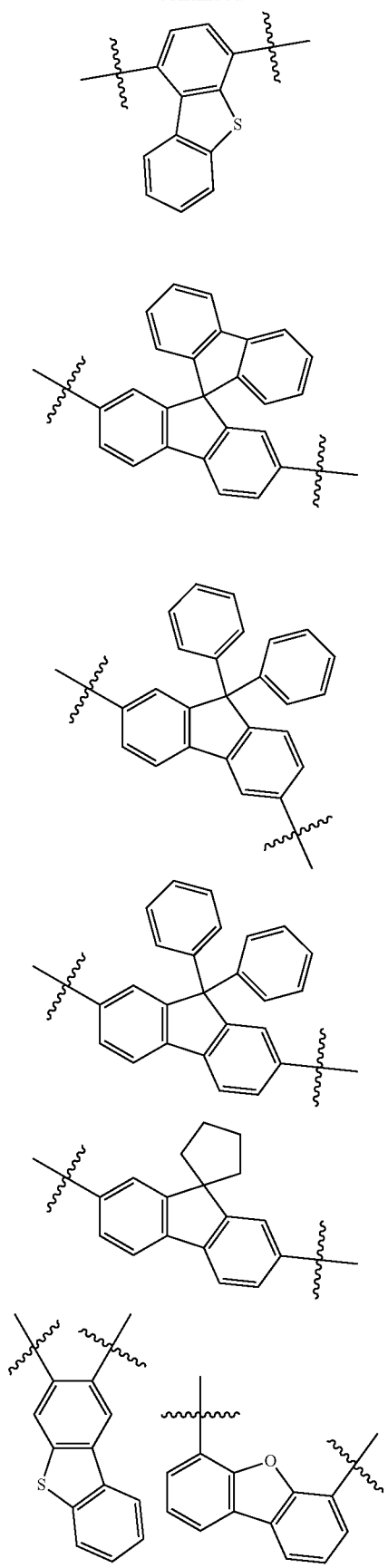
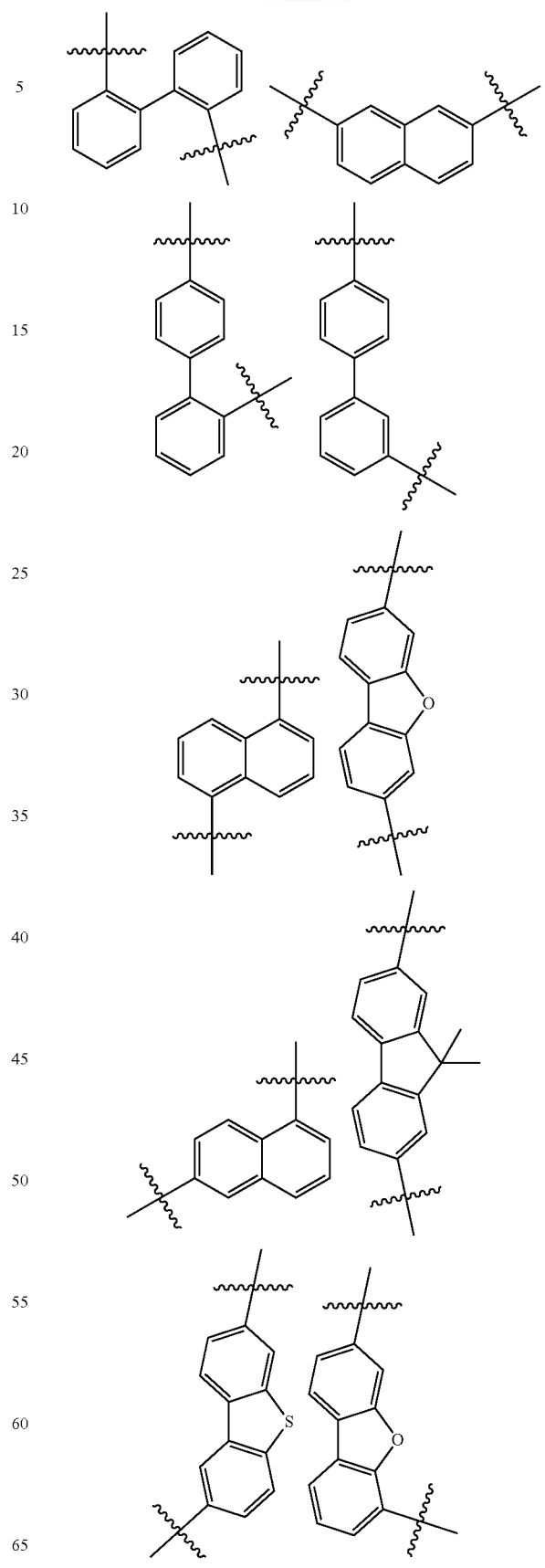

-continued
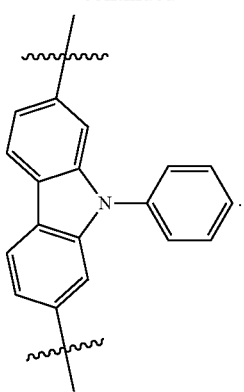
In one specific embodiment of the disclosure, the nitrogen-containing compound is selected from the group consisting of the following compounds:
A-1
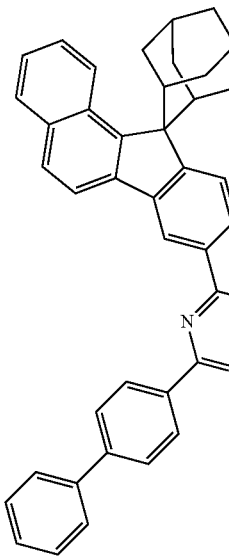
A-2
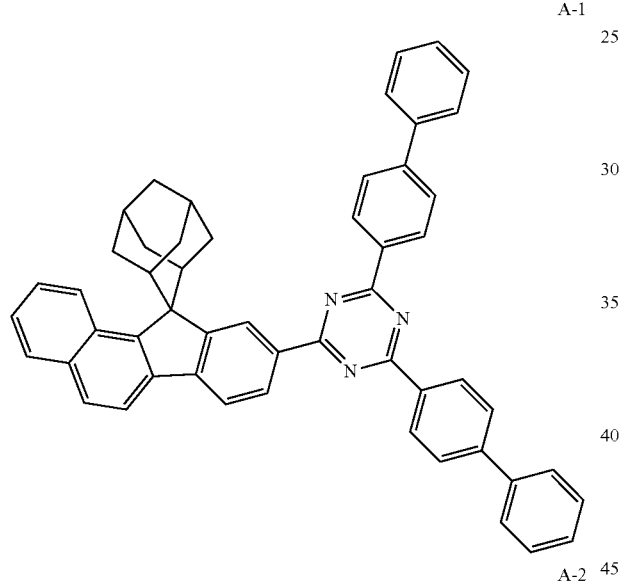
A-3
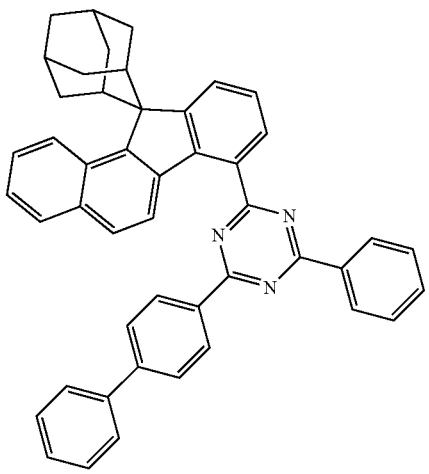
A-4
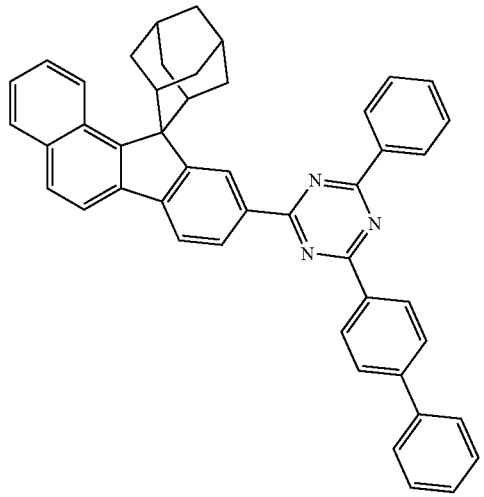
A-5
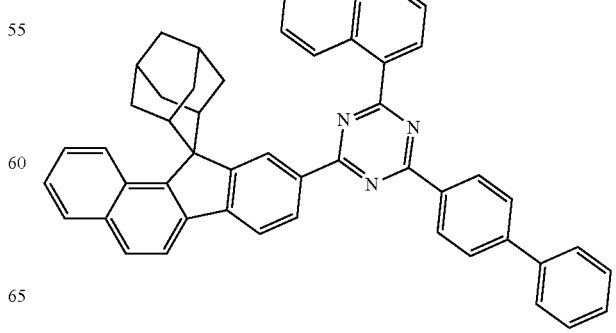

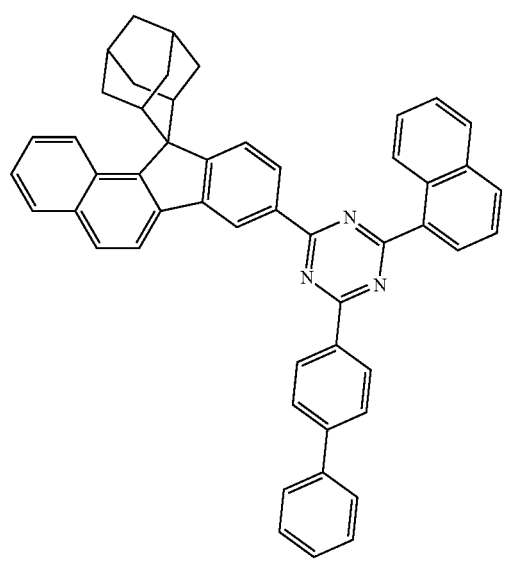
A-6
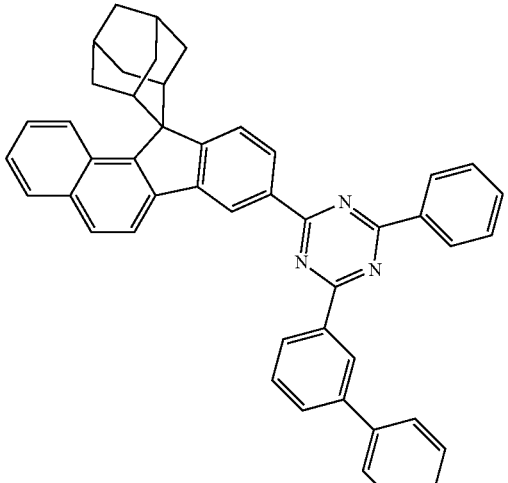
A-9
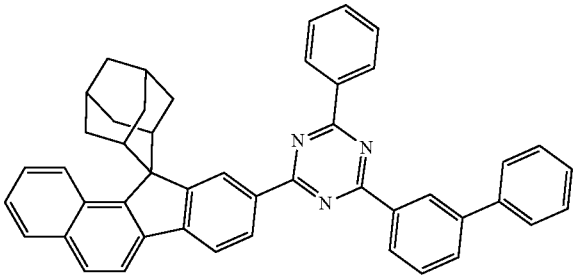
A-7
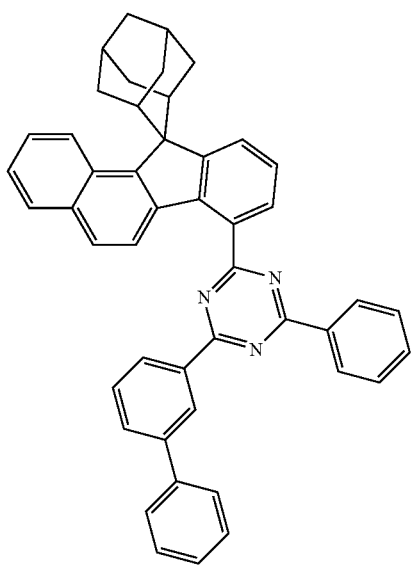
A-10
A-8

A-11
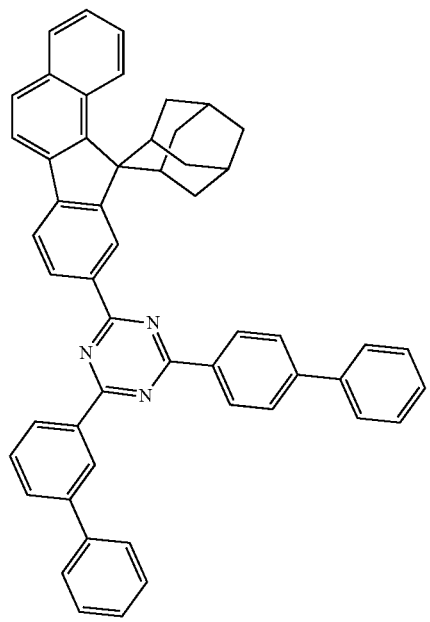
A-12
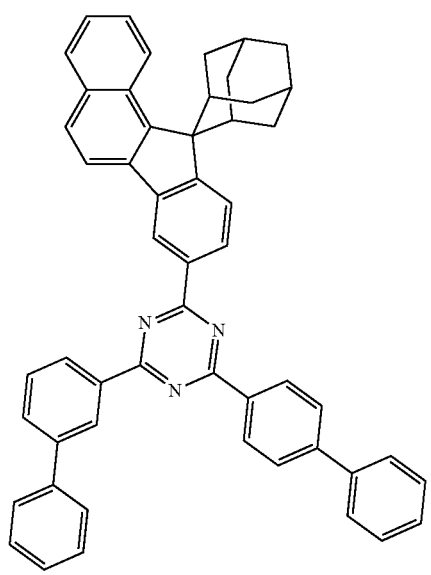
A-13
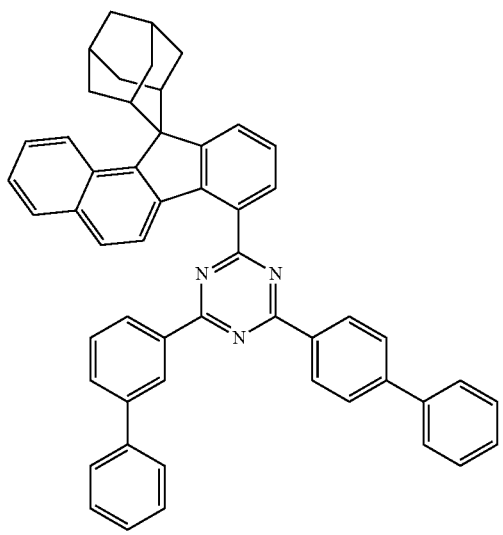
A-14
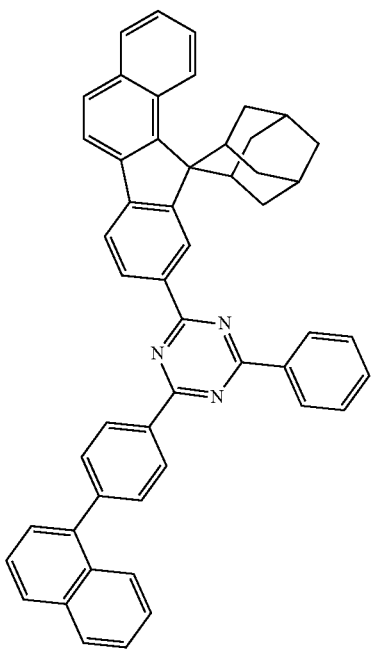

A-15
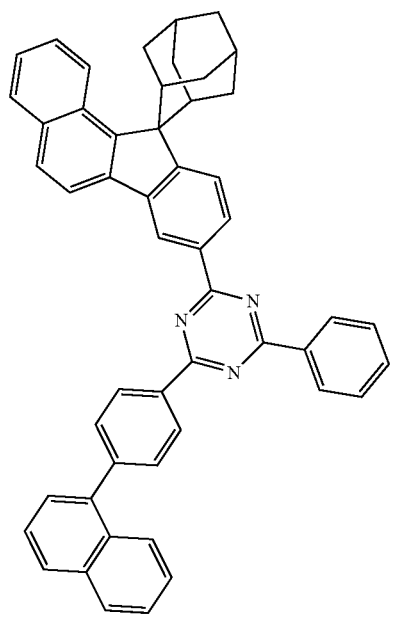
A-16
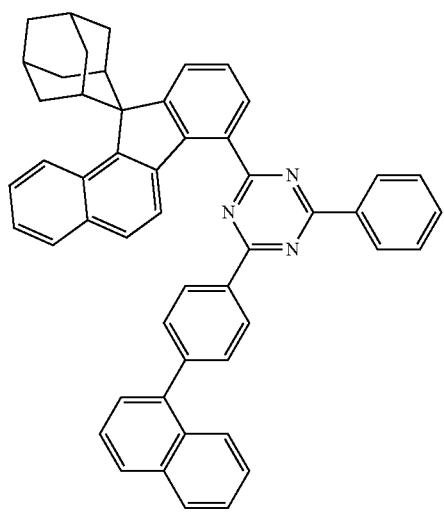
A-17
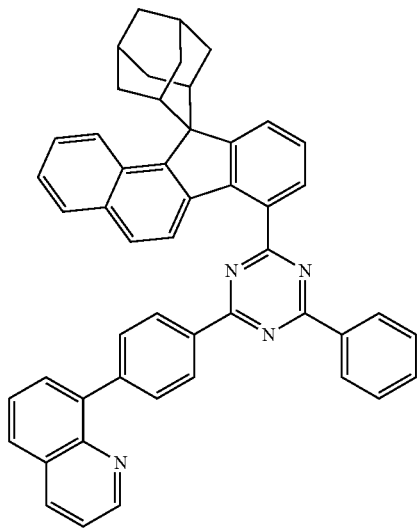
A-18
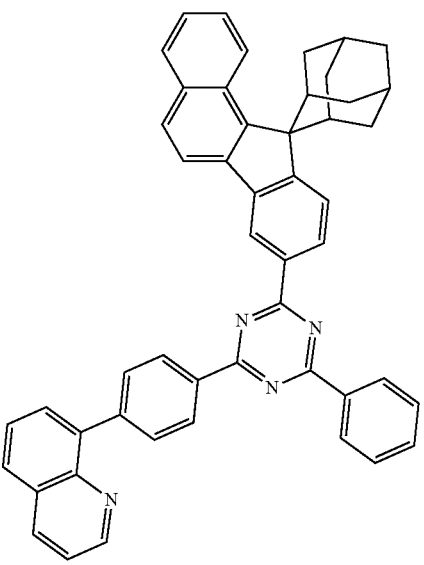
A-19
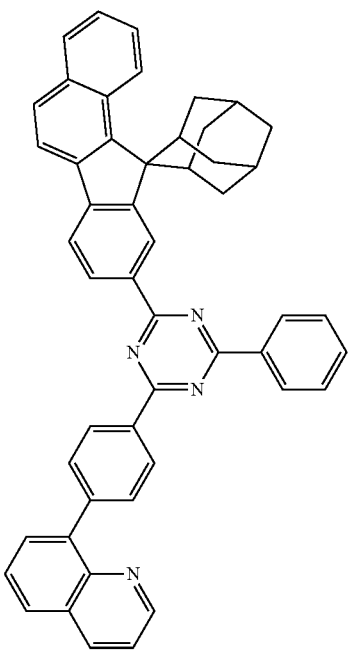

-continued
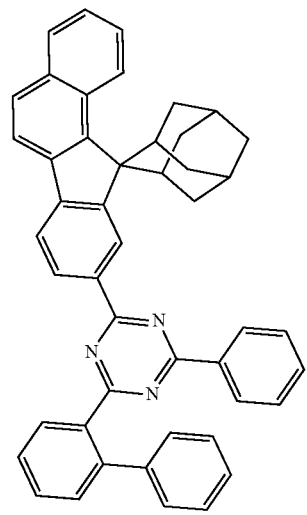
A-20
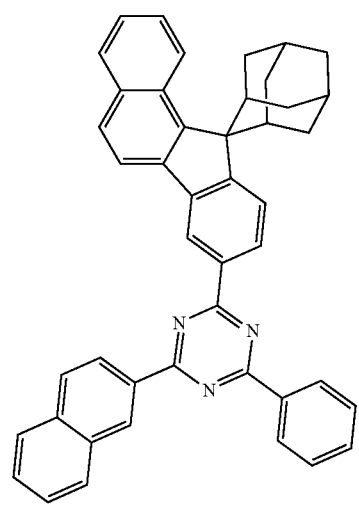
A-21
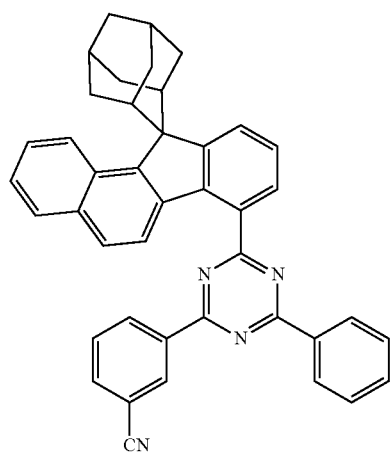
A-22
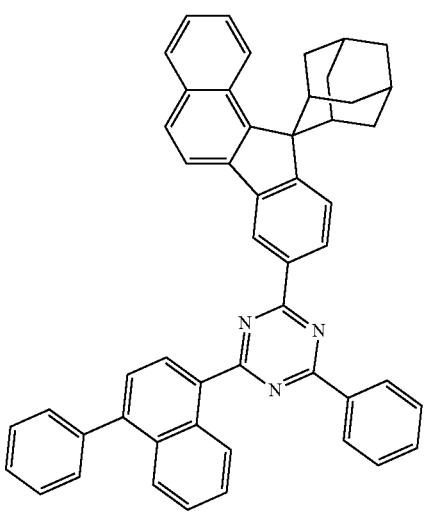
A-23
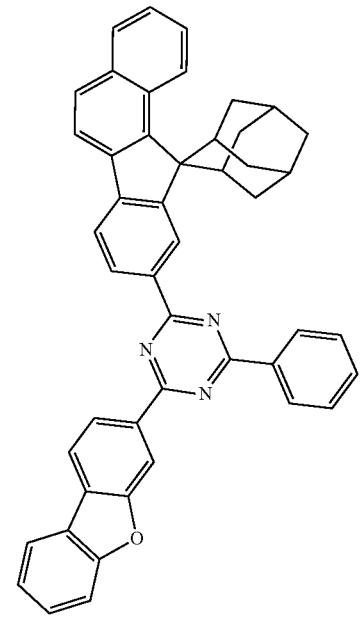
A-24
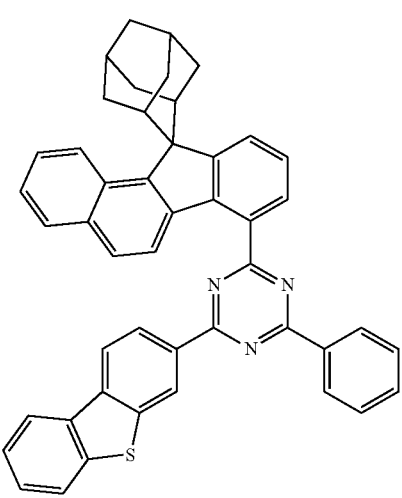
A-25

A-26
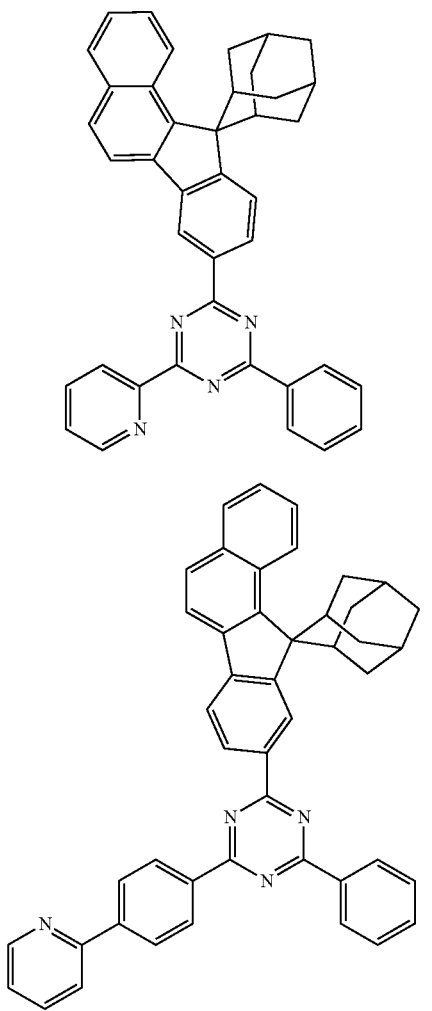
A-27
A-28
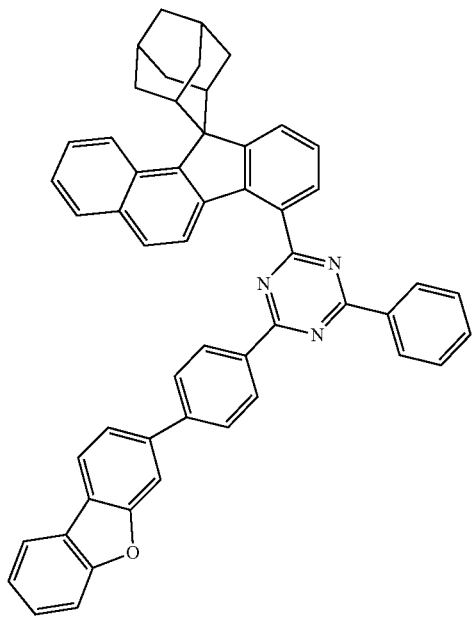
A-29
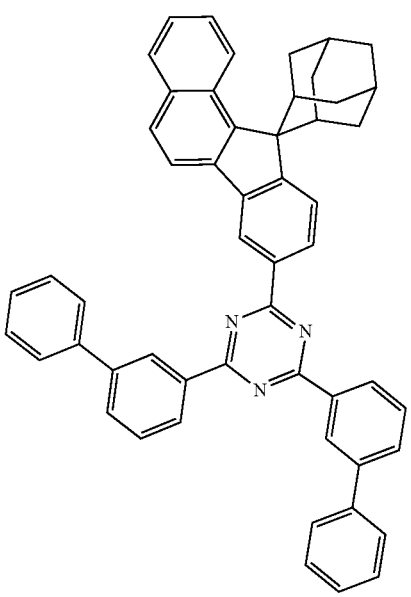
A-30
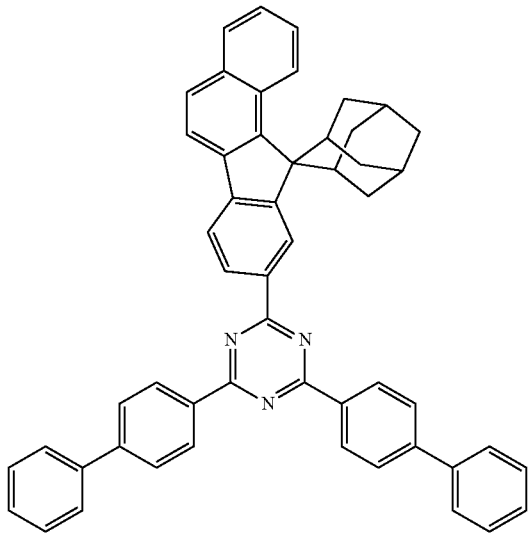

A-31
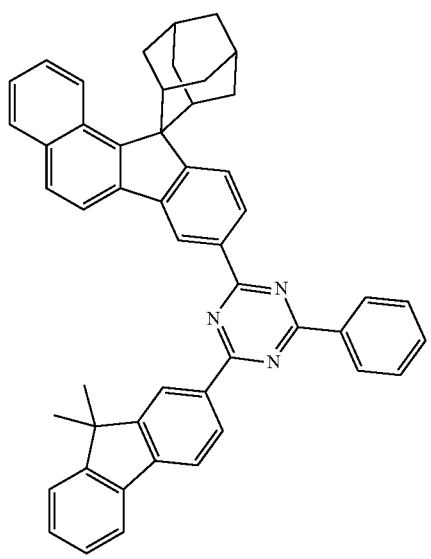
A-32
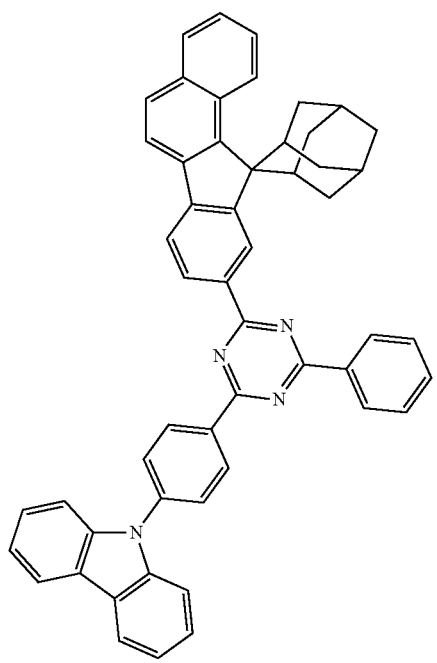
A-33
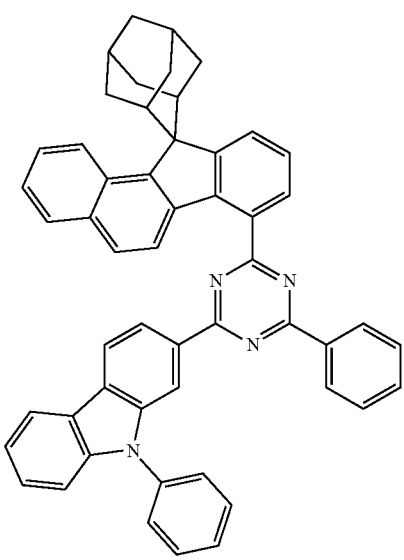
A-34
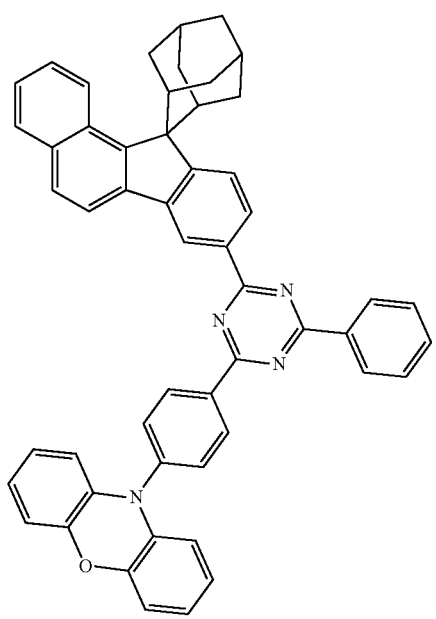

A-35
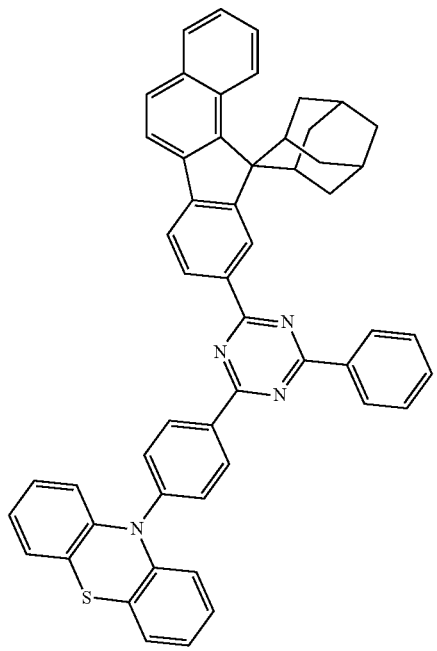
A-37
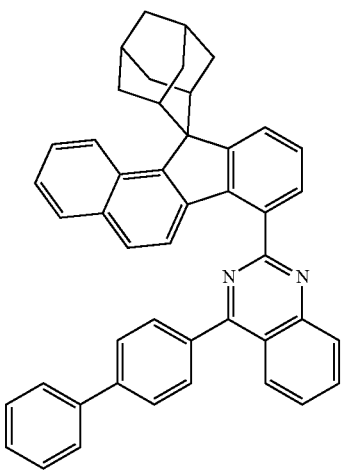
A-38
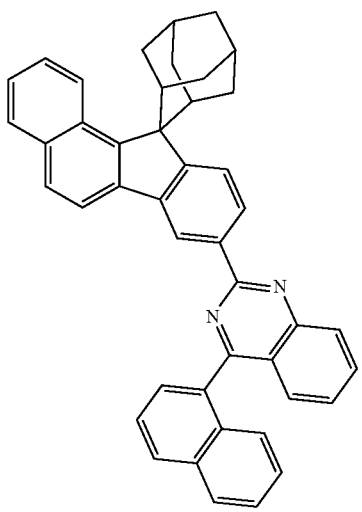
A-36
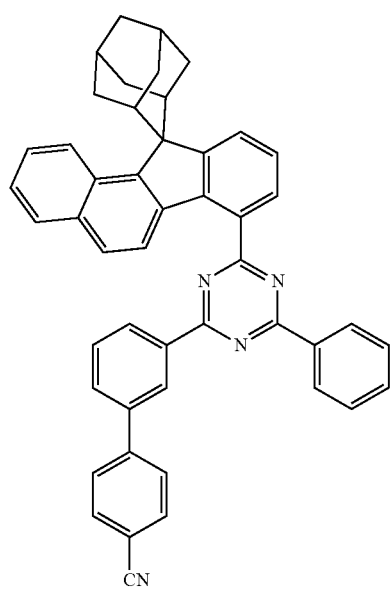
A-39
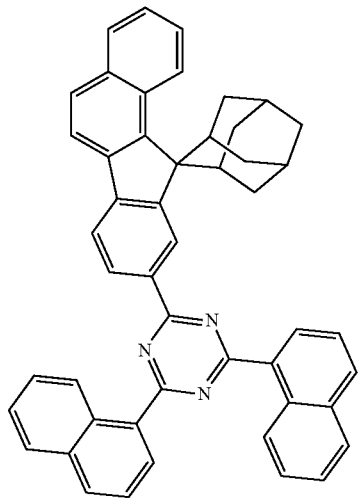

A-40
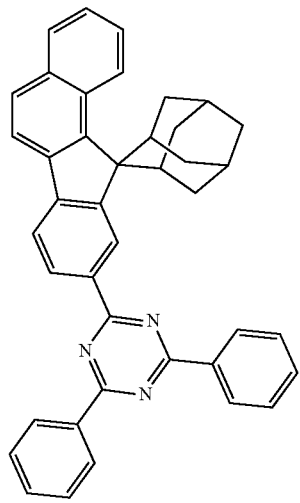
A-41
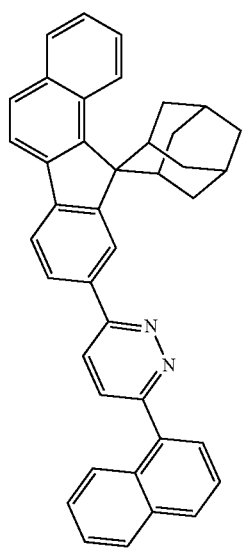
A-42
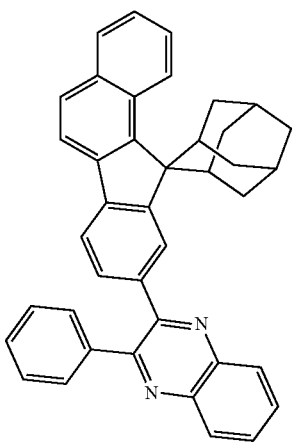
A-43
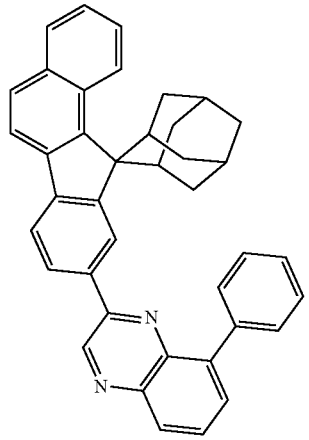
A-44
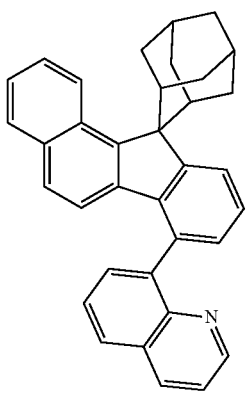
A-45
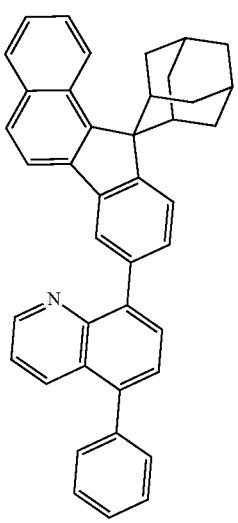

A-46
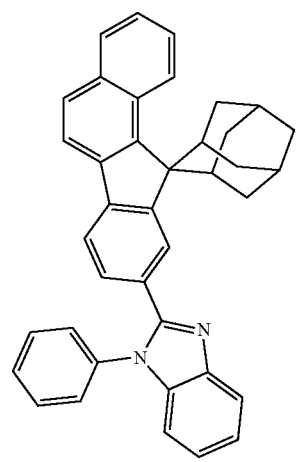
A-47
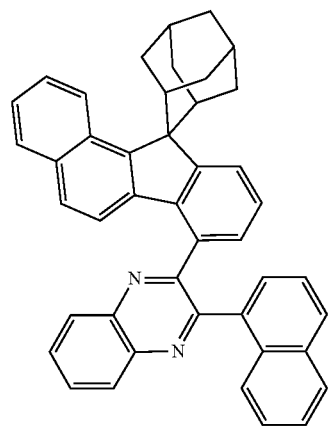
A-48
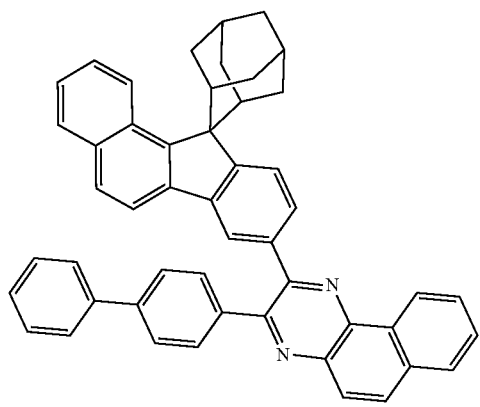
A-49
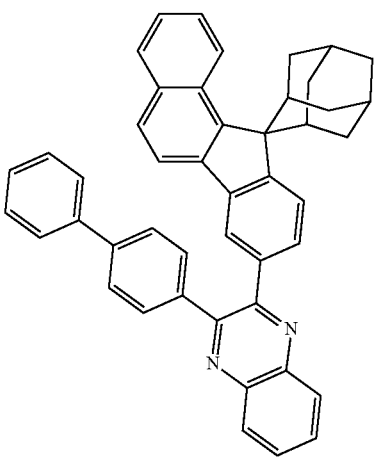
A-50
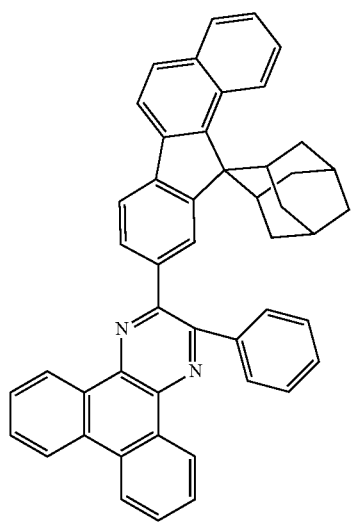
A-51
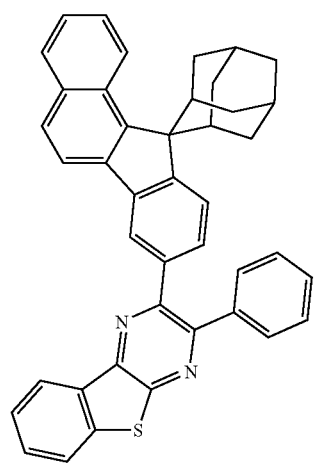

A-52
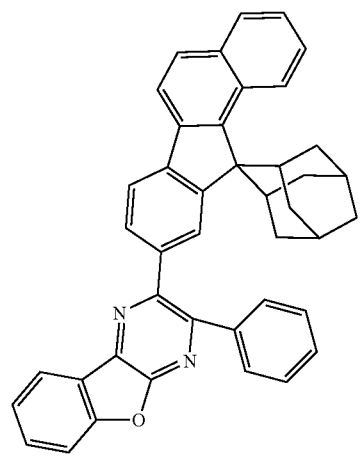
A-55
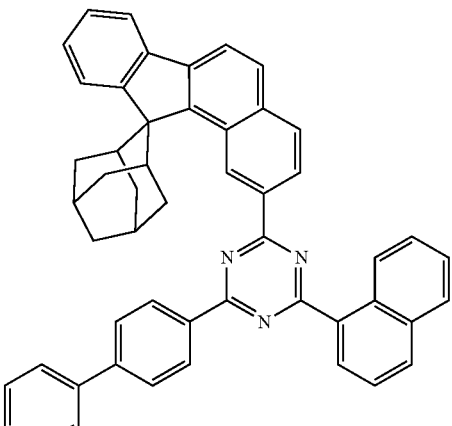
A-53
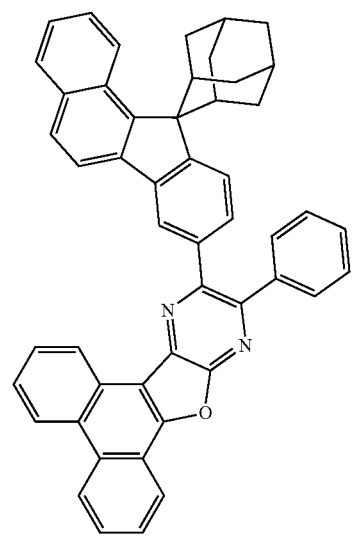
A-56
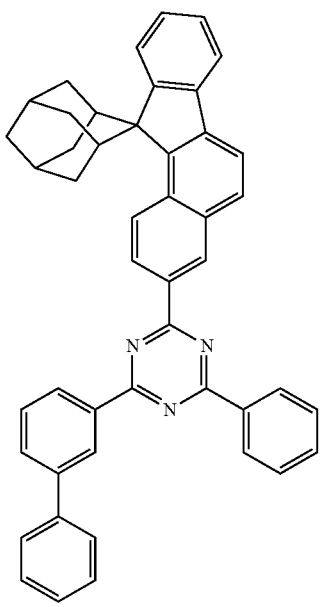
A-54
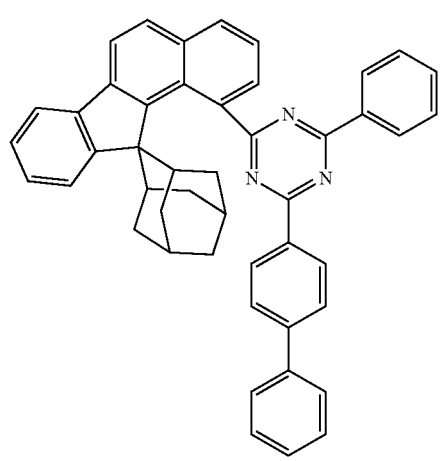

A-57
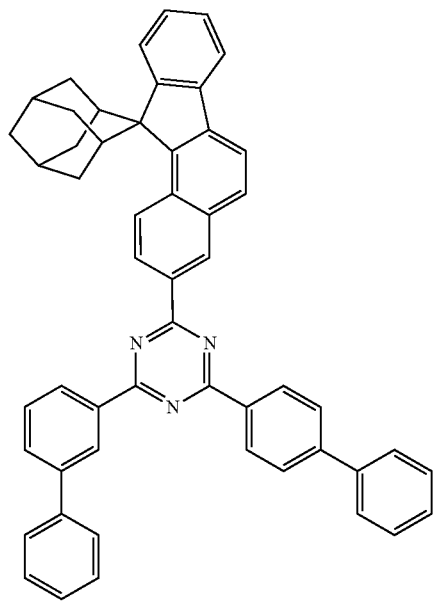
A-58
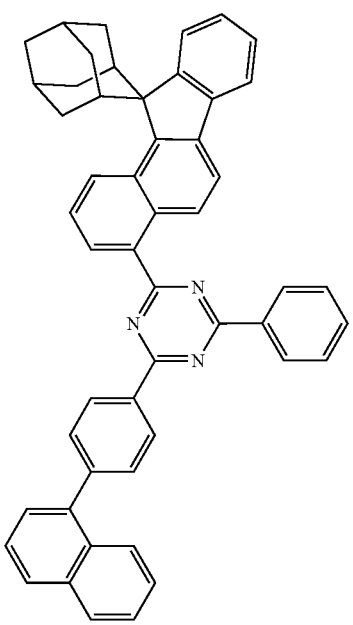
A-59
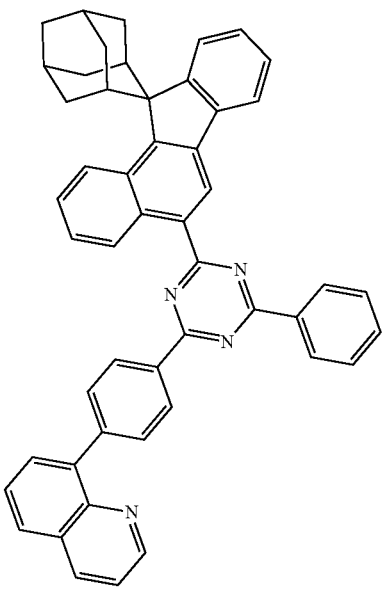
A-60
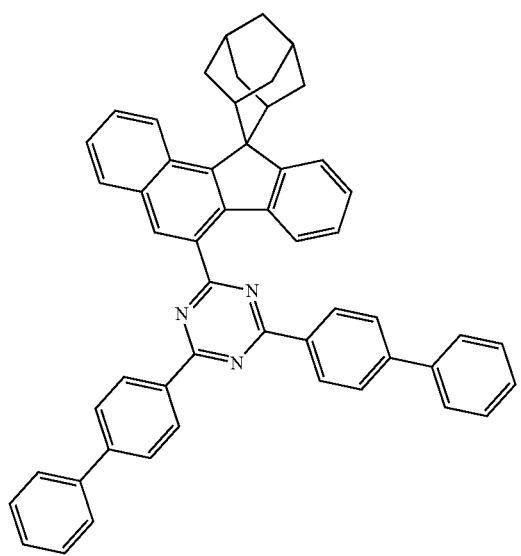

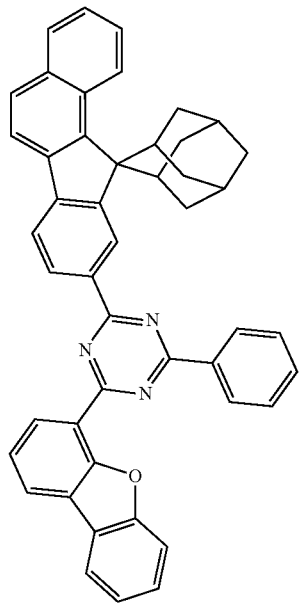
A-61
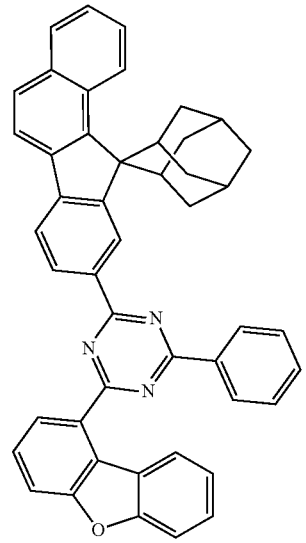
A-63
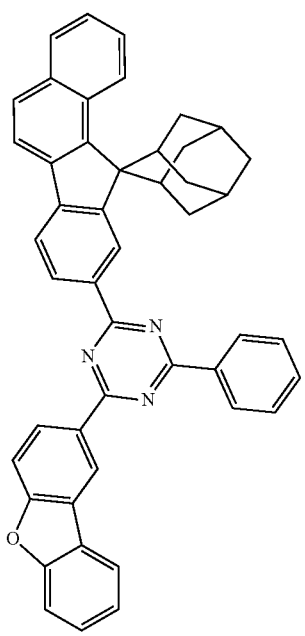
A-62
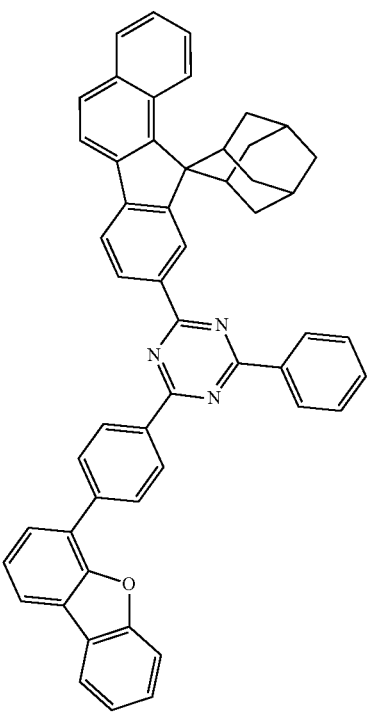
A-64

A-65
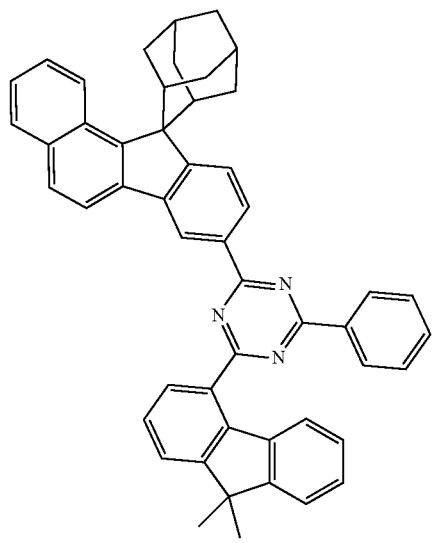
A-67
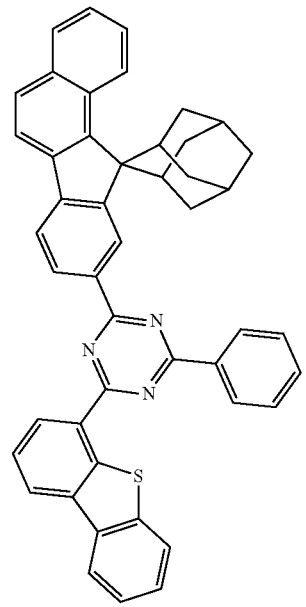
A-66
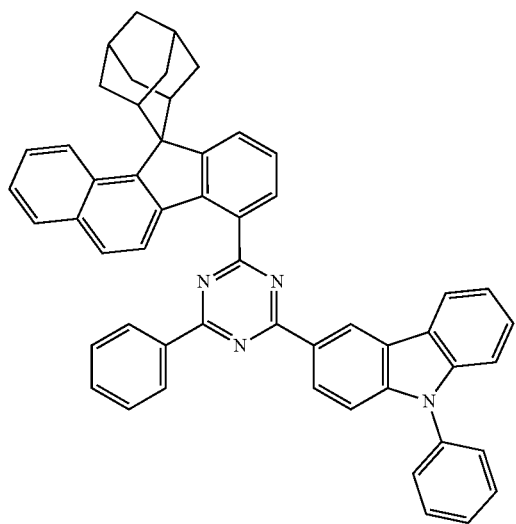
A-68
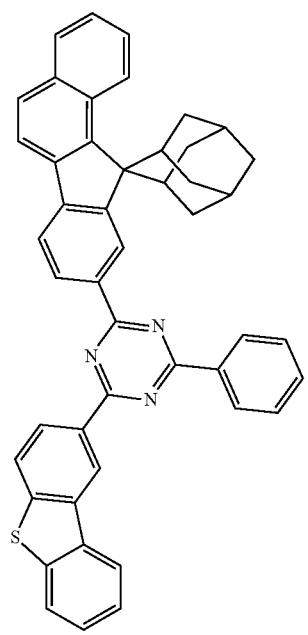

A-69
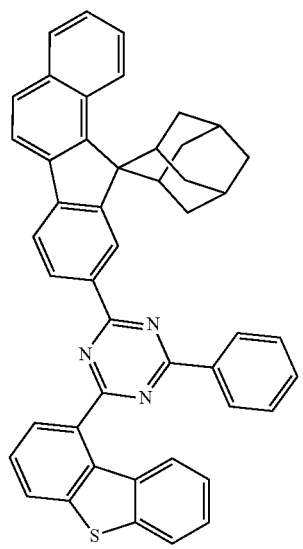
A-71
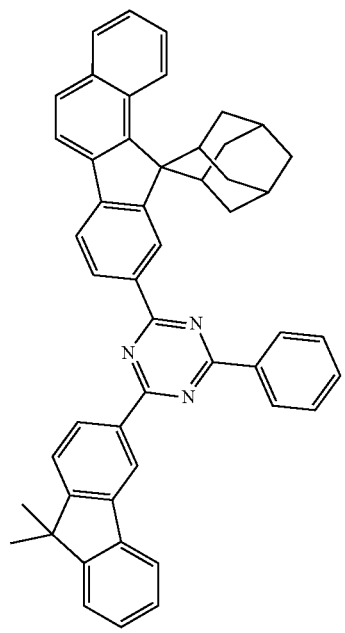
A-70
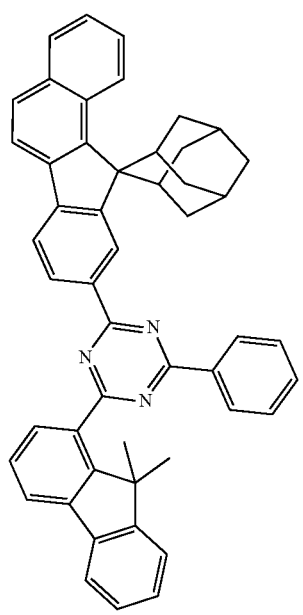
A-72
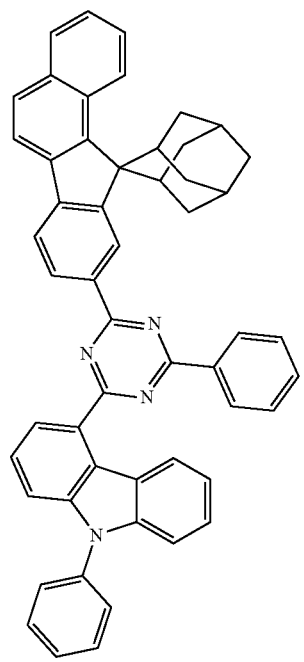

A-73
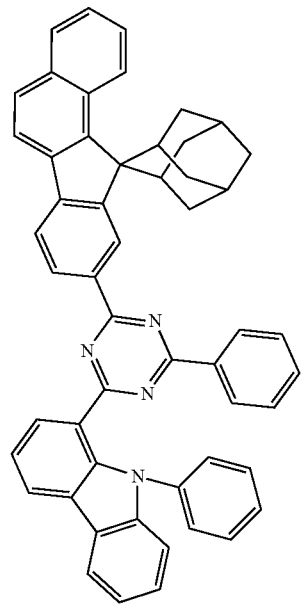
A-75
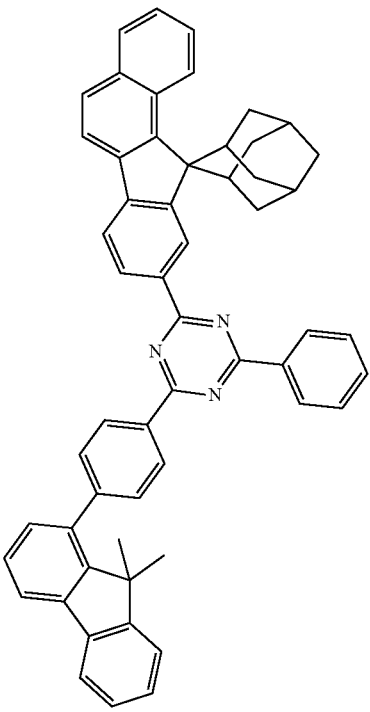
A-74
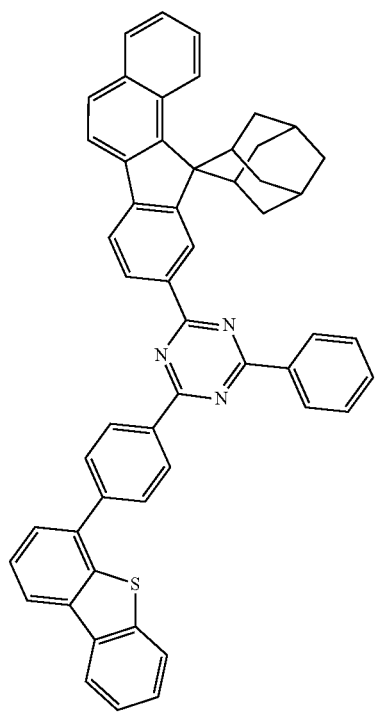
A-76
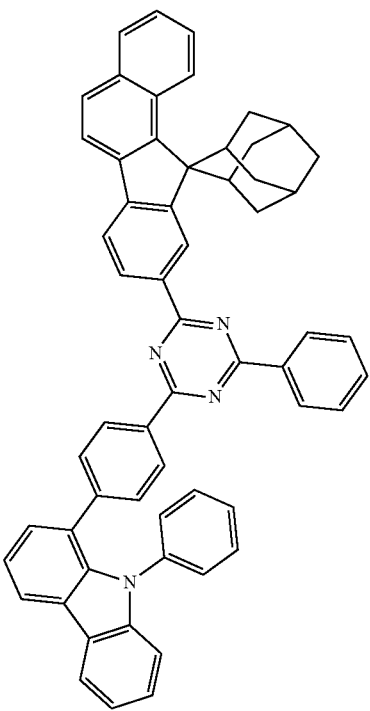

A-77
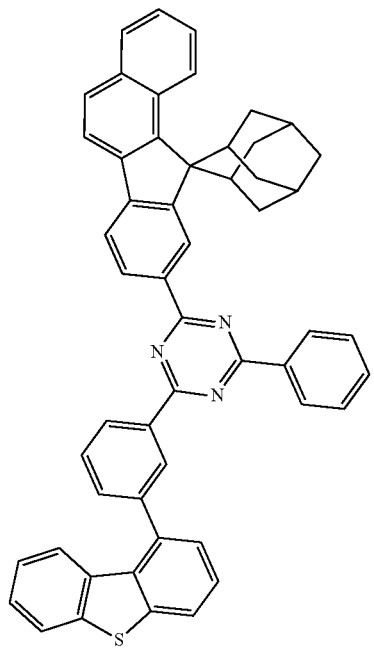
A-78
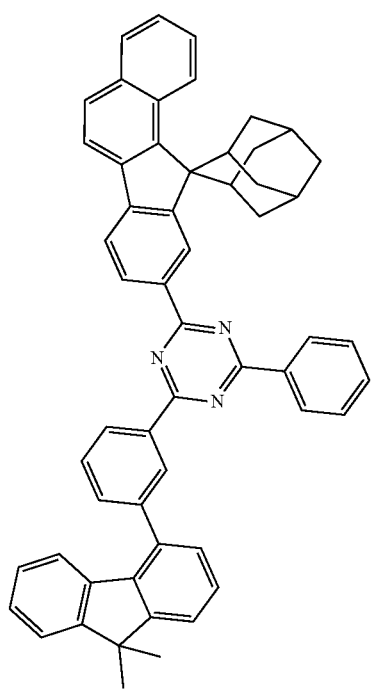
A-79
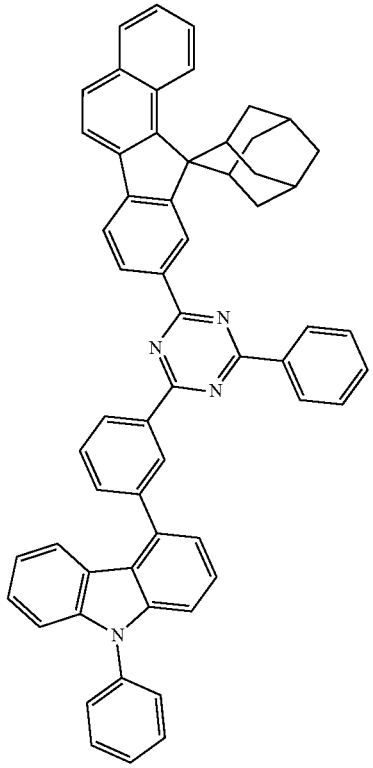
A-80
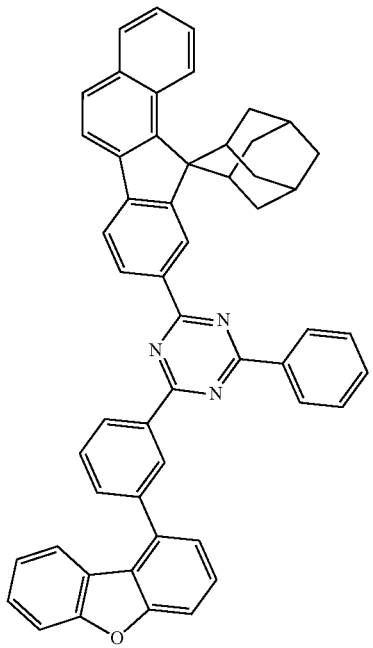

A-81
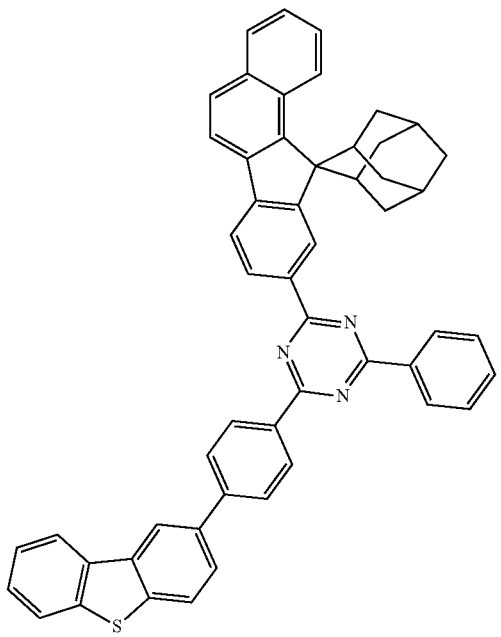
A-82
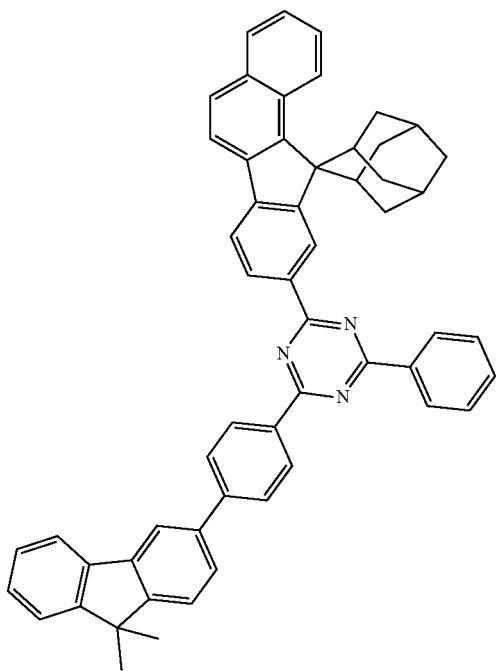
A-83
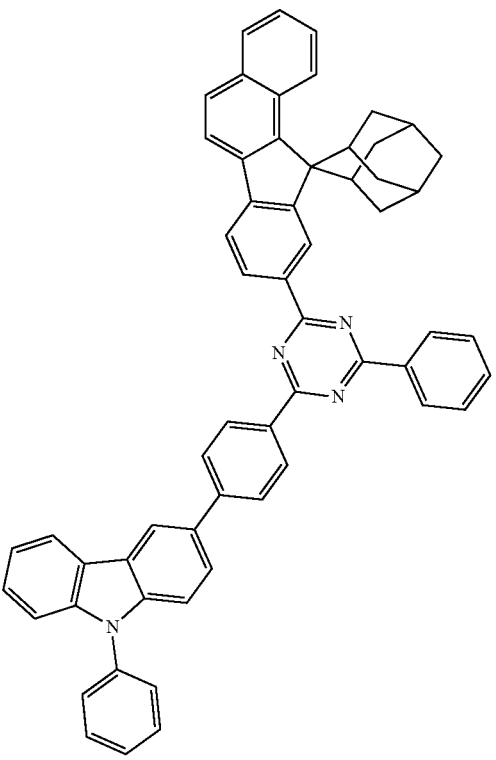
A-84
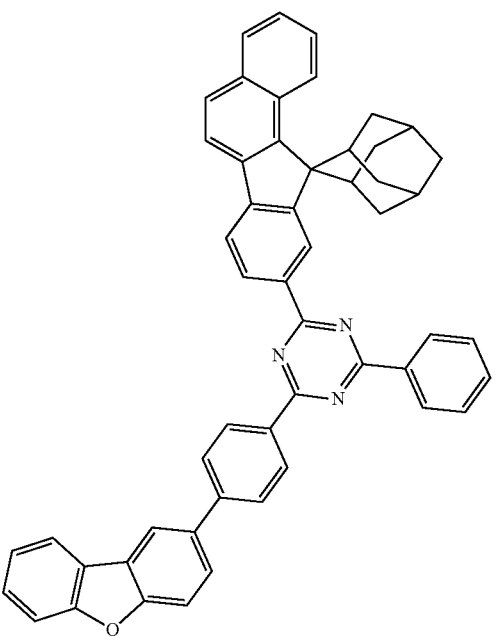

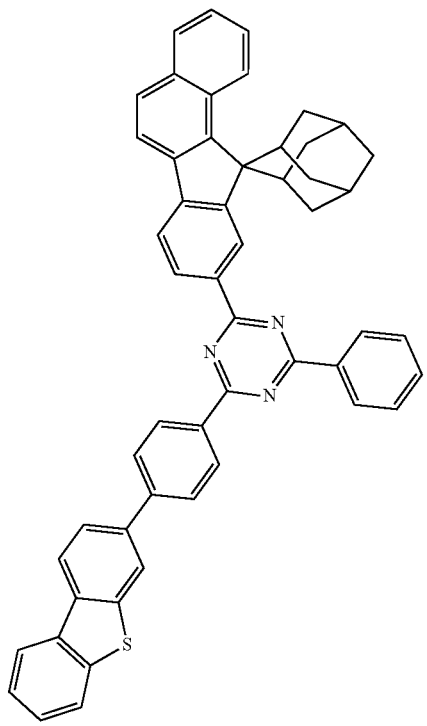
A-85
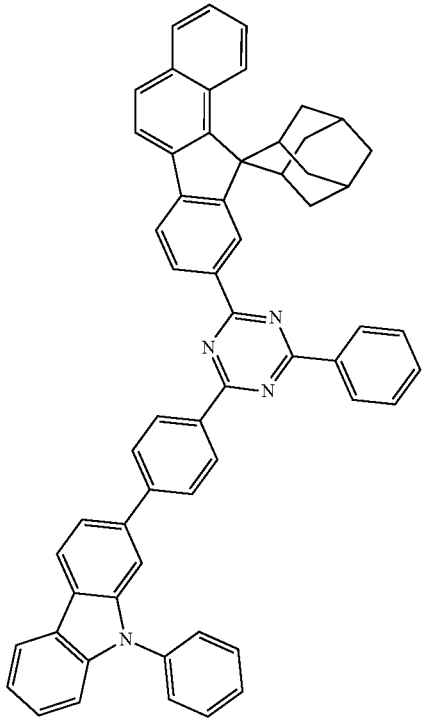
A-87
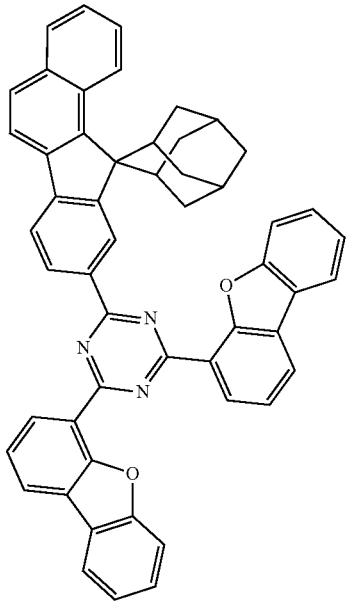
A-88
A-86

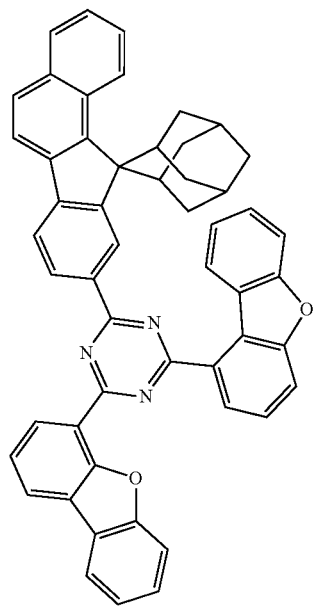
A-89
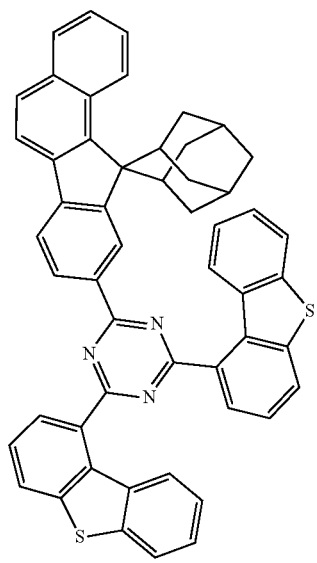
A-91
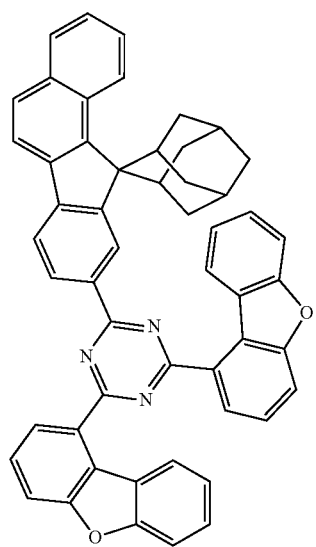
A-90
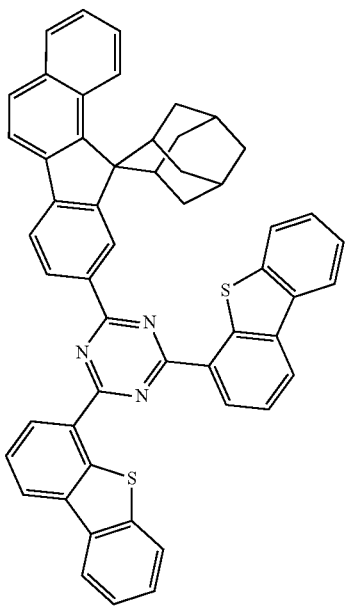
A-92

A-93
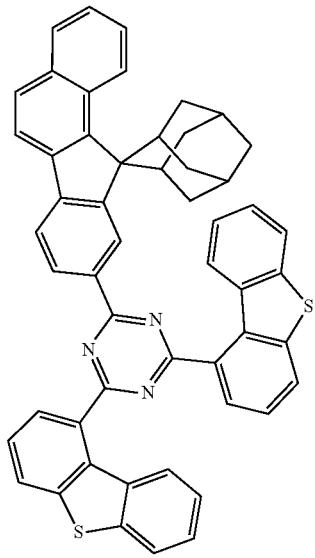
A-96
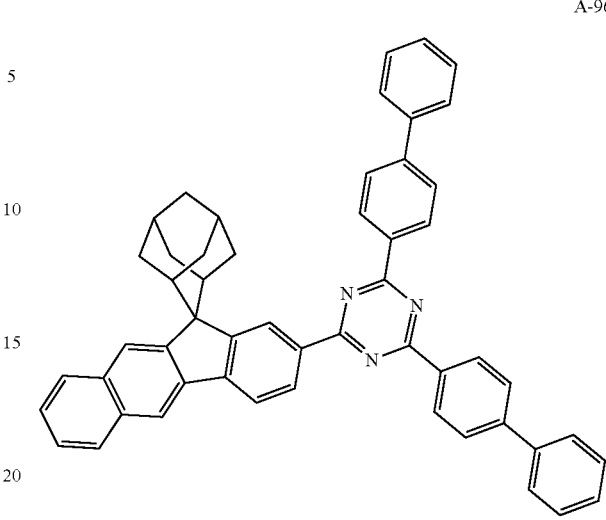
A-94
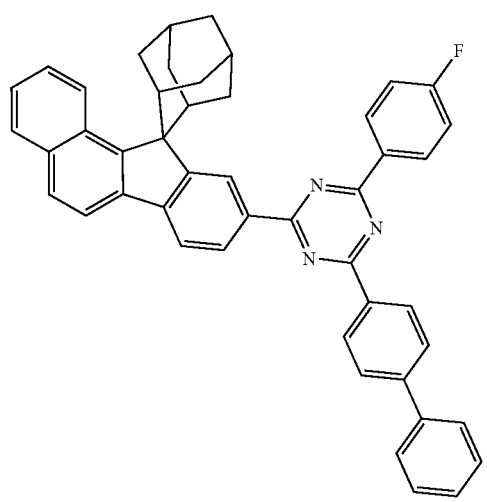
A-97
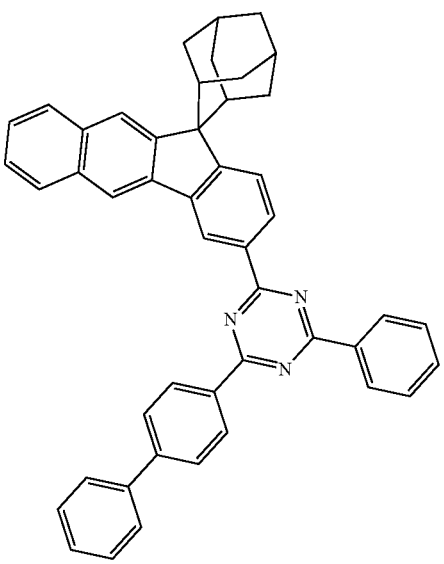
A-95
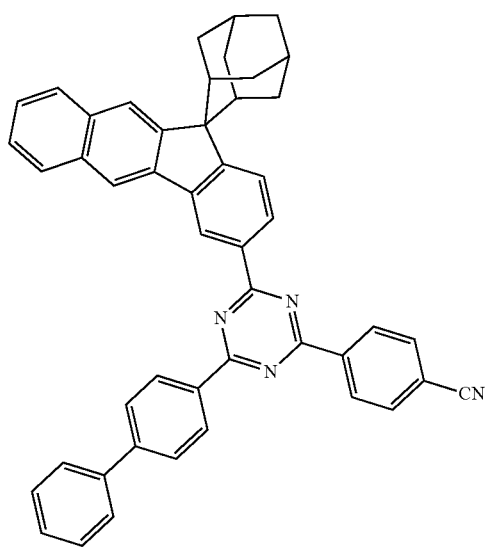
A-98
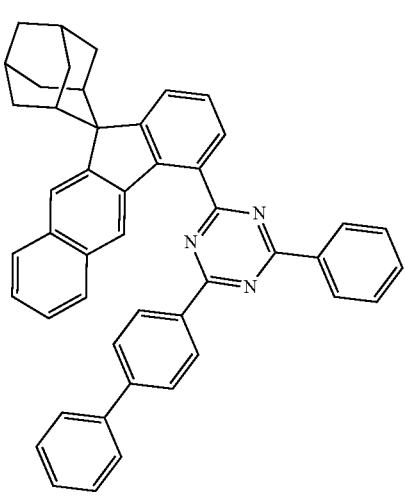

A-99
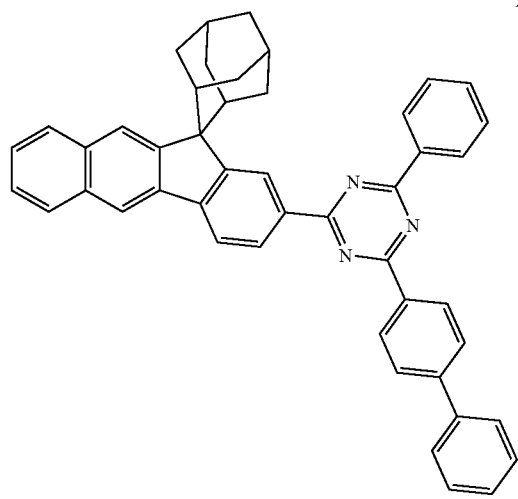
A-100
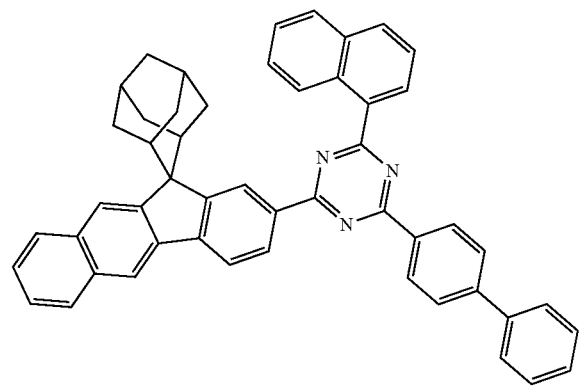
A-101
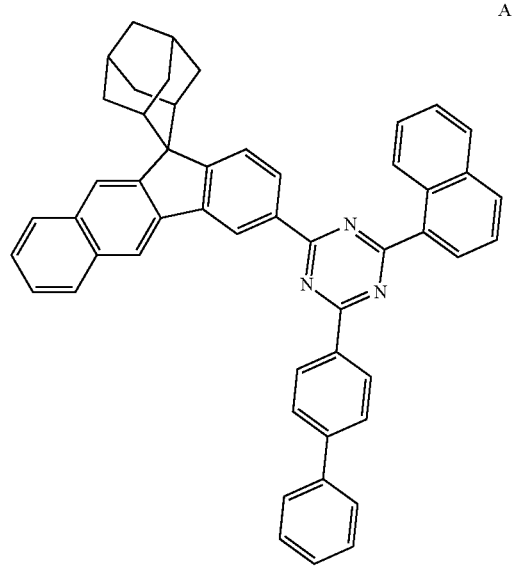
A-102
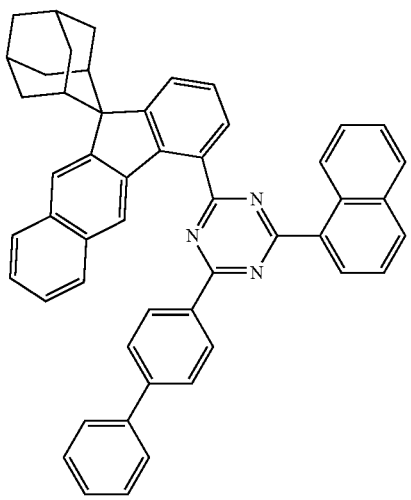
A-103
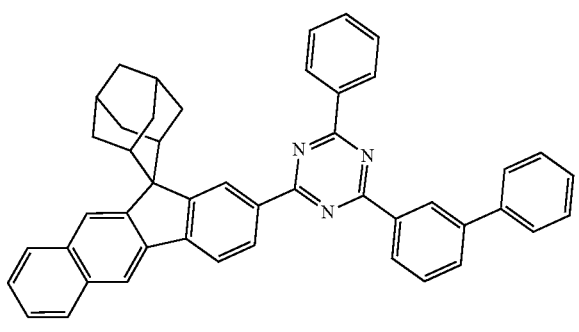
A-104
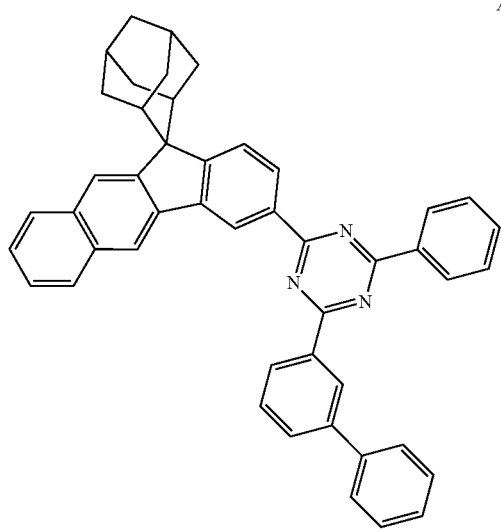

A-105
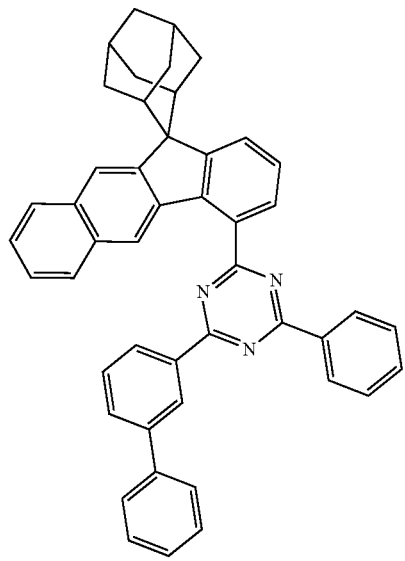
A-106
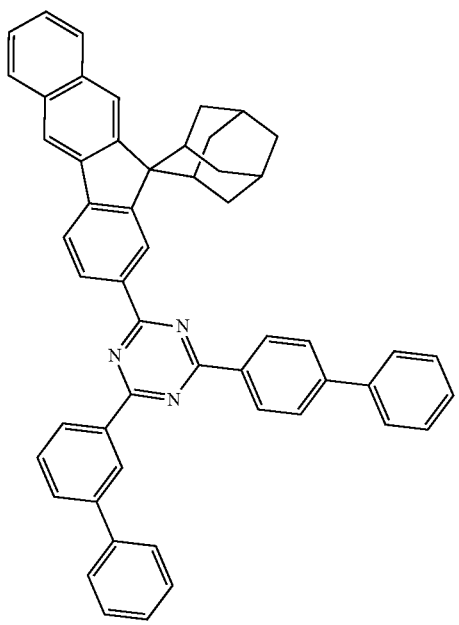
A-107
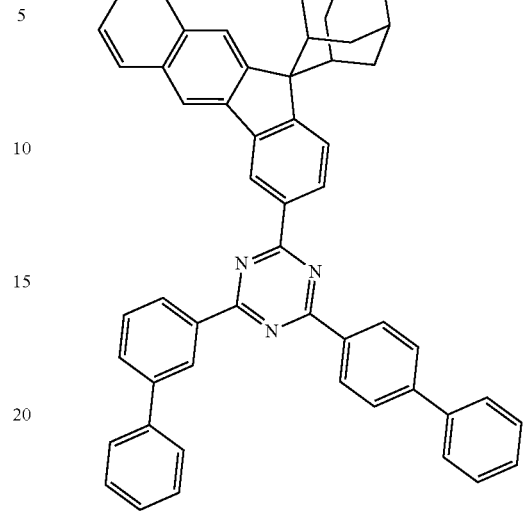
A-108
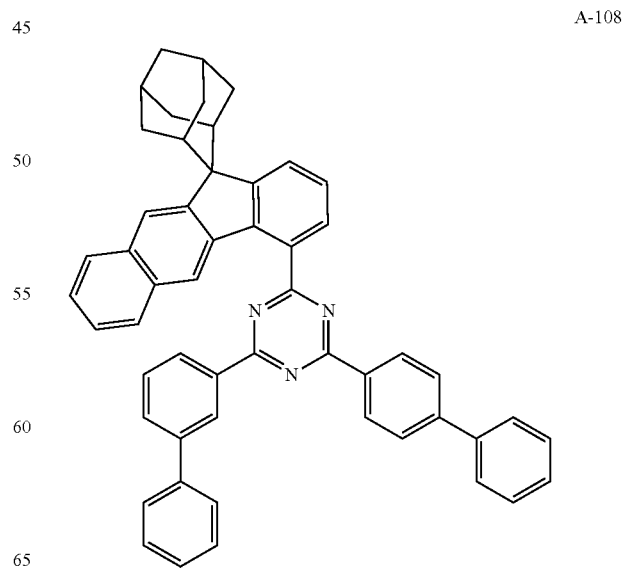

A-109
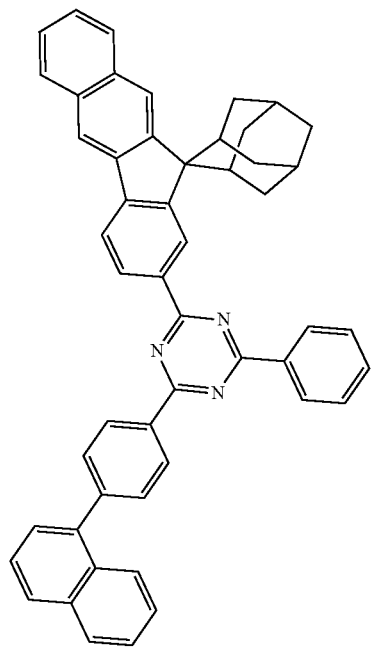
A-110
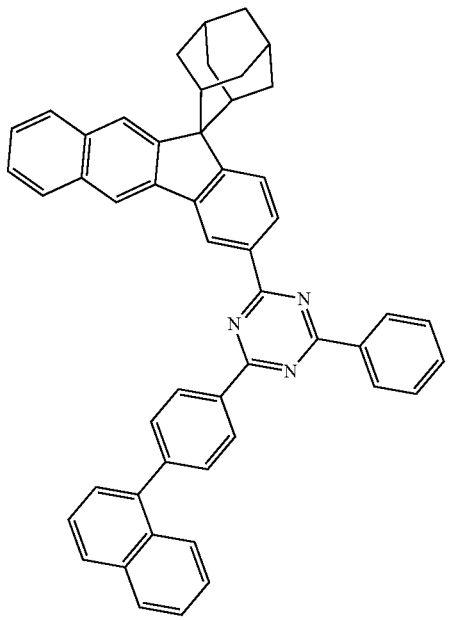
A-111
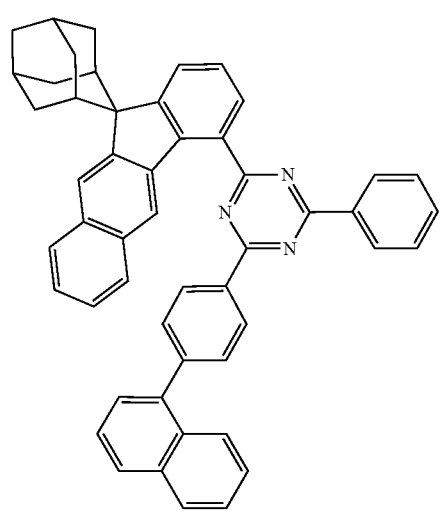
A-112
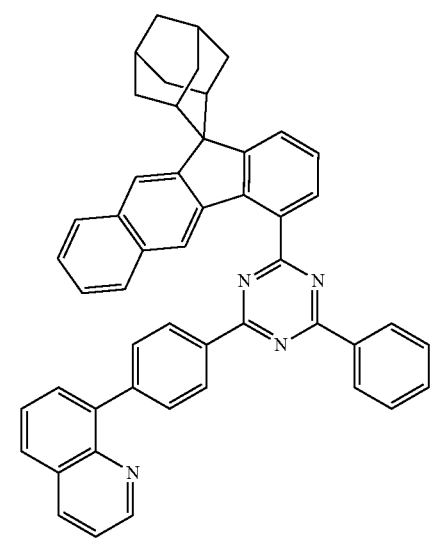
A-113
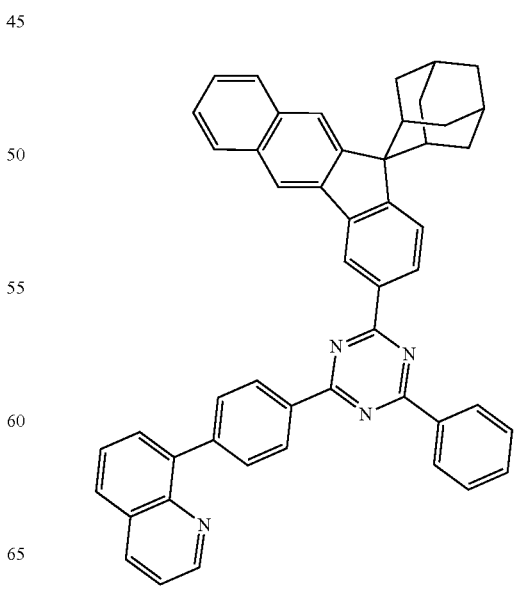

A-114
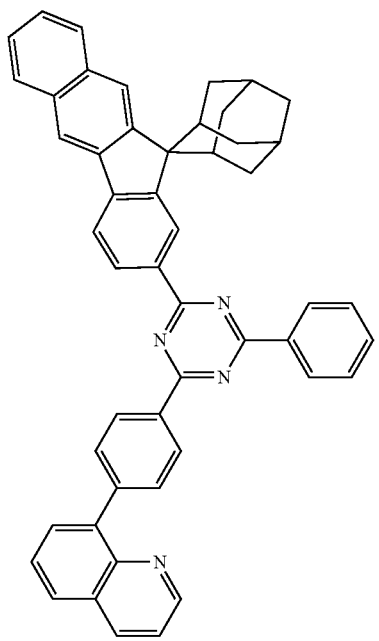
A-115
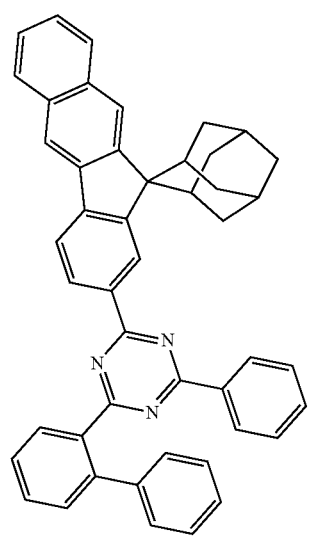
A-116
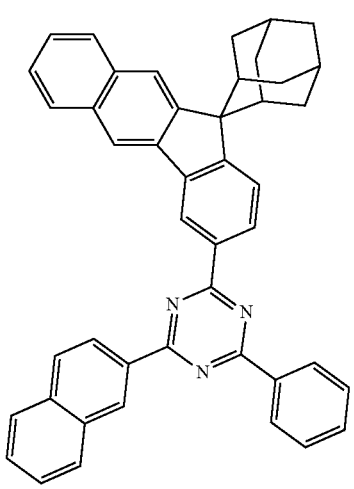
A-117
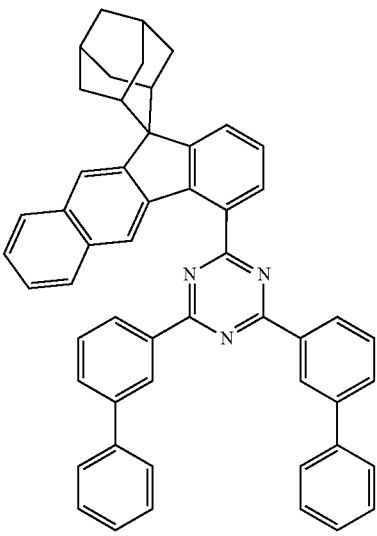
A-118
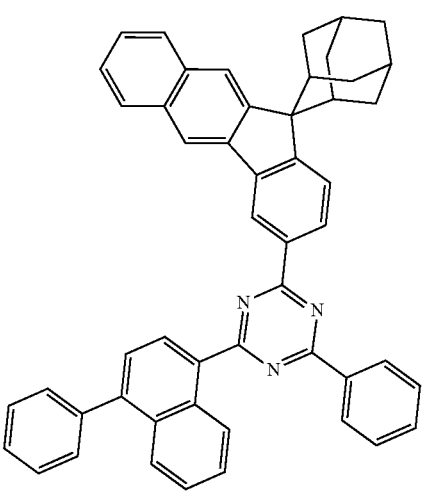
A-119
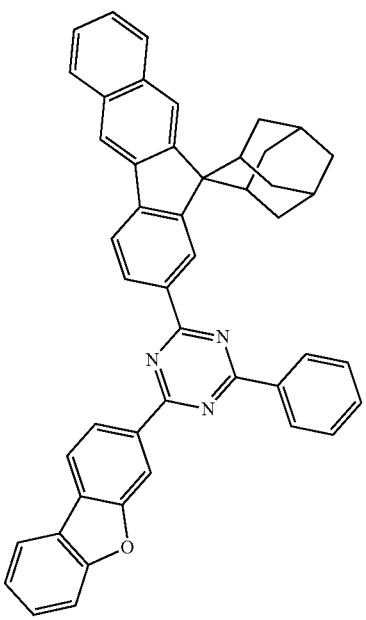

A-120
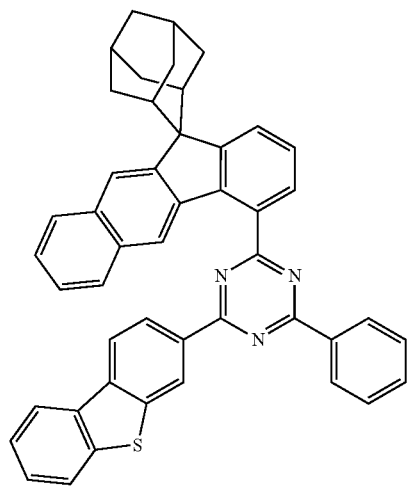
A-121
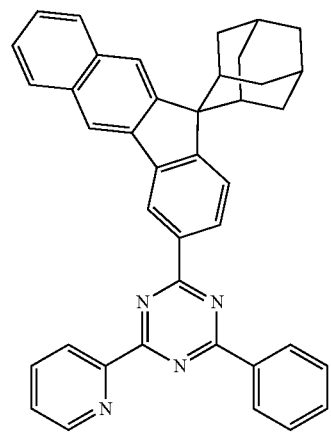
A-122
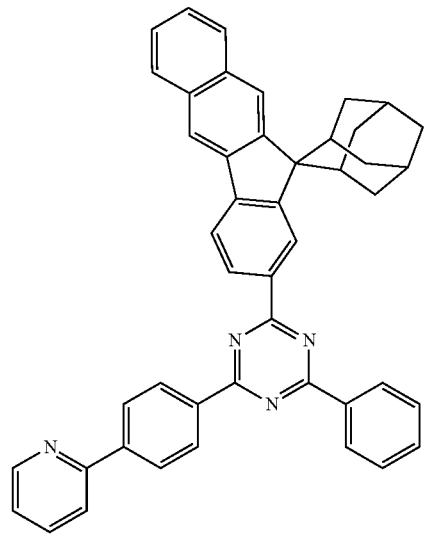
A-123
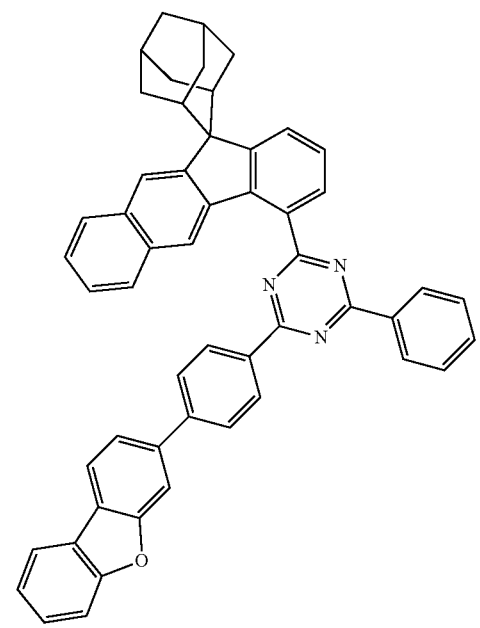
A-124
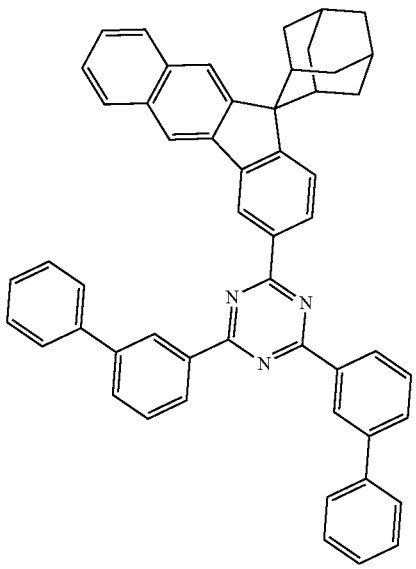

A-125
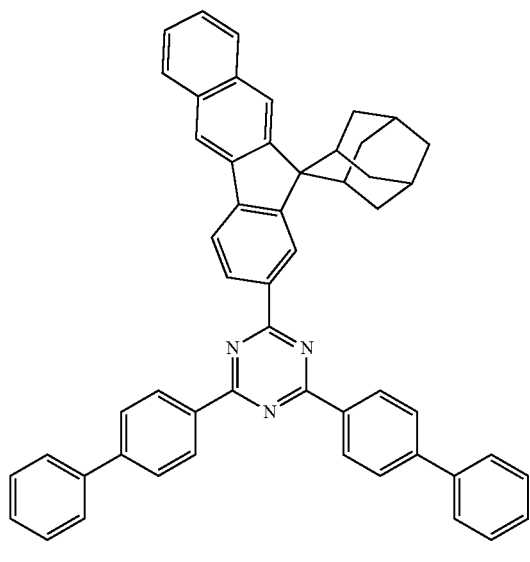
A-126
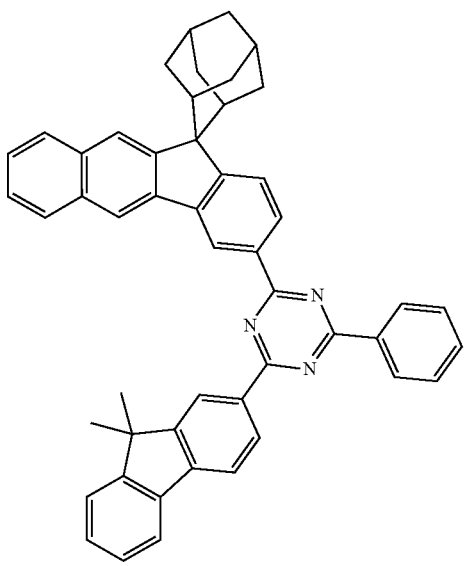
A-127
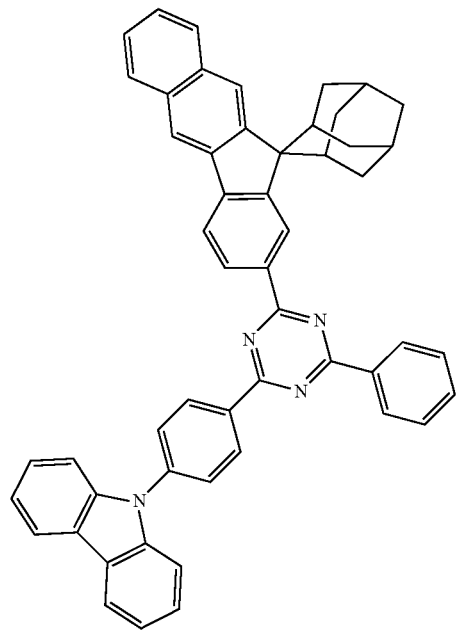
A-128
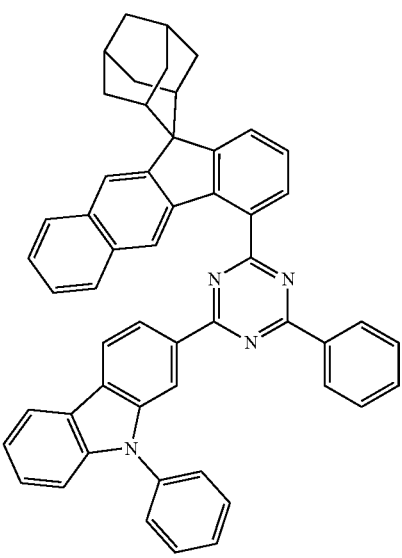

-continued
129
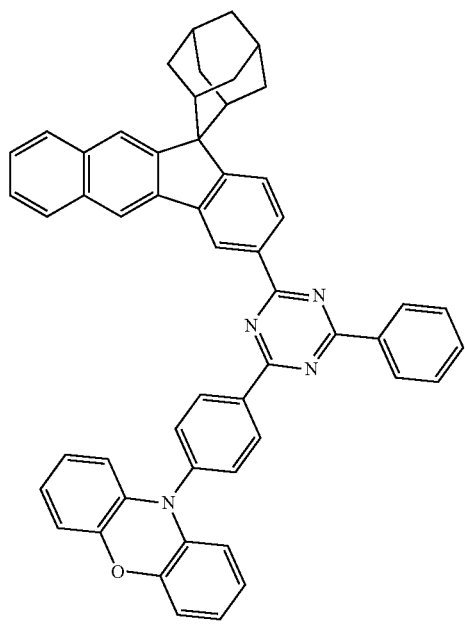
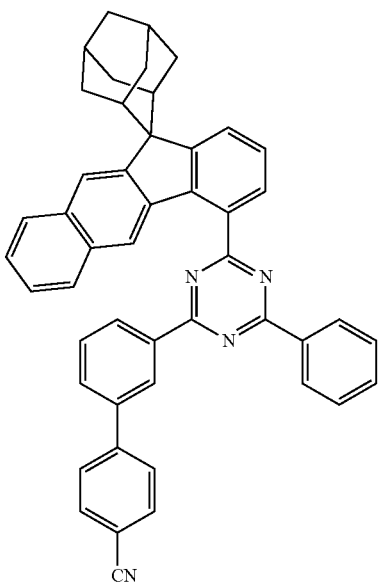
A-131
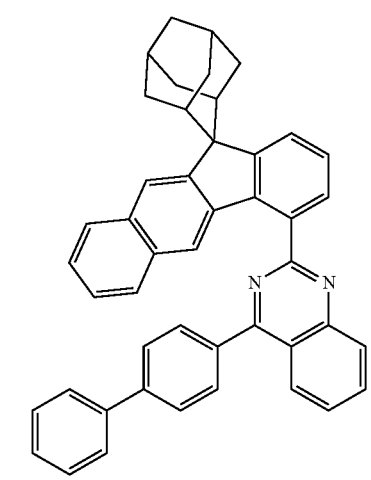
A-132
130
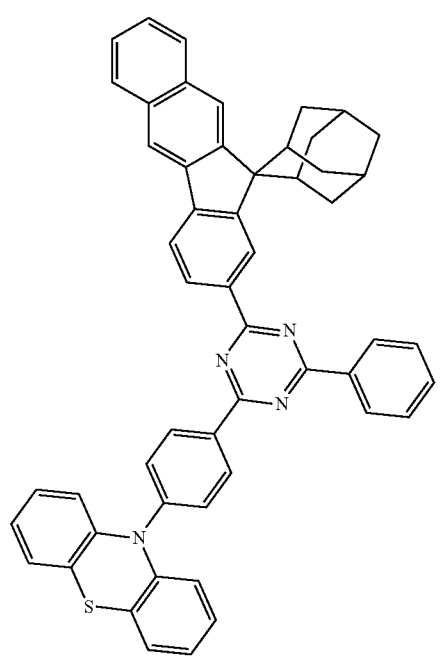
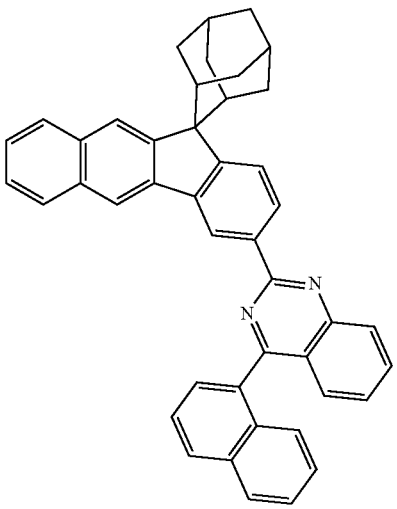
A-133

A-134
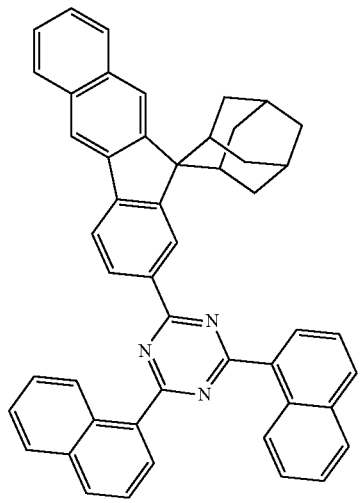
A-135
A-136
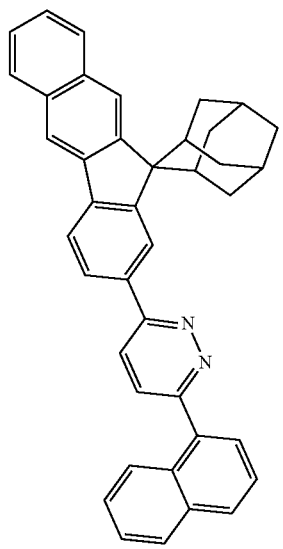
A-137
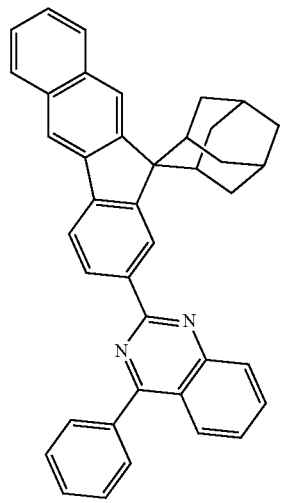
A-138
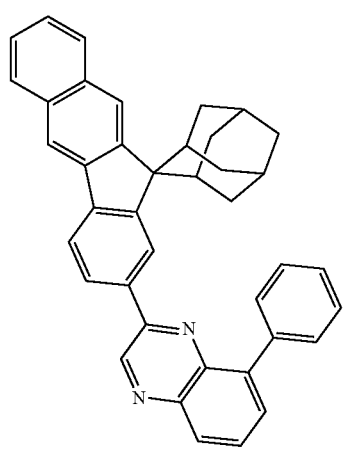
A-139
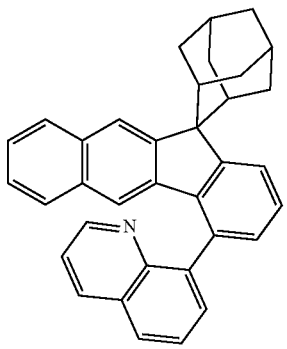

A-140
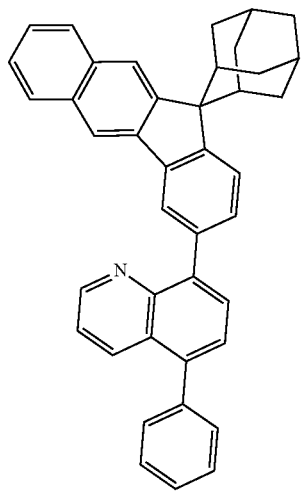
A-143
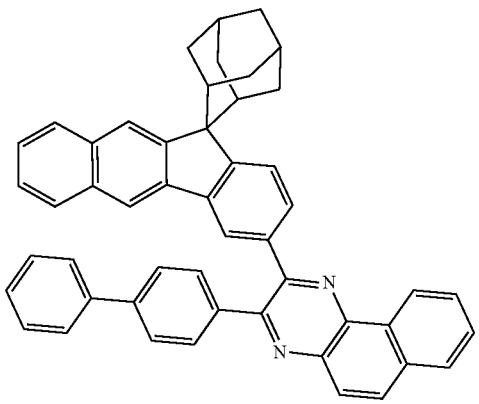
A-141
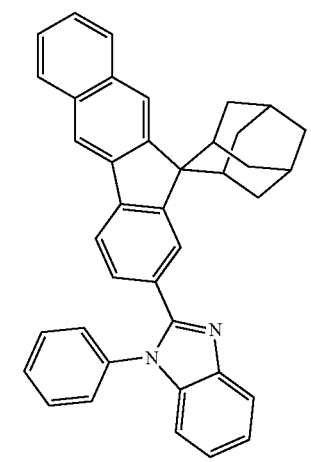
A-144
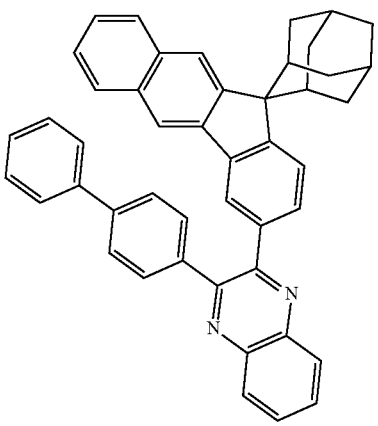
A-142
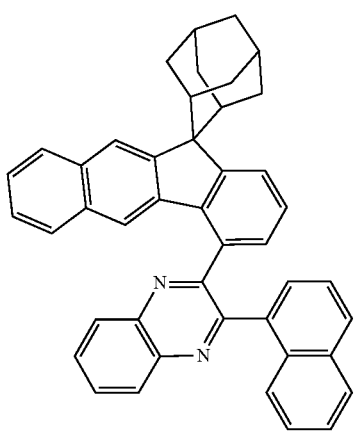
A-145
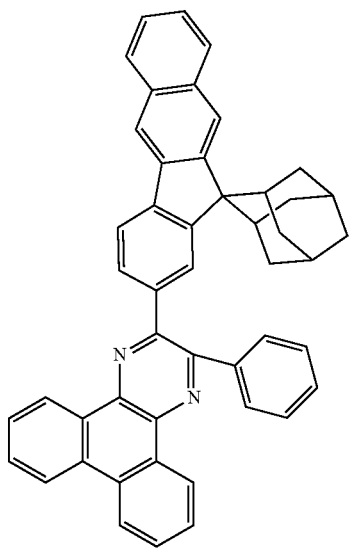

A-146
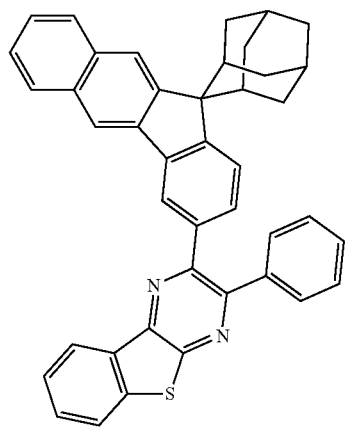
A-147
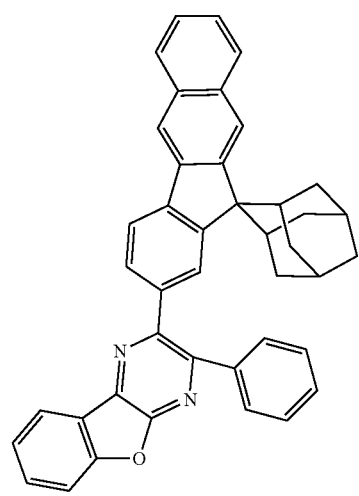
A-148
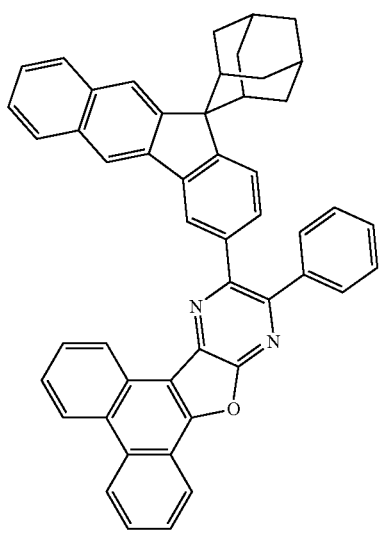
A-149
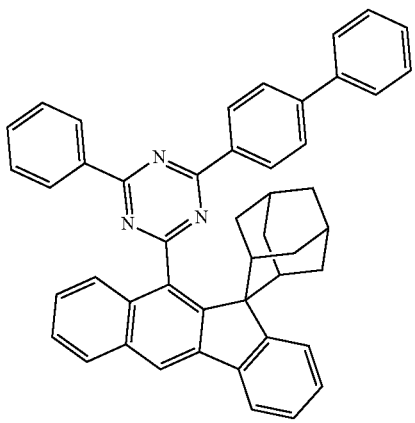
A-150
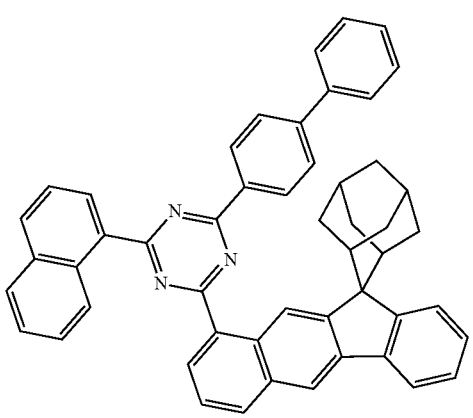
A-151
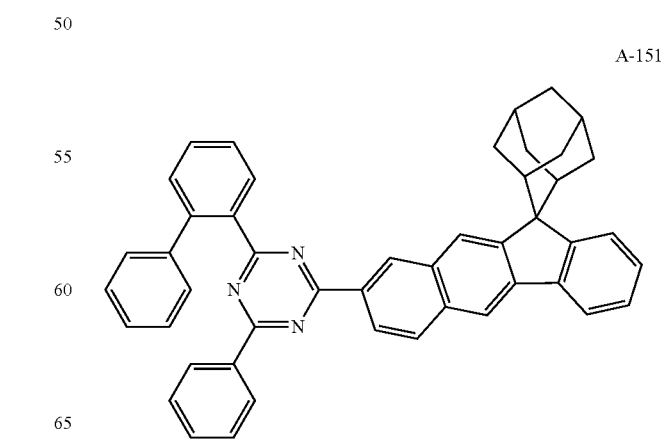

A-152
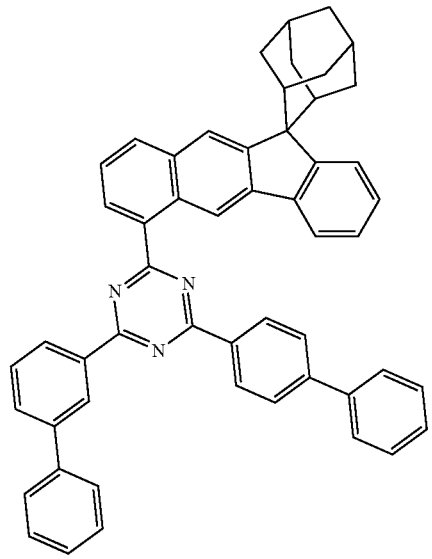
A-153
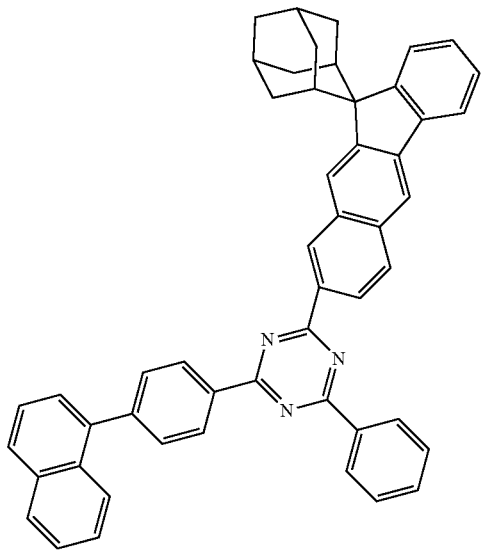
A-154
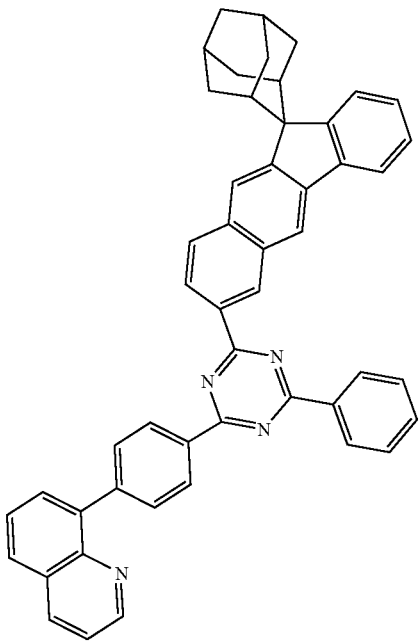
A-155
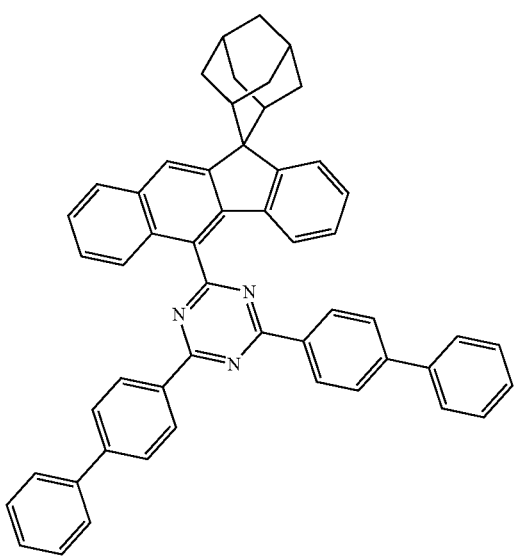

A-156
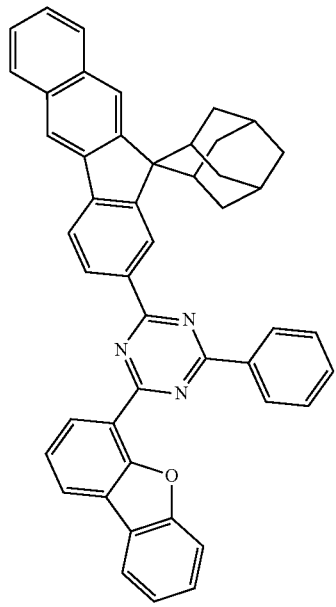
A-158
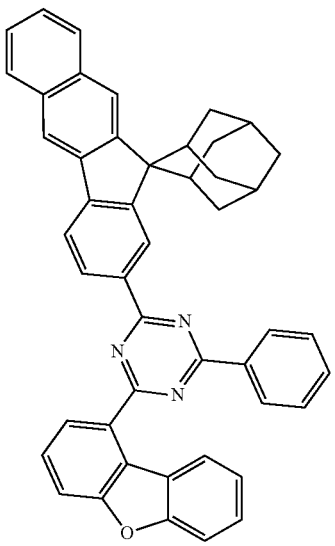
A-157
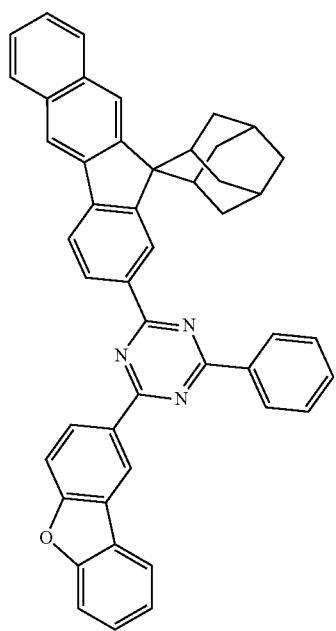
A-159
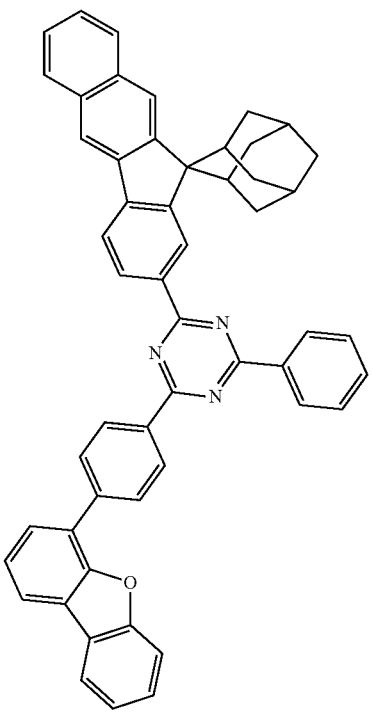

A-160
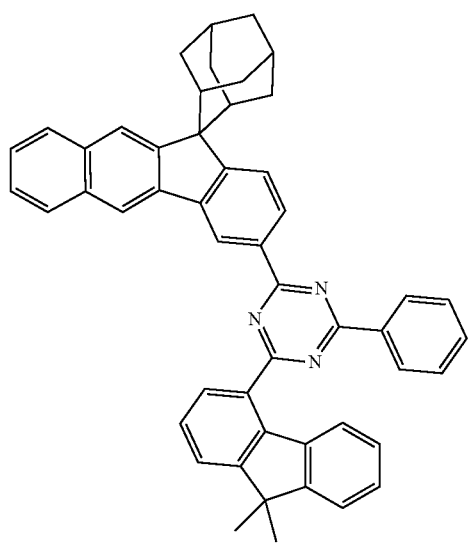
A-161
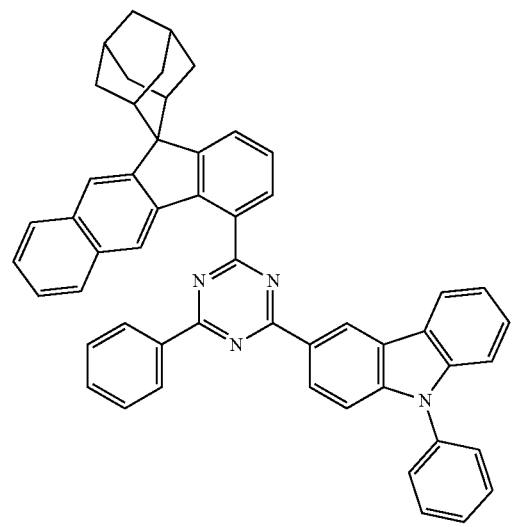
A-162
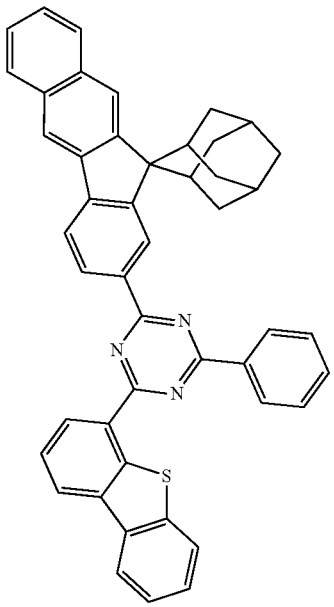
A-163
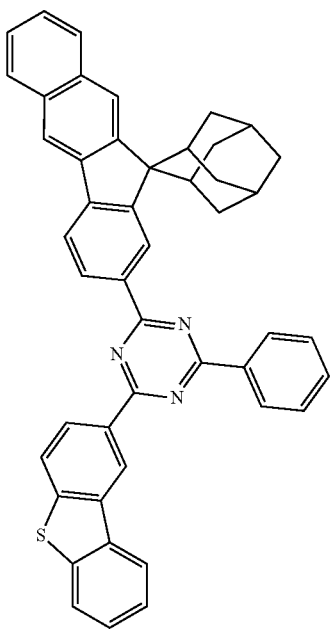

A-164
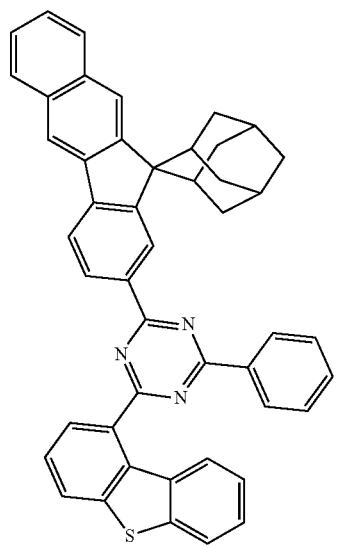
A-165
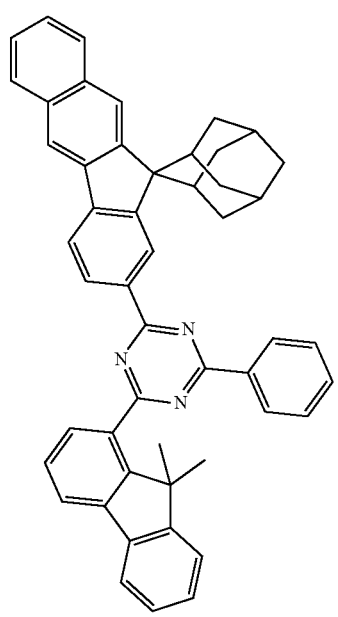
A-166
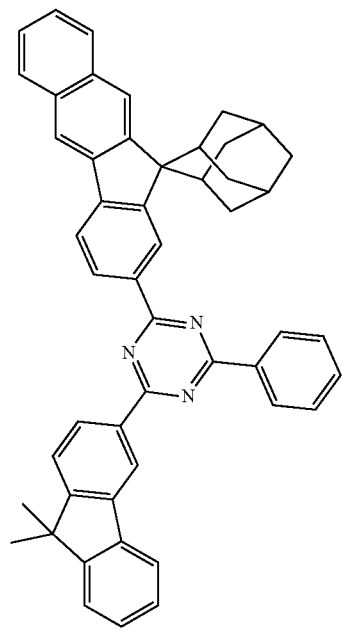
A-167
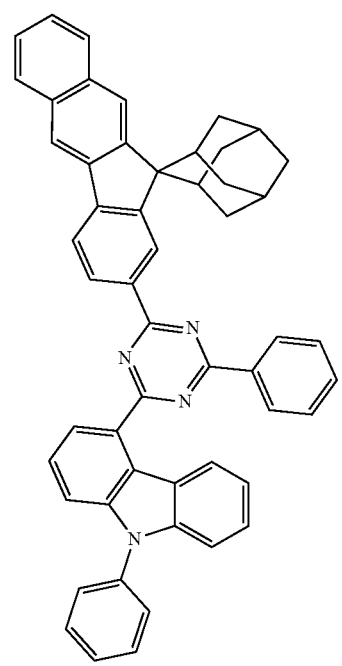

A-168
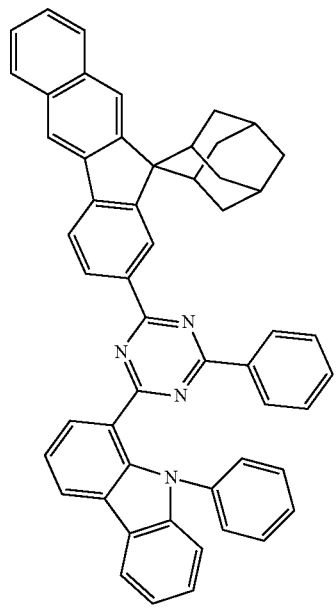
A-169
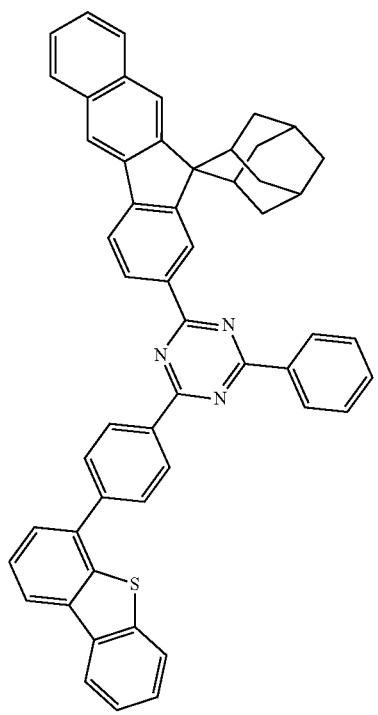
A-172
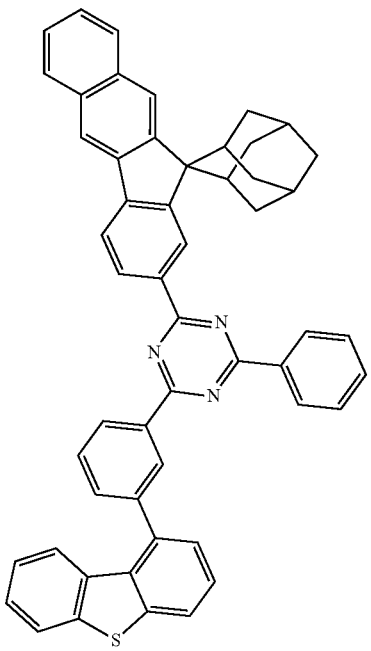
A-173
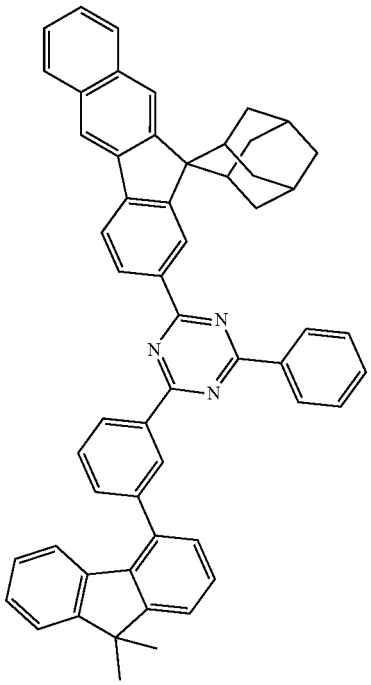

-continued
A-174
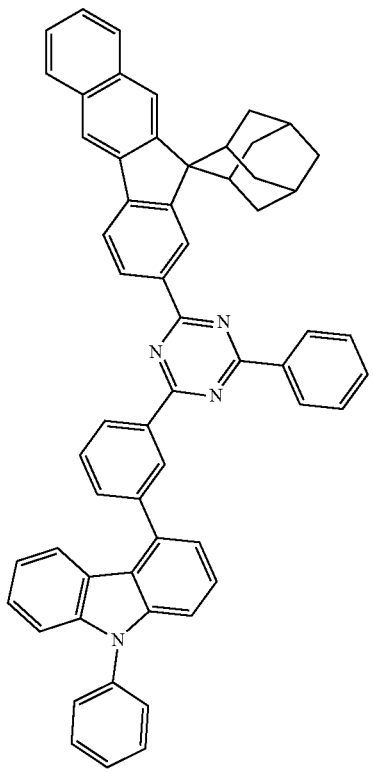
A-175
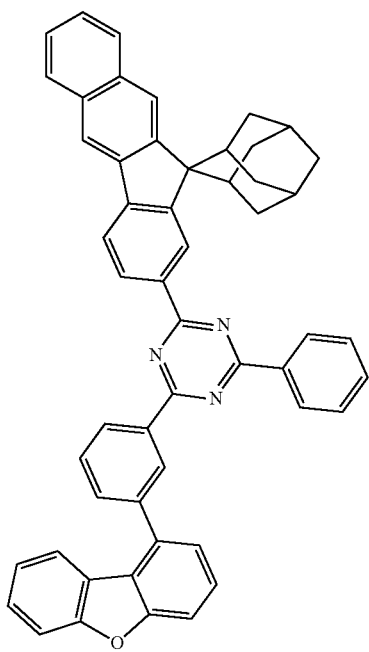
A-176
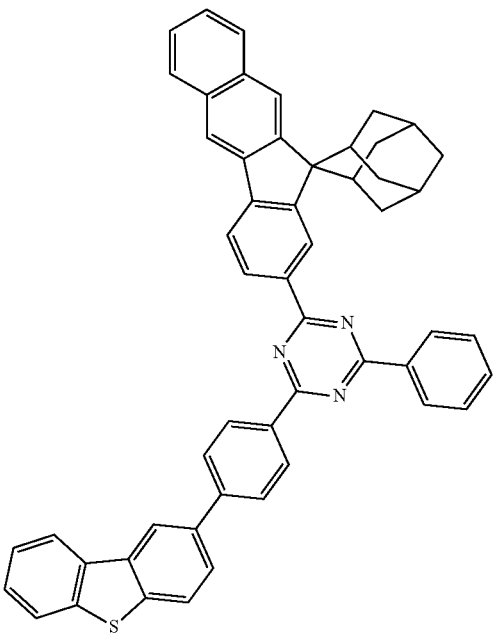
A-177
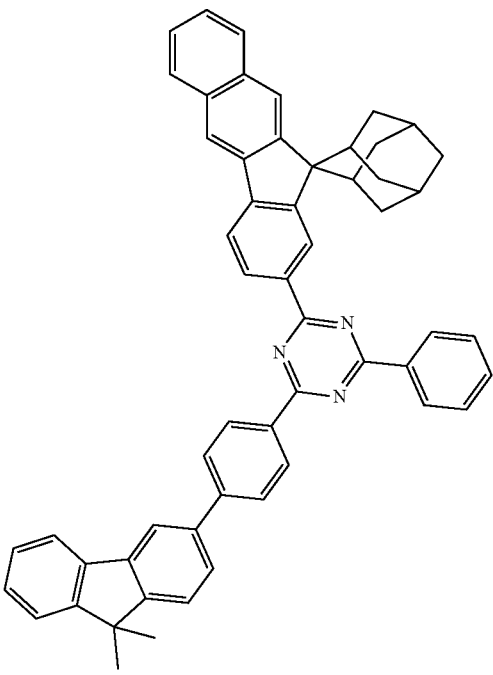

A-178
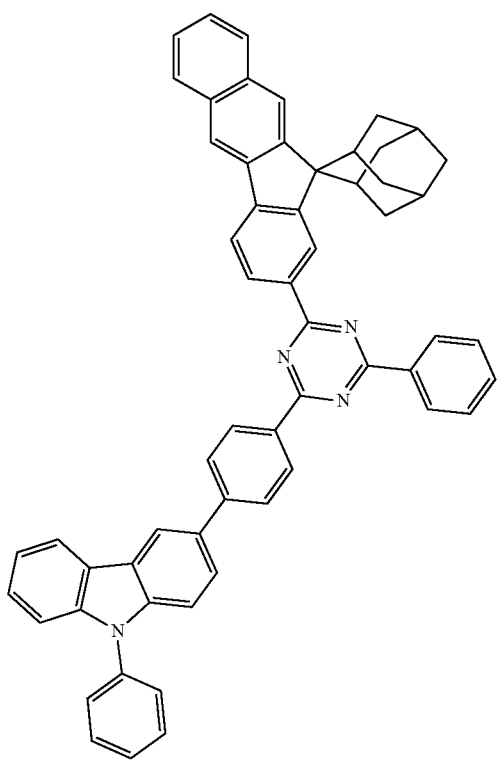
A-170
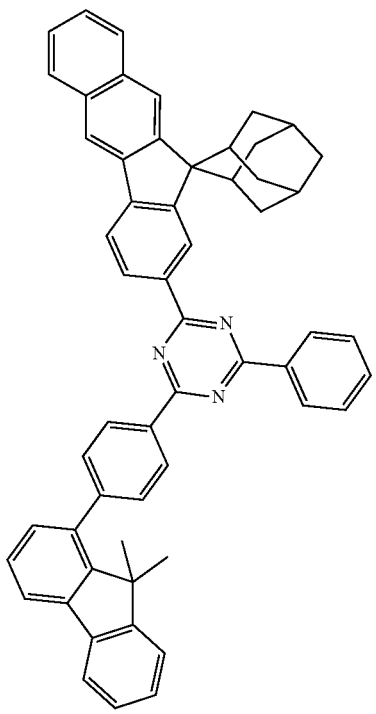
A-179
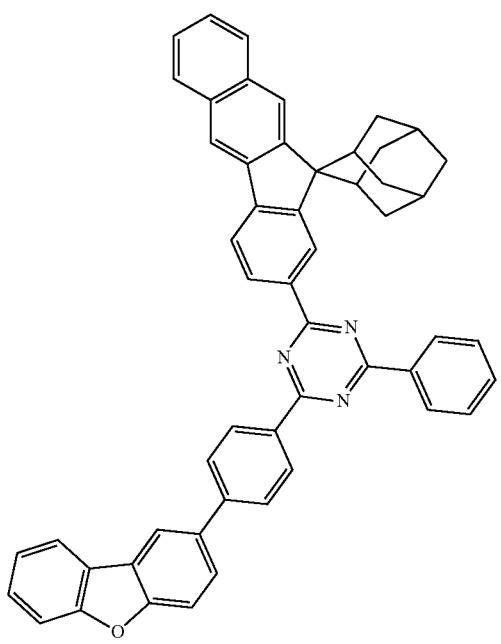
A-171
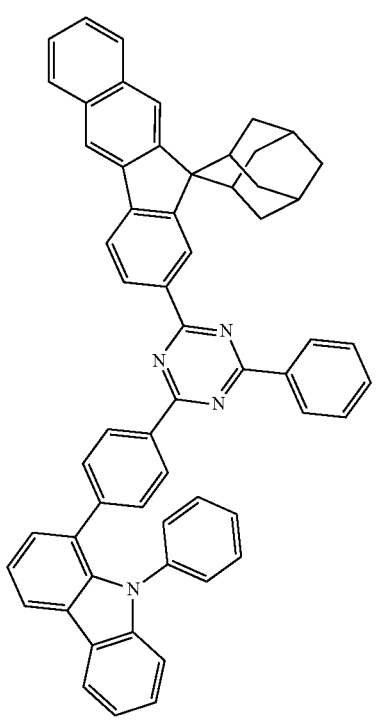

A-180
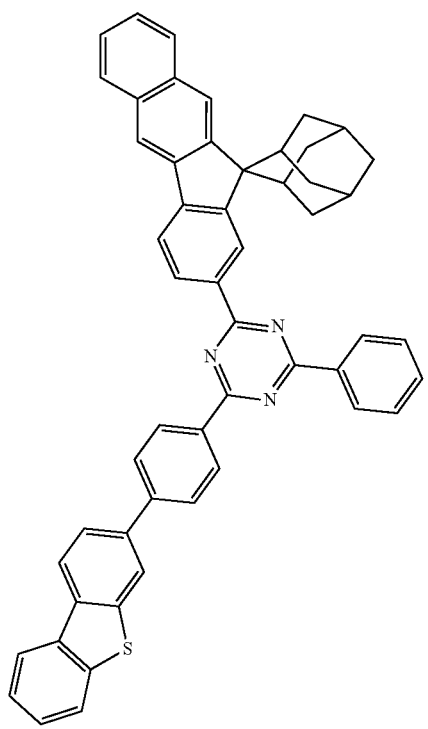
A-182
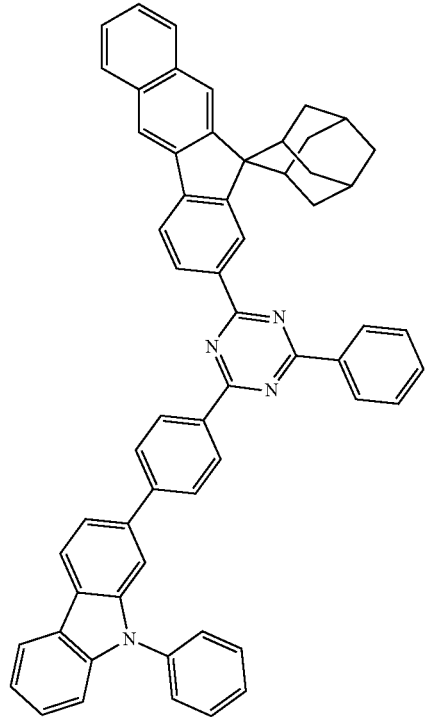
A-181
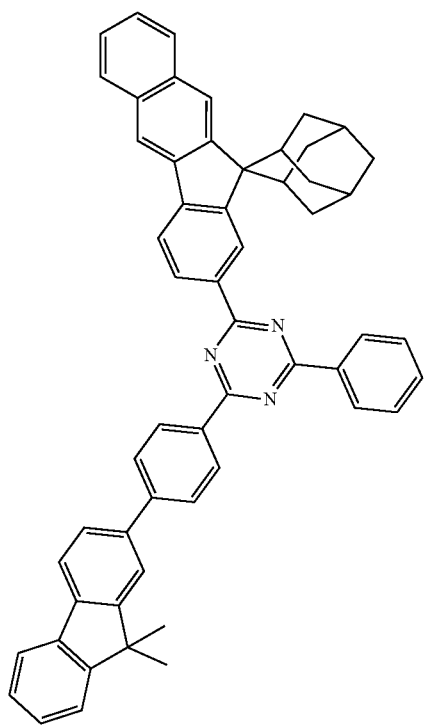
A-183
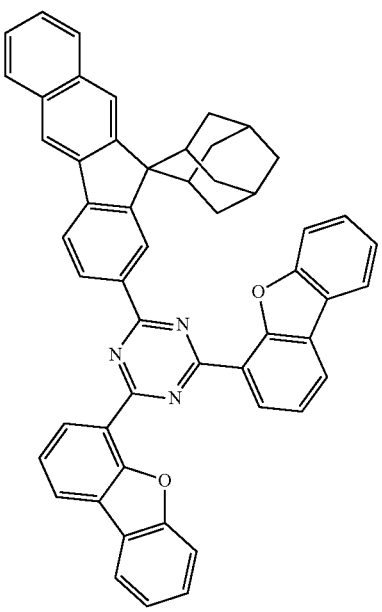

A-184
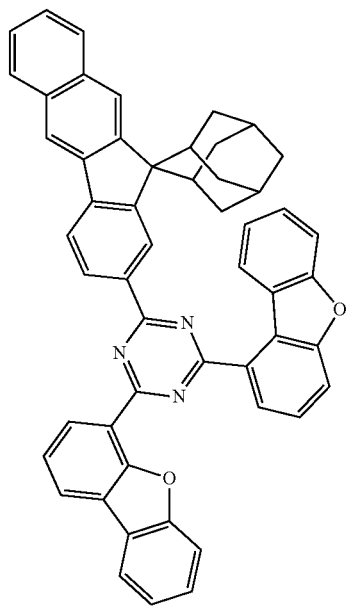
A-190
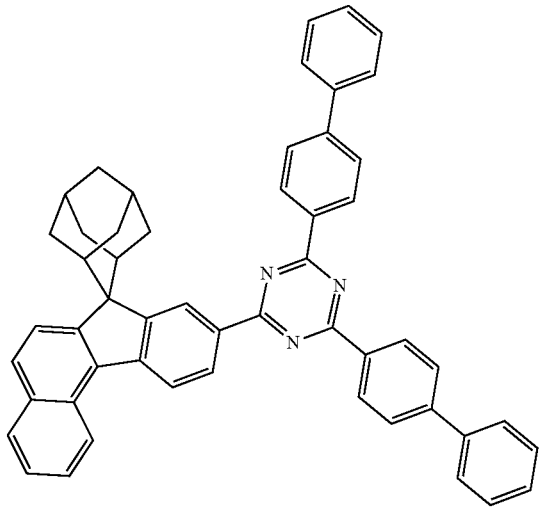
A-191
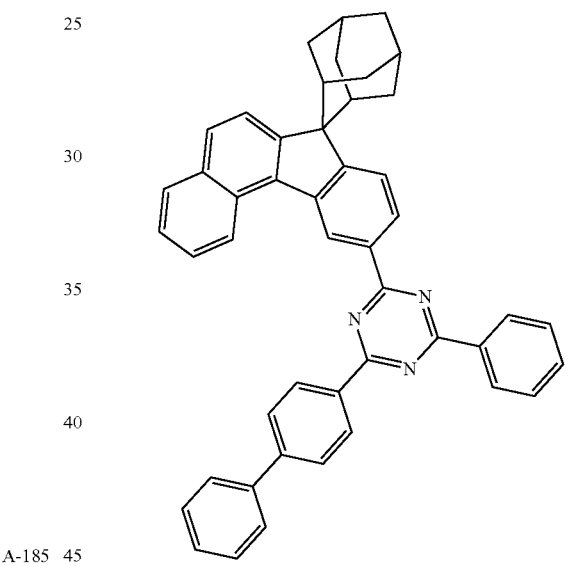
A-185
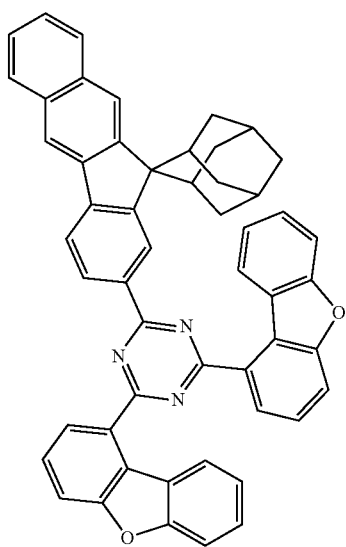
A-192
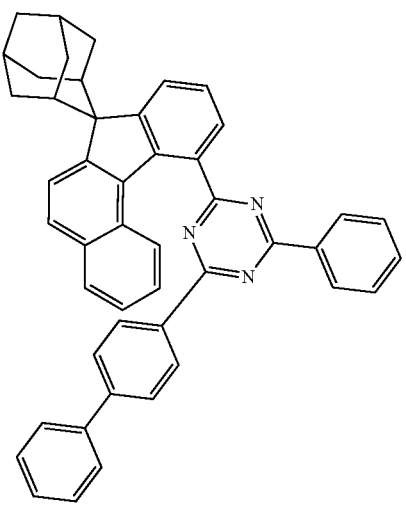

A-193
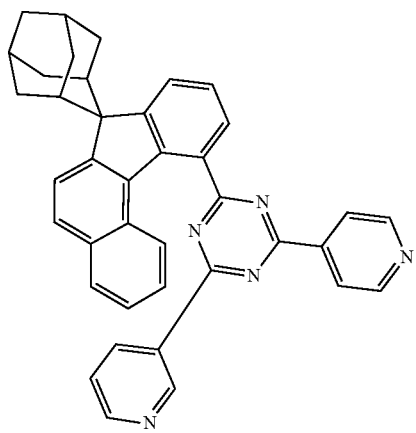
A-194
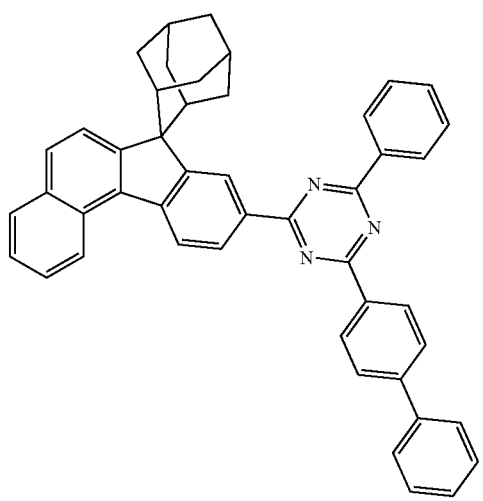
A-195
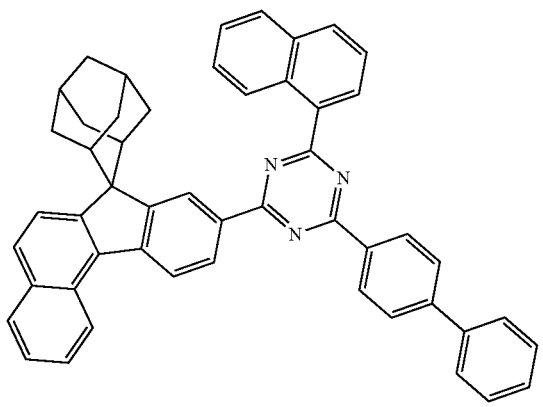
A-196
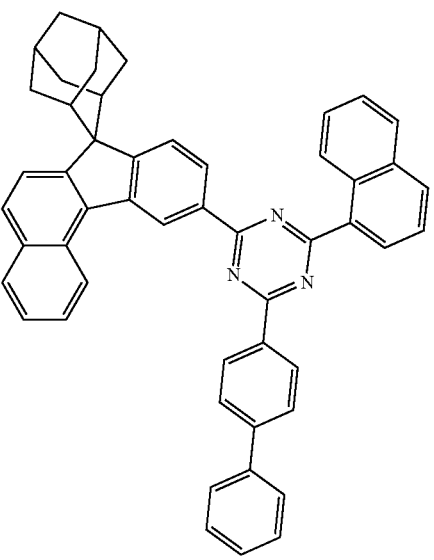
A-197
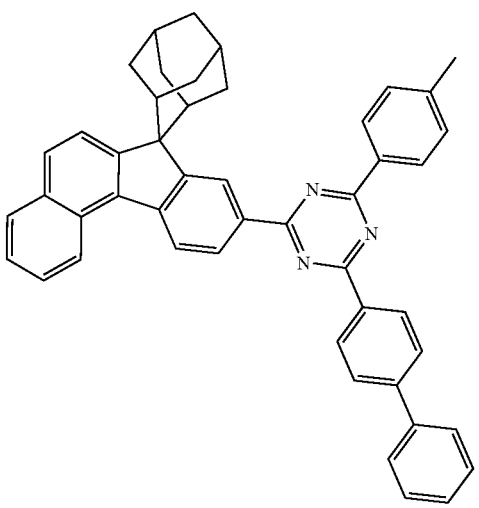
A-198
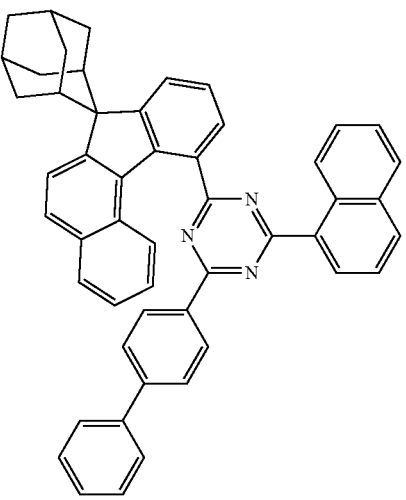

A-199
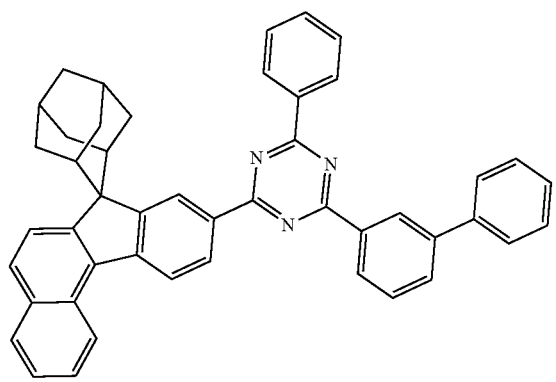
A-200
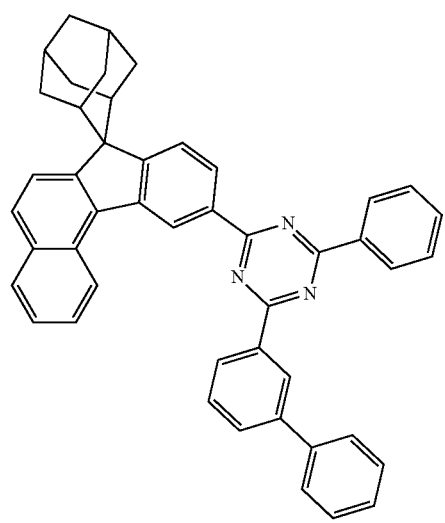
A-201
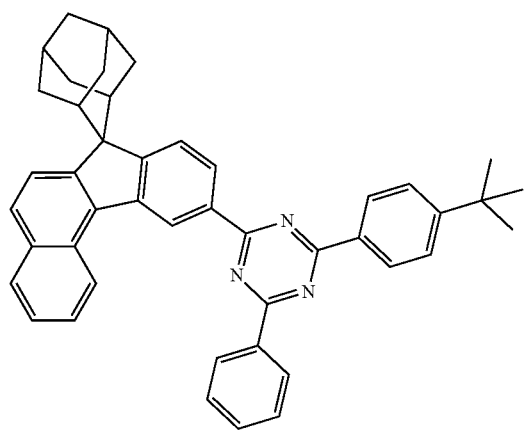
A-187
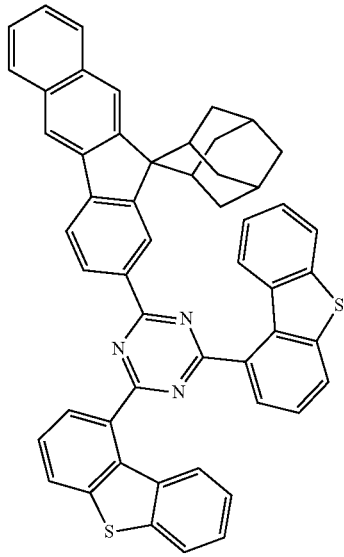
A-188
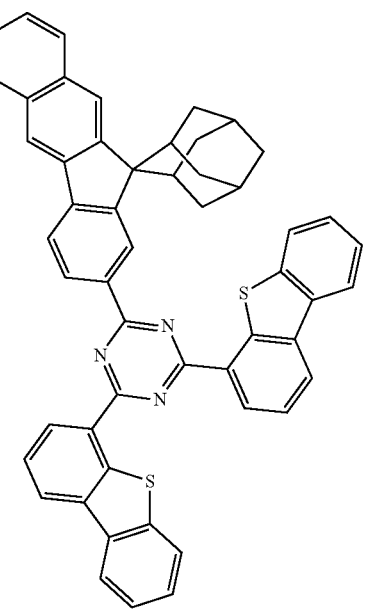

A-189
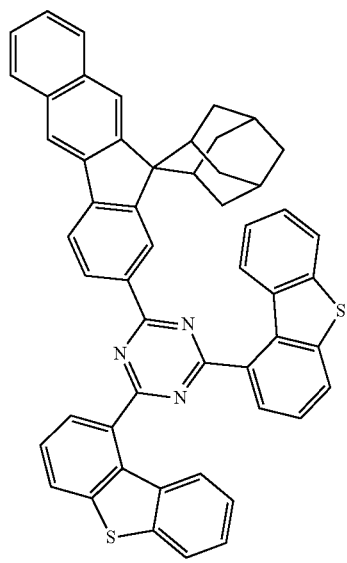
A-202
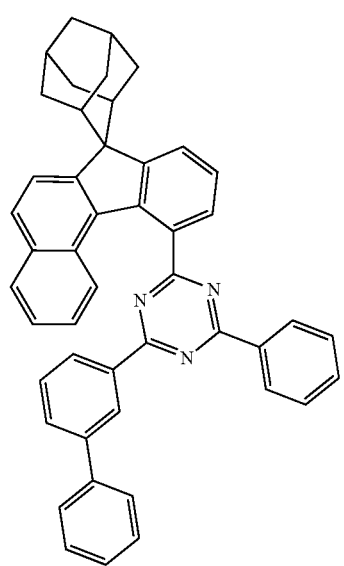
A-203
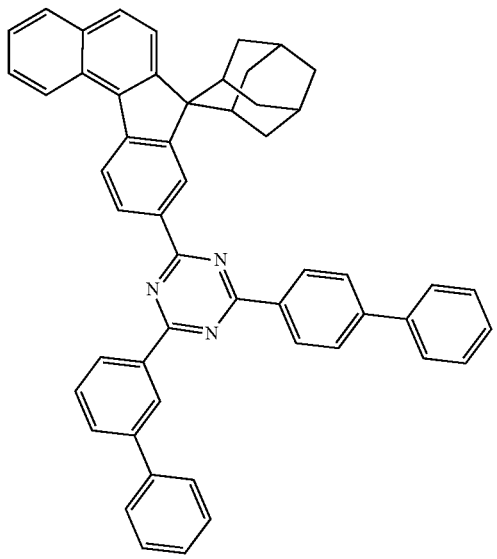
A-204
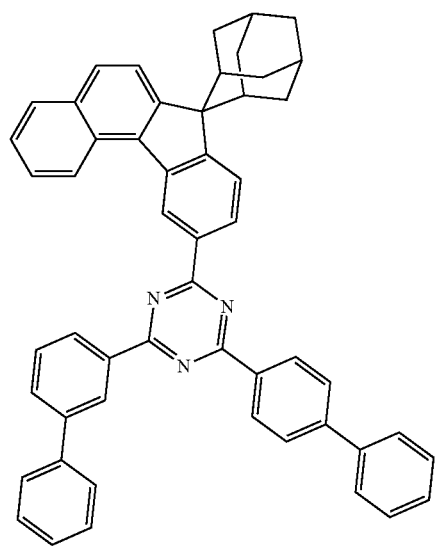
A-205
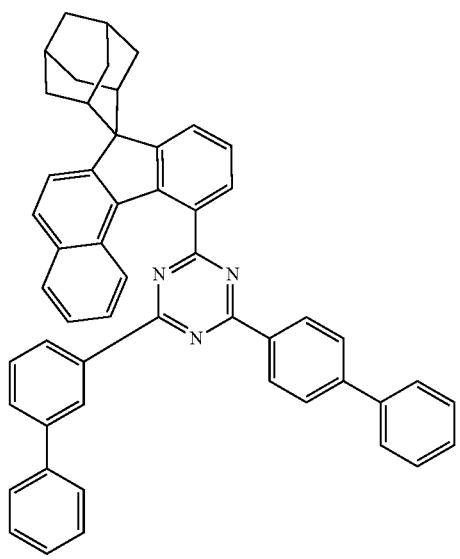

A-206
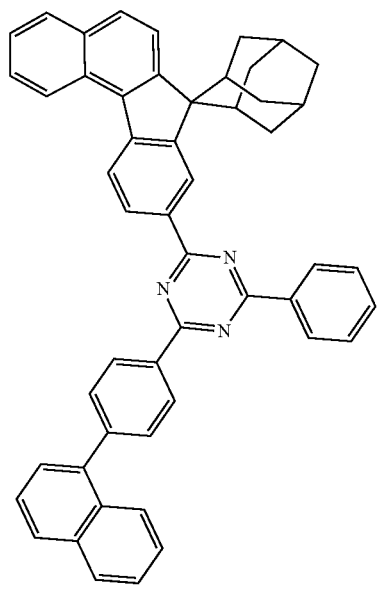
A-207
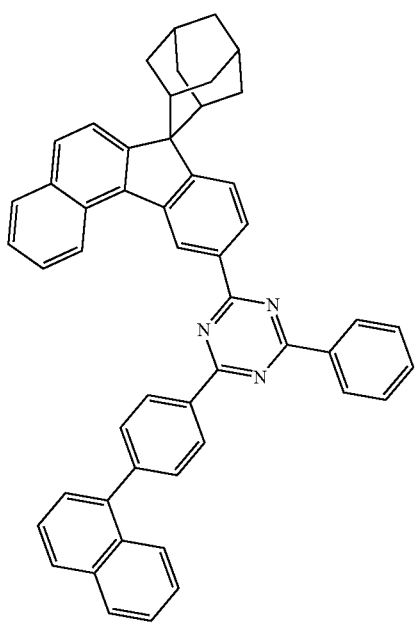
A-208
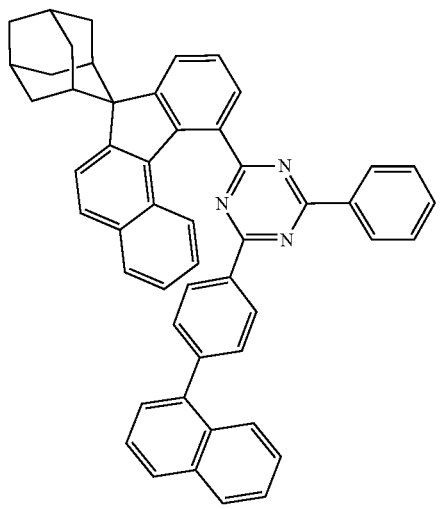
A-209
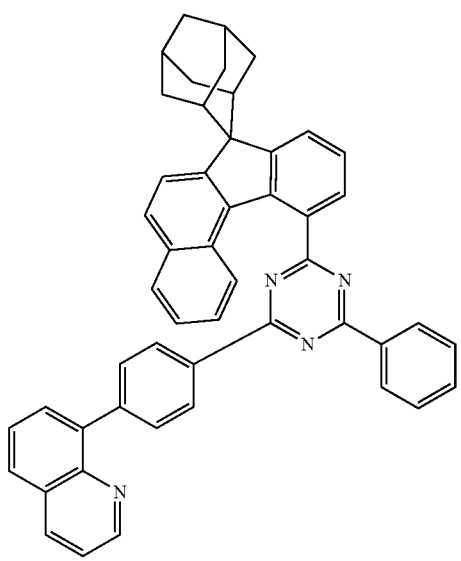
A-210
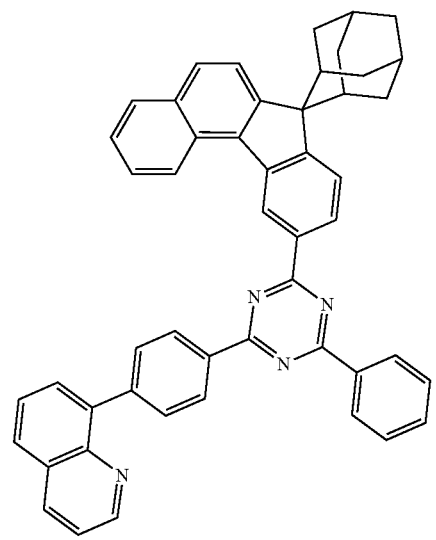

A-211
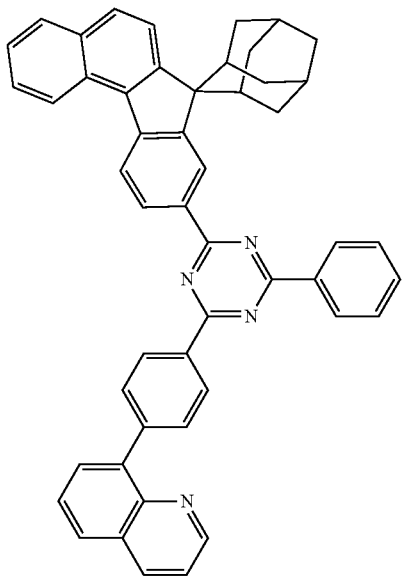
A-212
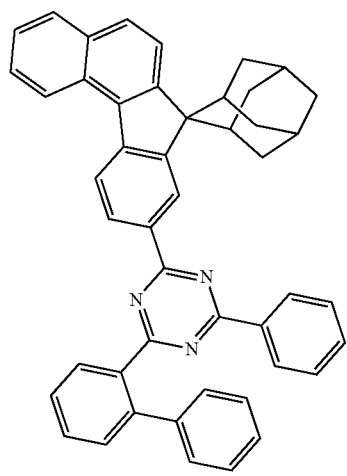
A-213
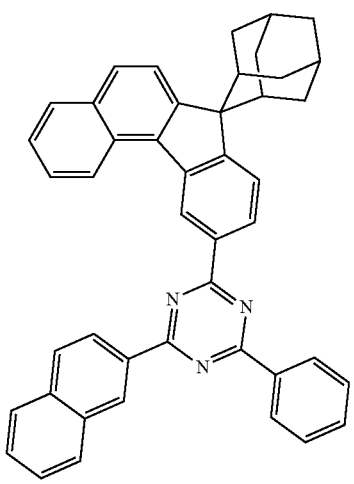
A-214
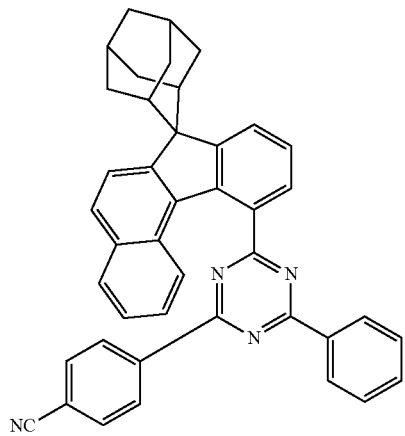
A-215
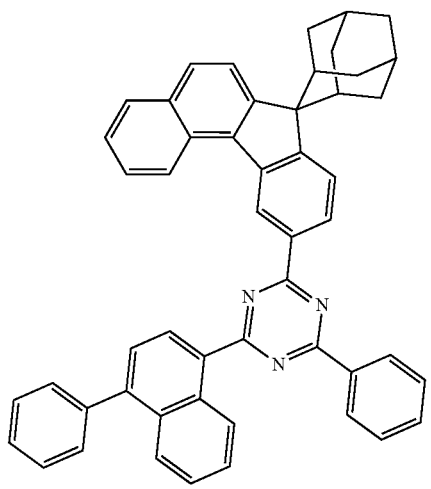
A-216
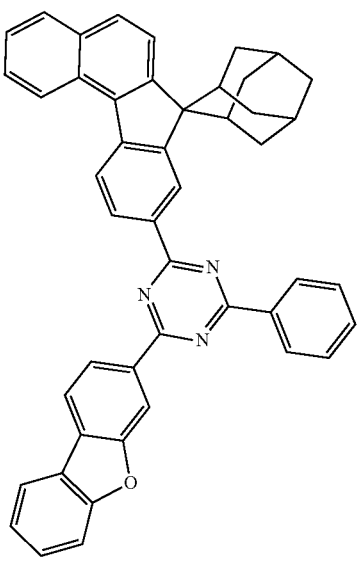

A-217
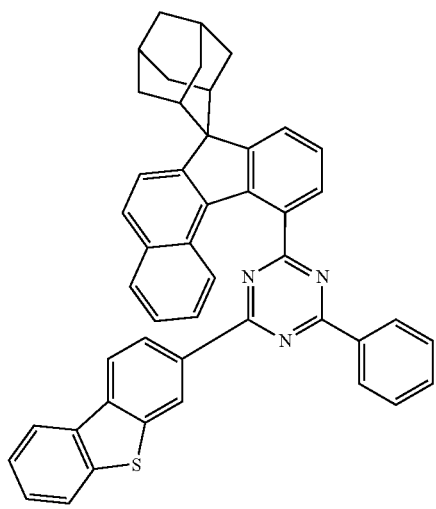
A-218
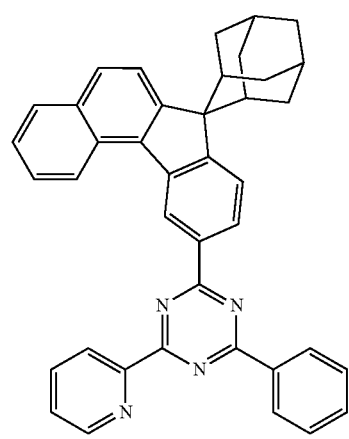
A-219
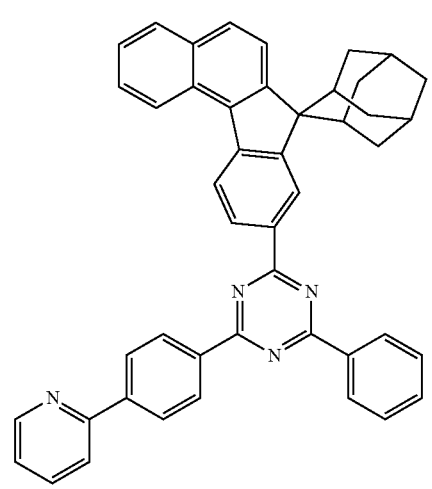
A-220
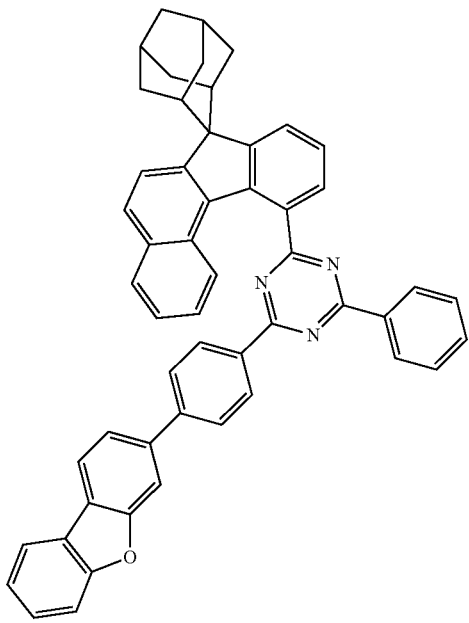
A-221
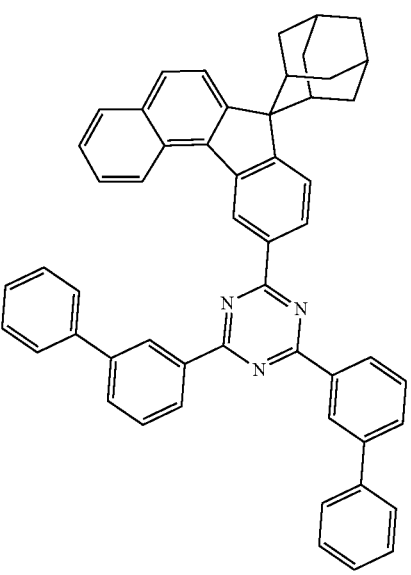

A-222
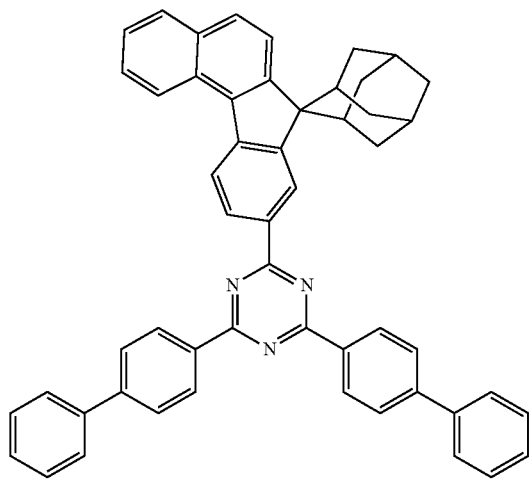
A-223
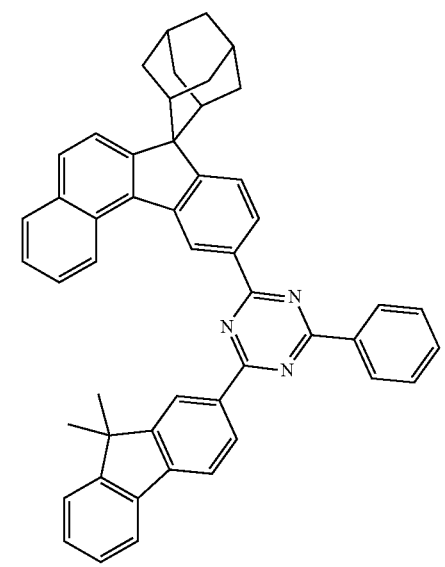
A-224
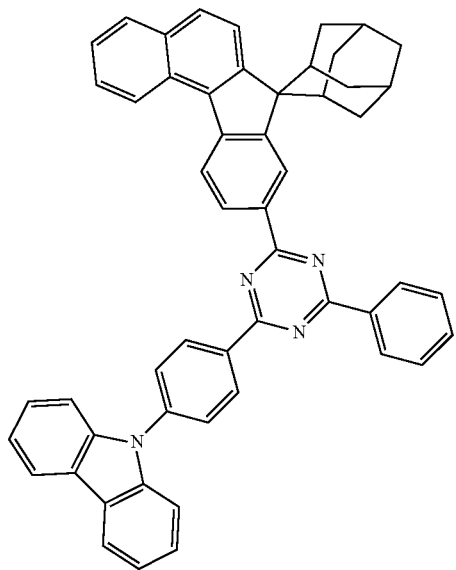
A-225
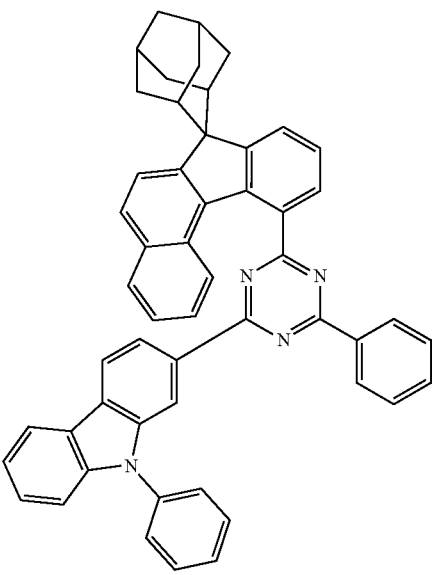
A-226
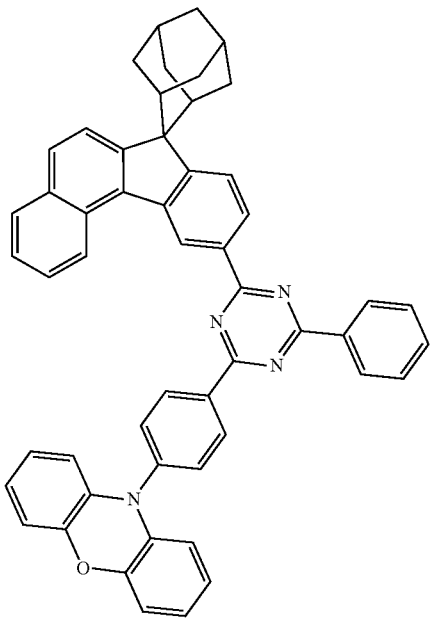

A-227

A-228

A-229

A-230

A-231

-continued
A-232
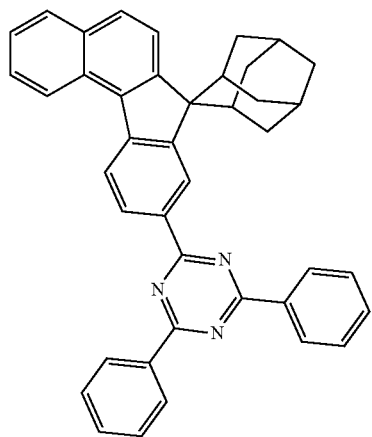
A-233
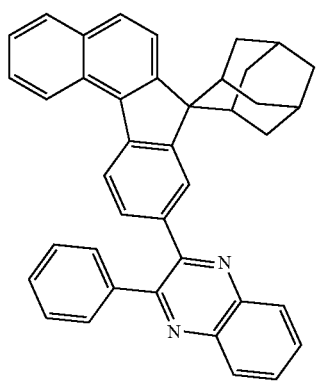
A-234
-continued
A-235
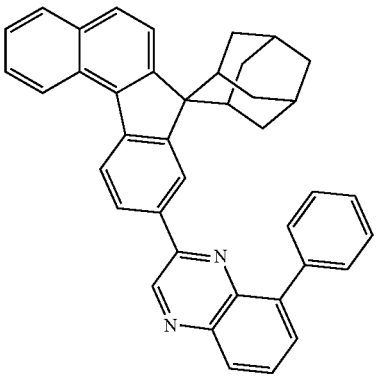
A-236
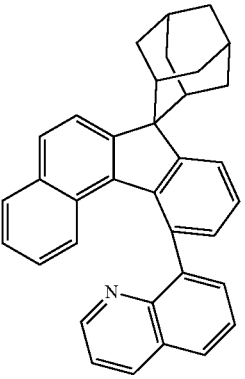
A-237
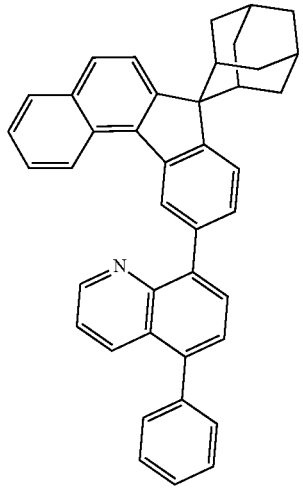
A-238
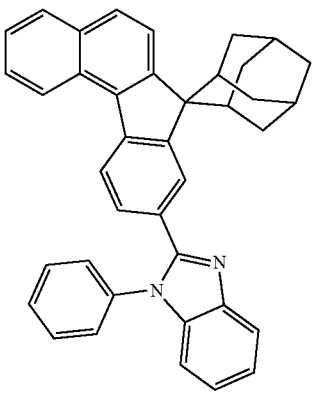

A-239
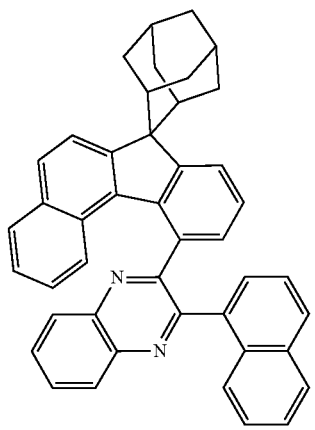
A-240
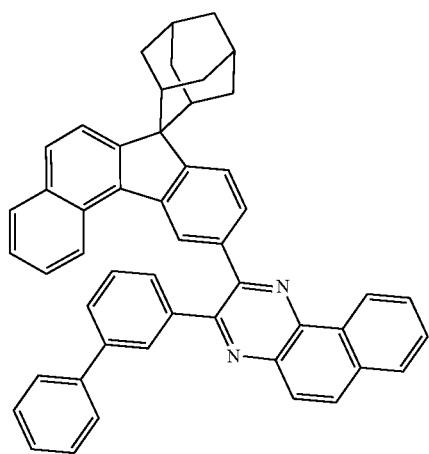
A-241
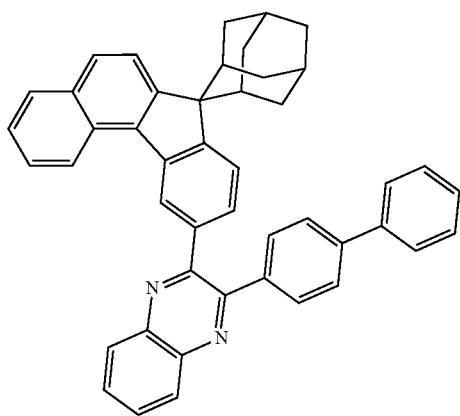
A-242
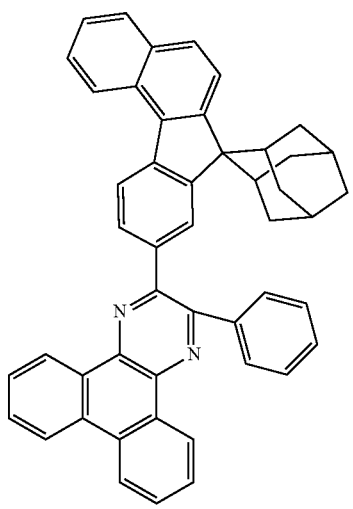
A-243
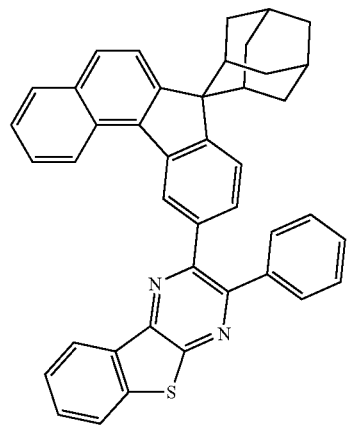
A-244
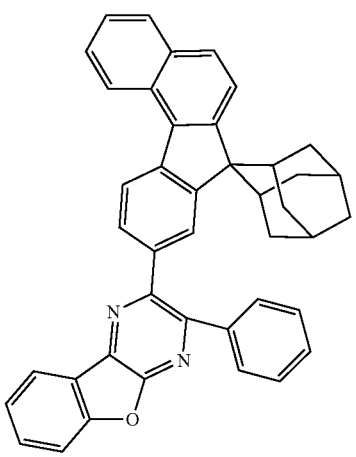

A-316
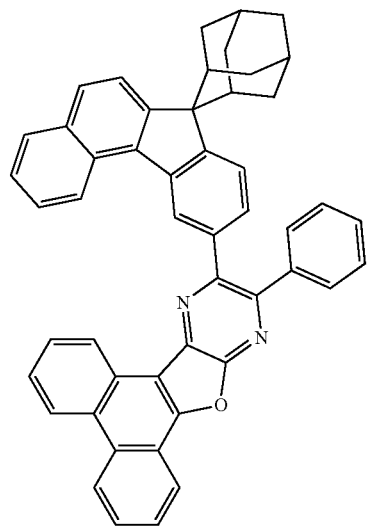
A-317
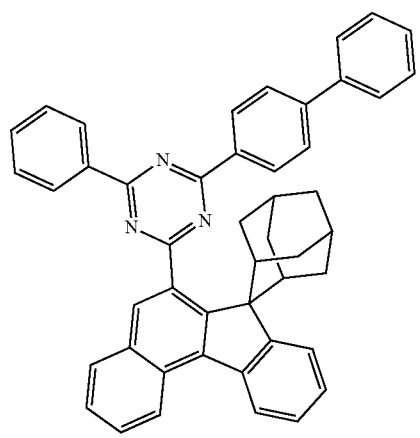
A-248
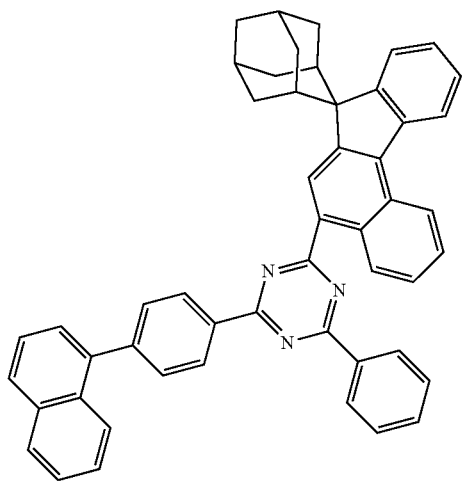
A-249
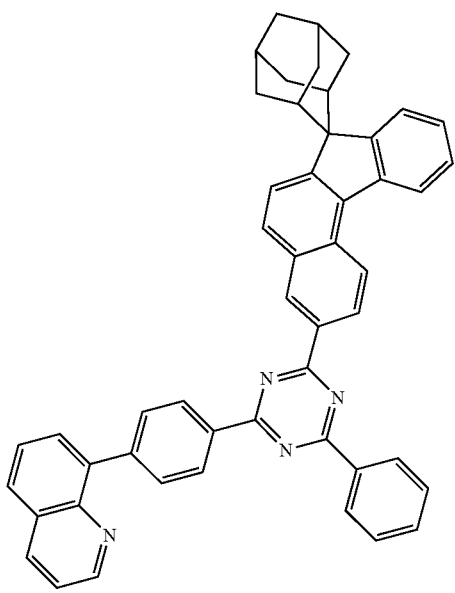
A-250
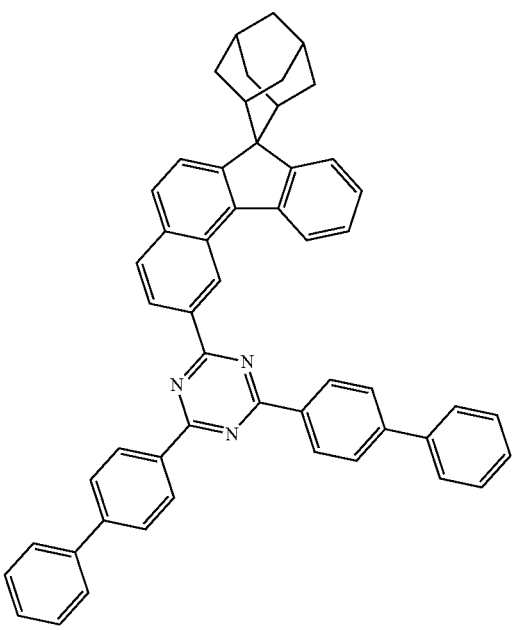

A-245
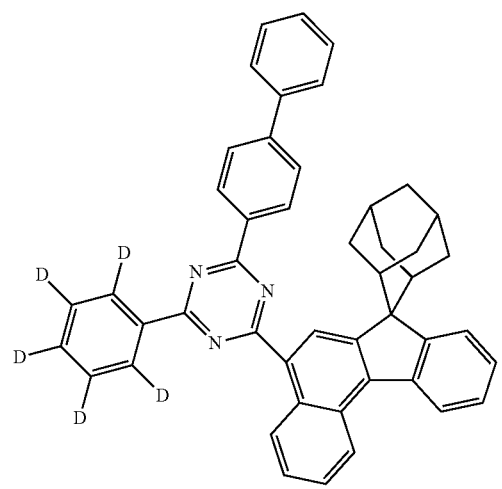
A-246
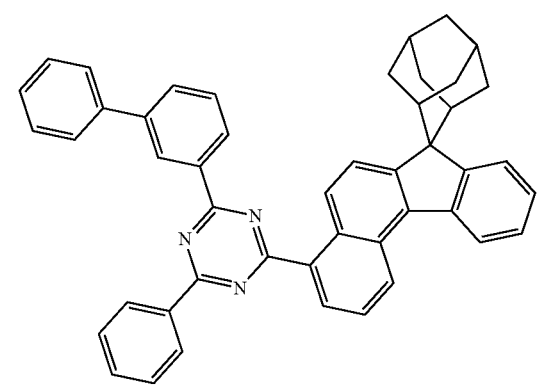
A-247
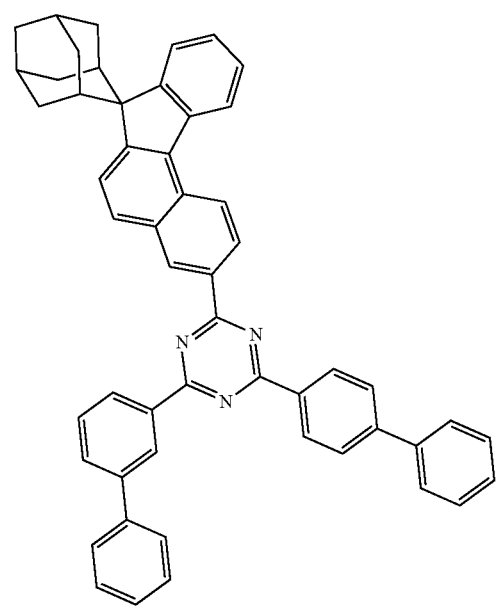
A-251
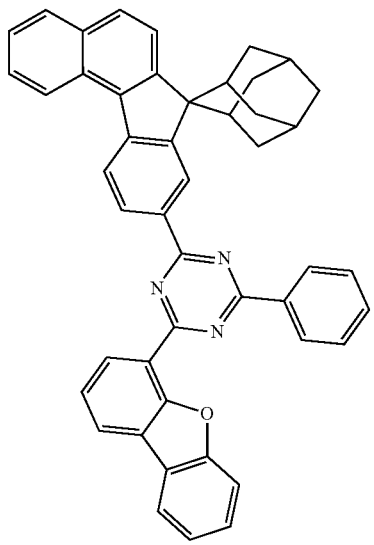
A-252
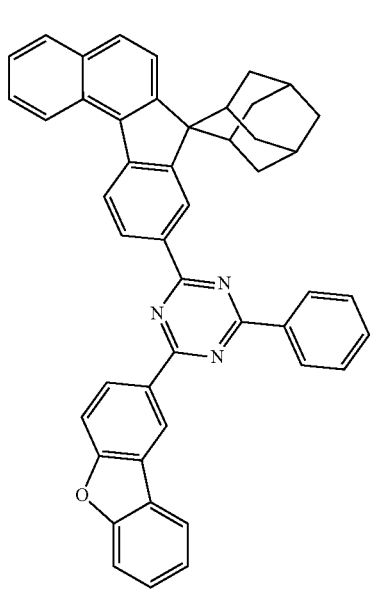
A-253
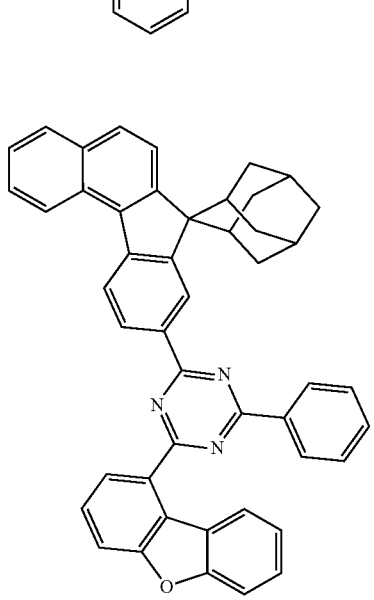

A-254
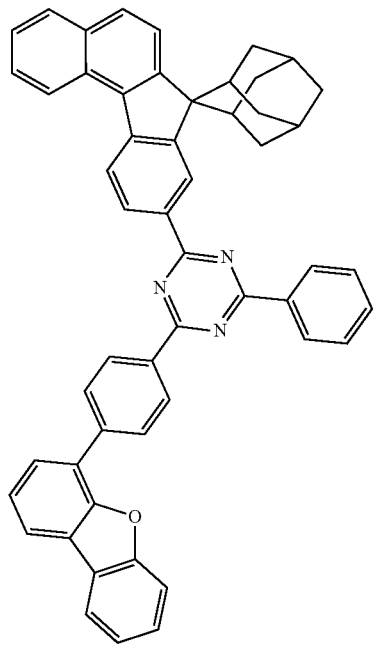
A-256
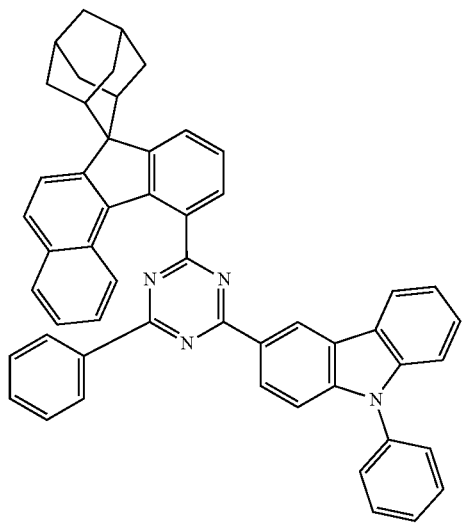
A-255
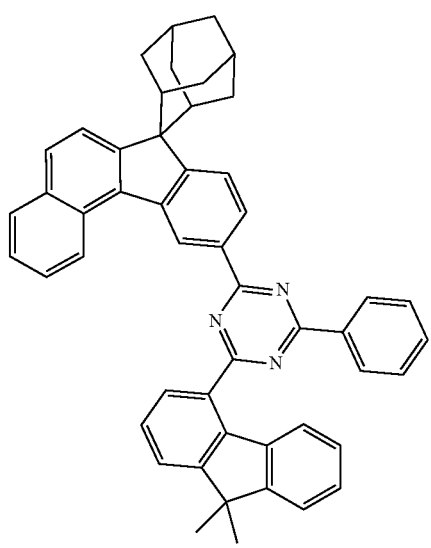
A-265
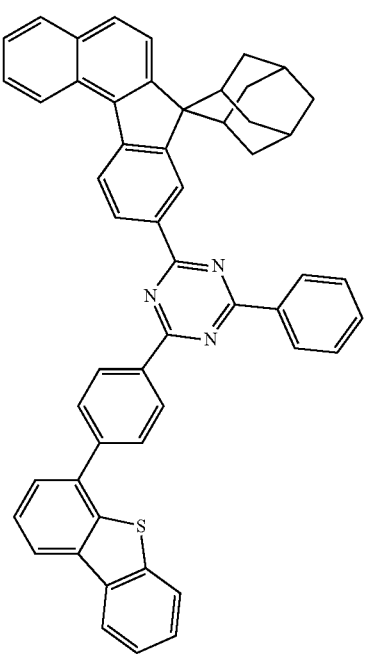

A-257
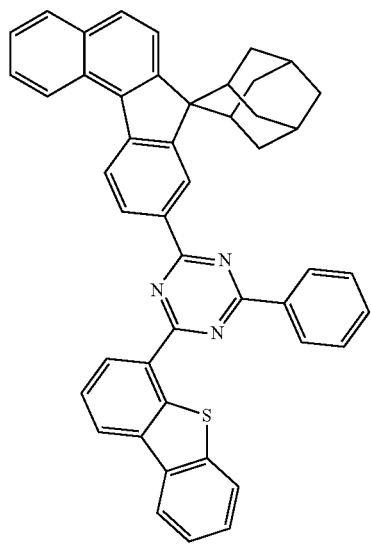
A-258
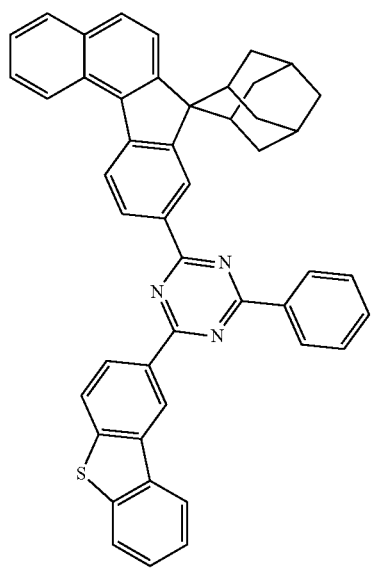
A-259
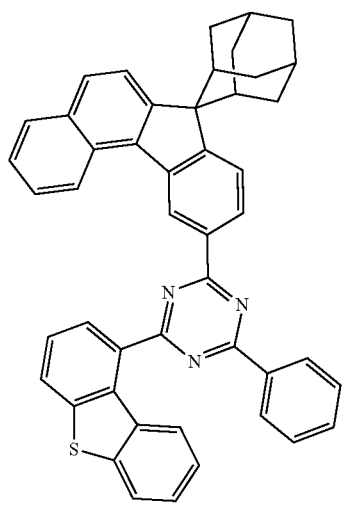
A-260
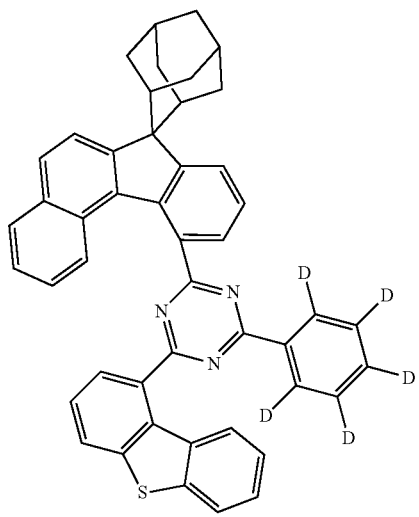
A-261
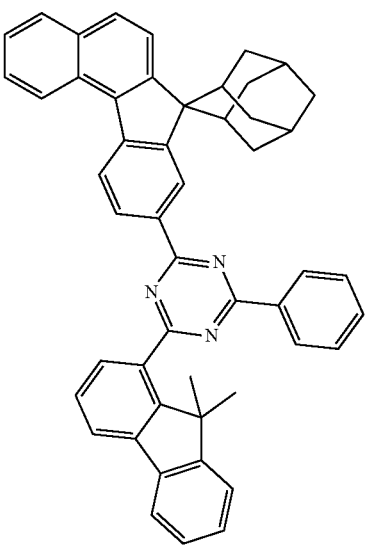
A-262
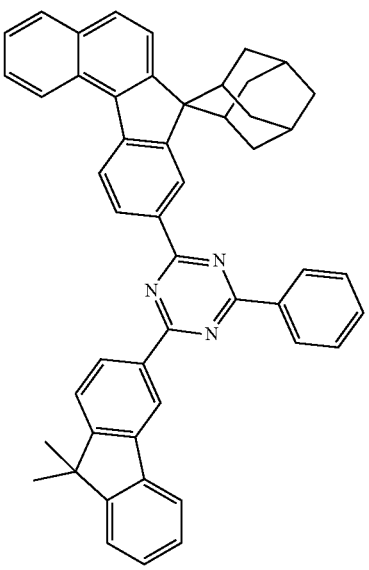

A-263
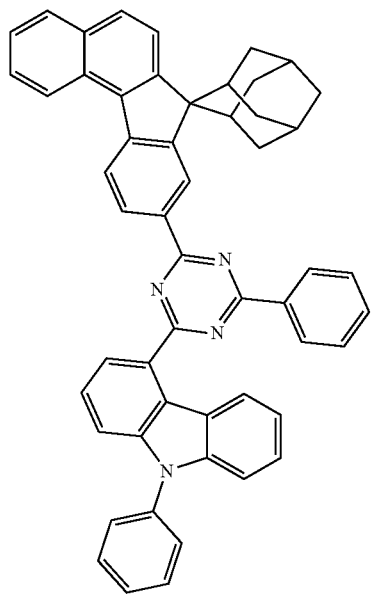
A-268
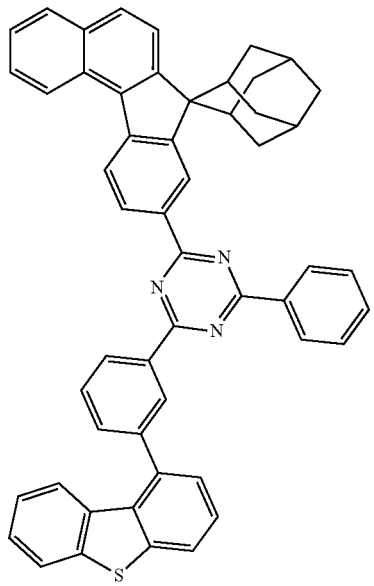
A-264
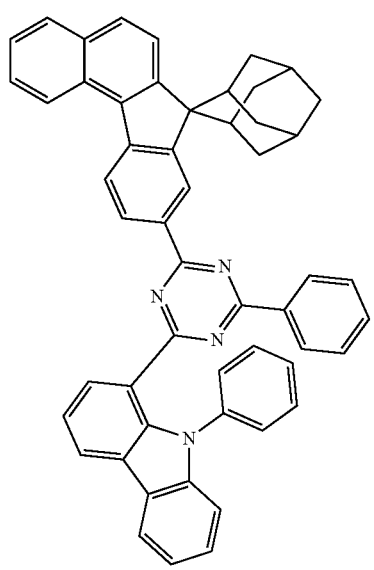
A-269
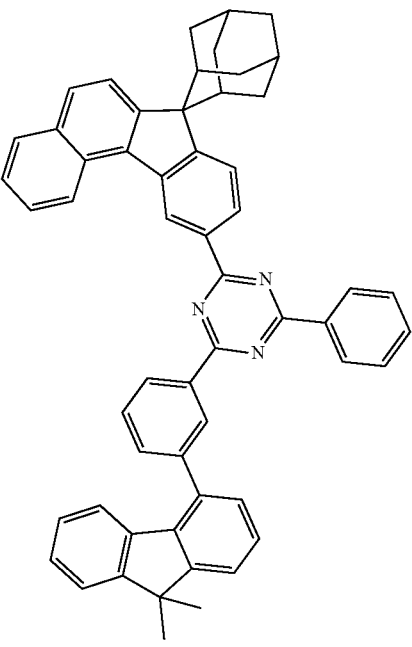

A-270
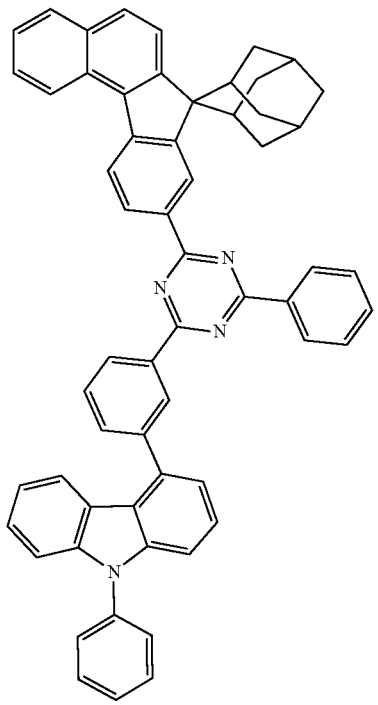
A-272
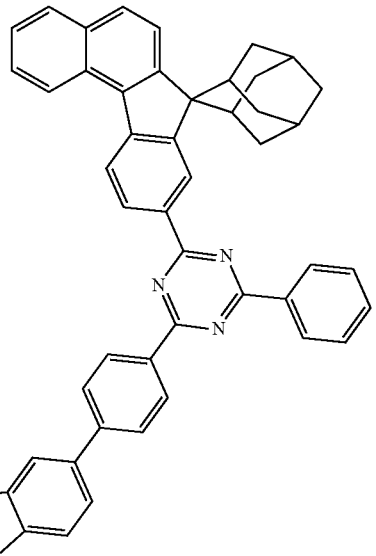
A-271
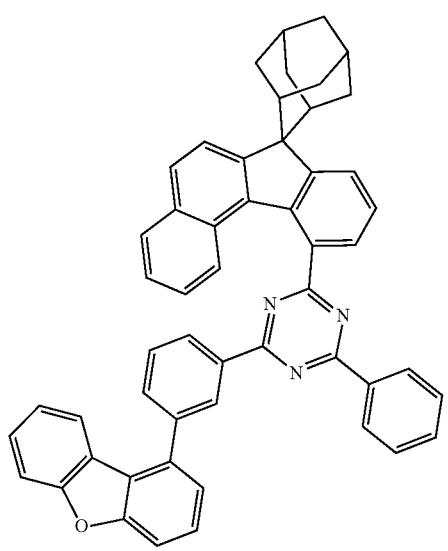
A-273
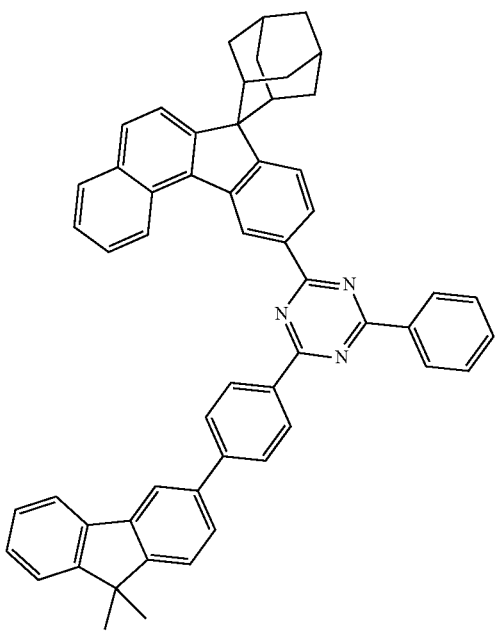

A-274
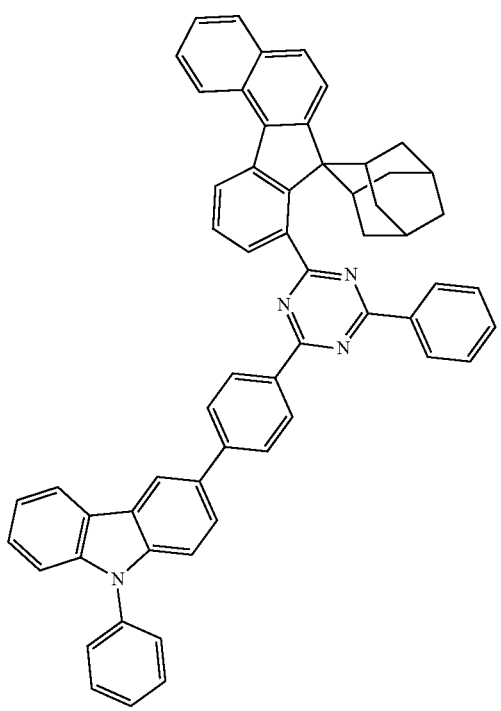
A-266
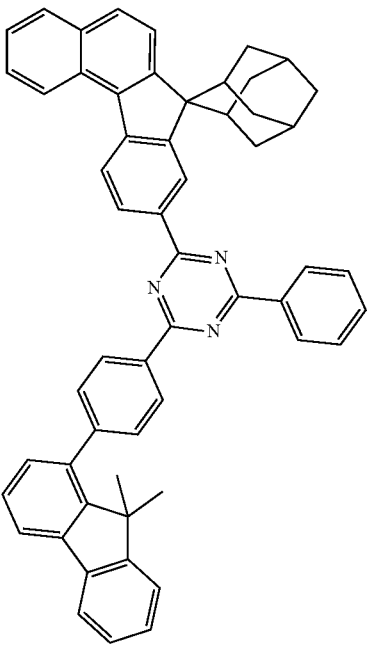
A-275
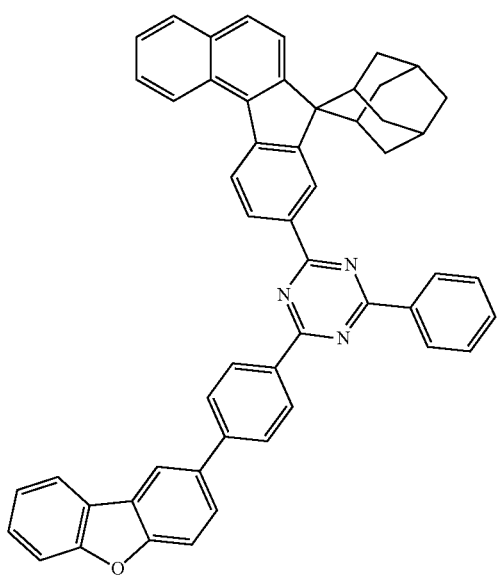
A-267

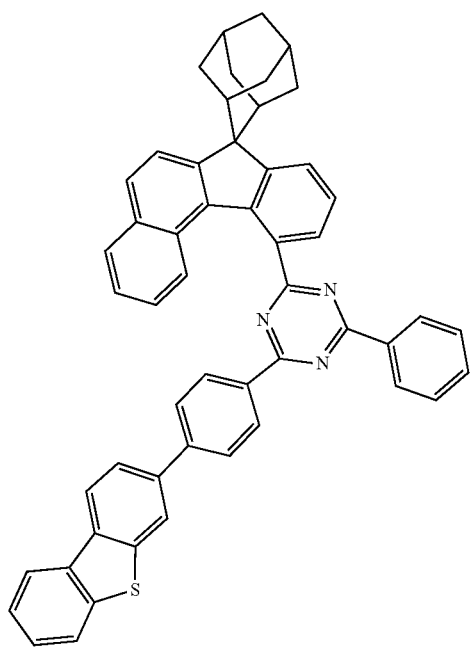
A-276
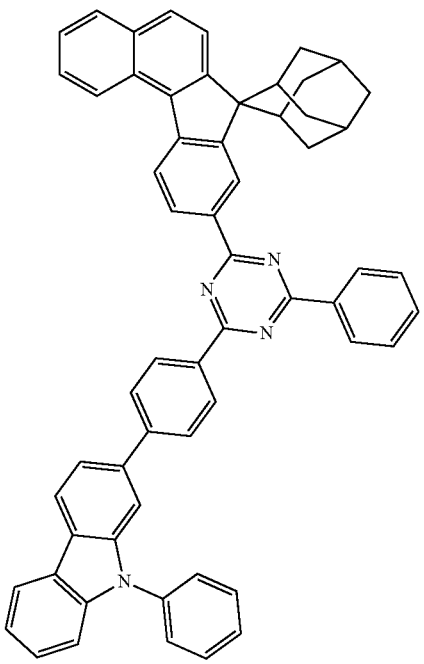
A-278
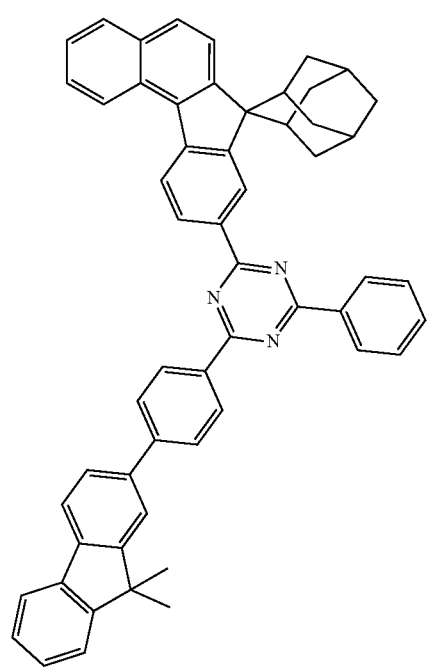
A-277
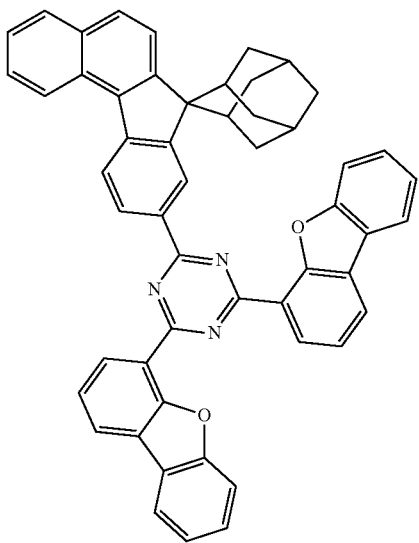
A-279

A-280
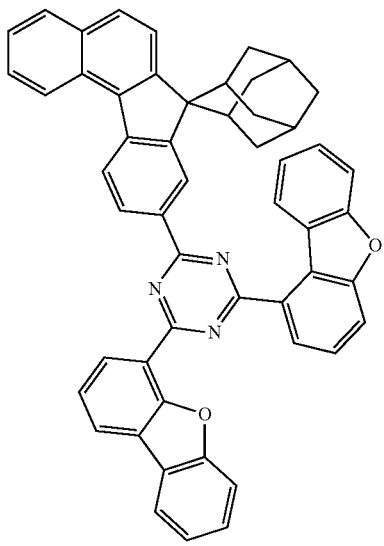
A-281
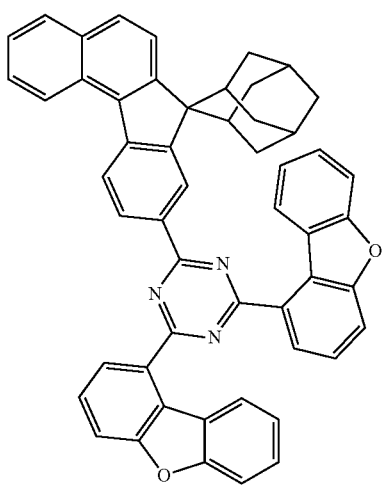
A-282
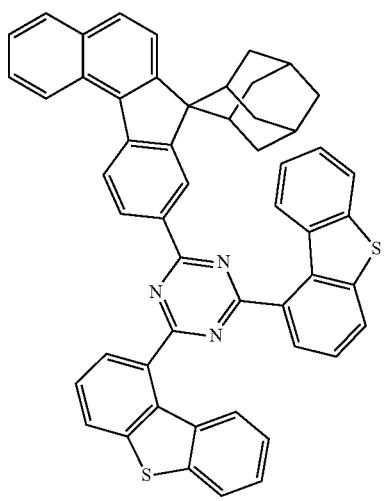
A-283
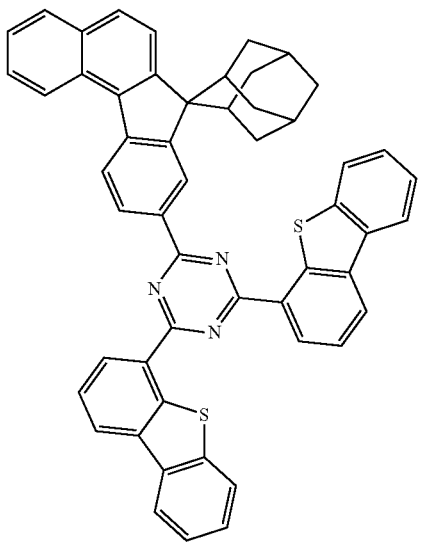
A-284
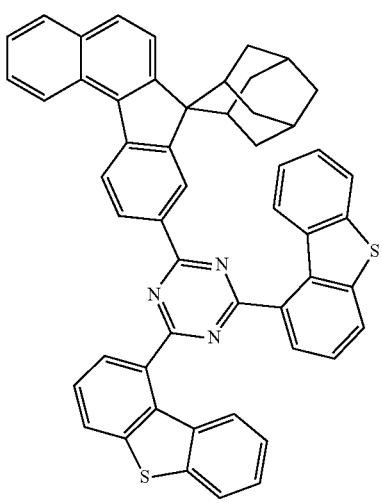
A-285
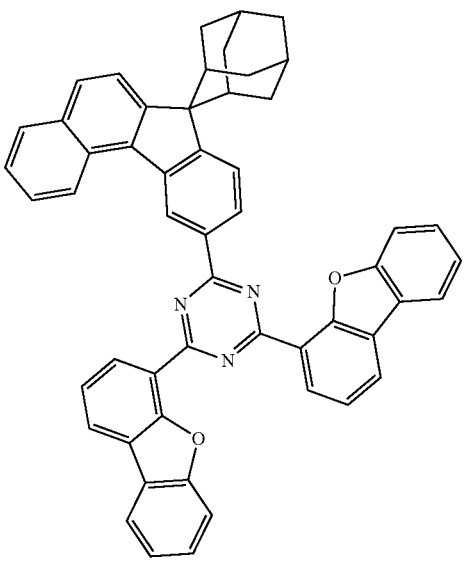

A-286
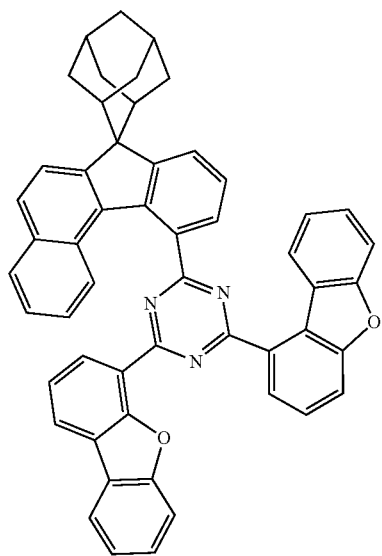
A-289
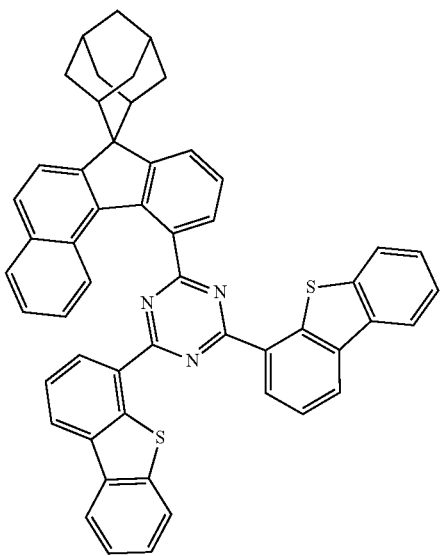
A-287
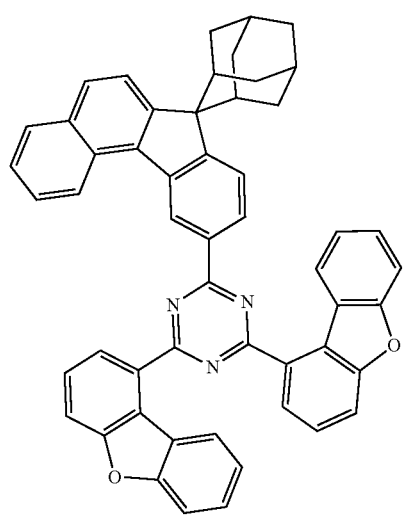
A-288
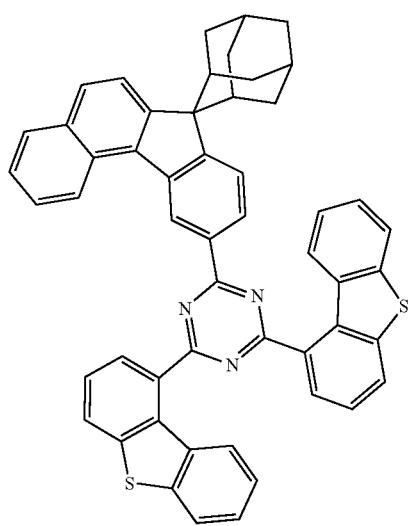
A-290
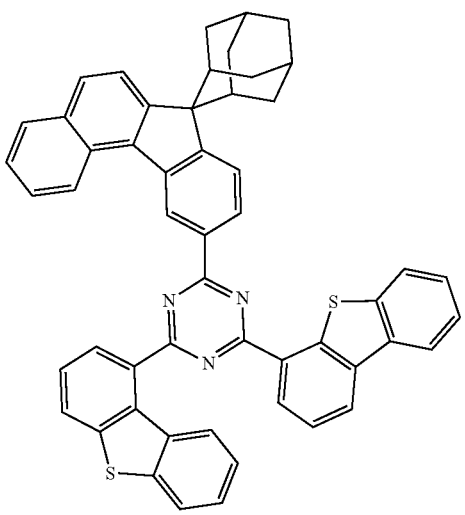

A-291
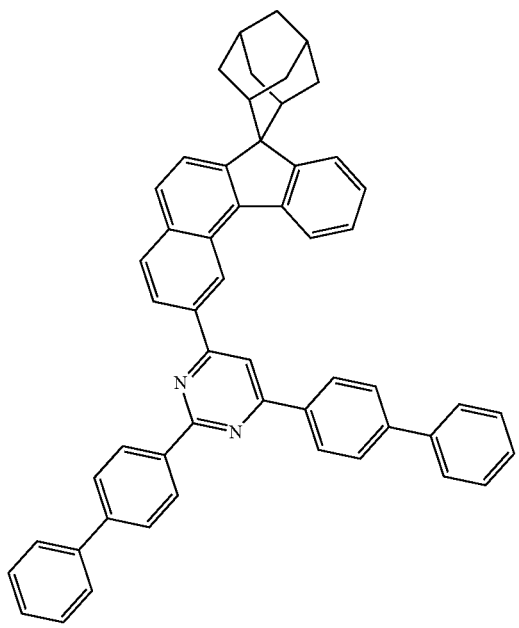
A-292
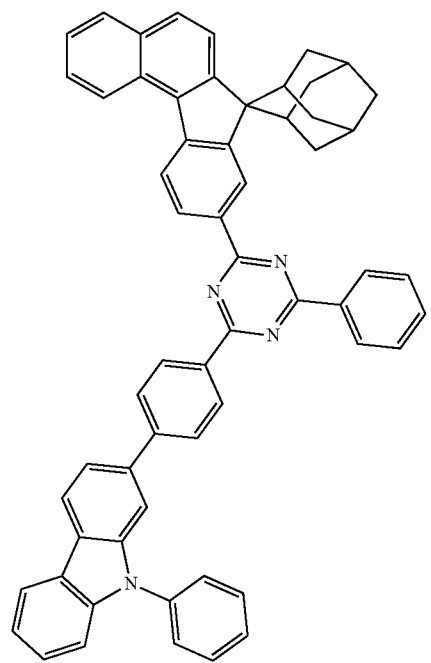
A-293
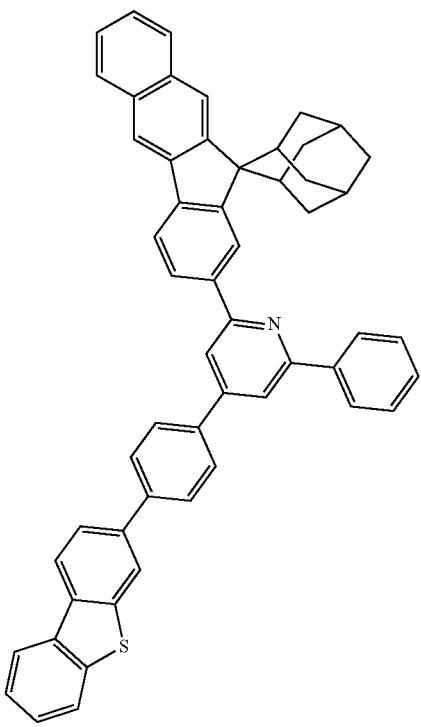
A-295
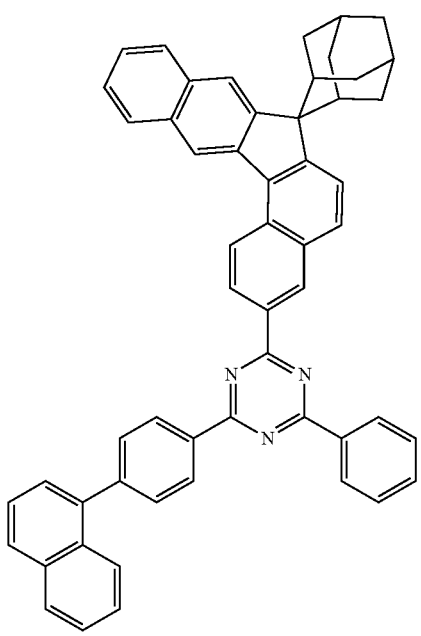

A-296
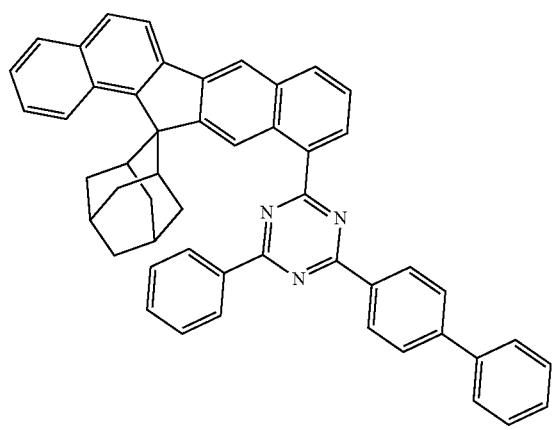
A-297
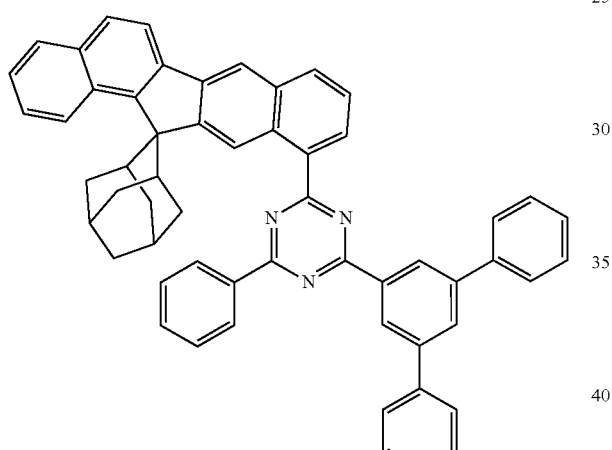
A-298
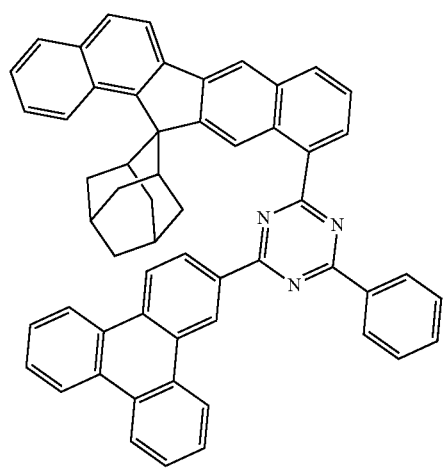
A-299
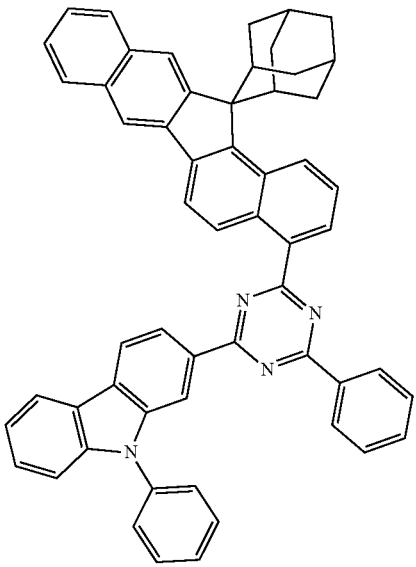
A-300
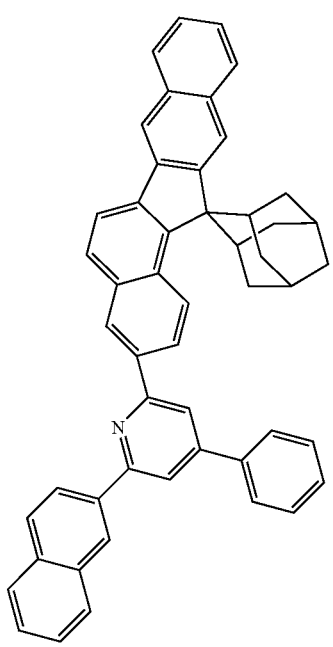

A-301
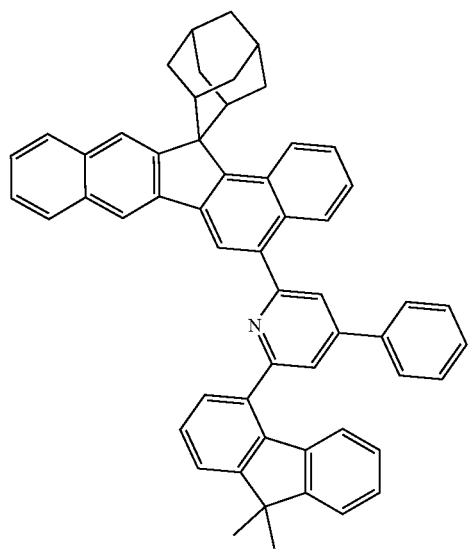
A-302
A-303
A-304
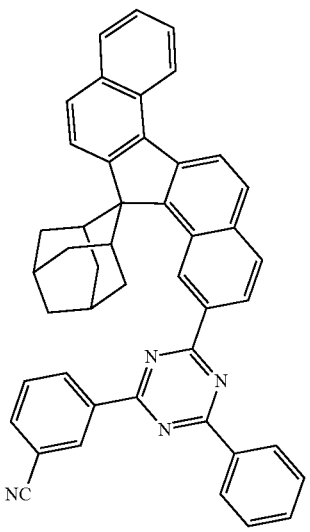
A-305
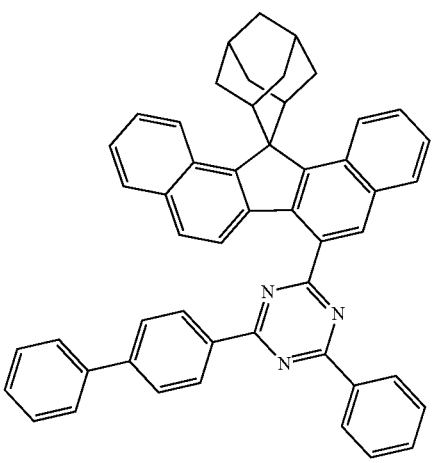
A-306
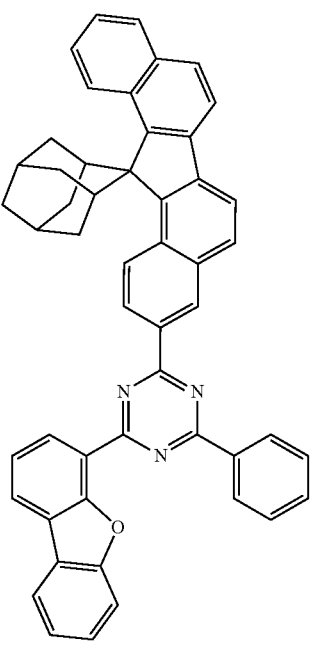

A-307
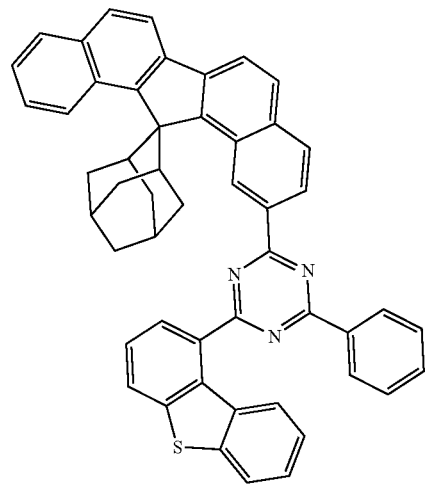
A-310
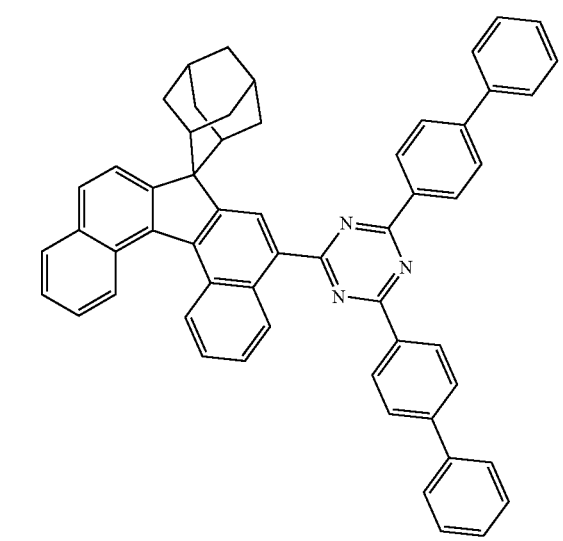
A-308
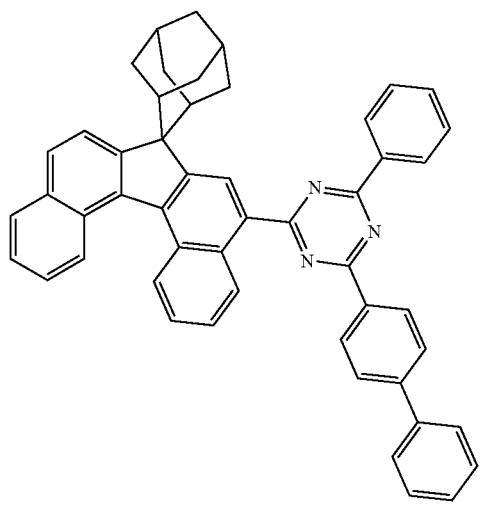
A-311
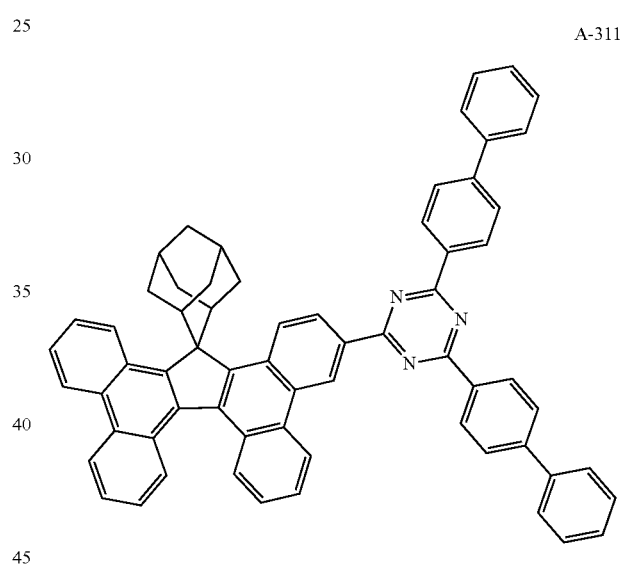
A-309
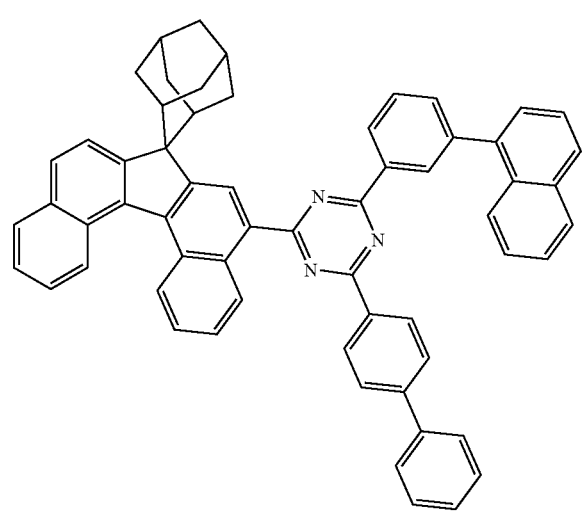
A-312
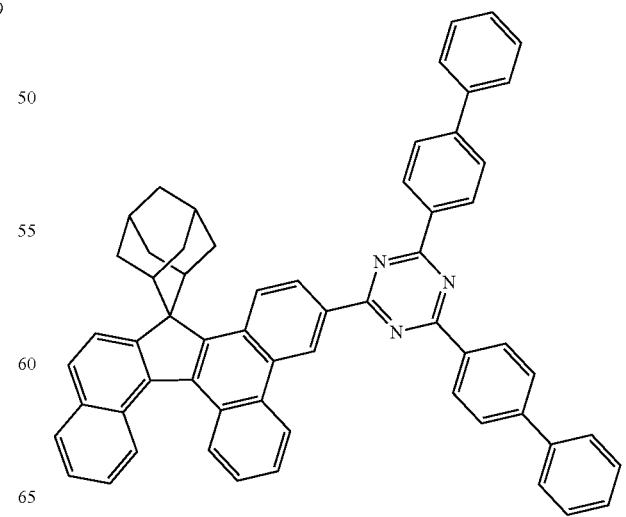

A-313
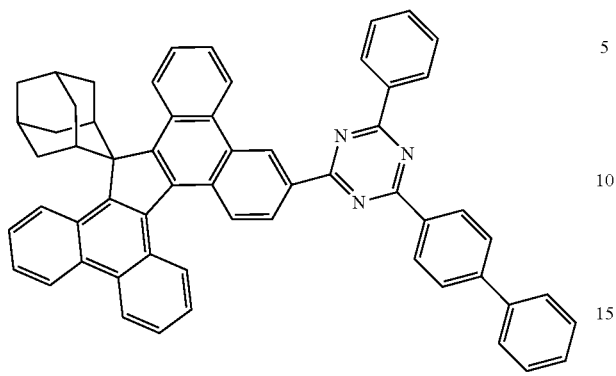
B-1
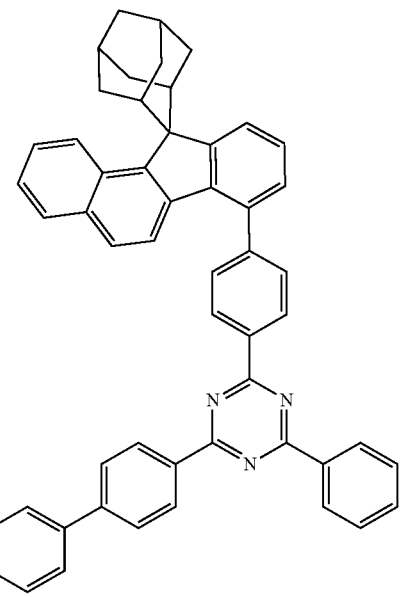
A-314
A-315
B-2
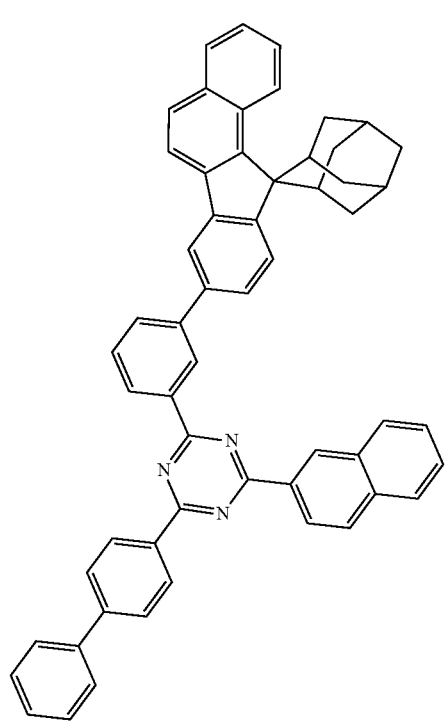

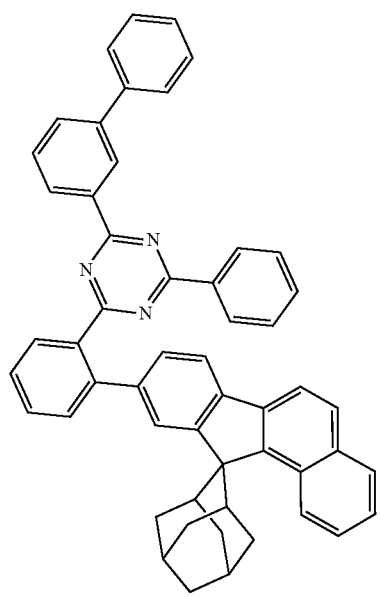
B-3
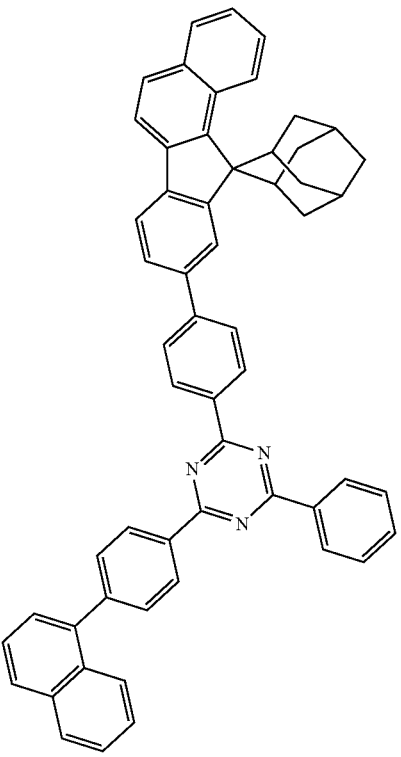
B-5
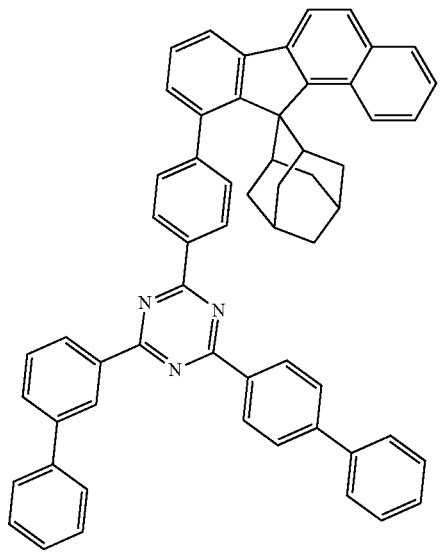
B-4
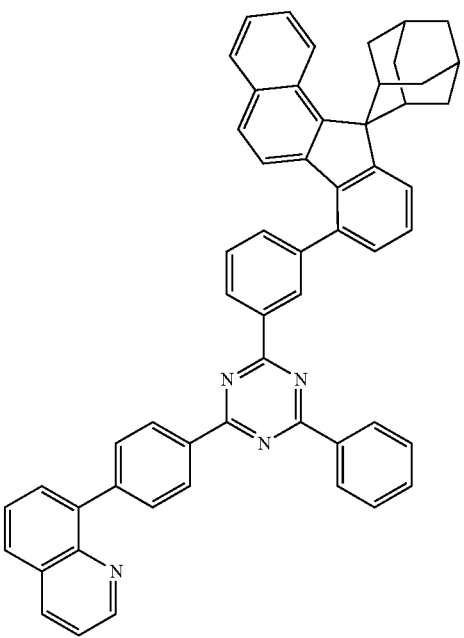
B-6

B-7
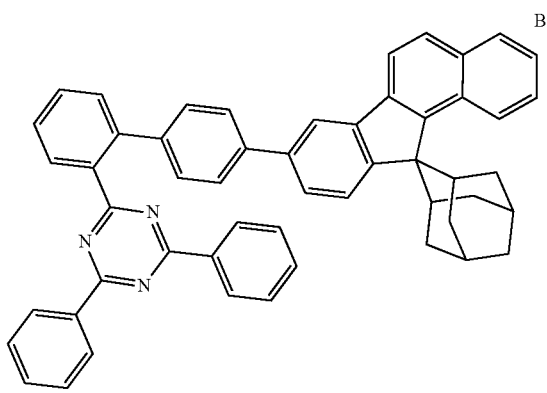
B-9
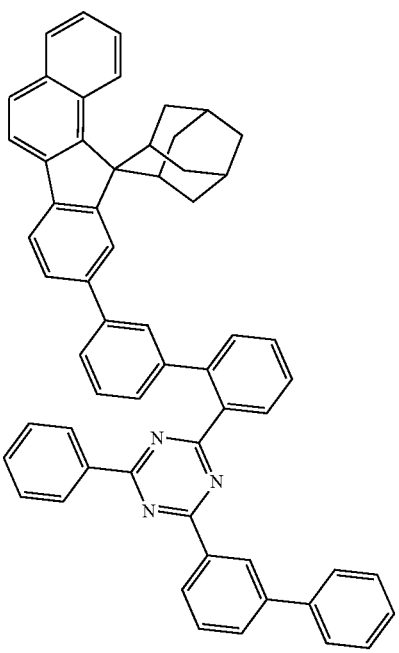
B-8
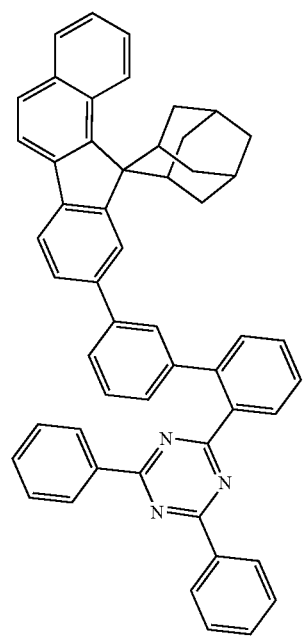
B-10
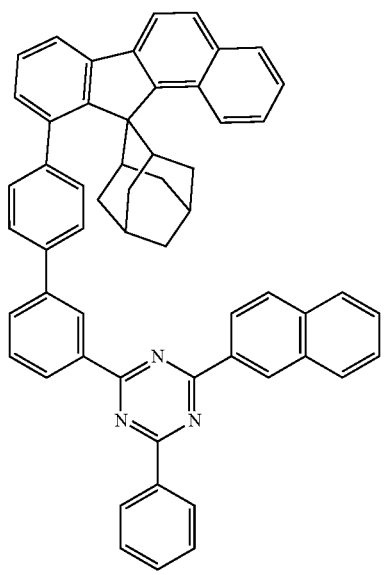

B-11
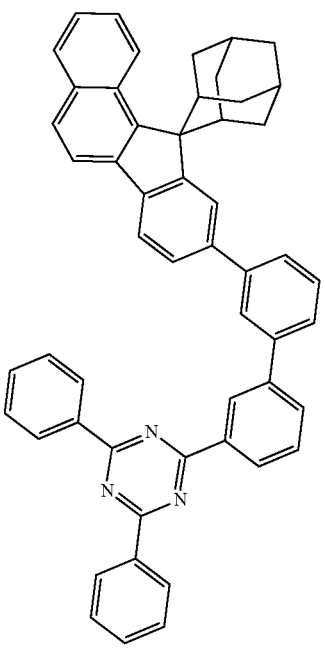
B-12
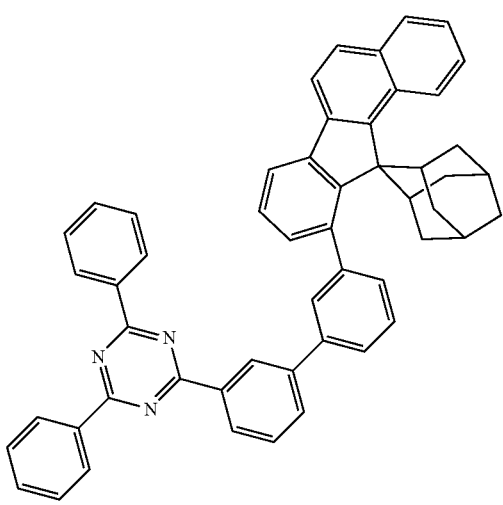
B-13
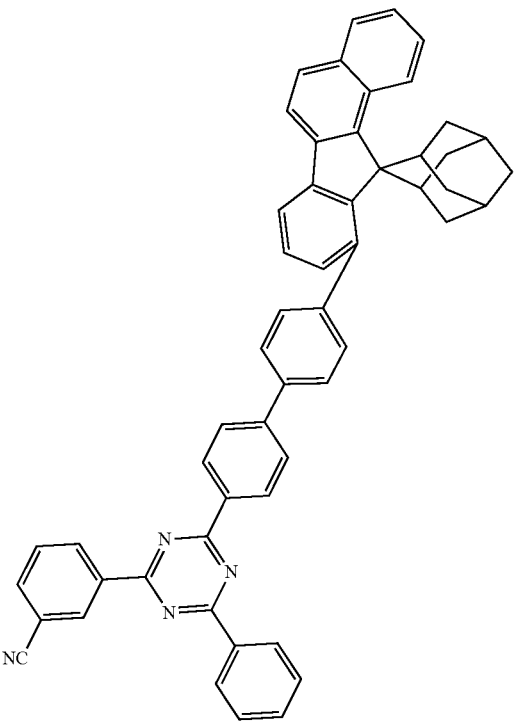
B-14
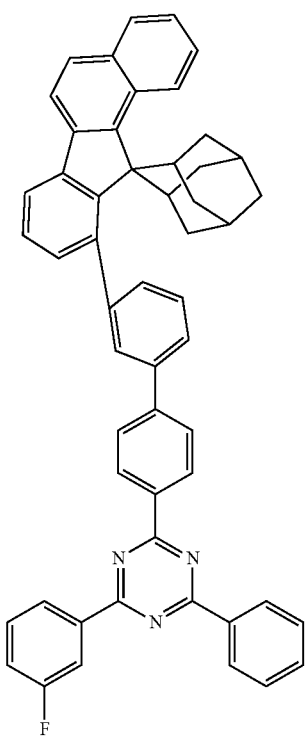

B-15
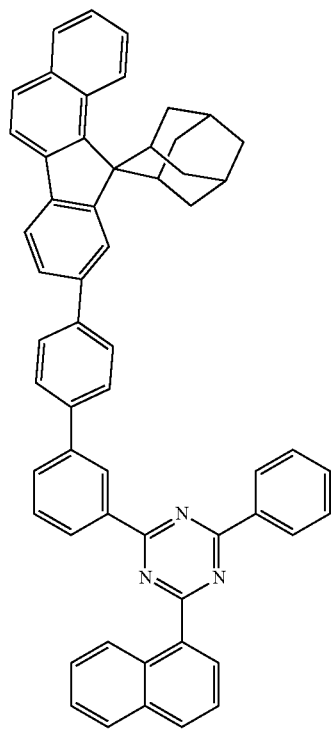
B-17
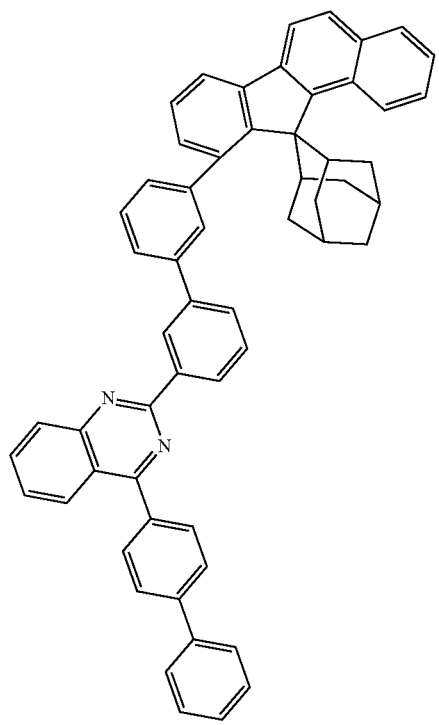
B-16
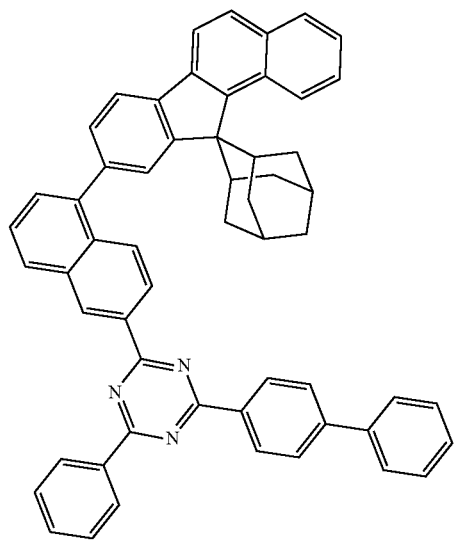
B-18
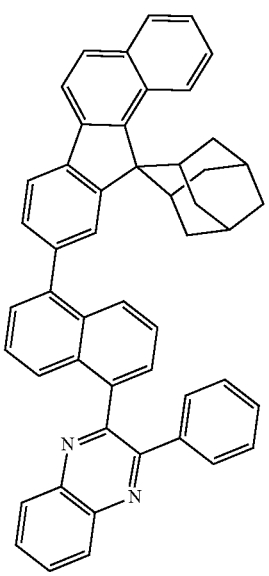

B-19
B-20
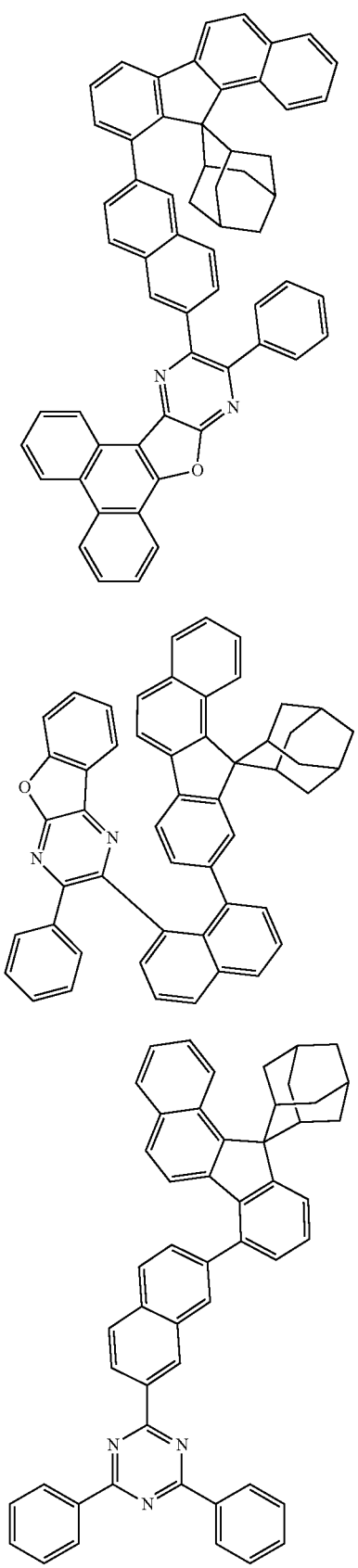
B-21
B-22
B-23

B-24
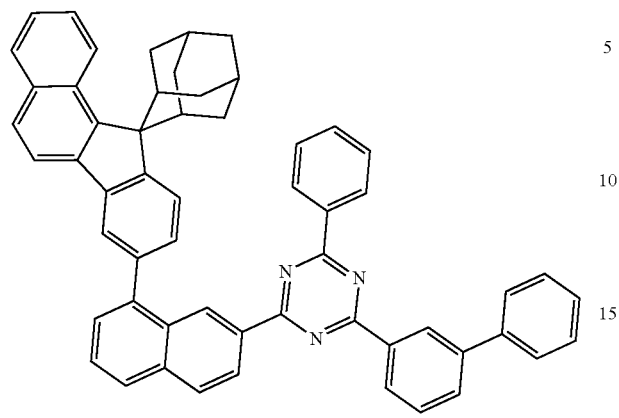
B-25
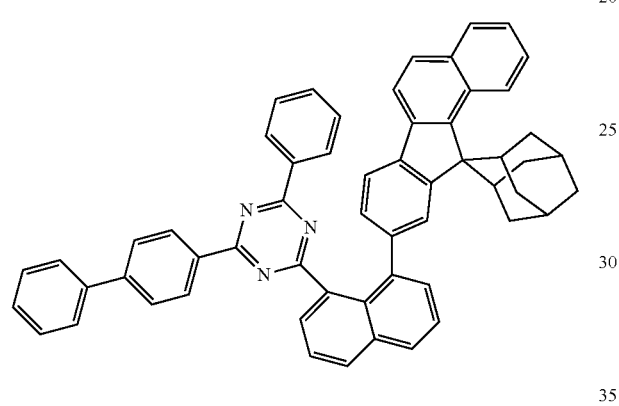
B-26
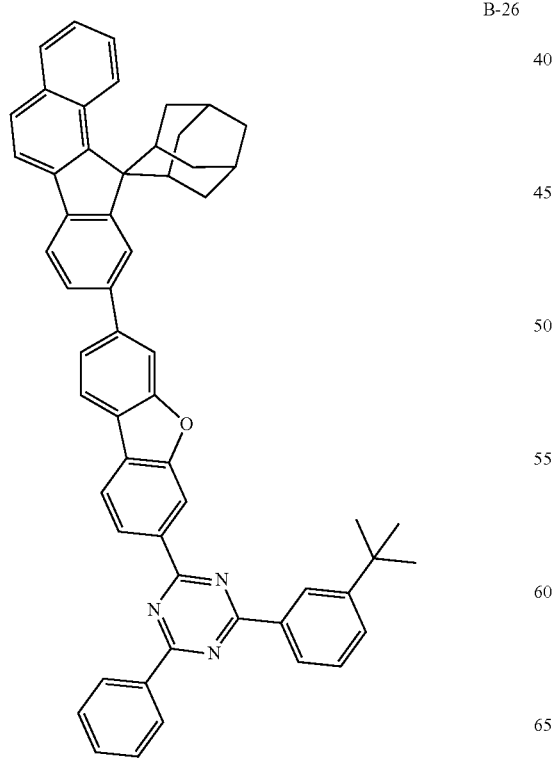
B-27
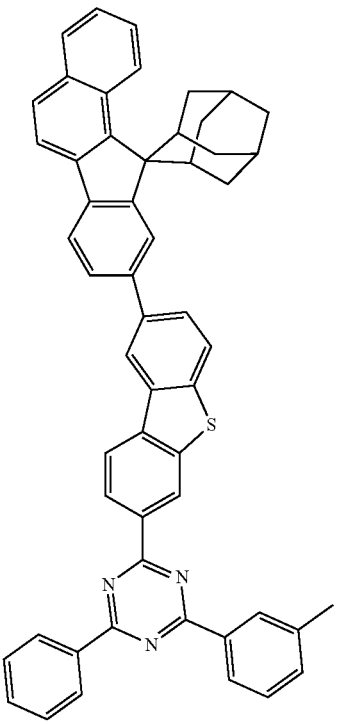
B-28
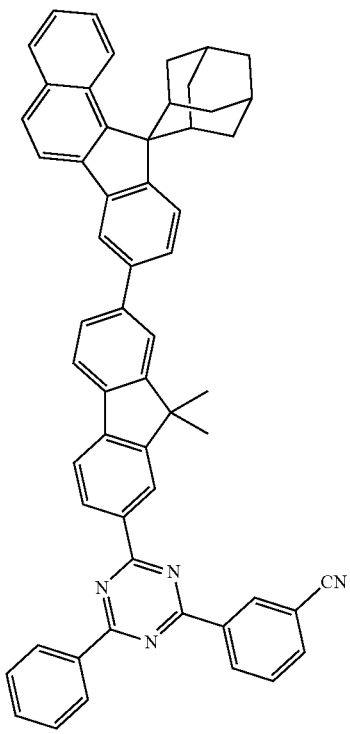

B-29
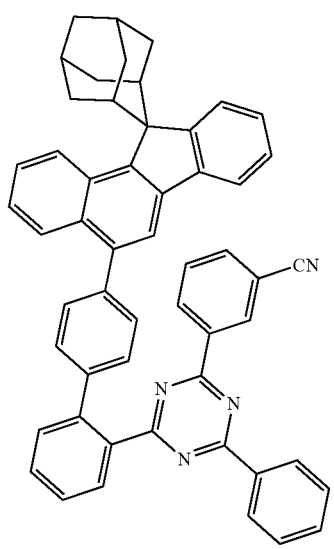
B-31
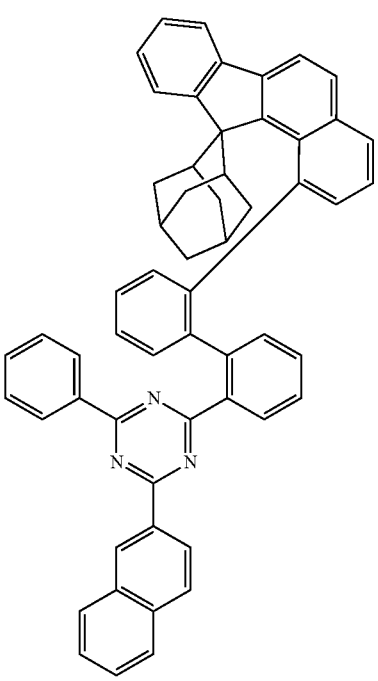
B-30
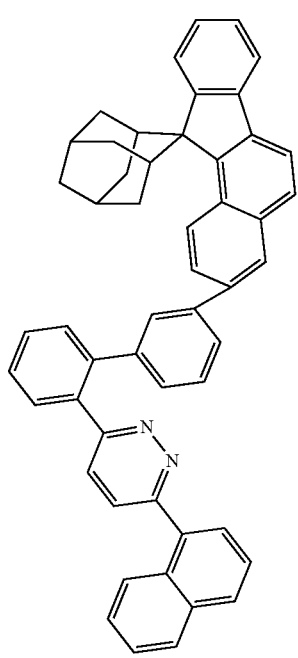
B-32
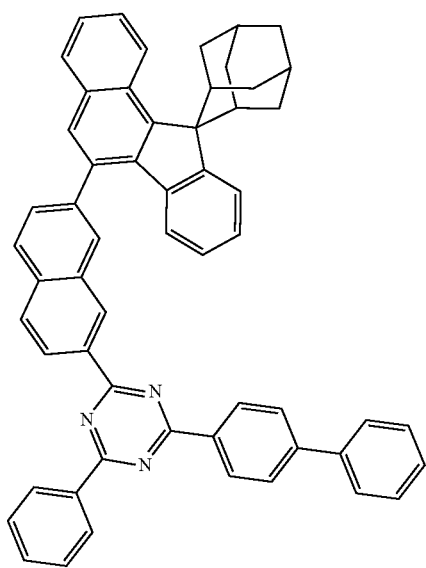

B-33
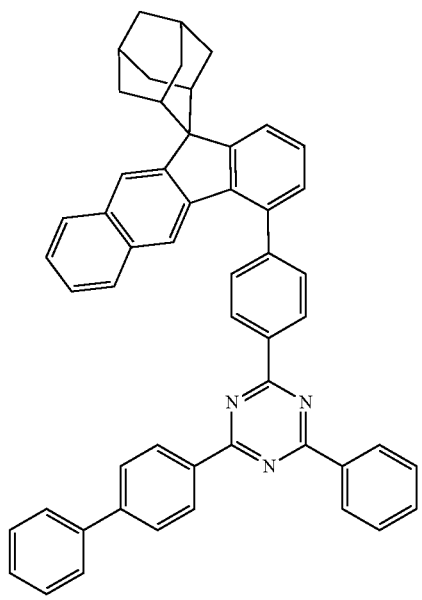
B-34
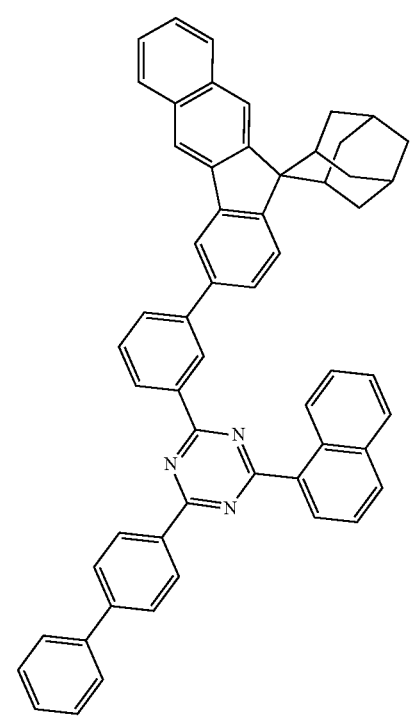
B-35
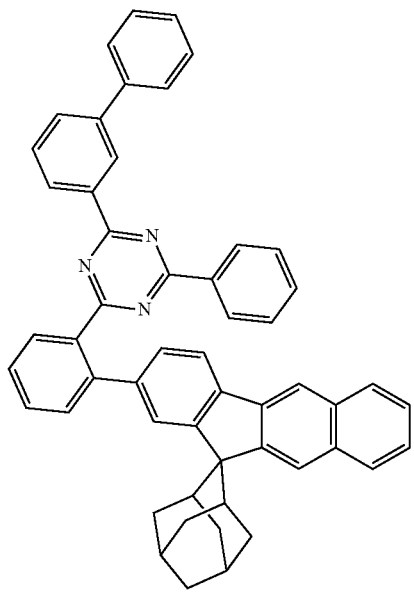
B-36
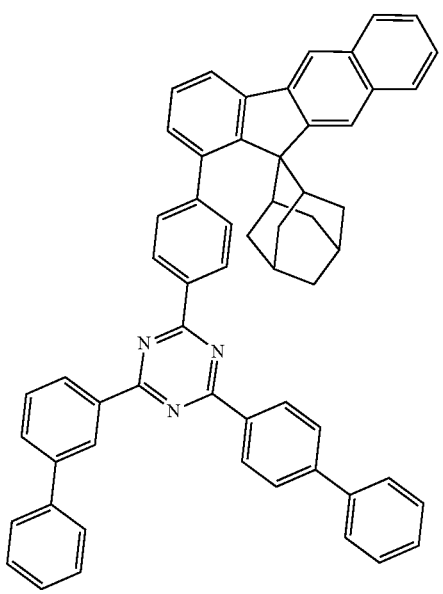

B-37
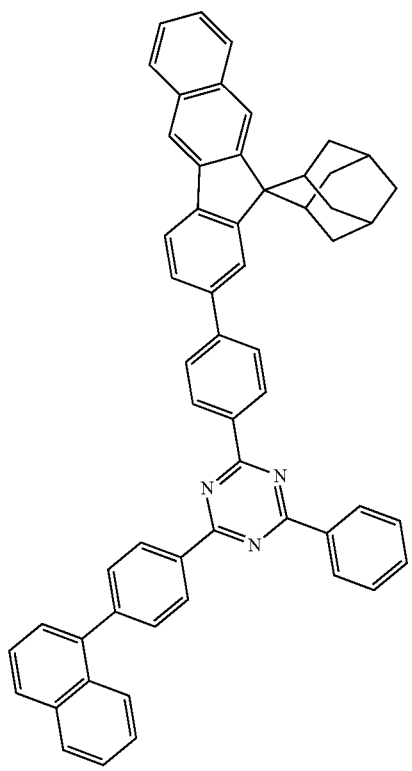
B-39
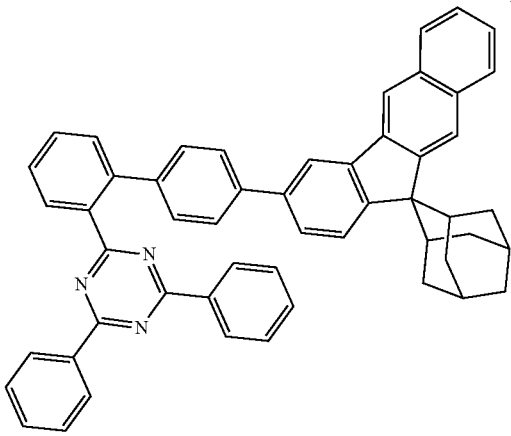
B-38
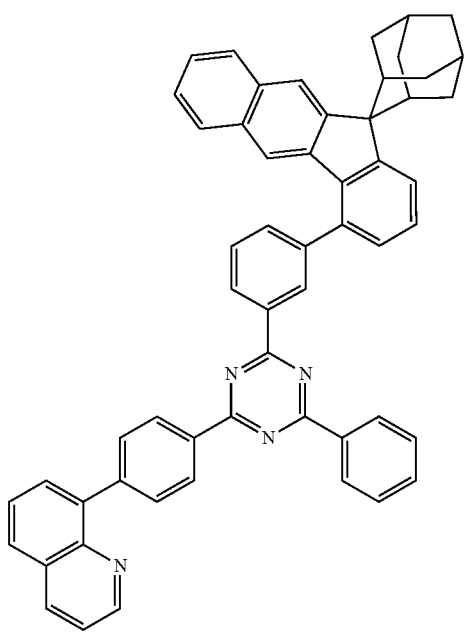
B-40
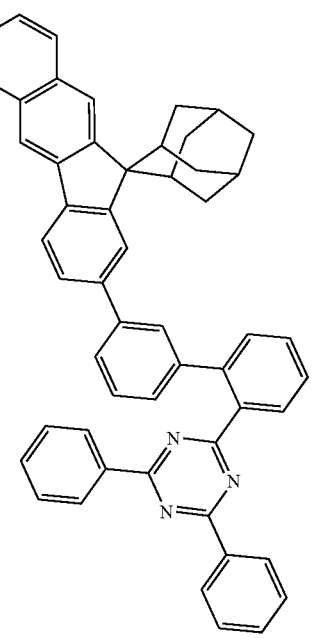

B-41
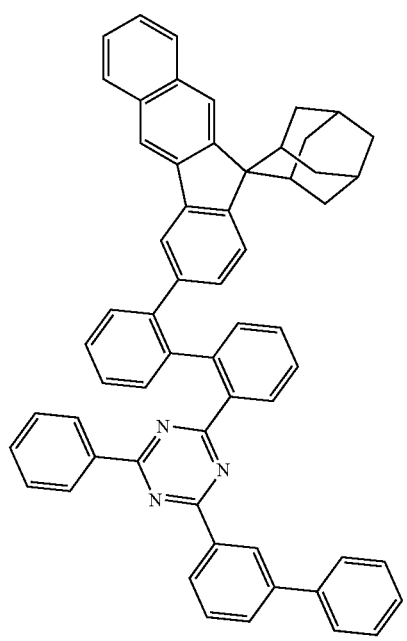
B-43
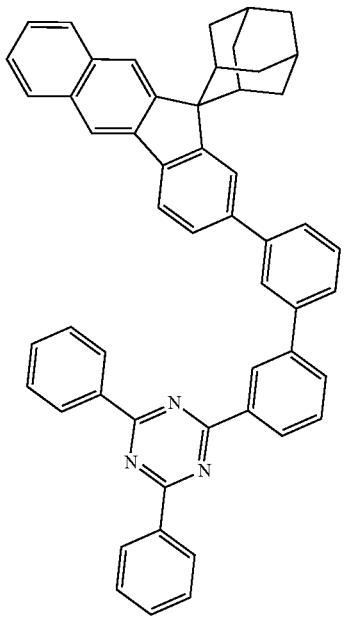
B-42
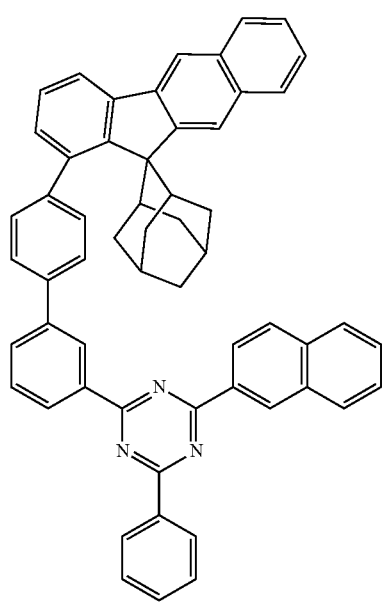
B-44
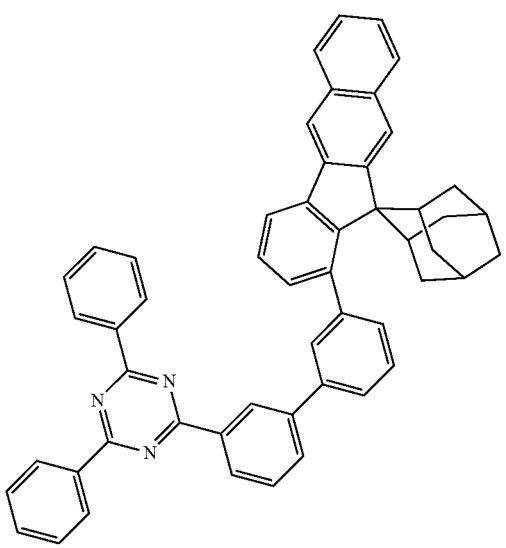

-continued
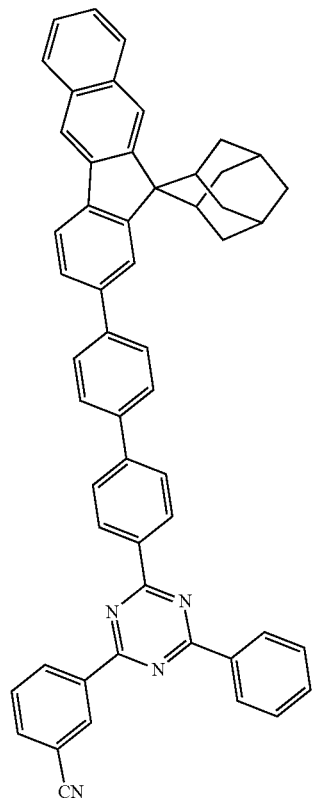
B-45
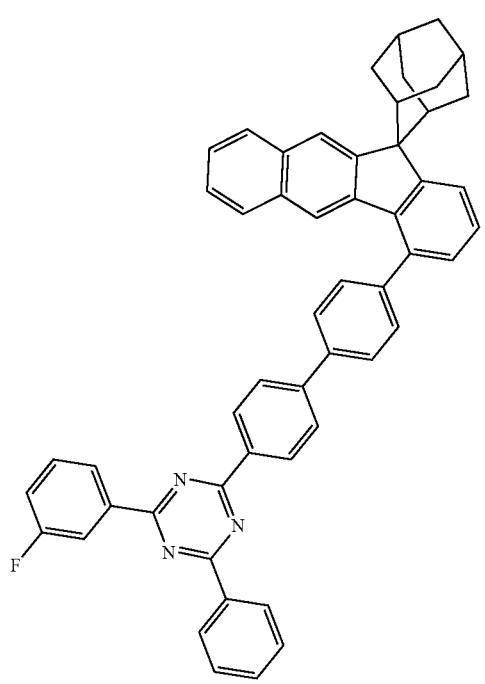
B-46
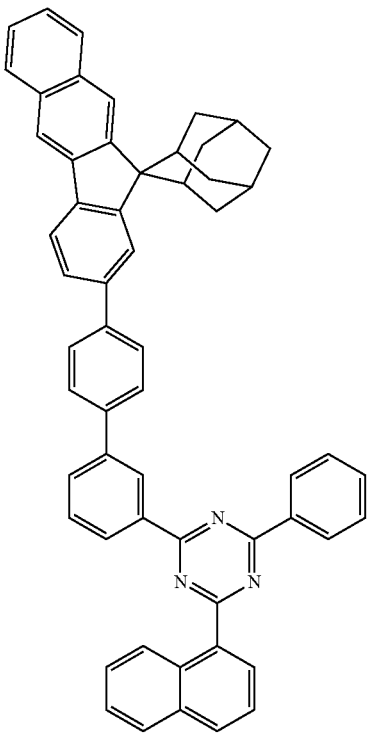
B-47
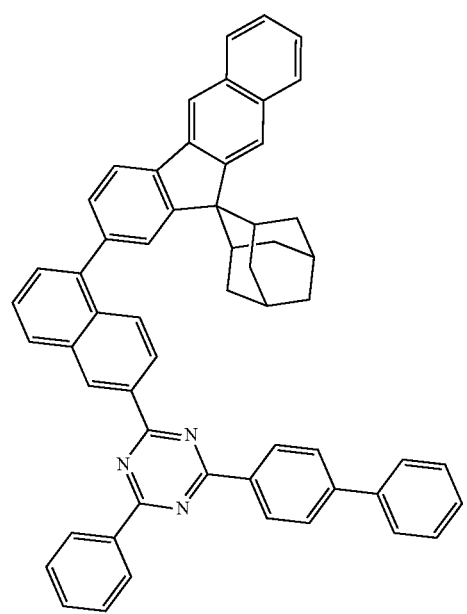
B-48

B-49
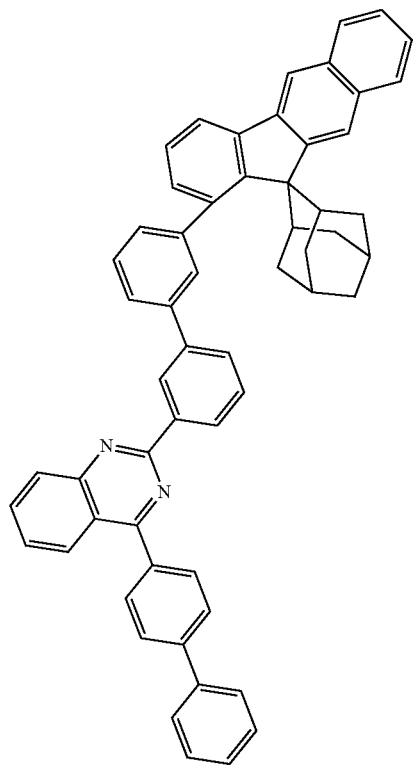
B-51
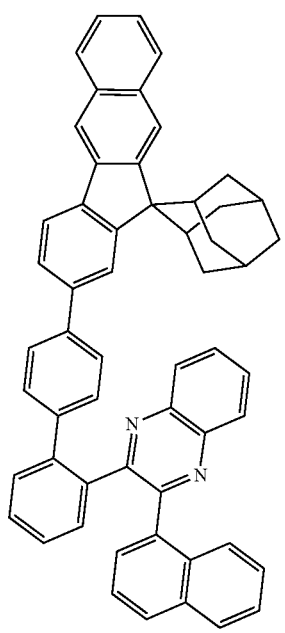
B-50
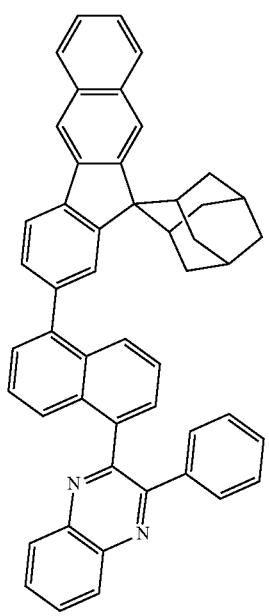
B-52
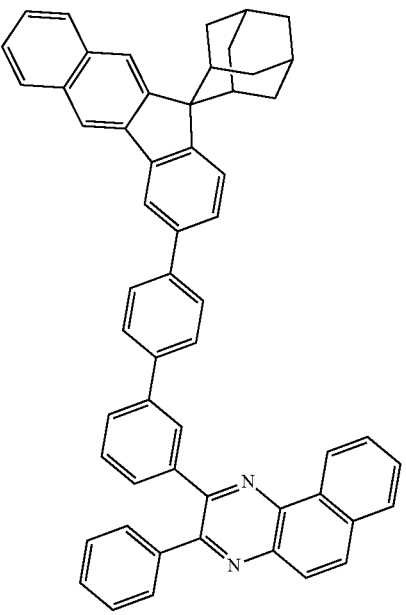

B-53
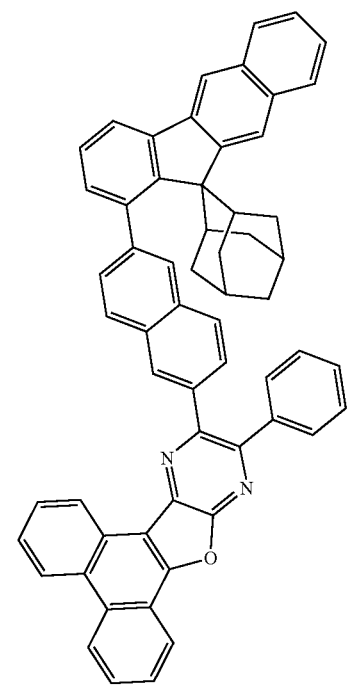
B-55
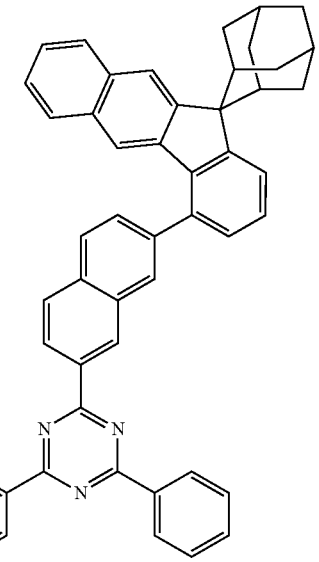
B-56
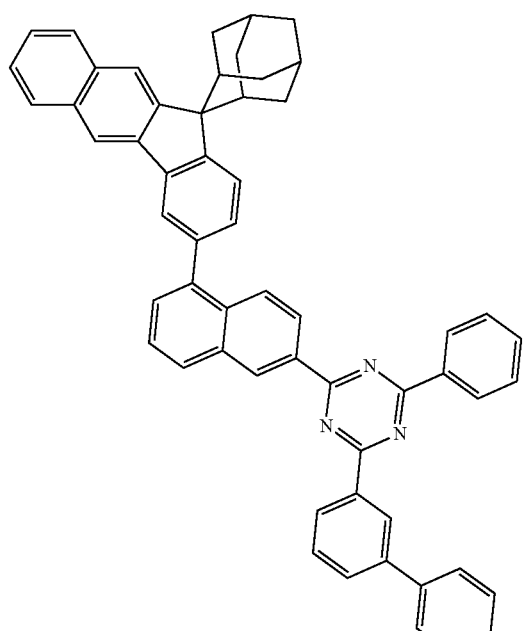
B-54
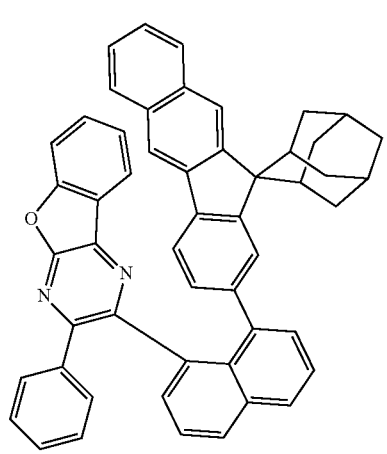
B-57
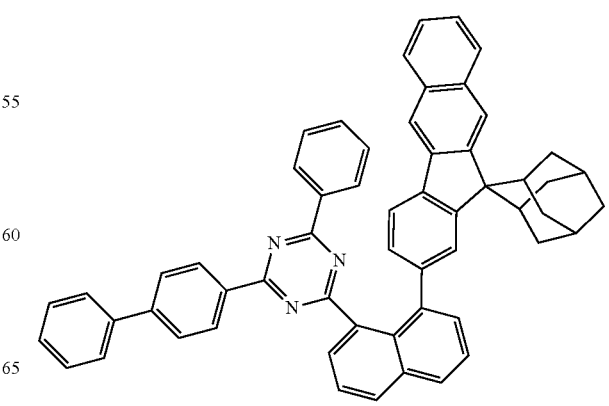

-continued
B-58
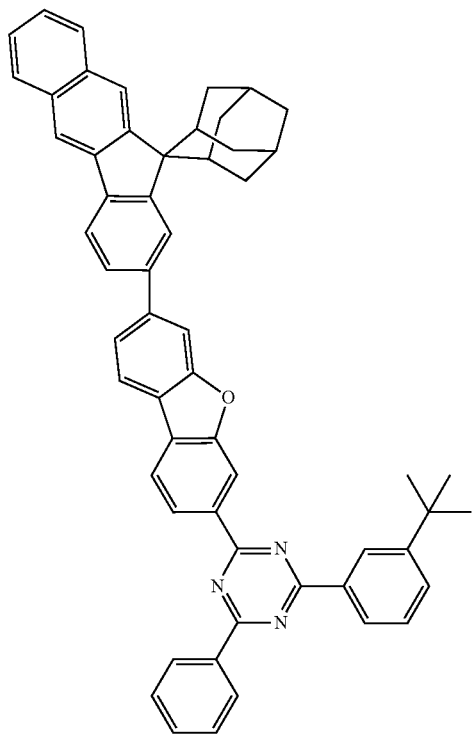
B-59
B-60
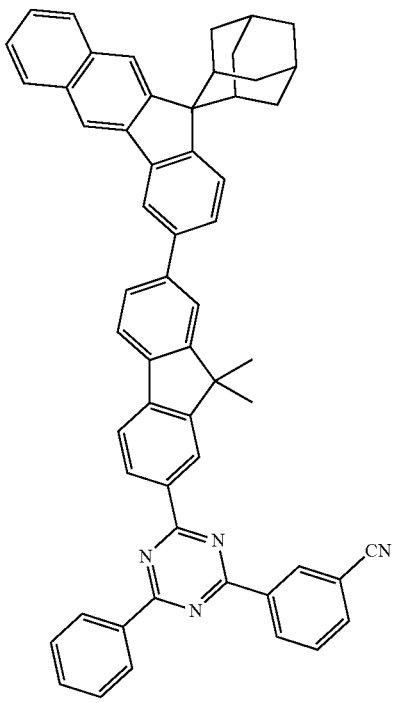
B-61

B-62
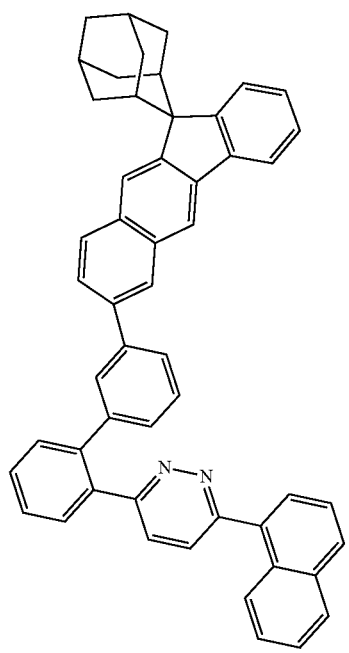
B-63
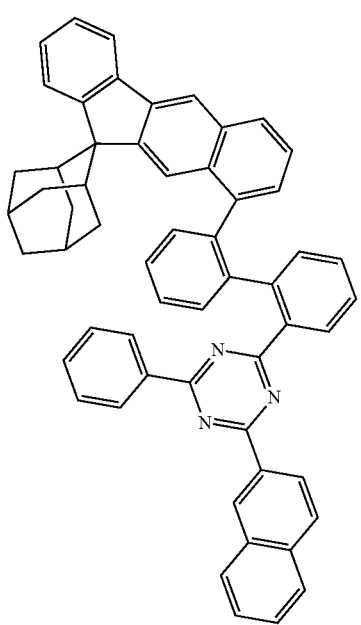
B-64
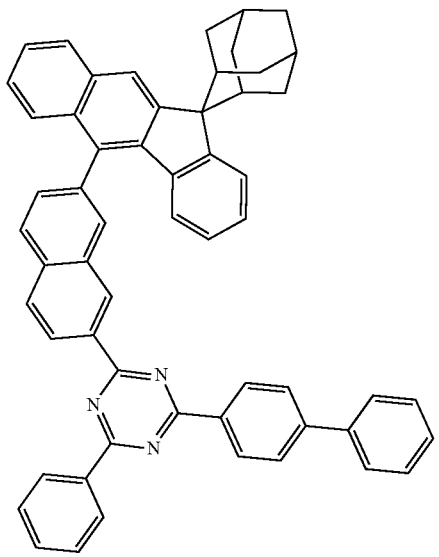
B-65
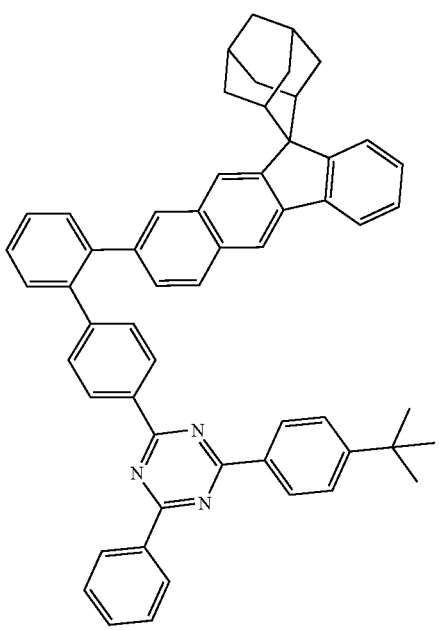

B-66
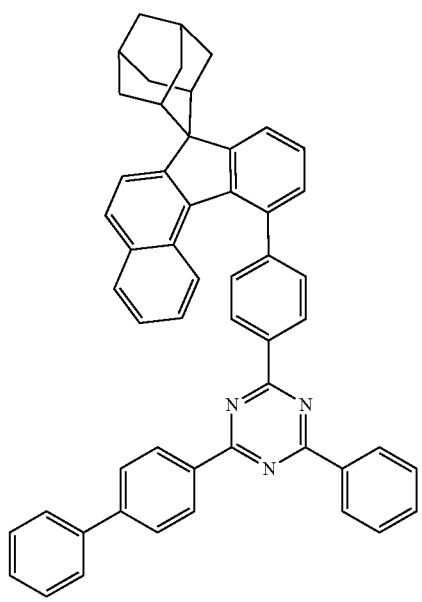
B-68
B-67
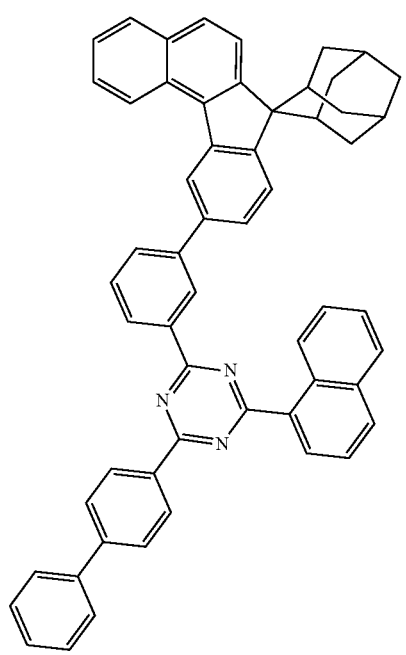
B-69
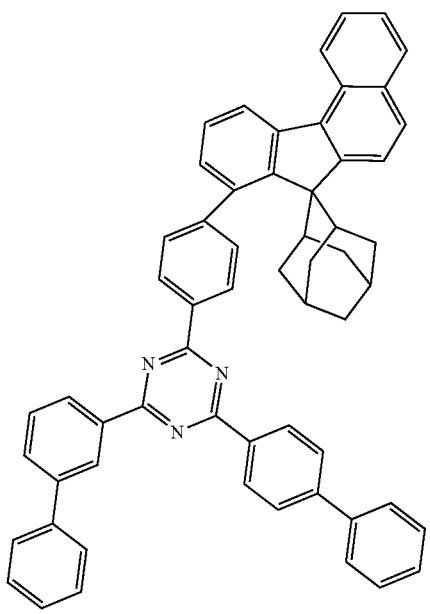

B-70
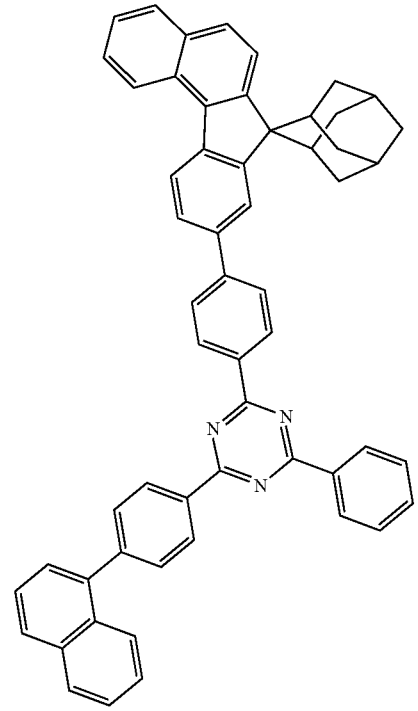
B-71
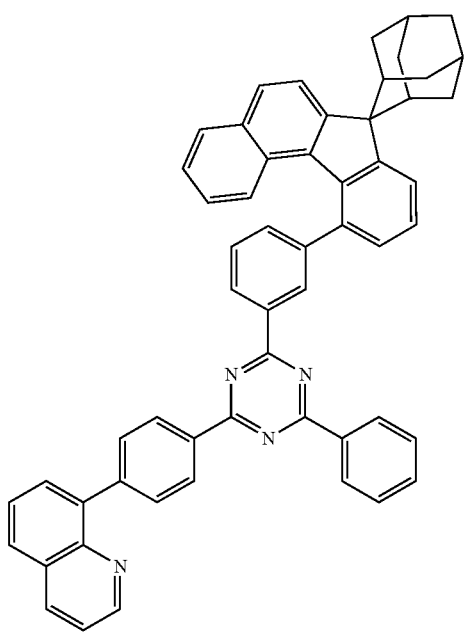
B-72
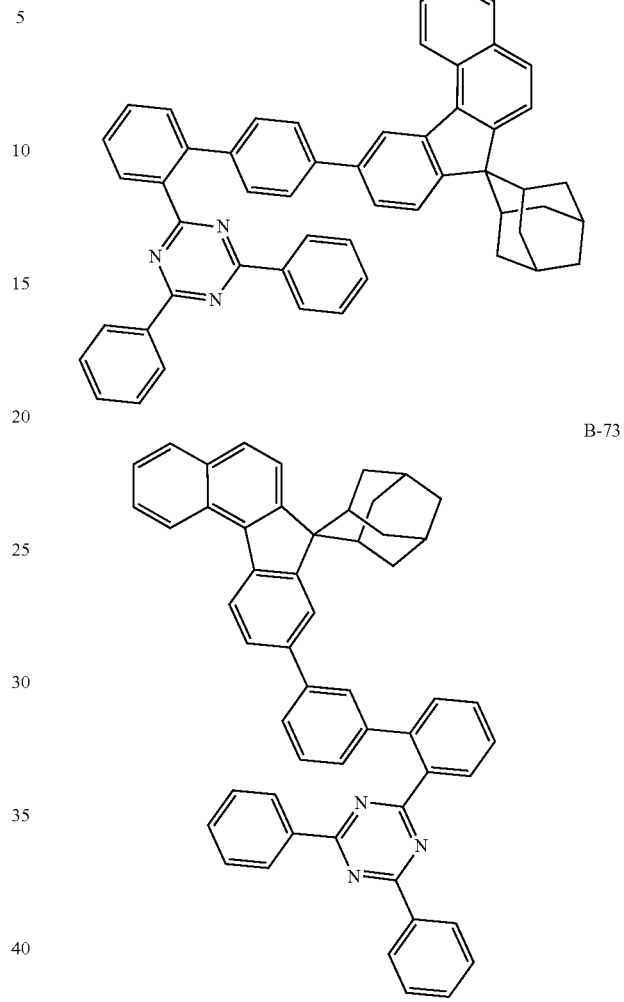
B-73
B-74
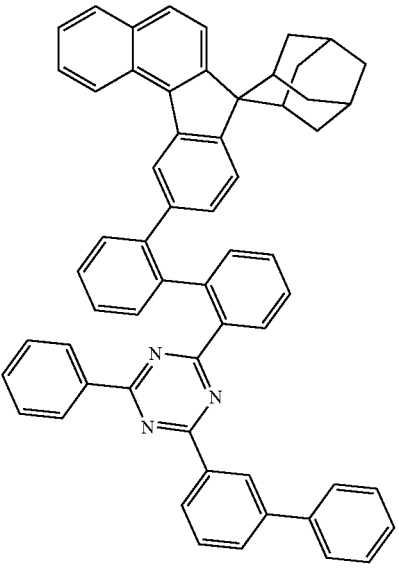

B-75
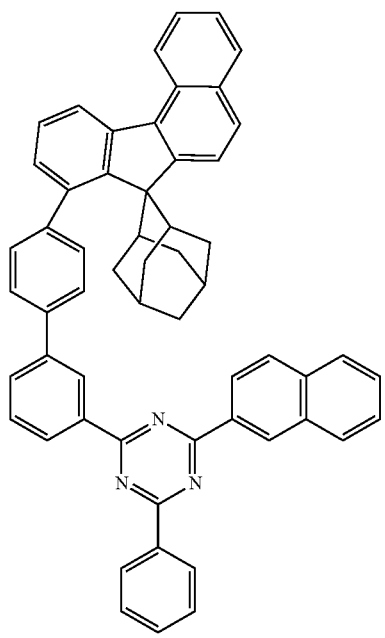
B-76
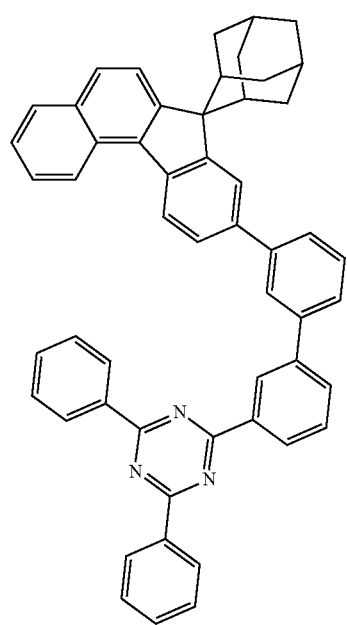
B-77
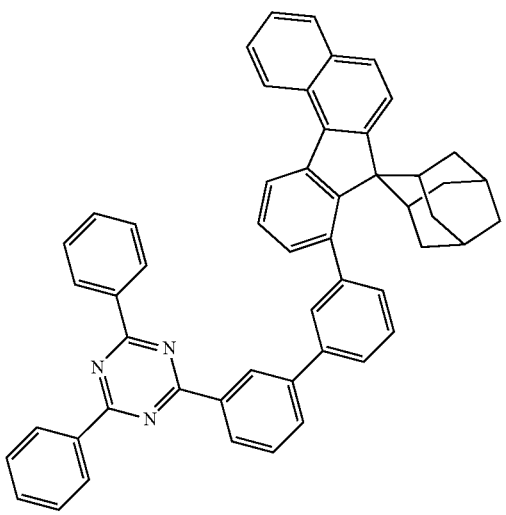
B-78
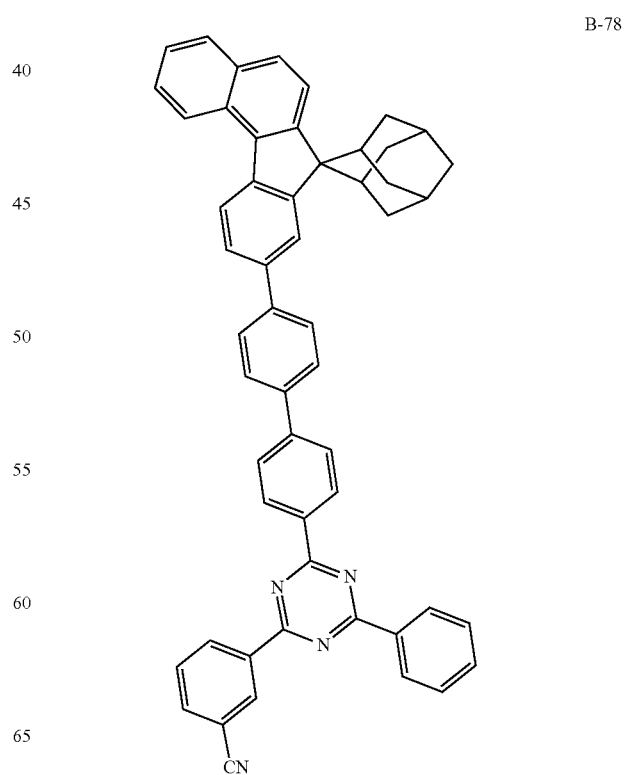

B-79
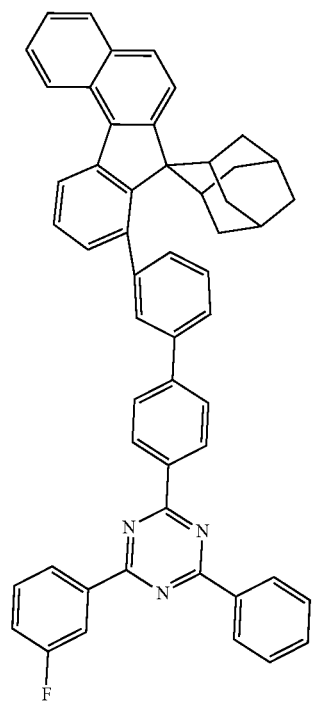
B-80
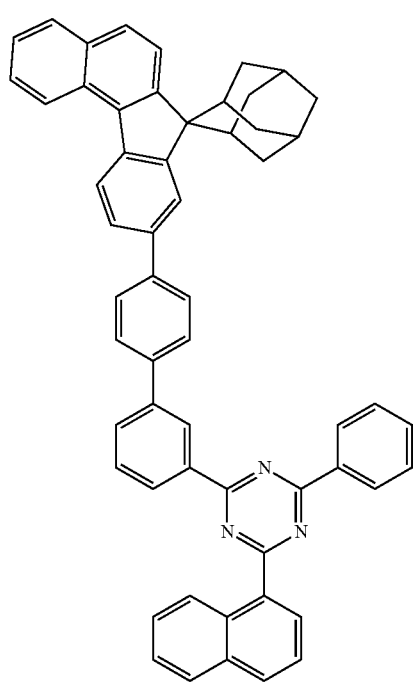
B-81
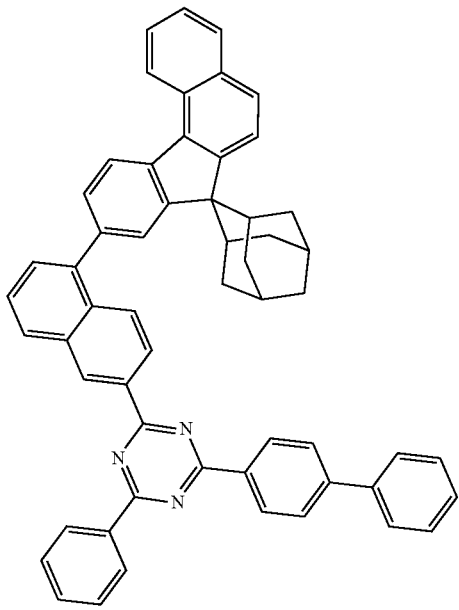
B-82
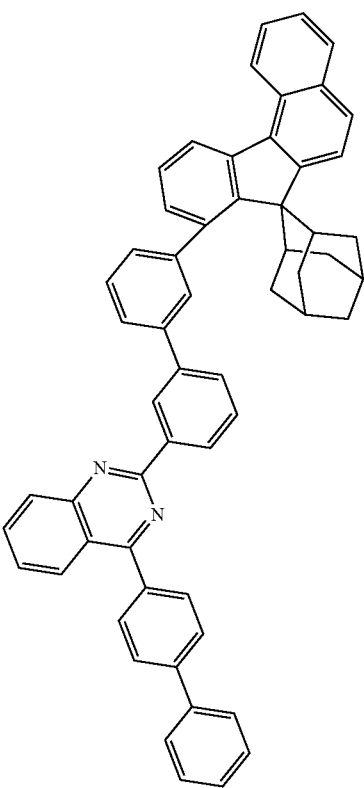

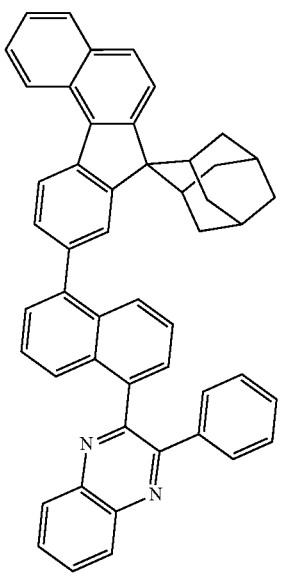
B-83
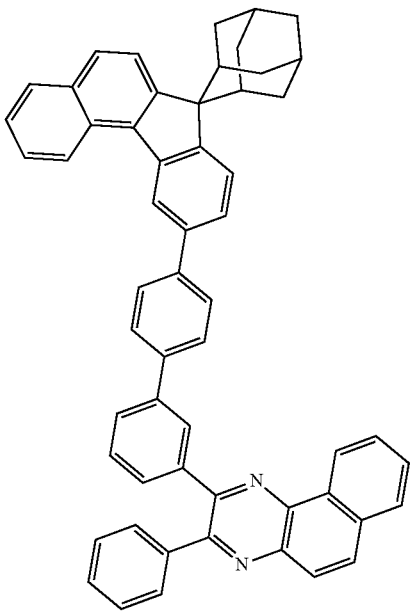
B-85
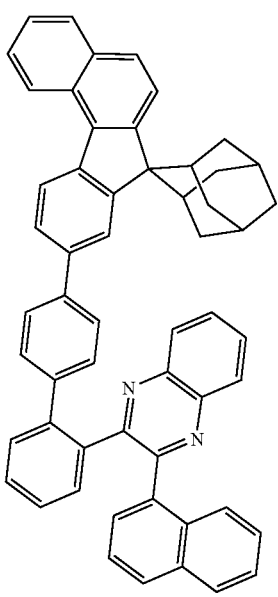
B-84
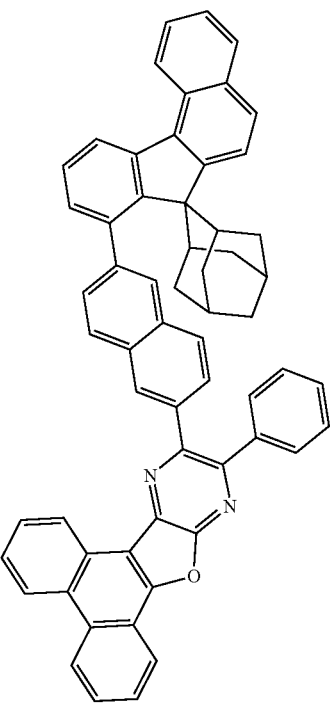
B-86

B-87
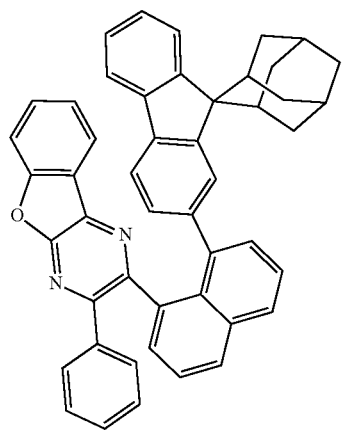
B-90
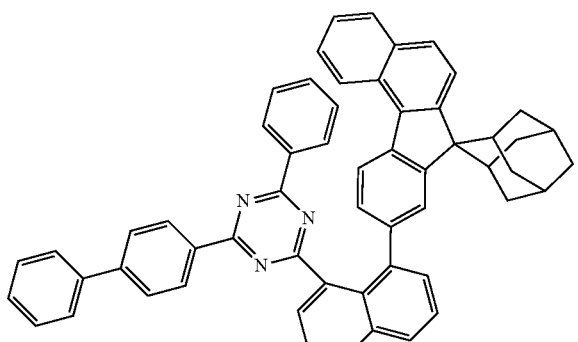
B-88
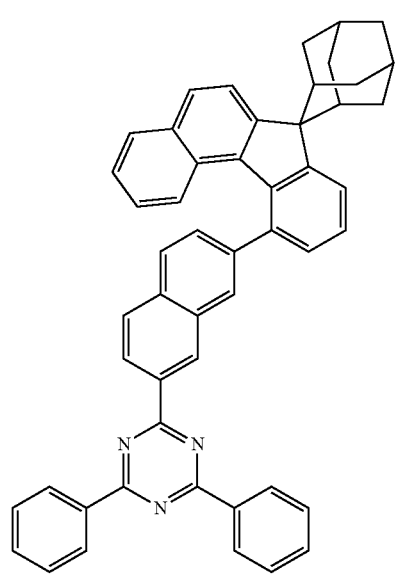
B-91
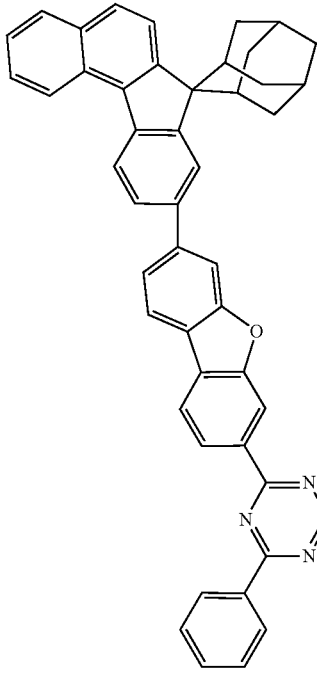
B-89
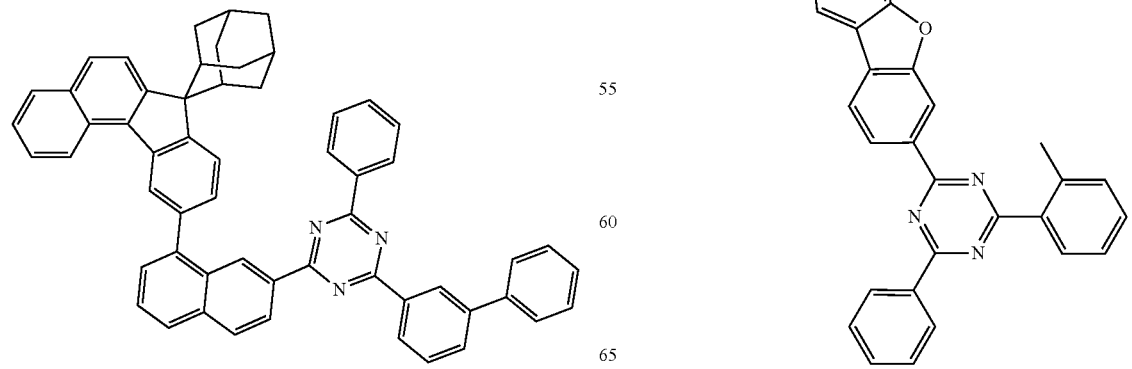

-continued
B-92
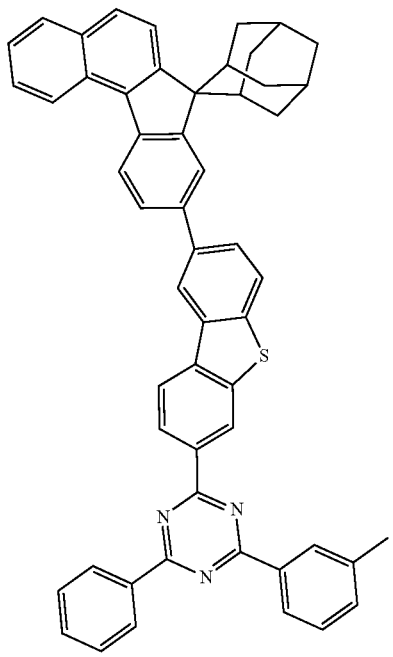
B-94
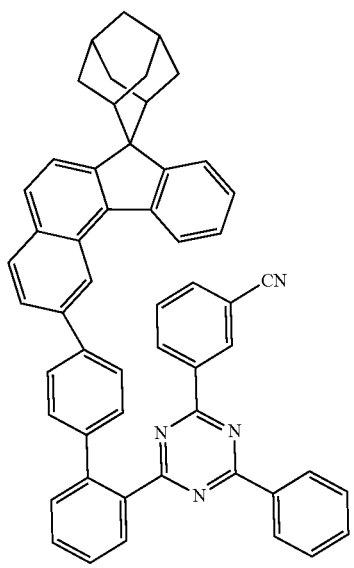
B-93
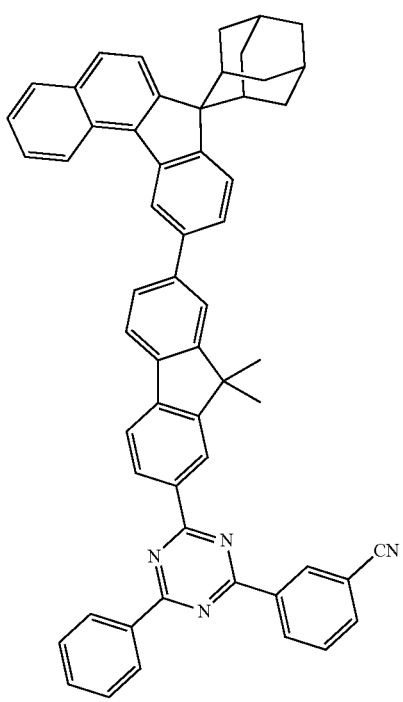
B-95
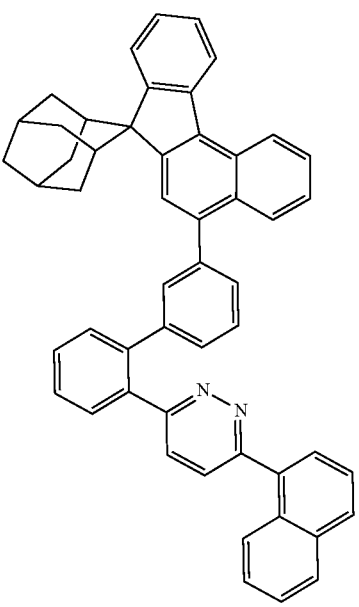

-continued
B-96
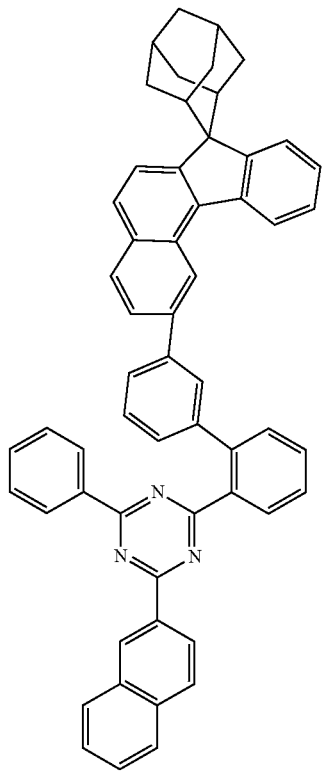
B-97
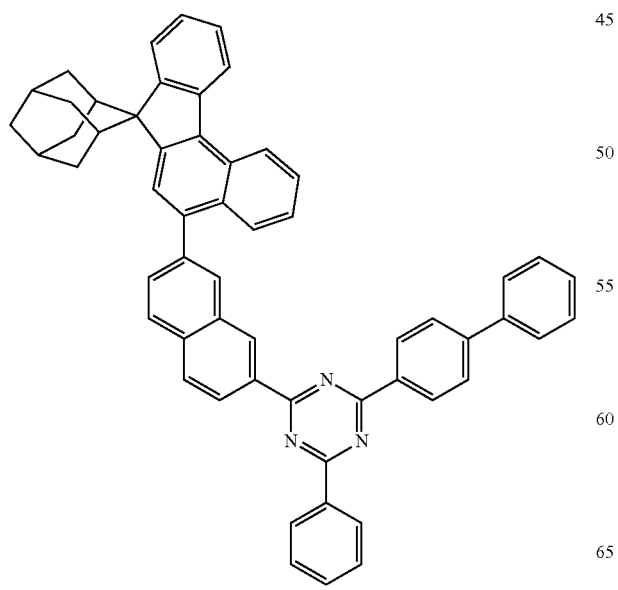
-continued
B-98
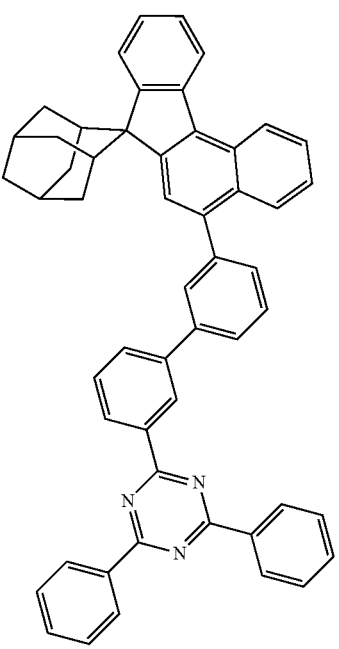
B-99
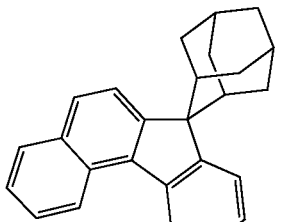
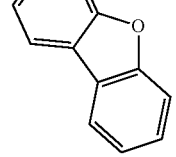

B-100
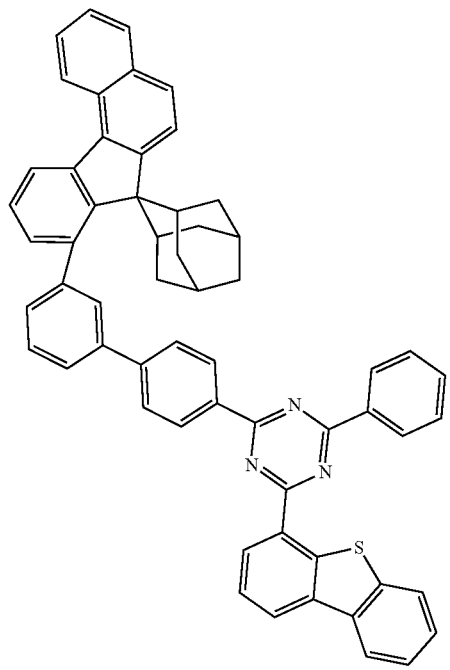
B-101
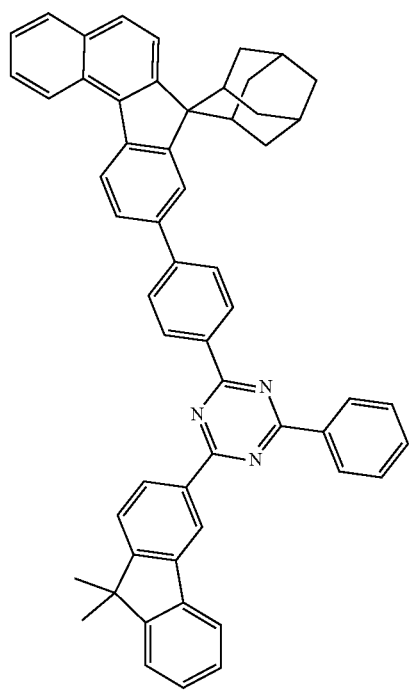
B-102
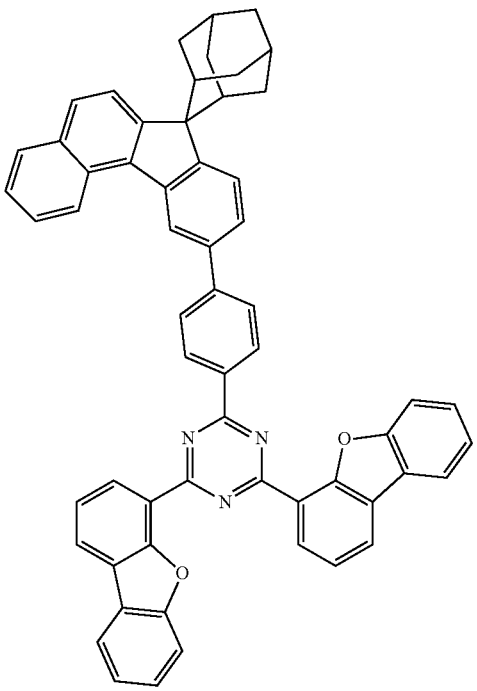
B-103
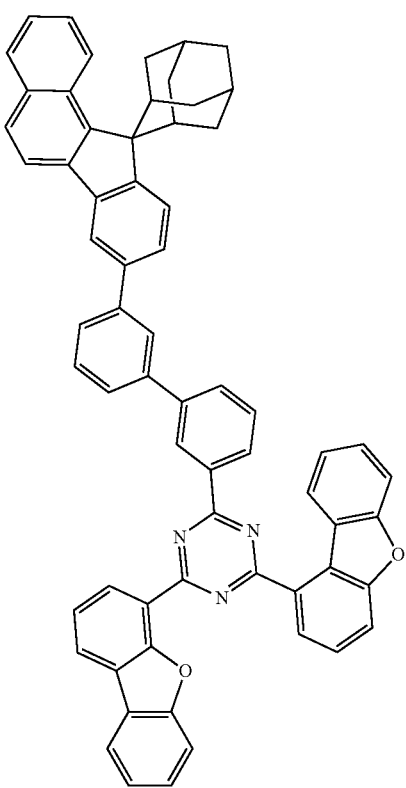

B-104
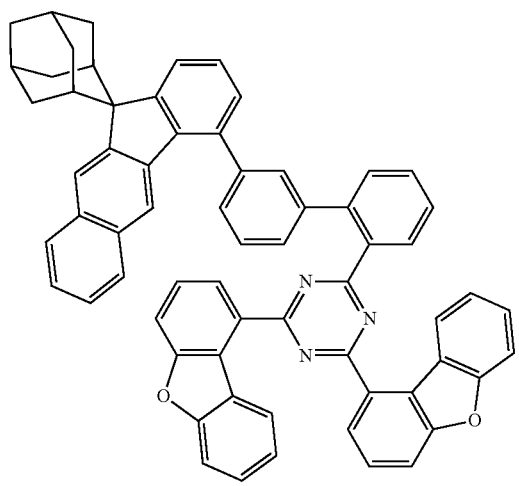
B-105
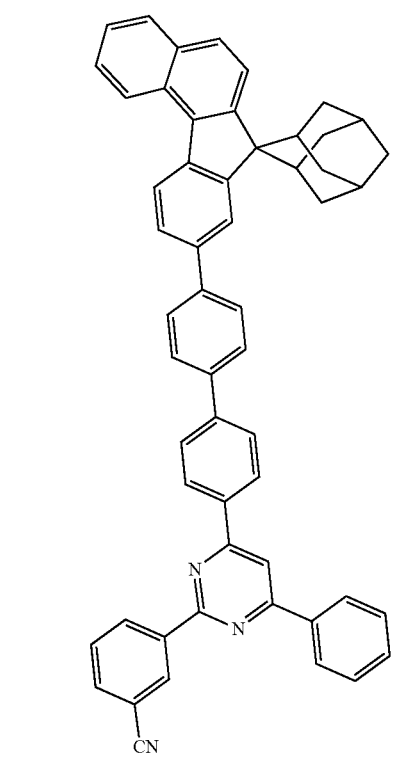
B-106
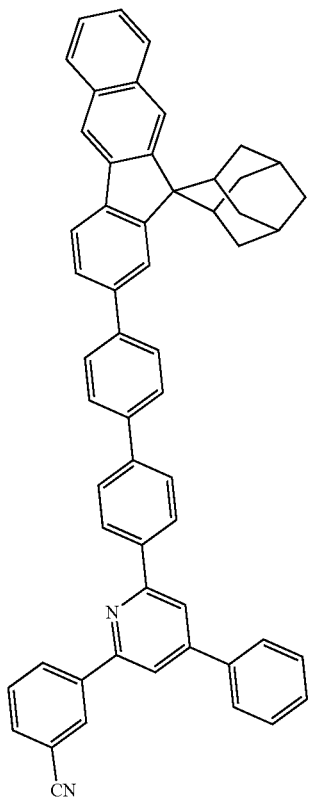
B-107
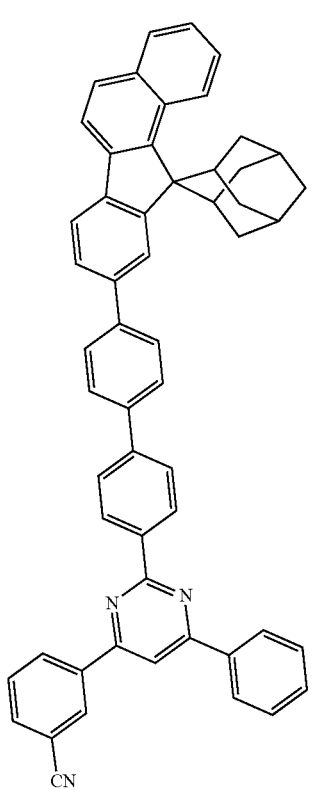

B-108
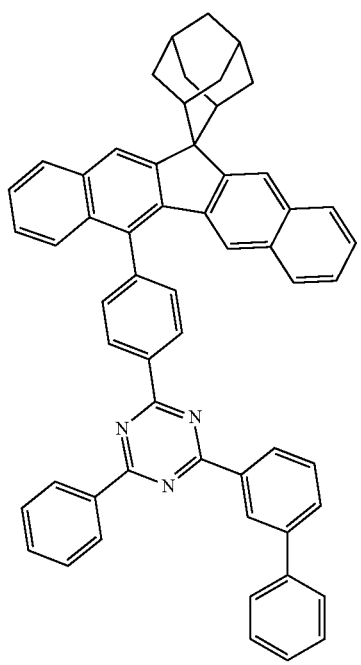
B-110
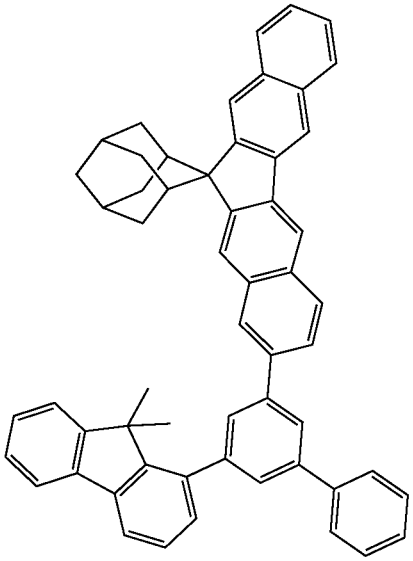
B-109
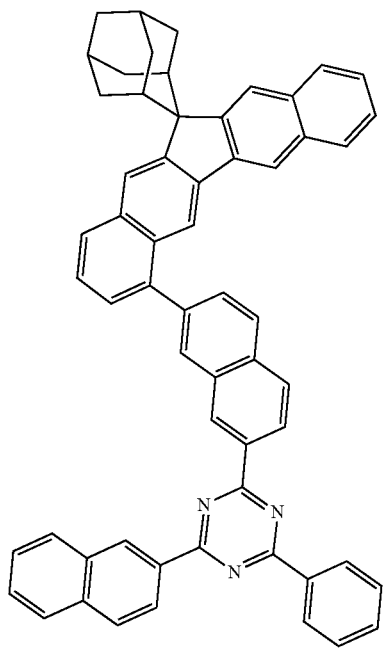
B-111
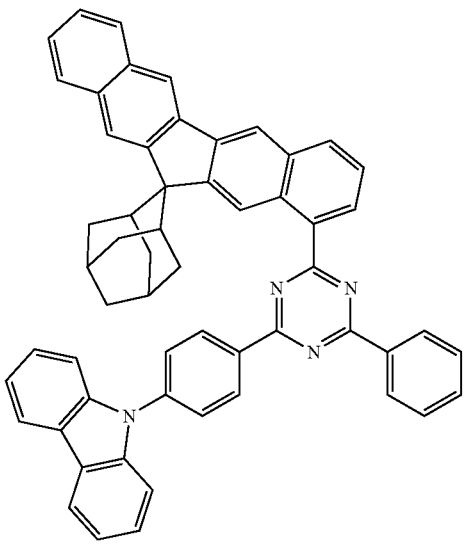

B-112
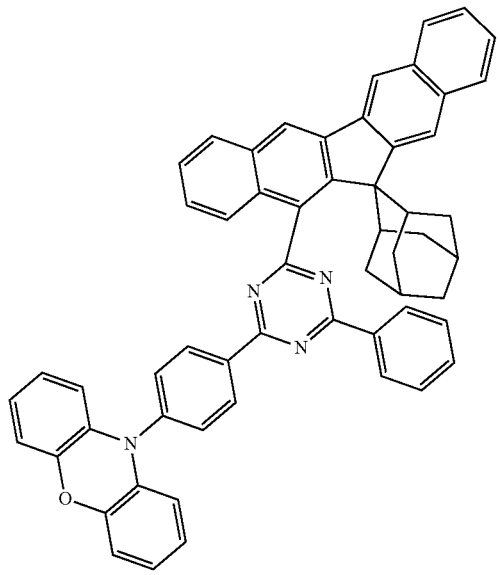
B-113
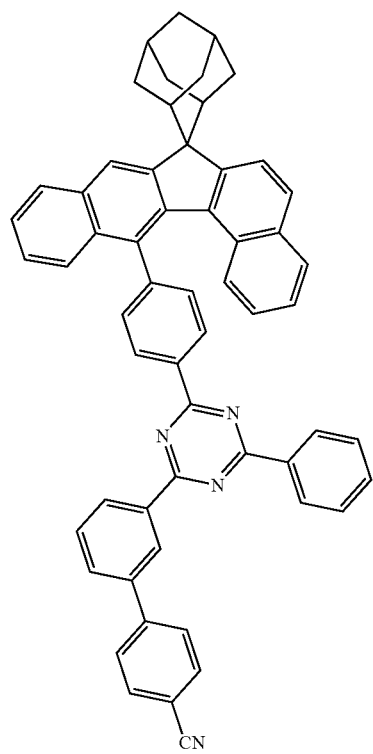
B-114
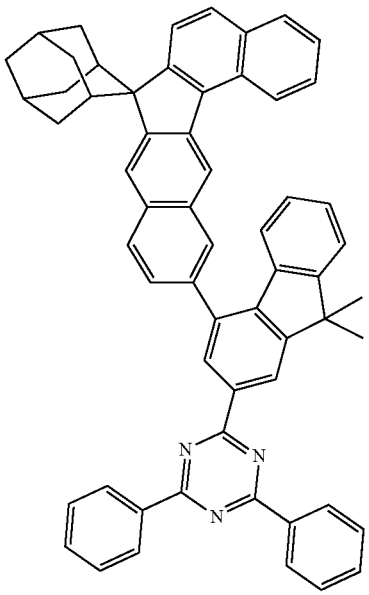
B-115
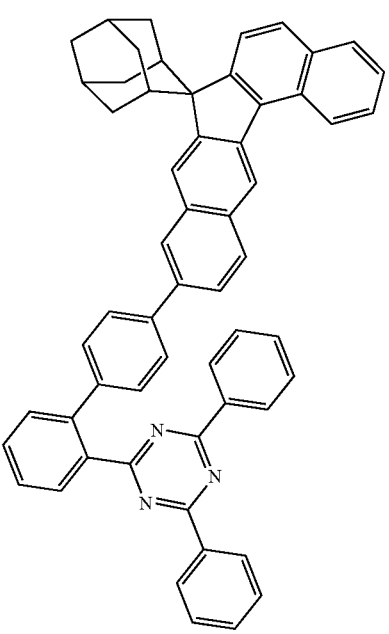

B-116
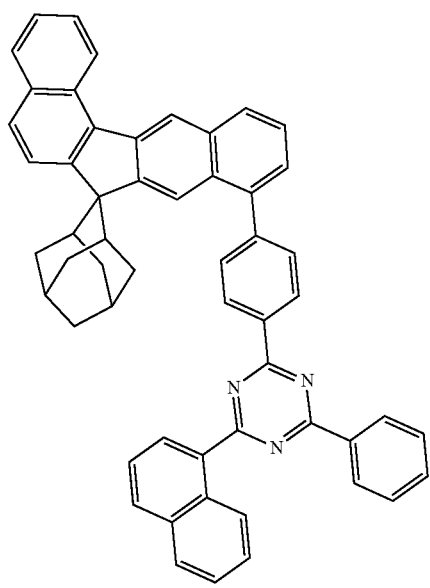
B-118
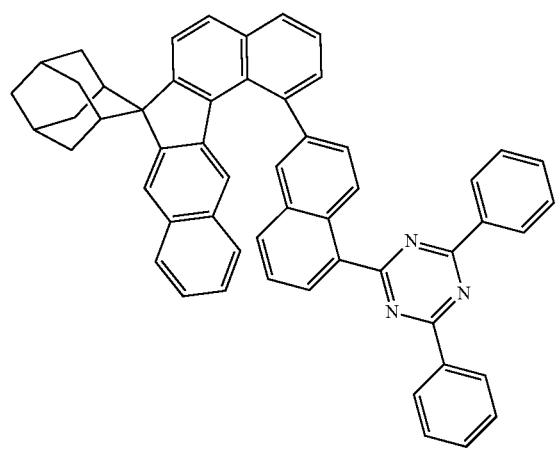
B-117
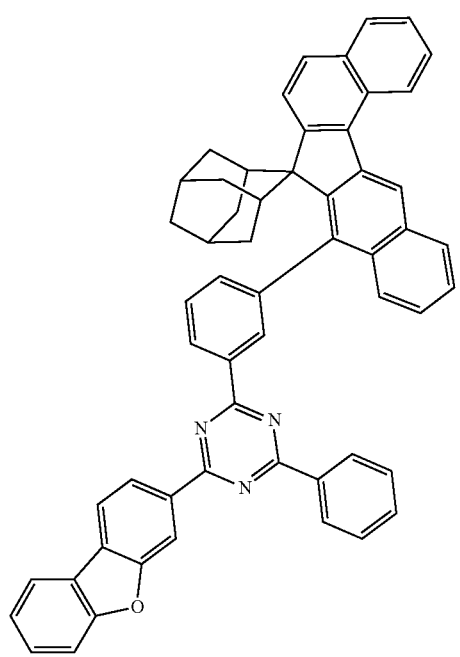
B-119

B-120
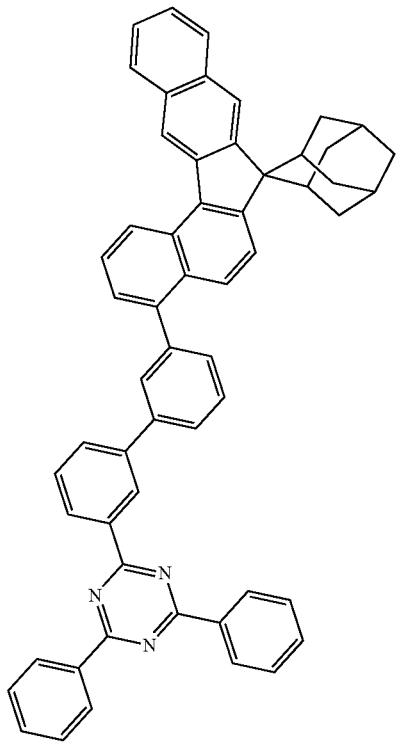
B-121
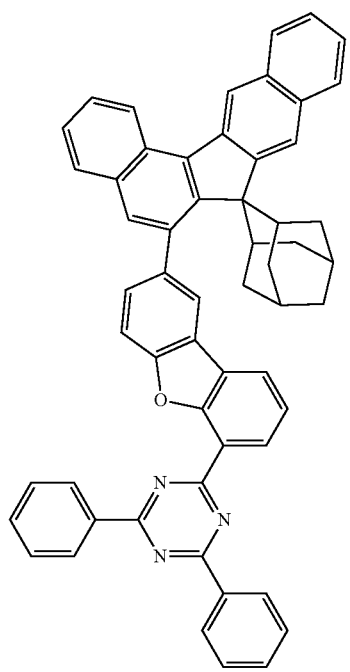
B-122
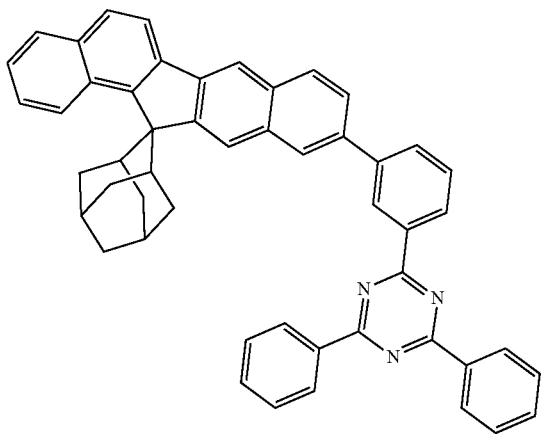
B-123
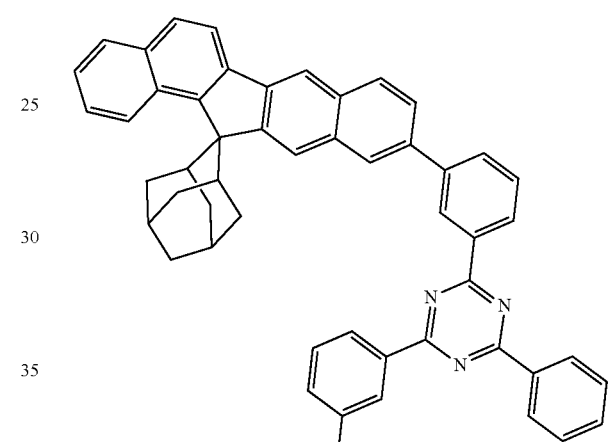
B-124
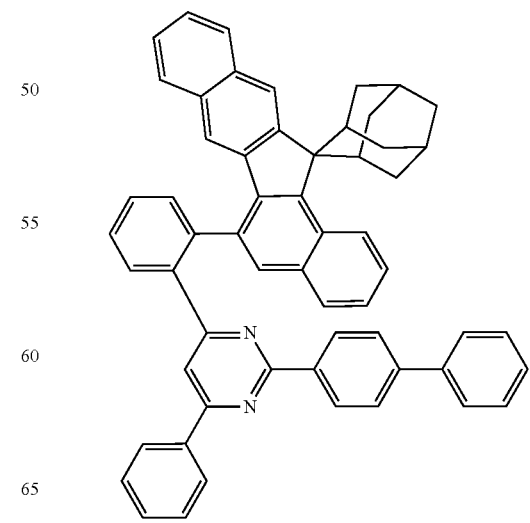

-continued
B-125
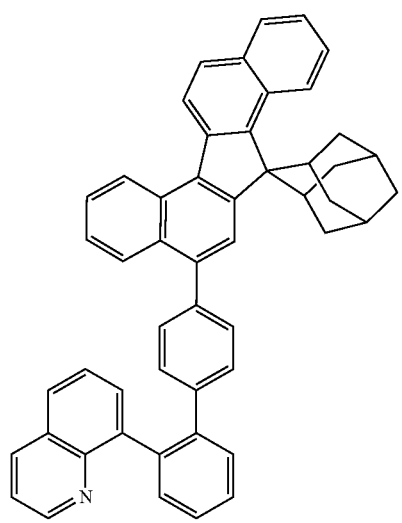
B-126
B-127
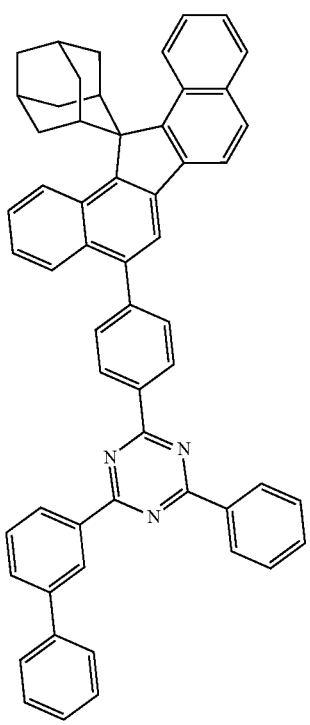
B-128
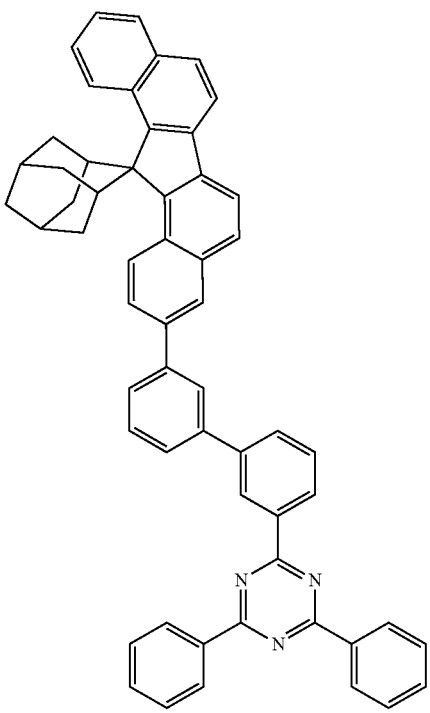

B-129
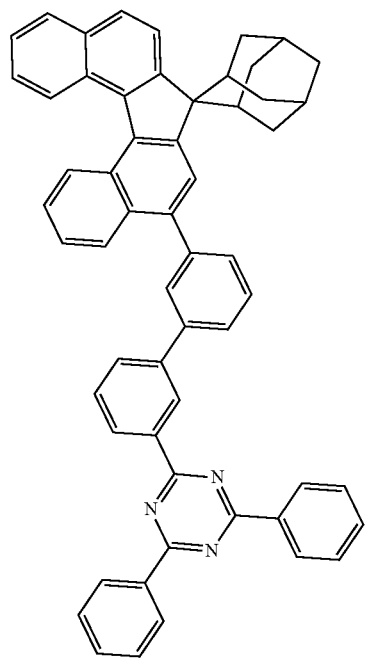
B-131
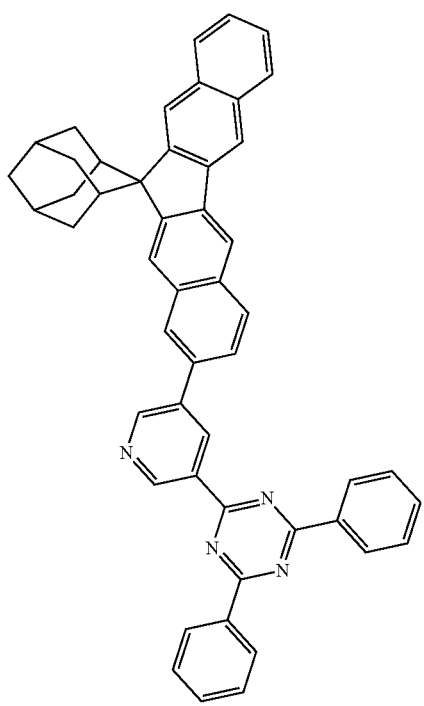
B-130
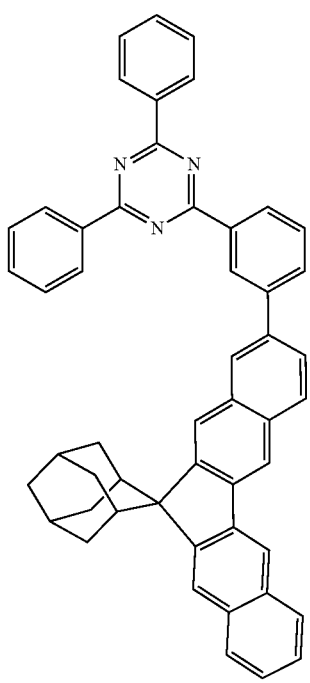
B-132
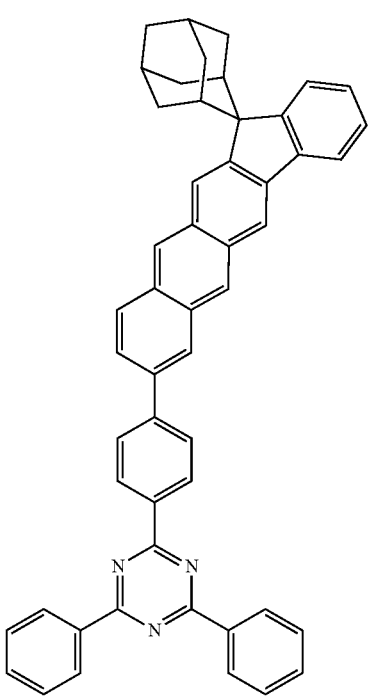

-continued
B-133
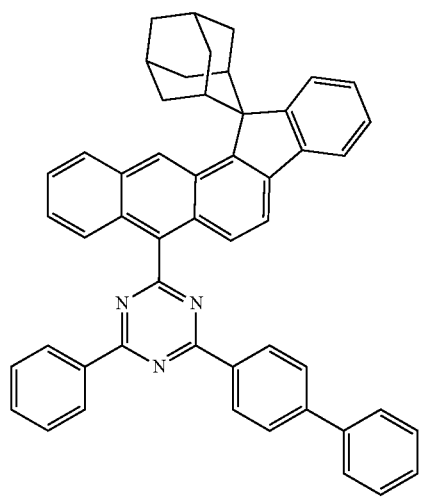
B-134
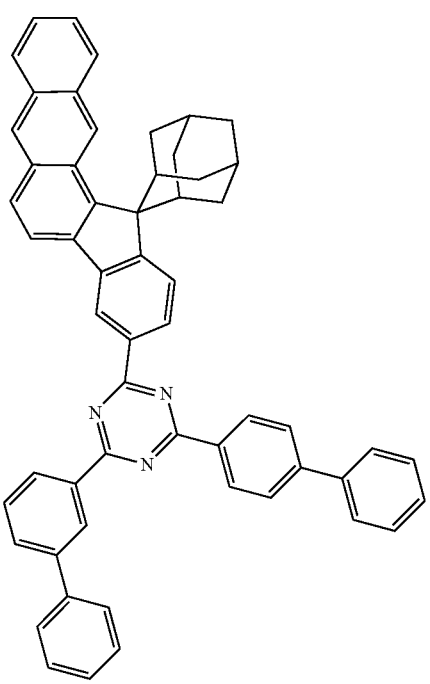
B-135
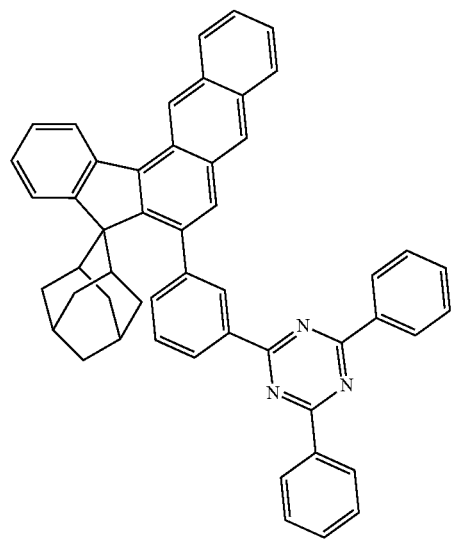
B-139
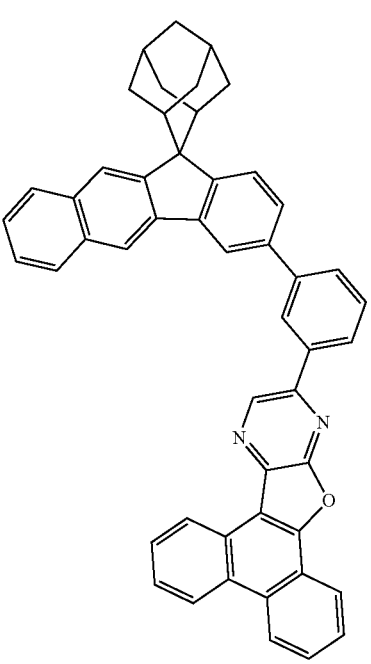

B-136
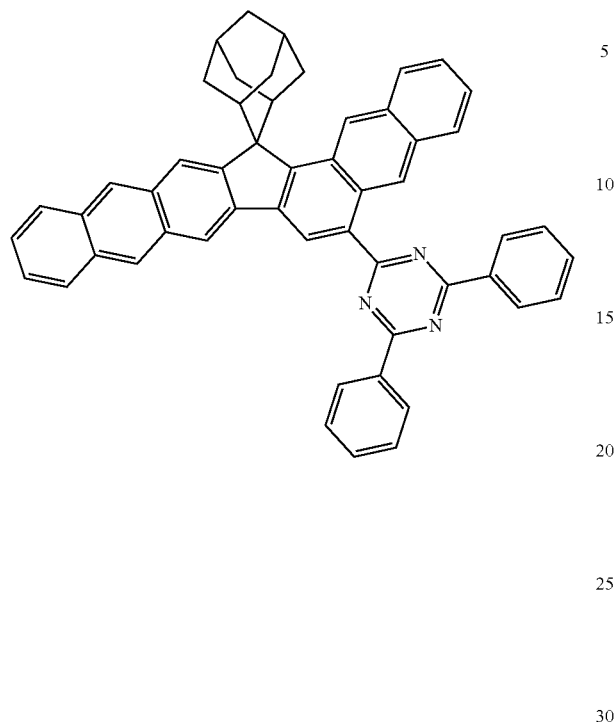
B-138
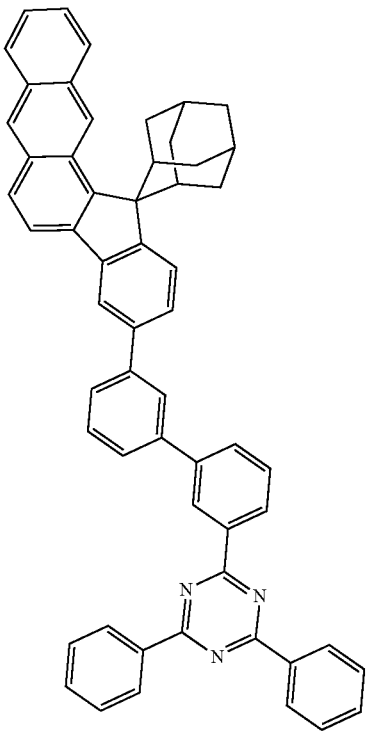
B-137
B-139'
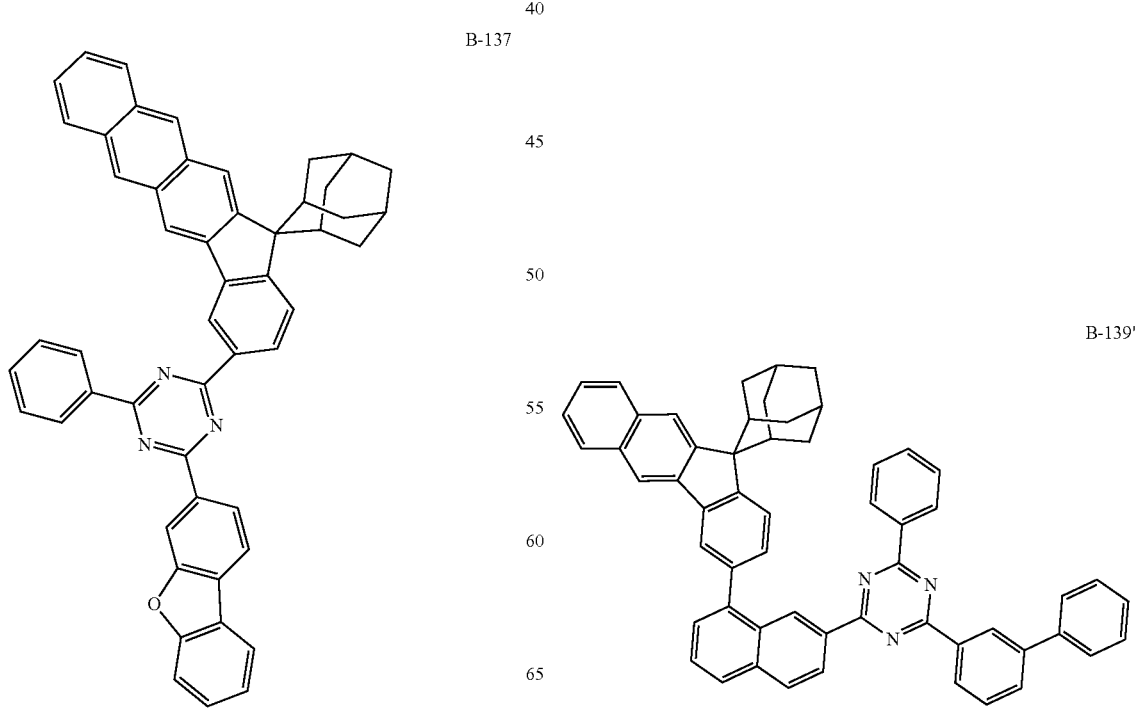

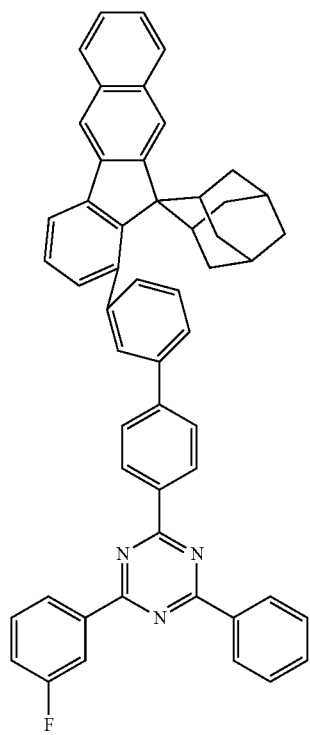
B-140
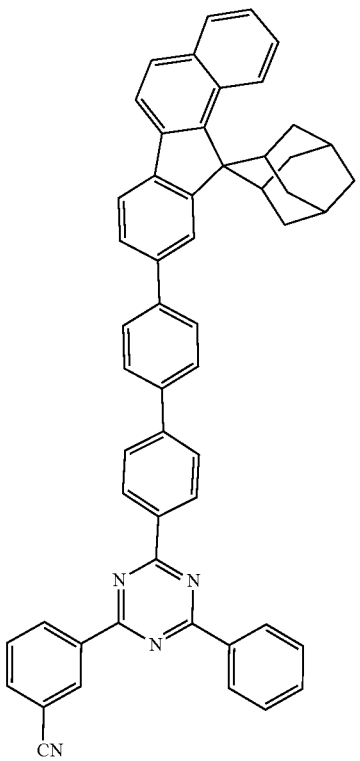
B-142
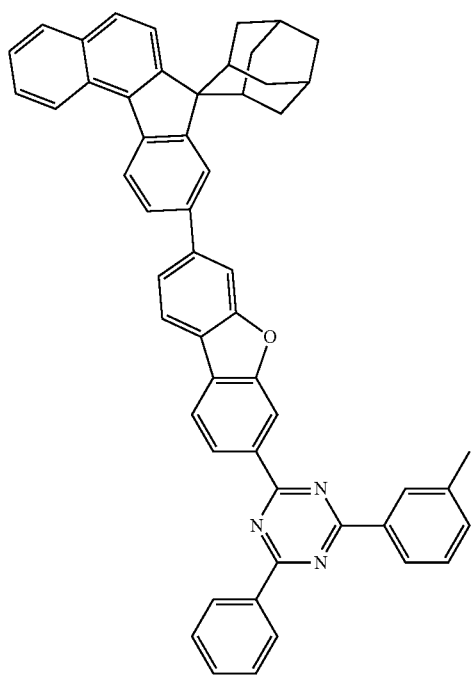
B-141
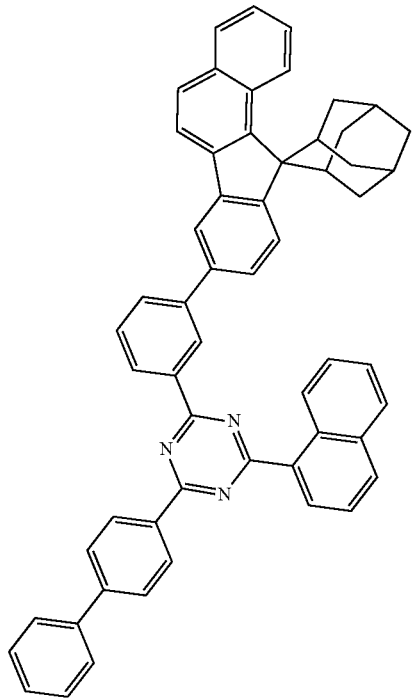
B-143

-continued

A-316

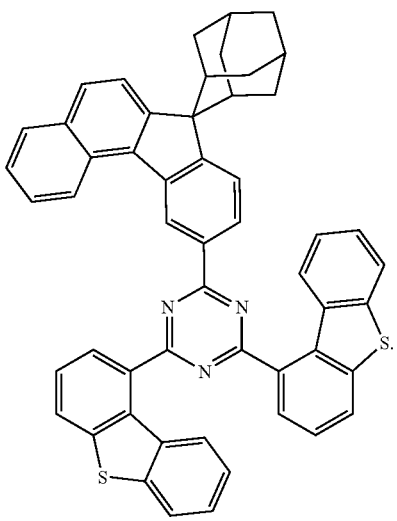

A synthesis method of the nitrogen-containing compound provided by the present disclosure is not specially limited, and those skilled in the art can determine a proper synthesis method according to the nitrogen-containing compound provided by the present disclosure in combination with a preparation method provided in the synthesis examples. In other words, the synthesis examples of the present disclosure exemplarily provide a preparation method of the nitrogen-containing compound, and the adopted raw materials can be obtained commercially or by a method well known in the field. All the nitrogen-containing compounds provided by the present disclosure can be obtained by those skilled in the art according to these exemplary preparation methods, and all specific preparation methods for preparing the nitrogen-containing compound are no longer detailed, which should not be understood by those skilled in the art as limiting the present disclosure.

In a second aspect, the present disclosure provides an electronic element, comprising an anode, a cathode which are arranged oppositely to the anode, and a functional layer arranged between the anode and the cathode; the functional layer contains the nitrogen-containing compound described in the first aspect of the present disclosure.

In one specific embodiment, the functional layer comprises an electron transport layer, and the electron transport layer contains the nitrogen-containing compound. The electron transport layer can be composed of the nitrogen-containing compound provided by the present disclosure, and can also be composed of the nitrogen-containing compound provided by the present disclosure and other materials. The electron transport layer can be one or two or more.

In one specific embodiment, the functional layer comprises a hole blocking layer, and the hole blocking layer contains the nitrogen-containing compound.

In one specific embodiment, the electronic element is an organic electroluminescent device or a photoelectric conversion device.

In one specific embodiment, the electronic element is an organic electroluminescent device, such as a blue light device or a green light device.

In one specific embodiment, the electronic element may be an organic electroluminescent device. As shown in FIG. 1, the organic electroluminescent device can comprise an anode 100, a hole injection layer 310, a hole transport layer 321, an electron blocking layer 322, an organic light-emitting layer 330 as an energy conversion layer, a hole blocking layer 341, an electron transport layer 340, an electron injection layer 350 and a cathode 200 which are sequentially stacked.

Optionally, the anode 100 contains the following anode materials. Preferably, it is a material having a large work function that facilitate hole injection into the functional layer. Specific examples of the anode materials comprise metals such as nickel, platinum, vanadium, chromium, copper, zinc, and gold, or an alloy thereof; metal oxides such as zinc oxide, indium oxide, indium tin oxide (ITO) and indium zinc oxide (IZO); combined metals and oxides, such as ZnO:Al or SnO$_2$:Sb; or a conductive polymer such as poly(3-methylthiophene), poly[3,4-(ethylene-1,2-dioxy)thiophene] (PEDT), polypyrrole, and polyaniline, but are not limited thereto. It is preferable to include a transparent electrode containing indium tin oxide (ITO) as the anode.

Optionally, the hole transport layer 321 and the electron blocking layer 322 respectively contain one or more hole transport materials, and the hole transport materials can be selected from a carbazole polymer, carbazole connected triarylamine compounds or other types of compounds, which are not specially limited in the present disclosure. For example, the hole transport layer 321 may be composed of a compound NPB or a compound HT-01, and the electron blocking layer 322 may contain a compound EB-01 or EB-02.

Optionally, the organic light-emitting layer 330 can be composed of a single light-emitting material, and can also contain a host material and a doping material. Optionally, the organic light-emitting layer 330 is composed of a host material and a doping material, holes injected into the organic light-emitting layer 330 and electrons injected into the organic light-emitting layer 330 can be recombined in the organic light-emitting layer 330 to form excitons, the excitons transfer energy to the host material, the host material transfers energy to the doping material, which in turn enables the doping material to emit light.

The host material of the organic light-emitting layer 330 can be a metal chelated compound, a distyryl derivative, an aromatic amine derivative, a dibenzofuran derivative or other types of materials, which is not specially limited in the present disclosure. In one embodiment of the present disclosure, the host material of the organic light-emitting layer 330 can be BH-01 or a mixed host material, such as a GH-n1 and GH-n2 mixed host material.

The doping material of the organic light-emitting layer 330 can be a compound having a condensed aryl ring or a derivative thereof, a compound with a heteroaryl ring or a derivative thereof, an aromatic amine derivative or other materials, which is not specially limited in the present disclosure. In one embodiment of the present disclosure, the doping material of the organic light-emitting layer 330 may be BD-01 or Ir(ppy)$_3$.

The electron transport layer 340 can be of a single-layer structure or a multi-layer structure and can contain one or more electron transport materials, and the electron transport materials can be selected from but are not limited to a benzimidazole derivative, an oxadiazole derivative, a quinoxaline derivative or other electron transport materials. In one embodiment of the present present disclosure, the electron transport layer material contains the nitrogen-containing compound provided in the present disclosure.

In the present disclosure, the specific structures of compounds such as EB-01, EB-02, BH-01, BD-01, GH-n1, GH-n2, ET-01 and the like are shown in the following examples, which will not be repeated here.

In the present disclosure, the cathode 200 may contain a cathode material, which is a material with a small work function that contributes to electron injection into the functional layer. Specific embodiments of the cathode material contain, but are not limited to, metals such as magnesium, calcium, sodium, potassium, titanium, indium, yttrium, lithium, gadolinium, aluminum, silver, tin, and lead, or an alloy thereof; or a plurality of layers of materials such as LiF/Al, Liq/Al, $LiO_2$/Al, LiF/Ca, LiF/Al, and $BaF_2$/Ca. It is preferable to include a metal electrode containing magnesium and silver as the cathode.

Optionally, as shown in FIG. 1, a hole injection layer 310 is arranged between the anode 100 and the hole transport layer 321 to enhance the ability of injecting holes into the hole transport layer 321. The hole injection layer 310 may be selected from a benzidine derivative, a starburst arylamine compound, a phthalocyanine derivative or other materials, which is not specially limited in the present disclosure. For example, the hole injection layer 310 may be composed of F4-TCNQ.

Optionally, as shown in FIG. 1, an electron injection layer 350 is arranged between the cathode 200 and the electron transport layer 340 to enhance the ability of injecting electrons into the electron transport layer 340. The electron injection layer 350 may include an inorganic material such as an alkali metal sulfide, and an alkali metal halide, or may contain a complex of an alkali metal and an organic substance. For example, the electron injection layer 350 may contain Yb.

Figure 3:
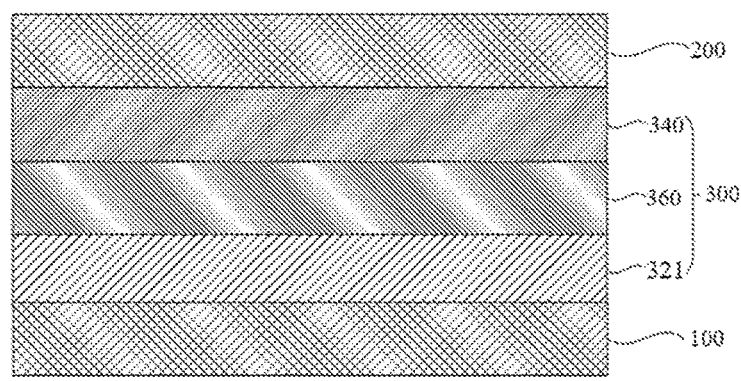
FIG. 3 is a structural schematic diagram of a photoelectric conversion device according to an embodiment of the present disclosure.

According to another embodiment, the electronic element may be a photoelectric conversion device. As shown in FIG. 3, the photoelectric conversion device can comprise an anode 100 and a cathode 200 which are oppositely arranged, and a functional layer 300 arranged between the anode 100 and the cathode 200; the functional layer 300 contains the nitrogen-containing compound provided in the present present disclosure.

According to one specific embodiment, as shown in FIG. 3, the photoelectric conversion device can comprise an anode 100, a hole transport layer 321, a photoelectric conversion layer 360, an electron transport layer 340 and a cathode 200 which are sequentially stacked.

Optionally, the photoelectric conversion device can be a solar cell, especially an organic thin-film solar cell. For example, in one example of the present disclosure, the solar cell can include an anode, a hole transport layer, a photoelectric conversion layer, an electron transport layer and a cathode which are sequentially stacked, and the photoelectric conversion layer contains the nitrogen-containing compound provided of the present disclosure.

In a third aspect, the present disclosure provides an electronic device, which includes the electronic element in the second aspect of the present disclosure.

Figure 2:
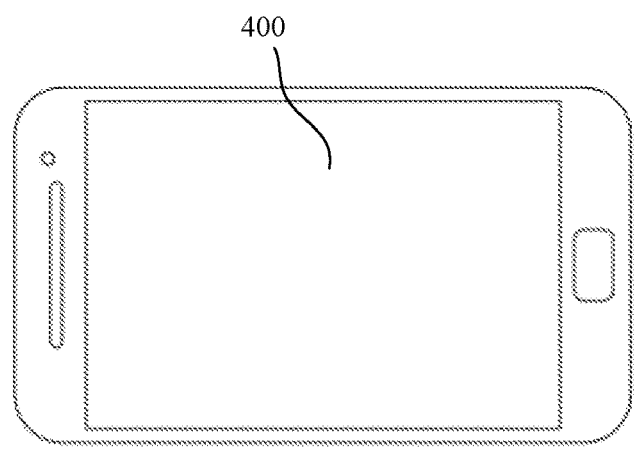
FIG. 2 is a structural schematic diagram of a first electronic device according to an embodiment of the present disclosure.

According to one embodiment, as shown in FIG. 2, the electronic device is a first electronic device 400, and the first electronic device 400 comprises the organic electroluminescent device. The first electronic device 400 may be a display device, a lighting device, an optical communication device or other types of electronic devices, for example, it may include, but is not limited to, a computer screen, a mobile phone screen, a television, electronic paper, an emergency lighting lamp, an optical module and the like.

Figure 4:
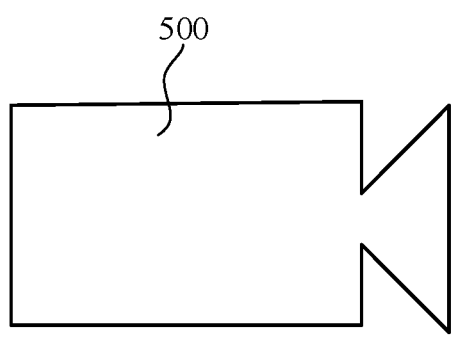
FIG. 4 is a structural schematic diagram of a second electronic device according to an embodiment of the present disclosure.

According to another embodiment, as shown in FIG. 4, the electronic device is a second electronic device 500, and the second electronic device 500 comprises the photoelectric conversion device. The second electronic device 500 may, for example, be a solar power plant, a light detector, a fingerprint identification device, a light module, a CCD camera, or other types of electronic devices.

The synthesis method of the nitrogen-containing compound of the present disclosure is specifically described below in combination with the synthesis examples, but the present disclosure is not limited thereby.

The compounds in the synthesis method which are not mentioned in the present disclosure are all commercially available raw material products.

An ICP-7700 mass spectrometer and an M5000 elemental analyzer are used for analysis and detection of intermediates and compounds in the present disclosure.

SYNTHETIC EXAMPLES

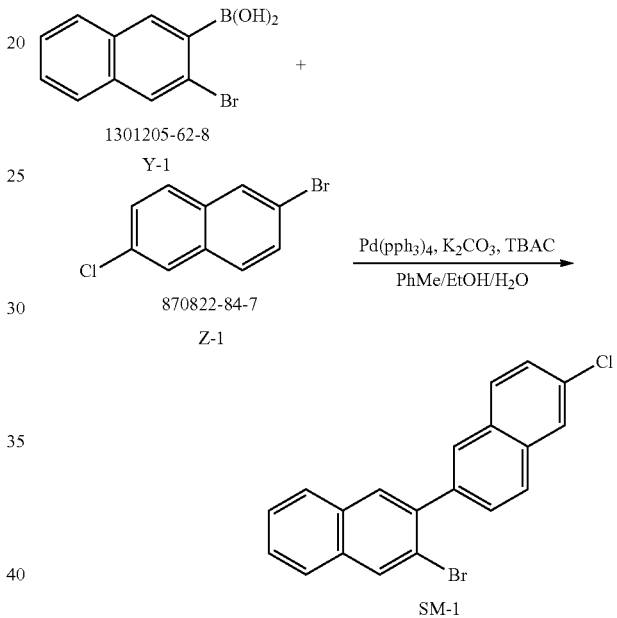

Y-1 (100 g, 398.5 mmol), Z-1 (96.3 g, 398.5 mmol), tetrakis(triphenylphosphine)palladium (2.3 g, 1.9 mmol), potassium carbonate (110.2 g, 797.1 mmol), tetrabutylammonium chloride (0.55 g, 1.9 mmol), toluene (800 mL), ethanol (400 mL) and deionized water (200 mL) were added into a three-necked flask, under the protection of nitrogen, the reaction solution was raised to 78° C. and stirred for 6 h; the resulting reaction solution was cooled to room temperature, toluene (300 mL) was added for extraction, organic phases were combined, dried with anhydrous magnesium sulfate, and filtered to obtain a filtrate, and the filtrate was concentrated under reduced pressure to obtain a crude product; and the obtained crude product was purified by silica gel column chromatography using n-heptane as a mobile phase, and then purified through recrystallization by using a dichloromethane/n-heptane system (a volume ratio of 1:3) to obtain SM-1 (112.8 g, yield: 77%).

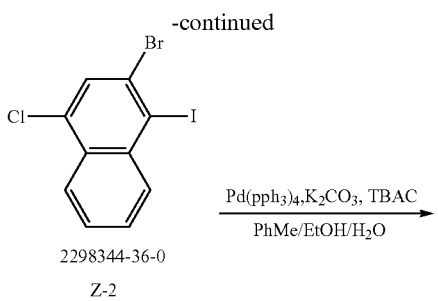

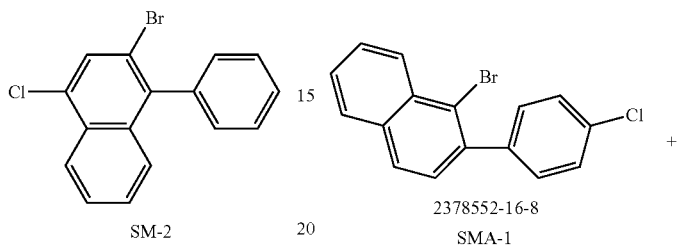

Y-2 (32.9 g, 272.2 mmol), Z-2 (100 g, 272.2 mmol), tetrakis(triphenylphosphine)palladium (9.4 g, 8.2 mmol), potassium carbonate (112.8 g, 816.5 mmol), tetrabutylammonium chloride (0.75 g, 2.72 mmol), toluene (800 mL), ethanol (400 mL) and deionized water (200 mL) were added into a three-necked flask, under the protection of nitrogen, the reaction solution was raised to 78° C., and stirred for 8 h; the resulting reaction solution was cooled to room temperature, toluene (300 mL) was added for extraction, organic phases were combined, dried with anhydrous magnesium sulfate, and filtered to obtain a filtrate, and the filtrate was concentrated under reduced pressure to obtain a crude product; and the obtained crude product was purified through recrystallization by using a dichloromethane/n-heptane system (a volume ratio of 1:3) to obtain SM-2 (64.8 g, yield: 75%).

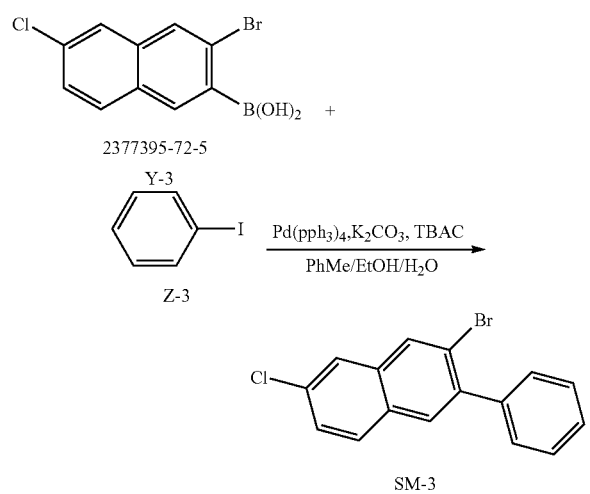

Y-3 (100 g, 350.5 mmol), Z-3 (71.5 g, 350.5 mmol), tetrakis(triphenylphosphine)palladium (12.1 g, 10.5 mmol), potassium carbonate (145.3 g, 1051.5 mmol), tetrabutylammonium chloride (0.97 g, 3.5 mmol), toluene (800 mL), ethanol (400 mL) and deionized water (200 mL) were added into a three-necked flask, under the protection of nitrogen, the reaction solution was raised to 78° C., and stirred for 6 h; the resulting reaction solution was cooled to room temperature, toluene (300 mL) was added for extraction, organic phases were combined, dried with anhydrous magnesium sulfate, and filtered to obtain a filtrate, and the filtrate was concentrated under reduced pressure to obtain a crude product; and the obtained crude product was purified by silica gel column chromatography using n-heptane as a mobile phase, and then purified through recrystallization by using a dichloromethane/n-heptane system (a volume ratio of 1:3) to obtain SM-3 (82.4 g, yield: 74%).

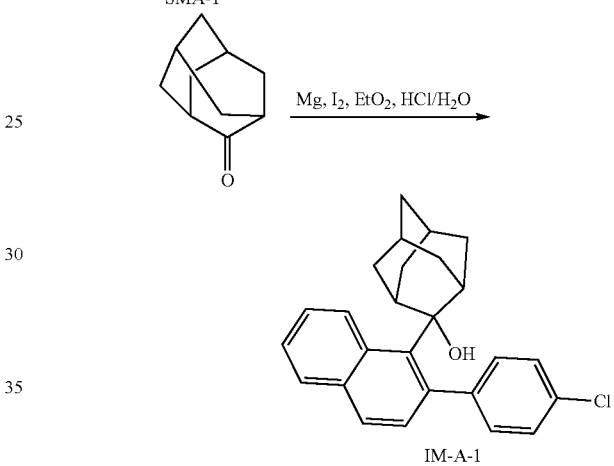

In a dry round-bottom flask, a magnesium ribbon (22.9, 944.5 mmol) and diethyl ether (250 mL) were placed under the protection of nitrogen, and 250 mg of iodine was added. Then, SMA-1 (100 g, 314.4 mmol) dissolved into diethyl ether (500 mL) was slowly dropped into the flask. After dropped, the temperature was raised to 35° C. and the reaction solution was stirred for 3 h; the resulting reaction solution was cooled to 0° C., the solution of adamantanone (37.8 g, 252 mmol) dissolved into diethyl ether (500 mL) was slowly added dropwise thereto. After the dropwise addition, the temperature was raised to 35° C., and stirred for 6 h; the resulting reaction solution was cooled to room temperature, and 5% hydrochloric acid was added into the reaction solution until a pH<7, and the stirring was performed for 1 h, diethyl ether (500 mL) was added into the reaction solution for extraction, organic phases were combined, dried with anhydrous magnesium sulfate, and filtered, and the solvent was removed under reduced pressure; and the obtained crude product was purified by silica gel column chromatography using n-heptane as a mobile phase to obtain a solid intermediate IM-A-1 (97.8 g, yield: 80%).

An intermediate IM-A-X was synthesized by adopting a method which is the same as intermediate IM-A-1, except that SMA-X (50 g) was used for replacing SMA-1 to prepare the intermediate IM-A-X, X can be 2 to 12, and the prepared intermediate IM-A-X is shown in Table 1.

TABLE 1
| SMA-X | Intermediate IM-A-X | Mass (g) | Yield (%) |
|---|---|---|---|
| 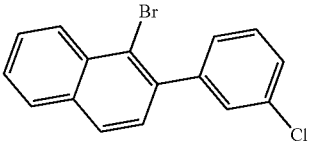 2378552-17-9 SMA-2 | 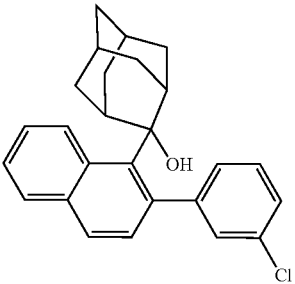 [SMILES: OC1(c2c(-c3cccc(Cl)c3)ccc3ccccc23)C2CC3CC(C2)CC1C3] IM-A-2 | 48.3 | 79 |
| 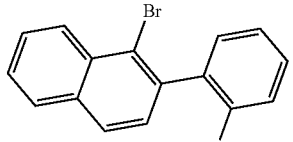 2378552-18-0 SMA-3 | 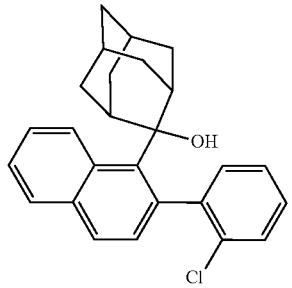 [SMILES: OC1(c2c(-c3ccccc3Cl)ccc3ccccc23)C2CC3CC(C2)CC1C3] IM-A-3 | 47.1 | 77 |
| 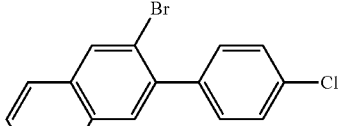 1421694-50-9 SMA-4 | 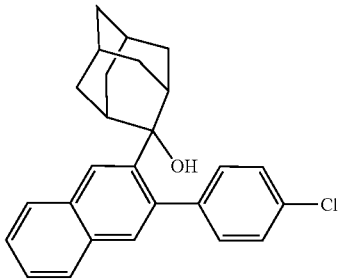 [SMILES: OC1(c2cc3ccccc3cc2-c2ccc(Cl)cc2)C2CC3CC(C2)CC1C3] IM-A-4 | 46.5 | 76 |
| 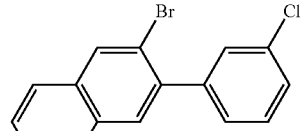 2378552-14-6 SMA-5 | 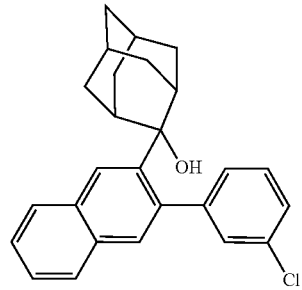 [SMILES: OC1(c2cc3ccccc3cc2-c2cccc(Cl)c2)C2CC3CC(C2)CC1C3] IM-A-5 | 47.1 | 77 |
| 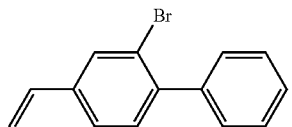 2378552-15-7 SMA-6 | 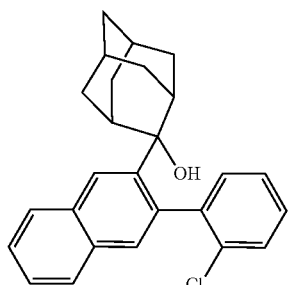 IM-A-6 | 45.9 | 75 |

TABLE 1-continued
| SMA-X | Intermediate IM-A-X | Mass (g) | Yield (%) |
|---|---|---|---|
| 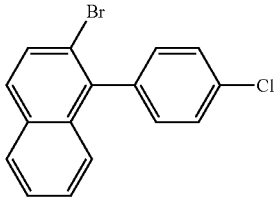<br>2378552-11-3<br>SMA-7 | 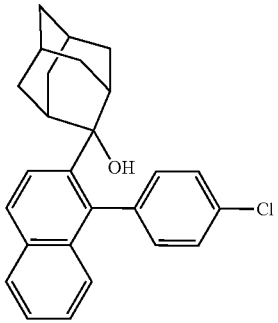 [SMILES: OC1(c2ccc3ccccc3c2-c2ccc(Cl)cc2)C2CC3CC(C2)CC1C3]<br>IM-A-7 | 45.3 | 74 |
| 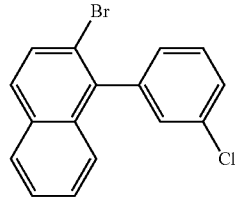<br>2378552-12-4<br>SMA-8 | 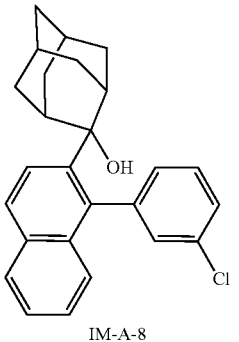<br>IM-A-8 | 47.7 | 78 |
| 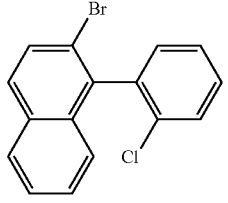<br>2378552-13-5<br>SMA-9 | 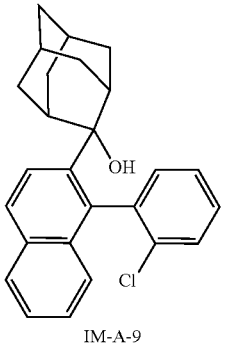<br>IM-A-9 | 47.1 | 77 |
| 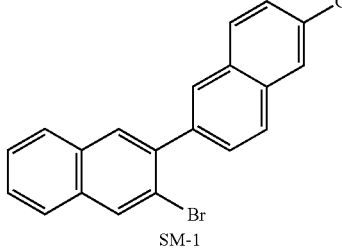<br>SM-1 | 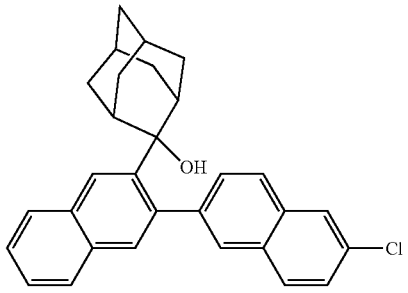 [SMILES: OC1(c2cc3ccccc3cc2-c2ccc3cc(Cl)ccc3c2)C2CC3CC(C2)CC1C3]<br>IM-A-10 | 46.6 | 78 |

TABLE 1-continued

| SMA-X | Intermediate IM-A-X | Mass (g) | Yield (%) |
|---|---|---|---|
| 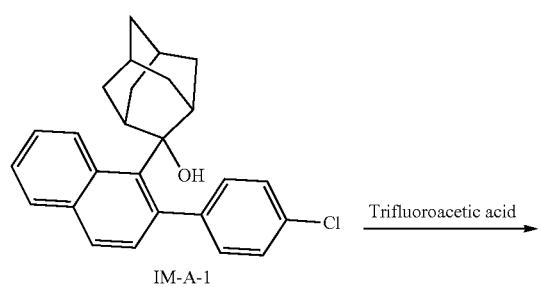 SM-2, SM-3 | IM-A-11 | 47.7 | 78 |
| | IM-A-12 | 47.1 | 77 |

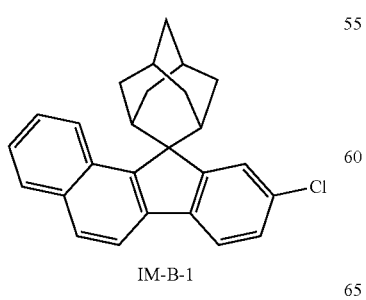

The intermediate IM-A-1 (40 g, 102.8 mmol) and trifluoroacetic acid (400 mL) were added into a reaction flask, stirring was started, then the mixture was gradually raised to 80° C., a reflux reaction was carried out for 12 h, after the reaction was completed, the resulting reaction solution was poured into water (in a volume ratio of 1:20), stirring was performed for 30 min, filtering was performed, drip washing was performed with water (in a volume ratio of 1:2), drip washing was performed with ethanol (in a volume ratio of 1:2), and the obtained crude product was recrystallized with dichloromethane and n-heptane in a volume ratio of 1:2 to obtain an intermediate IM-B-1 (30.5 g, yield: 80%).

An intermediate IM-B-X was synthesized by adopting a method which is the same as the method for synthesizing the intermediate IM-B-1, except that the intermediate IM-B-X and an intermediate IM-B-X-0 were prepared by replacing the intermediate IM-A-1 with the intermediate IM-A-X, X can be 2 to 12, and the prepared intermediate IM-B-X is shown in Table 2.

TABLE 2
| Intermediate IM-A-X | Intermediate IM-B-X | Mass (g) | Yield (%) |
|---|---|---|---|
| 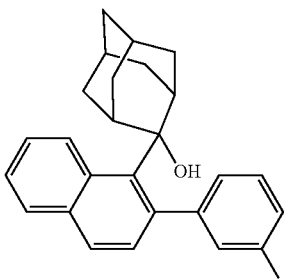 IM-A-2 | 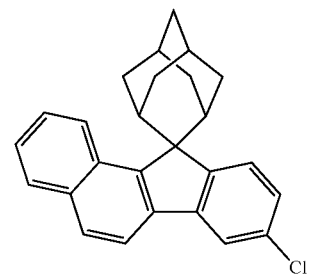 [SMILES: Clc1ccc2c(c1)-c1ccc3ccccc3c1C21C2CC3CC(C2)CC1C3] IM-B-2 | 17.1 | 41 |
|  | 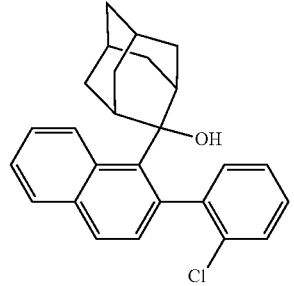 [SMILES: OC1(c2c(-c3ccccc3Cl)ccc3ccccc23)C2CC3CC(C2)CC1C3] IM-B-2-0 | 11.7 | 39 |
| 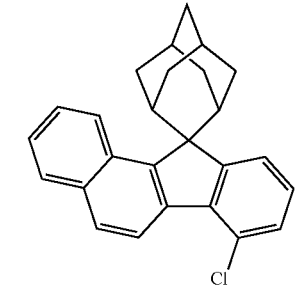 [SMILES: Clc1cccc2c1-c1ccc3ccccc3c1C21C2CC3CC(C2)CC1C3] IM-A-3 | 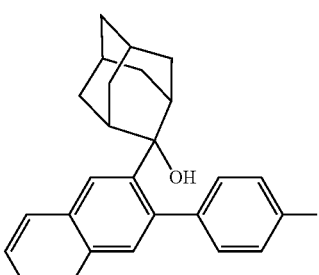 IM-B-3 | 24.4 | 81 |
| 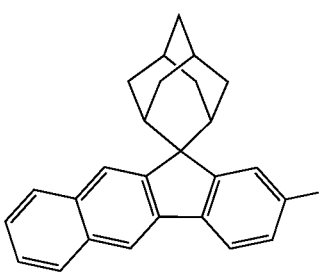 IM-A-4 | 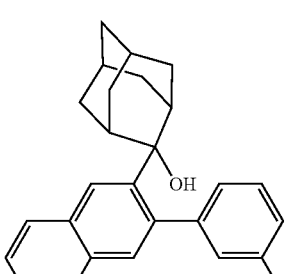 IM-B-4 | 24.9 | 83 |
| 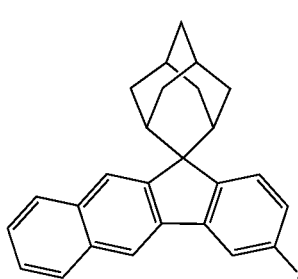 IM-A-5- | IM-B-5 | 11.4 | 38 |

TABLE 2-continued
| Intermediate IM-A-X | Intermediate IM-B-X | Mass (g) | Yield (%) |
|---|---|---|---|
| | 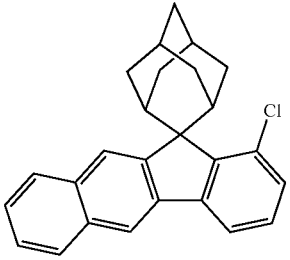 [SMILES: Clc1cccc2c1C1(c3cc4ccccc4cc3-2)C2CC3CC(C2)CC1C3]<br>IM-B-5-0 | 11.7 | 39 |
| 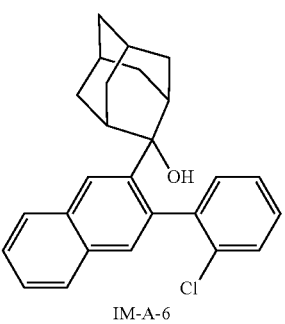<br>IM-A-6 | 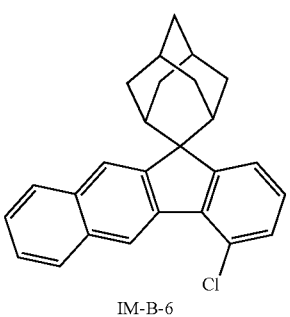<br>IM-B-6 | 25.3 | 84 |
| 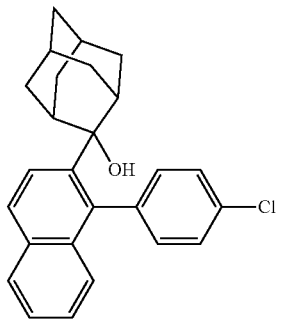 [SMILES: OC1(c2ccc3ccccc3c2-c2ccc(Cl)cc2)C2CC3CC(C2)CC1C3]<br>IM-A-7 | 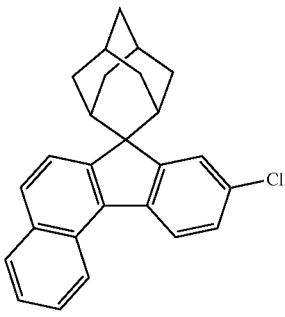 [SMILES: Clc1ccc2c(c1)C1(c3ccc4ccccc4c3-2)C2CC3CC(C2)CC1C3]<br>IM-B-7 | 24.9 | 83 |
| 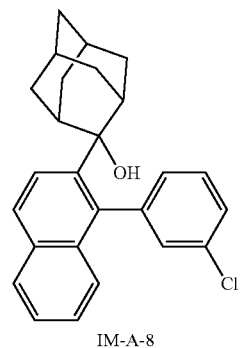<br>IM-A-8 | 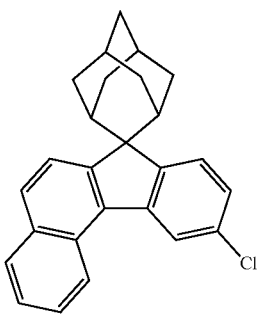 [SMILES: Clc1ccc2c(c1)-c1c(ccc3ccccc13)C21C2CC3CC(C2)CC1C3]<br>IM-B-8 | 11.4 | 38 |
| | 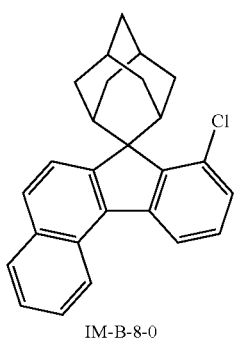<br>IM-B-8-0 | 11.1 | 37 |

TABLE 2-continued

| Intermediate IM-A-X | Intermediate IM-B-X | Mass (g) | Yield (%) |
|---|---|---|---|
| IM-A-9 | IM-B-9 | 24.6 | 82 |
| IM-A-10 | IM-B-10 | 31.4 | 82 |
| IM-A-11 | IM-B-11 | 25.3 | 84 |
| IM-A-12 | IM-B-12 | 24.9 | 83 |

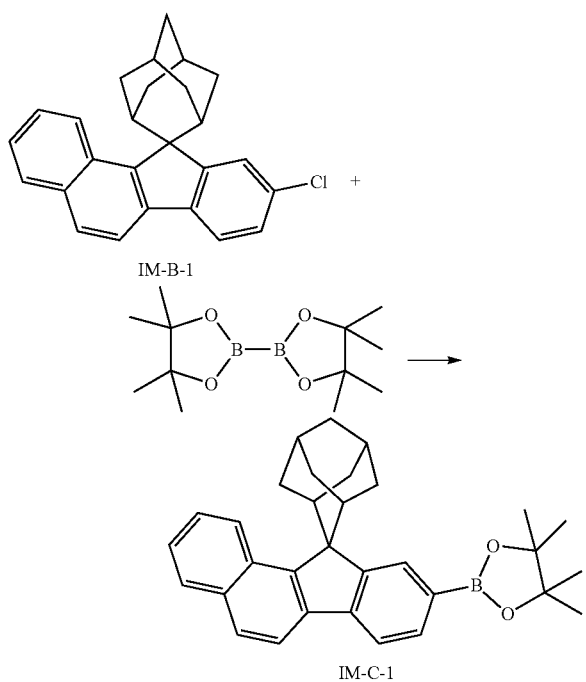

The intermediate IM-B-1 (15 g, 40.4 mmol), bis(pinacolato)diboron (10.3 g, 40.4 mmol), tris(dibenzylideneacetone)dipalladium (0.74 g, 0.81 mmol), 2-dicyclohexylphosphino-2,4,6-triisopropylbiphenyl (0.19 g, 0.40 mmol), potassium acetate (7.9 g, 80.8 mmol) and 1,4-dioxane (150 mL) were added into a reaction flask, under the protection of nitrogen, the reaction solution was raised to 110° C., and stirred under heating and refluxing for 5 h. The resulting reaction solution was cooled to room temperature, and extracted by using dichloromethane and water, an organic layer was dried with anhydrous magnesium sulfate, and filtered, the obtained filtrate was allowed to pass through a short silica gel column, the solvent was removed under reduced pressure, and the obtained crude product was purified through recrystallization by using a dichloromethane/n-heptane (a volume ratio of 1:3) system to obtain an intermediate IM-C-1 (14.0 g, yield: 75%).

An intermediate IM-C-X was synthesized by adopting a method which is the same as the method for synthesizing the intermediate IM-C-1, except that the intermediate IM-B-X was used for replacing the intermediate IM-B-1 to prepare the intermediate IM-C-X and an intermediate IM-C-X-0, X can be 1 to 12, and the prepared intermediate IM-C-X is shown in Table 3.

TABLE 3

| Intermediate IM-B-X | Intermediate IM-C-X | Mass (g) | Yield (%) |
|---|---|---|---|
| IM-B-2 | IM-C-2 | 14.0 | 75 |
| IM-B-2-0 | IM-C-2-0 | 13.6 | 73 |

TABLE 3-continued

| Intermediate IM-B-X | Intermediate IM-C-X | Mass (g) | Yield (%) |
|---|---|---|---|
| IM-B-3 | IM-C-3 | 13.3 | 71 |
| IM-B-4 | IM-C-4 | 13.8 | 74 |
| IM-B-5 | IM-C-5 | 13.6 | 73 |
| IM-B-5-0 | IM-C-5-0 | 14.2 | 76 |

TABLE 3-continued

| Intermediate IM-B-X | Intermediate IM-C-X | Mass (g) | Yield (%) |
|---|---|---|---|
| IM-B-6 | IM-C-6 | 13.6 | 73 |
| IM-B-7 | IM-C-7 | 13.8 | 74 |
| IM-B-8 | IM-C-8 | 14.0 | 75 |
| IM-B-8-0 | IM-C-8-0 | 13.8 | 74 |

TABLE 3-continued
| Intermediate IM-B-X | Intermediate IM-C-X | Mass (g) | Yield (%) |
|---|---|---|---|
| 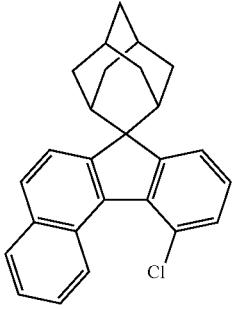 [SMILES: Clc1cccc2c1-c1c(ccc3ccccc13)C21C2CC3CC(C2)CC1C3] IM-B-9 | 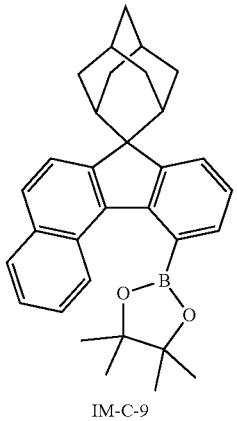 IM-C-9 | 14.2 | 76 |
| 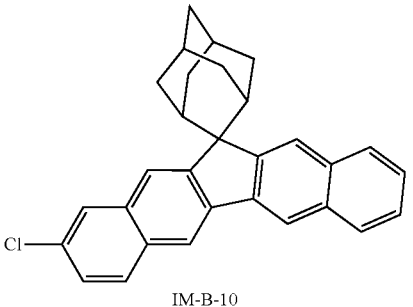 IM-B-10 | 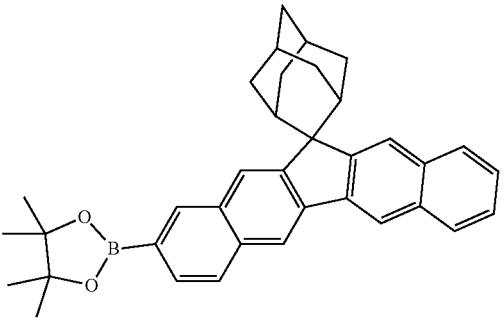 [SMILES: CC1(C)OB(c2ccc3cc4c(cc3c2)C2(c3cc5ccccc5cc3-4)C3CC4CC(C3)CC2C4)OC1(C)C] IM-C-10 | 13.6 | 75 |
| 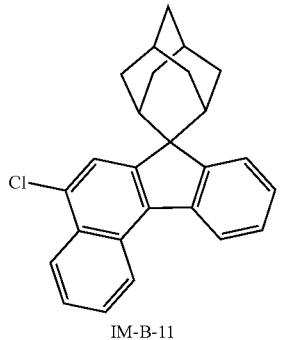 IM-B-11 | 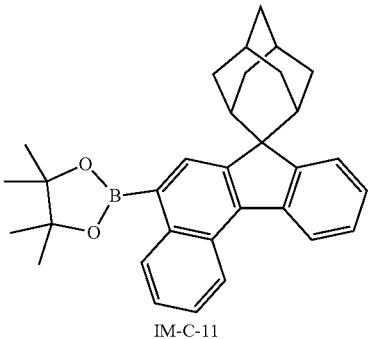 IM-C-11 | 13.6 | 73 |
| 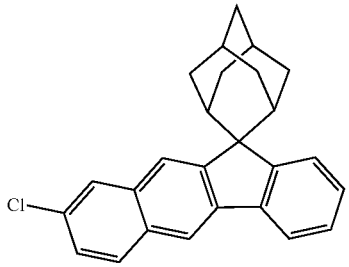 [SMILES: Clc1ccc2cc3c(cc2c1)C1(c2ccccc2-3)C2CC3CC(C2)CC1C3] IM-B-12 | 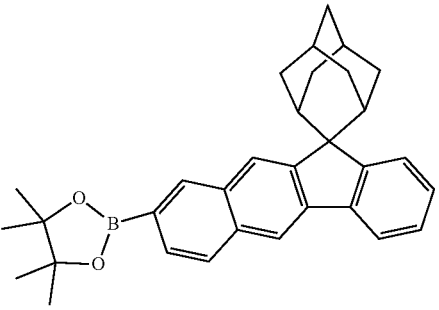 [SMILES: CC1(C)OB(c2ccc3cc4c(cc3c2)C2(c3ccccc3-4)C3CC4CC(C3)CC2C4)OC1(C)C] IM-C-12 | 13.8 | 74 |

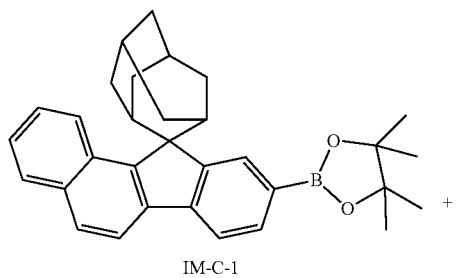

IM-C-1

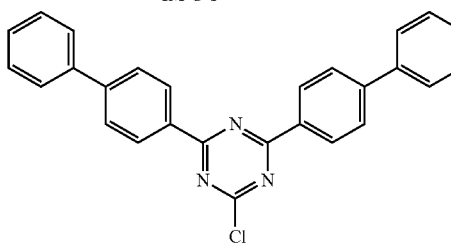

182918-13-4

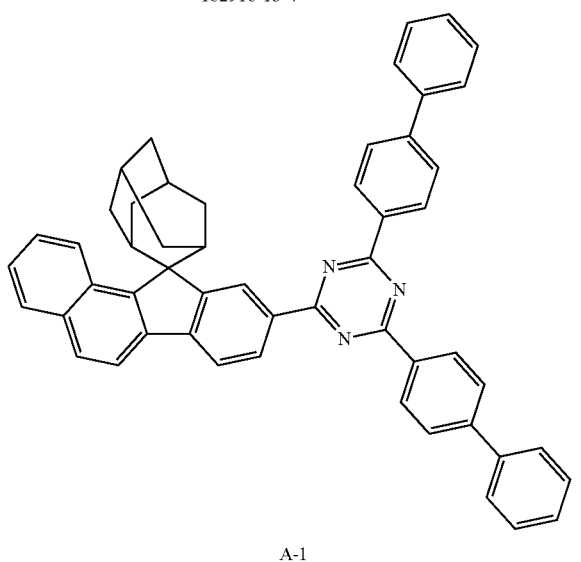

A-1

The intermediate IM-C-1 (5.00 g, 10.8 mmol), a raw material 1 (CAS. NO.: 182918-13-4) (5.46 g, 13.0 mmol), palladium acetate (0.12 g, 0.54 mmol), 2-dicyclohexylphosphino-2,4,6-triisopropylbiphenyl (0.26 g, 0.54 mmol), potassium carbonate (3.29 g, 23.8 mmol), toluene (40 mL), ethanol (20 mL) and water (10 mL) were added into a reaction flask, under the protection of nitrogen, the reaction solution was raised to 78° C., and stirred under heating and refluxing for 5 h. The resulting reaction solution was cooled to room temperature, and extracted by using dichloromethane and water, an organic layer was dried with anhydrous magnesium sulfate, and filtered, the obtained filtrate was allowed to pass through a short silica gel column, the solvent was removed under reduced pressure, and the obtained crude product was purified through recrystallization by using a dichloromethane/n-heptane (a volume ratio of 1:3) system to obtain a compound A-1 (6.24 g, yield: 80%). Mass spectrum: m/z=720.3[M+H]$^+$.

A compound A-X was synthesized by adopting a method which is the same as the method for synthesizing the compound A-1, except that the intermediate IM-C-X was used for replacing the intermediate IM-C-1, and a raw material M was used for replacing the raw material 1 (182918-13-4) to prepare the compound A-X or B-139. The prepared compounds A-X and B-139 are as shown in Table 4.

TABLE 4

| Intermediate IM-C-X | Raw Material M | Compound A-X | Mass (g)/yield (%)/mass spectrum |
|---|---|---|---|
| IM-C-2 | 1472062-94-4 | A-2 | 5.5/79/644.3 |

TABLE 4-continued
| Intermediate IM-C-X | Raw Material M | Compound A-X | Mass (g)/yield (%)/mass spectrum |
|---|---|---|---|
| | 2259346-78-4 | A-18 | 5.86/78/695.3 |
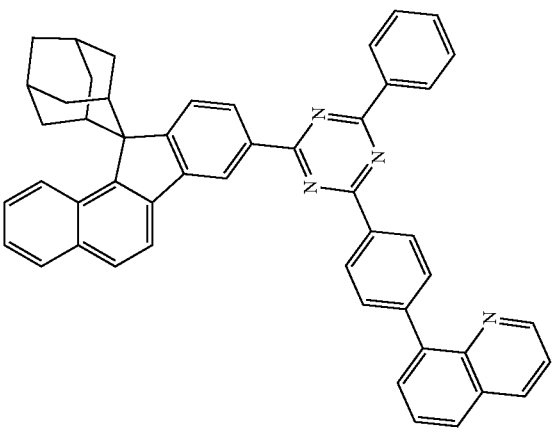

TABLE 4-continued
| Intermediate IM-C-X | Raw Material M | Compound A-X | Mass (g)/yield (%)/mass spectrum |
|---|---|---|---|
| 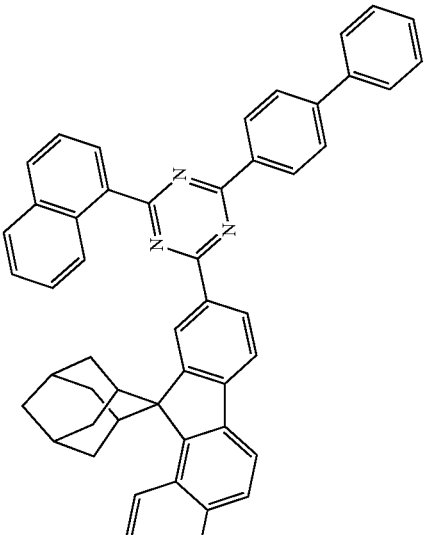 IM-C-1 | Naphthyl-triazine-biphenyl-Cl 2138467-53-3 | A-5 | 5.93/79/694.3 |

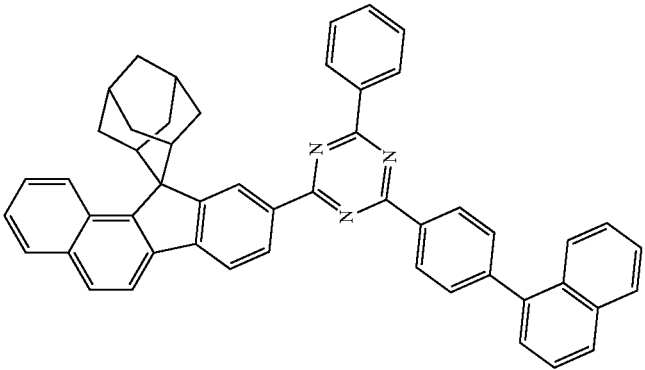

TABLE 4-continued

| Intermediate IM-C-X | Raw Material M | Compound A-X | Mass (g)/yield (%)/mass spectrum |
|---|---|---|---|
| IM-C-3 | 1689576-03-1 | A-10 | 5.43/78/644.3 |

TABLE 4-continued
| Intermediate IM-C-X | Raw Material M | Compound A-X | Mass (g)/yield (%)/mass spectrum |
|---|---|---|---|
| 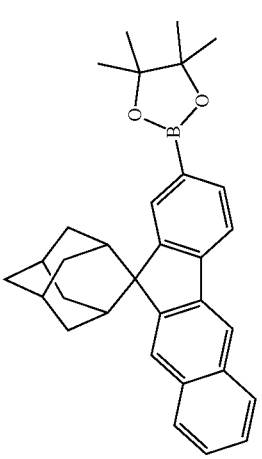<br>IM-C-4 | 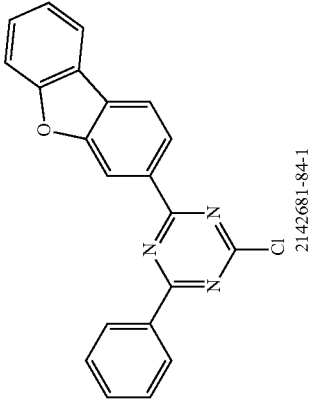<br>2142681-84-1 | 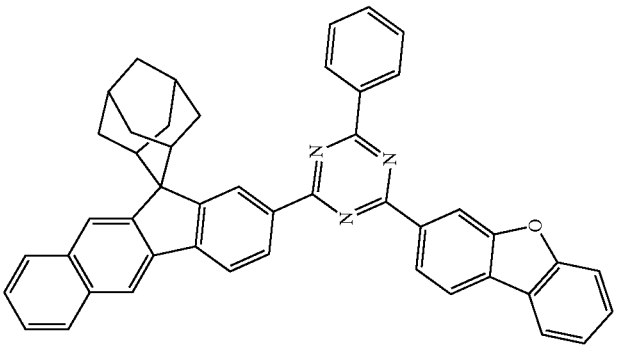<br>A-119 | 5.48/77/658.3 |

TABLE 4-continued
| Intermediate IM-C-X | Raw Material M | Compound A-X | Mass (g)/yield (%)/mass spectrum |
|---|---|---|---|
| | CAS.NO.29874-83-7 | A-137 | 4.38/75/541.3 |
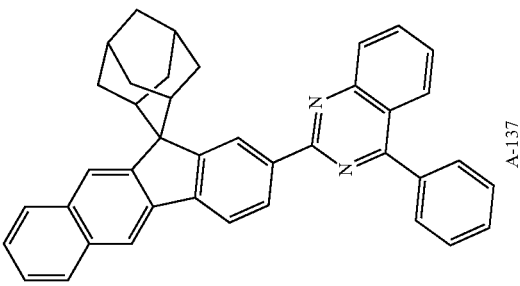

TABLE 4-continued
| Intermediate IM-C-X | Raw Material M | Compound A-X | Mass (g)/yield (%)/mass spectrum |
|---|---|---|---|
| | 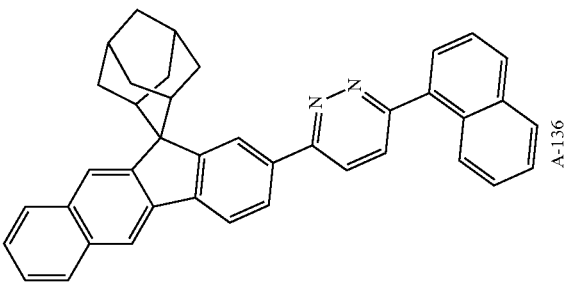 99708-50-6 | 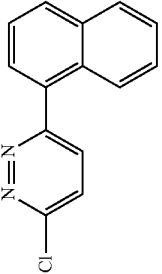 A-136 | 4.26/73/541.3 |

TABLE 4-continued
| Intermediate IM-C-X | Raw Material M | Compound A-X | Mass (g)/yield (%)/mass spectrum |
|---|---|---|---|
| | 2268733-10-2 | A-147 | 4.52/72/581.3 |
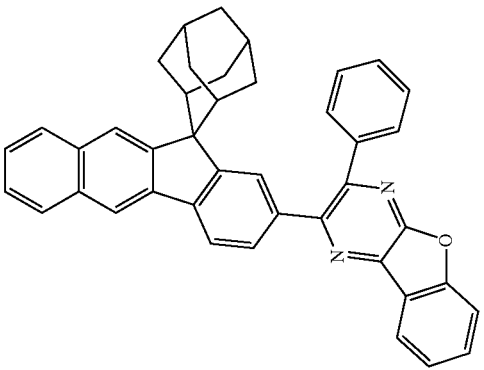

TABLE 4-continued

| Intermediate IM-C-X | Raw Material M | Compound A-X | Mass (g)/yield (%)/mass spectrum |
|---|---|---|---|
| IM-C-5 | 2305965-22-2 | A-95 | 5.50/76/669.3 |
| | | A-121 | 4.74/77/569.3 |

TABLE 4-continued
| Intermediate IM-C-X | Raw Material M | Compound A-X | Mass (g)/yield (%)/mass spectrum |
|---|---|---|---|
| | 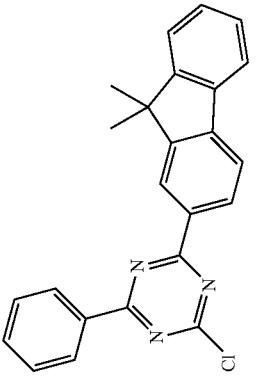 1618106-98-1 | 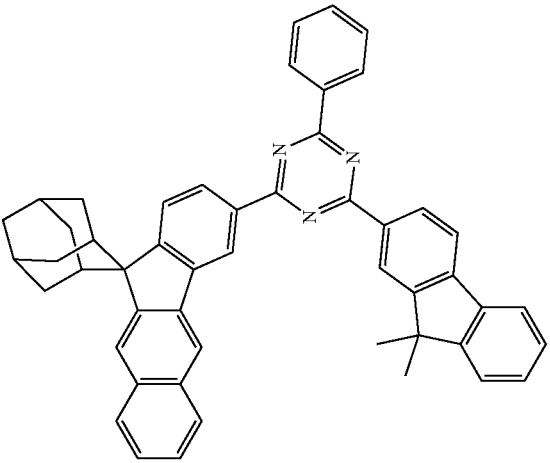 A-126 | 5.77/78/684.3 |

TABLE 4-continued

| Intermediate IM-C-X | Raw Material M | Compound A-X | Mass (g)/yield (%)/mass spectrum |
|---|---|---|---|
| | 2414306-25-3 | A-143 | 5.26/73/667.3 |
| IM-C-5 | 2286331-83-5 | A-146 | 4.77/74/597.3 |

TABLE 4-continued
| Intermediate IM-C-X | Raw Material M | Compound A-X | Mass (g)/yield (%)/mass spectrum |
|---|---|---|---|
| | 2271196-36-0 | B-139 | 5.15/70/681.3 |
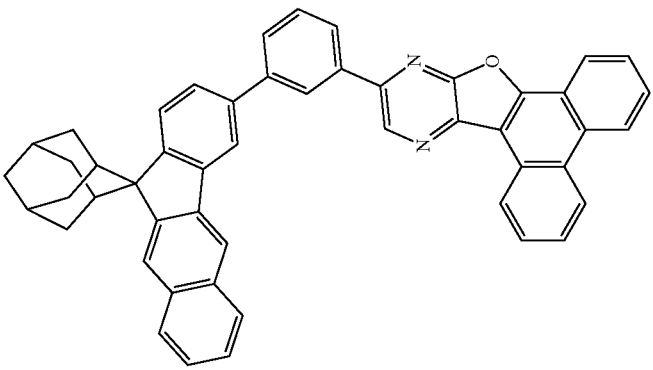

TABLE 4-continued

| Intermediate IM-C-X | Raw Material M | Compound A-X | Mass (g)/yield (%)/mass spectrum |
|---|---|---|---|
| IM-C-6 | 1205748-61-3 | A-117 | 5.92/76/720.3 |

TABLE 4-continued
| Intermediate IM-C-X | Raw Material M | Compound A-X | Mass (g)/yield (%)/mass spectrum |
|---|---|---|---|
| 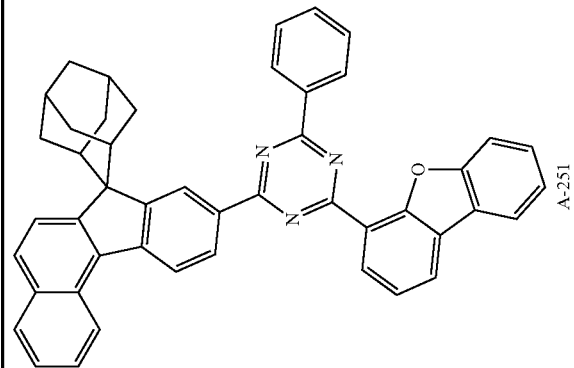<br>IM-C-7 | 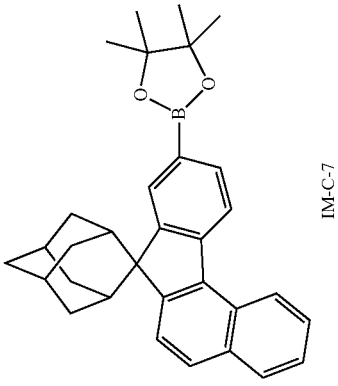<br>1472729-25-1 | 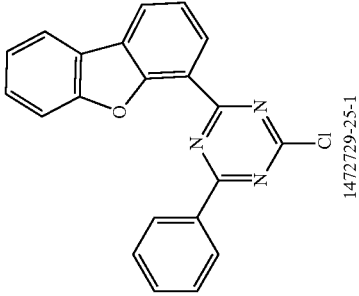<br>A-251 | 5.34/75/658.3 |

TABLE 4-continued

| Intermediate IM-C-X | Raw Material M | Compound A-X | Mass (g)/yield (%)/mass spectrum |
|---|---|---|---|
| | 1699739-83-7 | A-279 | 6.15/76/748.3 |
| IM-C-8 | 2244026-78-4 | A-201 | 5.13/76/624.3 |

TABLE 4-continued
| Intermediate IM-C-X | Raw Material M | Compound A-X | Mass (g)/yield (%)/mass spectrum |
|---|---|---|---|
|  | 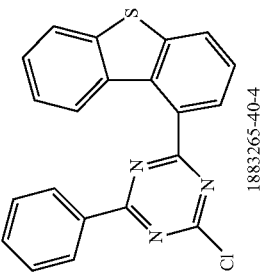 1883265-40-4 | 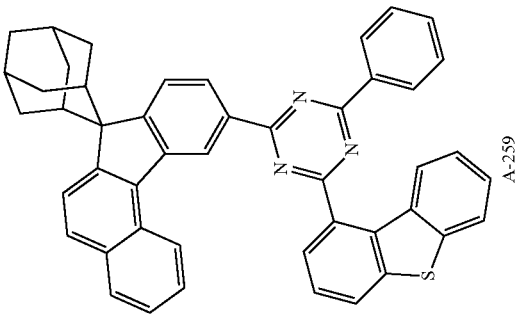 A-259 | 5.46/75/674.3 |

TABLE 4-continued

| Intermediate IM-C-X | Raw Material M | Compound A-X | Mass (g)/yield (%)/mass spectrum |
|---|---|---|---|
| | 1883265-33-5 | A-X | 6.25/74/780.3 |
| IM-C-10 | 3842-55-5 | A-290 | 4.69/78/618.3 |
| | | A-315 | |

TABLE 4-continued

| Intermediate IM-C-X | Raw Material M | Compound A-X | Mass (g)/yield (%)/mass spectrum |
|---|---|---|---|
| IM-C-11 | 2401923-63-3 | A-245 | 5.40/77/649.3 |
| IM-C-12 | 1835683-68-5 | A-151 | 5.22/75/644.3 |

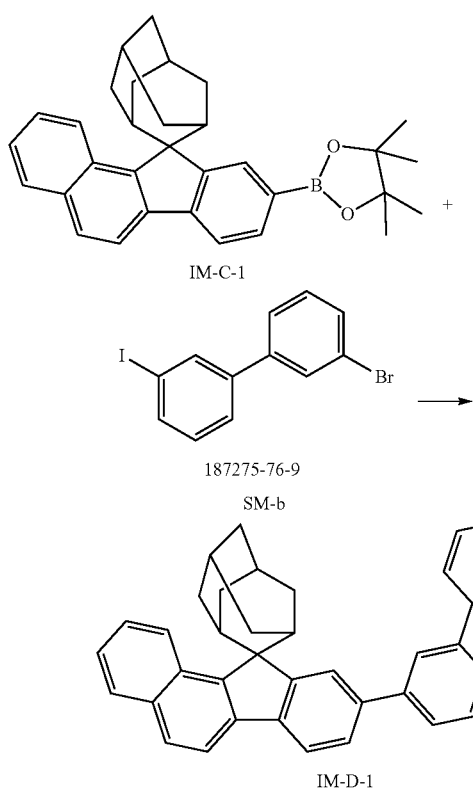

The intermediate IM-C-1 (5.00 g, 10.8 mmol), SM-b (187275-76-9) (4.66 g, 13.0 mmol), palladium acetate (0.12 g, 0.54 mmol), 2-dicyclohexylphosphino-2,4,6-triisopropylbiphenyl (0.26 g, 0.54 mmol), potassium carbonate (3.29 g, 23.8 mmol), toluene (40 mL), ethanol (20 mL) and water (10 mL) were added into a reaction flask, the reaction solution was heated to 78° C. under the protection of nitrogen, and stirred under heating and refluxing for 5 h. The resulting reaction solution was cooled to room temperature, and extracted by using dichloromethane and water, an organic layer was dried with anhydrous magnesium sulfate, and filtered, the obtained filtrate was allowed to pass through a short silica gel column, the solvent was removed under reduced pressure, and the obtained crude product was purified through recrystallization by using a dichloromethane/n-heptane (a volume ratio of 1:3) system to obtain an intermediate IM-D-1 (4.91 g, yield: 80%).

An intermediate IM-D-X was synthesized by adopting a method which is the same as the synthesis method of the intermediate IM-D-1, except that the intermediate IM-C-X was used for replacing the intermediate IM-C-1, and SM-X was used for replacing SM-b to prepare the intermediate IM-D-X. Where X can be 2 to 19, and the prepared intermediate IM-D-X is shown in Table 5.

TABLE 5
| Intermediate IM-C-X | SM-X | Intermediate IM-D-X | Mass (g)/yield (%) |
|---|---|---|---|
| 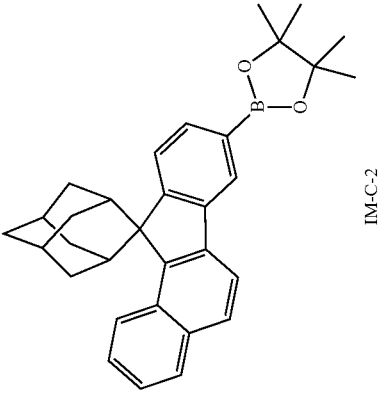 IM-C-2 | 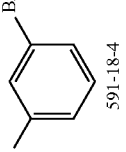 591-18-4 | 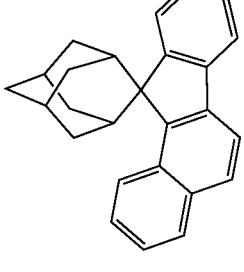 IM-D-2 | 4.14/78 |
| | 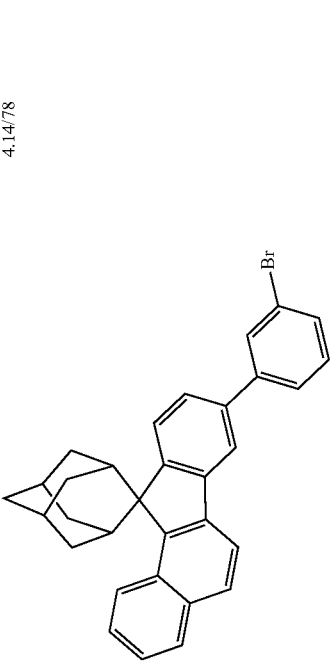 39655-12-4 | 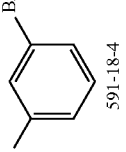 IM-D-3 | 4.66/76 |

TABLE 5-continued

| Intermediate IM-C-X | SM-X | Intermediate IM-D-X | Mass (g)/yield (%) |
|---|---|---|---|
| IM-C-2-0 | 105946-82-5 | IM-D-4 | 4.72/77 |
| IM-C-3 | 1261807-30-0 | IM-D-5 | 4.56/78 |
| IM-C-1 | 4044-58-0 | IM-D-6 | 4.39/75 |

TABLE 5-continued
| Intermediate IM-C-X | SM-X | Intermediate IM-D-X | Mass (g)/yield (%) |
|---|---|---|---|
| 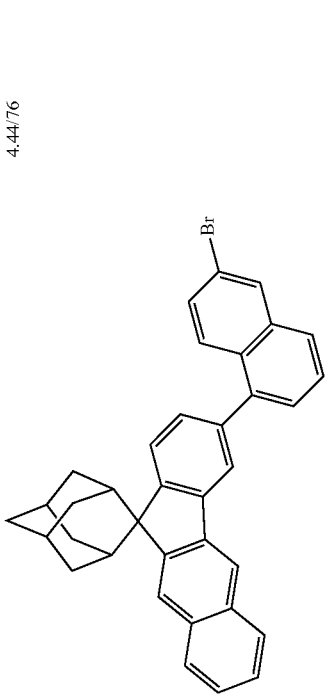 IM-C-4 | 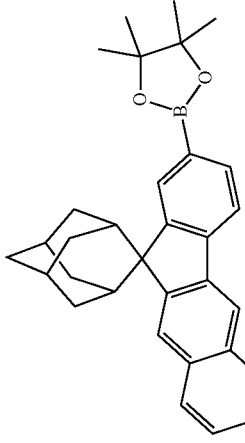 586-55-1 | 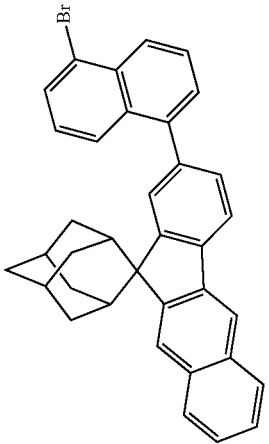 IM-D-7 | 4.14/78 |
| | 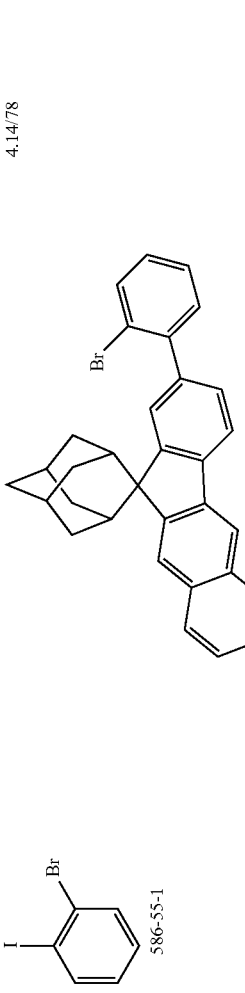 77332-64-0 | 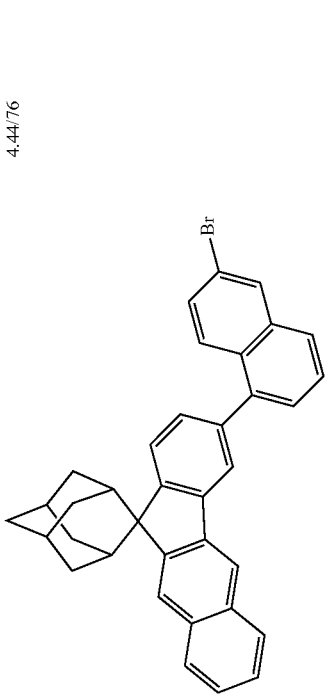 IM-D-10 | 4.50/77 |
| 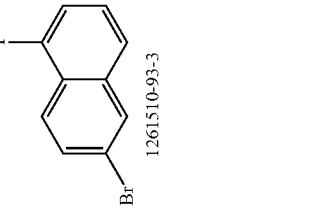 IM-C-5 | 1261510-93-3 | IM-D-11 | 4.44/76 |

TABLE 5-continued

| Intermediate IM-C-X | SM-X | Intermediate IM-D-X | Mass (g)/yield (%) |
|---|---|---|---|
| IM-C-5-0 | 187275-76-9 | IM-D-8 | 4.60/75 |
| IM-C-6 | 105946-82-5 | IM-D-9 | 4.78/78 |

TABLE 5-continued
| Intermediate IM-C-X | SM-X | Intermediate IM-D-X | Mass (g)/yield (%) |
|---|---|---|---|
| 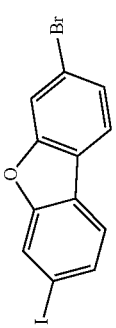 IM-C-7 | 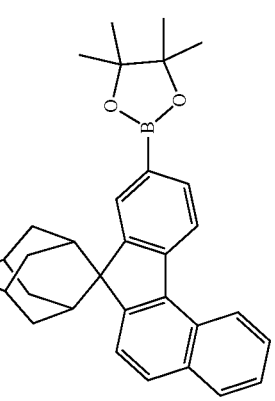 1448787-87-9 | 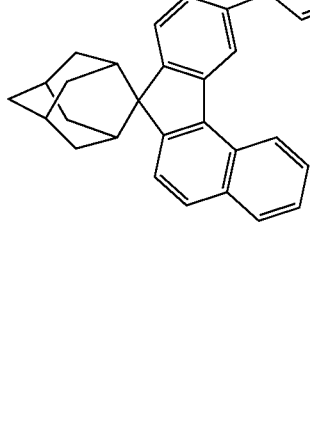 | 4.77/76 |
| 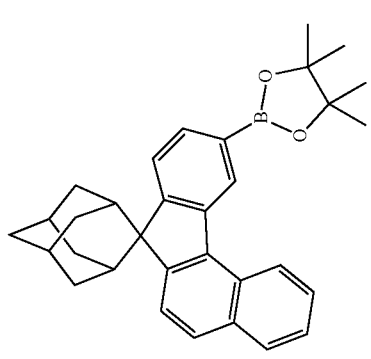 IM-C-8 | 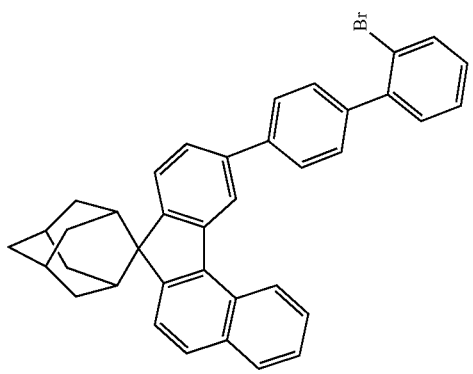 1779516-01-6 | IM-D-14 ... IM-D-13 | 4.60/75 |

TABLE 5-continued
| Intermediate IM-C-X | SM-X | Intermediate IM-D-X | Mass (g)/yield (%) |
|---|---|---|---|
| 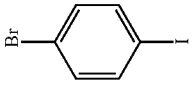 | 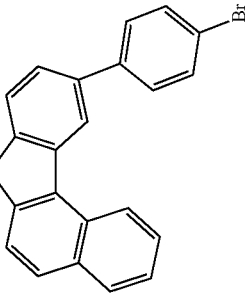 589-87-7 | 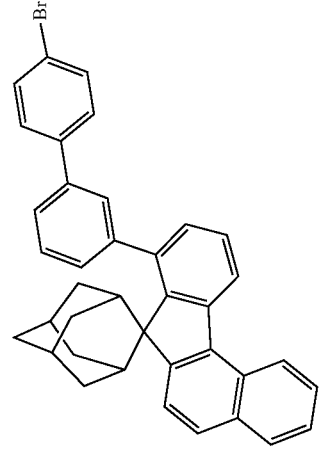 IM-D-16 | 4.09/77 |
| IM-C-8-0 | 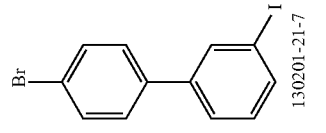 130201-21-7 | 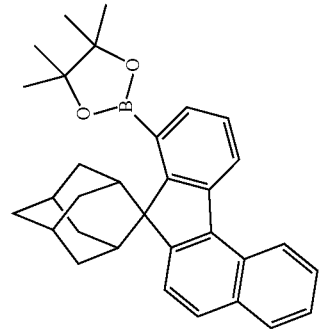 IM-D-15 | 4.60/75 |

TABLE 5-continued
| Intermediate IM-C-X | SM-X | Intermediate IM-D-X | Mass (g)/yield (%) |
|---|---|---|---|
| 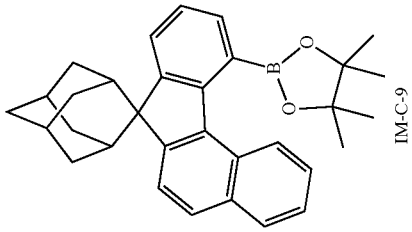 IM-C-9 | 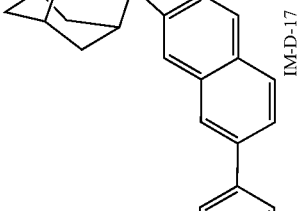 589-87-7 | 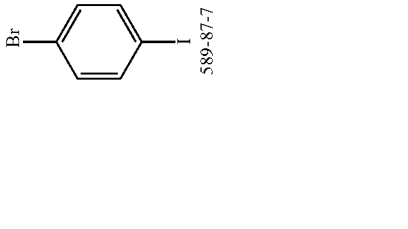 IM-D-12 | 4.14/78 |
| 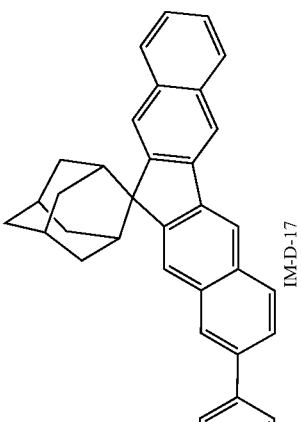 IM-C-10 | 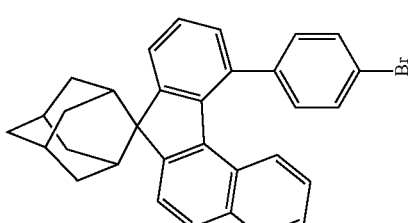 591-18-4 | 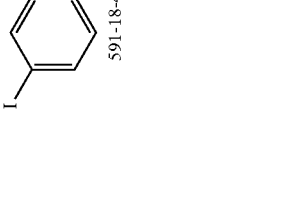 IM-D-17 | 4.06/77 |

TABLE 5-continued

| Intermediate IM-C-X | SM-X | Intermediate IM-D-X | Mass (g)/yield (%) |
|---|---|---|---|
| IM-C-11 | 187275-76-9 | IM-D-18 | 4.78/78 |
| IM-C-12 | 343945-63-1 | IM-D-19 | 4.66/76 |

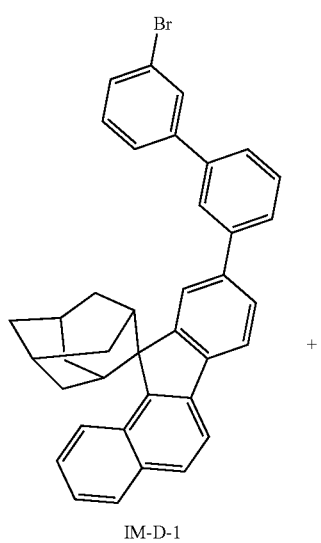

IM-D-1

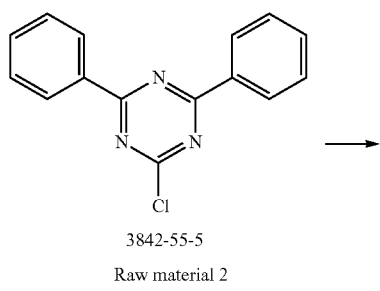

3842-55-5
Raw material 2

→

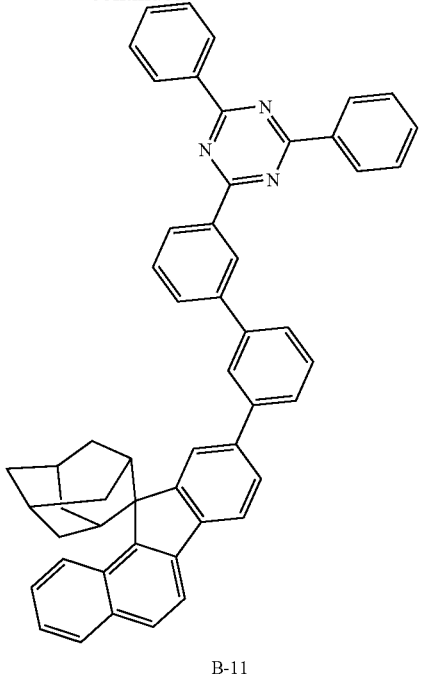

B-11

The intermediate IM-D-1 (4.00 g, 7.05 mmol) and tetrahydrofuran (40 mL) were added into a reaction flask, and the temperature was cooled to −78° C. in a nitrogen environment, n-butyllithium (0.52 g, 8.10 mmol) was dropwise added into the reaction solution. After the addition, the temperature of the reaction solution was maintained for 1 h, a raw material 2 (1.88 g, 7.05 mmol) was dropwise added, the temperature was continued to maintain for 1 h, and the temperature was naturally raised to room temperature 12 h, so that a solid was separated out from the reaction solution, filtering was performed by using a Buchner funnel to obtain a crude product, and the obtained crude product was purified through recrystallization by using a toluene (150 mL) system to obtain a compound B-11 (3.24, yield: 64%). Mass spectrum: m/z=720.3[M+H]$^+$.

A compound B-Y was synthesized by adopting a method which is the same as the method for synthesizing the compound B-11, except that the intermediate IM-D-X was used for replacing the intermediate IM-D-1, and a raw material SMX was used for replacing the raw material 2 (CAS. NO.: 3842-55-5) to prepare the compound B-Y. The prepared compound Y is shown in Table 6.

TABLE 6
| Intermediate IM-D-X | SMX | Compound B-Y | Mass (g)/yield (%)/mass spectrum |
|---|---|---|---|
| 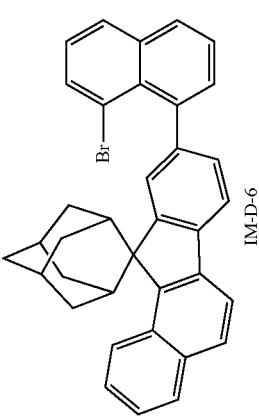<br>IM-D-6 | 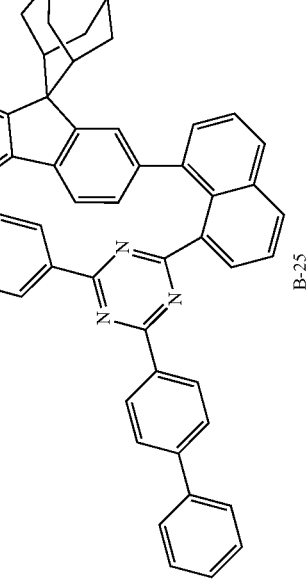<br>1472062-94-4 | 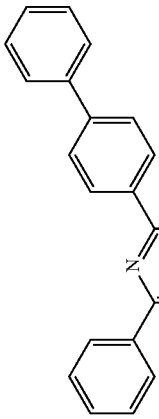<br>B-25 | 3.69/65/770.3 |

TABLE 6-continued

| Intermediate IM-D-X | SMX | Compound B-Y | Mass (g)/yield (%)/mass spectrum |
|---|---|---|---|
| IM-D-2 | 2307664-39-5 | B-2 | 4.13/66/770.3 |

TABLE 6-continued

| Intermediate IM-D-X | SMX | Compound B-Y | Mass (g)/yield (%)/mass spectrum |
|---|---|---|---|
| IM-D-3 | 1689576-03-1 | B-9 | 3.64/65/796.4 |

TABLE 6-continued
| Intermediate IM-D-X | SMX | Compound B-Y | Mass (g)/yield (%)/mass spectrum |
|---|---|---|---|
| IM-D-4 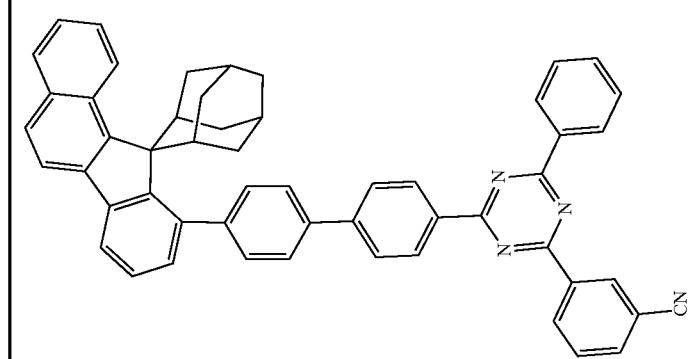 | 2183537-75-7 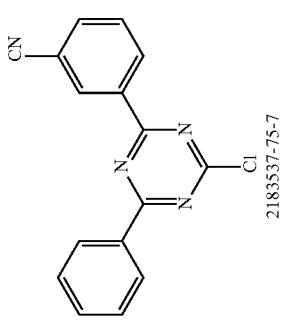 | B-13 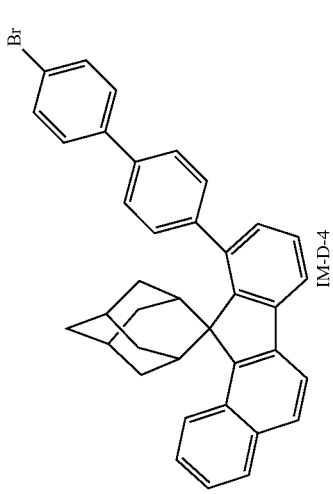 | 3.41/65/741.3 |

TABLE 6-continued

| Intermediate IM-D-X | SMX | Compound B-Y | Mass (g)/yield (%)/mass spectrum |
|---|---|---|---|
| IM-D-5 | 3842-55-5 | B-23 | 3.38/66/694.3 |

TABLE 6-continued
| Intermediate IM-D-X | SMX | Compound B-Y | Mass (g)/yield (%)/mass spectrum |
|---|---|---|---|
| 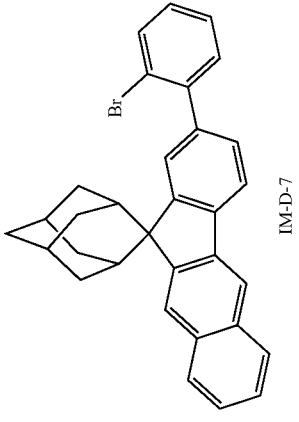<br>IM-D-7 | 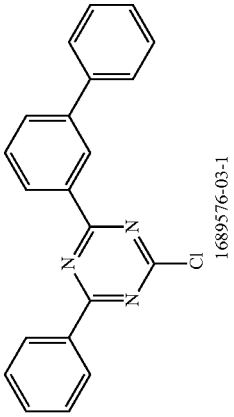<br>1689576-03-1 | 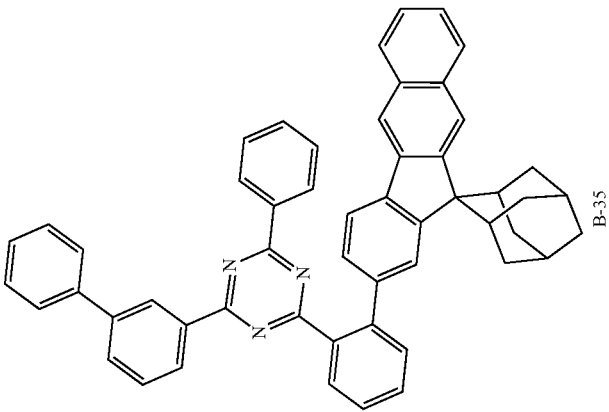<br>B-35 | 3.80/65/720.3 |

TABLE 6-continued

| Intermediate IM-D-X | SMX | Compound B-Y | Mass (g)/yield (%)/mass spectrum |
|---|---|---|---|
| IM-D-10 | 7065-92-1 | B-50 | 3.15/64/667.3 |

TABLE 6-continued

| Intermediate IM-D-X | SMX | Compound B-Y | Mass (g)/yield (%)/mass spectrum |
|---|---|---|---|
| IM-D-11 | 1689576-03-1 | B-56 | 3.58/63/770.3 |

TABLE 6-continued

| Intermediate IM-D-X | SMX | Compound B-Y | Mass (g)/yield (%)/mass spectrum |
|---|---|---|---|
| IM-D-8 | 3842-55-5 | B-44 | 3.24/64/720.3 |

TABLE 6-continued
| Intermediate IM-D-X | SMX | Compound B-Y | Mass (g)/yield (%)/mass spectrum |
|---|---|---|---|
| 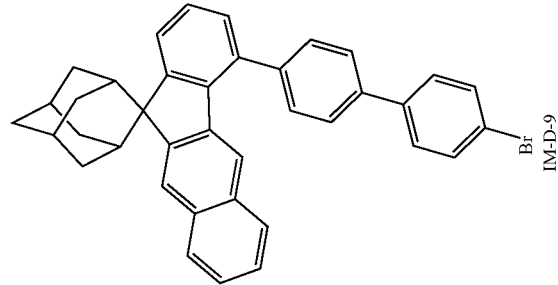<br>IM-D-9 | 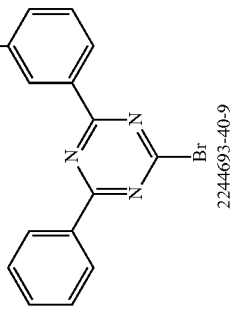<br>2244693-40-9 | 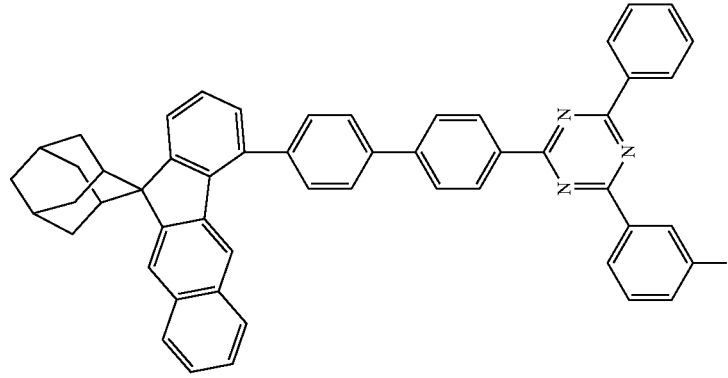<br>B-46 | 3.38/65/738.3 |

TABLE 6-continued
| Intermediate IM-D-X | SMX | Compound B-Y | Mass (g)/yield (%)/mass spectrum |
|---|---|---|---|
| 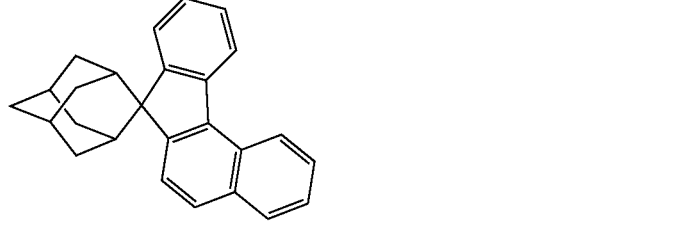 IM-D-14 | 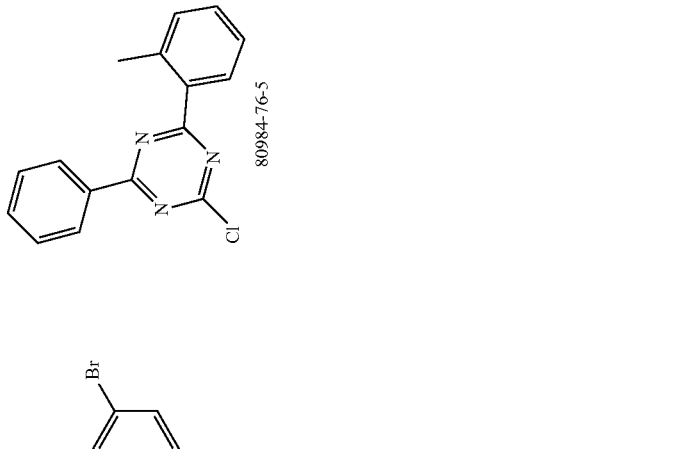 80984-76-5 | 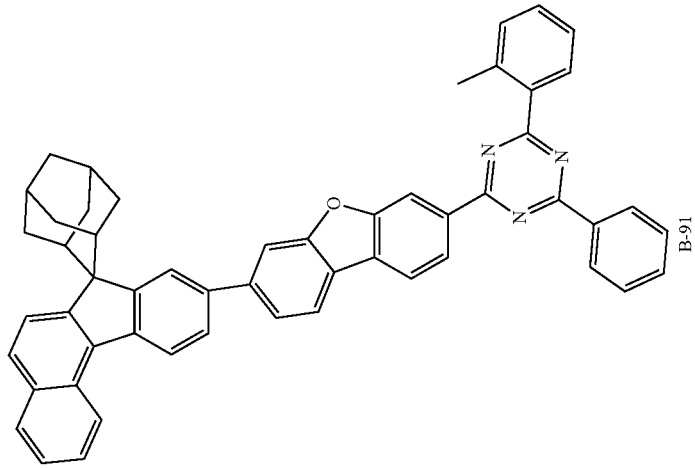 B-91 | 3.39/66/748.3 |

TABLE 6-continued

| Intermediate IM-D-X | SMX | Compound B-Y | Mass (g)/yield (%)/mass spectrum |
|---|---|---|---|
| IM-D-13 | 3842-55-5 | B-72 | 3.29/65/720.3 |

TABLE 6-continued
| Intermediate IM-D-X | SMX | Compound B-Y | Mass (g)/yield (%)/mass spectrum |
|---|---|---|---|
| 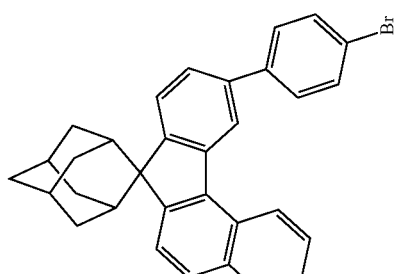<br>IM-D-16 | 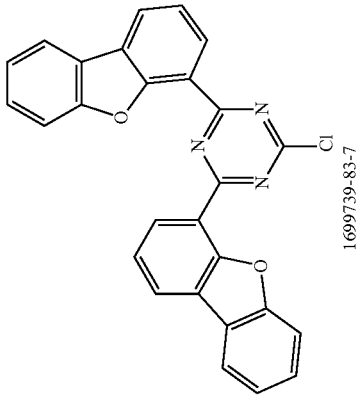<br>1699739-83-7 | 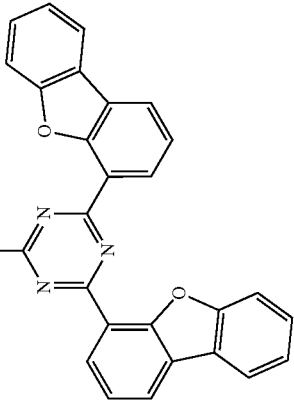<br>B-102 | 4.42/66/824.3 |

TABLE 6-continued

| Intermediate IM-D-X | SMX | Compound B-Y | Mass (g)/yield (%)/mass spectrum |
|---|---|---|---|
| IM-D-15 | 1476735-48-4 | B-100 | 3.90/67/826.3 |

TABLE 6-continued

| Intermediate IM-D-X | SMX | Compound B-Y | Mass (g)/yield (%)/mass spectrum |
|---|---|---|---|
| IM-D-12 | 1472062-94-4 | B-66 | 3.16/65/720.3 |
| IM-D-17 | 3842-55-5 | B-130 | 3.27/64/694.3 |

TABLE 6-continued

| Intermediate IM-D-X | SMX | Compound B-Y | Mass (g)/yield (%)/mass spectrum |
|---|---|---|---|
| IM-D-18 | 3842-55-5 | B-98 | 3.19/63/720.3 |

TABLE 6-continued

| Intermediate IM-D-X | SMX | Compound B-Y | Mass (g)/yield (%)/mass spectrum |
|---|---|---|---|
| IM-D-19 | 2244026-78-4 | B-65 | 3.50/64/776.4 |

NMR data of partial compounds is as shown in Table 7

TABLE 7

| Compound | NMR data |
| --- | --- |
| Compound A-1 | $^1$H NMR (400 Hz, CD$_2$Cl$_2$): 9.37 (s, 1H), 8.79(d, 4H), 8.49 (d, 1H), 7.91-7.85 (m, 6H), 7.79-7.73 (m, 2H), 7.68 (d,1H), 7.64-7.60 (m, 9H), 7.52-7.49 (m, 3H), 3.17 (d, 2H), 3.00 (d, 2H), 2.36 (s, 1H), 2.27 (s, 1H), 2.07 (s, 2H), 1.94 (t, 4H), 1.74 (s, 2H). |
| Compound B-11 | $^1$H NMR(400 Hz, CD$_2$Cl$_2$): 9.16 (s, 1H), 9.08 (d, 4H), 8.94 (d, 1H), 8.51 (s, 1H), 8.31-8.26 (m, 2H), 8.17-7.87 (m, 17H), 7.66 (d, 1H), 3.15 (d, 2H), 3.02 (d, 2H), 2.38 (s, 1H), 2.26 (s, 1H), 2.10 (s, 2H), 1.96 (t, 4H), 1.75 (s, 2H). |

An organic electroluminescent device was manufactured by adopting the following method:

Example 1 Blue Organic Electroluminescent Device

An anode was prepared by the following processes: an ITO substrate with a thickness of 1500 Å (manufactured by Corning) was cut into a size of 40 mm×40 mm×0.7 mm to be prepared into an experimental substrate with a cathode, an anode and an insulating layer pattern by adopting a photoetching process, and surface treatment was performed by utilizing ultraviolet ozone and O$_2$:N$_2$ plasma to increase the work function of the anode (the experiment substrate), and remove scum.

F4-TCNQ was vacuum-evaporated on the experiment substrate (the anode) to form a hole injection layer (HIL) having a thickness of 100 Å, and HT-01 was evaporated on the hole injection layer to form a hole transport layer having a thickness of 1000 Å.

EB-01 was vacuum-evaporated on the hole transport layer to form an electron blocking layer with a thickness of 100 Å.

BH-01 and BD-01 were co-evaporated on the electron blocking layer in a ratio of 98%:2% to form an organic light-emitting layer (EML) with a thickness of 220 Å.

A compound ET-01 was evaporated on the organic light-emitting layer to form a hole blocking layer (HBL) having a thickness of 50 Å.

A compound A-1 and LiQ were mixed at a weight ratio of 1:1 and evaporated on the hole blocking layer to form an electron transport layer (ETL) having a thickness of 300 Å.

Yb was evaporated on the electron transport layer to form an electron injection layer (EIL) having a thickness of 10 Å, and then magnesium (Mg) and silver (Ag) were mixed at an evaporation rate of 1:10 and vacuum-evaporated on the electron injection layer to form a cathode having a thickness of 140 Å.

In addition, CP-1 with a thickness of 630 Å was evaporated on the cathode to form an organic capping layer (CPL), so that the manufacturing of the organic light-emitting device was completed, and the structure is shown in FIG. 1.

Examples 2 to 26

An organic electroluminescent device was manufactured by adopting the same method that in Example 1, except that when the electron transport layer was manufactured, the nitrogen-containing compound A-1 was respectively replaced by the nitrogen-containing compounds shown in Table 9.

Example 27

An organic electroluminescent device was manufactured by adopting the same method that in Example 1, except that when the hole blocking layer was formed, the compound ET-01 was replaced by a nitrogen-containing compound B-11 of the present disclosure, and when the electron transport layer was formed, the nitrogen-containing compound A-1 of the present disclosure was replaced by the compound ET-01.

Examples 28 to 48

An organic electroluminescent device was manufactured by adopting the same method that in Example 27, except that when the hole blocking layer was formed, the nitrogen-containing compound B-11 was respectively replaced by the nitrogen-containing compounds shown in Table 9.

Example 49

An organic electroluminescent device was manufactured by adopting the same method that in Example 1, except that when the hole blocking layer was formed, the compound ET-01 was replaced by the nitrogen-containing compound A-1 of the present disclosure, and when the electron transport layer was formed, the nitrogen-containing compound A-1 was replaced by a nitrogen-containing compound B-9.

Example 50

An organic electroluminescent device was manufactured by adopting the same method that in Example 1, except that when the hole blocking layer was formed, the compound ET-01 was replaced by a nitrogen-containing compound A-5 of the present disclosure, and when the electron transport layer was formed, the nitrogen-containing compound A-1 was replaced by a nitrogen-containing compound B-13.

Example 51

An organic electroluminescent device was manufactured by adopting the same method that in Example 1, except that when the hole blocking layer was formed, the compound ET-01 was replaced by a nitrogen-containing compound A-14 of the present disclosure, and when the electron transport layer was formed, the nitrogen-containing compound A-1 was replaced by a nitrogen-containing compound B-23.

Example 52

An organic electroluminescent device was manufactured by adopting the same method that in Example 1, except that when the hole blocking layer was formed, the compound ET-01 was replaced by a nitrogen-containing compound A-10 of the present disclosure, and when the electron transport layer was formed, the nitrogen-containing compound A-1 was replaced by a nitrogen-containing compound B-56.

Example 53

An organic electroluminescent device was manufactured by adopting the same method that in Example 1, except that when the hole blocking layer was formed, the compound ET-01 was replaced by a nitrogen-containing compound A-201 of the present disclosure, and when the electron transport layer was formed, the nitrogen-containing compound A-1 was replaced by a nitrogen-containing compound B-102.

Comparative Example 1

An organic electroluminescent device was manufactured by adopting the same method that in Example 1, except that when the electron transport layer was manufactured, the nitrogen-containing compound A-1 was replaced by a compound A.

Comparative Example 2

An organic electroluminescent device was manufactured by adopting the same method that in Example 1, except that when the electron transport layer was manufactured, the nitrogen-containing compound A-1 was replaced by a compound B.

Comparative Example 3

An organic electroluminescent device was manufactured by adopting the same method that in Example 1, except that when the electron transport layer was manufactured, the nitrogen-containing compound A-1 was replaced by Alq3.

Comparative Example 4

An organic electroluminescent device was manufactured by adopting the same method that in Example 27, except that when the hole blocking layer was manufactured, the nitrogen-containing compound B-11 was replaced by the compound A.

Comparative Example 5

An organic electroluminescent device was manufactured by adopting the same method that in Example 27, except that when the hole blocking layer was manufactured, the nitrogen-containing compound B-11 was replaced by the compound B.

Comparative Example 6

An organic electroluminescent device was manufactured by adopting the same method that in Example 27, except that when the hole blocking layer was manufactured, the nitrogen-containing compound B-11 was replaced by Alq3.

The structures of the compounds adopted in the comparative examples and the compound ET-01 are shown in Table 8.

TABLE 8

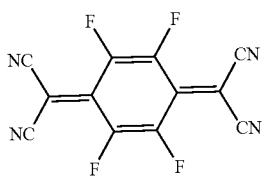 [SMILES: N#CC(C#N)=c1c(F)c(F)c(=C(C#N)C#N)c(F)c1F]

F4-TCNQ

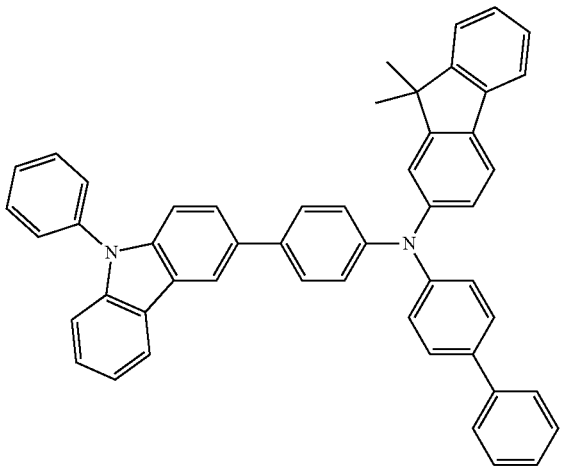 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

HT-01

TABLE 8-continued
EB-01
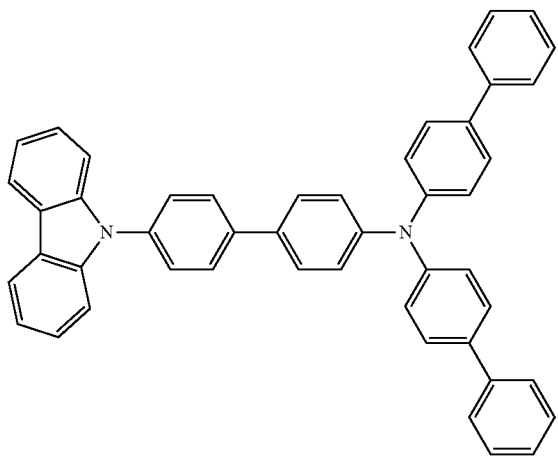 [SMILES: c1ccc(-c2ccc(N(c3ccc(-c4ccccc4)cc3)c3ccc(-c4ccc(-n5c6ccccc6c6ccccc65)cc4)cc3)cc2)cc1]
BH-01
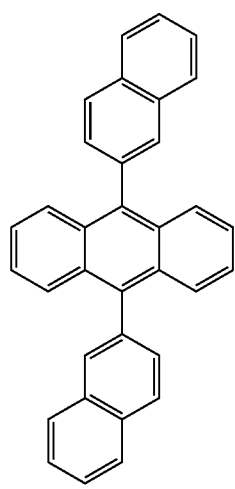 [SMILES: c1ccc2cc(-c3c4ccccc4c(-c4ccc5ccccc5c4)c4ccccc34)ccc2c1]
BD-01
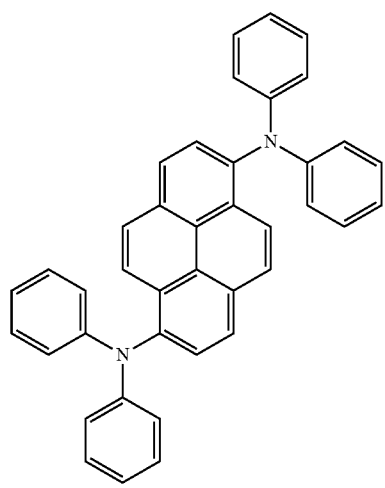 [SMILES: c1ccc(N(c2ccccc2)c2ccc3ccc4c(N(c5ccccc5)c5ccccc5)ccc5ccc2c3c54)cc1]

TABLE 8-continued
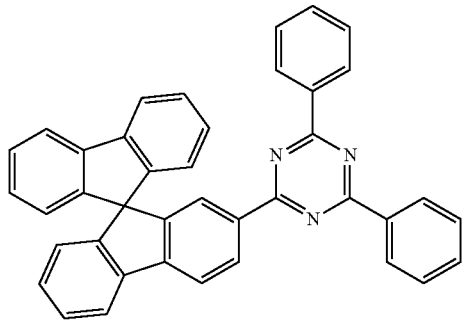 [SMILES: c1ccc(-c2nc(-c3ccccc3)nc(-c3ccc4c(c3)C3(c5ccccc5-c5ccccc53)c3ccccc3-4)n2)cc1]
ET-01
LiQ
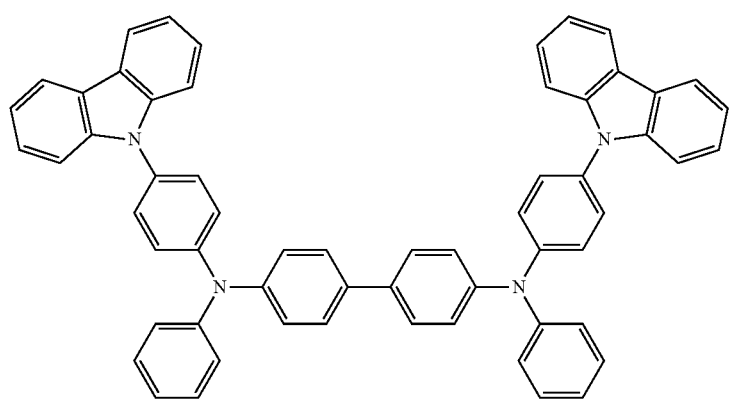 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
CP-01
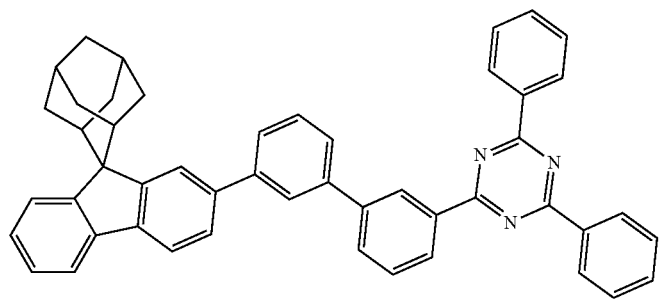 [SMILES: c1ccc(-c2nc(-c3ccccc3)nc(-c3cccc(-c4cccc(-c5ccc6c(c5)C5(c7ccccc7-6)C6CC7CC(C6)CC5C7)c4)c3)n2)cc1]
Compound A TABLE 8-continued

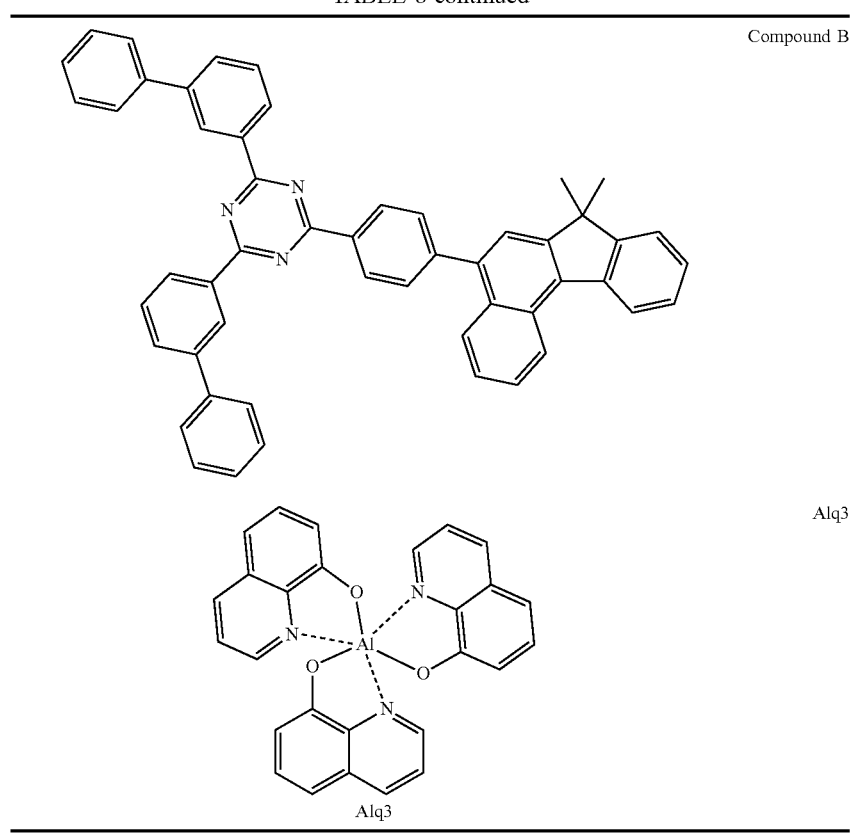

Compound B

Alq3

The photoelectric properties of the manufactured organic electroluminescent device were analyzed under the condition of 10 Å/cm² and 20 mA/cm², and the results are shown in the following Table 9:

TABLE 9

|  | HBL | ETL | Volt (V) | Cd/A | lm/W | CIE-x | CIE-y | EQE % | T95 (hrs)@ 20 mA/cm² |
|---|---|---|---|---|---|---|---|---|---|
| Example 1 | ET-01 | Compound A-1 | 3.88 | 6.91 | 5.59 | 0.14 | 0.05 | 14.21 | 213 |
| Example 2 | ET-01 | Compound A-2 | 3.89 | 6.61 | 5.34 | 0.14 | 0.05 | 13.61 | 211 |
| Example 3 | ET-01 | Compound A-18 | 3.94 | 6.78 | 5.41 | 0.14 | 0.05 | 13.95 | 192 |
| Example 4 | ET-01 | Compound A-5 | 3.89 | 6.92 | 5.59 | 0.14 | 0.05 | 14.23 | 211 |
| Example 5 | ET-01 | Compound A-14 | 3.92 | 6.84 | 5.51 | 0.14 | 0.05 | 14.07 | 193 |
| Example 6 | ET-01 | Compound A-10 | 3.82 | 6.84 | 5.63 | 0.14 | 0.05 | 14.07 | 198 |
| Example 7 | ET-01 | Compound A-119 | 3.90 | 6.69 | 5.39 | 0.14 | 0.05 | 13.76 | 190 |
| Example 8 | ET-01 | Compound A-137 | 3.92 | 6.67 | 5.35 | 0.14 | 0.05 | 13.72 | 207 |
| Example 9 | ET-01 | Compound A-95 | 3.81 | 6.89 | 5.68 | 0.14 | 0.05 | 14.17 | 187 |
| Example 10 | ET-01 | Compound A-121 | 3.82 | 6.59 | 5.42 | 0.14 | 0.05 | 13.56 | 190 |
| Example 11 | ET-01 | Compound A-126 | 3.92 | 6.57 | 5.27 | 0.14 | 0.05 | 13.51 | 195 |
| Example 12 | ET-01 | Compound A-117 | 3.83 | 6.73 | 5.52 | 0.14 | 0.05 | 13.78 | 204 |
| Example 13 | ET-01 | Compound A-251 | 3.87 | 6.56 | 5.33 | 0.14 | 0.05 | 13.49 | 209 |
| Example 14 | ET-01 | Compound A-279 | 3.91 | 6.79 | 5.46 | 0.14 | 0.05 | 13.97 | 197 |

TABLE 9-continued

| | HBL | ETL | Volt (V) | Cd/A | lm/W | CIE-x | CIE-y | EQE % | T95 (hrs)@ 20 mA/cm$^2$ |
|---|---|---|---|---|---|---|---|---|---|
| Example 15 | ET-01 | Compound A-201 | 3.86 | 6.88 | 5.62 | 0.14 | 0.05 | 14.15 | 199 |
| Example 16 | ET-01 | Compound A-259 | 3.83 | 6.62 | 5.43 | 0.14 | 0.05 | 13.62 | 215 |
| Example 17 | ET-01 | Compound A-290 | 3.92 | 6.78 | 5.43 | 0.14 | 0.05 | 13.95 | 183 |
| Example 18 | ET-01 | Compound B-9 | 3.98 | 6.33 | 5.00 | 0.14 | 0.05 | 13.02 | 188 |
| Example 19 | ET-01 | Compound B-13 | 3.99 | 6.27 | 4.94 | 0.14 | 0.05 | 12.90 | 182 |
| Example 20 | ET-01 | Compound B-23 | 4.02 | 6.30 | 4.92 | 0.14 | 0.05 | 12.96 | 182 |
| Example 21 | ET-01 | Compound B-56 | 4.00 | 6.24 | 4.90 | 0.14 | 0.05 | 12.84 | 187 |
| Example 22 | ET-01 | Compound B-102 | 4.01 | 6.24 | 4.89 | 0.14 | 0.05 | 12.84 | 207 |
| Example 23 | ET-01 | Compound A-136 | 4.01 | 6.77 | 4.94 | 0.14 | 0.05 | 13.93 | 202 |
| Example 24 | ET-01 | Compound A-147 | 3.97 | 6.73 | 4.94 | 0.14 | 0.05 | 13.83 | 192 |
| Example 25 | ET-01 | Compound A-143 | 3.95 | 6.77 | 4.94 | 0.14 | 0.05 | 13.84 | 197 |
| Example 26 | ET-01 | Compound A-146 | 3.99 | 6.67 | 4.94 | 0.14 | 0.05 | 13.60 | 195 |
| Example 27 | Compound B-11 | ET-01 | 3.88 | 6.68 | 5.41 | 0.14 | 0.05 | 13.74 | 184 |
| Example 28 | Compound B-25 | ET-01 | 3.84 | 6.56 | 5.37 | 0.14 | 0.05 | 13.49 | 183 |
| Example 29 | Compound B-2 | ET-01 | 3.89 | 6.59 | 5.32 | 0.14 | 0.05 | 13.56 | 186 |
| Example 30 | Compound B-9 | ET-01 | 3.92 | 6.82 | 5.47 | 0.14 | 0.05 | 14.03 | 193 |
| Example 31 | Compound B-13 | ET-01 | 3.89 | 6.75 | 5.45 | 0.14 | 0.05 | 13.88 | 192 |
| Example 32 | Compound B-23 | ET-01 | 3.88 | 6.68 | 5.41 | 0.14 | 0.05 | 13.74 | 199 |
| Example 33 | Compound B-35 | ET-01 | 3.89 | 6.60 | 5.33 | 0.14 | 0.05 | 13.58 | 199 |
| Example 34 | Compound B-50 | ET-01 | 3.91 | 6.58 | 5.29 | 0.14 | 0.05 | 13.54 | 184 |
| Example 35 | Compound B-56 | ET-01 | 3.88 | 6.80 | 5.51 | 0.14 | 0.05 | 13.99 | 198 |
| Example 36 | Compound B-44 | ET-01 | 3.86 | 6.61 | 5.38 | 0.14 | 0.05 | 13.60 | 194 |
| Example 37 | Compound B-46 | ET-01 | 3.88 | 6.69 | 5.42 | 0.14 | 0.05 | 13.76 | 189 |
| Example 38 | Compound B-91 | ET-01 | 3.87 | 6.69 | 5.43 | 0.14 | 0.05 | 13.76 | 192 |
| Example 39 | Compound B-72 | ET-01 | 3.87 | 6.60 | 5.36 | 0.14 | 0.05 | 13.58 | 200 |
| Example 40 | Compound B-102 | ET-01 | 3.85 | 6.84 | 5.58 | 0.14 | 0.05 | 14.07 | 182 |
| Example 41 | Compound B-100 | ET-01 | 3.87 | 6.67 | 5.41 | 0.14 | 0.05 | 13.72 | 193 |
| Example 42 | Compound B-66 | ET-01 | 3.90 | 6.76 | 5.45 | 0.14 | 0.05 | 13.91 | 194 |
| Example 43 | Compound B-139 | ET-01 | 3.95 | 6.58 | 5.05 | 0.14 | 0.05 | 13.42 | 193 |
| Example 44 | Compound A-1 | ET-01 | 3.97 | 6.31 | 4.99 | 0.14 | 0.05 | 12.98 | 177 |
| Example 45 | Compound A-5 | ET-01 | 4.03 | 6.34 | 4.94 | 0.14 | 0.05 | 13.04 | 175 |
| Example 46 | Compound A-14 | ET-01 | 3.98 | 6.42 | 5.07 | 0.14 | 0.05 | 13.21 | 176 |
| Example 47 | Compound A-10 | ET-01 | 4.05 | 6.26 | 4.86 | 0.14 | 0.05 | 12.88 | 176 |
| Example 48 | Compound A-201 | ET-01 | 3.99 | 6.24 | 4.91 | 0.14 | 0.05 | 12.84 | 179 |
| Example 49 | Compound A-1 | Compound B-9 | 3.79 | 6.53 | 5.52 | 0.14 | 0.05 | 13.43 | 194 |
| Example 50 | Compound A-5 | Compound B-13 | 3.81 | 6.56 | 5.33 | 0.14 | 0.05 | 13.49 | 189 |
| Example 51 | Compound A-14 | Compound B-23 | 3.82 | 6.49 | 5.42 | 0.14 | 0.05 | 13.35 | 190 |
| Example 52 | Compound A-10 | Compound B-56 | 3.78 | 6.57 | 5.27 | 0.14 | 0.05 | 13.51 | 195 |

TABLE 9-continued

| | HBL | ETL | Volt (V) | Cd/A | lm/W | CIE-x | CIE-y | EQE % | T95 (hrs)@ 20 mA/cm² |
|---|---|---|---|---|---|---|---|---|---|
| Example 53 | Compound A-201 | Compound B-102 | 3.76 | 6.49 | 5.68 | 0.14 | 0.05 | 13.35 | 187 |
| Comparative Example 1 | ET-01 | Compound A | 4.24 | 5.85 | 4.41 | 0.14 | 0.05 | 12.03 | 144 |
| Comparative Example 2 | ET-01 | Compound B | 4.17 | 5.72 | 4.31 | 0.14 | 0.05 | 11.77 | 118 |
| Comparative Example 3 | ET-01 | Alq3 | 4.39 | 5.33 | 3.98 | 0.14 | 0.05 | 10.96 | 96 |
| Comparative Example 4 | Compound A | ET-01 | 4.26 | 5.83 | 4.31 | 0.14 | 0.05 | 11.99 | 143 |
| Comparative Example 5 | Compound B | ET-01 | 4.27 | 5.72 | 4.16 | 0.14 | 0.05 | 11.75 | 122 |
| Comparative Example 6 | Alq3 | ET-01 | 4.37 | 5.22 | 3.89 | 0.14 | 0.05 | 10.74 | 93 |

From Table 9, it can be seen that when the compound provided of the present disclosure is used as an electron transport layer material in Examples 1 to 26, compared with Comparative Examples 1 to 3, the current efficiency and the service life of the device are obviously improved, the voltage is at least reduced by 0.15 V, the luminous efficiency is at least improved by 6.72%, the external quantum efficiency is at least improved by 6.73%, and the service life is at least improved by 26.39%. Compared with the devices using the compounds in which L is not a single bond in Examples 18 to 22, the devices using the compounds in which L is a single bond in Examples 1 to 17 are more excellent in various properties.

When the compound provided of the present disclosure is used as a hole blocking layer material in Examples 27 to 48, compared with Comparative Examples 4 to 6, the current efficiency and the service life of the device are obviously improved, the voltage is at least reduced by 0.21 V, the luminous efficiency is at least improved by 7.03%, the external quantum efficiency is at least improved by 7.09%, and the service life is at least improved by 22.4%. Compared with the devices using the compounds in which L is a single bond in Examples 44 to 48, the devices using the compounds in which L is not a single bond in Examples 27 to 43 are more excellent in various properties.

When the compounds provided of the present disclosure are simultaneously combined to serve as a hole blocking layer and an electron transport layer in Examples 49 to 53, compared with Comparative Examples 1 to 6, the voltage is obviously reduced and is at least reduced by 0.35 V, the luminous efficiency is at least improved by 10.94%, the external quantum efficiency is at least improved by 10.97%, and the service life is at least improved by 29.86%.

Example 54: Green Organic Electroluminescent Device

An anode was prepared by the following processes: a substrate with an ITO thickness of 1500 Å (manufactured by Corning) was cut into a size of 40 mm×40 mm×0.7 mm to be prepared into an experimental substrate with a cathode, an anode and an insulating layer pattern by adopting a photoetching process, and surface treatment was performed by utilizing ultraviolet ozone and $O_2:N_2$ plasma to increase the work function of the anode (the experiment substrate), and remove scum.

F4-TCNQ was vacuum-evaporated on the experiment substrate (the anode) to form a hole injection layer (HIL) having a thickness of 100 Å, and HT-01 was evaporated on the hole injection layer to form a hole transport layer having a thickness of 1000 Å.

EB-02 was vacuum-evaporated on the hole transport layer to form an electron blocking layer with a thickness of 400 Å.

GH-n1, GH-n2 and Ir(ppy)₃ were co-evaporated on the electron blocking layer in a ratio of 50%:45%:5% (an evaporation rate) to form a green organic light-emitting layer (EML) with a thickness of 400 Å.

A compound ET-01 was evaporated on the organic light-emitting layer to form a hole blocking layer (HBL) having a thickness of 50 Å.

A compound A-1 and LiQ were mixed at a weight ratio of 1:1 and evaporated on the hole blocking layer to form an electron transport layer (ETL) having a thickness of 300 Å.

Yb was evaporated on the electron transport layer to form an electron injection layer (EIL) having a thickness of 10 Å, and then magnesium (Mg) and silver (Ag) were mixed at an evaporation rate of 1:10 and vacuum-evaporated on the electron injection layer to form a cathode having a thickness of 140 Å.

In addition, CP-1 with a thickness of 650 Å was evaporated on the cathode to form an organic capping layer (CPL), so that the manufacturing of the organic light-emitting device was completed, and the structure is shown in FIG. 1.

Examples 55 to 62

An organic electroluminescent device was manufactured by adopting the same method that in Example 54, except that when the electron transport layer was manufactured, the nitrogen-containing compound A-1 was respectively replaced by the nitrogen-containing compounds shown in Table 11.

Example 63

An organic electroluminescent device was manufactured by adopting the same method that in Example 54, except that when the hole blocking layer was formed, the compound ET-01 was replaced by the nitrogen-containing compound B-9 of the present disclosure, and when the electron transport layer was formed, the nitrogen-containing compound A-1 of the present disclosure was replaced by the compound ET-01.

Examples 64 to 71

An organic electroluminescent device was manufactured by adopting the same method that in Example 63, except that when the hole blocking layer was formed, the nitrogen-containing compound B-9 was respectively replaced by the nitrogen-containing compounds shown in Table 11.

Comparative Example 7

An organic electroluminescent device was manufactured by adopting the same method that in Example 54, except that when the electron transport layer was manufactured, the nitrogen-containing compound A-1 was replaced by a compound A.

Comparative Example 8

An organic electroluminescent device was manufactured by adopting the same method that in Example 54, except that when the electron transport layer was manufactured, the nitrogen-containing compound A-1 was replaced by a compound B.

Comparative Example 9

An organic electroluminescent device was manufactured by adopting the same method that in Example 54, except that when the electron transport layer was manufactured, the nitrogen-containing compound A-1 was replaced by Alq3.

Comparative Example 10

An organic electroluminescent device was manufactured by adopting the same method that in Example 63, except that when the hole blocking layer was manufactured, the nitrogen-containing compound B-9 was replaced by the compound A.

Comparative Example 11

An organic electroluminescent device was manufactured by adopting the same method that in Example 63, except that when the hole blocking layer was manufactured, the nitrogen-containing compound B-9 was replaced by the compound B.

Comparative Example 12

An organic electroluminescent device was manufactured by adopting the same method that in Example 63, except that when the hole blocking layer was manufactured, the nitrogen-containing compound B-9 was replaced by Alq3.

The structural formula of each used material is shown in the following Table 10:

TABLE 10

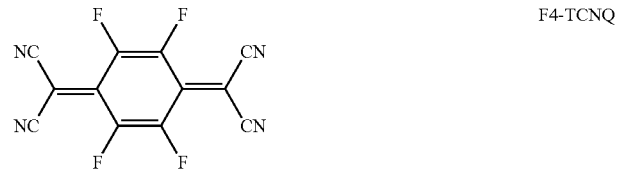

F4-TCNQ

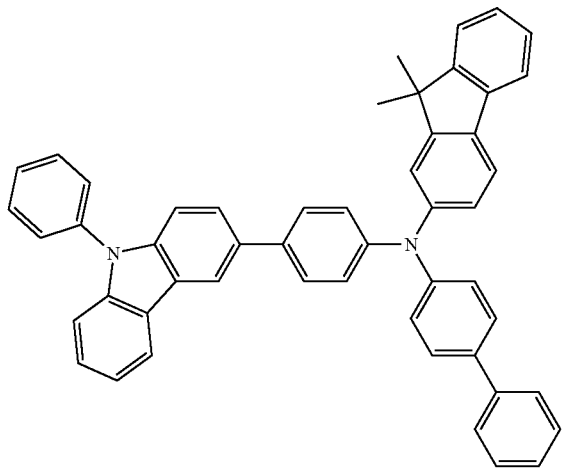 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

HT-01

TABLE 10-continued
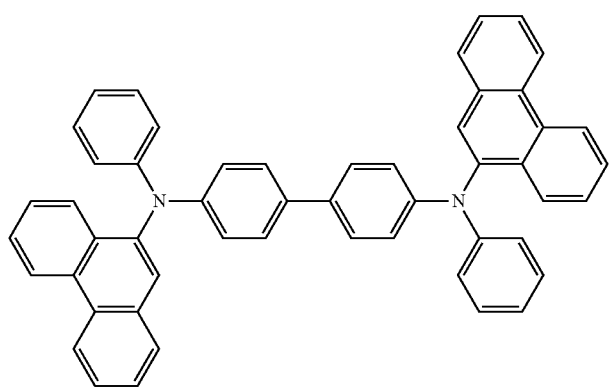 [SMILES: c1ccc(N(c2ccc(-c3ccc(N(c4ccccc4)c4cc5ccccc5c5ccccc45)cc3)cc2)c2cc3ccccc3c3ccccc23)cc1]
EB-02
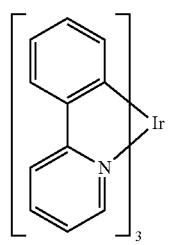
Ir(ppy)₃
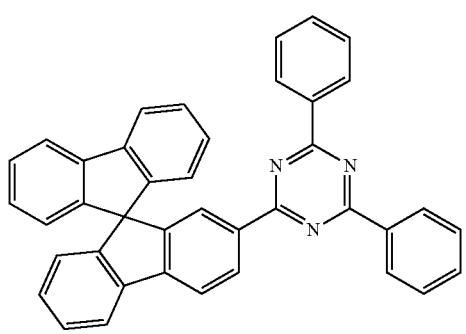 [SMILES: c1ccc(-c2nc(-c3ccccc3)nc(-c3ccc4c(c3)C3(c5ccccc5-c5ccccc53)c3ccccc3-4)n2)cc1]
ET-01
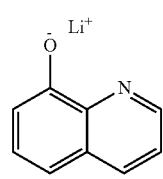 [SMILES: [Li+] ; Oc1cccc2cccnc12]
LiQ
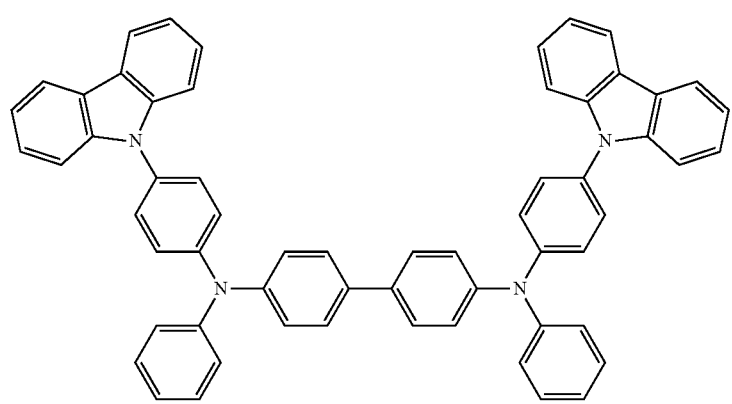 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
CP-01

TABLE 10-continued
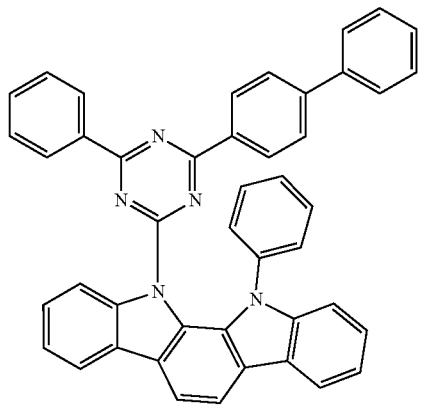 [SMILES: c1ccc(-c2ccc(-c3nc(-c4ccccc4)nc(-n4c5ccccc5c5ccc6c7ccccc7n(-c7ccccc7)c6c54)n3)cc2)cc1]
GH-n1
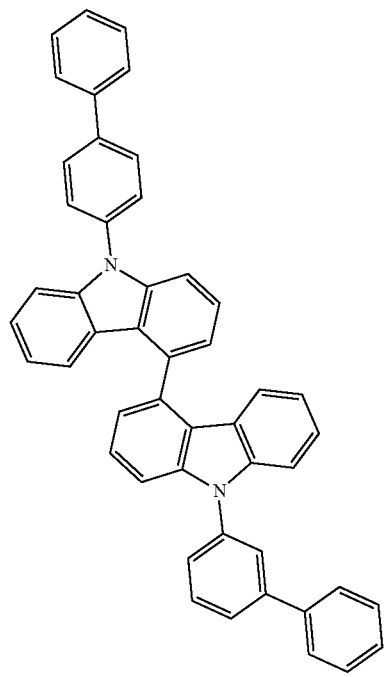 [SMILES: c1ccc(-c2ccc(-n3c4ccccc4c4c(-c5cccc6c5c5ccccc5n6-c5cccc(-c6ccccc6)c5)cccc43)cc2)cc1]
GH-n2
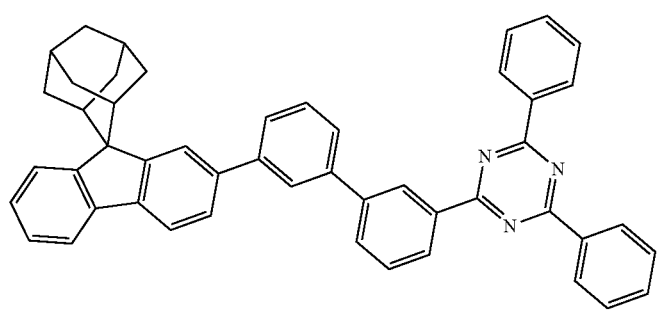 [SMILES: c1ccc(-c2nc(-c3ccccc3)nc(-c3cccc(-c4cccc(-c5ccc6c(c5)C5(c7ccccc7-6)C6CC7CC(C6)CC5C7)c4)c3)n2)cc1]
Compound A

TABLE 10-continued

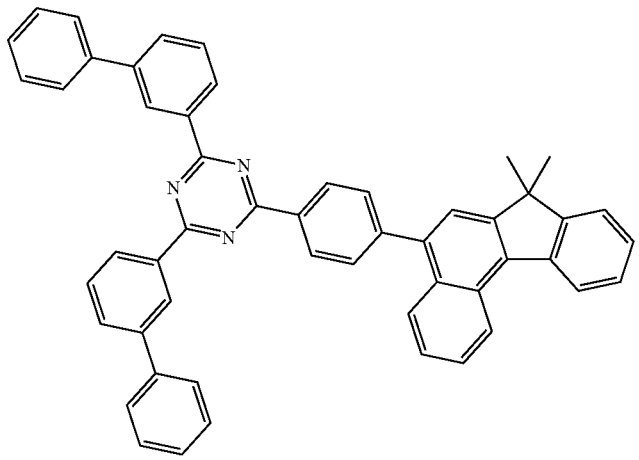 [SMILES: CC1(C)c2ccccc2-c2c1cc(-c1ccc(-c3nc(-c4cccc(-c5ccccc5)c4)nc(-c4cccc(-c5ccccc5)c4)n3)cc1)c1ccccc21]

Compound B

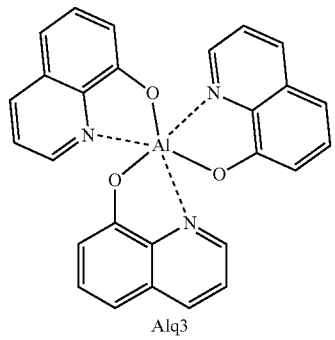

Alq3

The performance of the manufactured organic electroluminescent device was analyzed under the condition of 20 mA/cm², and the result is shown in the following Table 11:

TABLE 11

Performance test result of organic electroluminescent device

| | HBL | ETL | Volt (V) | Cd/A | lm/W | CIE-x | CIE-y | EQE % | T95 (hrs)@ 20 mA/cm² |
|---|---|---|---|---|---|---|---|---|---|
| Example 54 | ET-01 | Compound A-1 | 3.89 | 86.45 | 69.82 | 0.22 | 0.73 | 21.61 | 358 |
| Example 55 | ET-01 | Compound A-5 | 3.87 | 86.82 | 70.48 | 0.22 | 0.73 | 21.71 | 324 |
| Example 56 | ET-01 | Compound A-14 | 3.91 | 83.85 | 67.37 | 0.22 | 0.73 | 20.96 | 375 |
| Example 57 | ET-01 | Compound A-10 | 3.94 | 88.36 | 70.45 | 0.22 | 0.73 | 22.09 | 358 |
| Example 58 | ET-01 | Compound A-95 | 3.90 | 87.24 | 70.27 | 0.22 | 0.73 | 21.81 | 333 |
| Example 59 | ET-01 | Compound A-201 | 3.91 | 84.07 | 67.55 | 0.22 | 0.73 | 21.02 | 356 |
| Example 60 | ET-01 | Compound A-151 | 3.95 | 76.31 | 60.69 | 0.22 | 0.73 | 19.08 | 289 |
| Example 61 | ET-01 | Compound A-245 | 3.97 | 75.19 | 59.50 | 0.22 | 0.73 | 18.80 | 292 |
| Example 62 | ET-01 | Compound A-315 | 3.95 | 74.13 | 58.96 | 0.22 | 0.73 | 18.53 | 262 |
| Example 63 | Compound B-9 | ET-01 | 3.85 | 83.99 | 68.53 | 0.22 | 0.73 | 21.00 | 354 |
| Example 64 | Compound B-11 | ET-01 | 3.85 | 86.54 | 70.61 | 0.22 | 0.73 | 21.64 | 331 |
| Example 65 | Compound B-13 | ET-01 | 3.90 | 84.56 | 68.11 | 0.22 | 0.73 | 21.14 | 375 |
| Example 66 | Compound B-56 | ET-01 | 3.95 | 86.74 | 68.99 | 0.22 | 0.73 | 21.69 | 372 |

TABLE 11-continued

Performance test result of organic electroluminescent device

|  | HBL | ETL | Volt (V) | Cd/A | lm/W | CIE-x | CIE-y | EQE % | T95 (hrs)@ 20 mA/cm² |
|---|---|---|---|---|---|---|---|---|---|
| Example 67 | Compound B-66 | ET-01 | 3.89 | 86.76 | 70.07 | 0.22 | 0.73 | 21.69 | 362 |
| Example 68 | Compound B-102 | ET-01 | 3.92 | 84.56 | 67.77 | 0.22 | 0.73 | 21.14 | 371 |
| Example 69 | Compound B-65 | ET-01 | 3.98 | 75.91 | 59.92 | 0.22 | 0.73 | 18.98 | 288 |
| Example 70 | Compound B-98 | ET-01 | 3.96 | 74.52 | 59.12 | 0.22 | 0.73 | 18.63 | 293 |
| Example 71 | Compound B-130 | ET-01 | 3.97 | 73.97 | 58.53 | 0.22 | 0.73 | 18.49 | 260 |
| Comparative Example 7 | ET-01 | Compound A | 4.08 | 60.92 | 46.91 | 0.22 | 0.73 | 15.23 | 201 |
| Comparative Example 8 | ET-01 | Compound B | 4.11 | 62.69 | 47.92 | 0.22 | 0.73 | 15.67 | 182 |
| Comparative Example 9 | ET-01 | Alq3 | 4.07 | 64.75 | 49.98 | 0.22 | 0.73 | 16.19 | 192 |
| Comparative Example 10 | Compound A | ET-01 | 4.07 | 65.25 | 50.36 | 0.22 | 0.73 | 16.31 | 197 |
| Comparative Example 11 | Compound B | ET-01 | 4.05 | 62.41 | 48.41 | 0.22 | 0.73 | 15.60 | 180 |
| Comparative Example 12 | Alq3 | ET-01 | 4.11 | 63.13 | 48.25 | 0.22 | 0.73 | 15.78 | 186 |

From Table 11, it can be seen that when the compound provided of the present disclosure is used as an electron transport layer material in Examples 54 to 62, compared with Comparative Examples 7 to 9, the current efficiency and the service life of the device are obviously improved, the voltage is at least reduced by 0.10 V, the luminous efficiency is at least improved by 14.5%, the external quantum efficiency is at least improved by 14.5%, and the service life is at least improved by 30.3%.

When the compound provided of the present disclosure is used as a hole blocking layer material in Examples 63 to 71, compared with Comparative Examples 10 to 12, the current efficiency and the service life of the device are obviously improved, the voltage is at least reduced by 0.07 V, the luminous efficiency is at least improved by 13.4%, the external quantum efficiency is at least improved by 13.4%, and the service life is at least improved by 32.0%.

Therefore, when the novel compound provided by the present disclosure is used for manufacturing the organic electroluminescent device, the driving voltage of the device can be effectively reduced, and meanwhile, the service life of the device is improved.

The preferable embodiments of the present disclosure are described in detail above n combination with the drawings, however, the present disclosure is not limited to the specific details in the above embodiments, in the technical concept range of the present disclosure, the technical solution of the present disclosure can be subjected to various simple variations, and these simple variations all belong to the protection range of the present disclosure.

In addition, it should be noted that all the specific technical features described in the above specific embodiments can be combined in any appropriate mode without contradiction, and in order to avoid unnecessary repetition, various possible combinations are not described any more in the present disclosure.

In addition, various different embodiments of the present disclosure can also be combined at will, and as long as the embodiments do not violate the idea of the present disclosure, the embodiments also should be regarded as the contents disclosed by the present disclosure.

What is claimed is:

1. A nitrogen-containing compound, having a structural formula as shown in Formula 1:

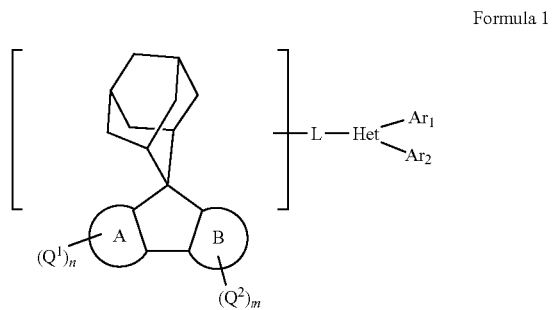

Formula 1 wherein ring A and ring B are the same or different, and are each independently selected from a benzene ring and a naphthalene ring, and the ring A and the ring B are not benzene rings at the same time;

L is selected from a single bond, unsubstituted phenylene, unsubstituted naphthylene, unsubstituted biphenylene, unsubstituted dibenzothienylidene, and unsubstituted dibenzofurylidene;

L is connected with the ring A or the ring B;

each $Q^1$ and each $Q^2$ are the same or different, and are each independently selected from deuterium, halogen group, cyano, haloalkyl with 1 to 10 carbon atoms, alkyl with 1 to 10 carbon atoms, cycloalkyl with 3 to 15 carbon atoms, alkoxy with 1 to 4 carbon atoms, alkylthio with 1 to 4 carbon atoms, trialkylsilyl with 3 to 12 carbon atoms, triarylsilyl with 18 to 24 carbon atoms, aryl with 6 to 12 carbon atoms, aralkyl with 7 to 13 carbon atoms, heteroaryl with 4 to 12 carbon atoms, and heteroaralkyl with 5 to 13 carbon atoms;

n represents the number of $Q^1$, which is selected from 0; and m represents the number of $Q^2$, which is selected from 0;

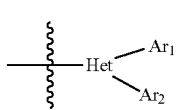

is selected from the following groups:

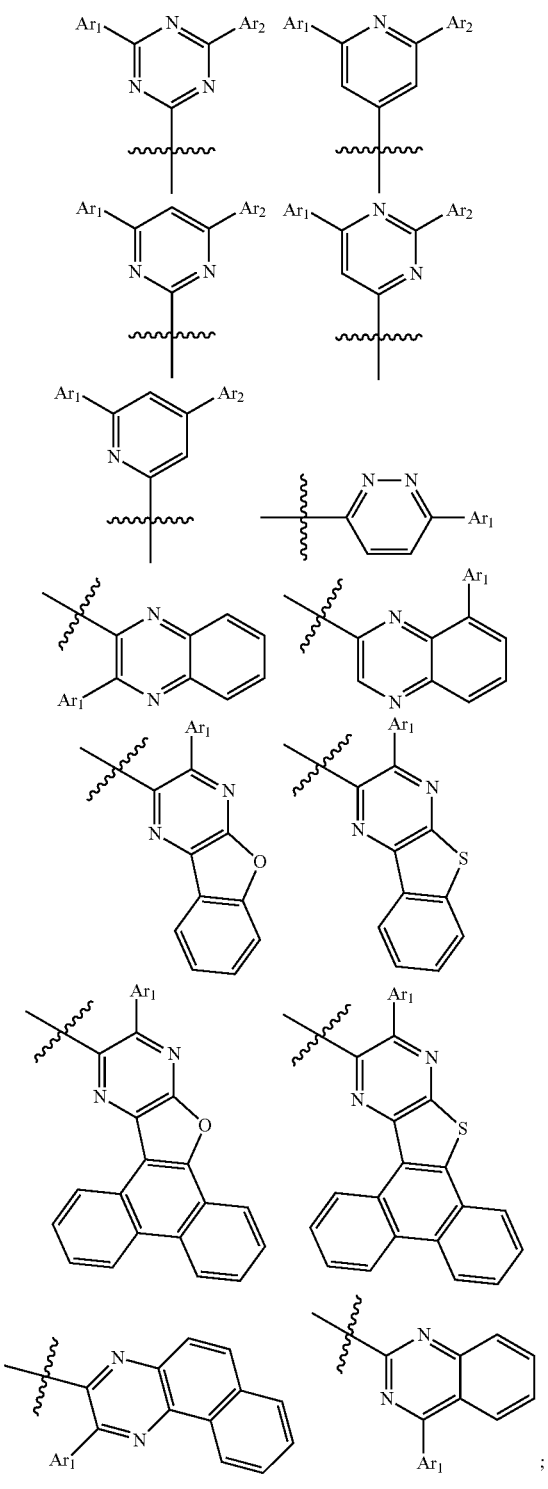

wherein, ⌇ represents a chemical bond;

Ar₁ and Ar₂ are the same or different, and are each independently selected from hydrogen, substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted pyridyl, substituted or unsubstituted dibenzofuranyl, and substituted or unsubstituted dibenzothienyl;

the substituents in Ar₁ and Ar₂ are the same or different, and are each independently selected from deuterium, fluorine, cyano, methyl, ethyl, n-propyl, isopropyl, tert-butyl, phenyl, naphthyl and quinolinyl.

2. The nitrogen-containing compound according to claim 1, wherein the nitrogen-containing compound as shown in the Formula 1 is selected from the group consisting of the following compounds:

Formula 2

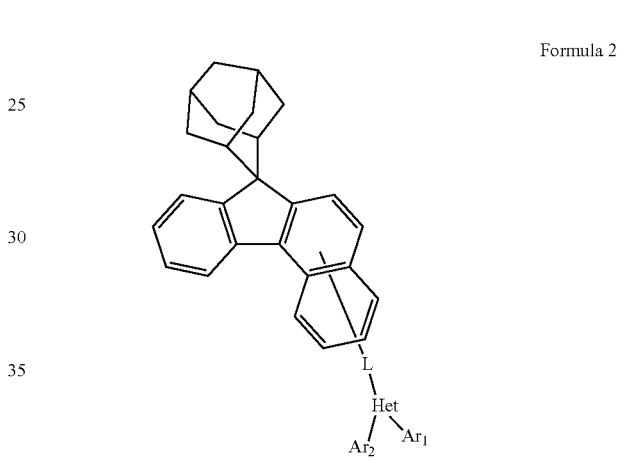

Formula 3

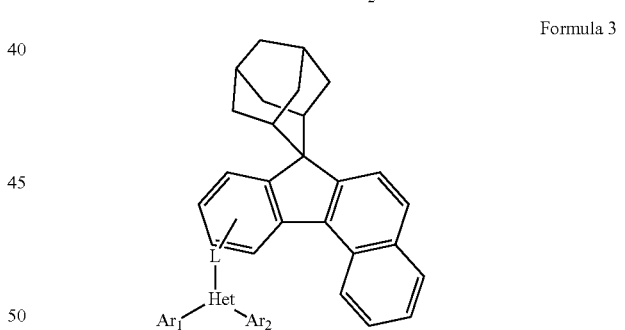

Formula 4

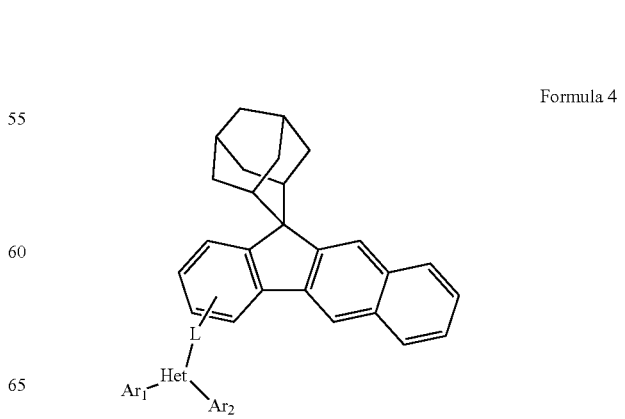

-continued
Formula 5
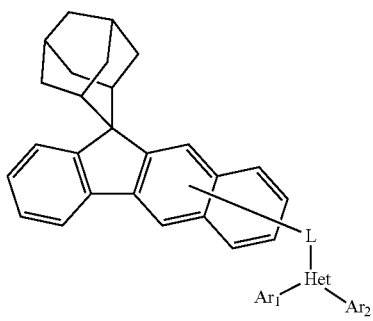
Formula 5'
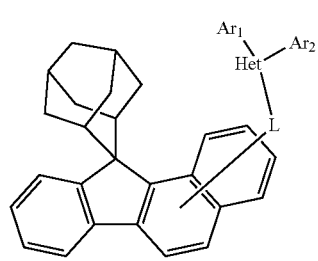
Formula 6
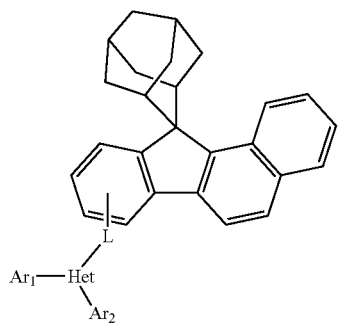
Formula 7
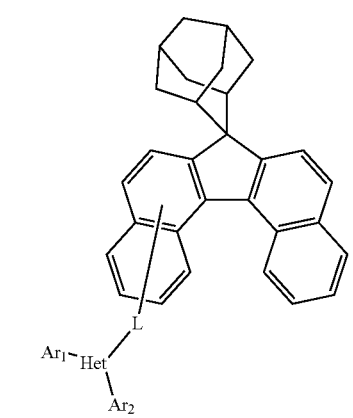
-continued
Formula 8
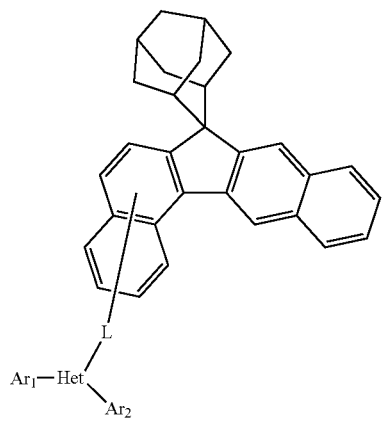
Formula 9'
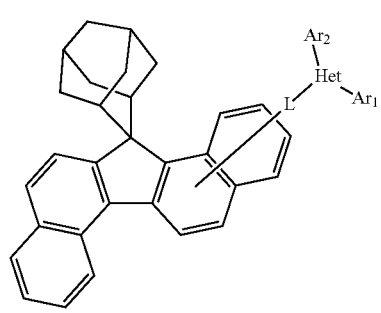
Formula 9
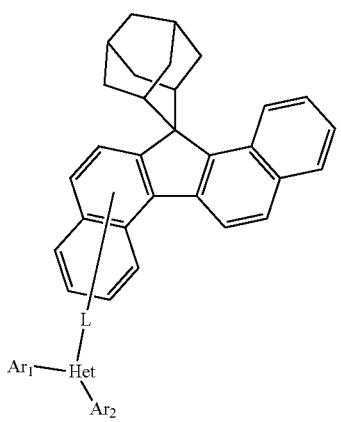
Formula 10
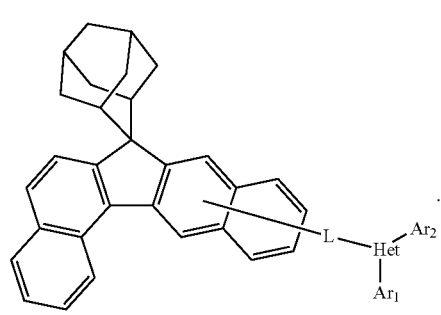

3. The nitrogen-containing compound according to claim 1, wherein

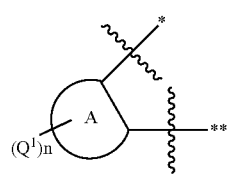

is selected from the group consisting of structures shown below:

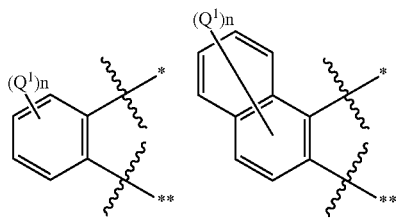

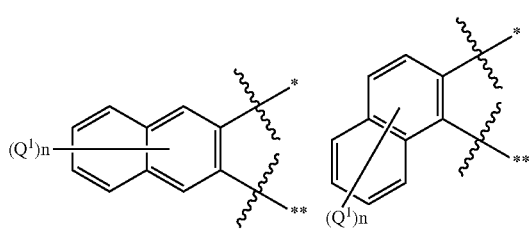

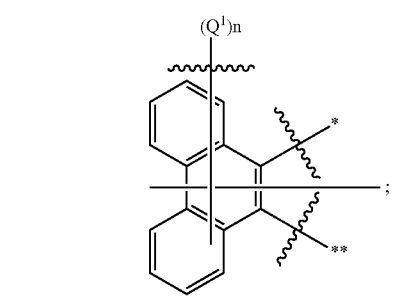

wherein ⁎ represents a chemical bond used for connection with

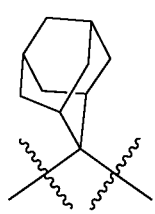 [SMILES: *C1(*)C2CC3CC(C2)CC1C3]

in the above structures, and ⁑ represents a chemical bond used for connection with

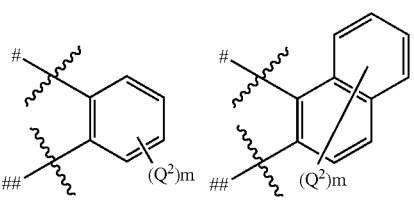

in the above structures.

4. The nitrogen-containing compound according to claim 1, wherein

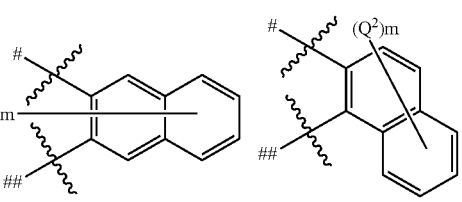

is selected from the group consisting of structures shown below:

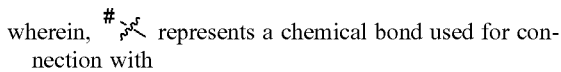

wherein, # represents a chemical bond used for connection with

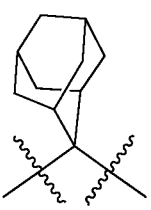 [SMILES: *C1(*)C2CC3CC(C2)CC1C3]

in the above structures, and ## ⁓ represents a chemical bond used for connection with
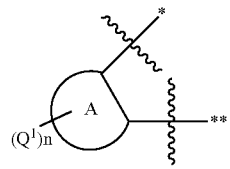
in the above structures.
5. The nitrogen-containing compound according to claim 1, wherein $Ar_1$ and $Ar_2$ are the same or different, and are each independently selected from hydrogen or the group consisting of the following groups:
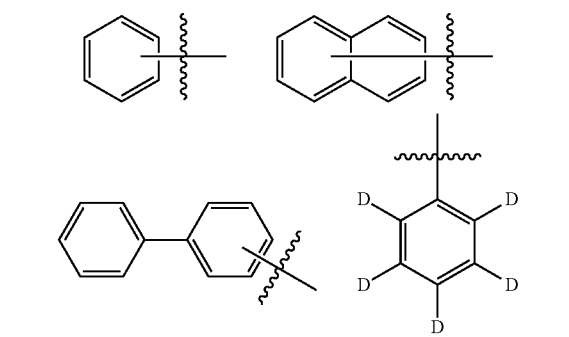
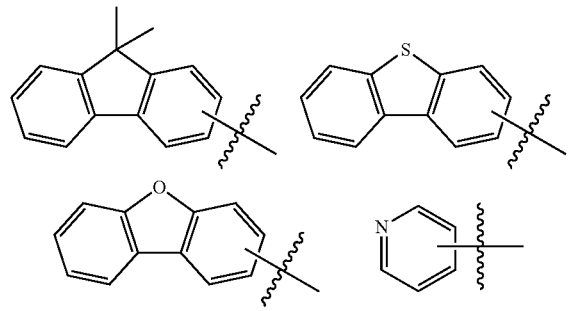
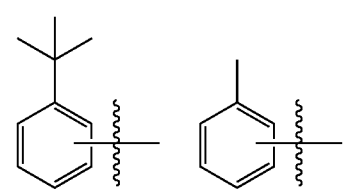
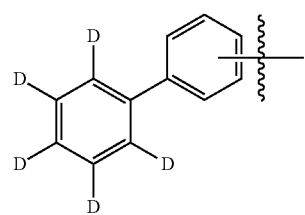
-continued
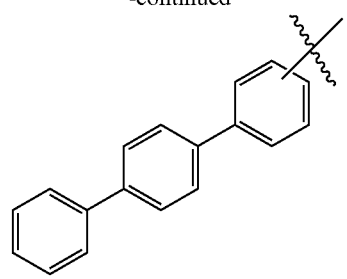
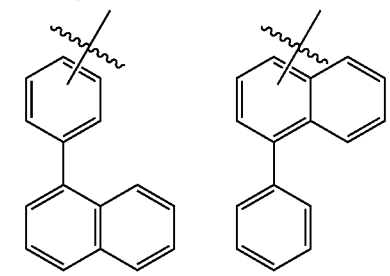
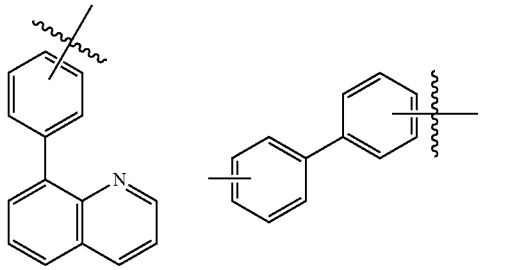
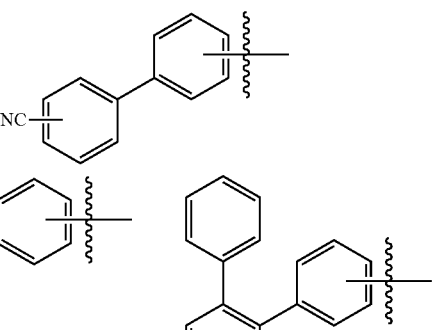
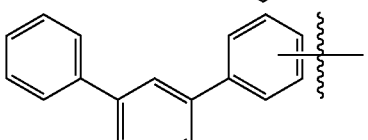
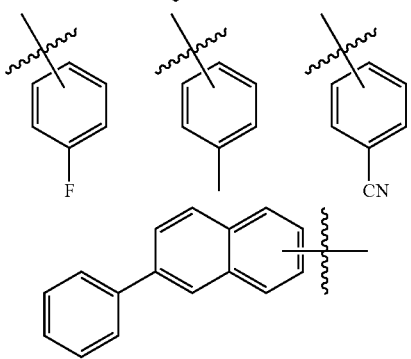

-continued
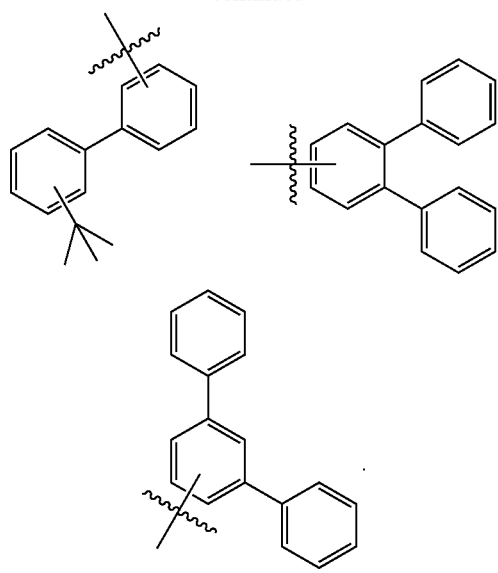
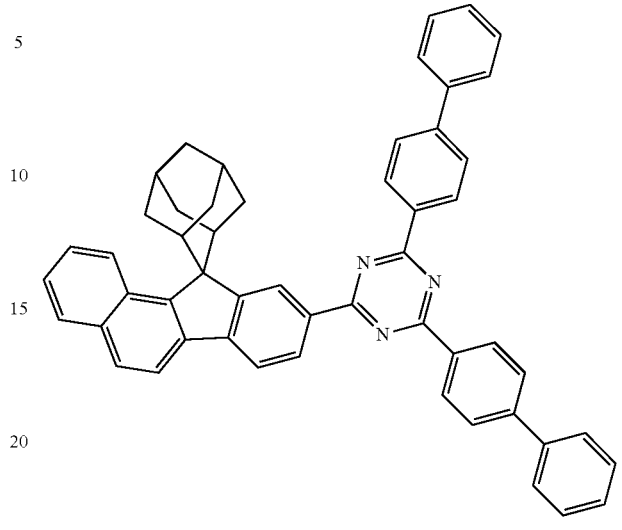
A-1
6. The nitrogen-containing compound according to claim 1, wherein L is selected from a single bond or the group consisting of the following groups:
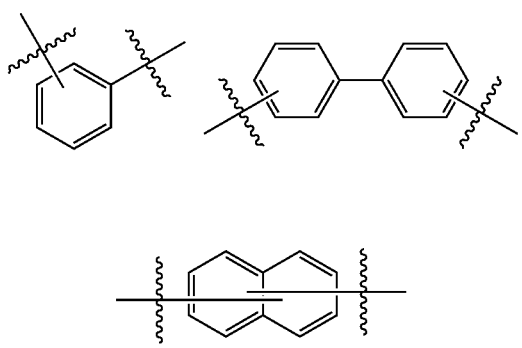
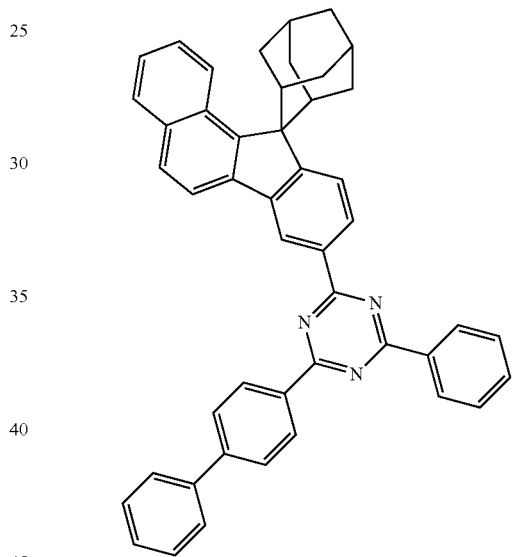
A-2
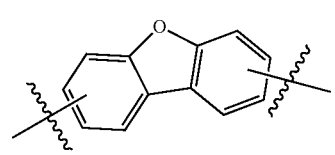
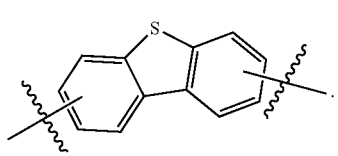
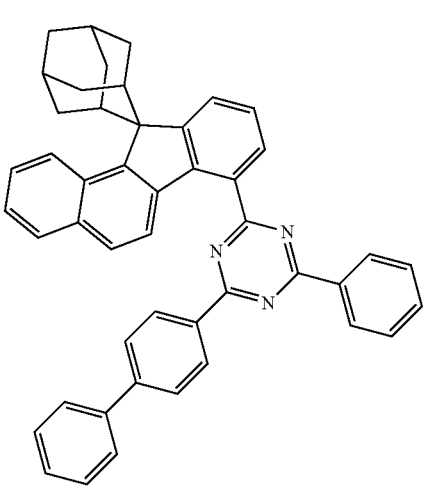
A-3
7. The nitrogen-containing compound according to claim 1, wherein the nitrogen-containing compound is selected from the group consisting of the following compounds:

A-4
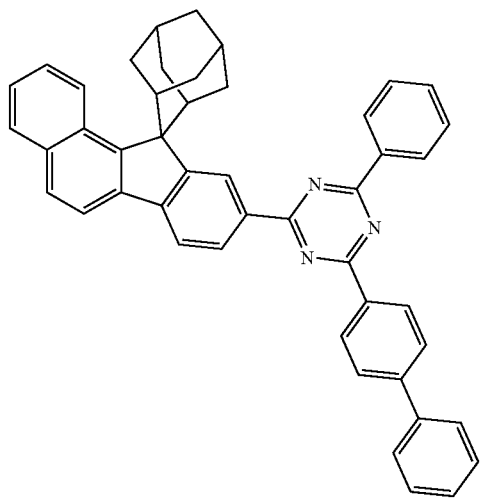
A-7
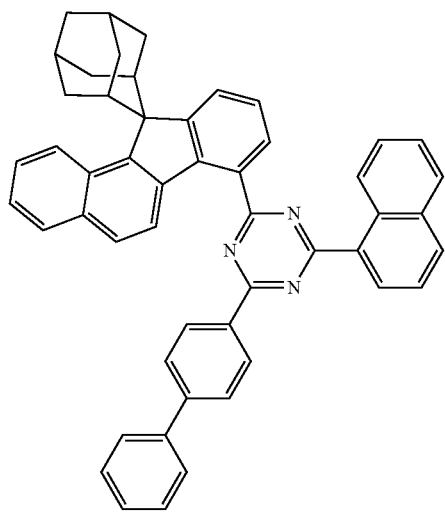
A-5
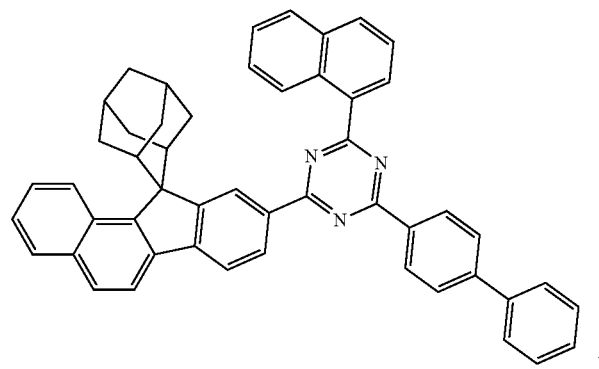
A-8
A-6
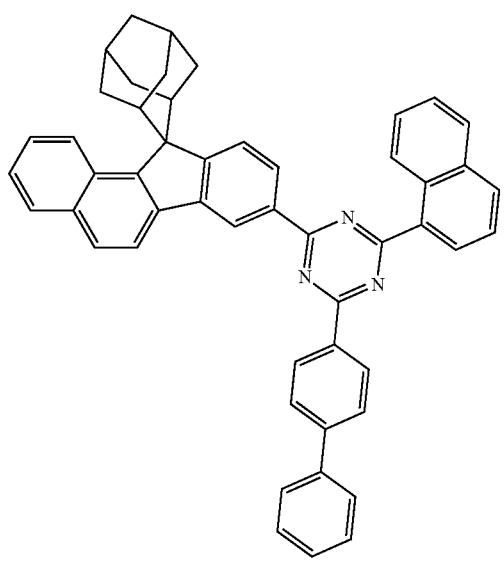
A-9
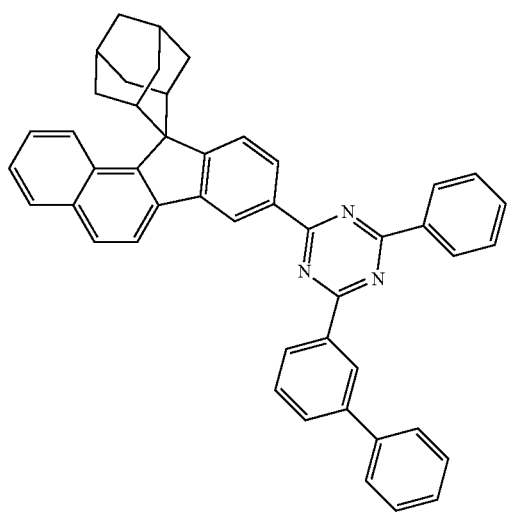

A-10
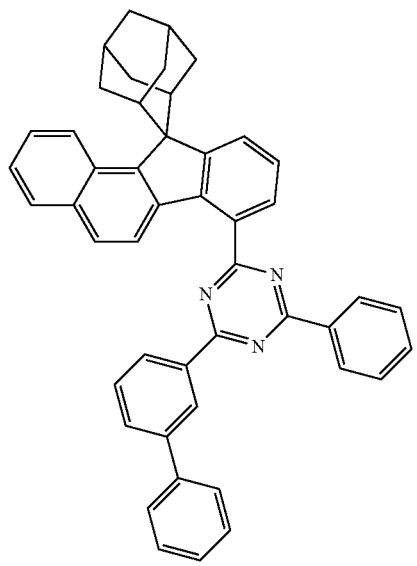
A-11
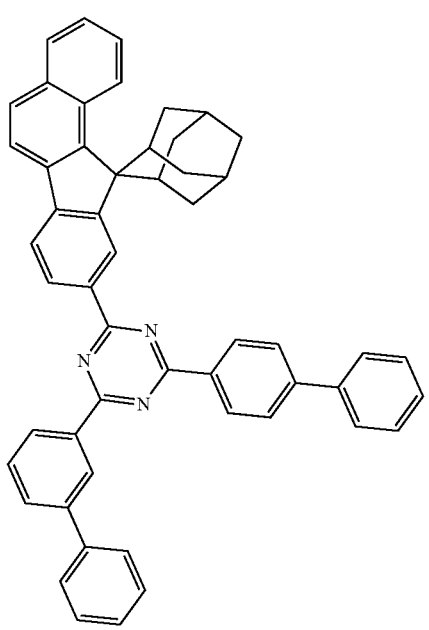
A-12
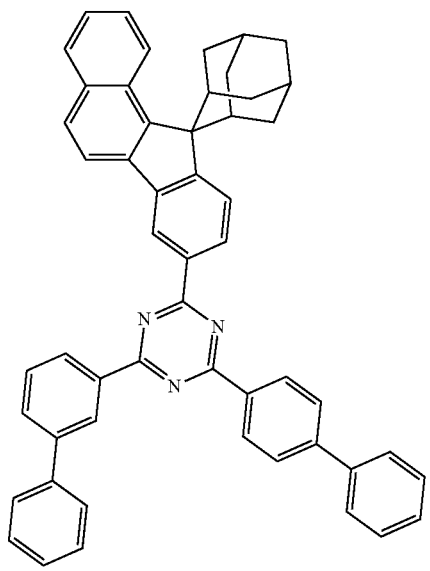
A-13
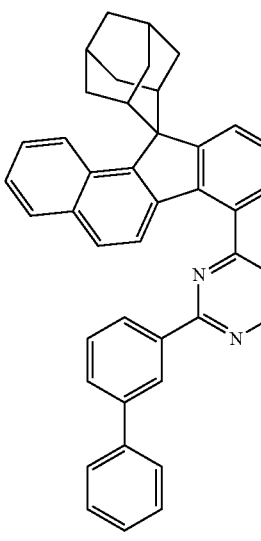

A-14
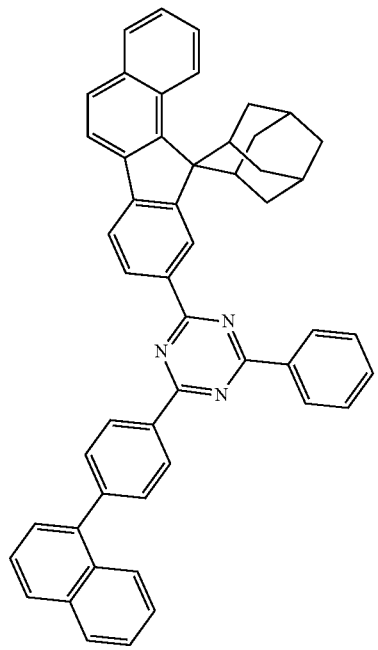
A-15
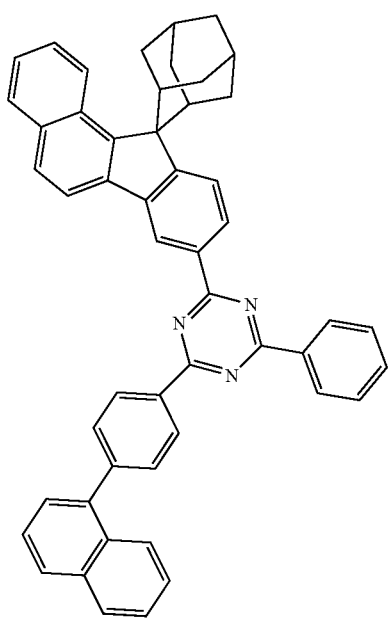
A-16
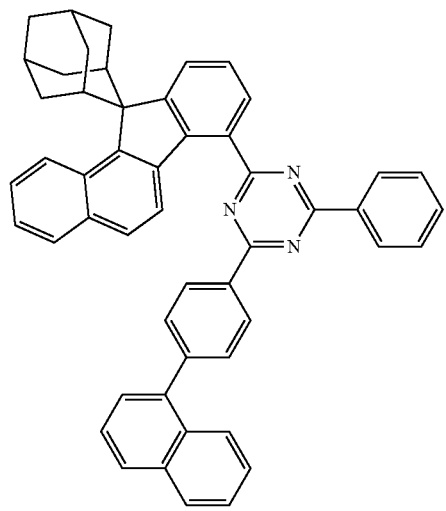
A-17
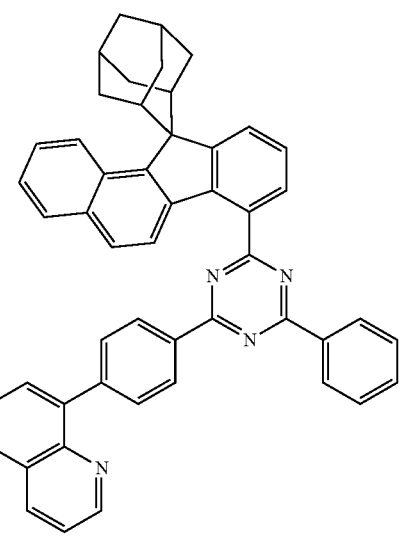
A-18
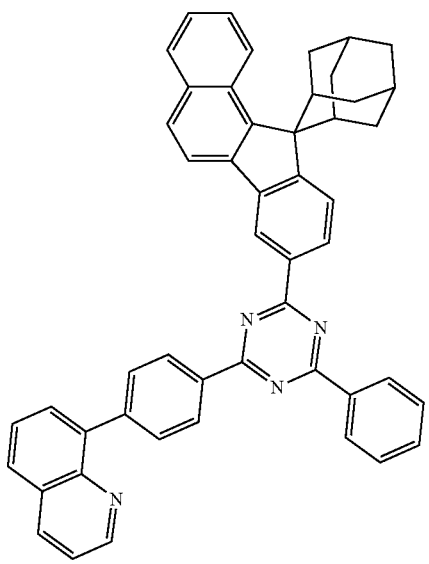

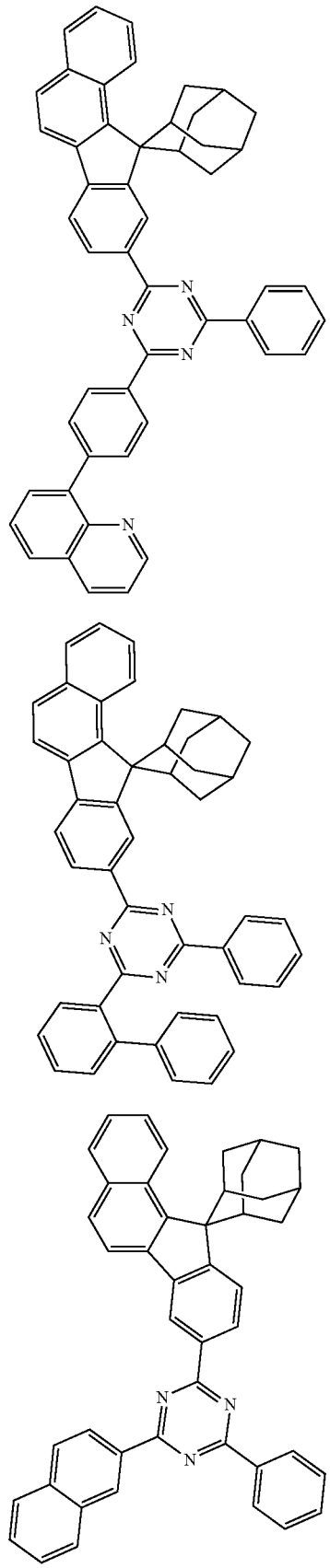
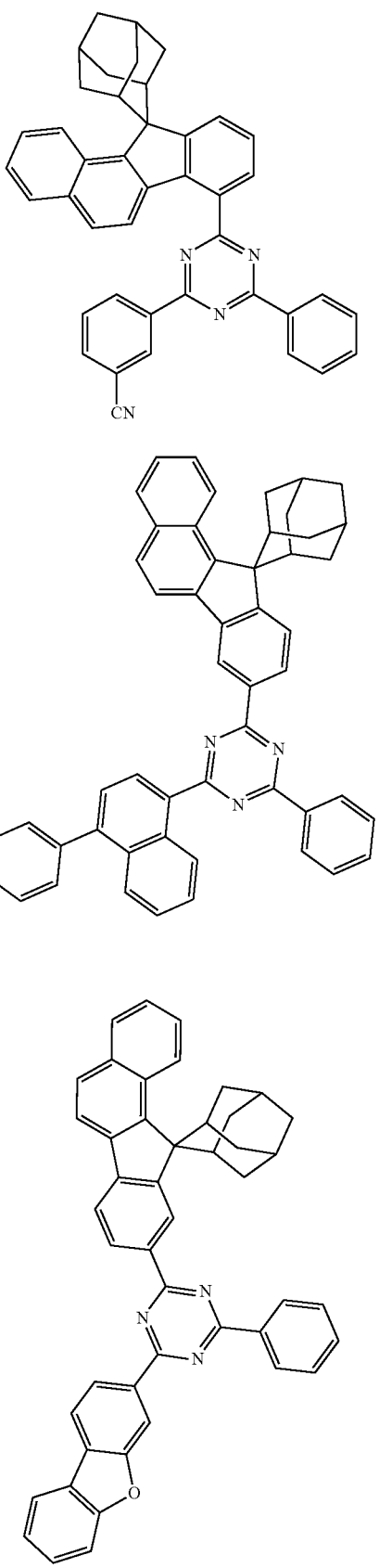

A-25
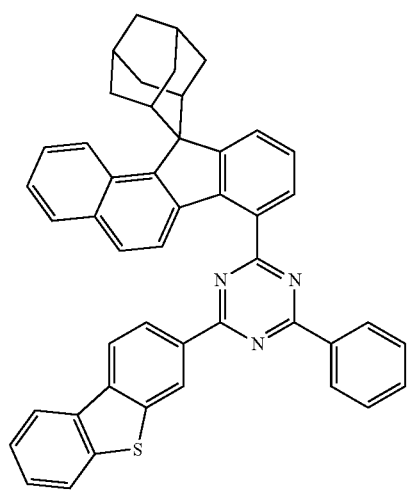
A-26
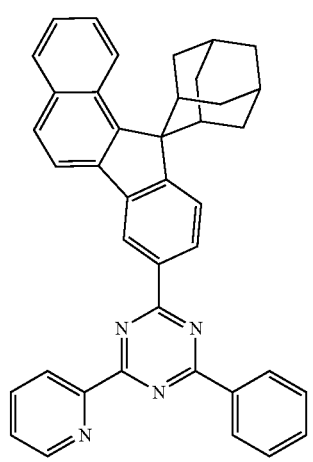
A-29
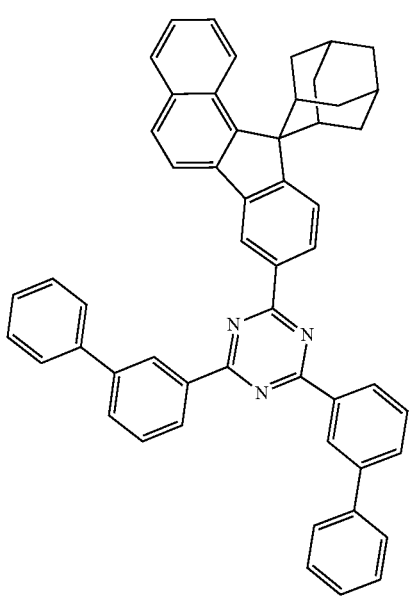
A-30
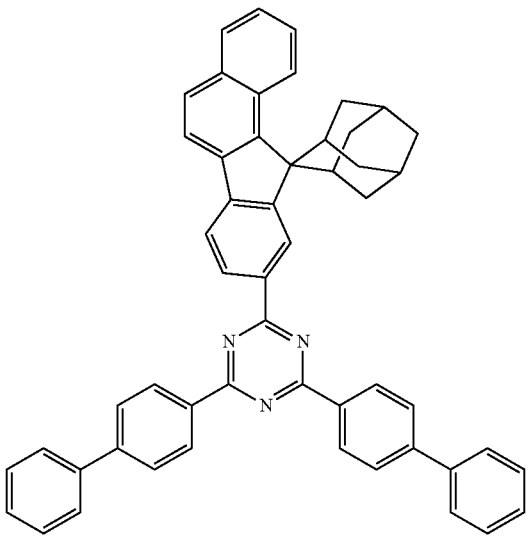
A-31
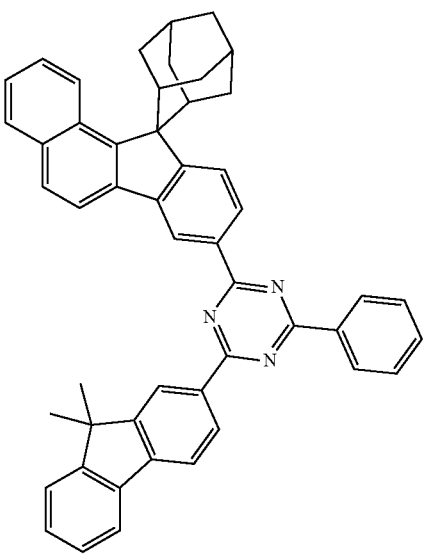

A-36
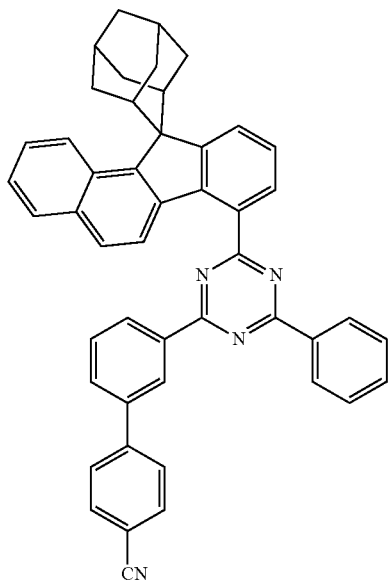
A-37
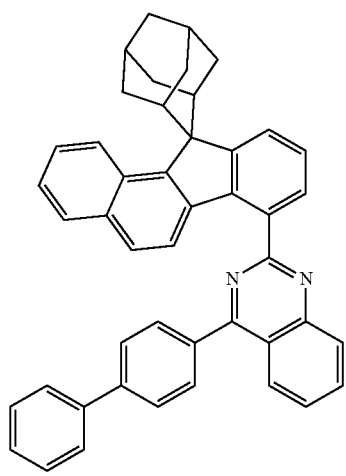
A-38
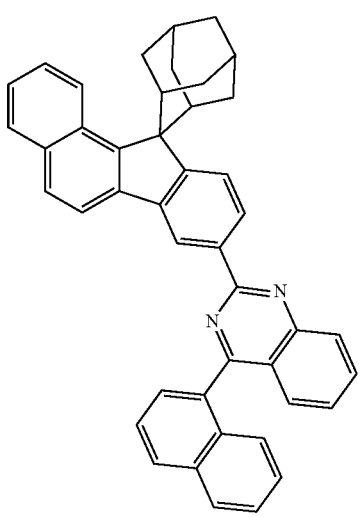
A-39
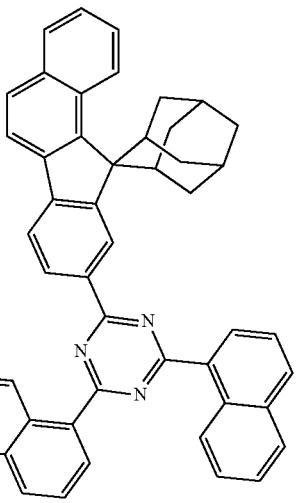
A-40
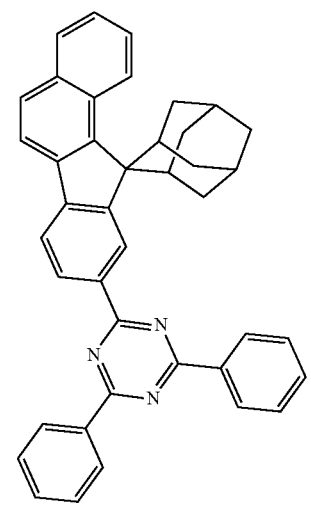
A-41
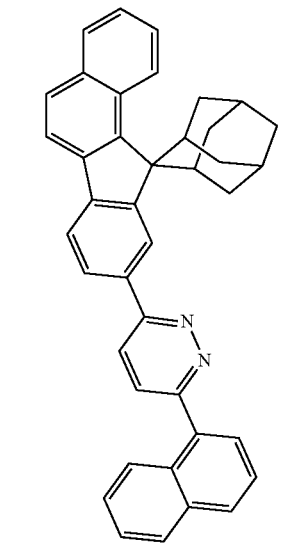

A-42
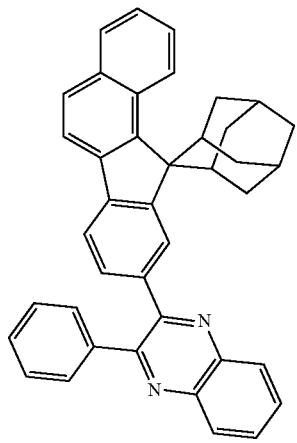
A-43
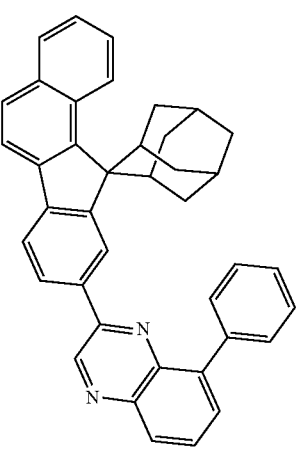
A-44
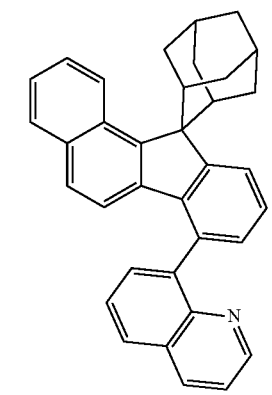
A-47
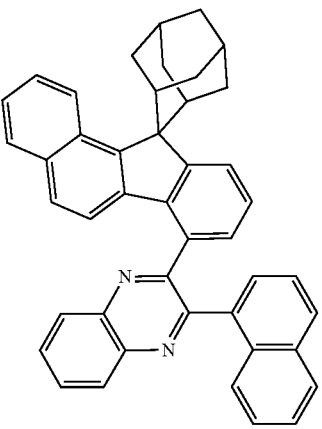
A-48
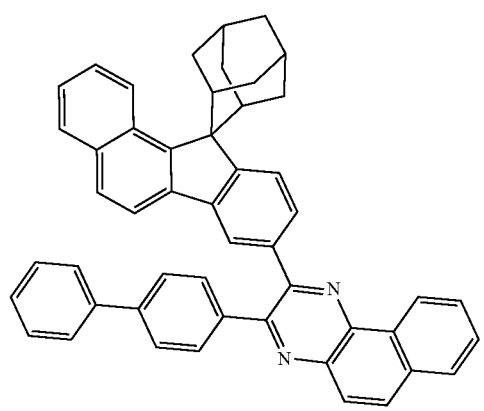
A-49
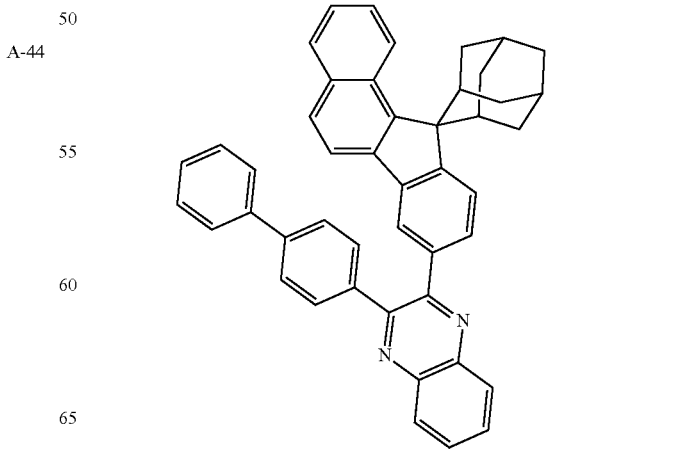

A-51 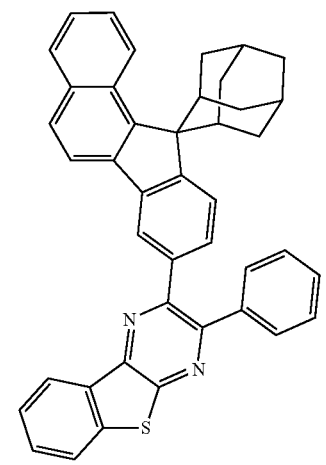
A-52 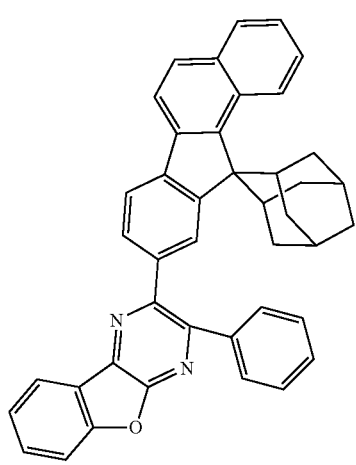
A-53 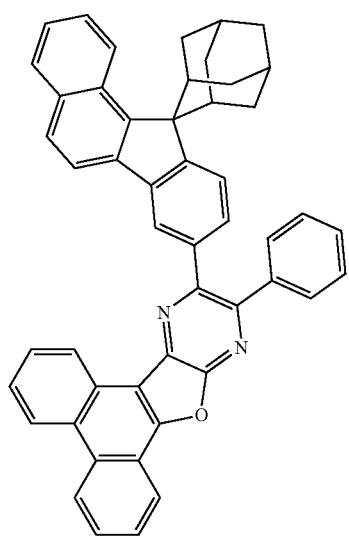
A-54 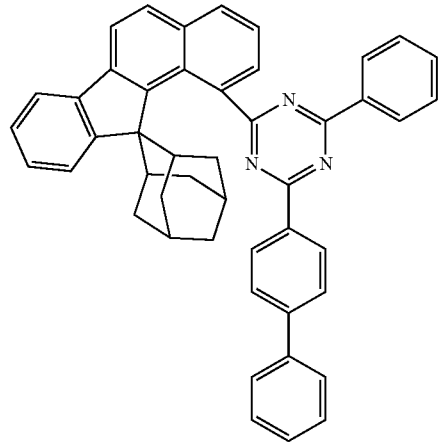
A-55 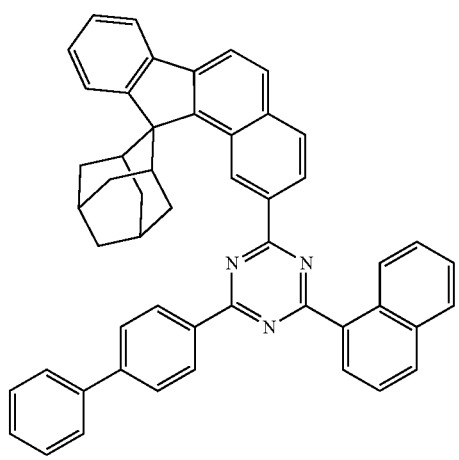
A-56 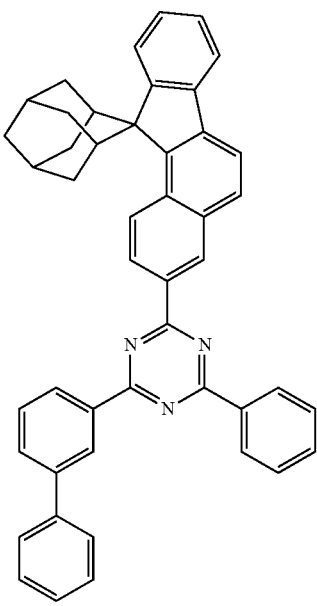

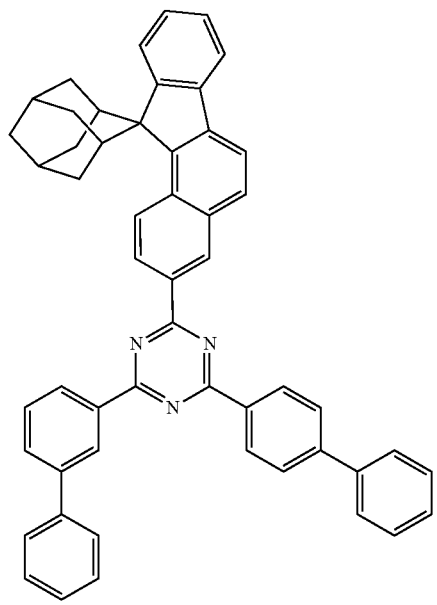
A-57
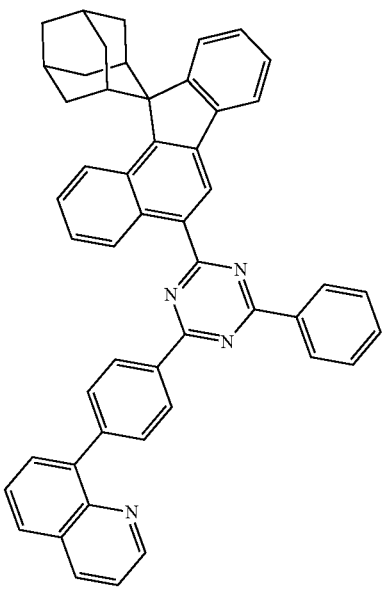
A-59
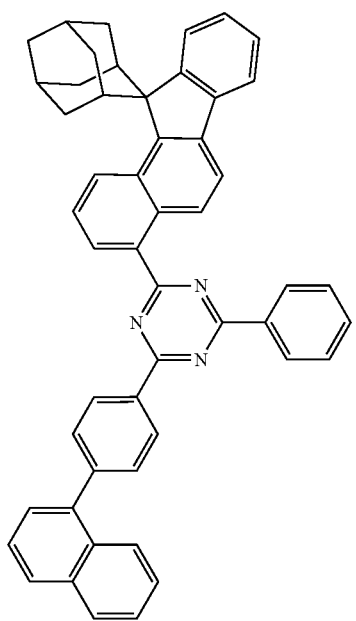
A-58
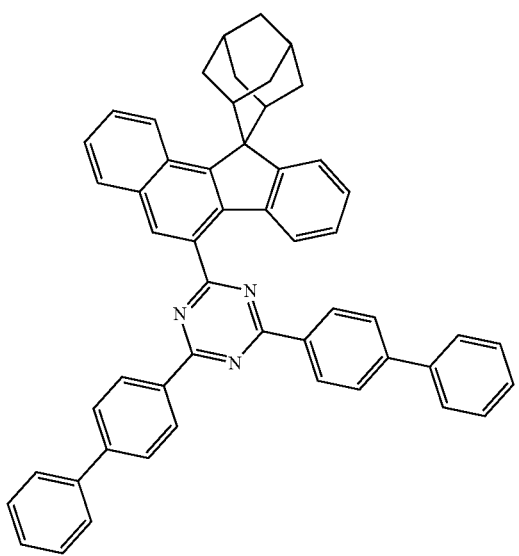
A-60

A-61
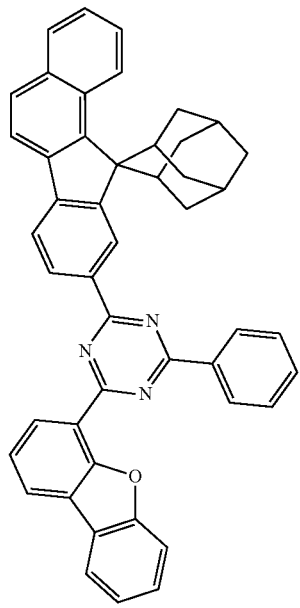
A-62
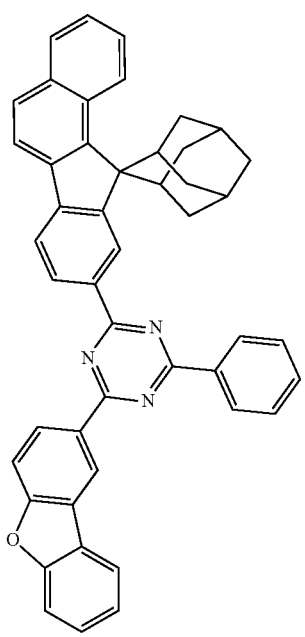
A-63
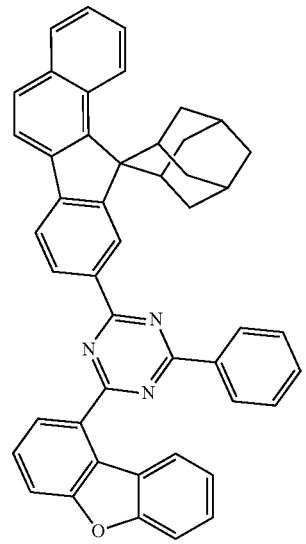
A-65
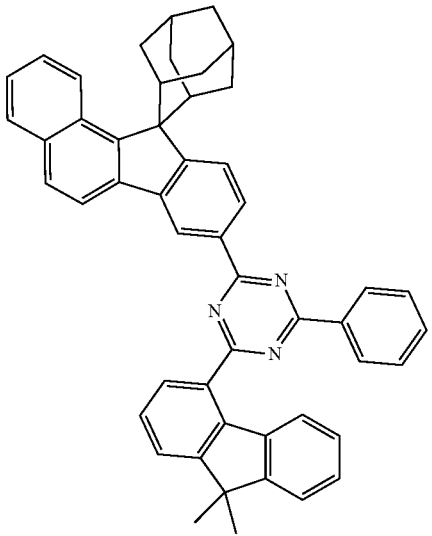

A-67
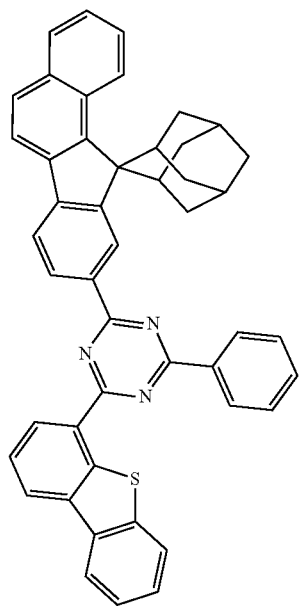
A-68
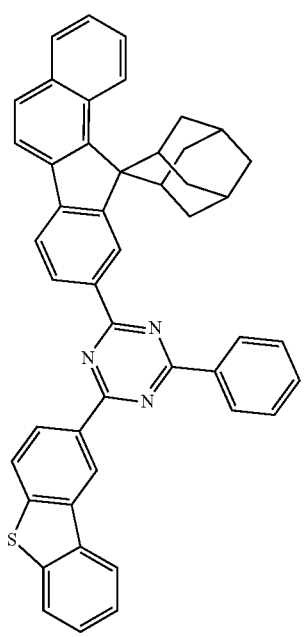
A-69
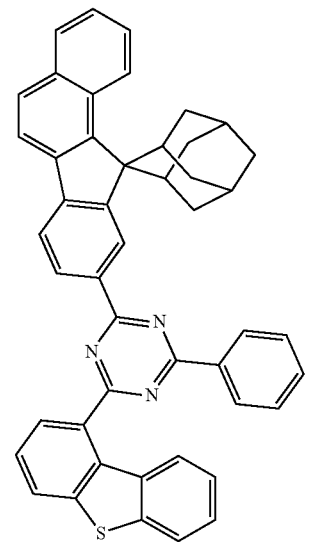
A-70
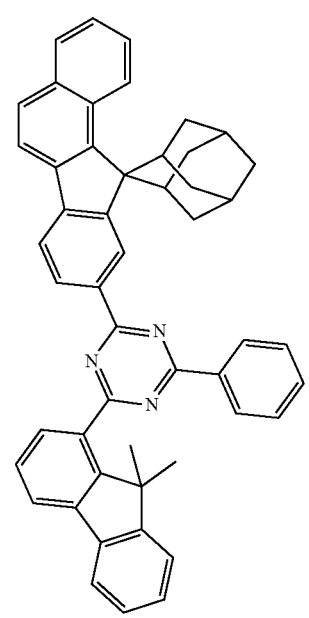

-continued
A-71
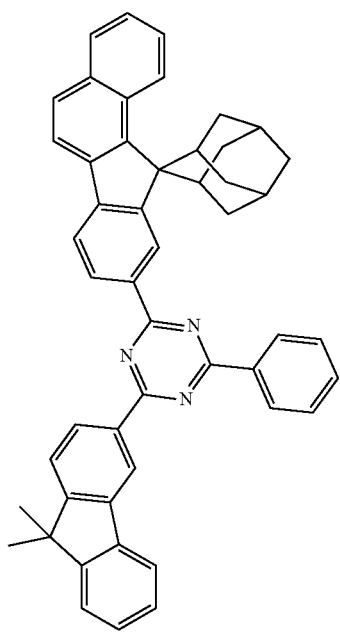
A-88
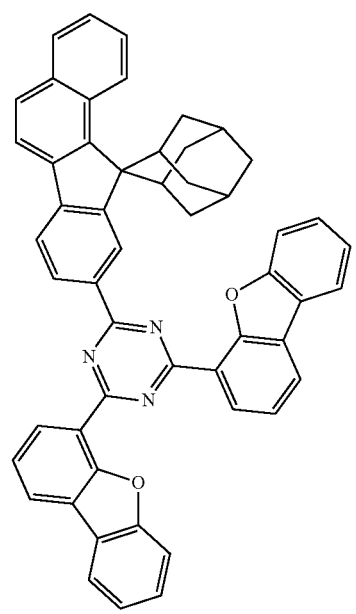
A-89
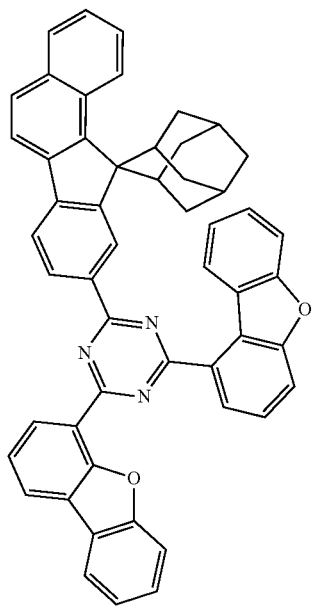
A-90
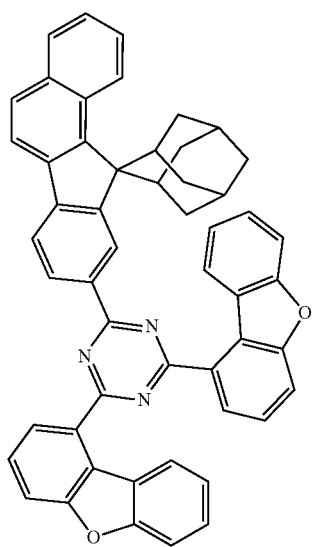

A-91
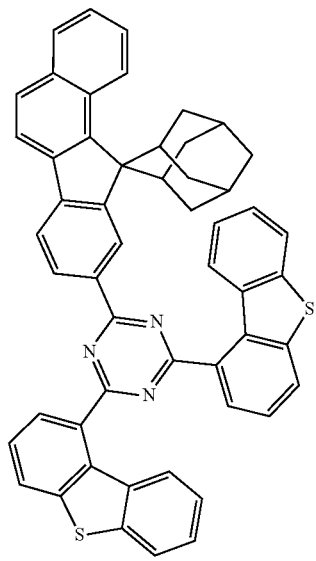
A-92
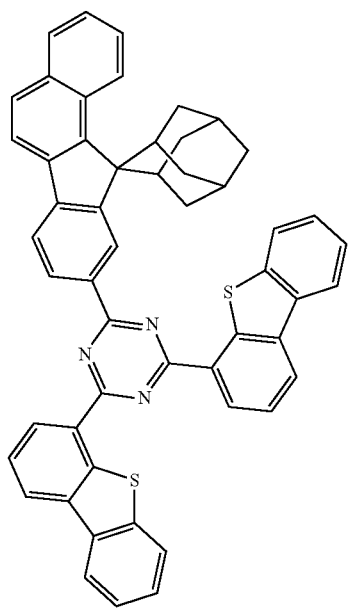
A-93
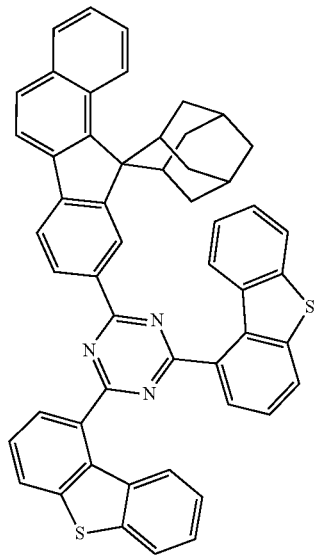
A-94
A-95
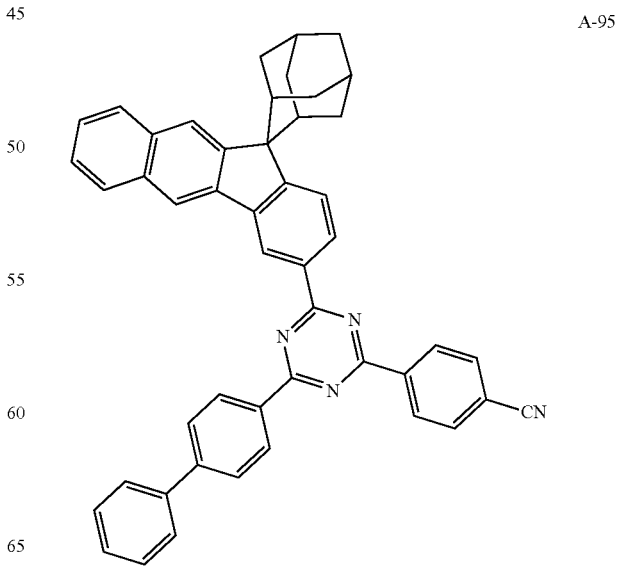

A-96
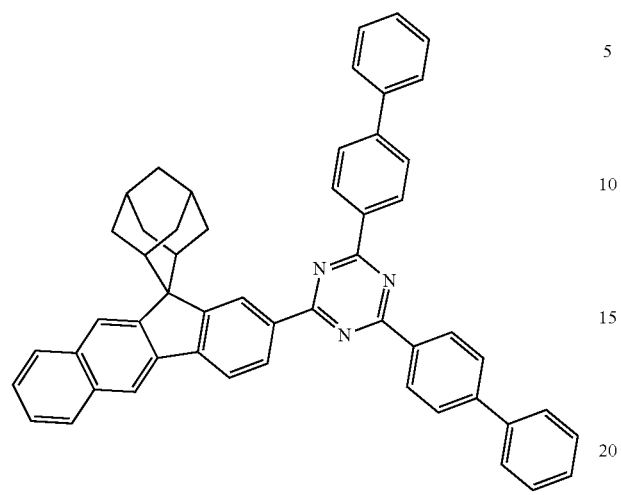
A-97
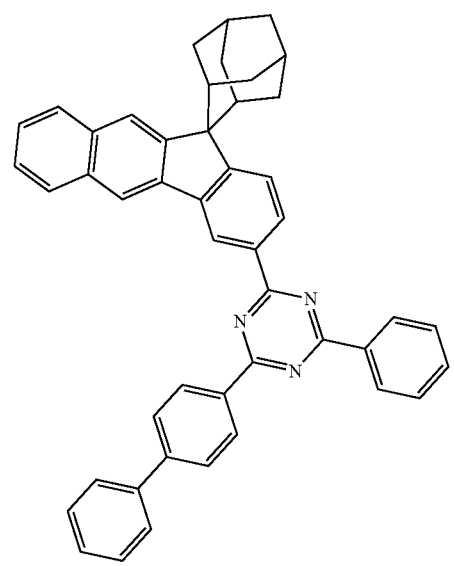
A-98
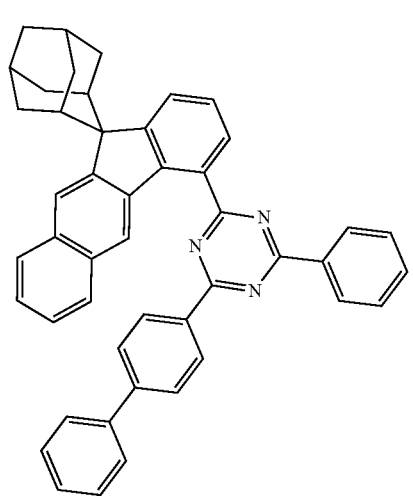
A-99
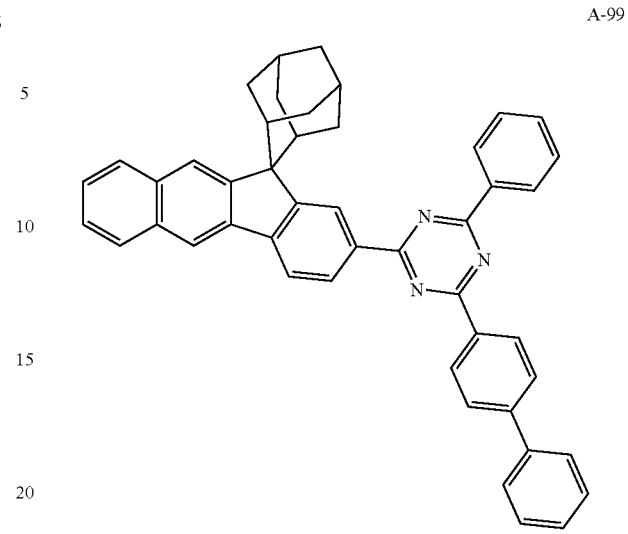
A-100
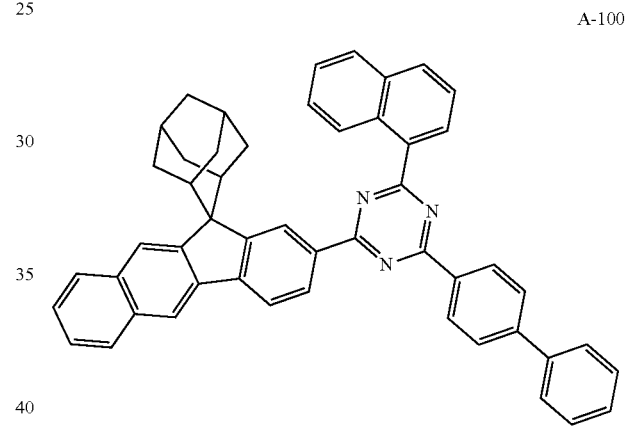
A-101
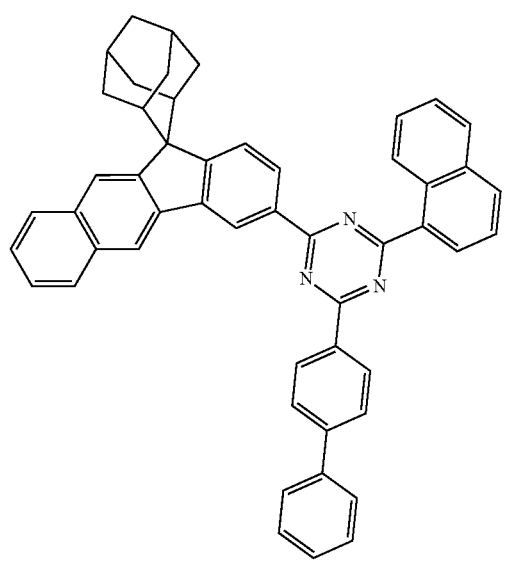

-continued
A-102
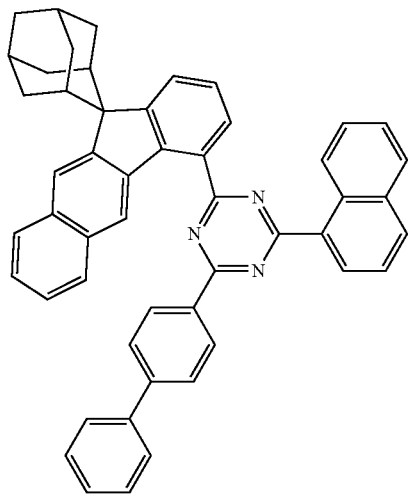
A-103
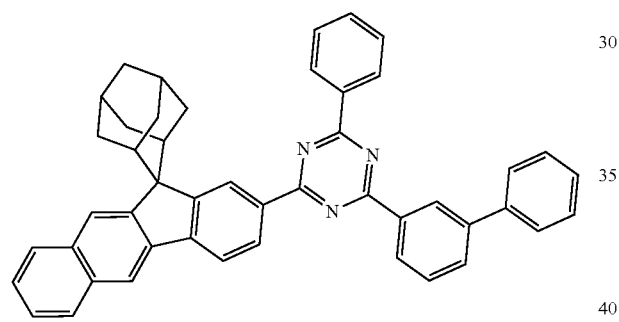
A-104
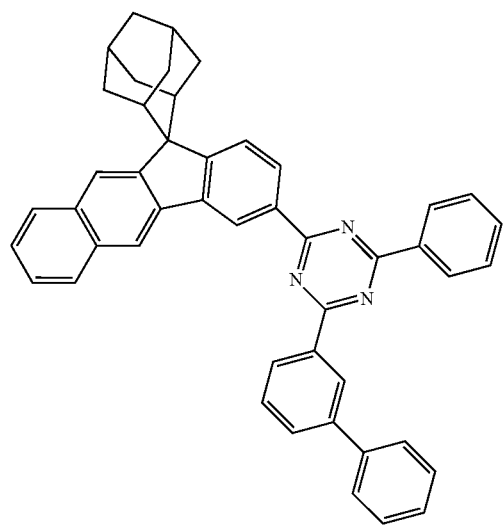
-continued
A-105
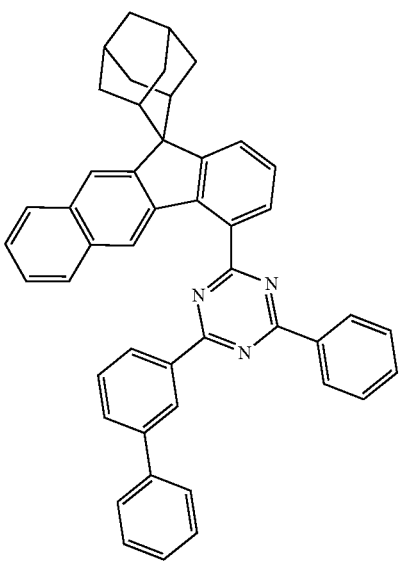
A-106
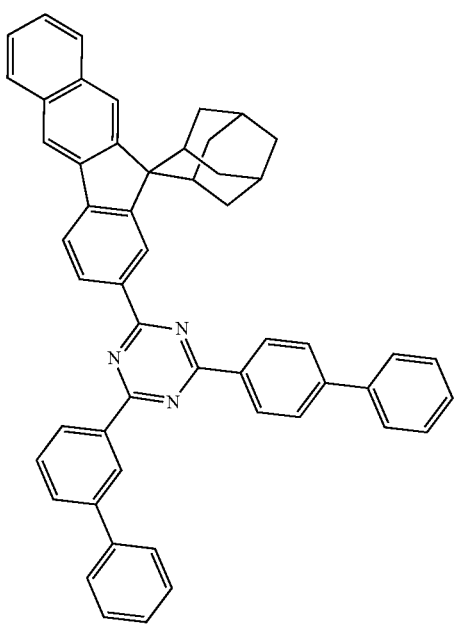

A-107
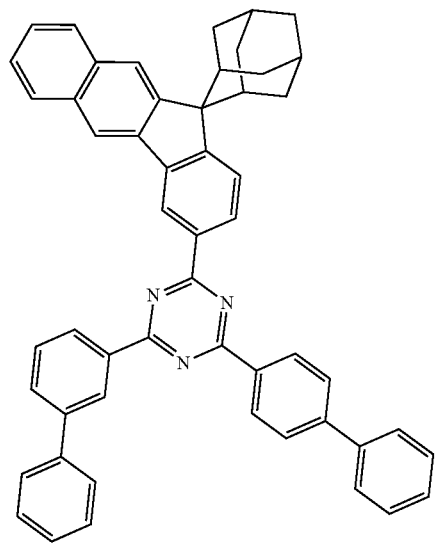
A-109
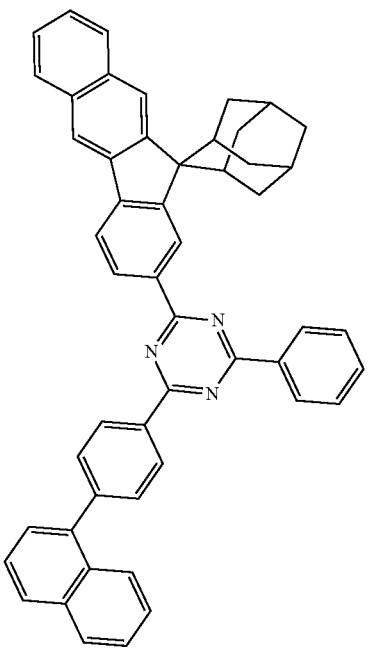
A-108
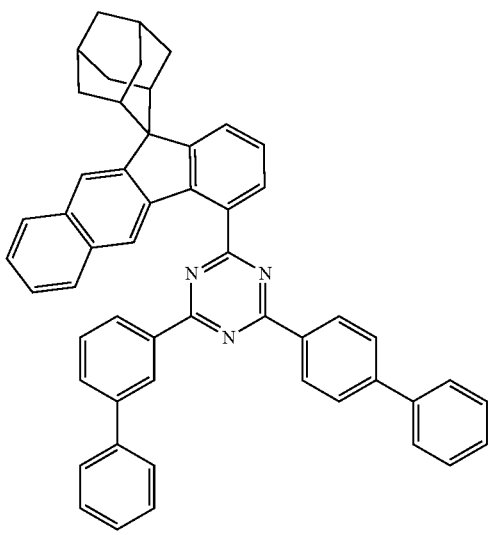
A-110
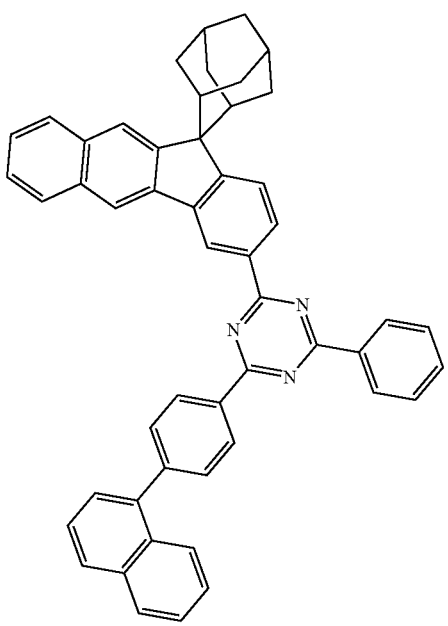

A-111
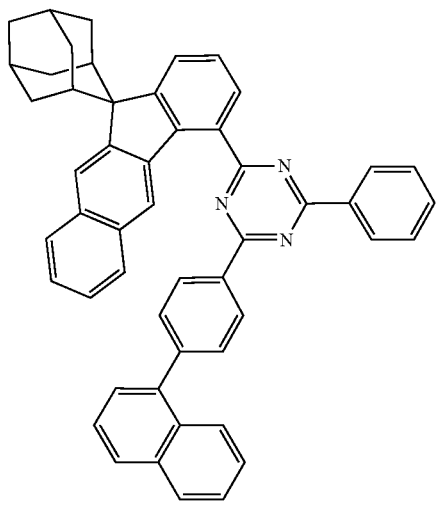
A-112
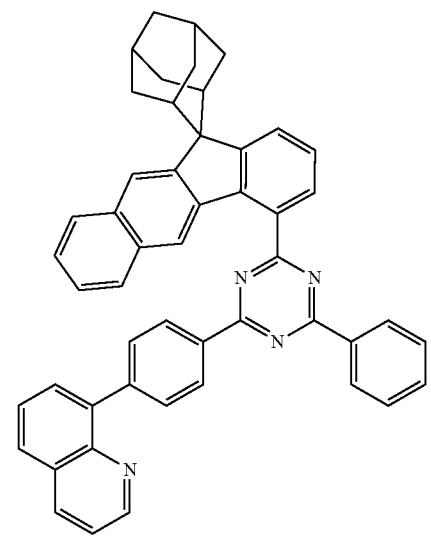
A-113
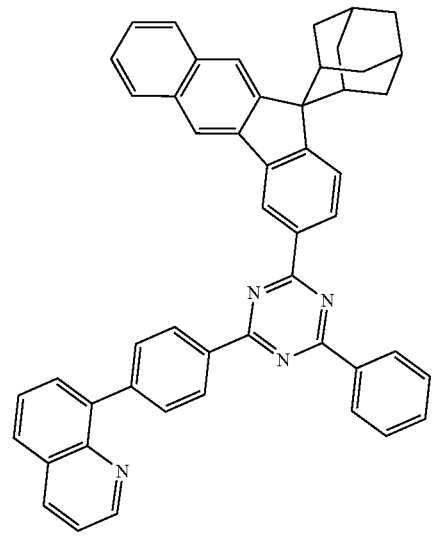
A-114
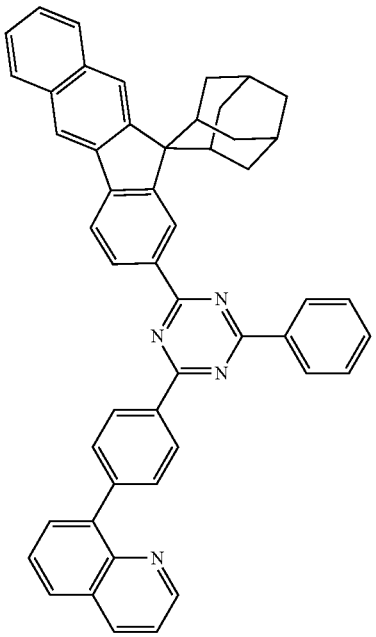
A-115
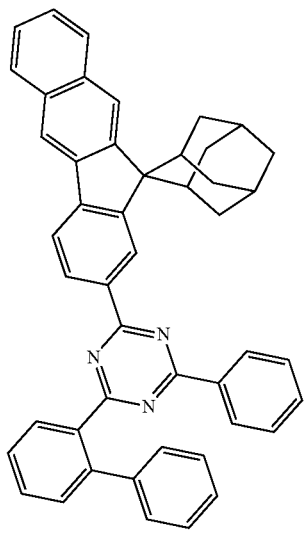
A-116
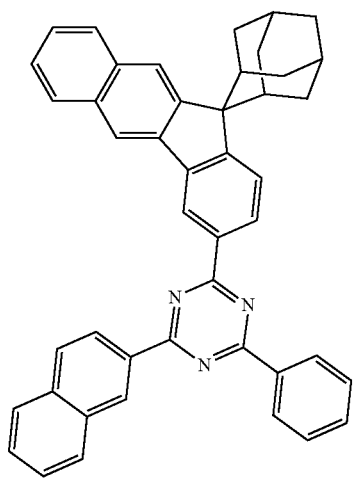

A-117
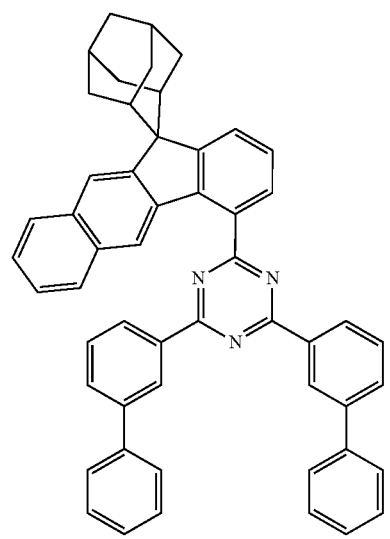
A-118
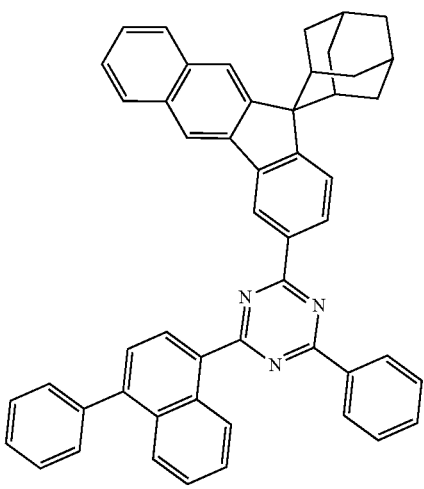
A-119
A-120
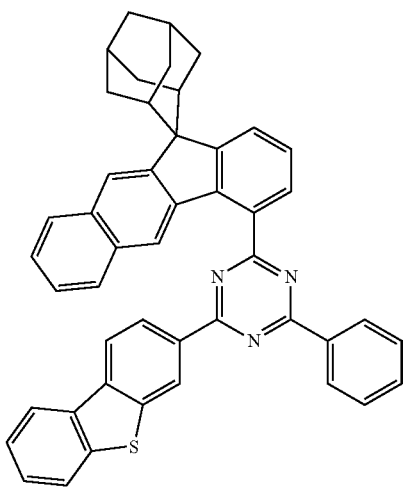
A-121
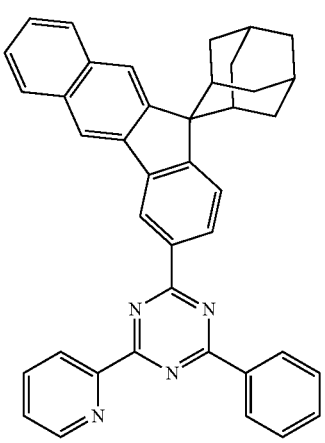
A-124
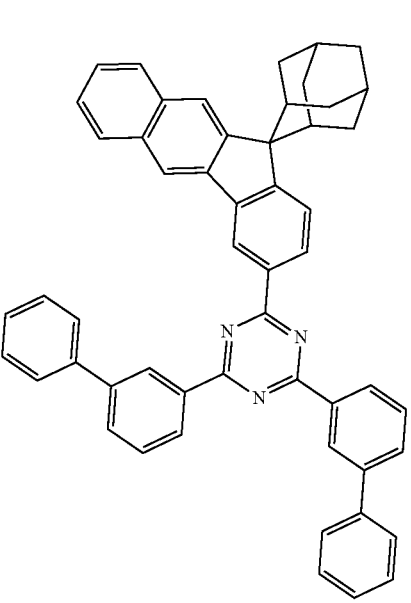

A-125
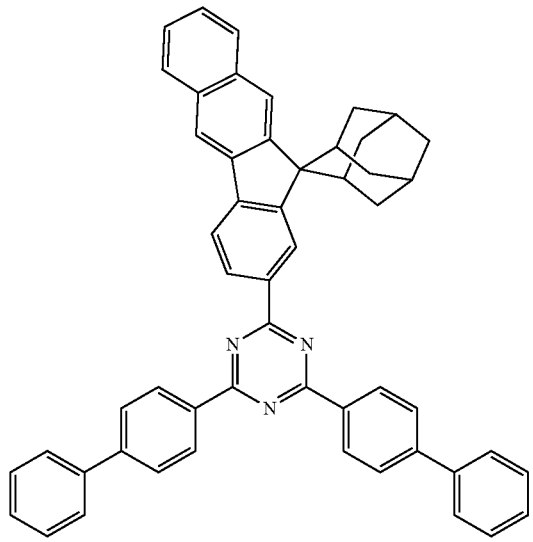
A-131
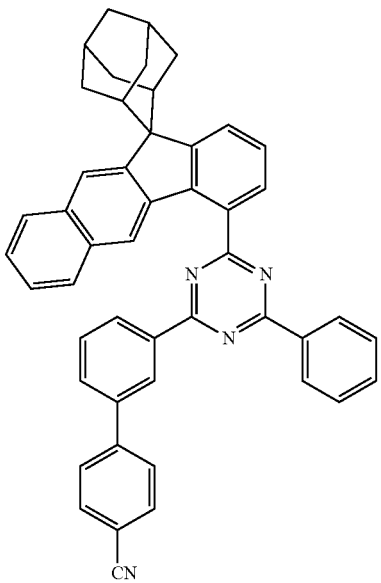
A-132
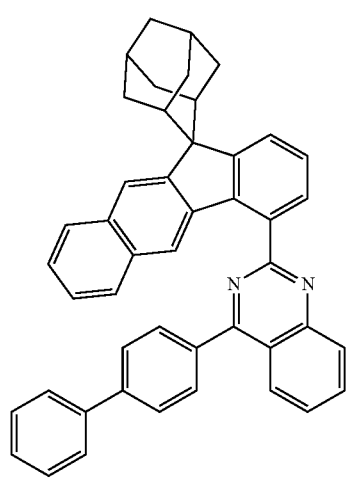
A-126
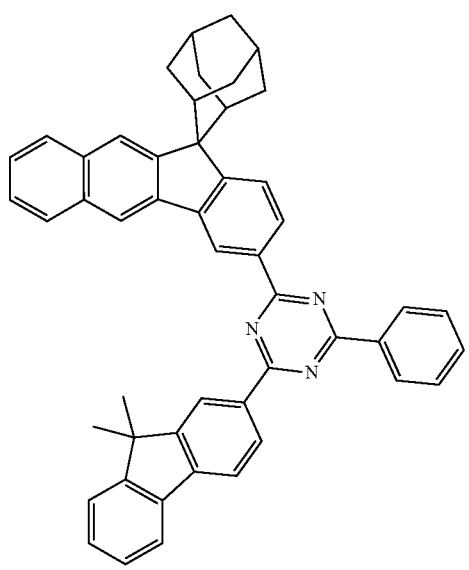
A-133
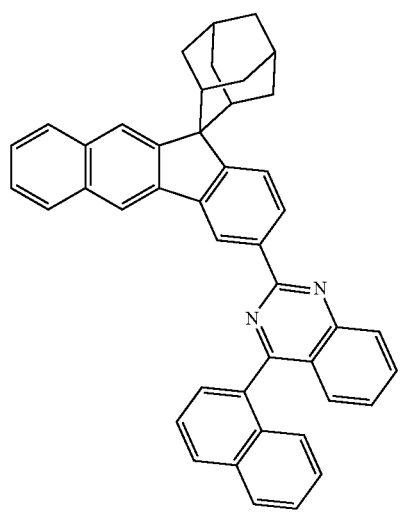

A-134
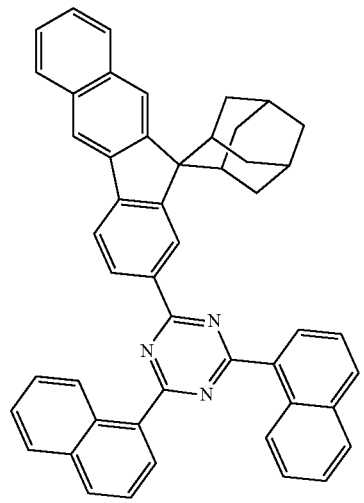
A-135
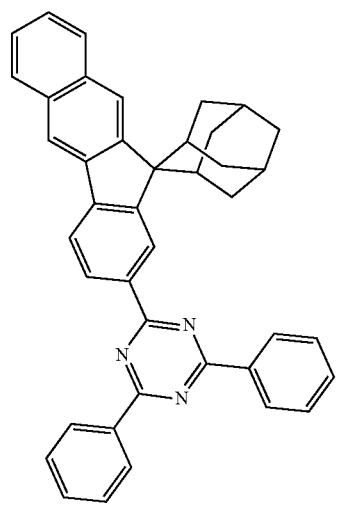
A-136
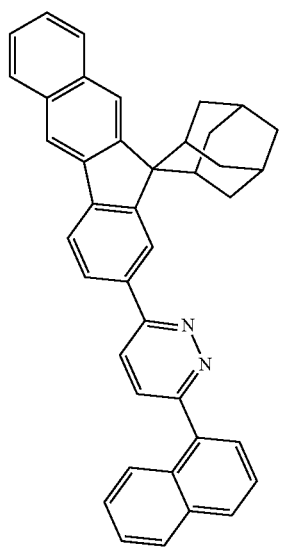
A-138
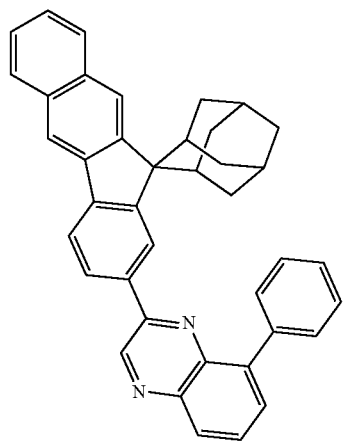
A-142
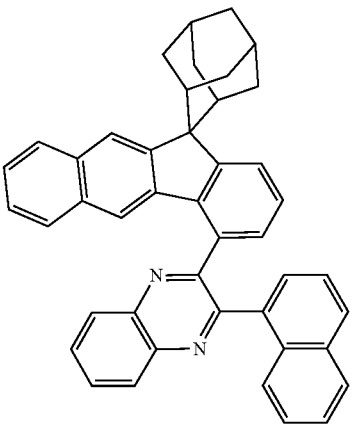
A-143
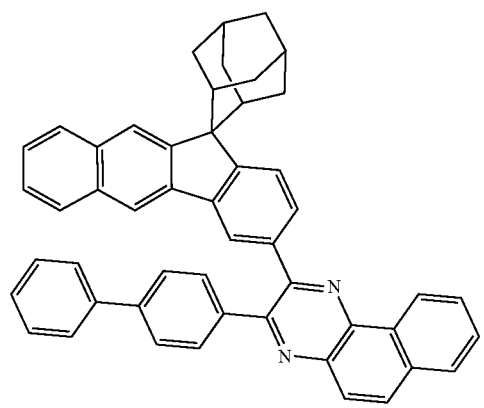

-continued
A-144
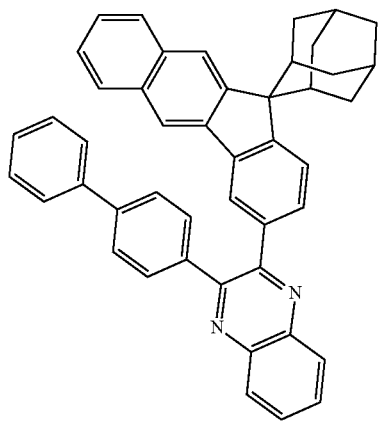
A-146
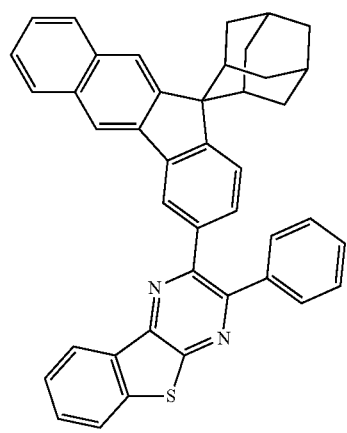
A-147
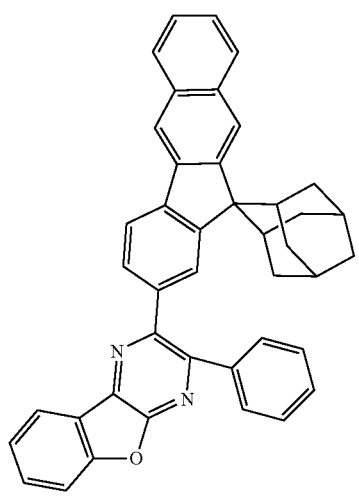
-continued
A-148
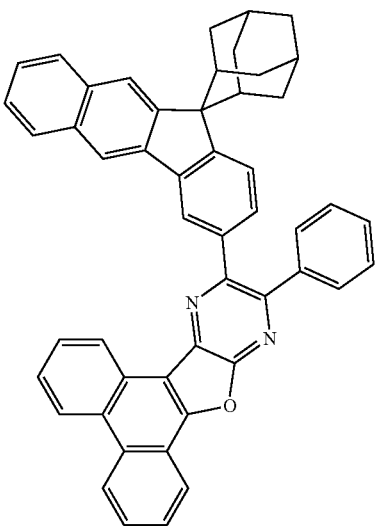
A-149
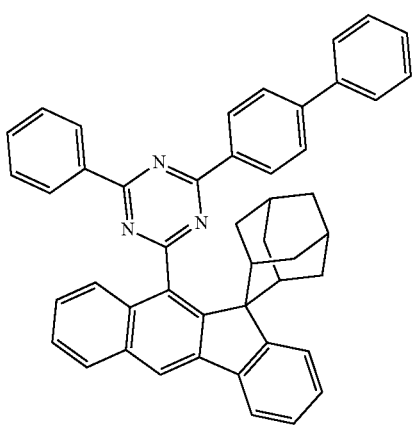
A-150
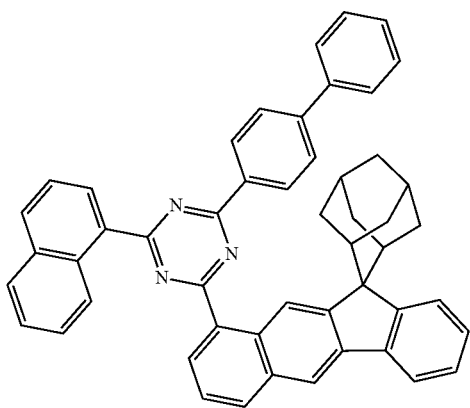

A-151
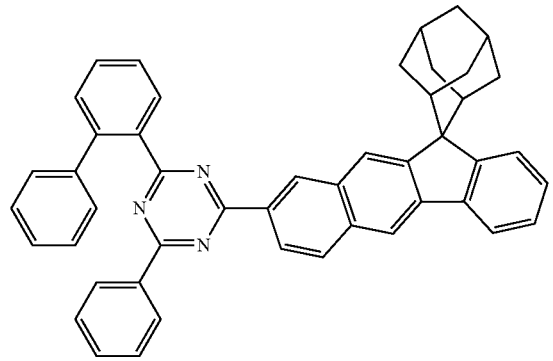
A-152
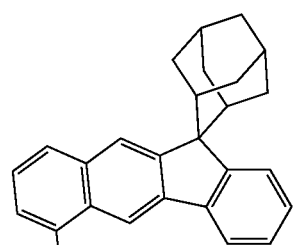
A-153
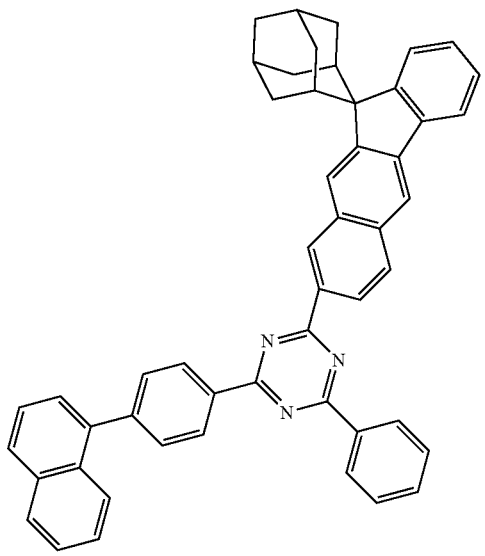
A-154
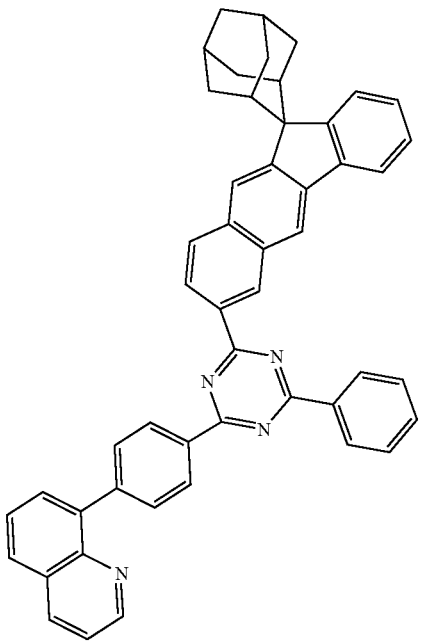
A-155
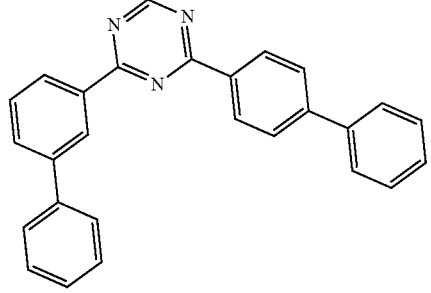

A-156
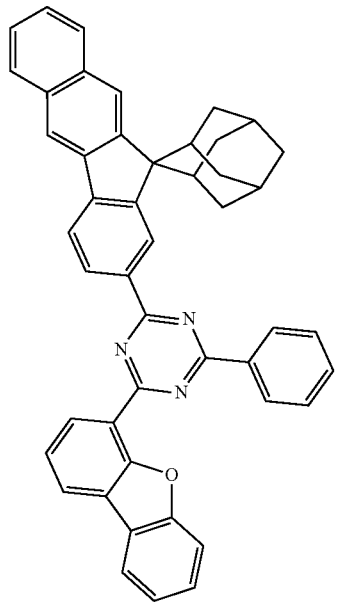
A-157
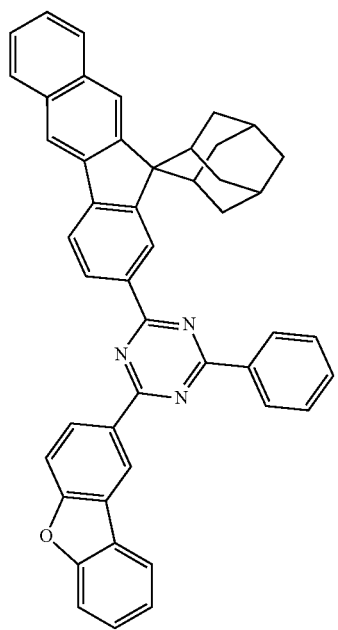
A-158
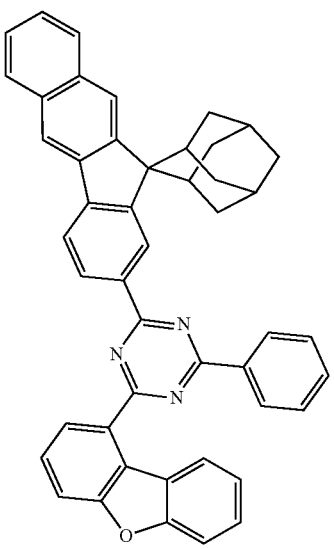
A-160
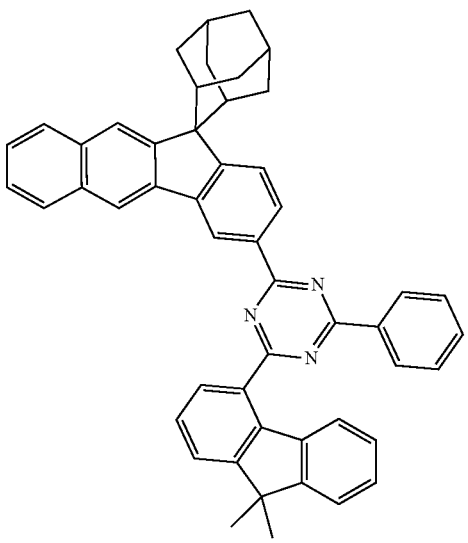

A-162
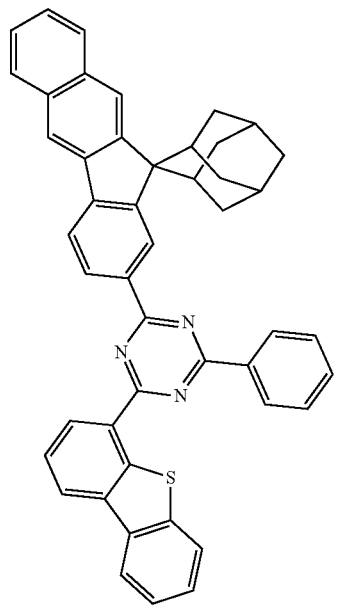
A-163
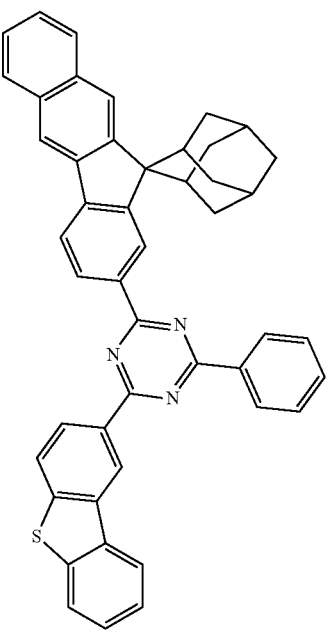
A-164
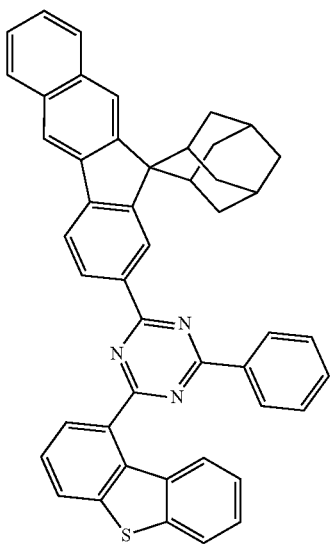
A-165
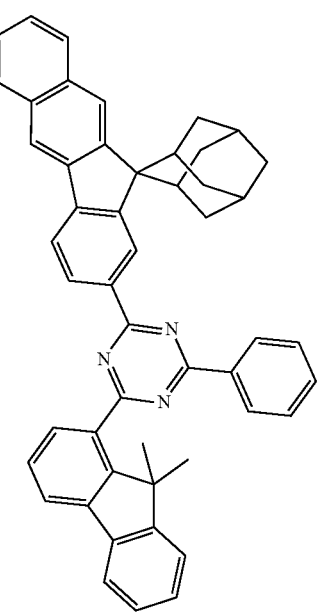

A-166
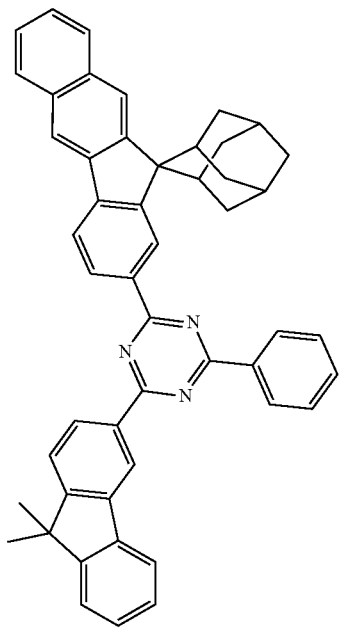
A-184
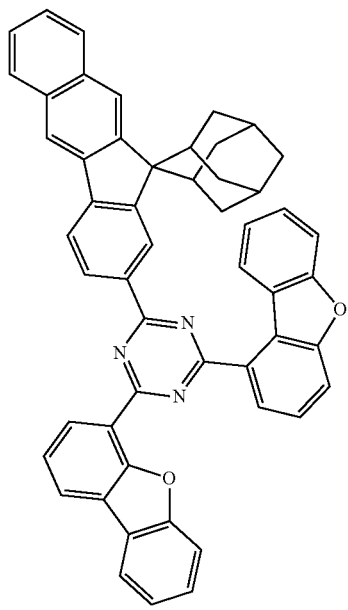
A-183
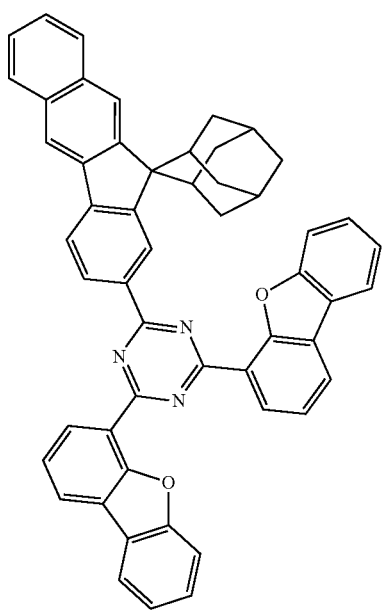
A-185
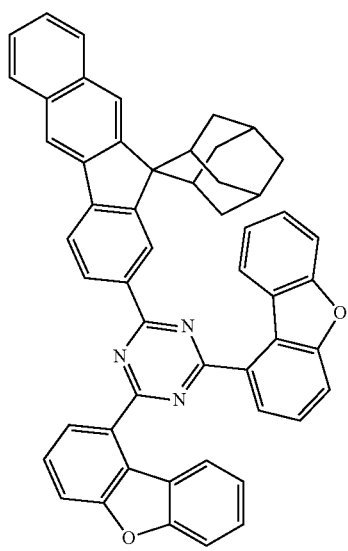

A-190
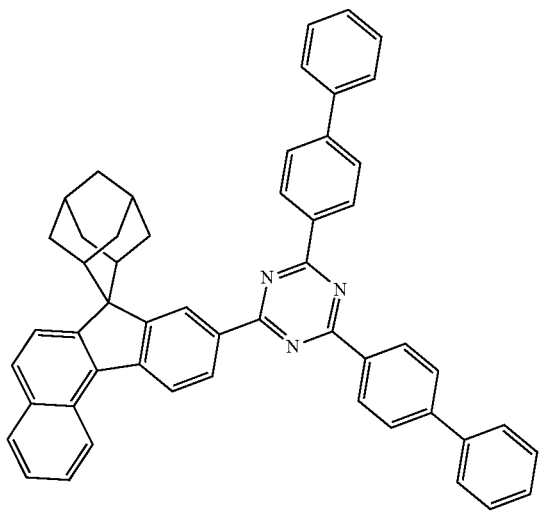
A-191
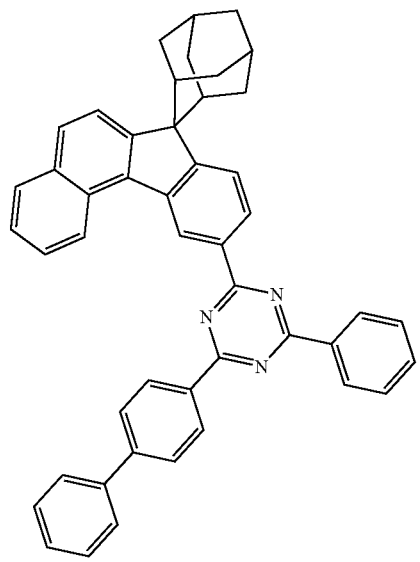
A-192
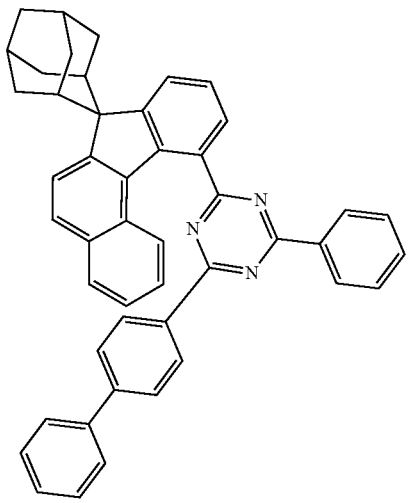
A-193
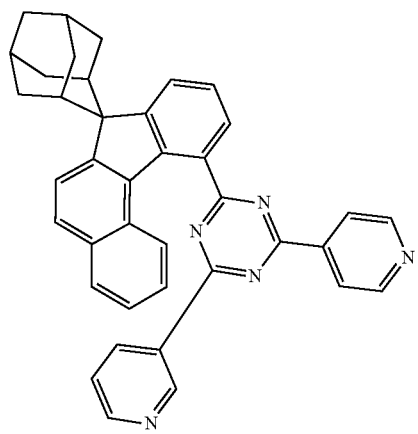
A-194
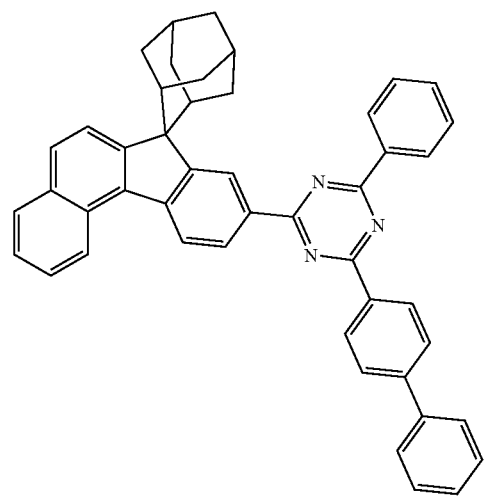
A-195
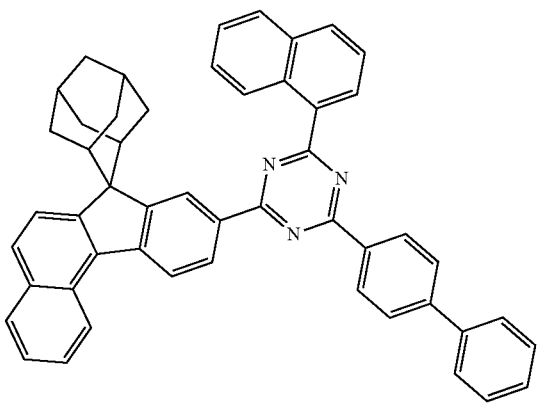

A-196
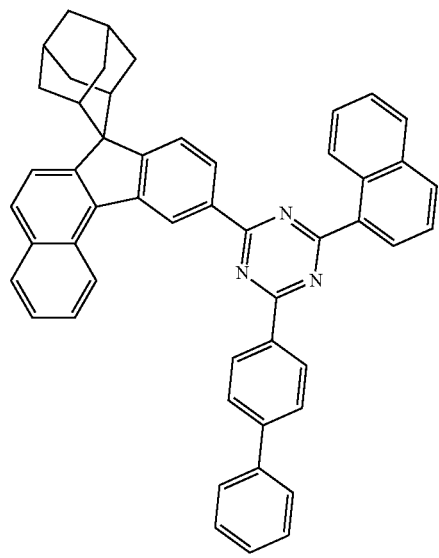
A-199
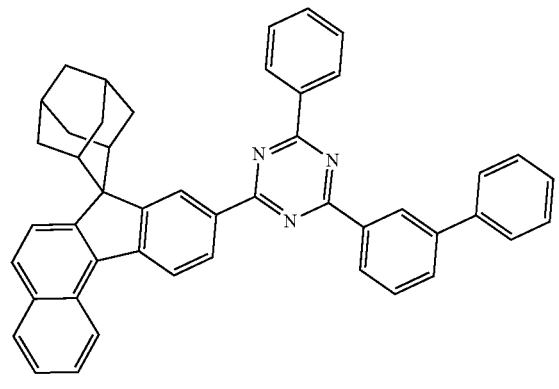
A-197
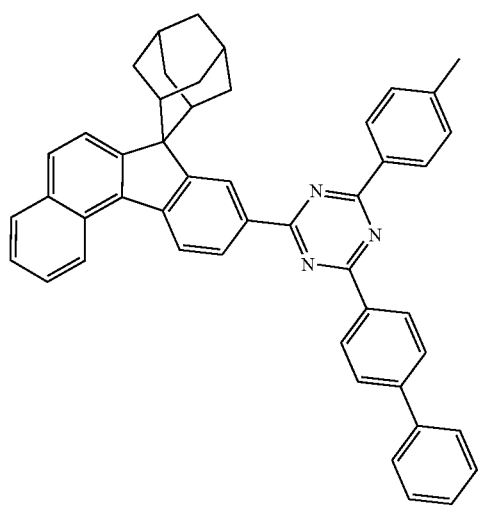
A-200
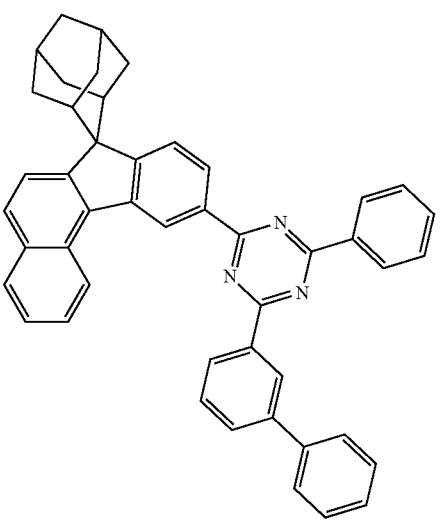
A-198
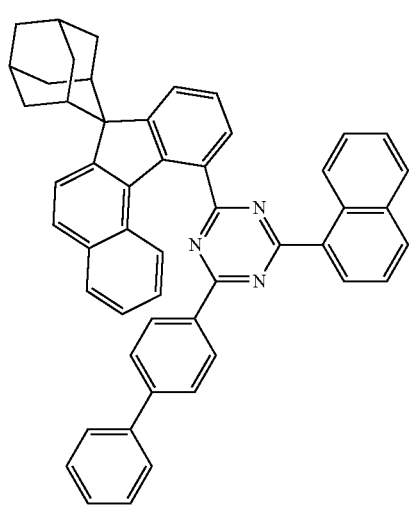
A-201
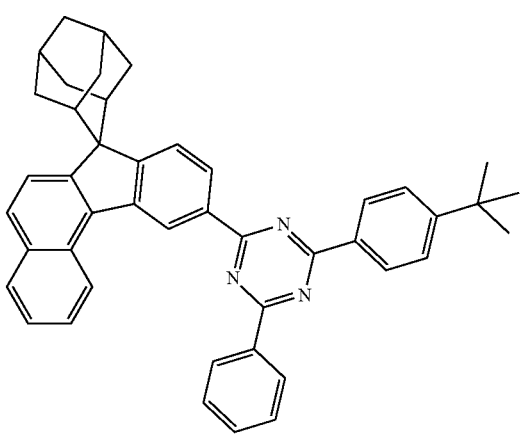

A-187
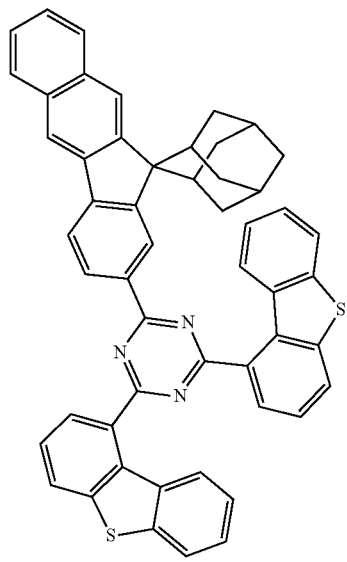
A-188
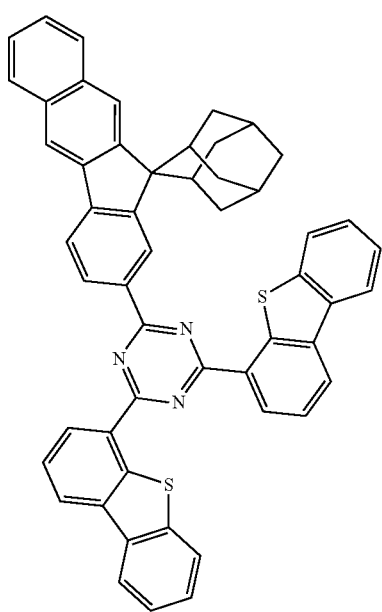
A-189
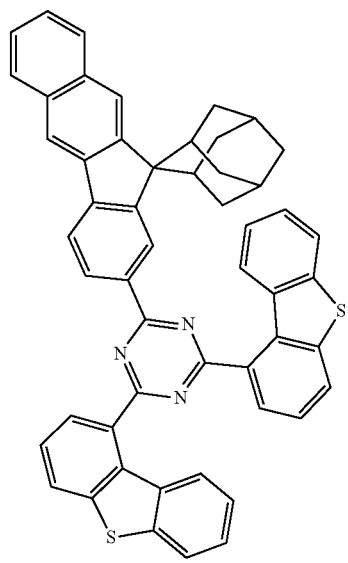
A-202
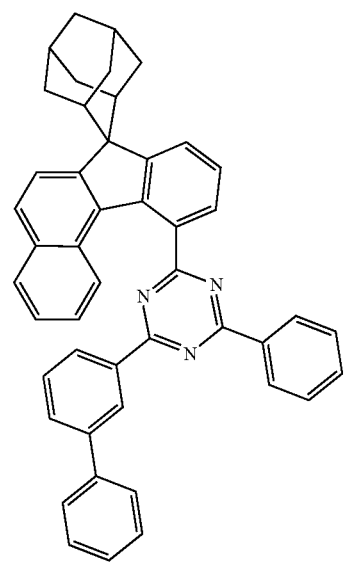

A-203
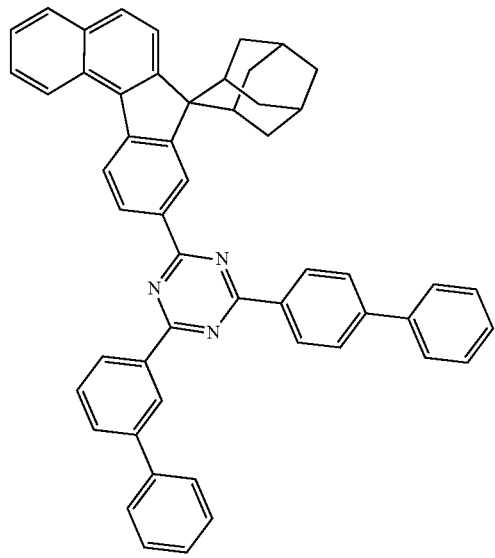
A-204
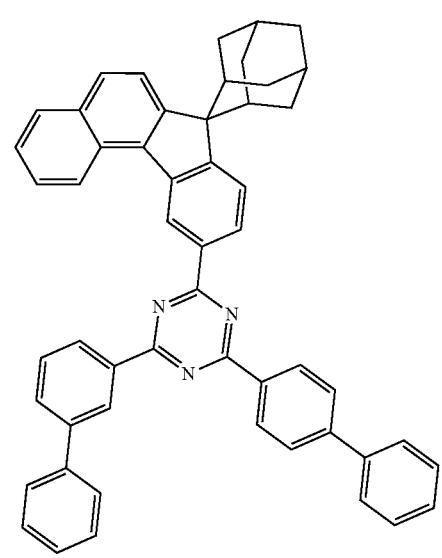
A-205
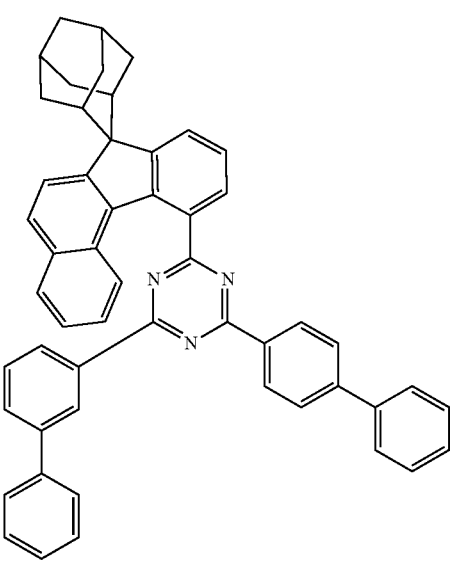
A-206
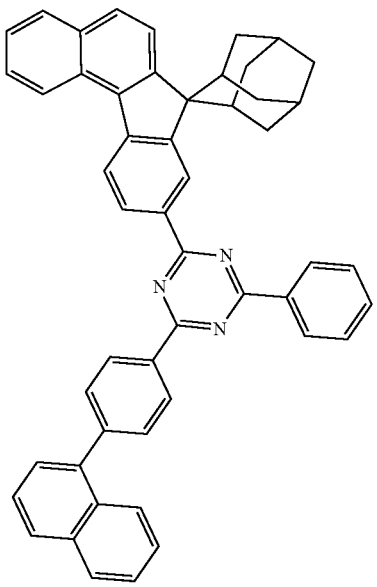
A-207
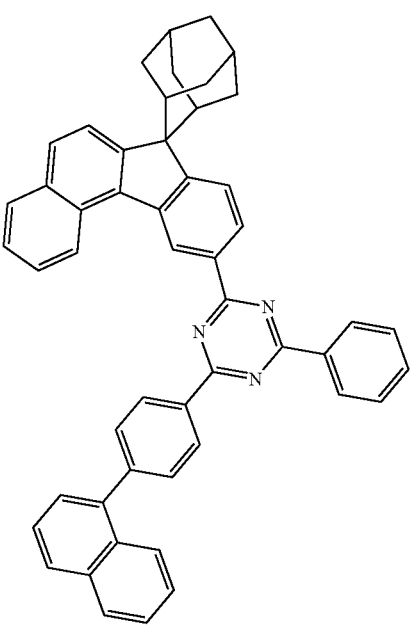

A-208
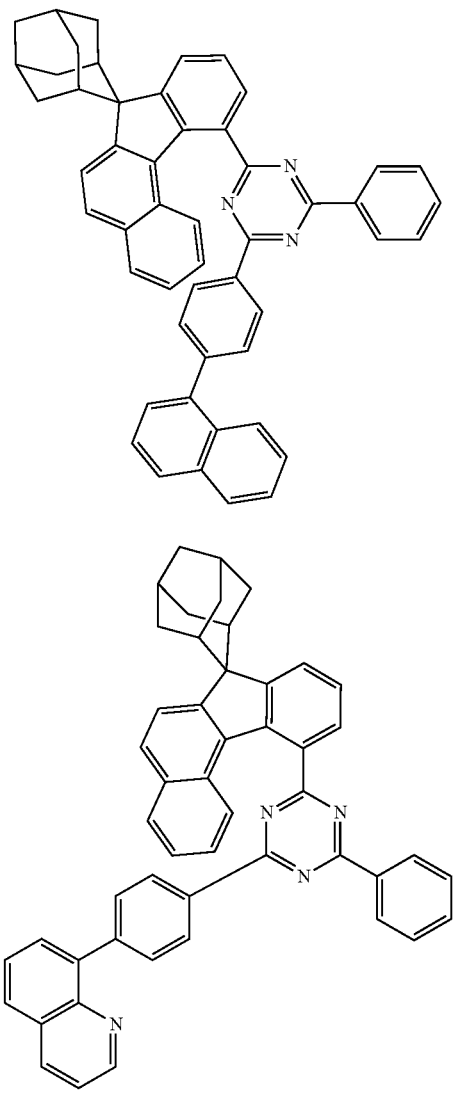
A-209
A-210
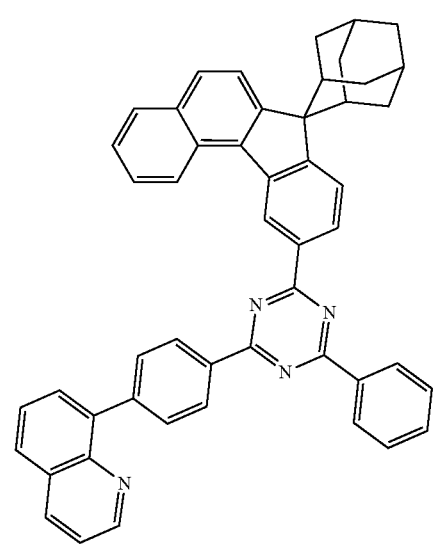
A-211
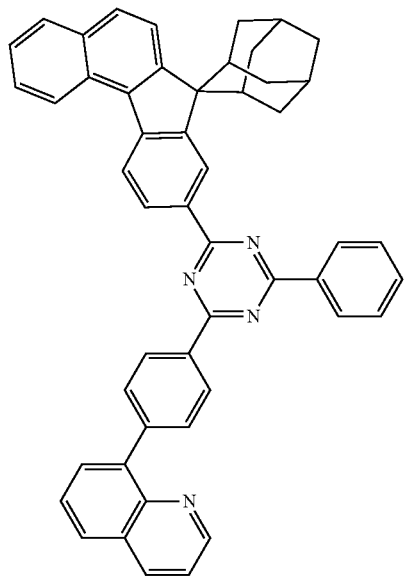
A-212
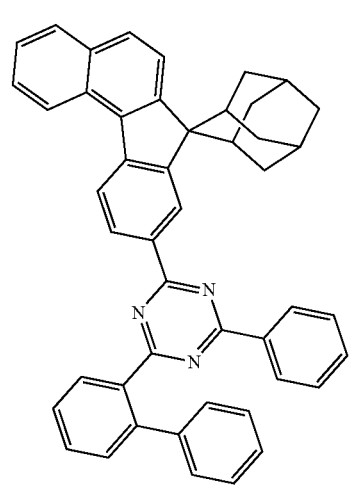
A-213
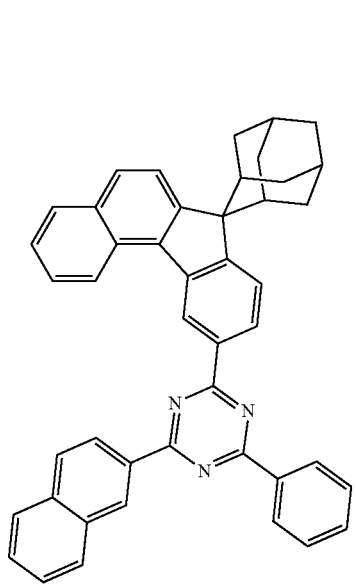

A-214
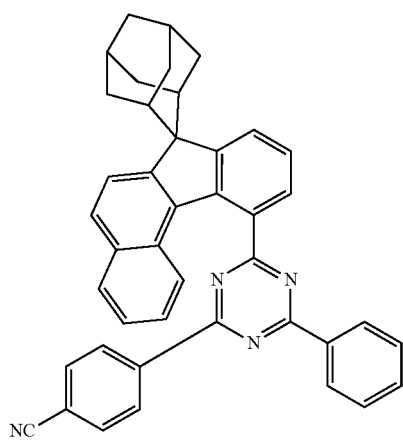
A-215
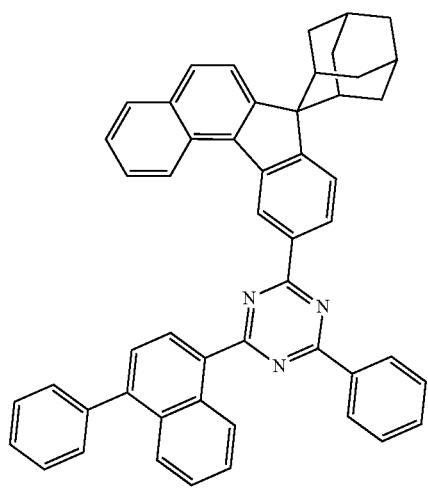
A-216
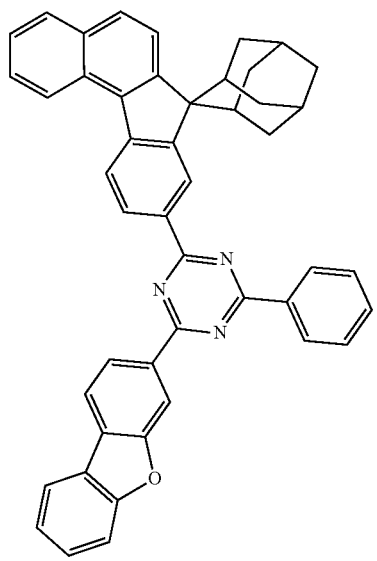
A-217
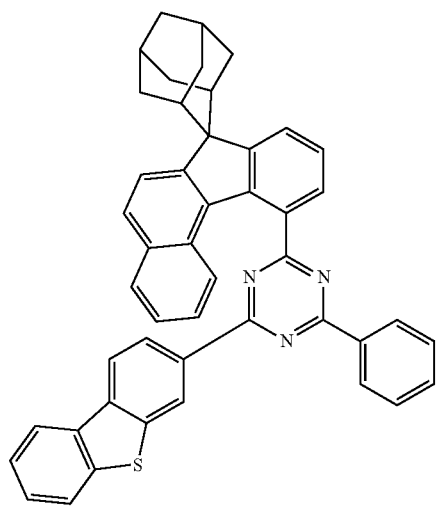
A-218
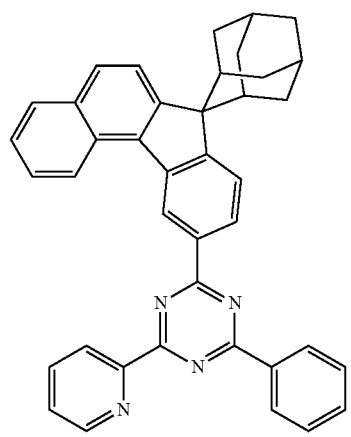
A-221
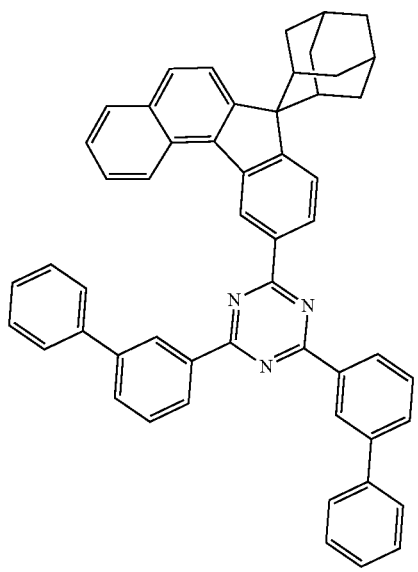

-continued
A-222
A-223
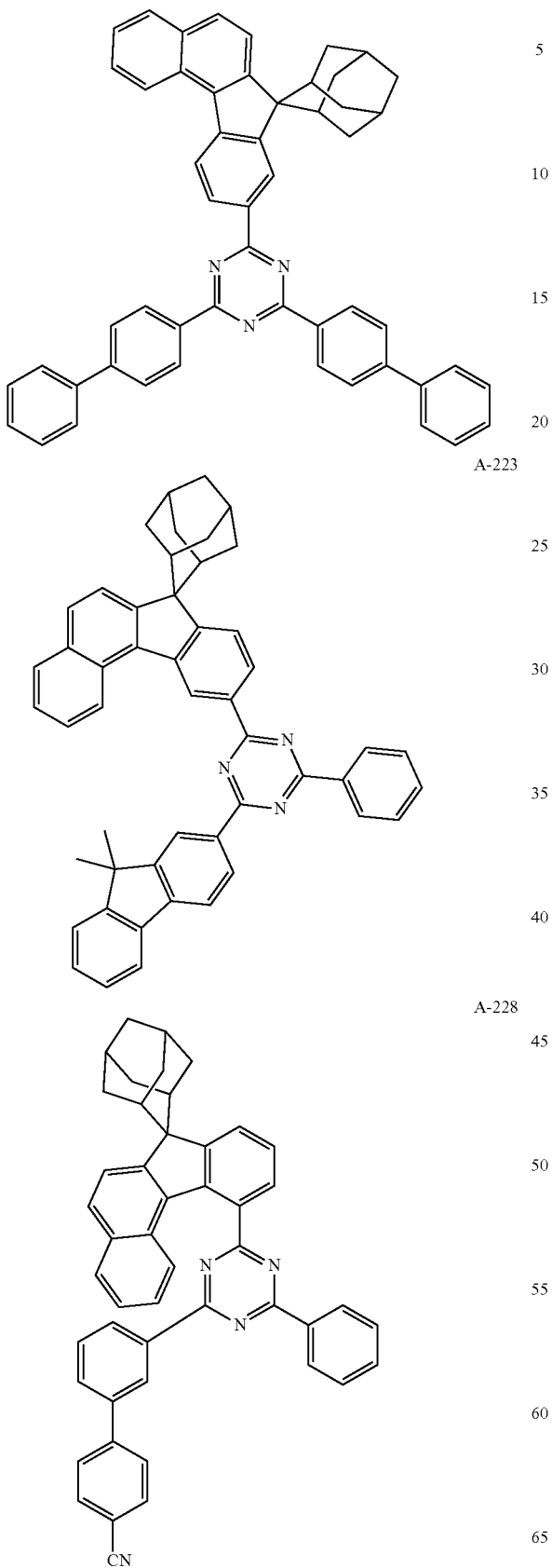
-continued
A-229
A-230
A-231
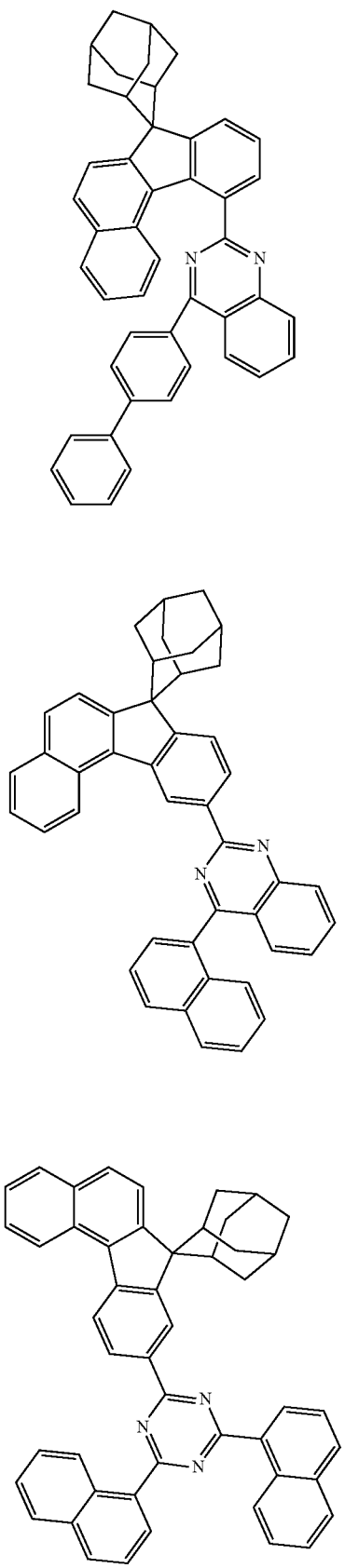
A-228

A-232
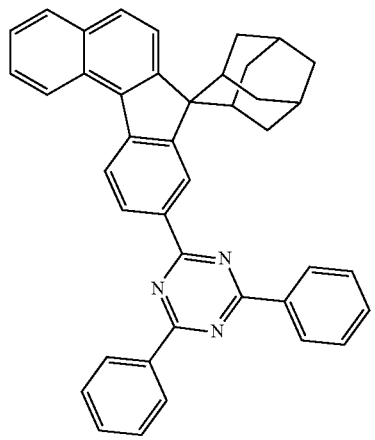
A-233
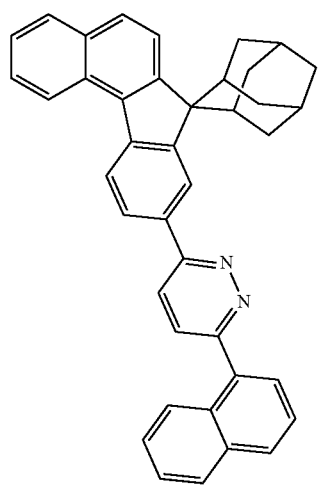
A-234
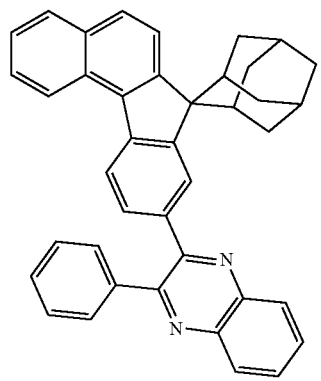
A-235
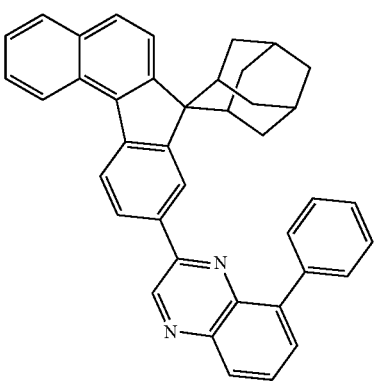
A-239
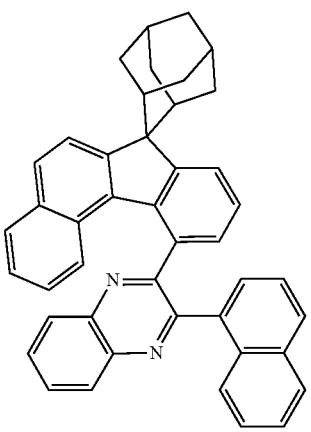
A-240
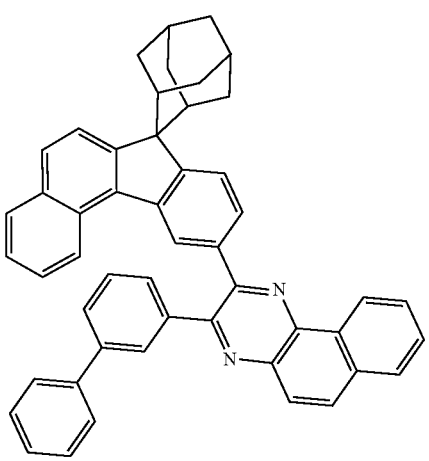

-continued
A-241
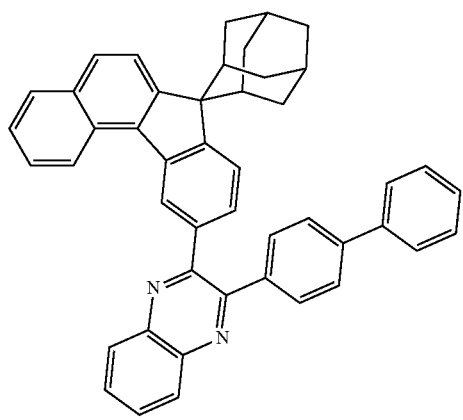
A-316
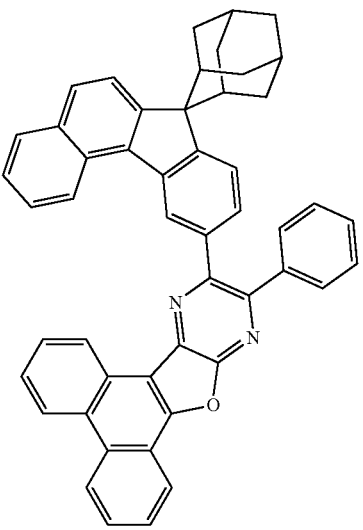
A-243
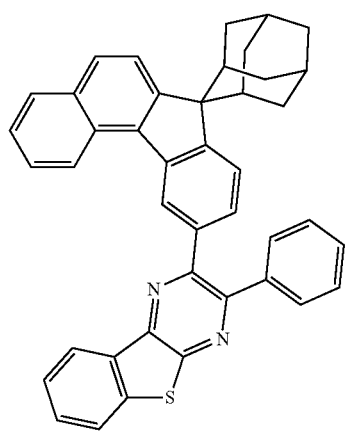
A-317
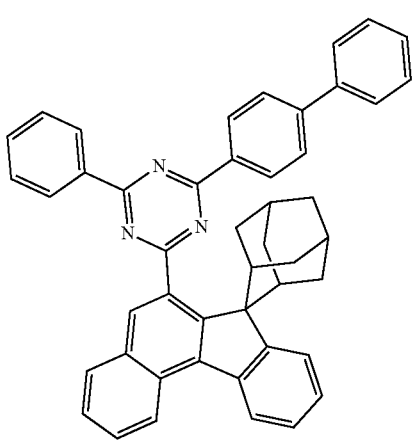
A-244
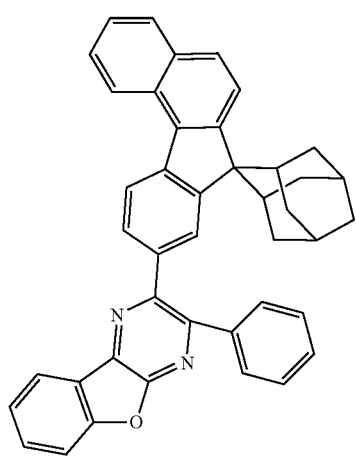
A-248
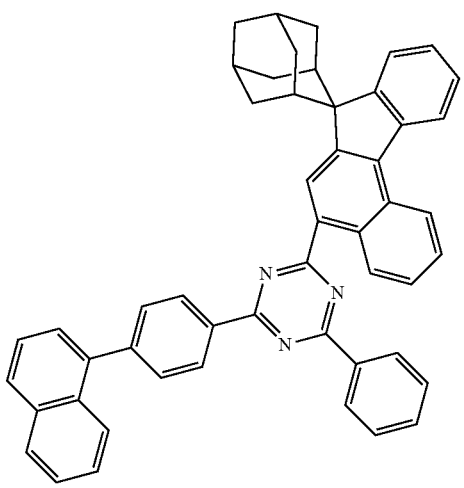

A-249
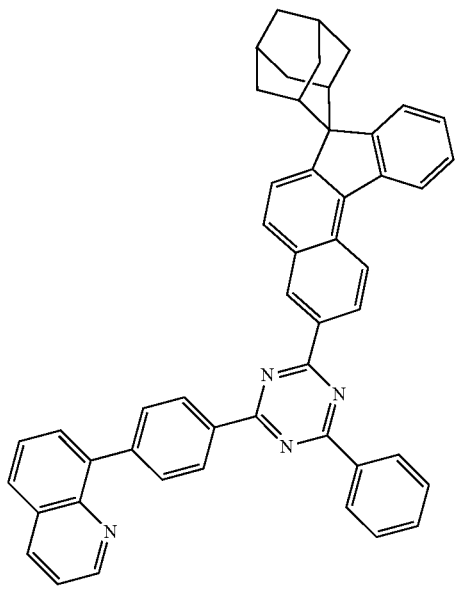
A-250
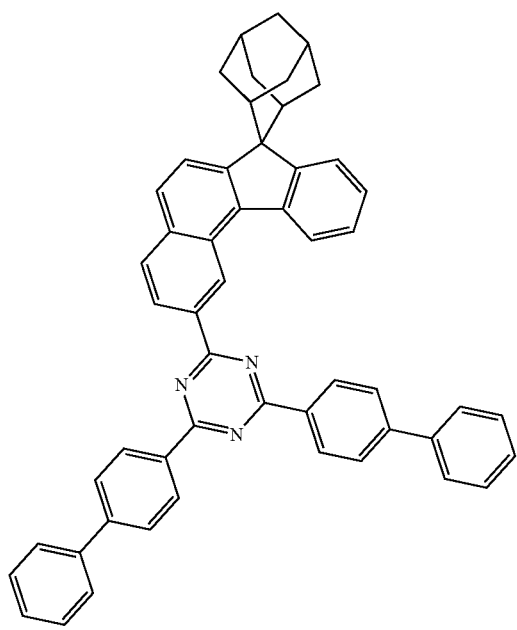
A-245
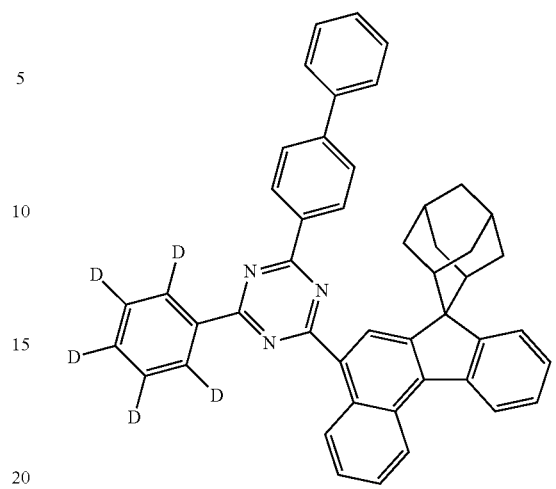
A-246
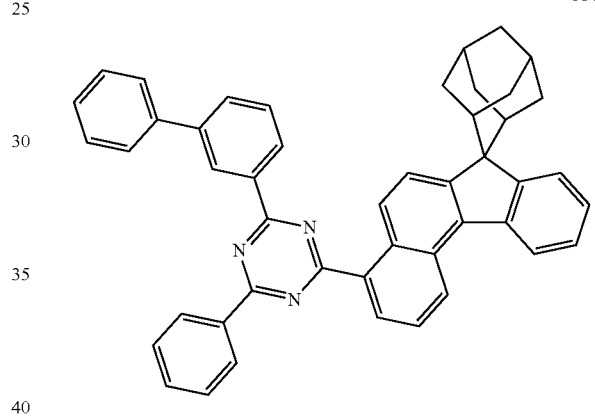
A-247
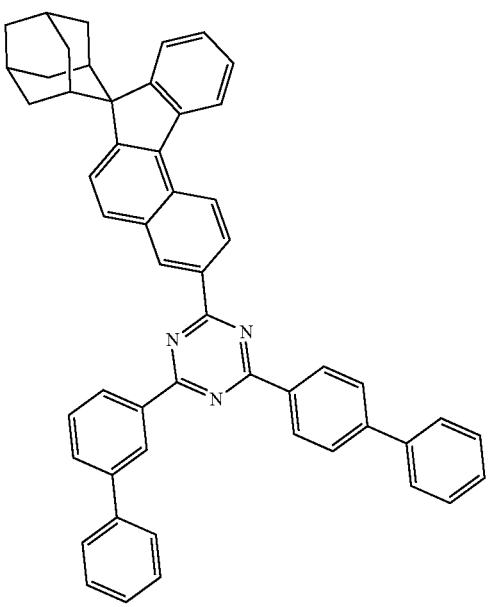

A-251
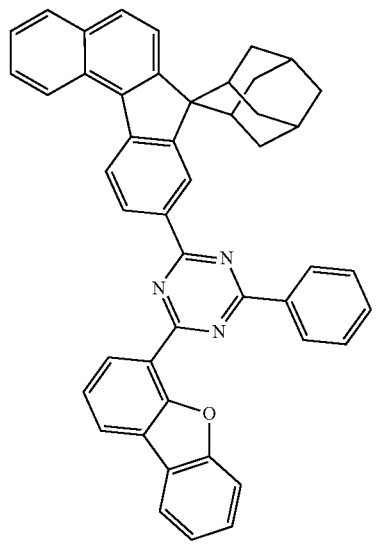
A-252
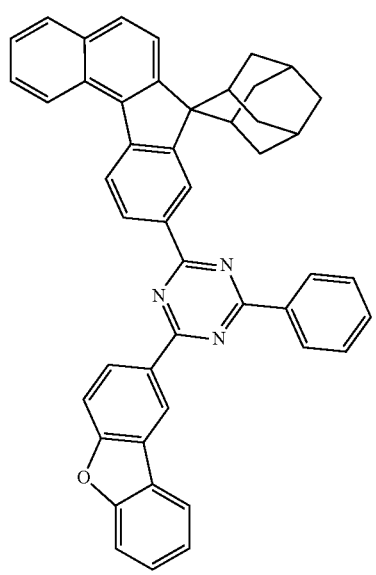
A-253
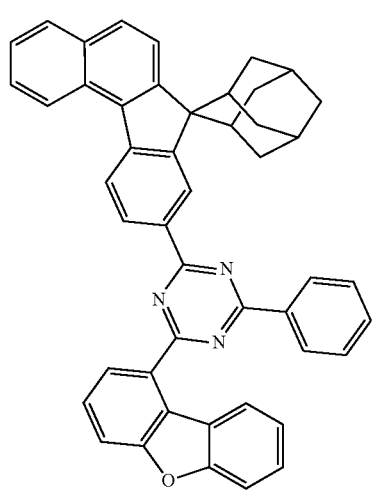
A-255
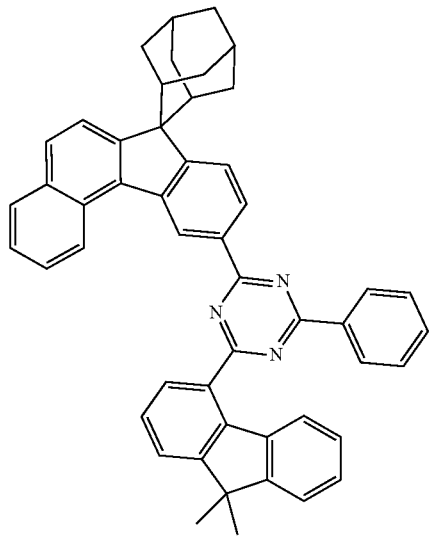
A-257
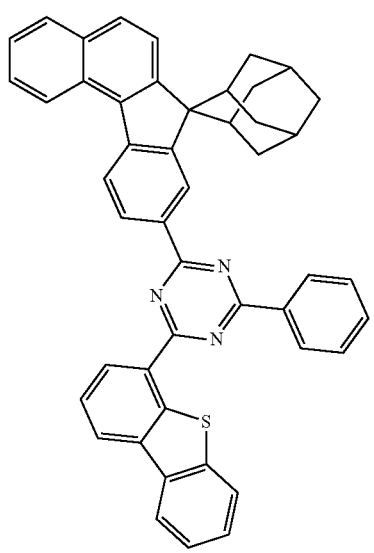
A-258
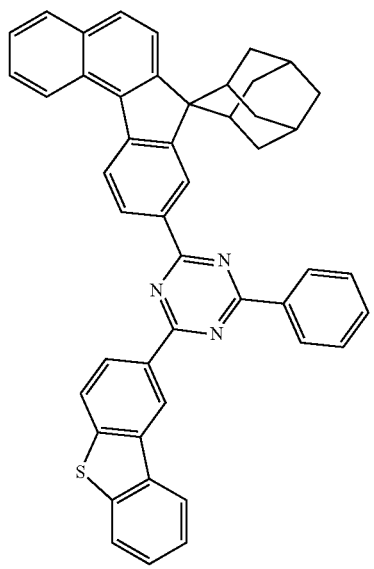

A-259
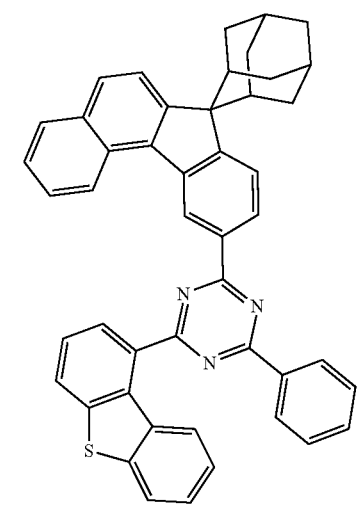
A-260
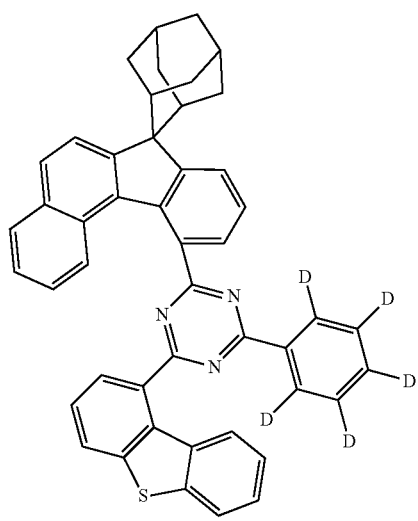
A-261
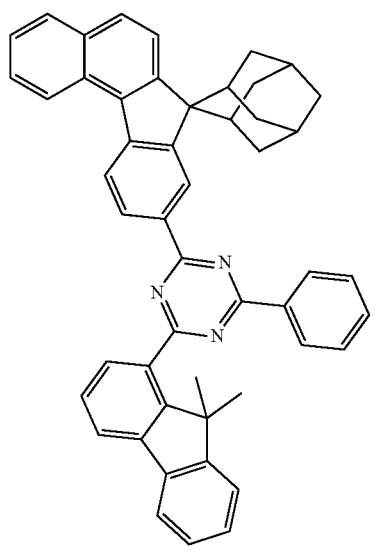
A-262
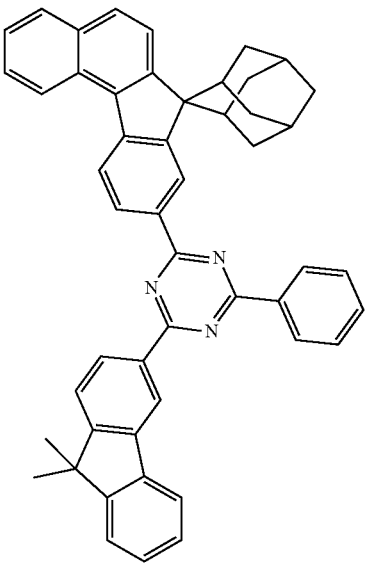
A-279
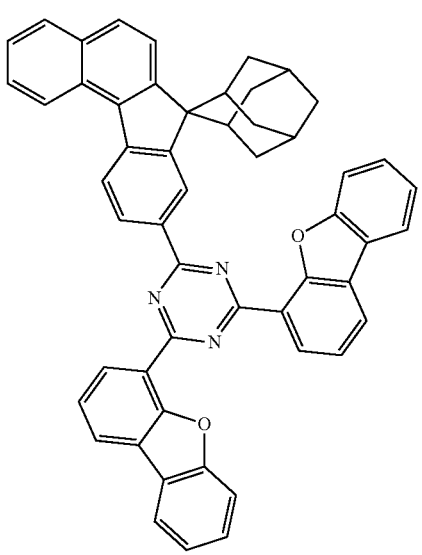
A-280
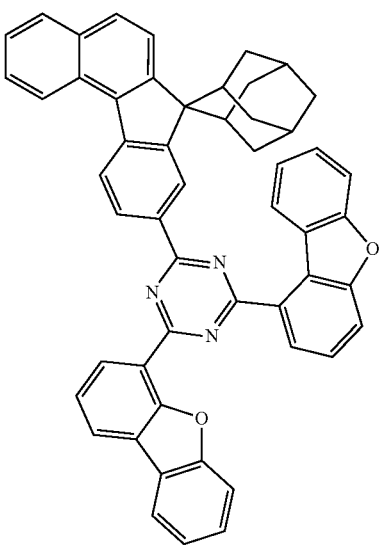

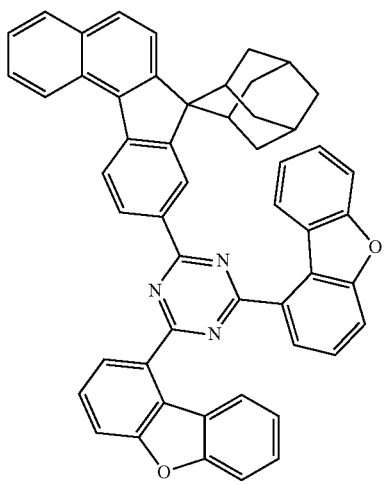
A-281
A-282
A-283
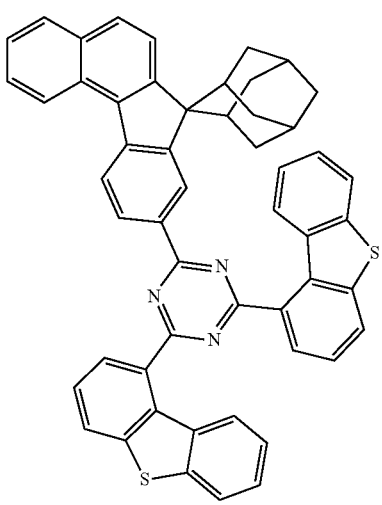
A-284
A-285
A-286

A-287
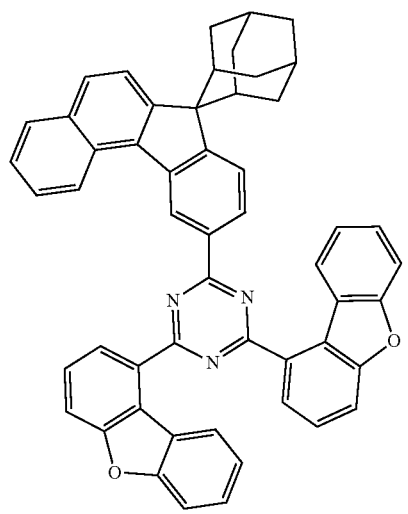
A-288
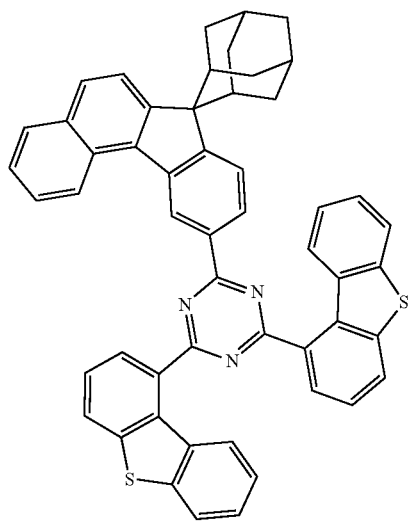
A-289
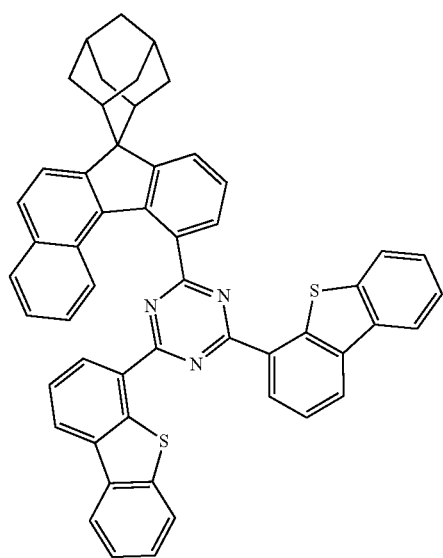
A-290
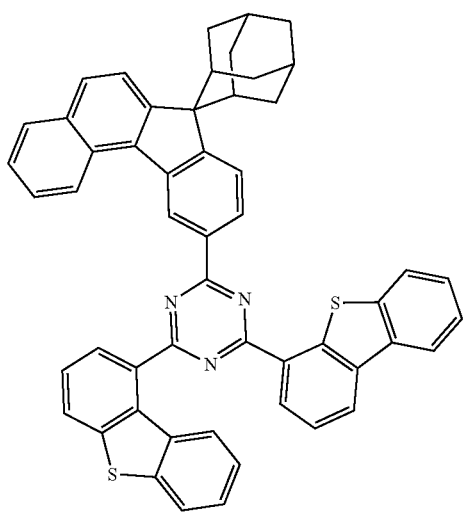
A-291
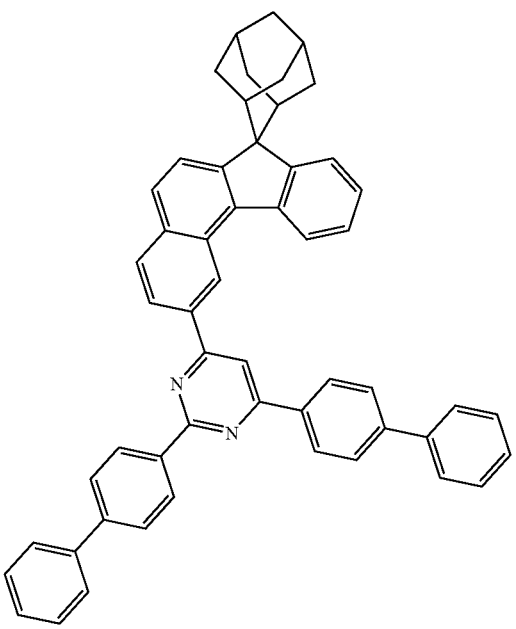

A-295
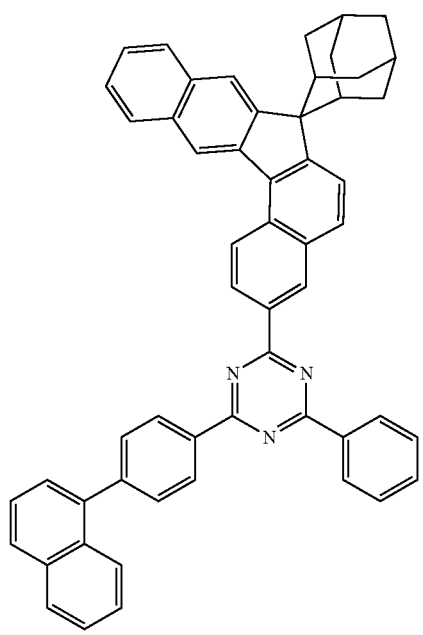
A-296
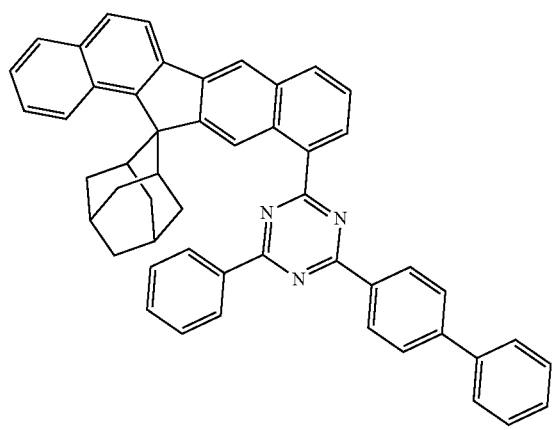
A-297
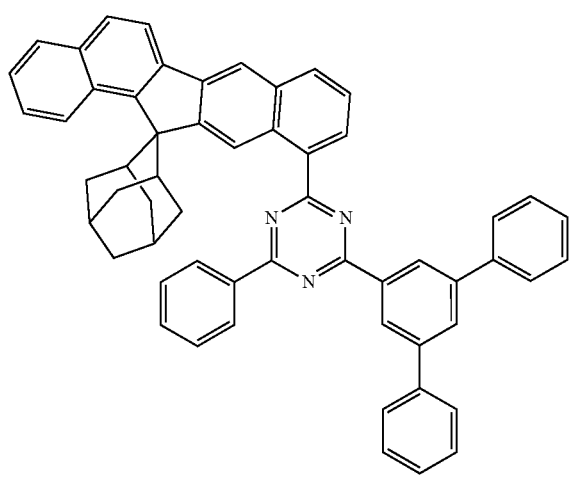
A-300
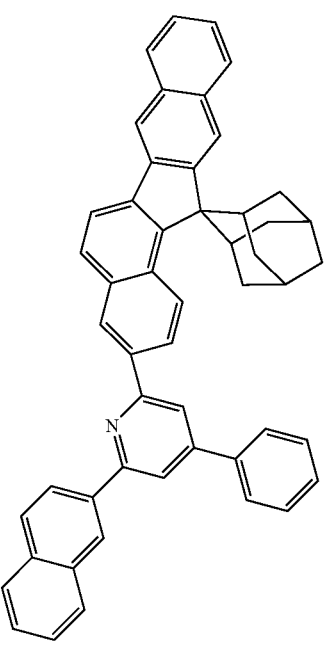
A-301
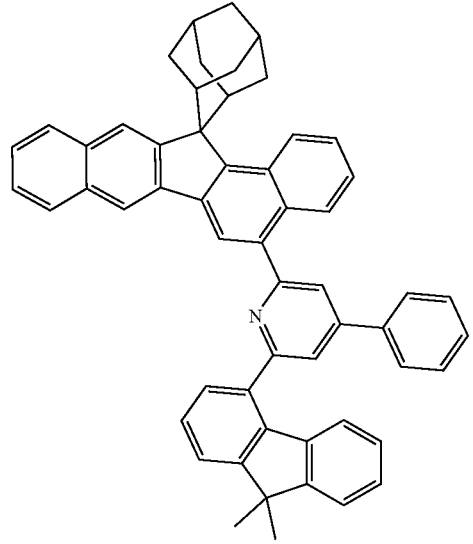
A-302
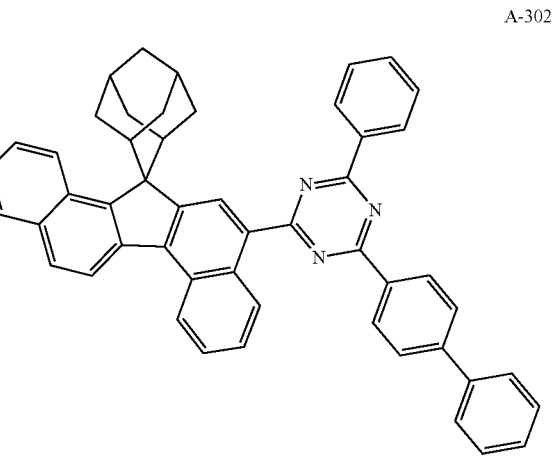

A-303
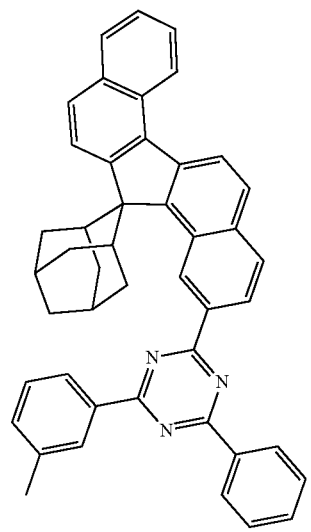
A-304
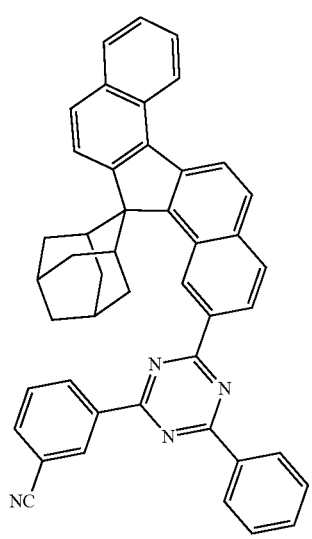
A-305
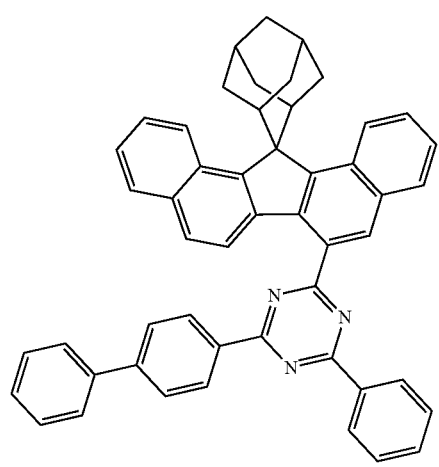
A-306
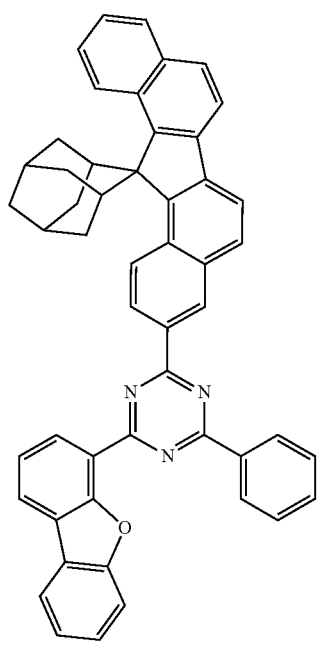
A-307
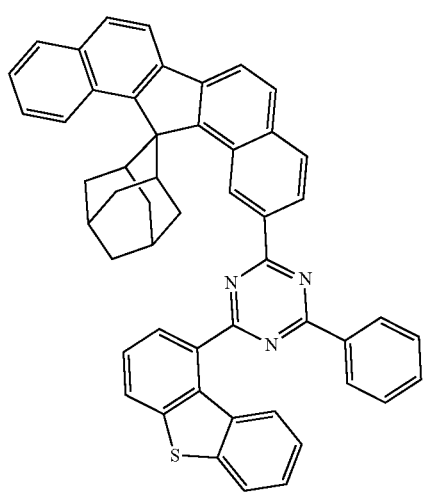
A-308
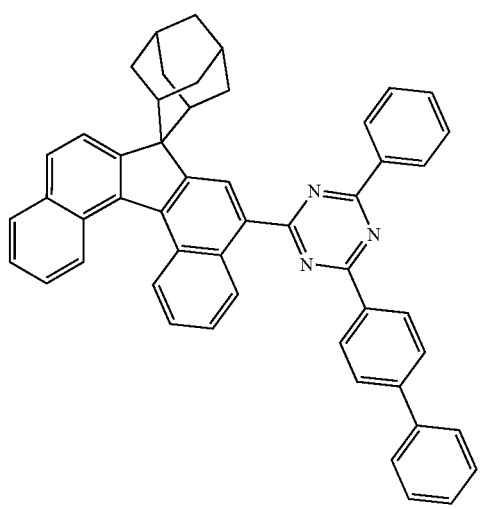

-continued
A-309
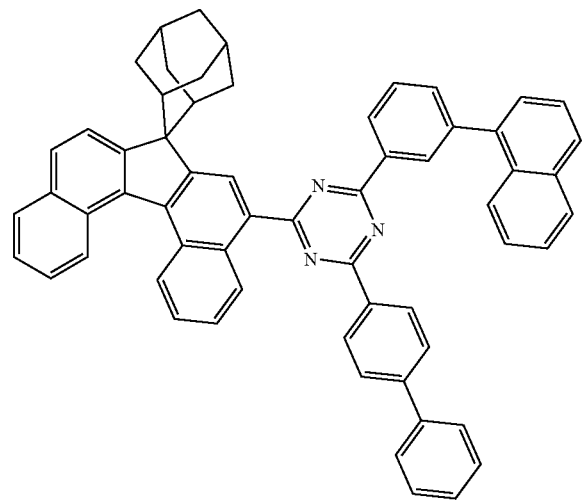
A-310
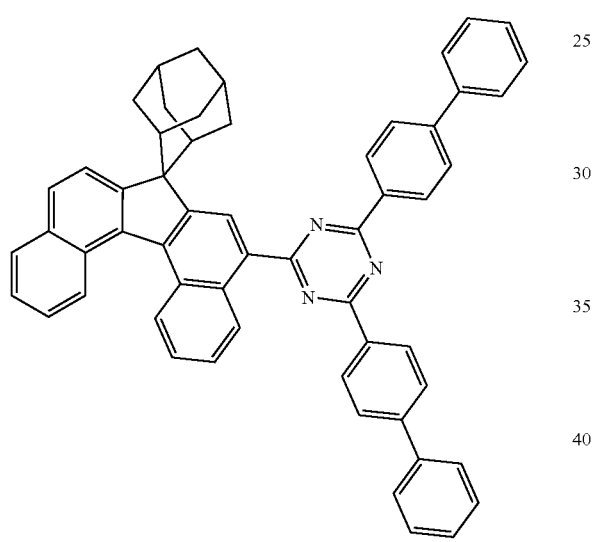
A-15
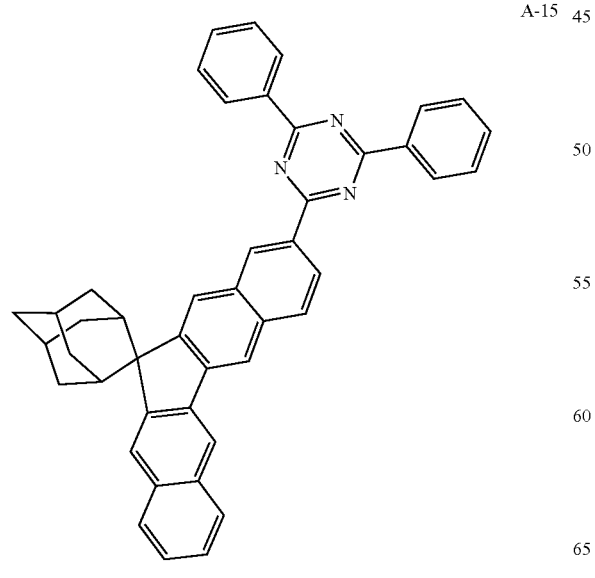
-continued
B-1
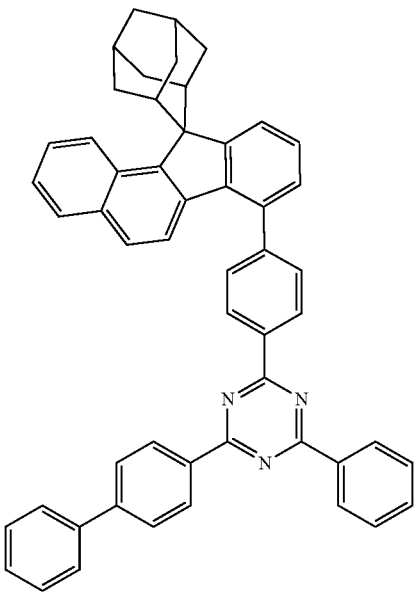
B-2
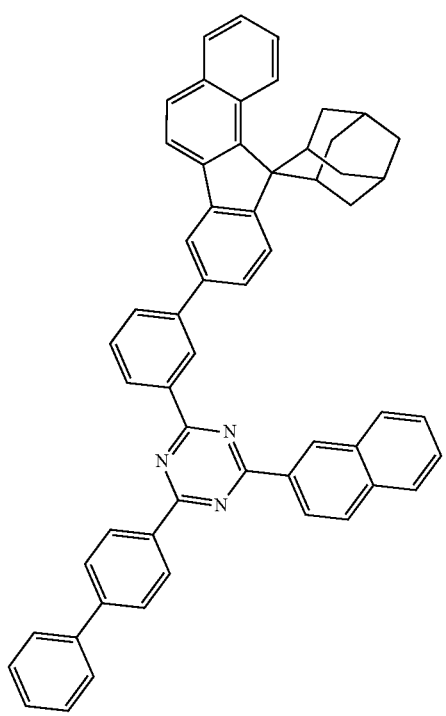

B-3
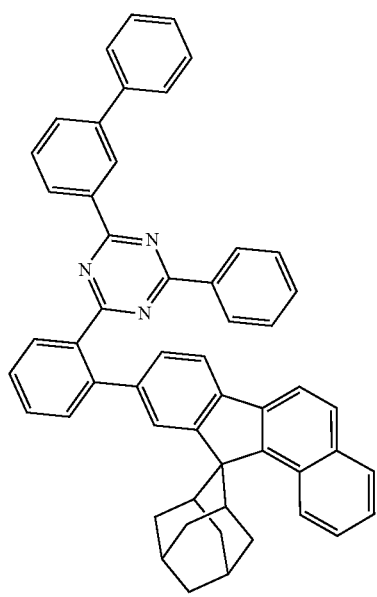
B-4
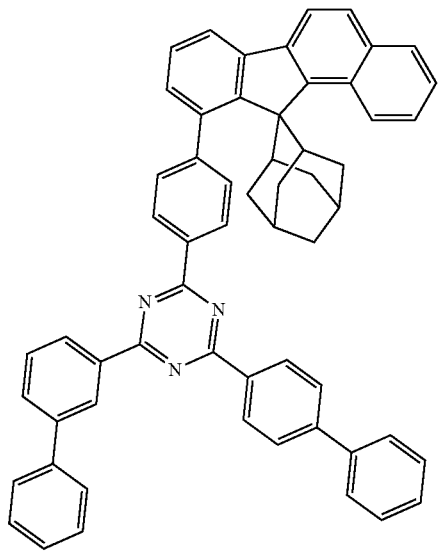
B-5
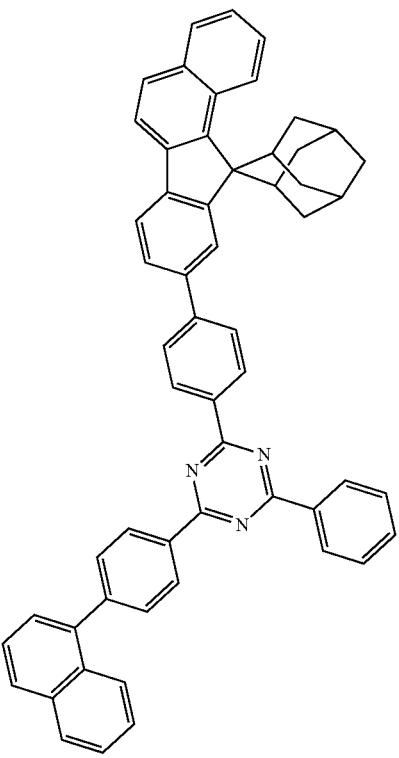
B-6
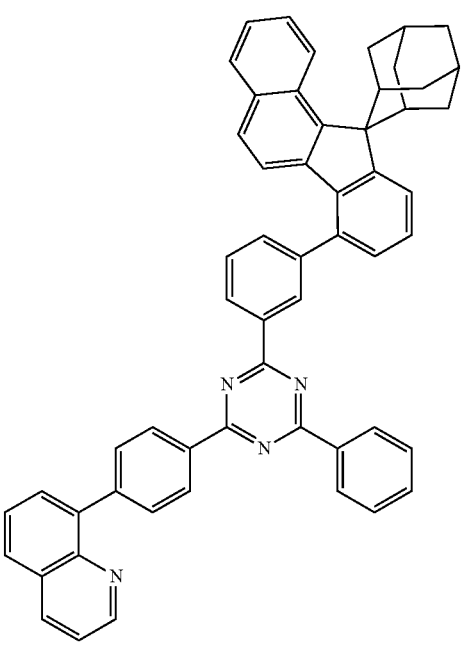

-continued
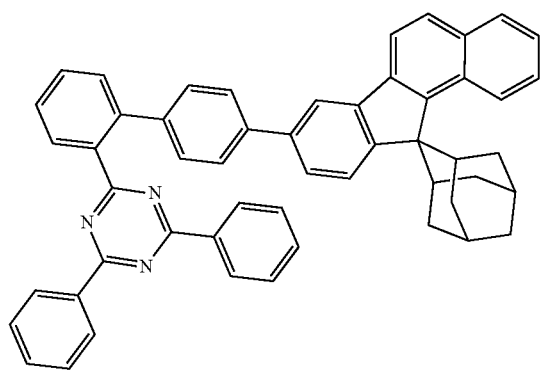
B-7
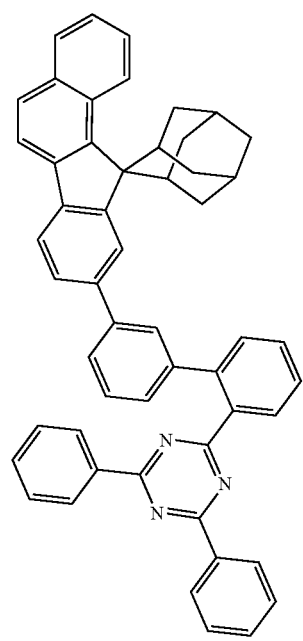
B-8
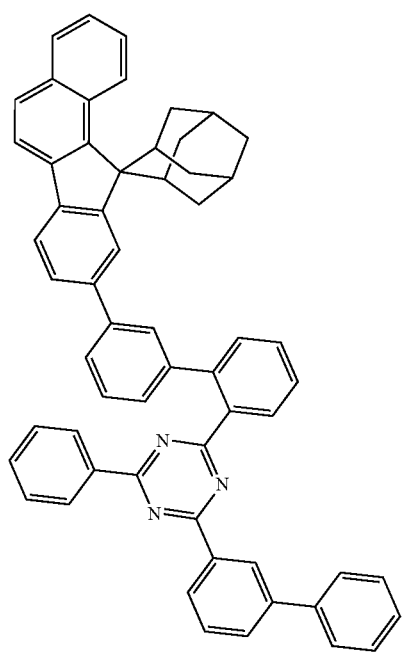
B-9
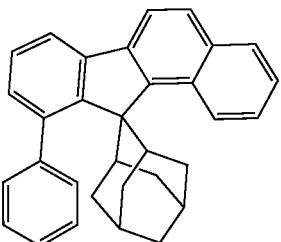
B-10
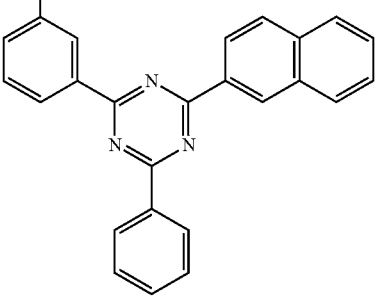
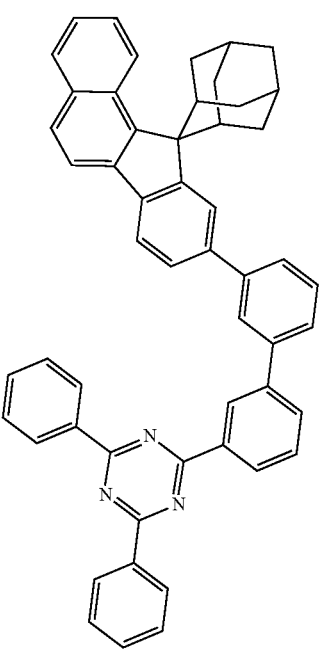
B-11

B-12
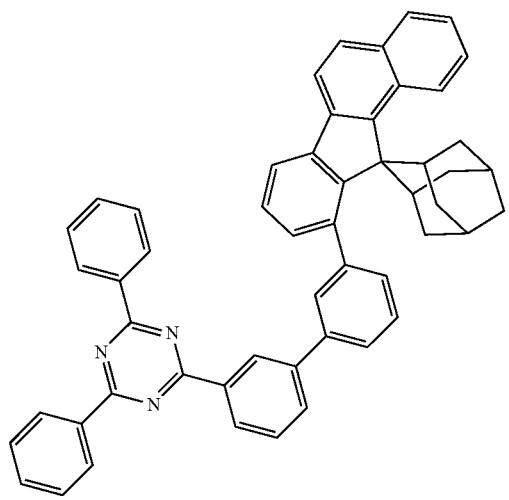
B-14
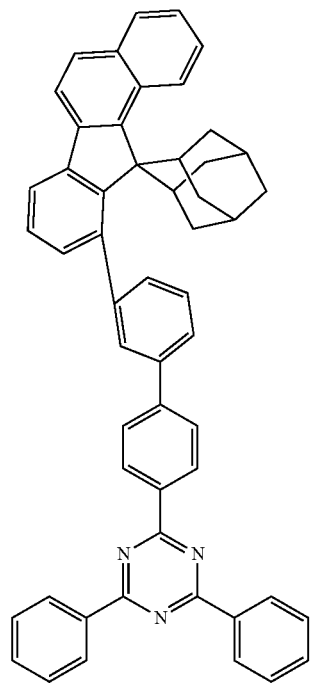
B-13
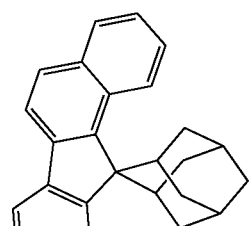
B-15
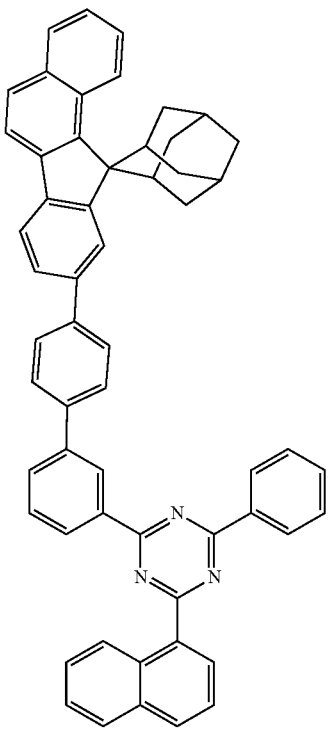
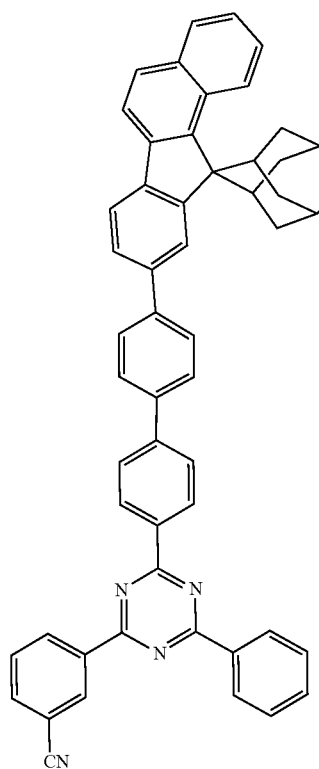

B-16
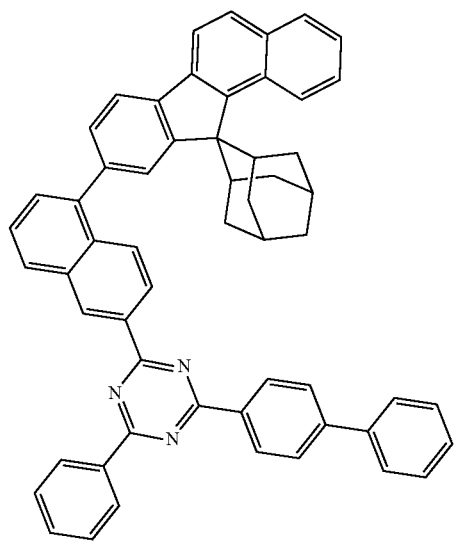
B-18
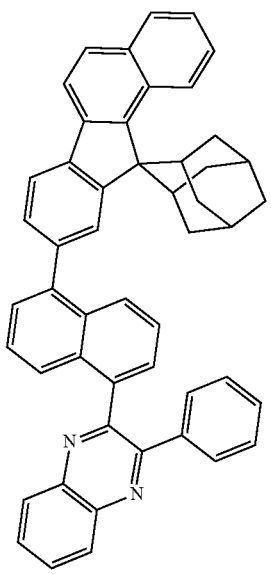
B-17
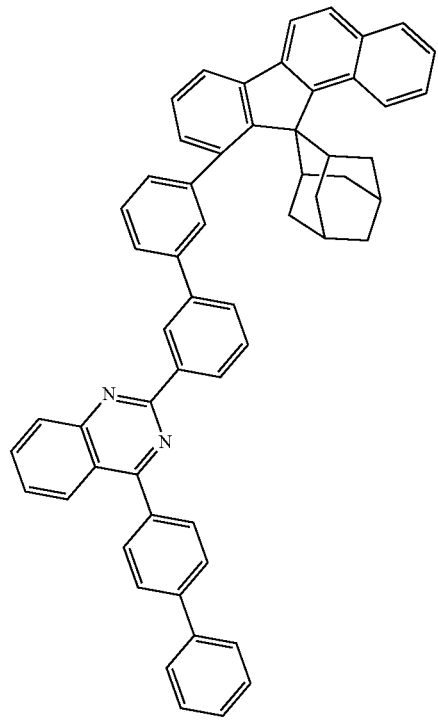
B-19
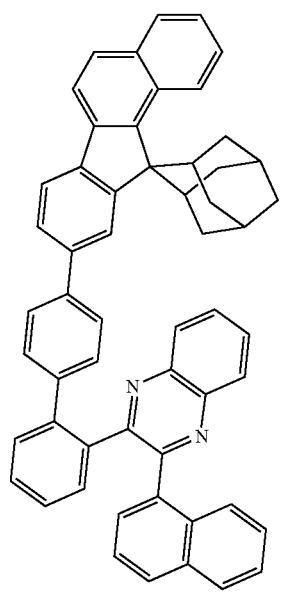

531
-continued
B-20
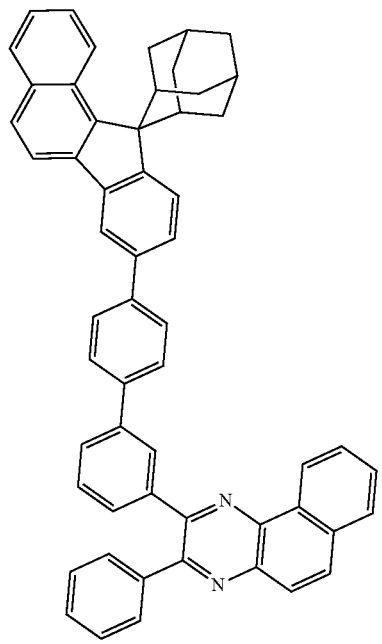
B-21
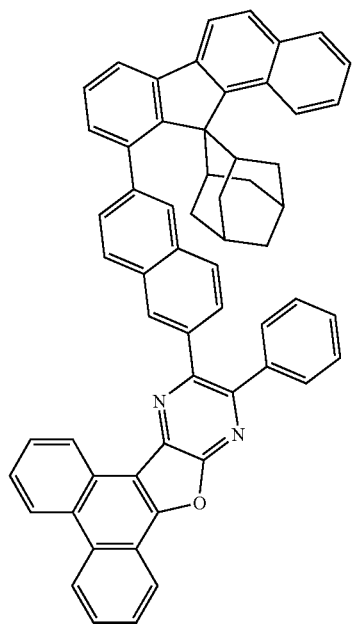
532
-continued
B-22
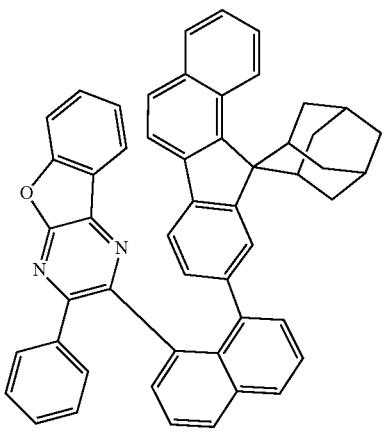
B-23
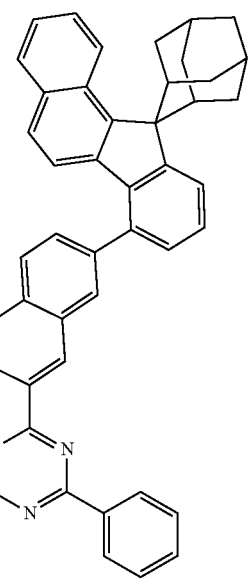
B-24
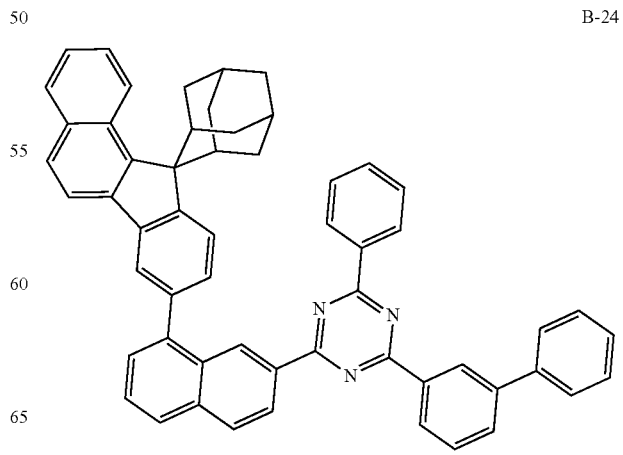

B-25
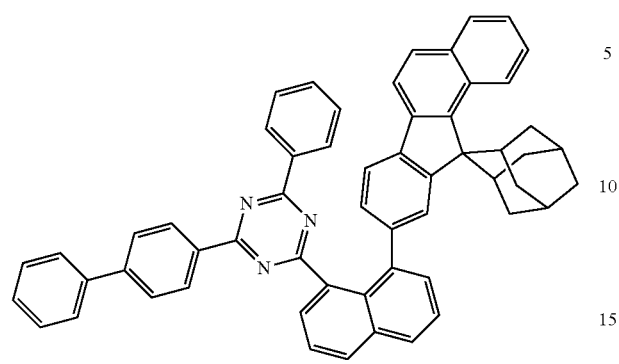
B-27
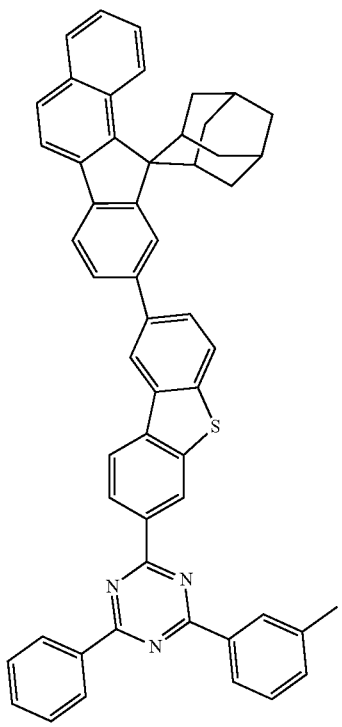
B-26
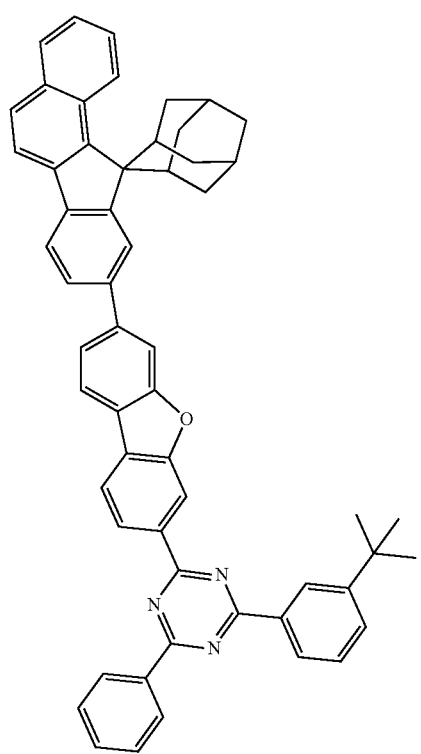
B-29
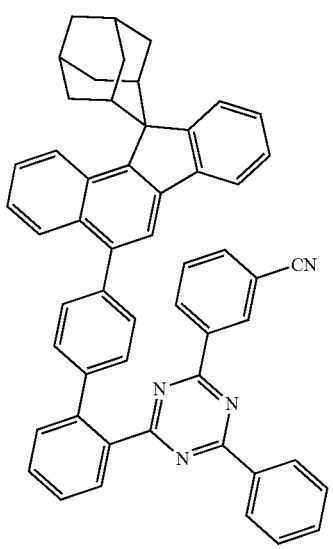

B-30
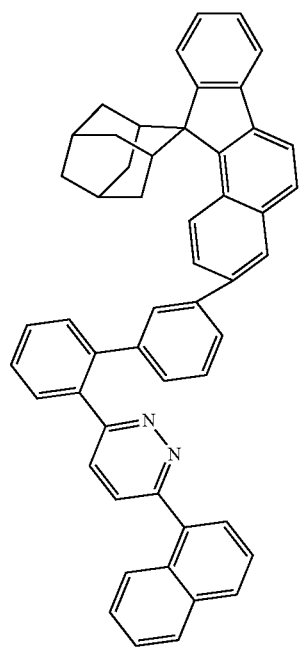
B-32
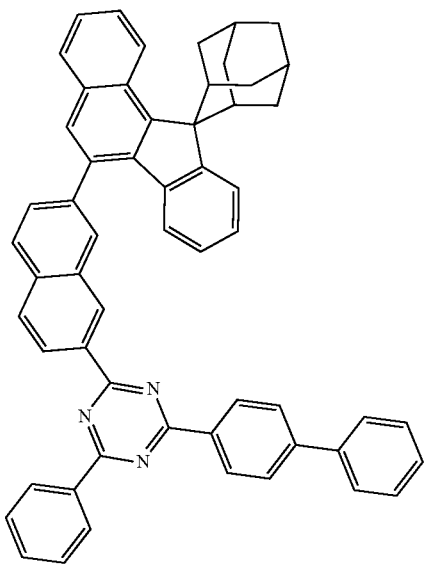
B-31
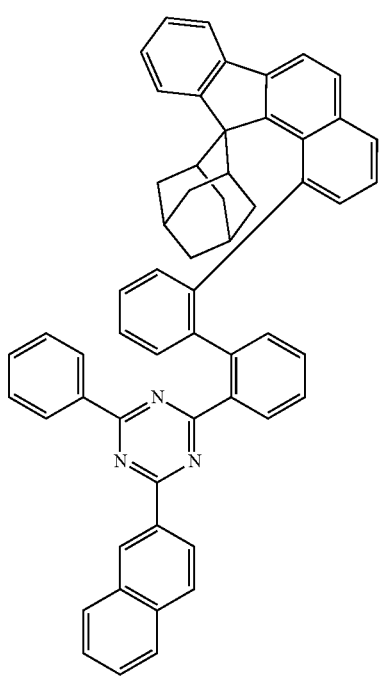
B-33
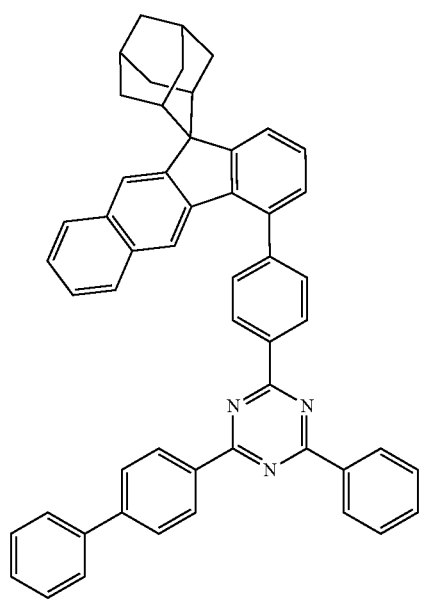

B-34
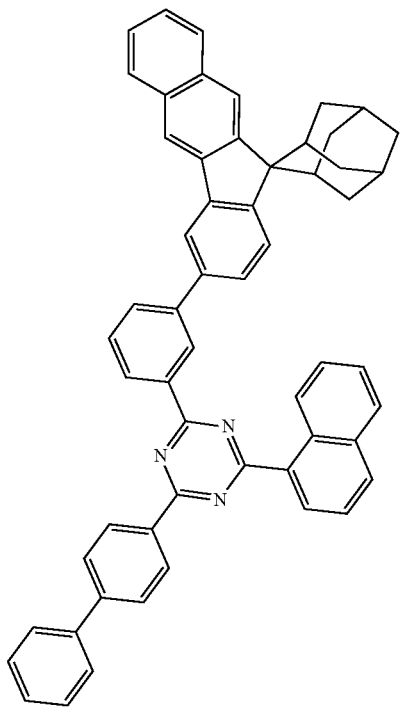
B-35
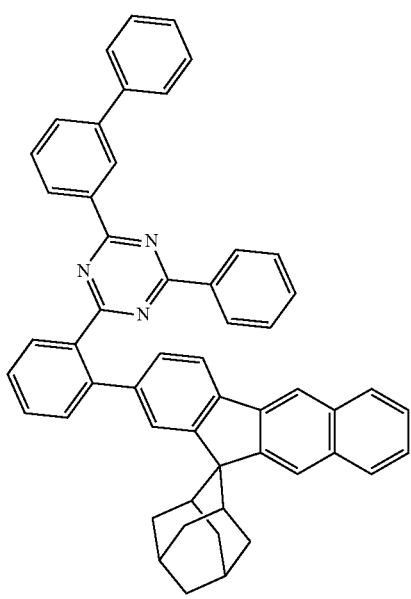
B-36
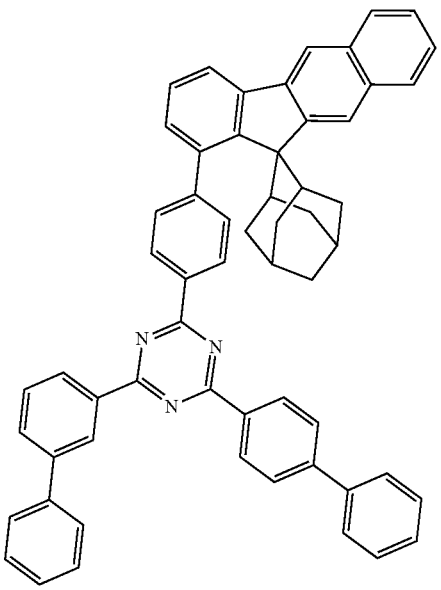
B-37
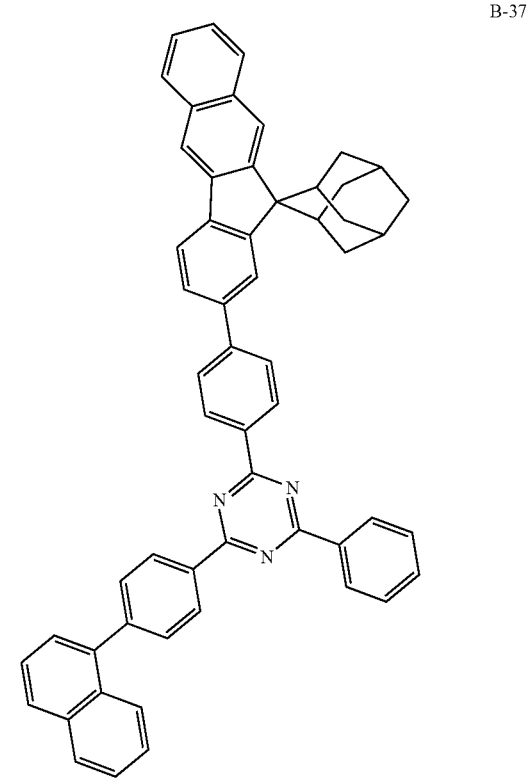

B-38
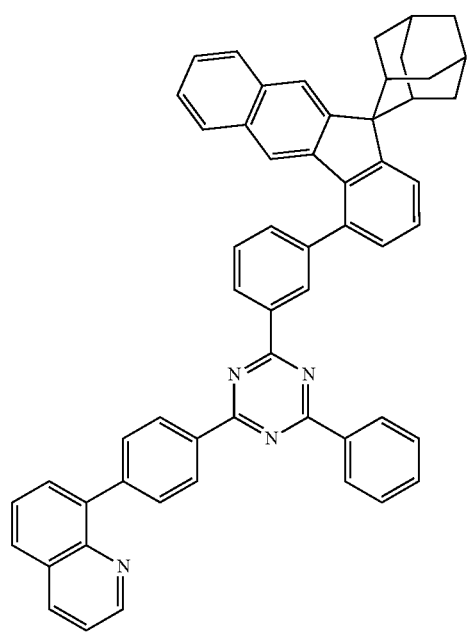
B-40
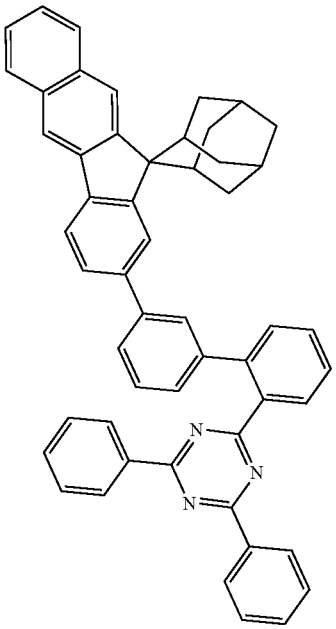
B-39
B-41
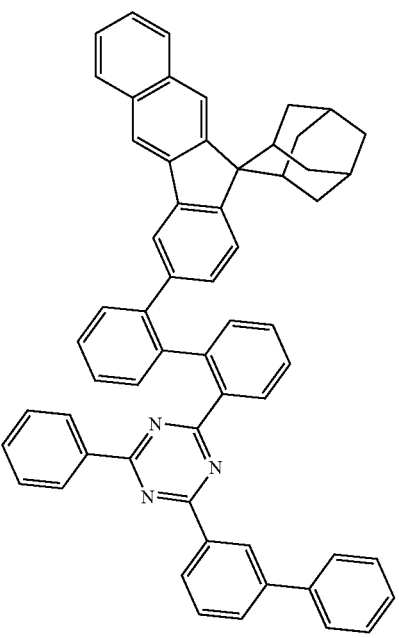

B-42
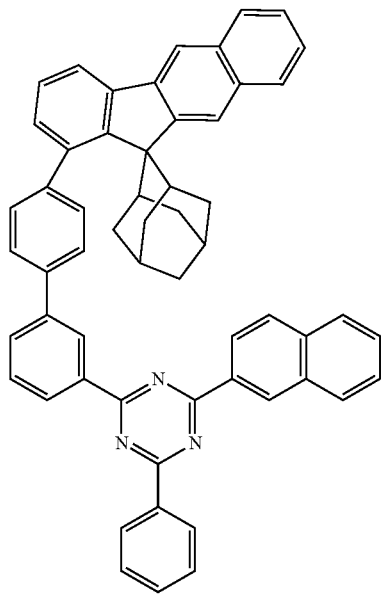
B-43
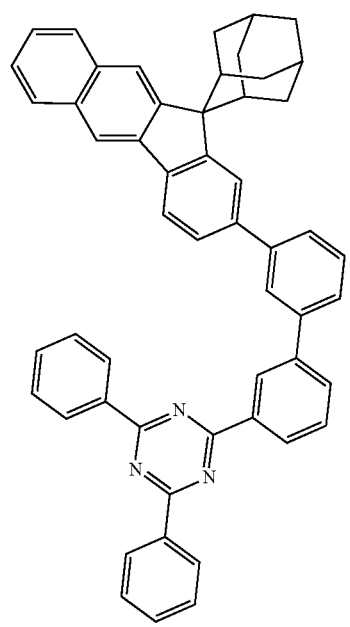
B-44
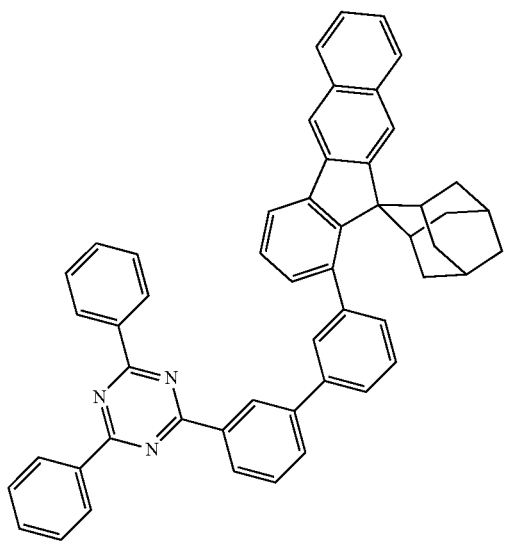
B-45
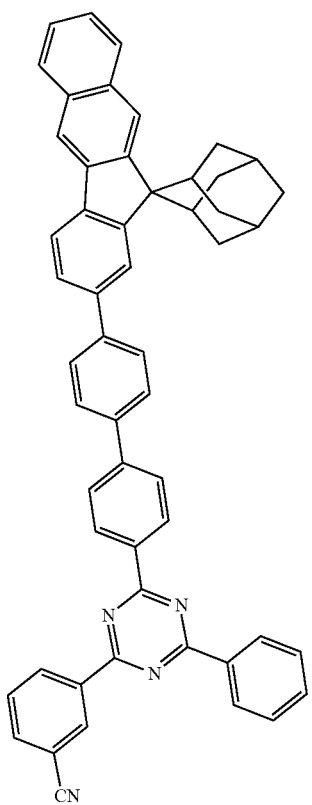

B-46
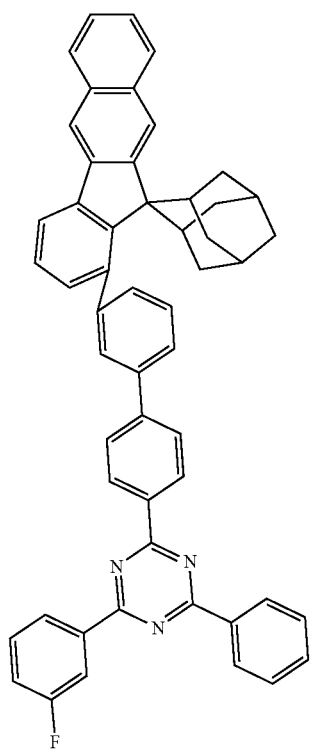
B-47
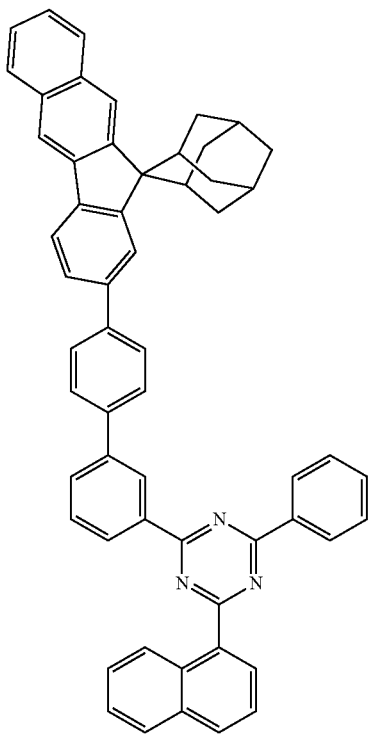
B-48
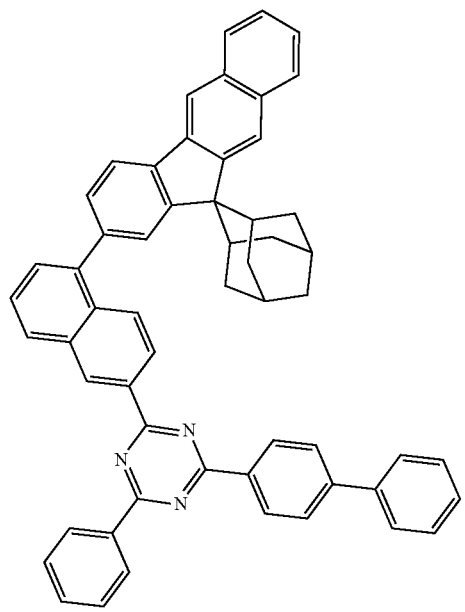
B-49
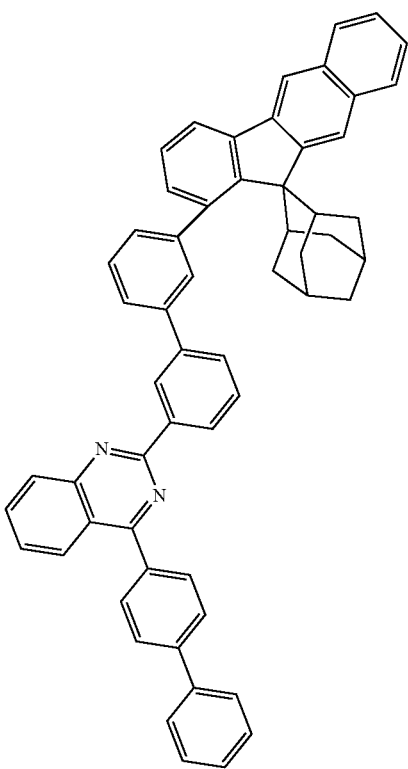

B-50
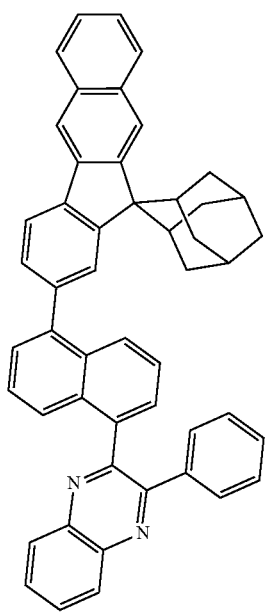
B-52
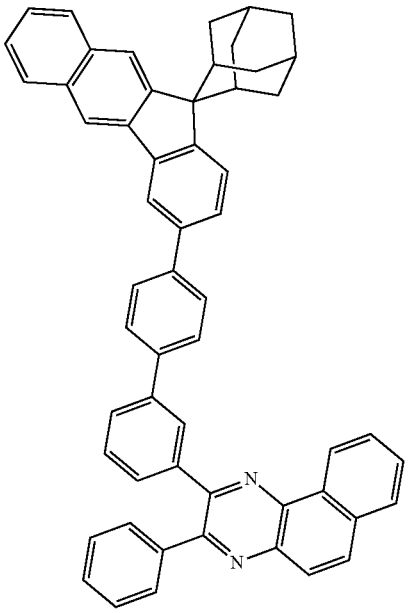
B-51
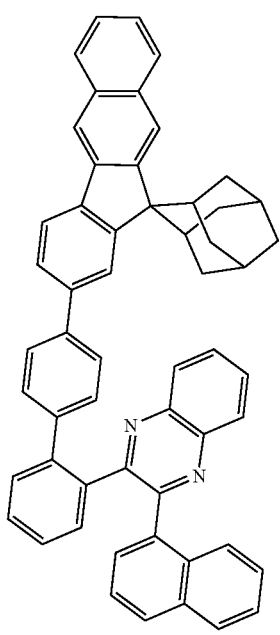
B-53
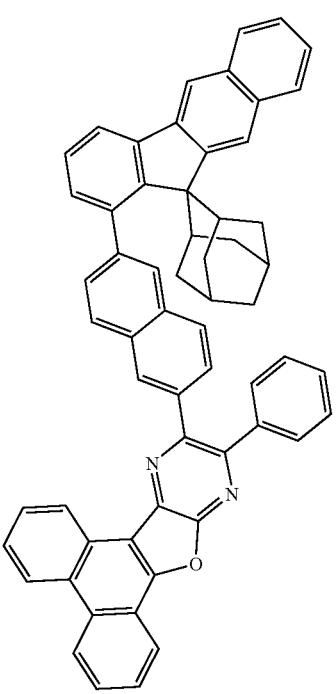

B-54
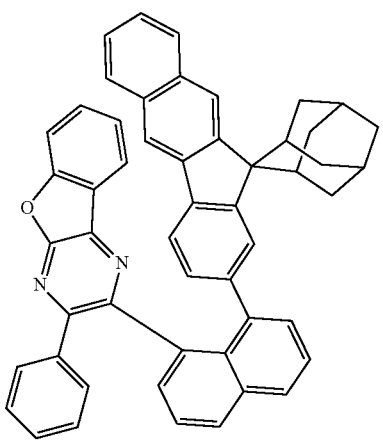
B-57
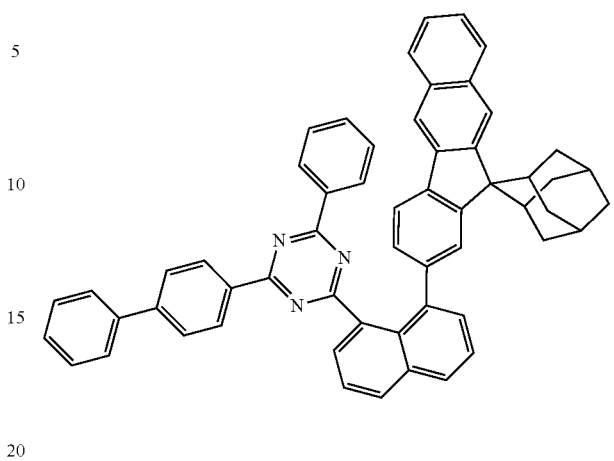
B-55
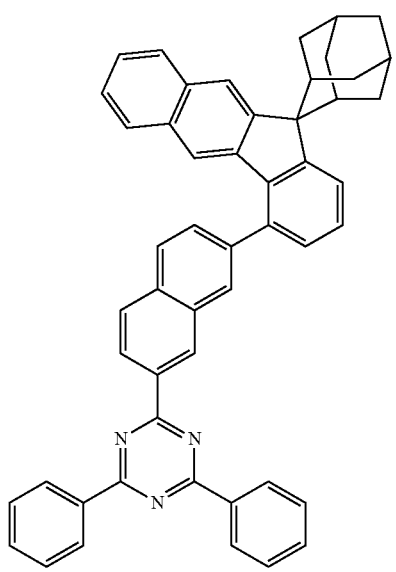
B-56
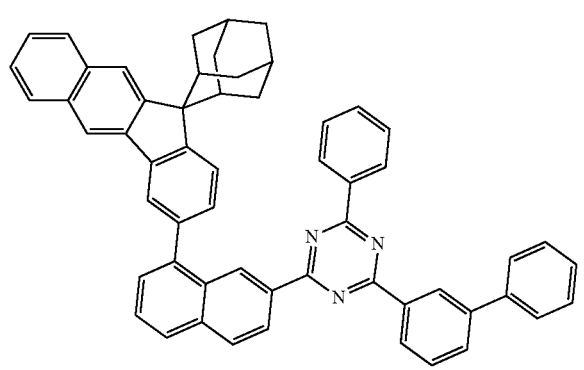
B-58
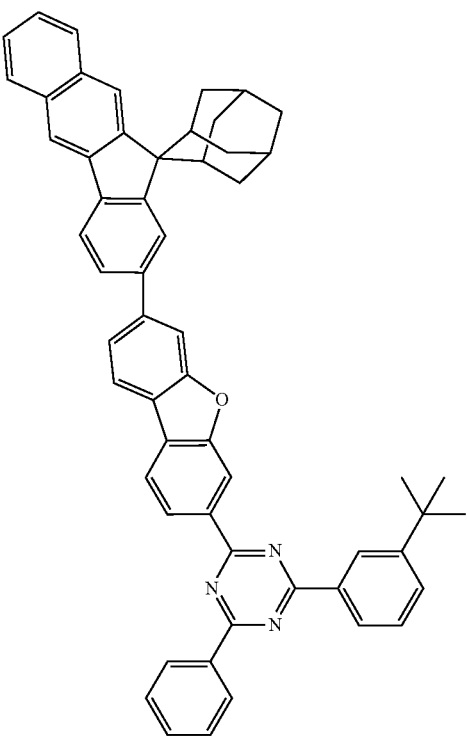

B-59
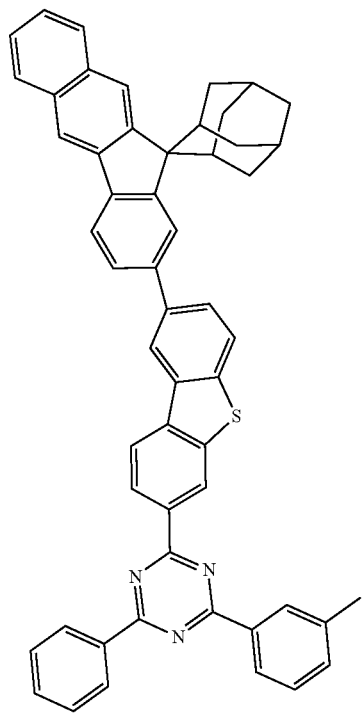
B-61
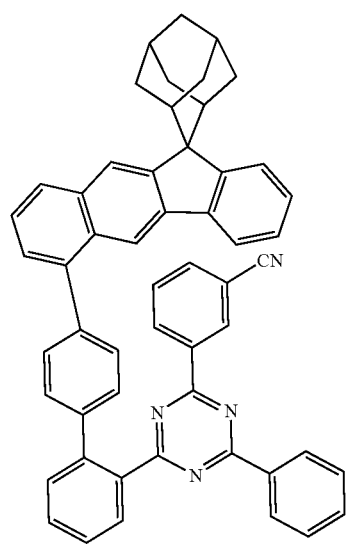
B-62
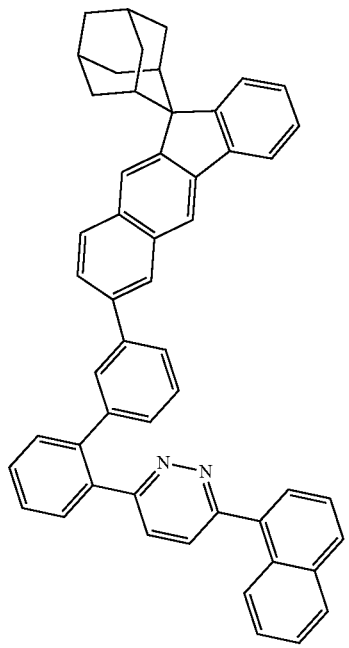
B-63
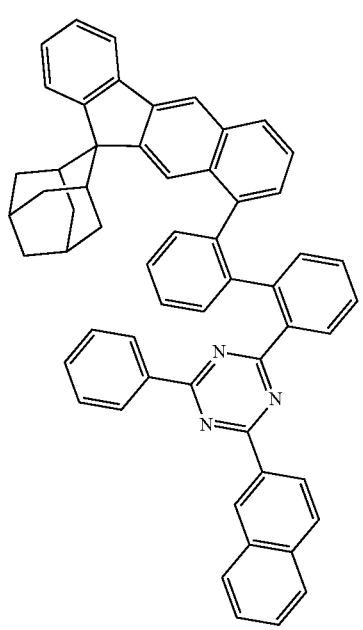

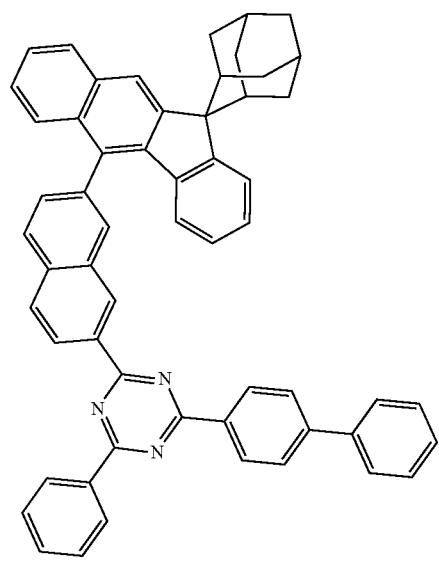
B-64
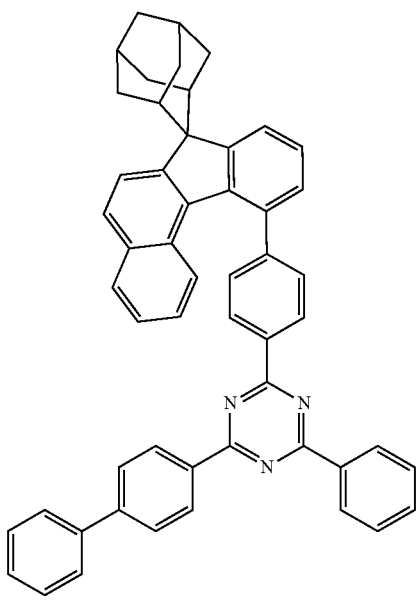
B-66
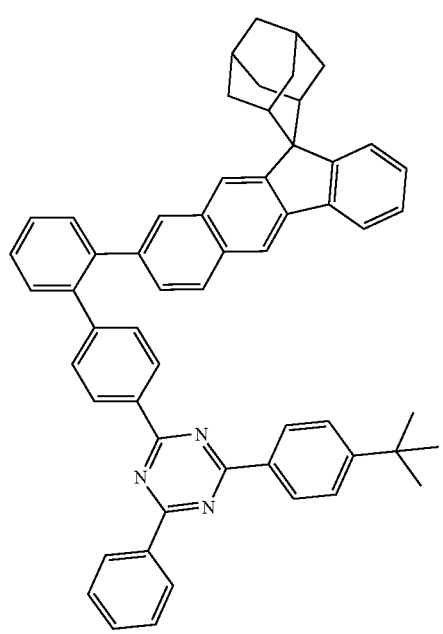
B-65
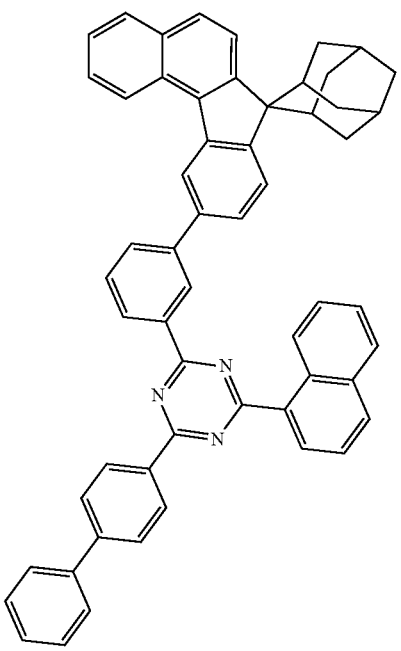
B-67

-continued
B-68
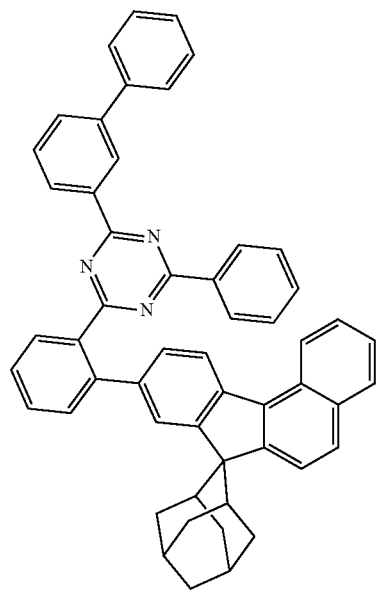
B-70
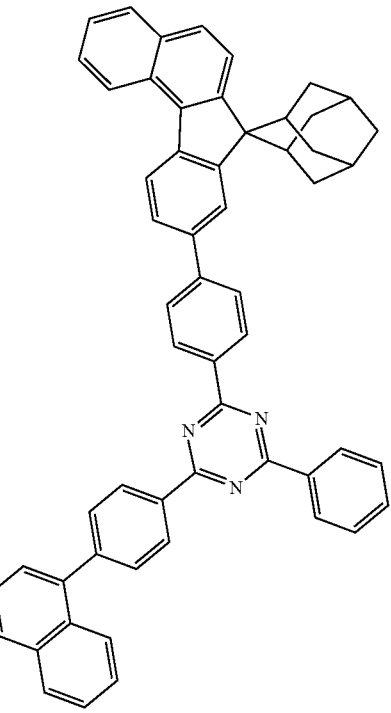
B-69
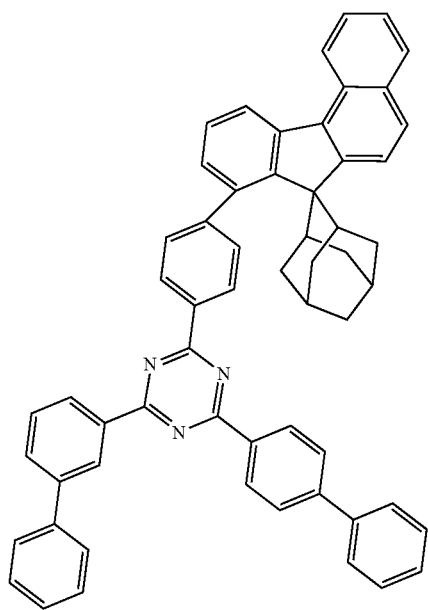
B-71
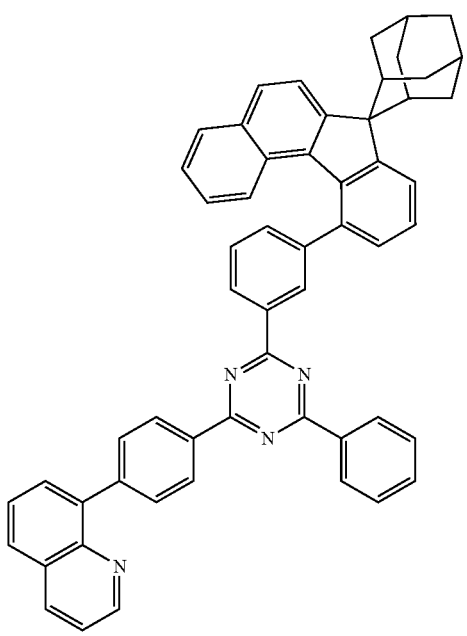

B-72
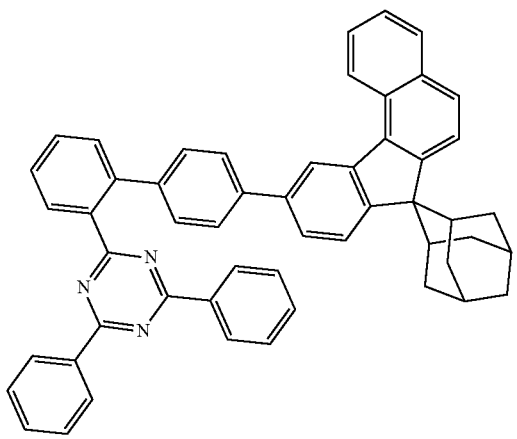
B-73
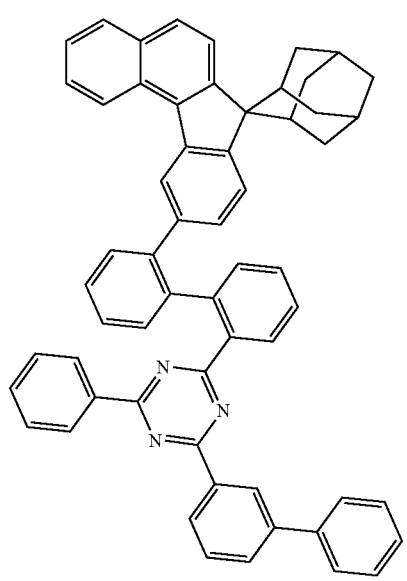
B-75
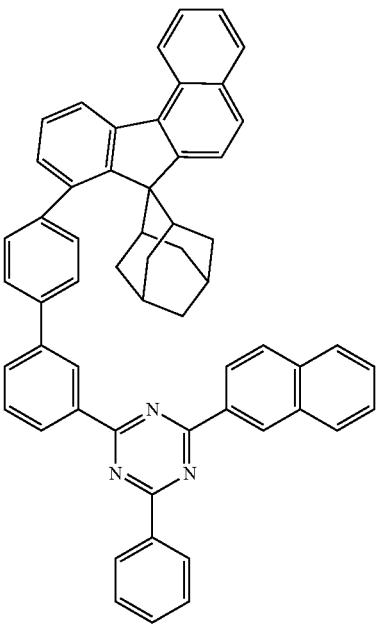
B-74
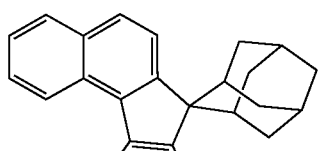
B-76
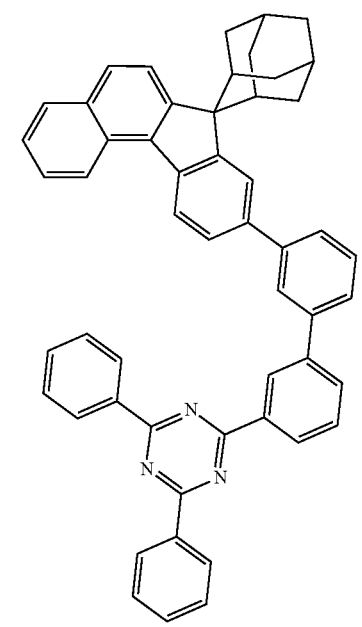

B-77
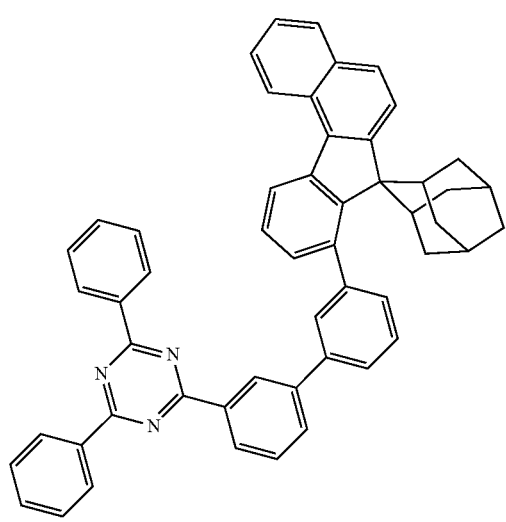
B-79
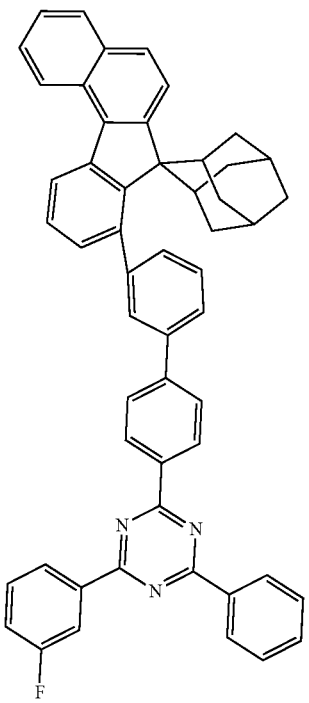
B-78
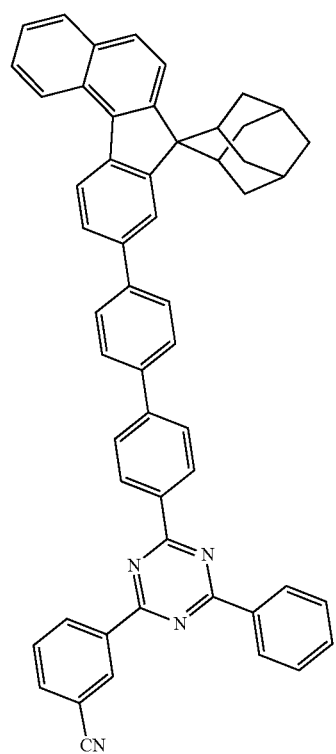
B-80
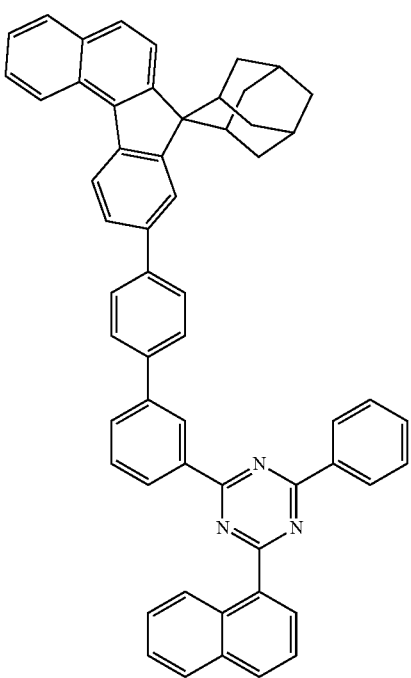

B-81
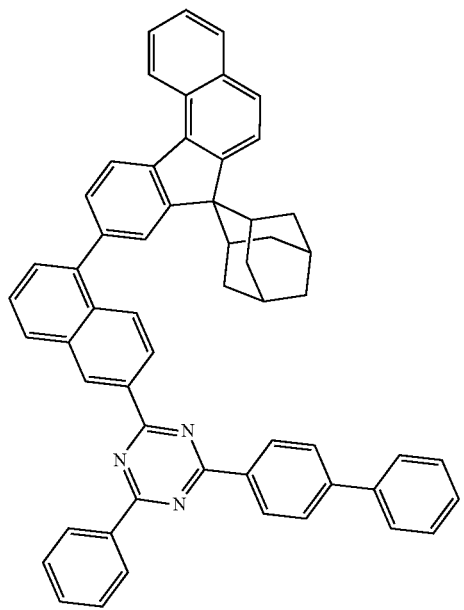
B-82
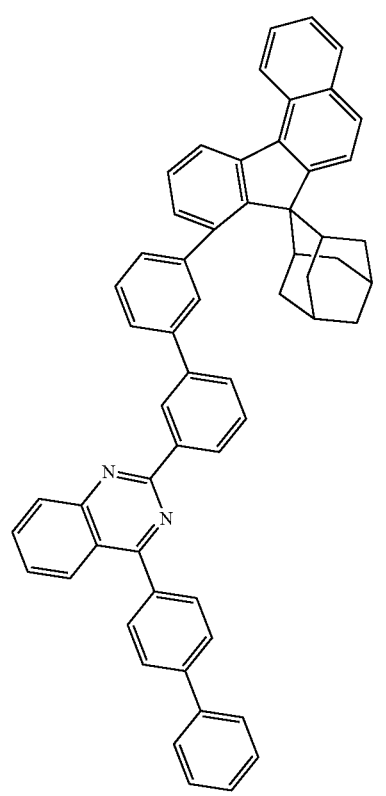
B-83
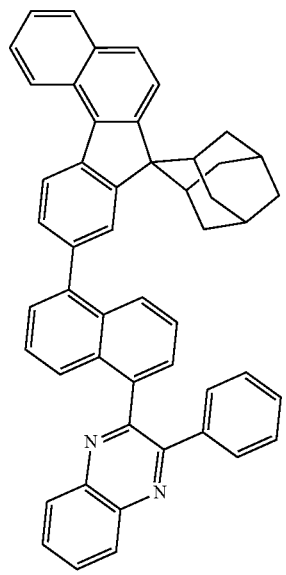
B-84
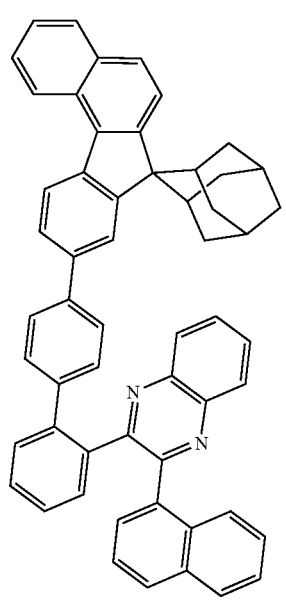

B-85
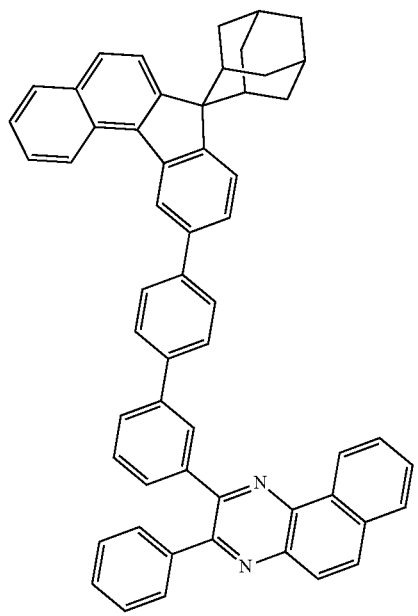
B-86
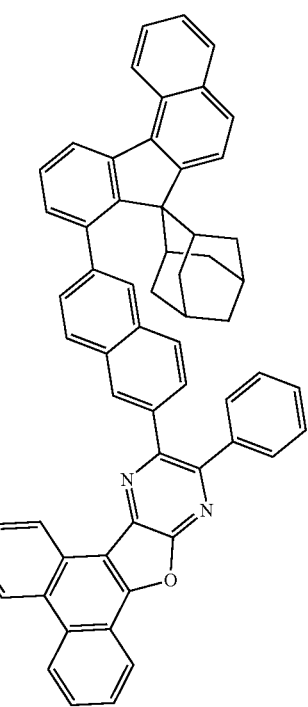
B-87
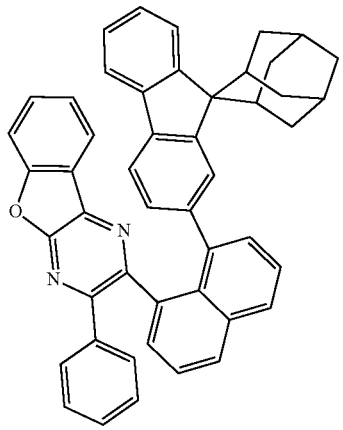
B-88
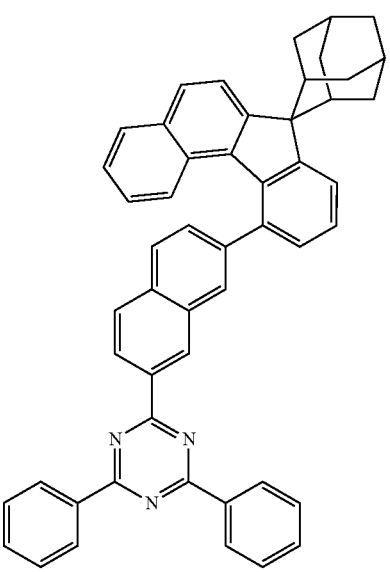
B-89
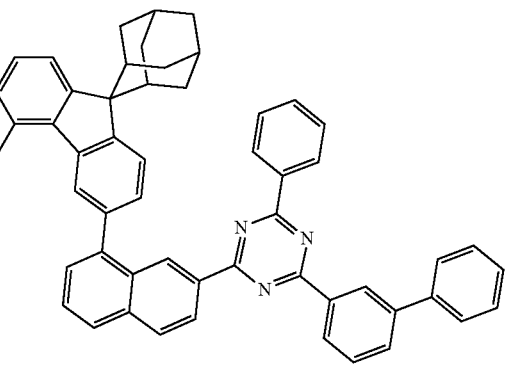

B-90
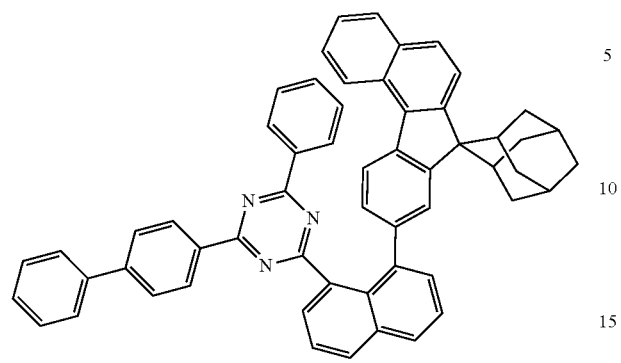
B-92
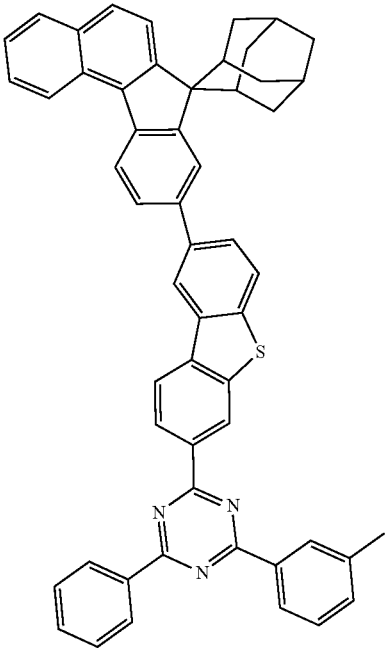
B-91
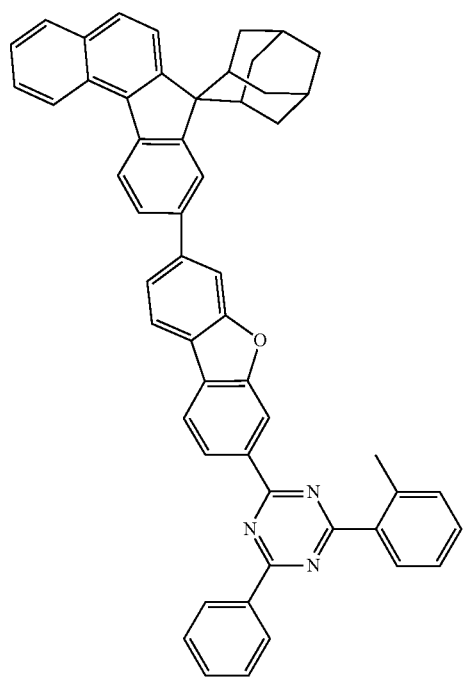
B-94
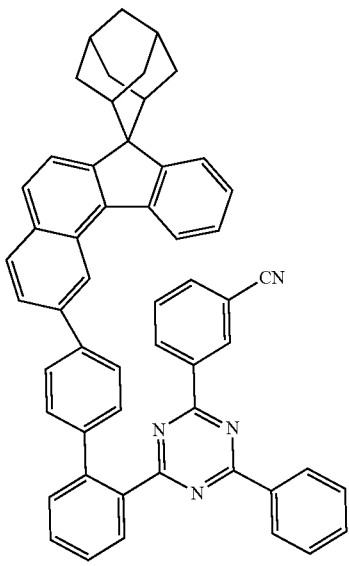

B-95
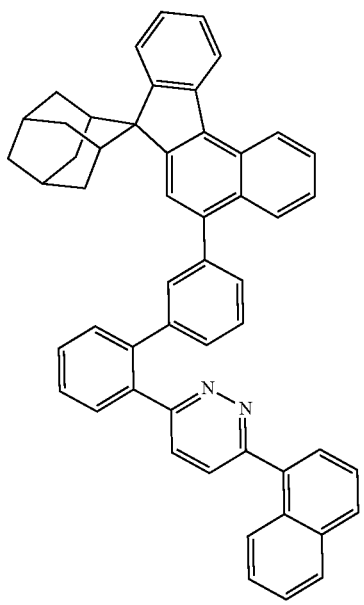
B-96
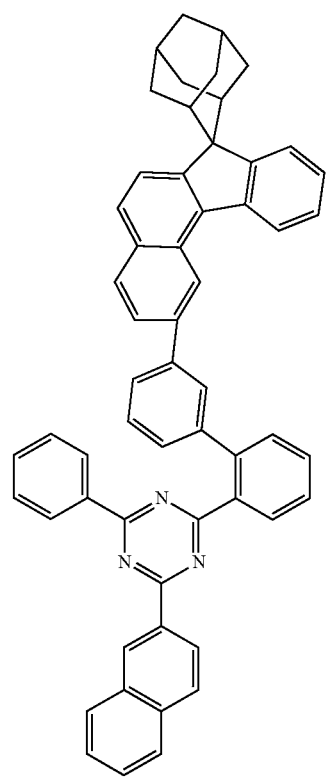
B-97
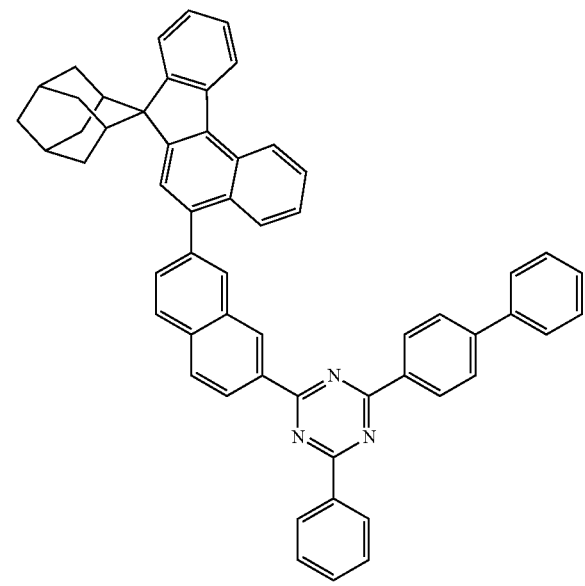
B-98
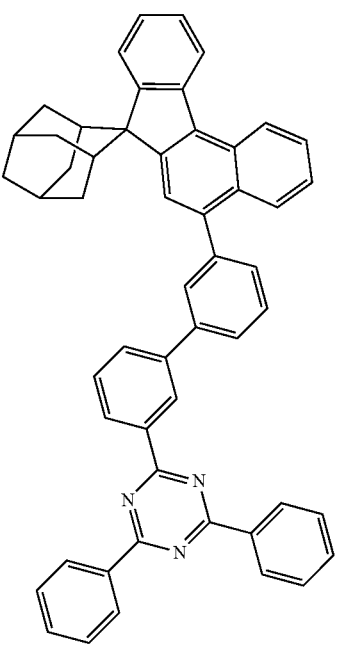

-continued
B-99
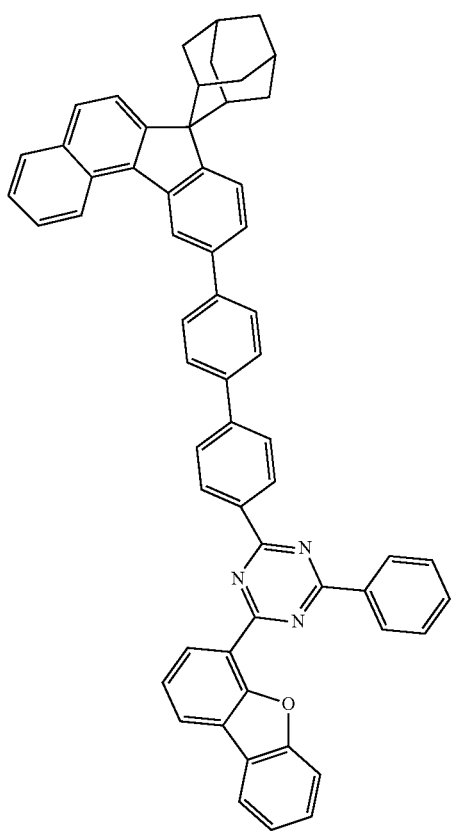
B-100
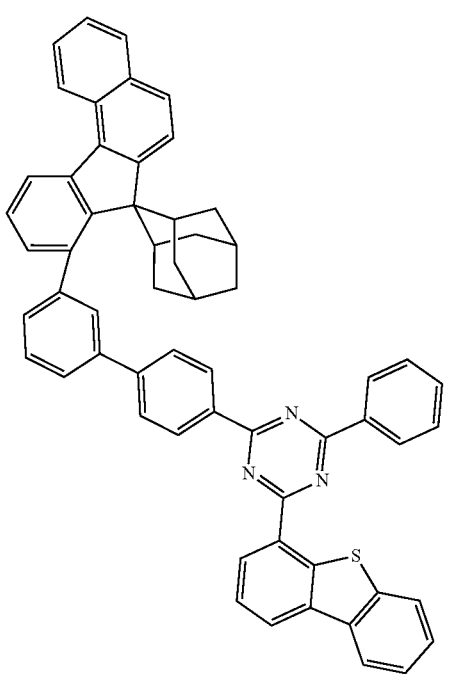
B-101
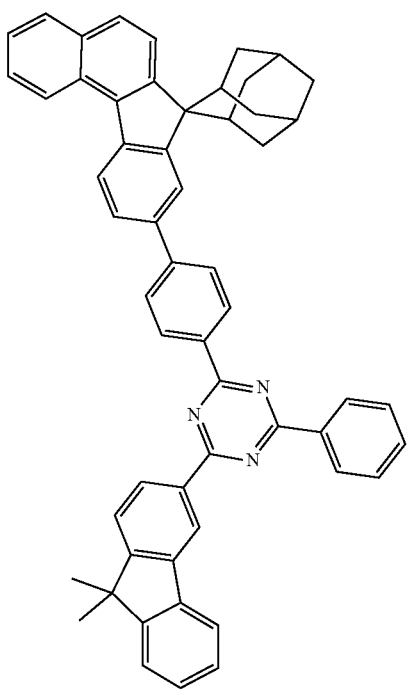
B-102
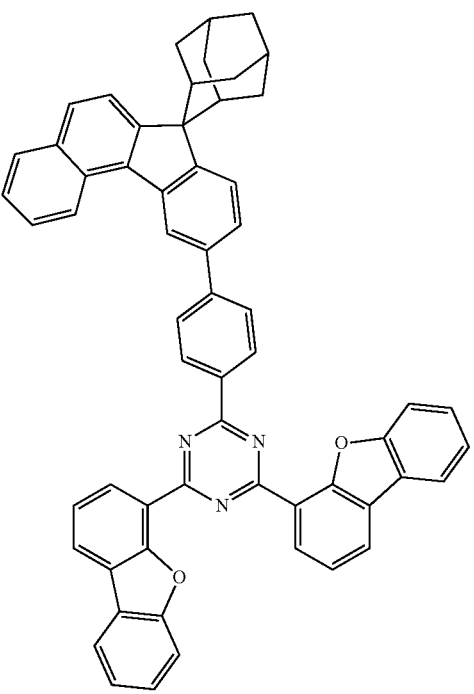

B-103
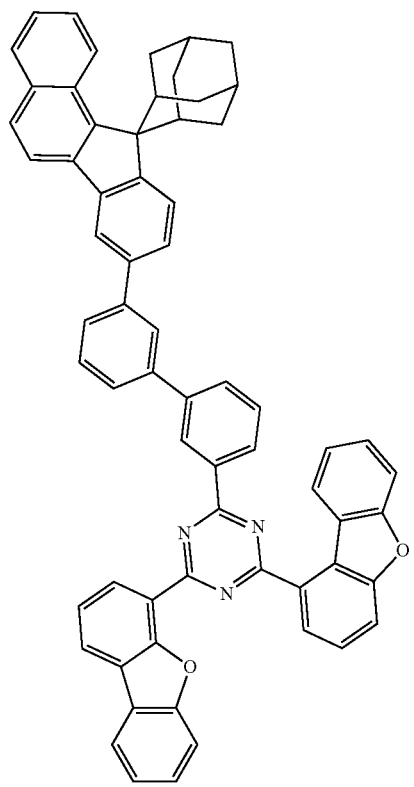
B-105
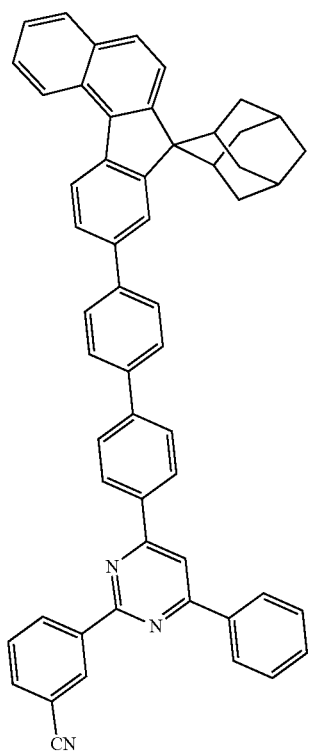
B-104
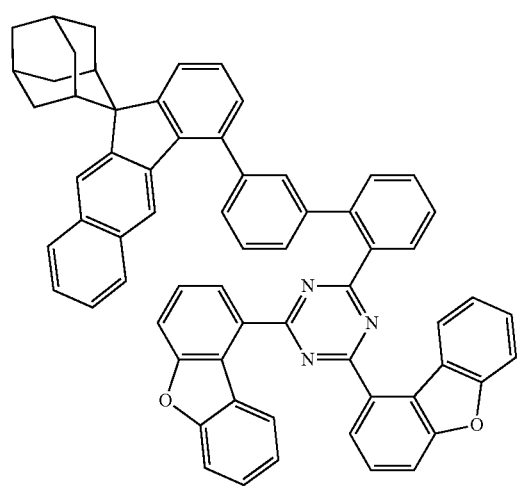
B-106
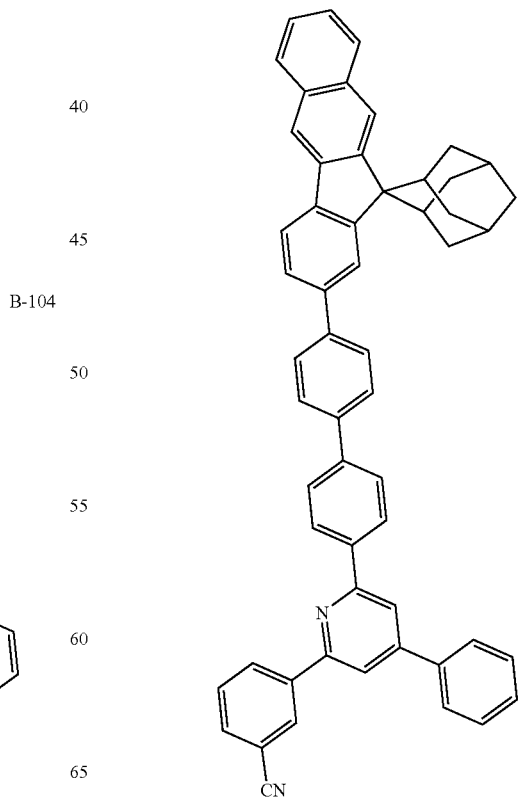

B-107
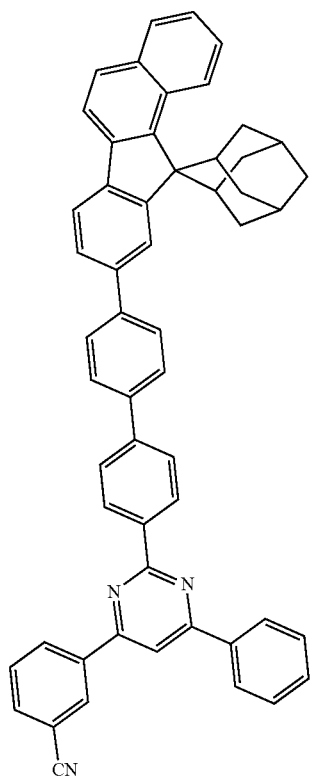
B-108
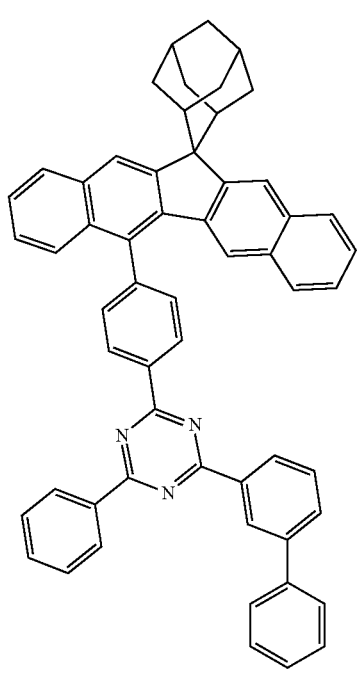
B-109
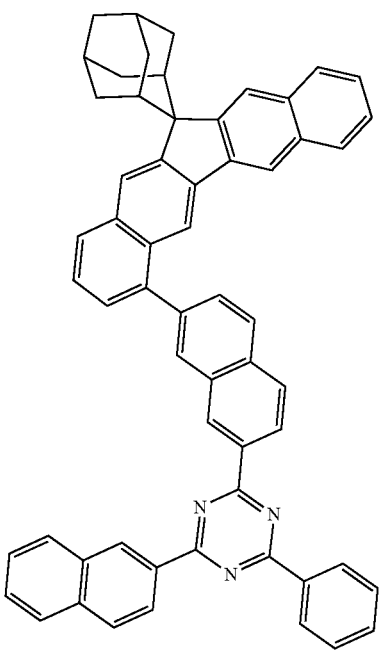
B-110
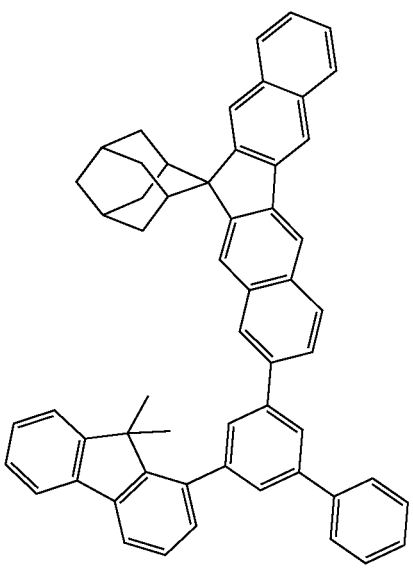

B-111
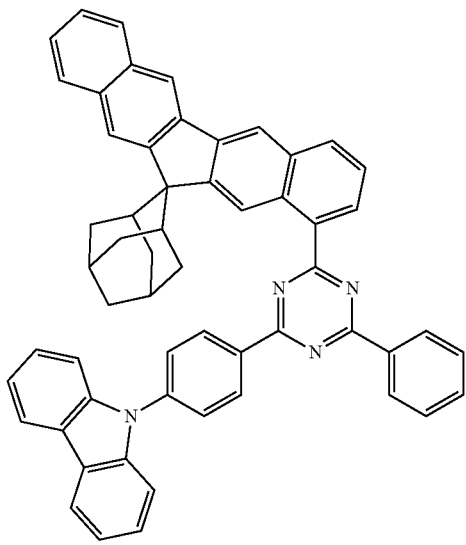
B-113
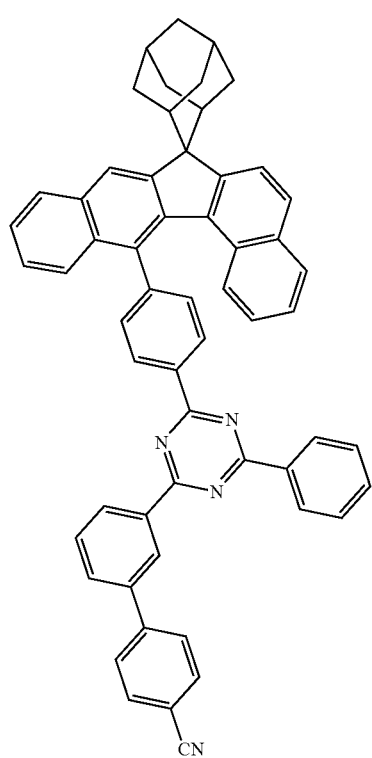
B-115
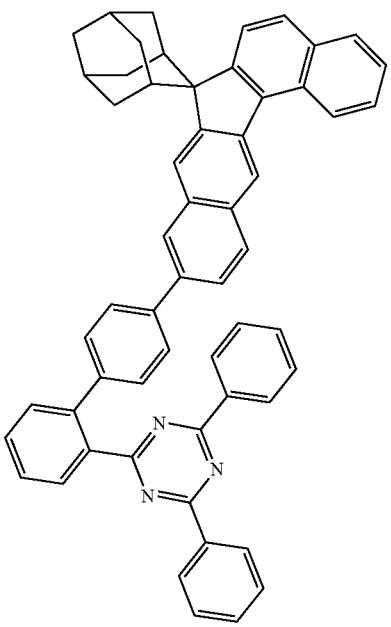
B-116
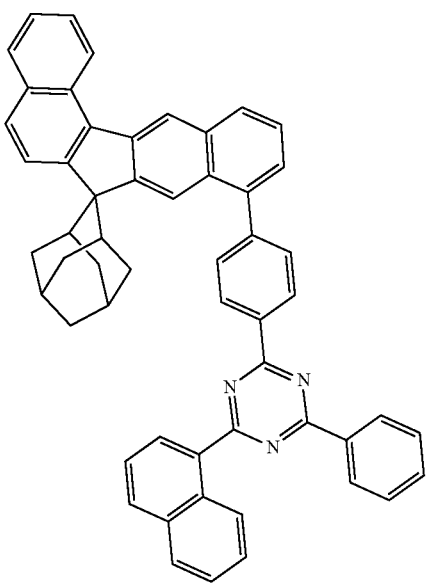

B-117
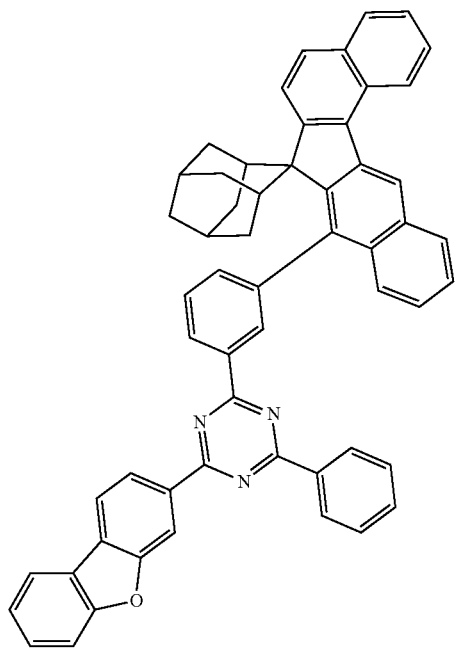
B-118
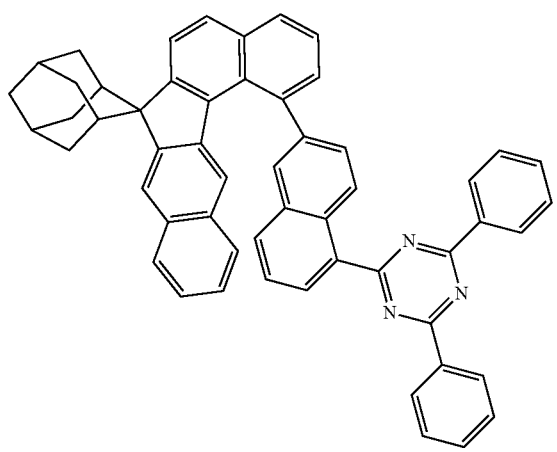
B-119
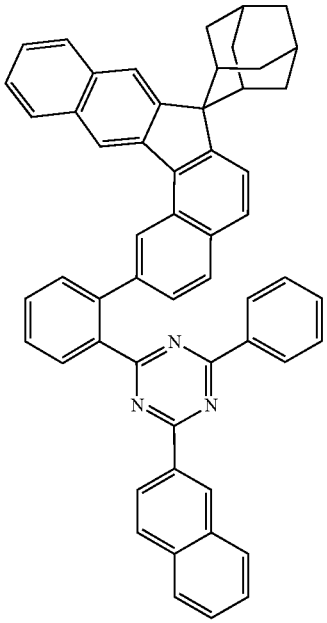
B-120
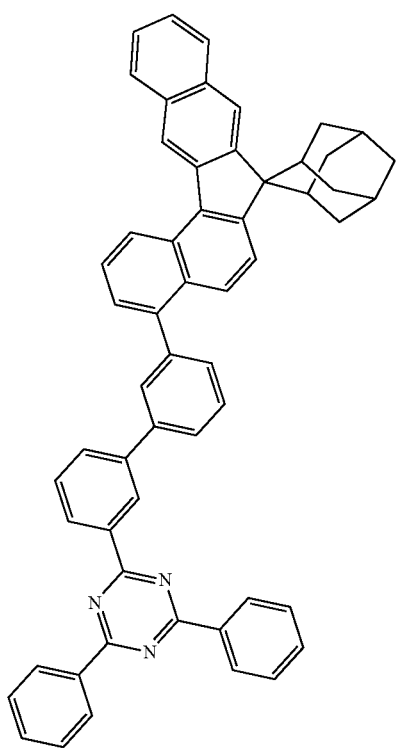

B-121
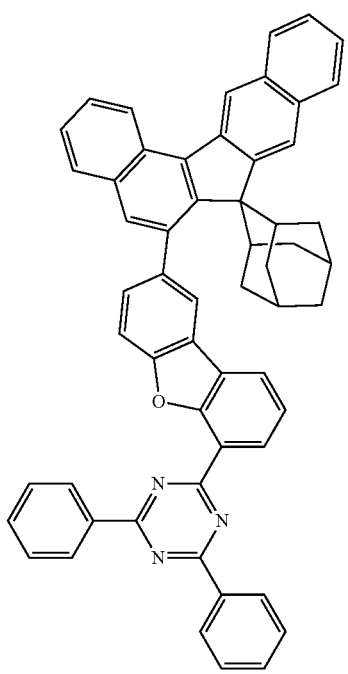
B-123
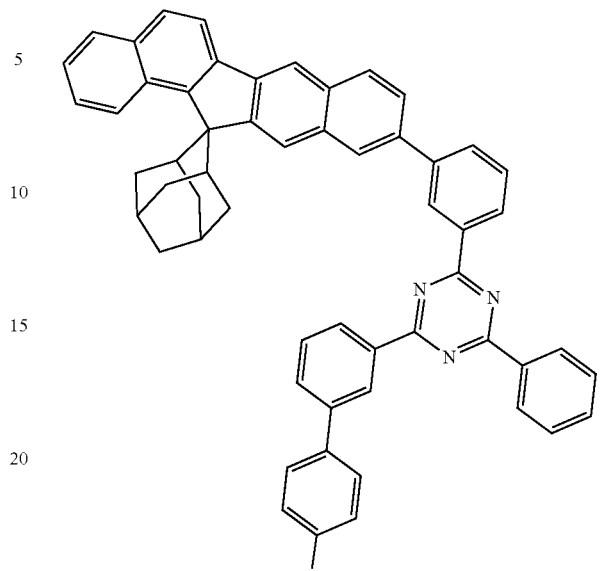
B-122
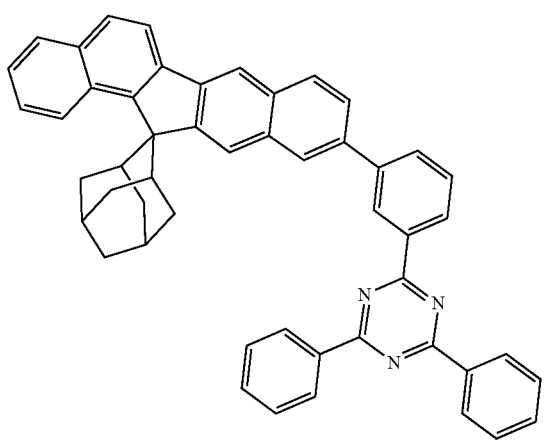
B-124
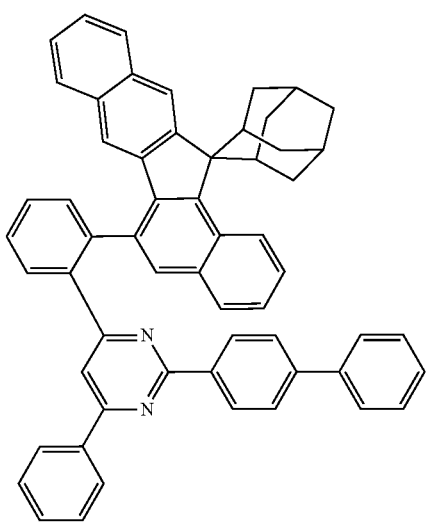

B-125
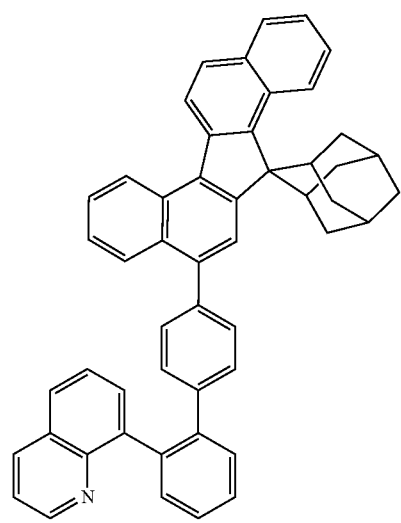
B-126
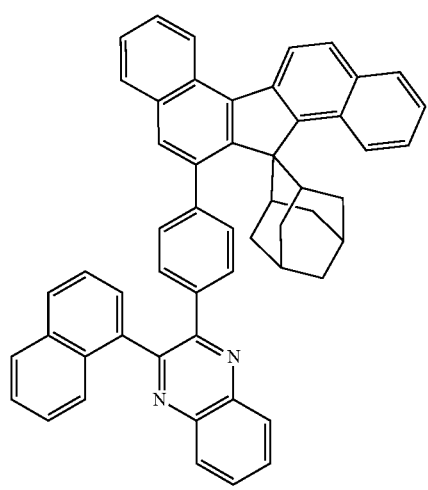
B-127
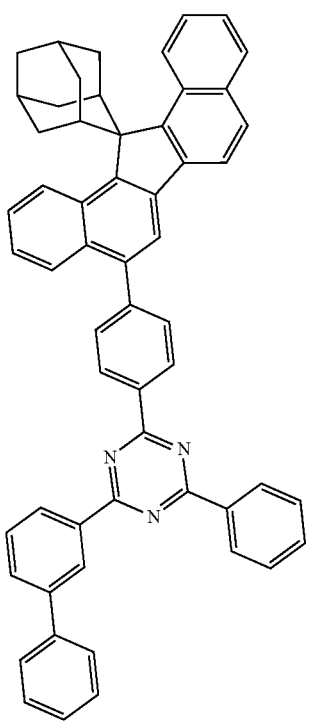
B-128
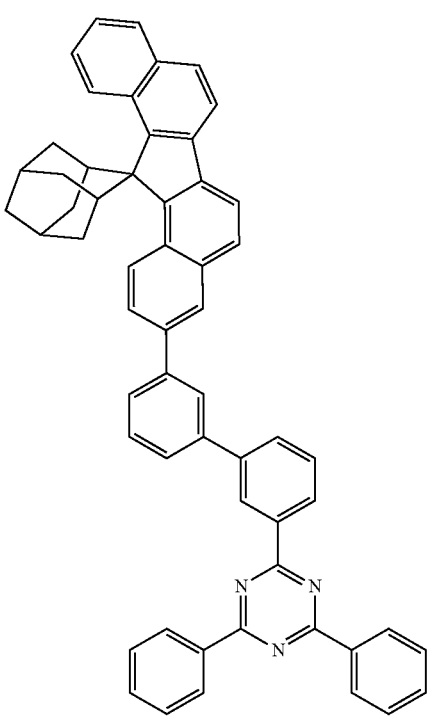

B-129

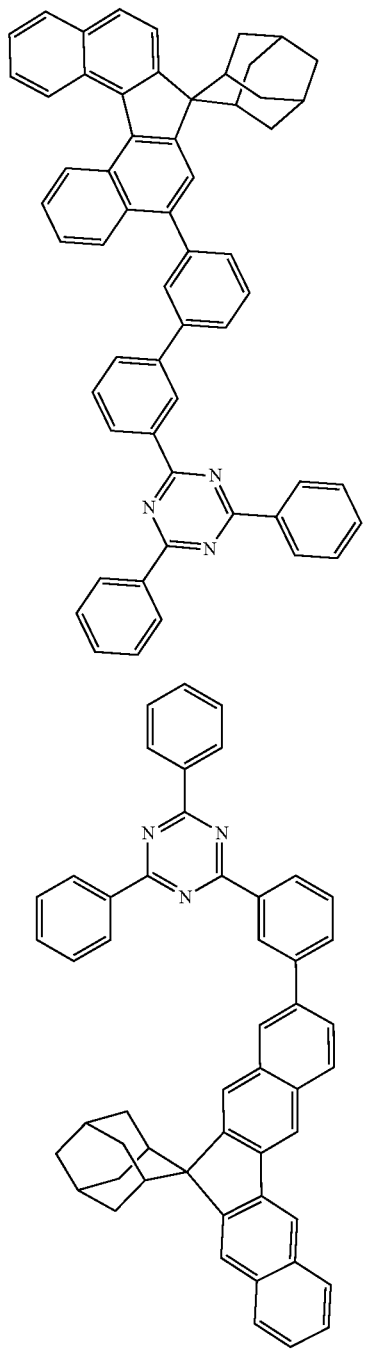

B-130

B-139

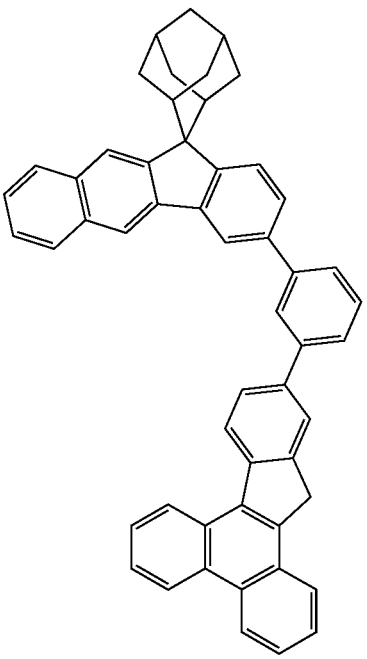

8. An electronic element, comprising an anode, a cathode which are arranged oppositely to the anode, and a functional layer arranged between the anode and the cathode; the functional layer contains the nitrogen-containing compound according to claim 1.

9. The electronic element according to claim 8, wherein the electronic element is an organic electroluminescent device or a photoelectric conversion device.

10. The electronic element according to claim 9, wherein the organic electroluminescent device is a blue light device or a green light device.

11. The electronic element according to claim 8, wherein the functional layer comprises an electron transport layer, and the electron transport layer contains the nitrogen-containing compound.

12. The electronic element according to claim 8, wherein the functional layer comprises a hole blocking layer, and the hole blocking layer contains the nitrogen-containing compound.

* * * * *

UNITED STATES PATENT AND TRADEMARK OFFICE
CERTIFICATE OF CORRECTION

PATENT NO. : 11,691,952 B2
APPLICATION NO. : 17/787656
DATED : July 4, 2023
INVENTOR(S) : Min Yang Page 1 of 1

It is certified that error appears in the above-identified patent and that said Letters Patent is hereby corrected as shown below:

In the Specification

Column 18, Line 62, formula (X'-3) " 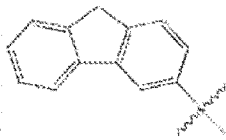 " should be -- 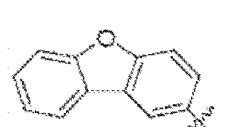 --.

Column 46, Line 30, formula " 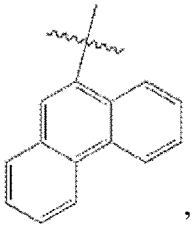 " should be -- 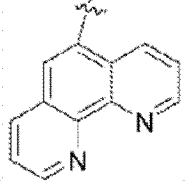 --.

Signed and Sealed this
Eighth Day of August, 2023

Katherine Kelly Vidal
*Director of the United States Patent and Trademark Office*